US011713308B2

(12) United States Patent
Han et al.

(10) Patent No.: US 11,713,308 B2
(45) Date of Patent: Aug. 1, 2023

(54) 3,3-DIFLUOROALLYLAMINES OR SALTS THEREOF AND PHARMACEUTICAL COMPOSITIONS COMPRISING THE SAME

(71) Applicant: YUHAN CORPORATION, Seoul (KR)

(72) Inventors: Tae Dong Han, Yongin-si (KR); Hee Jae Tak, Yongin-si (KR); Eun Kyung Kim, Seongnam-si (KR); Eui Chul Lee, Yongin-si (KR); Sol Park, Yongin-si (KR); Hyok Jun Cho, Hwaseong-si (KR); Cheol Hee Lim, Suwon-si (KR); So Young Kim, Suwon-si (KR); Hyun Ho Choi, Suwon-si (KR); Da Na Jeong, Seongnam-si (KR); Na Yeon Yang, Hwaseong-si (KR); Na Ry Ha, Seoul (KR)

(73) Assignee: YUHAN CORPORATION, Seoul (KR)

( * ) Notice: Subject to any disclaimer, the term of this patent is extended or adjusted under 35 U.S.C. 154(b) by 183 days.

(21) Appl. No.: 17/368,738

(22) Filed: Jul. 6, 2021

(65) Prior Publication Data
US 2023/0044255 A1    Feb. 9, 2023

Related U.S. Application Data

(63) Continuation of application No. 16/712,660, filed on Dec. 12, 2019, now Pat. No. 11,168,073.

(30) Foreign Application Priority Data

Dec. 14, 2018  (KR) .................... 10-2018-0161725
Oct. 31, 2019  (KR) .................... 10-2019-0137387

(51) Int. Cl.
| C07D 403/10 | (2006.01) |
| C07D 249/12 | (2006.01) |
| C07D 401/04 | (2006.01) |
| C07D 401/10 | (2006.01) |
| C07D 401/14 | (2006.01) |
| C07D 403/04 | (2006.01) |
| C07D 403/14 | (2006.01) |
| C07D 405/10 | (2006.01) |
| C07D 405/14 | (2006.01) |
| C07D 409/06 | (2006.01) |
| C07D 409/14 | (2006.01) |
| C07D 413/14 | (2006.01) |

(52) U.S. Cl.
CPC ......... *C07D 403/10* (2013.01); *C07D 249/12* (2013.01); *C07D 401/04* (2013.01); *C07D 401/10* (2013.01); *C07D 401/14* (2013.01); *C07D 403/04* (2013.01); *C07D 403/14* (2013.01); *C07D 405/10* (2013.01); *C07D 405/14* (2013.01); *C07D 409/06* (2013.01); *C07D 409/14* (2013.01); *C07D 413/14* (2013.01)

(58) Field of Classification Search
CPC ................ C07D 403/10; C07D 249/12; C07D 401/04; C07D 401/10; C07D 401/14; C07D 403/04; C07D 403/14; C07D 405/10; C07D 405/14; C07D 409/06; C07D 409/14; C07D 413/14; C07D 471/04; C07D 519/00
See application file for complete search history.

(56) References Cited

U.S. PATENT DOCUMENTS

| 10,562,865 | B2 | 2/2020 | Han et al. | |
| 10,899,719 | B2 | 1/2021 | Han et al. | |
| 10,995,086 | B2 * | 5/2021 | Han | .......... C07D 409/04 |
| 11,091,479 | B2 * | 8/2021 | Han | .......... A61P 1/16 |
| 11,168,073 | B2 * | 11/2021 | Han | .......... C07D 401/10 |
| 11,492,335 | B2 * | 11/2022 | Han | .......... C07D 403/10 |
| 2005/0096360 | A1 | 5/2005 | Salter-Cid et al. | |
| 2007/0293548 | A1 | 12/2007 | Wang et al. | |
| 2008/0249151 | A1 | 10/2008 | Sweeney et al. | |
| 2010/0029697 | A1 | 2/2010 | Debenham et al. | |
| 2010/0298330 | A1 | 11/2010 | McDonald et al. | |
| 2012/0225878 | A1 | 9/2012 | Bouillot et al. | |
| 2015/0158813 | A1 | 6/2015 | Deodhar et al. | |
| 2016/0009721 | A1 | 1/2016 | Wu et al. | |
| 2017/0360756 | A1 | 12/2017 | Brown et al. | |
| 2018/0104198 | A1 | 4/2018 | Rippmann et al. | |

(Continued)

FOREIGN PATENT DOCUMENTS

| EP | 0000014 | 12/1978 |
| WO | WO-2005014583 | 2/2005 |

(Continued)

OTHER PUBLICATIONS

Chemical Abstracts STN Registry Database record for RN 1700586-71-5, entered into STN on May 7, 2015.
Dobosz et al., Synthesis of 1-(3-amino-2-hydroksypropyl)-4-phenyl-1,2,4-triazolin-5-one and 1-(3-amino-2-hydroksypropyl)-3,4-diphenyl-1,2,4-triazolin-5-one derivatives. Acta Poloniae Pharmaceutica—Drug Research 2000, 57(5), pp. 363-368.
International Search Report and Written Opinion on PCT/IB2019/060736 dated Apr. 6, 2020.

(Continued)

*Primary Examiner* — Daniel R Carcanague
(74) *Attorney, Agent, or Firm* — Sheppard Mullin Richter & Hampton LLP

(57) ABSTRACT

The present technology provides 3,3-difluoroallylamines or pharmaceutically acceptable salts thereof, preparation processes thereof, pharmaceutical compositions comprising the same, and uses thereof. The 3,3-difluoroallylamines or their pharmaceutically acceptable salts exhibit potent inhibitory activity on VAP-1 and therefore can be usefully applied, e.g., for the treatment and prophylaxis of nonalcoholic hepatosteatosis (NASH).

9 Claims, No Drawings

(56) References Cited

U.S. PATENT DOCUMENTS

| | | | |
|---|---|---|---|
| 2018/0297987 A1 | 10/2018 | Coates et al. | |
| 2019/0308944 A1 | 10/2019 | Han et al. | |
| 2019/0322655 A1 | 10/2019 | Han et al. | |
| 2020/0223808 A1 | 7/2020 | Han et al. | |
| 2020/0223827 A1 | 7/2020 | Han et al. | |
| 2020/0223844 A1 | 7/2020 | Han et al. | |
| 2021/0317110 A1* | 10/2021 | Han | A61P 31/00 |
| 2022/0024918 A1* | 1/2022 | Han | A61P 1/16 |
| 2022/0380324 A1* | 12/2022 | Tak | C07D 401/14 |

FOREIGN PATENT DOCUMENTS

| | | |
|---|---|---|
| WO | WO-2006138695 | 12/2006 |
| WO | WO-2008119662 | 10/2008 |
| WO | WO-2009066152 | 5/2009 |
| WO | WO-2010096722 | 8/2010 |
| WO | WO-2013134562 | 9/2013 |
| WO | WO-2013163675 | 11/2013 |
| WO | WO-2016106106 | 6/2016 |
| WO | WO-2017046738 | 3/2017 |
| WO | WO-2017136870 | 8/2017 |
| WO | WO-2017191112 | 11/2017 |
| WO | WO-2018073154 | 4/2018 |
| WO | WO-2018157190 | 9/2018 |
| WO | WO-2018196677 | 11/2018 |
| WO | WO-2018233633 | 12/2018 |
| WO | WO-2019101086 | 5/2019 |
| WO | WO-2019129213 | 7/2019 |
| WO | WO-2019180644 | 9/2019 |
| WO | WO-2019180646 | 9/2019 |
| WO | WO-2020063696 | 4/2020 |
| WO | WO-2020063854 | 4/2020 |
| WO | WO-2020069330 | 4/2020 |
| WO | WO-2020069335 | 4/2020 |
| WO | WO-2020083264 | 4/2020 |
| WO | WO-2020086747 | 4/2020 |
| WO | WO-2020121261 | 6/2020 |
| WO | WO-2020121263 | 6/2020 |
| WO | WO-2020143763 | 7/2020 |

OTHER PUBLICATIONS

International Search Report and Written Opinion on PCT/IB2019/060738 dated Apr. 6, 2020.
International Search Report and Written Opinion, issued in Int'l. App. No. PCT/IB2019/052276, 13 pages (dated Aug. 1, 2019).
International Search Report and Written Opinion, issued in Int'l. App. No. PCT/IB2019/052278, 12 pages (dated Aug. 1, 2019).
Kirton et al., "Function-blocking antibodies to human vascular adhesion protein-1: A potential anti-inflammatory therapy", Eur. J. Immunol. 35: 3119-3130 (2005).
Mcdonald et al., "Semicarbazide Sensitive Amine Oxidase and Vascular Adhesion Protein-1: One Protein Being Validated as a Therapeutic Target for Inflammatory Diseases", Chapter 15, Annual Reports in Medicinal Chemistry 42: 229-243 (2007).
Noda et al., "Inhibition of vascular adhesion protein-1 suppresses endotoxin-induced uveitis", The FASEB Journal 22(4): 1094-1103 (2008).
Salmi et al., "VAP-1: an adhesin and an enzyme", Trends in Immunology 22(4): 211-216 (2001).
Salmi; Antioxidants & Redox Signalling 2019, 30, 314-332. (Year: 2019).
Salter-Cid et al., "Anti-Inflammatory Effects of Inhibiting the Amine Oxidase Activity of Semicarbazide-Sensitive Amine Oxidase", J. Pharmacol. Exp. Ther. 315(2): 553-562 (2005).
Sheng et al., "Design and synthesis of novel triazole antifungal derivatives by structure-based bioisosterism", Eur. J. Med. Chem. 46(11): 5276-5282 (2011).
Still et al., "Rapid Chromatographic Technique for Preparative Separations with Moderate Resolution", J. Org. Chem. 43(14): 2923-2925 (1978).
Stolen et al., "Absence of the Endothelial Oxidase AOC3 Leads to Abnormal Leukocyte Traffic In Vivo", Immunity 22: 105-115 (2005).
Sun et al., "Discovery of triazolone derivatives as novel, potent stearoyl-CoA desaturase-1 (SCD1) inhibitors", Bioorganic & Medicinal Chemistry 23(3): 455-465 (2015).
Weston et al., Vascular adhesion protein-1 promotes liver inflammation and drives hepatic fibrosis. The Journal of Clinical Investigation 2015, 125(2): 501-520.

* cited by examiner

3,3-DIFLUOROALLYLAMINES OR SALTS THEREOF AND PHARMACEUTICAL COMPOSITIONS COMPRISING THE SAME

CROSS-REFERENCE TO RELATED APPLICATIONS

This application is a continuation of U.S. patent application Ser. No. 16/712,660, filed Dec. 12, 2019, now U.S. Pat. No. 11,168,073, which application claims priority to and the benefit of Korean Patent Application No. 10-2018-0161725, filed Dec. 14, 2018, and Korean Patent Application No. 10-2019-0137387, filed Oct. 31, 2019, the entire contents of each of which are incorporated by reference herein in their entireties.

FIELD

The present technology relates to 3,3-difluoroallylamines or pharmaceutically acceptable salts thereof having inhibitory activity on vascular adhesion protein (VAP-1), a process for the preparation thereof, a pharmaceutical composition comprising the same, and uses thereof.

BACKGROUND

Vascular adhesion protein-1 (VAP-1) is a semicarbazide-sensitive amine oxidase (SSAO), which is abundantly present in human plasma. VAP-1 is an ectoenzyme comprising a short cytoplasmic tail, a single transmembrane domain, and an extracellular domain with large and high glycosylation containing the center of activity. In addition, VAP-1 exists not only as a membrane-bound form in the endothelium, but also as a soluble form in serums (soluble VAP-1, sVAP-1). This form was shown to be a product cleaved from the membrane-bound VAP-1, and appears to have similar properties as the tissue-bound form. It has been also reported that VAP-1 is normally stored in intracellular granules within endothelial cells, but when an inflammatory response is evoked in response to inflammatory stimuli, it is translocated onto the cell membrane, and its expression is upregulated, and therefore, it is expressed more strongly in inflamed tissues than in normal tissues.

Substrates for VAP-1 include endogenous methylamine and aminoacetone as well as some xenobiotic amines such as tyramine and benzylamine.

VAP-1 has two physiological functions: the first is amine oxidase activity stated earlier in this section, and the second is cell adhesion activity. Due to these two activities, VAP-1 has been shown to play a key role in the leakage of inflammatory cells as it acts as an adhesion protein for leukocytes in inflamed sites [Trends Immunol. (2001) 22: 211]. VAP-1-deficient transgenic mice are healthy, develop normally, and fertile, and phenotypically normal, but exhibit a marked decrease in the inflammatory responses evoked in response to various inflammatory stimuli [Immunity. (2005) 22: 105].

In addition, inhibitory activity of VAP-1 in multiple animal models of human diseases (e.g., carrageenan-induced paw inflammation, oxazolone-induced colitis, lipopolysaccharide-induced lung inflammation, collagen-induced arthritis, endotoxin-induced uveitis) by the use of antibodies or small molecules has been shown to prevent leukocyte from rolling, adhering, and leaking, and reduce levels of inflammatory cytokines and chemokines, thereby reducing the severity of the disease [Eur J Immunol. (2005) 35: 3119; J Pharmacol Exp Ther. (2005) 315: 553; Annu Rep Med Chem. (2007) 42: 229; FASEB J. (2008) 22: 1094]. Inflammation is the first reaction of the immune system to infection or stimulus, and in such a process, the movement of leukocytes into the tissue through circulation is an important step. The leukocytes are first bound to adhesion proteins and then adhered to the endothelium before they start to pass through blood vessel walls. VAP-1 is highly expressed in endothelial venules (HEV) such as high endothelial venules in lymphoid organs, as well as hepatic sinusoidal endothelial cells, (HSEC), smooth muscle cells, and adipocytes. The VAP-1 expression on the cell surface of endothelial cells is strictly regulated and is increased during inflammation. VAP-1 activates NF-κB when it is present in the substrate, and the NF-κB is activated within the HSEC while E-selectin and chemokine IL-8 that are other adhesion molecules are upregulated ex vivo. This suggests that VAP-1 may be a key factor for the regulation of the inflammatory response. Therefore, it seems likely that VAP-1 inhibitors may be effective anti-inflammatory drugs in a wide range of human diseases.

Nonalcoholic fatty liver disease (NAFLD), histologically, encompasses simple steatosis, nonalcoholic hepatosteatosis (NASH), and liver cirrhosis. Among these, unlike simple steatosis (non-alcoholic fatty liver, NAFL), NASH potentially progresses to liver cirrhosis and hepatoma (hepatocellular carcinoma). In NASH, insulin resistance is known to play an important role in the progression of disease, along with oxidative stress, inflammatory cascade, and fibrosis. In patients with NAFLD, sVAP-1 levels were found to be elevated, and in VAP-1 knockout (K/O) mice, carbon tetrachloride-induced liver fibrosis was reduced compared with that in wild type animals. In addition, improvement of liver fibrosis by VAP-1 inhibition following administration of VAP-1 antibody was identified by histological changes [J Clin Invest (2015) 125: 501], Thus, VAP-1 was found to be associated with NASH in clinical studies and animal models of diseases. Inhibitory activity of VAP-1 in the carbon tetrachloride-induced animal model appears to be due to a reduction in infiltration of leukocytes such as T cells, B cells, NKT cells, and NK cells observed in liver fibrosis, and VAP-1 inhibitors have the potential for treating fibrotic diseases.

Thus, a substance that inhibits VAP-1 may be applied to prevention and treatment of various inflammatory diseases and fibrotic diseases.

SUMMARY

The present inventors found that triazolones having 3,3-difluoroallylamine groups or their pharmaceutically acceptable salts exhibit inhibitory activity on VAP-1. Therefore, the 3,3-difluoroallylamines or their salts can be usefully used in the treatment and prophylaxis of various VAP-1 mediated diseases, for example, nonalcoholic hepatosteatosis (NASH).

Therefore, the present technology provides the 3,3-difluoroallylamines or their pharmaceutically acceptable salts, preparation processes thereof, pharmaceutical compositions comprising the same, and the use thereof.

In accordance with one aspect of the present technology, there is provided a 3,3-difluoroallylamine or its pharmaceutically acceptable salt.

In accordance with another aspect of the present technology, there is provided a preparation process of the 3,3-difluoroallylamine or its pharmaceutically acceptable salt.

In accordance with another aspect of the present technology, there is provided a pharmaceutical composition comprising the 3,3-difluoroallylamine or its pharmaceutically acceptable salt as an active ingredient.

In accordance with another aspect of the present technology, there is provided a method of treatment comprising administering the 3,3-difluoroallylamine or its pharmaceutically acceptable salt.

In accordance with another aspect of the present technology, there is provided the use of the 3,3-difluoroallylamine or its pharmaceutically acceptable salt in the manufacture of a medicament for inhibition of vascular adhesion protein-1.

It was found by the present technology that triazolones having 3,3-difluoroallylamine groups or their pharmaceutically acceptable salts exhibit inhibitory activity on VAP-1. Therefore, the compounds according to the present technology or pharmaceutically acceptable salts thereof can be usefully applied for the treatment and prophylaxis of VAP-1 mediated various diseases, for example, nonalcoholic hepatosteatosis (NASH).

Provided herein in one aspect is a compound of Formula X

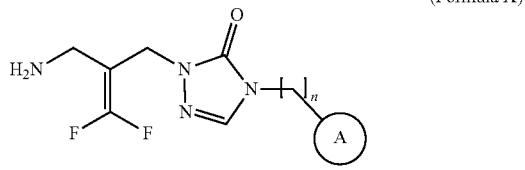

(Formula X)

or a stereoisomer thereof or a pharmaceutically acceptable salt thereof;
wherein
n is 0, 1 or 2; and
A is an aryl group or a heterocyclic group, wherein said heterocyclic group has 1 to 5 heteroatom ring members chosen from O, N, or S, and said heterocyclic group is aromatic or non-aromatic; and wherein said aryl group or said heterocyclic group is optionally substituted with one or two substituents selected from the group consisting of $C_{1-3}$ alkyl, halogen, benzyloxy, —R, —CH=CH—R, and —C≡C—R; and
R is a substituted or unsubstituted cyclic ring, optionally containing 1 to 5 heteroatom ring members chosen from O, N, or S, and said cyclic ring is aromatic or non-aromatic. In some embodiments, A is aryl optionally substituted with one or two substituents selected from the group consisting of $C_{1-3}$ alkyl, halogen, benzyloxy, —R, —CH=CH—R, and —C≡C—R. In some embodiments, A is phenyl substituted with one or two substituents selected from the group consisting of $C_{1-3}$ alkyl, halogen, benzyloxy, —R, —CH=CH—R, and —C≡C—R. In some embodiments, A is a heterocyclic group having 1 to 5 heteroatom ring members chosen from O, N, or S; said heterocyclic group is aromatic or non-aromatic; and said heterocyclic group is optionally substituted with one or two substituents selected from the group consisting of $C_{1-3}$ alkyl, halogen, benzyloxy, —R, —CH=CH—R, and —C≡C—R. In some embodiments, A is a heteroaryl group having 1 to 5 heteroatom ring members chosen from O, N, or S; and said heteroaryl group is optionally substituted with one or two substituents selected from the group consisting of $C_{1-3}$ alkyl, halogen, benzyloxy, —R, —CH=CH—R, and —C≡C—R. In some embodiments, A is pyridine, pyrazine, or thiophene, wherein A is optionally substituted with one or two substituents selected from the group consisting of $C_{1-3}$ alkyl, halogen, benzyloxy, —R, —CH=CH—R, and —C≡C—R. In some embodiments, R is a cyclic ring optionally containing 1-5 heteroatom ring members, and said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, $C_{1-6}$ alkylpyrazolyl, triazolyl, pyrrolidinonyl, and pyrrolidinyl. In some embodiments, n is 0. In some embodiments, n is 1. In some embodiments, n is 2.

Provided herein in another aspect is a compound, of Formula Y

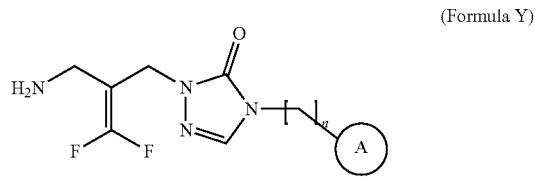

(Formula Y)

or a stereoisomer thereof or a pharmaceutically acceptable salt thereof;
wherein
n is 0, 1 or 2;
A is an aryl or heteroaryl group selected from the group consisting of phenyl, pyridine, pyrazine, thiophene, and benzothiophene;
wherein said aryl or heteroaryl group is optionally substituted with one or two substituents selected from the group consisting of $C_{1-3}$ alkyl, halogen, benzyloxy, —R, —CH=CH—R, and —C≡C—R;
wherein said R is a cyclic ring selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 3,4-dihydro-1,4-benzoxazine, 2,3-dihydro-1,4-benzoxazine, 1,4-benzoxazin-3-one, 1,4-dihydro-3,1-benzoxazin-2-one, 5,6,7,8-tetrahydronaphthyridine, triazolo[1,5-a]pyridine, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, 1,4-dihydroquinazolin-2-one, 1H-pyrrolo[2,3-b]pyridine, benzoxazole, and thiophene;
wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, $C_{1-6}$ alkylpyrazolyl, triazolyl, pyrrolidinonyl, and pyrrolidinyl.

In some embodiments, n is 0 or 1, and A is phenyl, pyridine or thiophene, optionally substituted with one or two substituents selected from the group consisting of $C_{1-3}$ alkyl, halogen, benzyloxy, —R, —CH=CH—R, and —C≡C—R. In some embodiments, said aryl or heteroaryl group is substituted with one or two substituents selected from the group consisting of $C_{1-3}$ alkyl, halogen, and —R. In some embodiments, said R is a cyclic ring selected from the group consisting of benzene, pyridine, pyridin-2-one, pyrazole and 3,4-dihydroquinolin-2-one, said cyclic ring is optionally substituted with one to three substituents selected from the group consisting of halogen, $C_{1-6}$ alkyl, difluoromethyl, trifluoromethyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl. In some embodiments, said cyclic ring is substituted with a substituent selected from the group consisting of $C_{1-6}$ alkyl, $C_{1-6}$ alkylsulfonyl, di-$C_{1-6}$ alkylamino, and piperazinyl. In some embodiments, n is 0; A is phenyl; wherein said phenyl is substituted with one or two substituents selected from the group consisting of halogen and —R; wherein said R is a cyclic ring selected from the group consisting of benzene, pyridine, 3,4-dihydroquinolin-2-one and pyrazole; and wherein said cyclic ring is substituted with a substituent selected from the group consisting of $C_{1-6}$ alkyl, $C_{1-6}$ alkylsulfonyl, di-$C_{1-6}$ alkylamino, and piperazinyl. In some embodiments, n is 0; A is pyridine; wherein said pyridine is substituted with one or two substituents selected from the group consisting of $C_{1-3}$ alkyl, halogen, and —R; wherein said R is a cyclic ring selected from the group consisting of benzene, pyridine, 3,4-dihydroquinolin-2-one and pyrazole; and wherein said cyclic ring is substituted with a substituent selected from the group consisting of $C_{1-6}$ alkyl, $C_{1-6}$ alkylsulfonyl, di-$C_{1-6}$ alkylamino, and piperazinyl. In some embodiments, n is 0; A is thiophene; wherein said thiophene is substituted with one or two cyclic rings selected from the group consisting of benzene, pyridine, pyridin-2-one, 3,4-dihydroquinolin-2-one and pyrazole; and wherein said cyclic ring is substituted with a substituent selected from the group consisting of $C_{1-6}$ alkyl, $C_{1-6}$ alkylsulfonyl, di-$C_{1-6}$ alkylamino, and piperazinyl. In some embodiments, A is phenyl optionally substituted with one or two substituents selected from the group consisting of $C_{1-3}$ alkyl, halogen, benzyloxy, —R, —CH=CH—R, and —C≡C—R. In some embodiments, A is phenyl substituted with —R. In some embodiments, —R is a cyclic ring selected from the group consisting of benzene, pyridine, pyridin-2-one, pyrazole, benzodioxole, and 3,4-dihydroquinolin-2-one; wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl. In some embodiments, A is pyridine substituted with —R. In some embodiments, —R is a cyclic ring selected from the group consisting of benzene, pyridine, pyridin-2-one, pyrimidine, pyrazole, benzodioxole, benzoxadiazole, benzothiazole, indazole, 2,3-dihydro-1,4-benzoxazine, 1,4-benzoxazin-3-one, 1,4-dihydro-3,1-benzoxazin-2-one, 1,4-dihydroquinazolin-2-one, 1H-pyrrolo[2,3-b]pyridine, benzoxazole, and thiophene, wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- $C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinonyl. In some embodiments, A is thiophene substituted with —R. In some embodiments, —R is a cyclic ring selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 2,3-dihydro-1,4-benzoxazine, 1,4-dihydro-3,1-benzoxazin-2-one, 5,6,7,8-tetrahydronaphthyridine, triazolo[1,5-a]pyridine, pyrido[2,3-b][1,4]oxazin-2-one, and 1,4-dihydroquinazolin-2-one; wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl. In some embodiments, A is benzothiophene substituted with —R. In some embodiments, —R is a cyclic ring selected from the group consisting of benzene, pyridine, pyridin-2-one, pyrazole, benzodioxole, and 3,4-dihydroquinolin-2-one, wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl. In some embodiments, n is 0. In some embodiments, n is 1. In some embodiments, n is 2.

Provided herein in another aspect is a compound of Formula 12

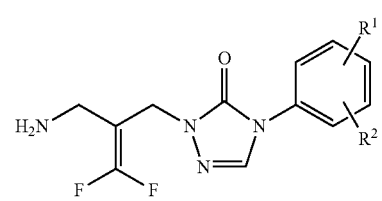

(Formula 12)

or a stereoisomer thereof or a pharmaceutically acceptable salt thereof;

wherein $R^1$ is hydrogen, halogen, or $C_{1-6}$ alkyl; and $R^2$ is a substituted or unsubstituted aryl group or a substituted or unsubstituted heteroaryl group, wherein said heteroaryl group has 1 to 5 heteroatom ring members chosen from O, N, or S.

In some embodiments, $R^1$ is hydrogen. In some embodiments, $R^1$ is halogen. In some embodiments, $R^1$ is $C_{1-6}$ alkyl. In some embodiments, $R^2$ is a substituted or unsubstituted aryl group. In some embodiments, $R^2$ is substituted or unsubstituted phenyl. In some embodiments, $R^2$ is phenyl substituted with triazolyl, $C_{1-6}$ alkylsulfonyl, or piperazinyl. In some embodiments, $R^2$ is benzodioxole or 3,4-dihydroquinolin-2-one, wherein said 3,4-dihydroquinolin-2-one is optionally substituted with $C_{1-6}$ alkyl. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with trifluoromethyl or mono- or di-$C_{1-6}$ alkylamino. In some embodiments, $R^2$ is substituted or unsubstituted pyrazole. In some embodiments, $R^2$ is pyrazole substituted with $C_{1-6}$ alkyl or difluoromethyl.

Provided herein in another aspect is a compound of Formula 13

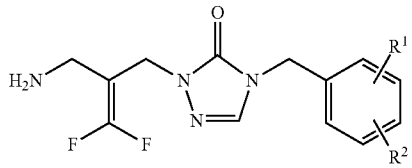

(Formula 13)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aralkoxy group, a substituted or unsubstituted aryl group, or a substituted or unsubstituted heterocyclic group, wherein said heterocyclic group has 1 to 5 heteroatom ring members chosen from O, N, or S, and said heterocyclic group is aromatic or non-aromatic.

In some embodiments, $R^1$ is hydrogen. In some embodiments, $R^1$ is halogen. In some embodiments, $R^1$ is $C_{1-6}$ alkyl. In some embodiments, $R^2$ is a substituted or unsubstituted aryl group. In some embodiments, $R^2$ is substituted or unsubstituted phenyl. In some embodiments, $R^2$ is phenyl substituted with $C_{1-6}$ alkylsulfonyl or piperazinyl. In some embodiments, $R^2$ is benzodioxole or 3,4-dihydroquinolin-2-one, wherein said 3,4-dihydroquinolin-2-one is optionally substituted with $C_{1-6}$ alkyl. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with mono- or di-$C_{1-6}$ alkylamino. In some embodiments, $R^2$ is substituted or unsubstituted pyrazole. In some embodiments, $R^2$ is pyrazole substituted with $C_{1-6}$ alkyl. In some embodiments, $R^2$ is substituted or unsubstituted pyridin-2-one. In some embodiments, $R^2$ is pyridin-2-one substituted with $C_{1-6}$ alkyl. In some embodiments, $R^2$ is substituted or unsubstituted aralkoxy group. In some embodiments, $R^2$ is substituted or unsubstituted benzyloxy.

Provided herein in another aspect is a compound of Formula 14

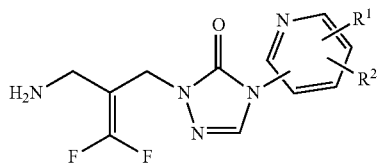

(Formula 14)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

In some embodiments, the compound is of Formula 14a

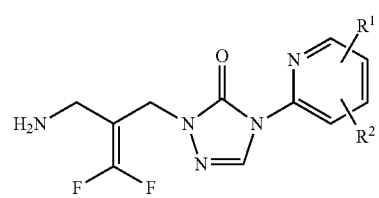

(Formula 14a)

or a stereoisomer thereof or a pharmaceutically acceptable salt thereof. In some embodiments, the compound is of Formula 14b

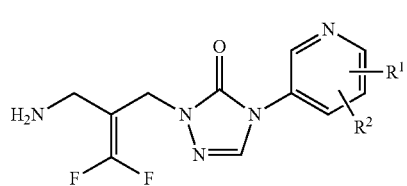

(Formula 14b)

or a stereoisomer thereof or a pharmaceutically acceptable salt thereof. In some embodiments, the compound is of Formula 14c

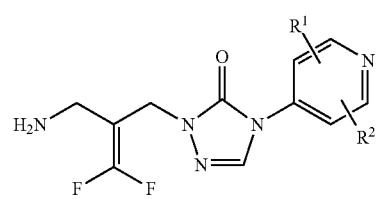

(Formula 14c)

or a stereoisomer thereof or a pharmaceutically acceptable salt thereof. In some embodiments, $R^1$ is hydrogen. In some embodiments, $R^1$ is halogen. In some embodiments, $R^1$ is $C_{1-6}$ alkyl. In some embodiments, $R^2$ is a substituted or unsubstituted aryl group. In some embodiments, $R^2$ is substituted or unsubstituted phenyl. In some embodiments, $R^2$ is phenyl substituted with one to three substituents selected from the group consisting of with halogen, $C_{1-6}$ alkoxy, mono- or di-$C_{1-6}$ alkylamino, mono- or di-$C_{1-6}$ alkylaminosulfonyl, $C_{1-6}$ alkylsulfonyl, morpholinylcarbonyl, piperazinyl, morpholinyl, pyrazolyl, $C_{1-6}$ alkylpyrazolyl, triazolyl, and pyrrolidinonyl. In some embodiments, $R^2$ is benzodioxole, benzoxadiazole, benzothiazole, indazole, 2,3-dihydro-1,4-benzoxazine, 1,4-benzoxazin-3-one, 1,4-dihydro-3,1-benzoxazin-2-one, 1,4-dihydroquinazolin-2-one, 3,4-dihydroquinolin-2-one, or benzoxazole, wherein $R^2$ is optionally substituted with $C_{1-6}$ alkyl or amino. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with $C_{1-6}$ alkoxy, trifluoromethyl, piperazinyl, morpholinyl, or mono- or di-$C_{1-6}$ alkylamino. In some embodiments, $R^2$ is pyrimidine, 1H-pyrrolo[2,3-b]pyridine, pyrazole, or thiophene, wherein $R^2$ is optionally substituted with $C_{1-6}$ alkyl, difluoromethyl, $C_{1-6}$ alkoxy-$C_{1-6}$ alkylamino, or $C_{1-6}$ alkylcarbonyl. In some embodiments, $R^2$ is substituted or unsubstituted pyridin-2-one. In some embodiments, $R^2$ is pyridin-2-one substituted with $C_{1-6}$ alkyl.

Provided herein in another aspect is a compound of Formula 15

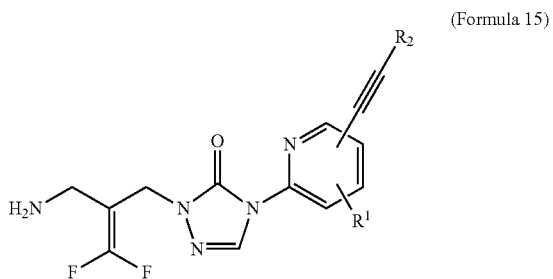

(Formula 15)

or a stereoisomer thereof or a pharmaceutically acceptable salt thereof;
wherein
$R^1$ is hydrogen or $C_{1-6}$ alkyl; and
$R^2$ is a substituted or unsubstituted aryl or a substituted or unsubstituted heteroaryl, wherein said heteroaryl group has 1 to 5 heteroatom ring members chosen from O, N, or S group.

In some embodiments, $R^1$ is hydrogen. In some embodiments, $R^1$ is $C_{1-6}$ alkyl. In some embodiments, $R^2$ is a substituted or unsubstituted aryl group. In some embodiments, $R^2$ is substituted or unsubstituted phenyl. In some embodiments, $R^2$ is 2,3-dihydro-1,4-benzoxazine or 3,4-dihydroquinolin-2-one, wherein said 3,4-dihydroquinolin-2-one is optionally substituted with $C_{1-6}$ alkyl. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with morpholinyl or mono- or di-$C_{1-6}$ alkylamino. In some embodiments, $R^2$ is 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, or pyrazole, wherein said pyrazole is optionally substituted with $C_{1-6}$ alkyl.

Provided herein in another aspect is a compound of Formula 16

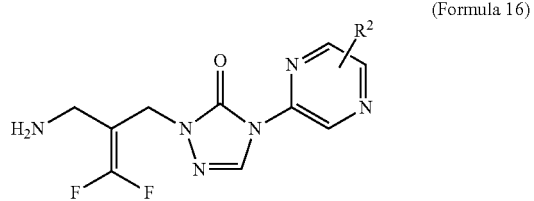

(Formula 16)

or a stereoisomer thereof or a pharmaceutically acceptable salt thereof;
wherein $R^2$ is a substituted or unsubstituted aryl or a substituted or unsubstituted heteroaryl group, wherein said heteroaryl group has 1 to 5 heteroatom ring members chosen from O, N, or S.

In some embodiments, $R^2$ is a substituted or unsubstituted aryl group. In some embodiments, $R^2$ is substituted or unsubstituted phenyl. In some embodiments, $R^2$ is phenyl substituted with $C_{1-6}$ alkylsulfonyl or piperazinyl. In some embodiments, $R^2$ is benzodioxole or 3,4-dihydroquinolin-2-one, wherein said 3,4-dihydroquinolin-2-one is optionally substituted with $C_{1-6}$ alkyl. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with trifluoromethyl or mono- or di-$C_{1-6}$ alkylamino. In some embodiments, $R^2$ is substituted or unsubstituted pyrazole. In some embodiments, $R^2$ is pyrazole substituted with $C_{1-6}$ alkyl.

Provided herein in another aspect is a compound of Formula 17

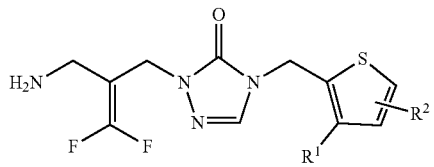

(Formula 17)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

In some embodiments, $R^1$ is hydrogen. In some embodiments, $R^1$ is halogen. In some embodiments, $R^1$ is $C_{1-6}$ alkyl. In some embodiments, $R^2$ is a substituted or unsubstituted aryl group. In some embodiments, $R^2$ is substituted or unsubstituted phenyl. In some embodiments, $R^2$ is phenyl substituted with one to three substituents selected from the group consisting of $C_{1-6}$ alkoxy, $C_{1-6}$ alkylcarbonyl, $C_{1-6}$ alkylsulfonyl, mono- or di-$C_{1-6}$ alkylaminosulfonyl, mono- or di-$C_{1-6}$ alkylaminocarbonyl, morpholinylcarbonyl, pyrazolyl, $C_{1-6}$ alkylpyrazolyl, triazolyl, piperazinyl, and acetylpiperazinyl. In some embodiments, $R^2$ is 3,4-dihydroisoquinolin-1-one, quinolin-2-one, 2,3-dihydro-1,4-benzoxazine, 1,4-benzoxazin-3-one, 1,4-dihydro-3,1-benzoxazin-2-one, 1,4-dihydroquinazolin-2-one, benzothiazole, benzoxadiazole, indazole, benzodioxole, 1,3-dihydroindol-2-one, or 3,4-dihydroquinolin-2-one; wherein $R^2$ is optionally substituted with $C_{1-6}$ alkyl, $C_{1-6}$ alkylcarbonylamino, or halogen. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with one to three substituents selected from the group consisting of halogen, trifluoromethyl, $C_{1-6}$ alkoxy, piperazinyl and mono- or di-$C_{1-6}$ alkylamino. In some embodiments, $R^2$ is substituted or unsubstituted pyrazole. In some embodiments, $R^2$ is pyrazole substituted with $C_{1-6}$ alkyl, difluoromethyl, benzyl, (cycloalkyl)alkyl, alkylsulfonyl, or cycloalkylsulfonyl. In some embodiments, $R^2$ is 5,6,7,8-tetrahydronaphthyridine, pyrimidine, imidazole, or triazolo[1,5-a]pyridine; wherein $R^2$ is optionally substituted with one to three substituents selected from the group consisting of halogen, $C_{1-6}$ alkyl, $C_{1-6}$ alkoxy, amino, and $C_{1-6}$ alkoxy-$C_{1-6}$ alkylamino. In some embodiments, $R^2$ is [1,2,4]triazolo[1,5-a]pyridine. In some embodiments, $R^2$ is tetrahydropyridine or pyridin-2-one, wherein said tetrahydropyridine and said pyridin-2-one are optionally substituted with $C_{1-6}$ alkyl or $C_{1-6}$ alkylcarbonyl.

Provided herein in another aspect is a compound of Formula 18

(Formula 18)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aryl or a substituted or unsubstituted heteroaryl group, wherein said heteroaryl group has 1 to 5 heteroatom ring members chosen from O, N, or S.

In some embodiments, $R^1$ is hydrogen. In some embodiments, $R^1$ is halogen. In some embodiments, $R^1$ is $C_{1-6}$ alkyl. In some embodiments, $R^2$ is a substituted or unsubstituted aryl group. In some embodiments, $R^2$ is substituted or unsubstituted phenyl. In some embodiments, $R^2$ is 2,3-dihydro-1,4-benzoxazine or 3,4-dihydroquinolin-2-one. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with morpholinyl or mono- or di-$C_{1-6}$ alkylamino. In some embodiments, $R^2$ is substituted or unsubstituted pyrazole. In some embodiments, $R^2$ is pyrazole substituted with $C_{1-6}$ alkyl. In some embodiments, $R^2$ is 2,3-dihydro-pyrido[2,3-b][1,4]oxazine, 3,4-dihydro-pyrido[3,2-b][1,4]oxazine, pyrido[2,3-b][1,4]oxazin-2-one, or pyrido[3,2-b][1,4]oxazin-3-one.

Provided herein in another aspect is a compound of Formula 19

(Formula 19)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aryl or a substituted or unsubstituted heteroaryl group, wherein said heteroaryl group has 1 to 5 heteroatom ring members chosen from O, N, or S.

In some embodiments, $R^1$ is hydrogen. In some embodiments, $R^1$ is halogen. In some embodiments, $R^1$ is $C_{1-6}$ alkyl. In some embodiments, $R^2$ is a substituted or unsubstituted aryl group. In some embodiments, $R^2$ is substituted or unsubstituted phenyl. In some embodiments, $R^2$ is phenyl substituted with $C_{1-6}$ alkylsulfonyl or piperazinyl. In some embodiments, $R^2$ is benzodioxole or 3,4-dihydroquinolin-2-one; wherein $R^2$ is optionally substituted with $C_{1-6}$ alkyl. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with trifluoromethyl or mono- or di-$C_{1-6}$ alkylamino. In some embodiments, $R^2$ is substituted or unsubstituted pyrazole. In some embodiments, $R^2$ is pyrazole substituted with $C_{1-6}$ alkyl.

Provided herein in another aspect is a compound of Formula 20

(Formula 20)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

In some embodiments, $R^1$ is hydrogen. In some embodiments, $R^1$ is halogen. In some embodiments, $R^1$ is $C_{1-6}$ alkyl. In some embodiments, $R^2$ is a substituted or unsubstituted aryl group. In some embodiments, $R^2$ is substituted or unsubstituted phenyl. In some embodiments, $R^2$ is phenyl substituted with $C_{1-6}$ alkylsulfonyl or piperazinyl. In some embodiments, $R^2$ is benzodioxole or 3,4-dihydroquinolin-2-one; wherein $R^2$ is optionally substituted with $C_{1-6}$ alkyl. In some embodiments, $R^2$ is a substituted or unsubstituted heteroaryl group, wherein said heteroaryl group has 1 to 5 heteroatom ring members chosen from O, N, or S. In some embodiments, $R^2$ is substituted or unsubstituted pyridine. In some embodiments, $R^2$ is pyridine substituted with trifluoromethyl or mono- or di-$C_{1-6}$ alkylamino. In some embodiments, $R^2$ is substituted or unsubstituted pyrazole. In some embodiments, $R^2$ is pyrazole substituted with $C_{1-6}$ alkyl. In some embodiments, $R^2$ is a substituted or unsubstituted pyridine-2-one. In some embodiments, $R^2$ is pyridine-2-one substituted with $C_{1-6}$ alkyl. In some embodiments, the compound, or a stereoisomer thereof or a pharmaceutically acceptable salt thereof, is selected from Table 1.

Provided herein in another aspect is a pharmaceutical composition comprising the compound disclosed herein, or a stereoisomer thereof, or a pharmaceutically acceptable salt thereof, and at least one pharmaceutically acceptable excipient Provided herein in another aspect is a method of inhibiting vascular adhesion protein (VAP-1), comprising administering to a mammal, a therapeutically effective amount of the compound disclosed herein, or a stereoisomer thereof, or a pharmaceutically acceptable salt thereof.

Provided herein in another aspect is a method of treating NASH in a subject in need thereof, the method comprising administering to the subject a therapeutically effective amount of the compound disclosed herein, or a stereoisomer thereof, or a pharmaceutically acceptable salt thereof, or a therapeutically effective amount of the pharmaceutical composition disclosed herein.

Provided herein in another aspect is a use of the compound disclosed herein, or a stereoisomer thereof, or a pharmaceutically acceptable salt thereof, for the manufacture of a medicament for the treatment of NASH.

Provided herein in another aspect is a compound disclosed herein, or a stereoisomer thereof, or a pharmaceutically acceptable salt thereof, for use in treating NASH.

Provided herein in another aspect is a composition disclosed herein for use in treating NASH.

Provided herein in another aspect is a compound disclosed herein, or a stereoisomer thereof, or a pharmaceutically acceptable salt thereof, for use in inhibiting VAP-1.

Provided herein in another aspect is a composition disclosed herein for use in inhibiting VAP-1.

Provided herein in another aspect is a method of treating a disease mediated by VAP-1 in a subject in need thereof, the method comprising administering to the subject a therapeutically effective amount of the compound disclosed herein, or a stereoisomer thereof, or a pharmaceutically acceptable salt thereof, or a therapeutically effective amount of the pharmaceutical composition disclosed herein. In some embodiments, the disease mediated by VAP-1 is selected from the group consisting of lipid and lipoprotein disorders, conditions and diseases which result from chronic fatty and fibrotic degeneration of organs due to accumulated lipid and specifically triglyceride accumulation and subsequent activation of profibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

Provided herein in another aspect is a method of preparing a compound of Formula 1aa, or a stereoisomer thereof, or a pharmaceutically acceptable salt thereof, (Formula 1aa)

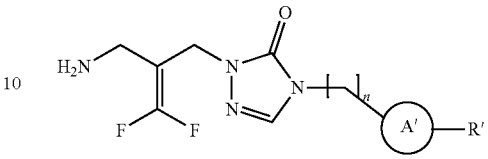

the method comprising
(a) reacting a compound of Formula 2 with a compound of Formula 3a or a compound of Formula 3b to obtain a compound of Formula 1a (Formula 2)

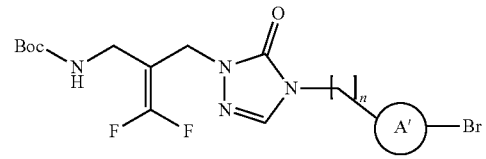

Z—R'    (Formula 3a)

HC≡CR    (Formula 3b)

(Formula 1a)

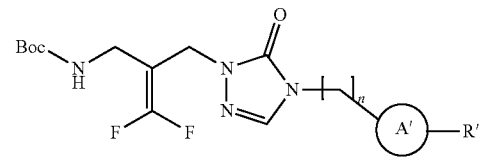

wherein
Boc is an amine protecting group;
n is 0, 1, or 2;
A' is aryl or heteroaryl group selected from the group consisting of phenyl, pyridine, pyrazine, thiophene, and benzothiophene; wherein said aryl or heteroaryl group is optionally substituted with $C_{1-3}$ alkyl or halogen;
Z is boronic acid ($B(OH)_2$) or boronic acid pinacol ester;
R' is —R, —CH═CH—R, or —C≡C—R; and
R is a substituted or unsubstituted cyclic ring, optionally containing 1 to 5 heteroatom ring members chosen from O, N, or S, and said cyclic ring is aromatic or non-aromatic; and
(b) removing Boc from the compound of Formula 1a under reaction conditions to obtain the compound of Formula 1aa, or the stereoisomer thereof, or the pharmaceutically acceptable salt thereof.
In some embodiments, the cyclic ring is selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 3,4-dihydro-1,4-benzoxazine, 2,3-dihydro-1,4-benzoxazine, 1,4-benzoxazin-3-one, 1,4-dihydro-3,1-benzoxazin-2-one, 5,6,7,8-tetrahydronaphthyridine, triazolo[1,5-a]pyridine, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, 1,4-dihydroquinazolin-2-one, 1H-pyrrolo[2,3-b]pyridine, benzoxazole, and thiophene; wherein said cyclic ring is optionally substituted with one to three substituents selected from the group consisting of halogen, $C_{1-6}$ alkyl, difluoromethyl, trifluoromethyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

DETAILED DESCRIPTION

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "comprising" or "comprises" is intended to mean that the compositions and methods include the recited elements, but not excluding others. A composition or method "consisting essentially" of the elements as defined herein would not exclude other materials or steps that do not materially affect the basic and novel characteristic(s) of the claimed technology. "Consisting of" shall mean excluding more than trace elements of other ingredients and substantial method steps. Embodiments defined by each of these transition terms are within the scope of this technology. When an embodiment is defined by one of these terms (e.g., "comprising") it should be understood that this disclosure also includes alternative embodiments, such as "consisting essentially of" and "consisting of" for said embodiment.

"Substantially" or "essentially" means nearly totally or completely, for instance, 95%, 96%, 97%, 98%, 99%, or greater of some given quantity.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Where a range of values is provided, it is understood that each intervening value, to the tenth of the unit of the lower limit unless the context clearly dictates otherwise, between the upper and lower limit of that range and any other stated or intervening value in that stated range, is encompassed within the present technology. The upper and lower limits of these smaller ranges may independently be included in the smaller ranges and are also encompassed within the present technology, subject to any specifically excluded limit in the stated range. Where the stated range includes one or both of the limits, ranges excluding either or both of those included limits are also included in the present technology.

In general, "substituted" refers to an organic group (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. The present disclosure is understood to include embodiments where, for instance a "substituted alkyl" optionally contains one or more alkene and/or alkyne. A substituted group will be substituted with one or more substituents, unless otherwise specified. In some embodiments, a substituted group is substituted with 1, 2, 3, 4, 5, or 6 substituents. Examples of substituent groups include: alkyl groups; haloalkyl groups; halogens (i.e., F, Cl, Br, and I); hydroxyls; alkoxy, alkenoxy, alkynoxy, aryloxy, aralkyloxy, heterocyclyloxy, and heterocyclylalkoxy groups; aryl groups; heteroaryl groups; cycloalkyl groups; heterocyclyl groups; carbonyls (oxo); carboxyls; esters; carbamates; urethanes; ureas; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. The substituent may be a substituted or unsubstituted cyclic ring. As used herein, an "optionally substituted" group refers to substituted or unsubstituted group. Accordingly, "optionally substituted" and "substituted or unsubstituted" may be used interchangeably.

Substituted ring groups such as substituted cyclic, substituted cycloalkyl, substituted aryl, substituted heterocyclic and substituted heteroaryl groups also include rings and fused ring systems in which a bond to a hydrogen atom is replaced with a bond to a carbon atom. Therefore, substituted cyclic, substituted cycloalkyl, substituted aryl, substituted heterocyclic and substituted heteroaryl groups may also be substituted with substituted or unsubstituted alkyl, alkenyl, and alkynyl groups as defined below.

As used herein, the term "cyclic ring" refers to an aromatic or non-aromatic ring, optionally containing one or more heteroatoms. Exemplary heteroatoms include, but are not limited to, N, O, S, or B. In some embodiments, the cyclic ring optionally contains 1 to 5 heteroatom ring members chosen from O, N, or S. In some embodiments, the cyclic ring optionally contains 1 to 4 heteroatom ring members chosen from O, N, or S. In some embodiments, the cyclic ring optionally contains 1 to 3 heteroatom ring members chosen from O, N, or S. Cyclic rings include aryl, cycloalkyl, and heterocyclic groups. In some embodiments, the cyclic ring is selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 3,4-dihydro-1,4-benzoxazine, 2,3-dihydro-1,4-benzoxazine, 1,4-benzoxazin-3-one, 1,4-dihydro-3,1-benzoxazin-2-one, 5,6,7,8-tetrahydronaphthyridine, triazolo[1,5-a]pyridine, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, 1,4-dihydroquinazolin-2-one, 1H-pyrrolo[2,3-b]pyridine, benzoxazole, and thiophene. As used herein, triazolo[1,5-a]pyridine includes [1,2,4]triazolo[1,5-a]pyridine and [1,2,3]triazolo[1,5-a]pyridine.

As used herein, an "aryl group" refers to a cyclic aromatic hydrocarbon that does not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., benzodioxole, indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

As used herein, the term "cycloalkyl group" refers to a cyclic alkyl group such as, but not limited to, cyclopropyl, cyclobutyl, cyclopentyl, cyclohexyl, cycloheptyl, and cyclooctyl groups. In some embodiments, the cycloalkyl group has 3 to 8 carbon ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-di-substituted cyclohexyl groups, which may be substituted with substituents such as those listed above. In some embodiments, a cycloalkyl group has one or more alkene bonds, but is not aromatic. As used herein, the term "(cycloalkyl)alkyl" refers to an alkyl group substituted with a cycloalkyl group.

As used herein, the term "heterocyclic" or "heterocyclyl" includes aromatic (also referred to as heteroaryl) and non-aromatic ring compounds containing 3 or more ring members, of which one or more is a heteroatom such as, but not limited to, N, O, S or B. In some embodiments, heterocyclic groups include 3 to 20 ring members, whereas other such groups have 3 to 6, 3 to 10, 3 to 12, or 3 to 15 ring members. The heterocyclic group may have 1 to 5 heteroatom ring members chosen from O, N, or S. Heterocyclic groups encompass unsaturated, partially saturated and saturated ring systems, such as, for example, imidazolyl, imidazolinyl and imidazolidinyl groups. The phrase "heterocyclic group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclic groups that have other groups, such as alkyl, oxo or halo groups, bonded to one of the ring members. Rather, these are referred to as "substituted heterocyclic groups". Heterocyclic groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclic groups may be mono-substituted or substituted more than once, such as, but not limited to, pyridyl or piperazinyl groups, which are 2-, 3-, 4-, 5-, or 6-substituted, or disubstituted with various substituents such as those listed above.

As used herein, the term "heteroaryl group" refers to an aromatic ring compound containing 5 or more ring members, of which, one or more is a heteroatom such as, but not limited to, N, O, S or B. In some embodiments, one or more heteroatoms are chosen from N, O, or S. In some embodiments, 1 to 4 heteroatoms are chosen from N, O, or S. In some embodiments, 1 to 5 heteroatoms are chosen from N, O, or S. In some embodiments, heteroaryl groups include 5 to 14 ring members, whereas other such groups have 5 to 6, 5 to 9, 5 to 10, 6 to 9, 6 to 10, or 6 to 14 ring members. For example, a 5-membered heteroaryl group has 5 ring members; a 6-membered heteroaryl group has 6 ring members; and a 9-membered heteroaryl group has 9 ring members (such as, but not limited to, benzothiophene). Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above. An azolyl group is a 5-membered heteroaryl group containing a nitrogen atom and at least one other atom selected from nitrogen, sulfur, and oxygen as part of the ring. Azolyl groups include imidazole, pyrazole, 1,2,3-triazole, 1,2,4-triazole, tetrazole, pentazole, oxazole, isoxazole, 1,2,4-oxadiazole, 1,2,5-oxadiazole, 1,3,4-oxadiazole, thiazole, isothiazole, 1,2,3-thiadiazole, 1,2,4-thiadiazole, 1,2,5-thiadiazole, and 1,3,4-thiadiazole.

As used herein, the term "alkyl" refers to an aliphatic hydrocarbon radical, which encompasses both straight and branched hydrocarbon radicals. In some embodiments, alkyl has from 1 to about 20 carbon atoms, from 1 to 12 carbons, from 1 to 8 carbons, 1 to 6 carbons, or 1 to 4 carbon atoms. For example, $C_{1-6}$ alkyl refers to an aliphatic hydrocarbon having 1 to 6 carbons, which includes methyl, ethyl, propyl, n-butyl, n-pentyl, n-hexyl, isopropyl, isobutyl, sec-butyl, tert-butyl, neopentyl, isopentyl, and the like.

As used herein, the term "hydroxy" is defined as —OH.

As used herein, the term "alkoxy," unless particularly defined herein, refers to a radical formed by substituting the hydrogen atom of a hydroxyl group with an alkyl. For example, $C_{1-6}$ alkoxy includes methoxy, ethoxy, propoxy, n-butoxy, n-pentyloxy, isopropoxy, sec-butoxy, tert-butoxy, neopentyloxy, isopentyloxy, and the like. An aralkoxy group is an alkoxy group substituted with an aryl group. One non-limiting example of an aralkoxy group is a substituted or unsubstituted benzyloxy group.

In addition, the term "halogen" refers to fluorine, bromine, chlorine, and iodine.

In addition, the term "amino" is defined as —NH$_2$, and the term "alkylamino" refers to a mono- or di-alkyl substituted amino. For example, $C_{1-6}$ alkylamino includes mono- or di-$C_{1-6}$ alkyl substituted amino.

In addition, the term "alkylthio" is defined as —SR (wherein R is alkyl), and the term "cyano" is defined as —CN.

Those of skill in the art will appreciate that compounds of the present technology may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the present technology encompasses any tautomeric, conformational isomeric, optical isomeric and/or geometric isomeric forms of the compounds having one or more of the utilities described herein, as well as mixtures of these various different forms. As used herein, "isomer" refers to a tautomer, conformation isomer, optical isomer, geometric isomer, or any combination thereof, of a compound. Structural isomers are not included in the meaning of "isomer" as used herein.

As readily understood by one skilled in the art, a wide variety of functional groups and other structures may exhibit tautomerism, and all tautomers of compounds as described herein are within the scope of the present technology.

Stereoisomers of compounds, also known as "optical isomers," include all chiral, diastereomeric, and racemic forms of a structure, unless the specific stereochemistry is expressly indicated. Thus, compounds used in the present technology include enriched or resolved optical isomers at any or all stereogenic atoms as are apparent from the depictions. Both racemic and diastereomeric mixtures, as well as the individual optical isomers can be isolated or synthesized so as to be substantially free of their enantiomeric or diastereomeric partners, and these are all within the scope of the present technology.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

Generally, reference to a certain moiety capable of being protected (such as hydroxy, amine, carbonyl, etc.) includes the protected groups in some embodiments of the disclosure. For example, in some embodiments, an —OH moiety as included herein also includes —OP, where P is a protecting group. Protecting groups, as referred to herein may be selected by one of ordinary skill in the art, and include the groups and strategies set forth in the art, for example, those such as described in R. Larock, *Comprehensive Organic Transformations*, VCH Publishers (1989); T. W. Greene and P. G. M. Wuts, *Greene's protective groups in organic synthesis*, John Wiley & Sons (2006); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

"Subject" refers to an animal, such as a mammal (including a human), that has been or will be the object of treatment, observation or experiment. "Subject" and "patient" may be used interchangeably, unless otherwise indicated. The methods described herein may be useful in human therapy and/or veterinary applications. In some embodiments, the subject is a mammal. In some embodiments, the subject is a human.

The terms "therapeutically effective amount" and "effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver.

The term "treatment" or "treating" means administering a compound disclosed herein for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

Unless defined otherwise, all technical and scientific terms used herein have the same meaning as commonly understood by one of ordinary skill in the art to which this present technology belongs. Although any methods and materials similar or equivalent to those described herein can also be used in the practice or testing of the present technology, representative illustrative methods and materials are described herein.

The present technology provides a compound having inhibitory activity on VAP-1 or its salt, that is, a compound of Formula X:

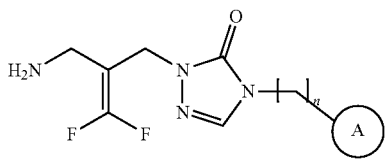

(Formula X)

or a stereoisomer thereof or a pharmaceutically acceptable salt thereof;
wherein
n is 0, 1 or 2; and
A is an aryl group or a heterocyclic group, wherein said heterocyclic group has 1 to 5 heteroatom ring members chosen from O, N, or S, and said heterocyclic group is aromatic or non-aromatic; and wherein said aryl group or said heterocyclic group is optionally substituted with one or two substituents selected from the group consisting of $C_{1-3}$ alkyl, halogen, benzyloxy, —R, —CH=CH—R, and —C≡C—R; and
R is a substituted or unsubstituted cyclic ring, optionally containing 1 to 5 heteroatom ring members chosen from O, N, or S, and said cyclic ring is aromatic or non-aromatic.

In another aspect, provided herein is a compound of Formula Y:

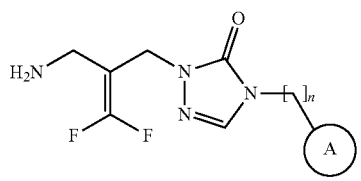

(Formula Y)

or a stereoisomer thereof, or a pharmaceutically acceptable salt thereof,
wherein
n is 0, 1 or 2,
A is an aryl or heteroaryl group selected from the group consisting of phenyl, pyridine, pyrazine, thiophene, and benzothiophene,
wherein said aryl or heteroaryl group is optionally substituted with one or two substituents selected from the group consisting of $C_{1-3}$ alkyl, halogen, benzyloxy, —R, —CH=CH—R, and —C≡C—R,
wherein said R is a cyclic ring selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 3,4-dihydro-1,4-benzoxazine, 2,3-dihydro-1,4-benzoxazine, 1,4-benzoxazin-3-one, 1,4-dihydro-3,1-benzoxazin-2-one, 5,6,7,8-tetrahydronaphthyridine, triazolo[1,5-a]pyridine, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, 1,4-dihydroquinazolin-2-one, 1H-pyrrolo[2,3-b]pyridine, benzoxazole, and thiophene,
wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, $C_{1-6}$ alkylpyrazolyl, triazolyl, pyrrolidinonyl, and pyrrolidinyl.

In some embodiments of a compound of Formula X or Y, or a stereoisomer thereof, or a pharmaceutically acceptable salt thereof, said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In another aspect, provided herein is a compound of Formula 1:

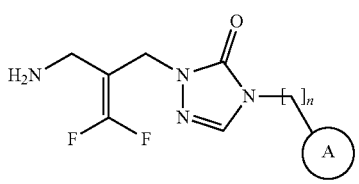

(Formula 1)

or a stereoisomer thereof, or a pharmaceutically acceptable salt thereof,
wherein
n is 0, 1 or 2,
A is an aryl or heteroaryl group selected from the group consisting of phenyl, pyridine, pyrazine, and thiophene,
wherein said aryl or heteroaryl group is optionally substituted with one or two substituents selected from the group consisting of $C_{1-3}$ alkyl, halogen, benzyloxy, —R, —CH=CH—R, and —C≡C—R,
wherein said R is a cyclic ring selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 3,4-dihydro-1,4-benzoxazine, 2,3-dihydro-1,4-benzoxazine, 1,4-benzoxazin-3-one, 1,4-dihydro-3,1-benzoxazin-2-one, 5,6,7,8-tetrahydronaphthyridine, triazolo[1,5-a]pyridine, 2,3-dihydro-pyrido[2,3-b][1,4]oxazine, 3,4-dihydro-pyrido[3,2-b][1,4]oxazine, pyrido[2,3-b][1,4]oxazin-2-one, and pyrido[3,2-b][1,4]oxazin-3-one,
wherein said cyclic ring is optionally substituted with one to three substituents selected from the group consisting of halogen, $C_{1-6}$ alkyl, trifluoromethyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono-$C_{1-6}$ alkylaminocarbonyl, mono- or di-$C_{1-6}$ alkylaminosulfonyl, $C_{1-6}$ alkylsulfonyl, $C_{1-6}$ alkylcarbonyl, morpholinylcarbonyl, piperazinyl, acetylpiperazinyl, morpholinyl, and pyrazolyl.

In some embodiments of a compound of Formulas X, Y, or 1, or a stereoisomer thereof, or a pharmaceutically acceptable salt thereof, A is aryl optionally substituted with one or two substituents selected from the group consisting of $C_{1-3}$ alkyl, halogen, benzyloxy, —R, —CH=CH—R, and —C≡C—R. In some embodiments of a compound of Formulas X, Y, or 1, or a stereoisomer thereof, or a pharmaceutically acceptable salt thereof, A is phenyl substituted with one or two substituents selected from the group consisting of $C_{1-3}$ alkyl, halogen, benzyloxy, —R, —CH=CH—R, and —C≡C—R.

In some embodiments of a compound of Formulas X, Y, or 1, or a stereoisomer thereof, or a pharmaceutically acceptable salt thereof, A is a heterocyclic group having 1 to 5 heteroatom ring members chosen from O, N, or S; said heterocyclic group is aromatic or non-aromatic; and said heterocyclic group is optionally substituted with one or two substituents selected from the group consisting of $C_{1-3}$ alkyl, halogen, benzyloxy, —R, —CH=CH—R, and —C≡C—R.

In some embodiments of a compound of Formulas X, Y, or 1, or a stereoisomer thereof, or a pharmaceutically acceptable salt thereof, A is a heteroaryl group having 1 to 5 heteroatom ring members chosen from O, N, or S; and said heteroaryl group is optionally substituted with one or two substituents selected from the group consisting of $C_{1-3}$ alkyl, halogen, benzyloxy, —R, —CH=CH—R, and —C≡C—R. In some embodiments of a compound of Formulas X, Y, or 1, or a stereoisomer thereof, or a pharmaceutically acceptable salt thereof, A is pyridine, pyrazine, or thiophene, wherein A is optionally substituted with one or two substituents selected from the group consisting of $C_{1-3}$ alkyl, halogen, benzyloxy, —R, —CH=CH—R, and —C≡C—R.

In the compound of Formulas X, Y, or 1, or the stereoisomer thereof, or its pharmaceutically acceptable salt thereof according to the present technology, n may preferably be 0 or 1. In some embodiments, n is 0. In some embodiments, n is 1. In some embodiments, n is 2.

Further, in the compound of Formulas X, Y, or 1, or the stereoisomer thereof, or its pharmaceutically acceptable salt thereof according to the present technology, A may preferably be phenyl, pyridine, or thiophene, each of which is optionally substituted as described above.

In some embodiments of a compound of Formulas X, Y, or 1, or a stereoisomer thereof, or a pharmaceutically acceptable salt thereof, A is phenyl, optionally substituted with one or two substituents selected from the group consisting of $C_{1-3}$ alkyl, halogen, benzyloxy, —R, —CH=CH—R, and —C≡C—R. In further embodiments, A is phenyl substituted with —R. In some embodiments, A is phenyl substituted with —CH=CH—R or —C≡C—R. In some embodiments, A is phenyl substituted with —CH=CH—R. In some embodiments, A is phenyl substituted with —C≡C—R. In still further embodiments, —R is a cyclic ring selected from the group consisting of benzene, pyridine, pyridin-2-one, pyrazole, benzodioxole, and 3,4-dihydroquinolin-2-one. In still further embodiments, —R is a cyclic ring selected from the group consisting of benzene, pyridine, pyridin-2-one, pyrazole, benzodioxole, and 3,4-dihydroquinolin-2-one, wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, A is pyridine, optionally substituted with one or two substituents selected from the group consisting of $C_{1-3}$ alkyl, halogen, benzyloxy, —R, —CH=CH—R, and —C≡C—R. In further embodiments, A is pyridine substituted with —R. In some embodiments, A is pyridine substituted with —CH=CH—R or —C≡C—R. In some embodiments, A is pyridine substituted with —CH=CH—R. In some embodiments, A is pyridine substituted with —C≡C—R. In still further embodiments, —R is a cyclic ring selected from the group consisting of benzene, pyridine, pyridin-2-one, pyrimidine, pyrazole, benzodioxole, benzoxadiazole, benzothiazole, indazole, 2,3-dihydro-1,4-benzoxazine, 1,4-benzoxazin-3-one, 1,4-dihydro-3,1-benzoxazin-2-one, 1,4-dihydroquinazolin-2-one, 1H-pyrrolo[2,3-b]pyridine, benzoxazole, and thiophene. In still further embodiments, —R is a cyclic ring selected from the group consisting of benzene, pyridine, pyridin-2-one, pyrimidine, pyrazole, benzodioxole, benzoxadiazole, benzothiazole, indazole, 2,3-dihydro-1,4-benzoxazine, 1,4-benzoxazin-3-one, 1,4-dihydro-3,1-benzoxazin-2-one, 1,4-dihydroquinazolin-2-one, 1H-pyrrolo[2,3-b]pyridine, benzoxazole, and thiophene, wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, A is thiophene, optionally substituted with one or two substituents selected from the group consisting of $C_{1-3}$ alkyl, halogen, benzyloxy, —R, —CH=CH—R, and —C≡C—R. In further embodiments, A is thiophene substituted with —R. In some embodiments, A is thiophene substituted with —CH=CH—R or —C≡C—R. In some embodiments, A is thiophene substituted with —CH=CH—R. In some embodiments, A is thiophene substituted with —C≡C—R. In still further embodiments, —R is a cyclic ring selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 2,3-dihydro-1,4-benzoxazine, 1,4-dihydro-3,1-benzoxazin-2-one, 5,6,7,8-tetrahydronaphthyridine, triazolo[1,5-a]pyridine, pyrido[2,3-b][1,4]oxazin-2-one, and 1,4-dihydroquinazolin-2-one. In still further embodiments, —R is a cyclic ring selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 2,3-dihydro-1,4-benzoxazine, 1,4-dihydro-3,1-benzoxazin-2-one, 5,6,7,8-tetrahydronaphthyridine, triazolo[1,5-a]pyridine, pyrido[2,3-b][1,4]oxazin-2-one, and 1,4-dihydroquinazolin-2-one; wherein said cyclic ring is optionally substituted with one to three substituents selected from the group consisting of halogen, $C_{1-6}$ alkyl, difluoromethyl, trifluoromethyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, A is benzothiophene, optionally substituted with one or two substituents selected from the group consisting of $C_{1-3}$ alkyl, halogen, benzyloxy, —R, —CH=CH—R, and —C≡C—R. In further embodiments, A is benzothiophene substituted with —R. In some embodiments, A is benzothiophene substituted with —CH=CH—R or —C≡C—R. In some embodiments, A is benzothiophene substituted with —CH=CH—R. In some embodiments, A is benzothiophene substituted with —C≡C—R. In still further embodiments, —R is a cyclic ring selected from the group consisting of benzene, pyridine, pyridin-2-one, pyrazole, benzodioxole, and 3,4-dihydroquinolin-2-one. In still further embodiments, —R is a cyclic ring selected from the group consisting of benzene, pyridine, pyridin-2-one, pyrazole, benzodioxole, and 3,4-dihydroquinolin-2-one; wherein said cyclic ring is optionally substituted with one to three substituents selected from the group consisting of halogen, $C_{1-6}$ alkyl, difluoromethyl, trifluoromethyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

Further, in the compound of Formulas X, Y, or 1, or the stereoisomer thereof, or its pharmaceutically acceptable salt thereof according to the present technology, said aryl or heteroaryl group may preferably be substituted with one or two substituents selected from the group consisting of $C_{1-3}$ alkyl, halogen, and —R. Preferably, said R may be a cyclic ring selected from the group consisting of benzene, pyridine, pyridin-2-one, pyrazole, and 3,4-dihydroquinolin-2-one. More preferably, said cyclic ring may be substituted with a substituent selected from the group consisting of $C_{1-6}$ alkyl, $C_{1-6}$ alkylsulfonyl, di-$C_{1-6}$ alkylamino, and piperazinyl.

In one embodiment of the present technology, a compound, wherein n is 0; A is phenyl; said phenyl is substituted with one or two substituents selected from the group consisting of halogen and —R; said R is a cyclic ring selected from the group consisting of benzene, pyridine, 3,4-dihydroquinolin-2-one, and pyrazole; and said cyclic ring is substituted with a substituent selected from the group consisting of $C_{1-6}$ alkyl, $C_{1-6}$ alkylsulfonyl, di-$C_{1-6}$ alkylamino, and piperazinyl; or a pharmaceutically acceptable salt thereof is provided.

In another embodiment of the present technology, a compound wherein n is 0; wherein A is pyridine; wherein said pyridine is substituted with one or two substituents selected from the group consisting of $C_{1-3}$ alkyl, halogen, and —R; wherein said R is a cyclic ring selected from the group consisting of benzene, pyridine, 3,4-dihydroquinolin-2-one, and pyrazole; wherein said cyclic ring is substituted with a substituent selected from the group consisting of $C_{1-6}$ alkyl, $C_{1-6}$ alkylsulfonyl, di-$C_{1-6}$ alkylamino, and piperazinyl, or a pharmaceutically acceptable salt thereof is provided.

In another embodiment of the present technology, a compound wherein n is 0; A is thiophene; wherein said thiophene is substituted with one or two cyclic rings selected from the group consisting of benzene, pyridine, pyridin-2-one, 3,4-dihydroquinolin-2-one, and pyrazole; and said cyclic ring is substituted with a substituent selected from the group consisting of $C_{1-6}$ alkyl, $C_{1-6}$ alkylsulfonyl, di-$C_{1-6}$ alkylamino, and piperazinyl; or a pharmaceutically acceptable salt thereof is provided.

In some embodiments of a compound of Formulas X, Y, or 1, or a stereoisomer thereof, or a pharmaceutically acceptable salt thereof, R is substituted or unsubstituted benzene. In some embodiments, R is benzene substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, $C_{1-6}$ alkylpyrazolyl, triazolyl, pyrrolidinonyl, and pyrrolidinyl. In some embodiments, R is benzene substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted pyridine. In some embodiments, R is pyridine substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted tetrahydropyridine. In some embodiments, R is tetrahydropyridine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted pyridin-2-one. In some embodiments, R is pyridin-2-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted pyrimidine. In some embodiments, R is pyrimidine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted imidazole. In some embodiments, R is imidazole, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted pyrazole. In some embodiments, R is pyrazole, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted benzodioxole. In some embodiments, R is benzodioxole, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted benzoxadiazole. In some embodiments, R is benzoxadiazole, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted benzothiazole. In some embodiments, R is benzothiazole, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted indazole. In some embodiments, R is indazole, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 1,3-dihydroindol-2-one. In some embodiments, R is 1,3-dihydroindol-2-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted quinolin-2-one. In some embodiments, R is quinolin-2-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 3,4-dihydroisoquinolin-1-one. In some embodiments, R is 3,4-dihydroisoquinolin-1-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 3,4-dihydroquinolin-2-one. In some embodiments, R is 3,4-dihydroquinolin-2-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 3,4-dihydro-1,4-benzoxazine. In some embodiments, R is 3,4-dihydro-1,4-benzoxazine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 2,3-dihydro-1,4-benzoxazine. In some embodiments, R is 2,3-dihydro-1,4-benzoxazine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 1,4-benzoxazin-3-one. In some embodiments, R is 1,4-benzoxazin-3-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 1,4-dihydro-3,1-benzoxazin-2-one. In some embodiments, R is 1,4-dihydro-3,1-benzoxazin-2-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 5,6,7,8-tetrahydronaphthyridine. In some embodiments, R is 5,6,7,8-tetrahydronaphthyridine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted triazolo[1,5-a]pyridine. In some embodiments, R is triazolo[1,5-a]pyridine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 2,3-dihydro-pyrido[2,3-b][1,4]oxazine. In some embodiments, R is 2,3-dihydro-pyrido[2,3-b][1,4]oxazine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 3,4-dihydro-pyrido[3,2-b][1,4]oxazine. In some embodiments, R is 3,4-dihydro-pyrido[3,2-b][1,4]oxazine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted pyrido[2,3-b][1,4]oxazin-2-one. In some embodiments, R is pyrido[2,3-b][1,4]oxazin-2-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted pyrido[3,2-b][1,4]oxazin-3-one. In some embodiments, R is pyrido[3,2-b][1,4]oxazin-3-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 1,4-dihydroquinazolin-2-one. In some embodiments, R is 1,4-dihydroquinazolin-2-one, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted 1H-pyrrolo[2,3-b]pyridine. In some embodiments, R is 1H-pyrrolo[2,3-b]pyridine, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted benzoxazole. In some embodiments, R is benzoxazole, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In some embodiments of a compound of Formulas X, Y, or 1, or a stereoisomer thereof, or a pharmaceutically acceptable salt thereof, R is substituted or unsubstituted thiophene. In some embodiments, R is thiophene, optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

In another aspect, provided herein is a compound of Formula 12

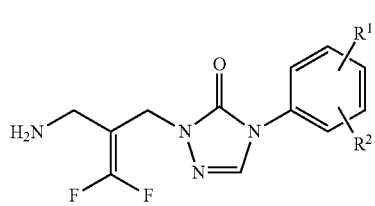

(Formula 12)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aryl group or a substituted or unsubstituted heteroaryl group, wherein said heteroaryl group has 1 to 5 heteroatom ring members chosen from O, N, or S.

In some embodiments of a compound of Formula 12, or a stereoisomer thereof or a pharmaceutically acceptable salt thereof, $R^2$ is a substituted or unsubstituted aryl group. In further embodiments, $R^2$ is substituted or unsubstituted phenyl. In still further embodiments, $R^2$ is phenyl substituted with triazolyl, $C_{1-6}$ alkylsulfonyl, or piperazinyl. In other embodiments, $R^2$ is benzodioxole or 3,4-dihydroquinolin-2-one, wherein said 3,4-dihydroquinolin-2-one is optionally substituted with $C_{1-6}$ alkyl.

In some embodiments of a compound of Formula 12, or a stereoisomer thereof or a pharmaceutically acceptable salt thereof, $R^2$ is a substituted or unsubstituted heteroaryl group, wherein said heteroaryl group has 1 to 5 heteroatom ring members chosen from O, N, or S. In further embodiments, $R^2$ is substituted or unsubstituted pyridine. In still further embodiments, $R^2$ is pyridine substituted with trifluoromethyl or mono- or di-$C_{1-6}$ alkylamino. In other embodiments, $R^2$ is substituted or unsubstituted pyrazole. In further embodiments, $R^2$ is pyrazole substituted with $C_{1-6}$ alkyl or difluoromethyl.

In another aspect, provided herein is a compound of Formula 13

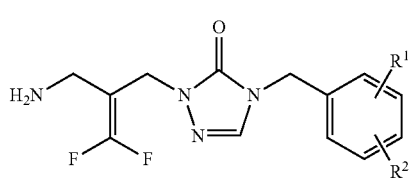

(Formula 13)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aralkoxy group, a substituted or unsubstituted aryl group, or a substituted or unsubstituted heterocyclic group, wherein said heterocyclic group has 1 to 5 heteroatom ring members chosen from O, N, or S, and said heterocyclic group is aromatic or non-aromatic.

In some embodiments of a compound of Formula 13, or a stereoisomer thereof or a pharmaceutically acceptable salt thereof, R² is a substituted or unsubstituted aralkoxy group. In further embodiments, R² is substituted or unsubstituted benzyloxy.

In some embodiments of a compound of Formula 13, or a stereoisomer thereof or a pharmaceutically acceptable salt thereof, R² is a substituted or unsubstituted aryl group. In further embodiments, R² is substituted or unsubstituted phenyl. In still further embodiments, R² is phenyl substituted with $C_{1-6}$ alkylsulfonyl or piperazinyl. In other embodiments, R² is benzodioxole or 3,4-dihydroquinolin-2-one, wherein said 3,4-dihydroquinolin-2-one is optionally substituted with $C_{1-6}$ alkyl.

In some embodiments of a compound of Formula 13, or a stereoisomer thereof or a pharmaceutically acceptable salt thereof, R² is a substituted or unsubstituted heteroaryl group, wherein said heteroaryl group has 1 to 5 heteroatom ring members chosen from O, N, or S. In further embodiments, R² is substituted or unsubstituted pyridine. In still further embodiments, R² is pyridine substituted with mono- or di-$C_{1-6}$ alkylamino. In other embodiments, R² is substituted or unsubstituted pyrazole. In further embodiments, R² is pyrazole substituted with $C_{1-6}$ alkyl.

In some embodiments of a compound of Formula 13, or a stereoisomer thereof or a pharmaceutically acceptable salt thereof, R² is substituted or unsubstituted pyridin-2-one. In further embodiments, R² is pyridin-2-one substituted with $C_{1-6}$ alkyl.

In another aspect, provided herein is a compound of Formula 14

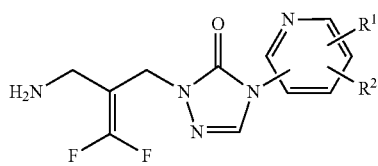

(Formula 14)

or a stereoisomer thereof or a pharmaceutically acceptable salt thereof;
wherein
R¹ is hydrogen, halogen, or $C_{1-6}$ alkyl; and
R² is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

In some embodiments of a compound of Formula 14, or a stereoisomer thereof or a pharmaceutically acceptable salt thereof, the compound is of Formula 14a

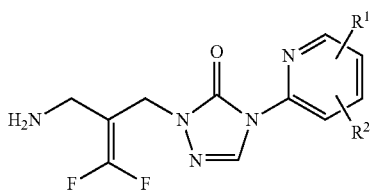

(Formula 14a)

or a stereoisomer thereof or a pharmaceutically acceptable salt thereof.

In some embodiments of a compound of Formula 14, or a stereoisomer thereof or a pharmaceutically acceptable salt thereof, the compound is of Formula 14b

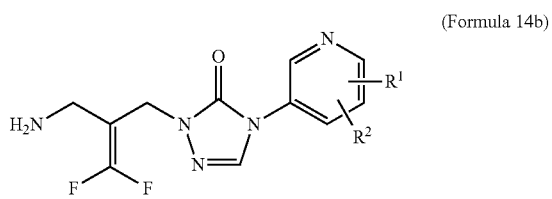

(Formula 14b)

or a stereoisomer thereof or a pharmaceutically acceptable salt thereof.

In some embodiments of a compound of Formula 14, or a stereoisomer thereof or a pharmaceutically acceptable salt thereof, the compound is of Formula 14c

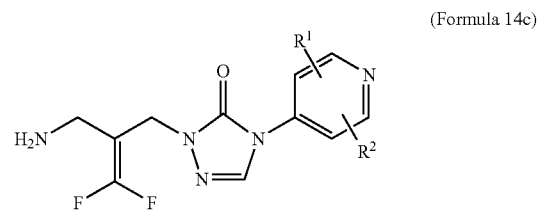

(Formula 14c)

or a stereoisomer thereof or a pharmaceutically acceptable salt thereof.

In some embodiments of a compound of Formula 14, or a stereoisomer thereof or a pharmaceutically acceptable salt thereof, R² is a substituted or unsubstituted aryl group. In further embodiments, R² is substituted or unsubstituted phenyl. In still further embodiments, R² is phenyl substituted with one to three substituents selected from the group consisting of with halogen, $C_{1-6}$ alkoxy, mono- or di-$C_{1-6}$ alkylamino, mono- or di-$C_{1-6}$ alkylaminosulfonyl, $C_{1-6}$ alkylsulfonyl, morpholinylcarbonyl, piperazinyl, morpholinyl, pyrazolyl, $C_{1-6}$ alkylpyrazolyl, triazolyl, and pyrrolidinonyl. In other embodiments, R² is benzodioxole, benzoxadiazole, benzothiazole, indazole, 2,3-dihydro-1,4-benzoxazine, 1,4-benzoxazin-3-one, 1,4-dihydro-3,1-benzoxazin-2-one, 1,4-dihydroquinazolin-2-one, 3,4-dihydroquinolin-2-one, or benzoxazole, wherein R² is optionally substituted with $C_{1-6}$ alkyl or amino.

In some embodiments of a compound of Formula 14, or a stereoisomer thereof or a pharmaceutically acceptable salt thereof, R² is a substituted or unsubstituted heteroaryl group, wherein said heteroaryl group has 1 to 5 heteroatom ring members chosen from O, N, or S. In further embodiments, R² is substituted or unsubstituted pyridine. In still further embodiments, R² is pyridine substituted with $C_{1-6}$ alkoxy, trifluoromethyl, piperazinyl, morpholinyl, or mono- or di-$C_{1-6}$ alkylamino. In other embodiments, R² is pyrimidine, 1H-pyrrolo[2,3-b]pyridine, pyrazole, or thiophene, wherein R² is optionally substituted with $C_{1-6}$ alkyl, difluoromethyl, $C_{1-6}$ alkoxy-$C_{1-6}$ alkylamino, or $C_{1-6}$ alkylcarbonyl.

In some embodiments of a compound of Formula 14, or a stereoisomer thereof or a pharmaceutically acceptable salt thereof, R² is substituted or unsubstituted pyridin-2-one. In further embodiments, R² is pyridin-2-one substituted with $C_{1-6}$ alkyl.

In another aspect, provided herein is a compound of Formula 15

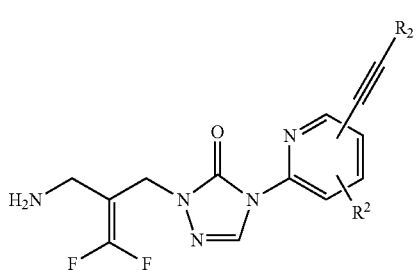

(Formula 15)

or a stereoisomer thereof or a pharmaceutically acceptable salt thereof;
wherein
$R^1$ is hydrogen or $C_{1-6}$ alkyl; and
$R^2$ is a substituted or unsubstituted aryl or a substituted or unsubstituted heteroaryl, wherein said heteroaryl group has 1 to 5 heteroatom ring members chosen from O, N, or S group.

In some embodiments of a compound of Formula 15, or a stereoisomer thereof or a pharmaceutically acceptable salt thereof, $R^2$ is a substituted or unsubstituted aryl group. In further embodiments, $R^2$ is substituted or unsubstituted phenyl. In still further embodiments, $R^2$ is 2,3-dihydro-1,4-benzoxazine or 3,4-dihydroquinolin-2-one, wherein said 3,4-dihydroquinolin-2-one is optionally substituted with $C_{1-6}$ alkyl.

In some embodiments of a compound of Formula 15, or a stereoisomer thereof or a pharmaceutically acceptable salt thereof, $R^2$ is a substituted or unsubstituted heteroaryl group, wherein said heteroaryl group has 1 to 5 heteroatom ring members chosen from O, N, or S. In further embodiments, $R^2$ is substituted or unsubstituted pyridine. In still further embodiments, $R^2$ is pyridine substituted with morpholinyl or mono- or di-$C_{1-6}$ alkylamino. In other embodiments, $R^2$ is 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, or pyrazole, wherein said pyrazole is optionally substituted with $C_{1-6}$ alkyl.

In another aspect, provided herein is a compound of Formula 16

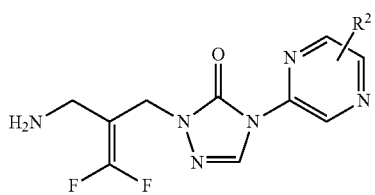

(Formula 16)

or a stereoisomer thereof or a pharmaceutically acceptable salt thereof;
wherein $R^2$ is a substituted or unsubstituted aryl or a substituted or unsubstituted heteroaryl group, wherein said heteroaryl group has 1 to 5 heteroatom ring members chosen from O, N, or S.

In some embodiments of a compound of Formula 16, or a stereoisomer thereof or a pharmaceutically acceptable salt thereof, $R^2$ is a substituted or unsubstituted aryl group. In further embodiments, $R^2$ is substituted or unsubstituted phenyl. In still further embodiments, $R^2$ is phenyl substituted with $C_{1-6}$ alkylsulfonyl or piperazinyl. In other embodiments, $R^2$ is benzodioxole or 3,4-dihydroquinolin-2-one, wherein said 3,4-dihydroquinolin-2-one is optionally substituted with $C_{1-6}$ alkyl.

In some embodiments of a compound of Formula 16, or a stereoisomer thereof or a pharmaceutically acceptable salt thereof, $R^2$ is a substituted or unsubstituted heteroaryl group, wherein said heteroaryl group has 1 to 5 heteroatom ring members chosen from O, N, or S. In further embodiments, $R^2$ is substituted or unsubstituted pyridine. In still further embodiments, $R^2$ is pyridine substituted with trifluoromethyl or mono- or di-$C_{1-6}$ alkylamino. In other embodiments, $R^2$ is substituted or unsubstituted pyrazole. In further embodiments, $R^2$ is pyrazole substituted with $C_{1-6}$ alkyl.

In another aspect, provided herein is a compound of Formula 17

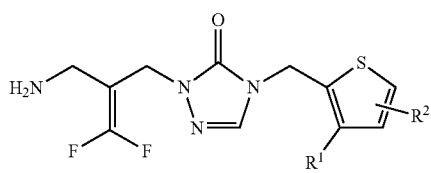

(Formula 17)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

In some embodiments of a compound of Formula 17, or a stereoisomer thereof or a pharmaceutically acceptable salt thereof, $R^2$ is a substituted or unsubstituted aryl group. In further embodiments, $R^2$ is substituted or unsubstituted phenyl. In still further embodiments, $R^2$ is phenyl substituted with one to three substituents selected from the group consisting of $C_{1-6}$ alkoxy, $C_{1-6}$ alkylcarbonyl, $C_{1-6}$ alkylsulfonyl, mono- or di-$C_{1-6}$ alkylaminosulfonyl, mono- or di-$C_{1-6}$ alkylaminocarbonyl, morpholinylcarbonyl, pyrazolyl, triazolyl, piperazinyl, and acetylpiperazinyl. In some embodiments, $R^2$ is phenyl substituted with one to three substituents selected from the group consisting of $C_{1-6}$ alkoxy, $C_{1-6}$ alkylcarbonyl, $C_{1-6}$ alkylsulfonyl, mono- or di-$C_{1-6}$ alkylaminosulfonyl, mono- or di-$C_{1-6}$ alkylaminocarbonyl, morpholinylcarbonyl, pyrazolyl, $C_{1-6}$ alkylpyrazolyl, triazolyl, piperazinyl, and acetylpiperazinyl. In other embodiments, $R^2$ is 3,4-dihydroisoquinolin-1-one, quinolin-2-one, 2,3-dihydro-1,4-benzoxazine, 1,4-benzoxazin-3-one, 1,4-dihydro-3,1-benzoxazin-2-one, 1,4-dihydroquinazolin-2-one, benzothiazole, benzoxadiazole, indazole, benzodioxole, 1,3-dihydroindol-2-one, or 3,4-dihydroquinolin-2-one; wherein $R^2$ is optionally substituted with $C_{1-6}$ alkyl, $C_{1-6}$ alkylcarbonylamino, or halogen.

In some embodiments of a compound of Formula 17, or a stereoisomer thereof or a pharmaceutically acceptable salt thereof, $R^2$ is a substituted or unsubstituted heteroaryl group, wherein said heteroaryl group has 1 to 5 heteroatom ring members chosen from O, N, or S. In further embodiments, $R^2$ is substituted or unsubstituted pyridine. In still further embodiments, R² is pyridine substituted with one to three substituents selected from the group consisting of halogen, trifluoromethyl, $C_{1-6}$ alkoxy, piperazinyl and mono- or di-$C_{1-6}$ alkylamino. In other embodiments, R² is substituted or unsubstituted pyrazole. In further embodiments, R² is pyrazole substituted with $C_{1-6}$ alkyl, difluoromethyl, benzyl, (cycloalkyl)alkyl, alkylsulfonyl, or cycloalkylsulfonyl. In other embodiments, R² is 5,6,7,8-tetrahydronaphthyridine, pyrimidine, imidazole, or triazolo[1,5-a]pyridine; wherein R² is optionally substituted with one to three substituents selected from the group consisting of halogen, $C_{1-6}$ alkyl, $C_{1-6}$ alkoxy, amino, and $C_{1-6}$ alkoxy-$C_{1-6}$ alkylamino.

In some embodiments of a compound of Formula 17, or a stereoisomer thereof or a pharmaceutically acceptable salt thereof, R² is tetrahydropyridine or pyridin-2-one, wherein said tetrahydropyridine and said pyridin-2-one are optionally substituted with $C_{1-6}$ alkyl or $C_{1-6}$ alkylcarbonyl.

In another aspect, provided herein is a compound of Formula 18

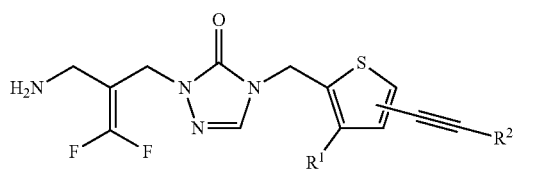

(Formula 18)

or a stereoisomer thereof or a pharmaceutically acceptable salt thereof;
wherein
R¹ is hydrogen, halogen, or $C_{1-6}$ alkyl; and
R² is a substituted or unsubstituted aryl or a substituted or unsubstituted heteroaryl group, wherein said heteroaryl group has 1 to 5 heteroatom ring members chosen from O, N, or S.

In some embodiments of a compound of Formula 18, or a stereoisomer thereof or a pharmaceutically acceptable salt thereof, R² is a substituted or unsubstituted aryl group. In further embodiments, R² is substituted or unsubstituted phenyl. In other embodiments, R² is 2,3-dihydro-1,4-benzoxazine or 3,4-dihydroquinolin-2-one.

In some embodiments of a compound of Formula 18, or a stereoisomer thereof or a pharmaceutically acceptable salt thereof, R² is a substituted or unsubstituted heteroaryl group, wherein said heteroaryl group has 1 to 5 heteroatom ring members chosen from O, N, or S. In further embodiments, R² is substituted or unsubstituted pyridine. In still further embodiments, R² is pyridine substituted with morpholinyl or mono- or di-$C_{1-6}$ alkylamino. In other embodiments, R² is substituted or unsubstituted pyrazole. In further embodiments, R² is pyrazole substituted with $C_{1-6}$ alkyl. In other embodiments, R² is 2,3-dihydro-pyrido[2,3-b][1,4]oxazine, 3,4-dihydro-pyrido[3,2-b][1,4]oxazine, pyrido[2,3-b][1,4]oxazin-2-one, or pyrido[3,2-b][1,4]oxazin-3-one.

In another aspect, provided herein is a compound of Formula 19

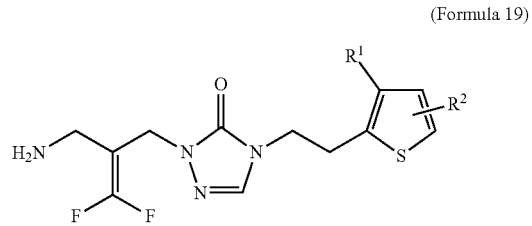

(Formula 19)

or a stereoisomer thereof or a pharmaceutically acceptable salt thereof;
wherein
R¹ is hydrogen, halogen, or $C_{1-6}$ alkyl; and
R² is a substituted or unsubstituted aryl or a substituted or unsubstituted heteroaryl group, wherein said heteroaryl group has 1 to 5 heteroatom ring members chosen from O, N, or S.

In some embodiments of a compound of Formula 19, or a stereoisomer thereof or a pharmaceutically acceptable salt thereof, R² is a substituted or unsubstituted aryl group. In further embodiments, R² is substituted or unsubstituted phenyl. In still further embodiments, R² is phenyl substituted with $C_{1-6}$ alkylsulfonyl or piperazinyl. In other embodiments, R² is benzodioxole or 3,4-dihydroquinolin-2-one; wherein R² is optionally substituted with $C_{1-6}$ alkyl.

In some embodiments of a compound of Formula 19, or a stereoisomer thereof or a pharmaceutically acceptable salt thereof, R² is a substituted or unsubstituted heteroaryl group, wherein said heteroaryl group has 1 to 5 heteroatom ring members chosen from O, N, or S. In further embodiments, R² is substituted or unsubstituted pyridine. In still further embodiments, R² is pyridine substituted with trifluoromethyl or mono- or di-$C_{1-6}$ alkylamino. In other embodiments, R² is substituted or unsubstituted pyrazole. In further embodiments, R² is pyrazole substituted with $C_{1-6}$ alkyl.

In another aspect, provided herein is a compound of Formula 20

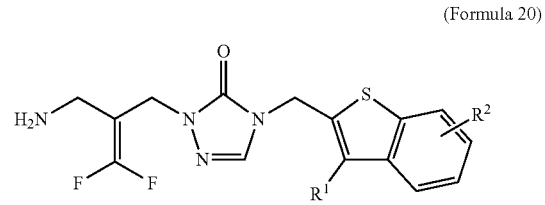

(Formula 20)

or a stereoisomer thereof or a pharmaceutically acceptable salt thereof;
wherein
R¹ is hydrogen, halogen, or $C_{1-6}$ alkyl; and
R² is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

In some embodiments of a compound of Formula 20, or a stereoisomer thereof or a pharmaceutically acceptable salt thereof, R² is a substituted or unsubstituted aryl group. In further embodiments, R² is substituted or unsubstituted phenyl. In still further embodiments, R² is phenyl substituted with $C_{1-6}$ alkylsulfonyl or piperazinyl. In other embodiments, $R^2$ is benzodioxole or 3,4-dihydroquinolin-2-one; wherein $R^2$ is optionally substituted with $C_{1-6}$ alkyl.

In some embodiments of a compound of Formula 20, or a stereoisomer thereof or a pharmaceutically acceptable salt thereof, $R^2$ is a substituted or unsubstituted heteroaryl group, wherein said heteroaryl group has 1 to 5 heteroatom ring members chosen from O, N, or S. In further embodiments, $R^2$ is substituted or unsubstituted pyridine. In still further embodiments, $R^2$ is pyridine substituted with trifluoromethyl or mono- or di-$C_{1-6}$ alkylamino. In other embodiments, $R^2$ is substituted or unsubstituted pyrazole. In further embodiments, $R^2$ is pyrazole substituted with $C_{1-6}$ alkyl.

In some embodiments of a compound of Formula 20, or a stereoisomer thereof or a pharmaceutically acceptable salt thereof, $R^2$ is a substituted or unsubstituted pyridine-2-one. In further embodiments, $R^2$ is pyridine-2-one substituted with $C_{1-6}$ alkyl.

In some embodiments of a compound of Formulas 12, 13, 14, 15, 16, 17, 18, 19, or 20, or a stereoisomer thereof or a pharmaceutically acceptable salt thereof, $R^1$ is hydrogen.

In some embodiments of a compound of Formulas 12, 13, 14, 15, 16, 17, 18, 19, or 20, or a stereoisomer thereof or a pharmaceutically acceptable salt thereof, $R^1$ is halogen.

In some embodiments of a compound of Formulas 12, 13, 14, 15, 16, 17, 18, 19, or 20, or a stereoisomer thereof or a pharmaceutically acceptable salt thereof, $R^1$ is $C_{1-6}$ alkyl.

The compounds provided in the description are inhibitors of VAP-1. VAP-1 inhibition may be measured, for example, by determining the half maximal inhibitory concentration ($IC_{50}$). One method for determining an $IC_{50}$ for VAP-1 is provided herein.

In one embodiment, the compounds are inhibitors of VAP-1. Selectivity may be determined, for example, by comparing inhibition of VAP-1 to inhibition of other aminooxidaxes such as MAO-A (monoamine oxidase-A), MAO-B (monoamine oxidase-B), and DAO (diamine oxidase). In one embodiment, said "significantly high inhibitory activity" means that $IC_{50}$ for VAP-1 obtained from the in vitro enzyme assay test is at least 3000 times lower than $IC_{50}$ of MAO-A, at least 100 times lower than $IC_{50}$ of MAO-B, and at least 100 times lower than $IC_{50}$ of DAO. In an alternative embodiment, "significantly high inhibitory activity" means the $IC_{50}$ for VAP-1 obtained from the in vitro enzyme analysis (in vitro enzyme assay) test is at least 3000 times lower than $IC_{50}$ of MAO-A, at least 100 times lower than $IC_{50}$ of MAO-B, or at least 100 times lower than $IC_{50}$ of DAO.

In another aspect, a compound of Formulas X, Y, or 1, or a stereoisomer thereof, or a pharmaceutically acceptable salt thereof is selected from the following compounds or a pharmaceutically acceptable salt thereof:

2-[2-(aminomethyl)-3,3-difluoro-allyl]-4-(4-fluorophenyl)-1,2,4-triazol-3-one;

2-[2-(aminomethyl)-3,3-difluoro-allyl]-4-(3-bromophenyl)-1,2,4-triazol-3-one;

2-[2-(aminomethyl)-3,3-difluoro-allyl]-4-(3,4-difluorophenyl)-1,2,4-triazol-3-one;

2-[2-(aminomethyl)-3,3-difluoro-allyl]-4-(4-bromo-3-fluoro-phenyl)-1,2,4-triazol-3-one;

2-[2-(aminomethyl)-3,3-difluoro-allyl]-4-(4-bromo-2-fluoro-phenyl)-1,2,4-triazol-3-one;

2-[2-(aminomethyl)-3,3-difluoro-allyl]-4-(4-bromo-2-methyl-phenyl)-1,2,4-triazol-3-one;

2-[2-(aminomethyl)-3,3-difluoro-allyl]-4-(6-bromo-3-pyridyl)-1,2,4-triazol-3-one;

2-[2-(aminomethyl)-3,3-difluoro-allyl]-4-(6-bromo-2-pyridyl)-1,2,4-triazol-3-one;

2-[2-(aminomethyl)-3,3-difluoro-allyl]-4-(4-bromo-2-pyridyl)-1,2,4-triazol-3-one;

2-[2-(aminomethyl)-3,3-difluoro-allyl]-4-(2-bromo-4-pyridyl)-1,2,4-triazol-3-one;

2-[2-(aminomethyl)-3,3-difluoro-allyl]-4-(5-bromo-3-methyl-2-pyridyl)-1,2,4-triazol-3-one;

2-[2-(aminomethyl)-3,3-difluoro-allyl]-4-(6-bromo-4-methyl-3-pyridyl)-1,2,4-triazol-3-one;

2-[2-(aminomethyl)-3,3-difluoro-allyl]-4-(6-bromo-5-methyl-3-pyridyl)-1,2,4-triazol-3-one;

2-[2-(aminomethyl)-3,3-difluoro-allyl]-4-(5-bromo-3-fluoro-2-pyridyl)-1,2,4-triazol-3-one;

2-[2-(aminomethyl)-3,3-difluoro-allyl]-4-(6-bromo-3-methyl-2-pyridyl)-1,2,4-triazol-3-one;

2-[2-(aminomethyl)-3,3-difluoro-allyl]-4-(5-bromopyrazin-2-yl)-1,2,4-triazol-3-one;

2-[2-(aminomethyl)-3,3-difluoro-allyl]-4-[3-(4-methylsulfonylphenyl)phenyl]-1,2,4-triazol-3-one;

2-[2-(aminomethyl)-3,3-difluoro-allyl]-4-[3-(4-piperazin-1-ylphenyl)phenyl]-1,2,4-triazol-3-one;

2-[2-(aminomethyl)-3,3-difluoro-allyl]-4-[3-[6-(trifluoromethyl)-3-pyridyl]phenyl]-1,2,4-triazol-3-one;

2-[2-(aminomethyl)-3,3-difluoro-allyl]-4-[3-[6-(dimethylamino)-3-pyridyl]phenyl]-1,2,4-triazol-3-one;

2-[2-(aminomethyl)-3,3-difluoro-allyl]-4-[3-(1,3-benzodioxol-5-yl)phenyl]-1,2,4-triazol-3-one;

6-[3-[1-[2-(aminomethyl)-3,3-difluoro-allyl]-5-oxo-1,2,4-triazol-4-yl]phenyl]-8-methyl-3,4-dihydro-1H-quinolin-2-one;

2-[2-(aminomethyl)-3,3-difluoro-allyl]-4-[3-(1-ethylpyrazol-4-yl)phenyl]-1,2,4-triazol-3-one;

2-[2-(aminomethyl)-3,3-difluoro-allyl]-4-[3-fluoro-4-(4-methylsulfonylphenyl)phenyl]-1,2,4-triazol-3-one;

2-[2-(aminomethyl)-3,3-difluoro-allyl]-4-[3-fluoro-4-(4-piperazin-1-ylphenyl)phenyl]-1,2,4-triazol-3-one;

2-[2-(aminomethyl)-3,3-difluoro-allyl]-4-[3-fluoro-4-[6-(trifluoromethyl)-3-pyridyl]phenyl]-1,2,4-triazol-3-one;

2-[2-(aminomethyl)-3,3-difluoro-allyl]-4-[4-[6-(dimethylamino)-3-pyridyl]-3-fluoro-phenyl]-1,2,4-triazol-3-one;

2-[2-(aminomethyl)-3,3-difluoro-allyl]-4-[4-(1,3-benzodioxol-5-yl)-3-fluoro-phenyl]-1,2,4-triazol-3-one;

6-[4-[1-[2-(aminomethyl)-3,3-difluoro-allyl]-5-oxo-1,2,4-triazol-4-yl]-2-fluoro-phenyl]-8-methyl-3,4-dihydro-1H-quinolin-2-one;

2-[2-(aminomethyl)-3,3-difluoro-allyl]-4-[4-(1-ethylpyrazol-4-yl)-3-fluoro-phenyl]-1,2,4-triazol-3-one;

2-[2-(aminomethyl)-3,3-difluoro-allyl]-4-[2-fluoro-4-(4-methylsulfonylphenyl)phenyl]-1,2,4-triazol-3-one;

2-[2-(aminomethyl)-3,3-difluoro-allyl]-4-[2-fluoro-4-(4-piperazin-1-ylphenyl)phenyl]-1,2,4-triazol-3-one;

2-[2-(aminomethyl)-3,3-difluoro-allyl]-4-[2-fluoro-4-[6-(trifluoromethyl)-3-pyridyl]phenyl]-1,2,4-triazol-3-one;

2-[2-(aminomethyl)-3,3-difluoro-allyl]-4-[4-[6-(dimethylamino)-3-pyridyl]-2-fluoro-phenyl]-1,2,4-triazol-3-one;

2-[2-(aminomethyl)-3,3-difluoro-allyl]-4-[4-(1,3-benzodioxol-5-yl)-2-fluoro-phenyl]-1,2,4-triazol-3-one;

6-[4-[1-[2-(aminomethyl)-3,3-difluoro-allyl]-5-oxo-1,2,4-triazol-4-yl]-3-fluoro-phenyl]-8-methyl-3,4-dihydro-1H-quinolin-2-one;

2-[2-(aminomethyl)-3,3-difluoro-allyl]-4-[4-(1-ethylpyrazol-4-yl)-2-fluoro-phenyl]-1,2,4-triazol-3-one;

2-[2-(aminomethyl)-3,3-difluoro-allyl]-4-[6-(4-methylsulfonylphenyl)-3-pyridyl]-1,2,4-triazol-3-one;

2-[2-(aminomethyl)-3,3-difluoro-allyl]-4-[6-(4-piperazin-1-ylphenyl)-3-pyridyl]-1,2,4-triazol-3-one;

2-[2-(aminomethyl)-3,3-difluoro-allyl]-4-[6-[6-(trifluoromethyl)-3-pyridyl]-3-pyridyl]-1,2,4-triazol-3-one;

2-[2-(aminomethyl)-3,3-difluoro-allyl]-4-[6-[6-(dimethylamino)-3-pyridyl]-3-pyridyl]-1,2,4-triazol-3-one;
2-[2-(aminomethyl)-3,3-difluoro-allyl]-4-[6-(1,3-benzodioxol-5-yl)-3-pyridyl]-1,2,4-triazol-3-one;
6-[5-[1-[2-(aminomethyl)-3,3-difluoro-allyl]-5-oxo-1,2,4-triazol-4-yl]-2-pyridyl]-8-methyl-3,4-dihydro-1H-quinolin-2-one:
6-[5-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[6-(1-ethylpyrazol-4-yl)-3-pyridyl]-1,2,4-triazol-3-one;
2-[2-(aminomethyl)-3,3-difluoro-allyl]-4-[6-(4-methylsulfonylphenyl)-2-pyridyl]-1,2,4-triazol-3-one;
2-[2-(aminomethyl)-3,3-difluoro-allyl]-4-[6-(4-piperazin-1-ylphenyl)-2-pyridyl]-1,2,4-triazol-3-one;
2-[2-(aminomethyl)-3,3-difluoro-allyl]-4-[6-[6-(trifluoromethyl)-3-pyridyl]-2-pyridyl]-1,2,4-triazol-3-one;
2-[2-(aminomethyl)-3,3-difluoro-allyl]-4-[6-[6-(dimethylamino)-3-pyridyl]-2-pyridyl]-1,2,4-triazol-3-one;
2-[2-(aminomethyl)-3,3-difluoro-allyl]-4-[6-(1,3-benzodioxol-5-yl)-2-pyridyl]-1,2,4-triazol-3-one;
6-[6-[1-[2-(aminomethyl)-3,3-difluoro-allyl]-5-oxo-1,2,4-triazol-4-yl]-2-pyridyl]-8-methyl-3,4-dihydro-1H-quinolin-2-one:
6-[6-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[6-(1-ethylpyrazol-4-yl)-2-pyridyl]-1,2,4-triazol-3-one;
2-[2-(aminomethyl)-3,3-difluoro-allyl]-4-[4-(4-methylsulfonylphenyl)-2-pyridyl]-1,2,4-triazol-3-one;
2-[2-(aminomethyl)-3,3-difluoro-allyl]-4-[4-(4-piperazin-1-ylphenyl)-2-pyridyl]-1,2,4-triazol-3-one;
2-[2-(aminomethyl)-3,3-difluoro-allyl]-4-[4-[6-(trifluoromethyl)-3-pyridyl]-2-pyridyl]-1,2,4-triazol-3-one;
2-[2-(aminomethyl)-3,3-difluoro-allyl]-4-[4-[6-(dimethylamino)-3-pyridyl]-2-pyridyl]-1,2,4-triazol-3-one;
2-[2-(aminomethyl)-3,3-difluoro-allyl]-4-[4-(1,3-benzodioxol-5-yl)-2-pyridyl]-1,2,4-triazol-3-one;
6-[2-[1-[2-(aminomethyl)-3,3-difluoro-allyl]-5-oxo-1,2,4-triazol-4-yl]-4-pyridyl]-8-methyl-3,4-dihydro-1H-quinolin-2-one:
2-[2-(aminomethyl)-3,3-difluoro-allyl]-4-[4-(1-ethylpyrazol-4-yl)-2-pyridyl]-1,2,4-triazol-3-one;
2-[2-(aminomethyl)-3,3-difluoro-allyl]-4-[2-(4-methylsulfonylphenyl)-4-pyridyl]-1,2,4-triazol-3-one;
2-[2-(aminomethyl)-3,3-difluoro-allyl]-4-[2-(4-piperazin-1-ylphenyl)-4-pyridyl]-1,2,4-triazol-3-one;
2-[2-(aminomethyl)-3,3-difluoro-allyl]-4-[2-[6-(dimethylamino)-3-pyridyl]-4-pyridyl]-1,2,4-triazol-3-one;
2-[2-(aminomethyl)-3,3-difluoro-allyl]-4-[2-(1,3-benzodioxol-5-yl)-4-pyridyl]-1,2,4-triazol-3-one;
6-[4-[1-[2-(aminomethyl)-3,3-difluoro-allyl]-5-oxo-1,2,4-triazol-4-yl]-2-pyridyl]-8-methyl-3,4-dihydro-1H-quinolin-2-one:
6-[4-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[2-(1-ethylpyrazol-4-yl)-4-pyridyl]-1,2,4-triazol-3-one;
2-[2-(aminomethyl)-3,3-difluoro-allyl]-4-[3-methyl-5-(4-methylsulfonylphenyl)-2-pyridyl]-1,2,4-triazol-3-one;
2-[2-(aminomethyl)-3,3-difluoro-allyl]-4-[3-methyl-5-(4-piperazin-1-ylphenyl)-2-pyridyl]-1,2,4-triazol-3-one;
2-[2-(aminomethyl)-3,3-difluoro-allyl]-4-[3-methyl-5-[6-(trifluoromethyl)-3-pyridyl]-2-pyridyl]-1,2,4-triazol-3-one;
2-[2-(aminomethyl)-3,3-difluoro-allyl]-4-[5-[6-(dimethylamino)-3-pyridyl]-3-methyl-2-pyridyl]-1,2,4-triazol-3-one;
2-[2-(aminomethyl)-3,3-difluoro-allyl]-4-[5-(1,3-benzodioxol-5-yl)-3-methyl-2-pyridyl]-1,2,4-triazol-3-one;
6-[6-[1-[2-(aminomethyl)-3,3-difluoro-allyl]-5-oxo-1,2,4-triazol-4-yl]-5-methyl-3-pyridyl]-8-methyl-3,4-dihydro-1H-quinolin-2-one:
6-[6-[1-[2-(aminomethyl)-3,3-difluoro-allyl]-5-oxo-1,2,4-triazol-4-yl]-5-methyl-3-pyridyl]-1-methyl-3,4-dihydroquinolin-2-one;
2-[2-(aminomethyl)-3,3-difluoro-allyl]-4-[5-(1-ethylpyrazol-4-yl)-3-methyl-2-pyridyl]-1,2,4-triazol-3-one;
2-[2-(aminomethyl)-3,3-difluoro-allyl]-4-[5-methyl-6-(4-methylsulfonylphenyl)-3-pyridyl]-1,2,4-triazol-3-one;
2-[2-(aminomethyl)-3,3-difluoro-allyl]-4-[5-methyl-6-[6-(trifluoromethyl)-3-pyridyl]-3-pyridyl]-1,2,4-triazol-3-one;
2-[2-(aminomethyl)-3,3-difluoro-allyl]-4-[6-[6-(dimethylamino)-3-pyridyl]-5-methyl-3-pyridyl]-1,2,4-triazol-3-one;
2-[2-(aminomethyl)-3,3-difluoro-allyl]-4-[6-(1,3-benzodioxol-5-yl)-5-methyl-3-pyridyl]-1,2,4-triazol-3-one;
6-[5-[1-[2-(aminomethyl)-3,3-difluoro-allyl]-5-oxo-1,2,4-triazol-4-yl]-3-methyl-2-pyridyl]-8-methyl-3,4-dihydro-1H-quinolin-2-one:
6-[5-[1-[2-(aminomethyl)-3,3-difluoro-allyl]-5-oxo-1,2,4-triazol-4-yl]-3-methyl-2-pyridyl]-1-methyl-3,4-dihydroquinolin-2-one;
2-[2-(aminomethyl)-3,3-difluoro-allyl]-4-[3-fluoro-5-(4-methylsulfonylphenyl)-2-pyridyl]-1,2,4-triazol-3-one;
2-[2-(aminomethyl)-3,3-difluoro-allyl]-4-[3-fluoro-5-(4-piperazin-1-ylphenyl)-2-pyridyl]-1,2,4-triazol-3-one;
2-[2-(aminomethyl)-3,3-difluoro-allyl]-4-[3-fluoro-5-[6-(trifluoromethyl)-3-pyridyl]-2-pyridyl]-1,2,4-triazol-3-one;
2-[2-(aminomethyl)-3,3-difluoro-allyl]-4-[5-(1,3-benzodioxol-5-yl)-3-fluoro-2-pyridyl]-1,2,4-triazol-3-one;
6-[6-[1-[2-(aminomethyl)-3,3-difluoro-allyl]-5-oxo-1,2,4-triazol-4-yl]-5-fluoro-3-pyridyl]-8-methyl-3,4-dihydro-1H-quinolin-2-one:
6-[6-[1-[2-(aminomethyl)-3,3-difluoro-allyl]-5-oxo-1,2,4-triazol-4-yl]-5-fluoro-3-pyridyl]-1-methyl-3,4-dihydroquinolin-2-one;
2-[2-(aminomethyl)-3,3-difluoro-allyl]-4-[5-(1-ethylpyrazol-4-yl)-3-fluoro-2-pyridyl]-1,2,4-triazol-3-one;
2-[2-(aminomethyl)-3,3-difluoro-allyl]-4-[5-(4-methylsulfonylphenyl)-pyrazin-2-yl]-1,2,4-triazol-3-one;
2-[2-(aminomethyl)-3,3-difluoro-allyl]-4-[5-(4-piperazin-1-ylphenyl)pyrazin-2-yl]-1,2,4-triazol-3-one;
2-[2-(aminomethyl)-3,3-difluoro-allyl]-4-[5-[6-(trifluoromethyl)-3-pyridyl]pyrazin-2-yl]-1,2,4-triazol-3-one;
2-[2-(aminomethyl)-3,3-difluoro-allyl]-4-[5-[6-(dimethylamino)-3-pyridyl]pyrazin-2-yl]-1,2,4-triazol-3-one;
2-[2-(aminomethyl)-3,3-difluoro-allyl]-4-[5-(1,3-benzodioxol-5-yl)pyrazin-2-yl]-1,2,4-triazol-3-one;
6-[5-[1-[2-(aminomethyl)-3,3-difluoro-allyl]-5-oxo-1,2,4-triazol-4-yl]pyrazin-2-yl]-1-methyl-3,4-dihydro-1H-quinolin-2-one:
2-[2-(aminomethyl)-3,3-difluoro-allyl]-4-[5-(1-ethylpyrazol-4-yl)pyrazin-2-yl]-1,2,4-triazol-3-one;
2-[2-(aminomethyl)-3,3-difluoro-allyl]-4-[(4-benzyloxyphenyl)methyl]-1,2,4-triazol-3-one;

2-[2-(aminomethyl)-3,3-difluoro-allyl]-4-[(5-bromo-2-thie-nyl)methyl]-1,2,4-triazol-3-one;
2-[2-(aminomethyl)-3,3-difluoro-allyl]-4-[(4-bromo-2-thie-nyl)methyl]-1,2,4-triazol-3-one;
2-[2-(aminomethyl)-3,3-difluoro-allyl]-4-[(5-bromo-3-methyl-2-thienyl)methyl]-1,2,4-triazol-3-one;
4-[[5-(4-acetylphenyl)-2-thienyl]methyl]-2-[2-(aminom-ethyl)-3,3-difluoro-allyl]-1,2,4-triazol-3-one;
2-[2-(aminomethyl)-3,3-difluoro-allyl]-4-[[5-(4-methyl-sulfonylphenyl)-2-thienyl]methyl]-1,2,4-triazol-3-one;
2-[2-(aminomethyl)-3,3-difluoro-allyl]-4-[[5-(3-methyl-sulfonylphenyl)-2-thienyl]methyl]-1,2,4-triazol-3-one;
3-[5-[[1-[2-(aminomethyl)-3,3-difluoro-allyl]-5-oxo-1,2,4-triazol-4-yl]methyl]-2-thienyl]-N,N-dimethyl-benzene-sulfonamide:
4-[5-[[1-[2-(aminomethyl)-3,3-difluoro-allyl]-5-oxo-1,2,4-triazol-4-yl]methyl]-2-thienyl]-N-methyl-benzamide;
2-[2-(aminomethyl)-3,3-difluoro-allyl]-4-[[5-(3,4,5-trimethoxyphenyl)-2-thienyl]methyl]-1,2,4-triazol-3-one;
2-[2-(aminomethyl)-3,3-difluoro-allyl]-4-[[5-(4-piperazin-1-ylphenyl)-2-thienyl]methyl]-1,2,4-triazol-3-one;
2-[2-(aminomethyl)-3,3-difluoro-allyl]-4-[[5-(3-piperazin-1-ylphenyl)-2-thienyl]methyl]-1,2,4-triazol-3-one;
4-[[5-[4-(4-acetylpiperazin-1-yl)phenyl]-2-thienyl]methyl]-2-[2-(aminomethyl)-3,3-difluoro-allyl]-1,2,4-triazol-3-one;
2-[2-(aminomethyl)-3,3-difluoro-allyl]-4-[[5-(4-morpho-line-4-carbonyl)phenyl]-2-thienyl]methyl]-1,2,4-triazol-3-one;
2-[2-(aminomethyl)-3,3-difluoro-allyl]-4-[[5-[3-(1H-pyra-zol-3-yl)phenyl]-2-thienyl]methyl]-1,2,4-triazol-3-one;
2-[2-(aminomethyl)-3,3-difluoro-allyl]-4-[[5-[6-(trifluo-romethyl)-3-pyridyl]-2-thienyl]methyl]-1,2,4-triazol-3-one;
2-[2-(aminomethyl)-3,3-difluoro-allyl]-4-[[5-[6-(dimethyl-amino)-3-pyridyl]-2-thienyl]methyl]-1,2,4-triazol-3-one;
2-[2-(aminomethyl)-3,3-difluoro-allyl]-4-[[5-(6-methoxy-3-pyridyl)-2-thienyl]methyl]-1,2,4-triazol-3-one;
2-[2-(aminomethyl)-3,3-difluoro-allyl]-4-[[5-(6-piperazin-1-yl-3-pyridyl)-2-thienyl]methyl]-1,2,4-triazol-3-one;
2-[2-(aminomethyl)-3,3-difluoro-allyl]-4-[[5-[6-(dimethyl-amino)-5-fluoro-3-pyridyl]-2-thienyl]methyl]-1,2,4-tri-azol-3-one;
2-[2-(aminomethyl)-3,3-difluoro-allyl]-4-[[5-(2-aminopy-rimidin-5-yl)-2-thienyl]methyl]-1,2,4-triazol-3-one;
2-[2-(aminomethyl)-3,3-difluoro-allyl]-4-[[5-(2-ethoxypy-rimidin-5-yl)-2-thienyl]methyl]-1,2,4-triazol-3-one;
2-[2-(aminomethyl)-3,3-difluoro-allyl]-4-[[5-[2-(2-methoxyethylamino)pyrimidin-5-yl]-2-thienyl]methyl]-1,2,4-triazol-3-one;
2-[2-(aminomethyl)-3,3-difluoro-allyl]-4-[[5-(1-ethylpyra-zol-4-yl)-2-thienyl]methyl]-1,2,4-triazol-3-one;
2-[2-(aminomethyl)-3,3-difluoro-allyl]-4-[[5-(2-chloro-3-methyl-imidazol-4-yl)-2-thienyl]methyl]-1,2,4-triazol-3-one;
5-[5-[[1-[2-(aminomethyl)-3,3-difluoro-allyl]-5-oxo-1,2,4-triazol-4-yl]methyl]-2-thienyl]-1-methyl-pyridin-2-one;
5-[5-[[1-[2-(aminomethyl)-3,3-difluoro-allyl]-5-oxo-1,2,4-triazol-4-yl]methyl]-2-thienyl]-1-ethyl-pyridin-2-one;
5-[5-[[1-[2-(aminomethyl)-3,3-difluoro-allyl]-5-oxo-1,2,4-triazol-4-yl]methyl]-2-thienyl]-1-isopropyl-pyridin-2-one;
2-[2-(aminomethyl)-3,3-difluoro-allyl]-4-[[5-(1-methyl-3,6-dihydro-2H-pyridin-4-yl)-2-thienyl]methyl]-1,2,4-tri-azol-3-one;

2-[2-(aminomethyl)-3,3-difluoro-allyl]-4-[[5-(1-acetyl-3,6-dihydro-2H-pyridin-4-yl)-2-thienyl]methyl]-1,2,4-tri-azol-3-one;
2-[2-(aminomethyl)-3,3-difluoro-allyl]-4-[[5-(1,3-benzodi-oxol-5-yl)-2-thienyl]methyl]-1,2,4-triazol-3-one;
2-[2-(aminomethyl)-3,3-difluoro-allyl]-4-[[5-(1H-indazol-6-yl)-2-thienyl]methyl]-1,2,4-triazol-3-one;
2-[2-(aminomethyl)-3,3-difluoro-allyl]-4-[[5-([1,2,4]tri-azolo[1,5-a]pyridin-7-yl)-2-thienyl]methyl]-1,2,4-triazol-3-one;
2-[2-(aminomethyl)-3,3-difluoro-allyl]-4-[[5-(2,1,3-benzo-xadiazol-5-yl)-2-thienyl]methyl]-1,2,4-triazol-3-one;
5-[5-[[1-[2-(aminomethyl)-3,3-difluoro-allyl]-5-oxo-1,2,4-triazol-4-yl]methyl]-2-thienyl]-7-fluoro-indolin-2-one;
N-[6-[5-[[1-[2-(aminomethyl)-3,3-difluoro-allyl]-5-oxo-1,2,4-triazol-4-yl]methyl]-2-thienyl]-1,3-benzothiazol-2-yl]acetamide;
7-[5-[[1-[2-(aminomethyl)-3,3-difluoro-allyl]-5-oxo-1,2,4-triazol-4-yl]methyl]-2-thienyl]-3,4-dihydro-2H-isoquino-lin-1-one:
6-[5-[[1-[2-(aminomethyl)-3,3-difluoro-allyl]-5-oxo-1,2,4-triazol-4-yl]methyl]-2-thienyl]-3,4-dihydro-1H-quinolin-2-one:
6-[5-[[1-[2-(aminomethyl)-3,3-difluoro-allyl]-5-oxo-1,2,4-triazol-4-yl]methyl]-2-thienyl]-8-methyl-3,4-dihydro-1H-quinolin-2-one:
6-[5-[[1-[2-(aminomethyl)-3,3-difluoro-allyl]-5-oxo-1,2,4-triazol-4-yl]methyl]-2-thienyl]-8-methyl-1H-quinolin-2-one:
6-[5-[[1-[2-(aminomethyl)-3,3-difluoro-allyl]-5-oxo-1,2,4-triazol-4-yl]methyl]-2-thienyl]-8-fluoro-3,4-dihydro-1H-quinolin-2-one:
6-[5-[[1-[2-(aminomethyl)-3,3-difluoro-allyl]-5-oxo-1,2,4-triazol-4-yl]methyl]-2-thienyl]-8-fluoro-1H-quinolin-2-one:
6-[5-[[1-[2-(aminomethyl)-3,3-difluoro-allyl]-5-oxo-1,2,4-triazol-4-yl]methyl]-2-thienyl]-1-methyl-3,4-dihydroqui-nolin-2-one;
2-[2-(aminomethyl)-3,3-difluoro-allyl]-4-[[5-(5-methyl-3,4-dihydro-2H-1,4-benzoxazin-6-yl)-2-thienyl]methyl]-1,2,4-triazol-3-one;
2-[2-(aminomethyl)-3,3-difluoro-allyl]-4-[[5-(4-methyl-2,3-dihydro-1,4-benzoxazin-7-yl)-2-thienyl]methyl]-1,2,4-triazol-3-one;
6-[5-[[1-[2-(aminomethyl)-3,3-difluoro-allyl]-5-oxo-1,2,4-triazol-4-yl]methyl]-2-thienyl]-4H-1,4-benzoxazin-3-one:
7-[5-[[1-[2-(aminomethyl)-3,3-difluoro-allyl]-5-oxo-1,2,4-triazol-4-yl]methyl]-2-thienyl]-1,4-dihydro-3,1-benzo-xazin-2-one;
6-[5-[[1-[2-(aminomethyl)-3,3-difluoro-allyl]-5-oxo-1,2,4-triazol-4-yl]methyl]-2-thienyl]-1,4-dihydro-3,1-benzo-xazin-2-one;
7-[5-[[1-[2-(aminomethyl)-3,3-difluoro-allyl]-5-oxo-1,2,4-triazol-4-yl]methyl]-2-thienyl]-4-methyl-1,4-benzoxazin-3-one;
2-[2-(aminomethyl)-3,3-difluoro-allyl]-4-[[5-(5,6,7,8-tetra-hydro-1,8-naphthyridin-3-yl)-2-thienyl]methyl]-1,2,4-tri-azol-3-one;
2-[2-(aminomethyl)-3,3-difluoro-allyl]-4-[[4-(4-methyl-sulfonylphenyl)-2-thienyl]methyl]-1,2,4-triazol-3-one;
2-[2-(aminomethyl)-3,3-difluoro-allyl]-4-[[4-(4-piperazin-1-ylphenyl)-2-thienyl]methyl]-1,2,4-triazol-3-one;
2-[2-(aminomethyl)-3,3-difluoro-allyl]-4-[[4-[6-(trifluo-romethyl)-3-pyridyl]-2-thienyl]methyl]-1,2,4-triazol-3-one;

2-[2-(aminomethyl)-3,3-difluoro-allyl]-4-[[4-[6-(dimethylamino)-3-pyridyl]-2-thienyl]methyl]-1,2,4-triazol-3-one;

2-[2-(aminomethyl)-3,3-difluoro-allyl]-4-[[4-(1,3-benzodioxol-5-yl)-2-thienyl]methyl]-1,2,4-triazol-3-one;

6-[5-[[1-[2-(aminomethyl)-3,3-difluoro-allyl]-5-oxo-1,2,4-triazol-4-yl]methyl]-3-thienyl]-8-methyl-3,4-dihydro-1H-quinolin-2-one:

6-[5-[[1-[2-(aminomethyl)-3,3-difluoro-allyl]-5-oxo-1,2,4-triazol-4-yl]methyl]-3-thienyl]-1-methyl-3,4-dihydroquinolin-2-one;

2-[2-(aminomethyl)-3,3-difluoro-allyl]-4-[[4-(1-ethylpyrazol-4-yl)-2-thienyl]methyl]-1,2,4-triazol-3-one;

2-[2-(aminomethyl)-3,3-difluoro-allyl]-4-[[3-methyl-5-(4-methylsulfonylphenyl)-2-thienyl]methyl]-1,2,4-triazol-3-one;

2-[2-(aminomethyl)-3,3-difluoro-allyl]-4-[[3-methyl-5-(4-piperazin-1-ylphenyl)-2-thienyl]methyl]-1,2,4-triazol-3-one;

2-[2-(aminomethyl)-3,3-difluoro-allyl]-4-[[3-methyl-5-[6-(trifluoromethyl)-3-pyridyl]-2-thienyl]methyl]-1,2,4-triazol-3-one;

2-[2-(aminomethyl)-3,3-difluoro-allyl]-4-[[5-[6-(dimethylamino)-3-pyridyl]-3-methyl-2-thienyl]methyl]-1,2,4-triazol-3-one;

2-[2-(aminomethyl)-3,3-difluoro-allyl]-4-[[5-(1,3-benzodioxol-5-yl)-3-methyl-2-thienyl]methyl]-1,2,4-triazol-3-one;

2-[2-(aminomethyl)-3,3-difluoro-allyl]-4-[[5-(1-ethylpyrazol-4-yl)-3-methyl-2-thienyl]methyl]-1,2,4-triazol-3-one;

2-[2-(aminomethyl)-3,3-difluoro-allyl]-4-[6-[2-(1-methylpyrazol-4-yl)ethynyl]-2-pyridyl]-1,2,4-triazol-3-one;

7-[(E)-2-[5-[[1-[2-(aminomethyl)-3,3-difluoro-allyl]-5-oxo-1,2,4-triazol-4-yl]methyl]-2-thienyl]vinyl]-1H-pyrido[2,3-b][1,4]oxazin-2-one;

2-[2-(aminomethyl)-3,3-difluoro-allyl]-4-[[5-[2-[6-(dimethylamino)-3-pyridyl]ethynyl]-2-thienyl]methyl]-1,2,4-triazol-3-one;

2-[2-(aminomethyl)-3,3-difluoro-allyl]-4-[[5-[2-(6-morpholino-3-pyridyl)ethynyl]-2-thienyl]methyl]-1,2,4-triazol-3-one;

2-[2-(aminomethyl)-3,3-difluoro-allyl]-4-[[5-[2-(3,4-dihydro-2H-1,4-benzoxazin-6-yl)ethynyl]-2-thienyl]methyl]-1,2,4-triazol-3-one;

6-[2-[5-[[1-[2-(aminomethyl)-3,3-difluoro-allyl]-5-oxo-1,2,4-triazol-4-yl]methyl]-2-thienyl]ethynyl]-3,4-dihydro-1H-quinolin-2-one:

2-[2-(aminomethyl)-3,3-difluoro-allyl]-4-[[5-[2-(2,3-dihydro-1H-pyrido[2,3-b][1,4]oxazin-7-yl)ethynyl]-2-thienyl]methyl]-1,2,4-triazol-3-one;

2-[2-(aminomethyl)-3,3-difluoro-allyl]-4-[[5-[2-(3,4-dihydro-2H-pyrido[3,2-b][1,4]oxazin-7-yl)ethynyl]-2-thienyl]methyl]-1,2,4-triazol-3-one;

2-[2-(aminomethyl)-3,3-difluoro-allyl]-4-[[5-[2-(2,3-dihydro-1H-pyrido[2,3-b][1,4]oxazin-6-yl)ethynyl]-2-thienyl]methyl]-1,2,4-triazol-3-one;

7-[2-[5-[[1-[2-(aminomethyl)-3,3-difluoro-allyl]-5-oxo-1,2,4-triazol-4-yl]methyl]-2-thienyl]ethynyl]-1H-pyrido[2,3-b][1,4]oxazin-2-one;

7-[2-[5-[[1-[2-(aminomethyl)-3,3-difluoro-allyl]-5-oxo-1,2,4-triazol-4-yl]methyl]-2-thienyl]ethynyl]-4H-pyrido[3,2][b 1,4]oxazin-3-one:

2-[2-(aminomethyl)-3,3-difluoro-allyl]-4-[[5-[2-(1-methylpyrazol-4-yl)ethynyl]-2-thienyl]methyl]-1,2,4-triazol-3-one;

2-[2-(aminomethyl)-3,3-difluoro-allyl]-4-[2-(2-thienyl)ethyl]-1,2,4-triazol-3-one;

2-[2-(aminomethyl)-3,3-difluoro-allyl]-4-[2-[5-(4-methylsulfonylphenyl)-2-thienyl]ethyl]-1,2,4-triazol-3-one;

2-[2-(aminomethyl)-3,3-difluoro-allyl]-4-[2-[5-(4-piperazin-1-ylphenyl)-2-thienyl]ethyl]-1,2,4-triazol-3-one;

2-[2-(aminomethyl)-3,3-difluoro-allyl]-4-[2-[5-[6-(trifluoromethyl)-3-pyridyl]-2-thienyl]ethyl]-1,2,4-triazol-3-one;

2-[2-(aminomethyl)-3,3-difluoro-allyl]-4-[2-[5-[6-(dimethylamino)-3-pyridyl]-2-thienyl]ethyl]-1,2,4-triazol-3-one;

2-[2-(aminomethyl)-3,3-difluoro-allyl]-4-[2-[5-(1,3-benzodioxol-5-yl)-2-thienyl]ethyl]-1,2,4-triazol-3-one;

6-[5-[2-[1-[2-(aminomethyl)-3,3-difluoro-allyl]-5-oxo-1,2,4-triazol-4-yl]ethyl]-2-thienyl]-8-methyl-3,4-dihydro-1H-quinolin-2-one:

6-[5-[2-[1-[2-(aminomethyl)-3,3-difluoro-allyl]-5-oxo-1,2,4-triazol-4-yl]ethyl]-2-thienyl]-1-methyl-3,4-dihydroquinolin-2-one;

2-[2-(aminomethyl)-3,3-difluoro-allyl]-4-[2-[5-(1-ethylpyrazol-4-yl)-2-thienyl]ethyl]-1,2,4-triazol-3-one;

3-[5-[[1-[2-(aminomethyl)-3,3-difluoro-allyl]-5-oxo-1,2,4-triazol-4-yl]methyl]-2-thienyl]-N,N-dimethyl-benzamide;

6-[5-[[1-[2-(aminomethyl)-3,3-difluoro-allyl]-5-oxo-1,2,4-triazol-4-yl]methyl]-2-thienyl]-3-methyl-1,4-dihydroquinazolin-2-one;

2-[2-(aminomethyl)-3,3-difluoro-allyl]-4-[[5-[1-(difluoromethyl)pyrazol-4-yl]-2-thienyl]methyl]-1,2,4-triazol-3-one;

2-[2-(aminomethyl)-3,3-difluoro-allyl]-4-[[5-(1-isopropylpyrazol-4-yl)-2-thienyl]methyl]-1,2,4-triazol-3-one;

2-[2-(aminomethyl)-3,3-difluoro-allyl]-4-[[5-[3-(1H-1,2,4-triazol-3-yl)phenyl]-2-thienyl]methyl]-1,2,4-triazol-3-one;

6-[5-[[1-[2-(aminomethyl)-3,3-difluoro-allyl]-5-oxo-1,2,4-triazol-4-yl]methyl]-3-thienyl]-3-methyl-1,4-dihydroquinazolin-2-one;

5-[5-[[1-[2-(aminomethyl)-3,3-difluoro-allyl]-5-oxo-1,2,4-triazol-4-yl]methyl]-3-thienyl]-1-isopropyl-pyridin-2-one;

4-[[4-[4-(4-acetylpiperazin-1-yl)phenyl]-2-thienyl]methyl]-2-[2-(aminomethyl)-3,3-difluoro-allyl]-1,2,4-triazol-3-one;

6-[5-[[1-[2-(aminomethyl)-3,3-difluoro-allyl]-5-oxo-1,2,4-triazol-4-yl]methyl]-3-thienyl]-8-fluoro-1H-quinolin-2-one;

5-[5-[[1-[2-(aminomethyl)-3,3-difluoro-allyl]-5-oxo-1,2,4-triazol-4-yl]methyl]-3-thienyl]-1-methyl-pyridin-2-one;

6-[5-[[1-[2-(aminomethyl)-3,3-difluoro-allyl]-5-oxo-1,2,4-triazol-4-yl]methyl]-3-thienyl]-1,4-dihydro-3,1-benzoxazin-2-one;

6-[5-[[1-[2-(aminomethyl)-3,3-difluoro-allyl]-5-oxo-1,2,4-triazol-4-yl]methyl]-3-thienyl]-3,4-dihydro-1H-quinolin-2-one;

5-[5-[[1-[2-(aminomethyl)-3,3-difluoro-allyl]-5-oxo-1,2,4-triazol-4-yl]methyl]-3-thienyl]-1-ethyl-pyridin-2-one;

2-[2-(aminomethyl)-3,3-difluoro-allyl]-4-[[4-[1-(difluoromethyl)pyrazol-4-yl]-2-thienyl]methyl]-1,2,4-triazol-3-one;

2-[2-(aminomethyl)-3,3-difluoro-allyl]-4-[[4-(1-isopropylpyrazol-4-yl)-2-thienyl]methyl]-1,2,4-triazol-3-one;

2-[2-(aminomethyl)-3,3-difluoro-allyl]-4-[[4-[3-(1H-1,2,4-triazol-3-yl)phenyl]-2-thienyl]methyl]-1,2,4-triazol-3-one;

2-[2-(aminomethyl)-3,3-difluoro-allyl]-4-[[6-(4-methylsulfonylphenyl)benzothiophen-2-yl]methyl]-1,2,4-triazol-3-one;

2-[2-(aminomethyl)-3,3-difluoro-allyl]-4-[[6-(4-piperazin-1-ylphenyl)benzothiophen-2-yl]methyl]-1,2,4-triazol-3-one;

2-[2-(aminomethyl)-3,3-difluoro-allyl]-4-[[6-[6-(trifluoromethyl)-3-pyridyl]benzothiophen-2-yl]methyl]-1,2,4-triazol-3-one;

2-[2-(aminomethyl)-3,3-difluoro-allyl]-4-[[6-[6-(dimethylamino)-3-pyridyl]benzothiophen-2-yl]methyl]-1,2,4-triazol-3-one;

2-[2-(aminomethyl)-3,3-difluoro-allyl]-4-[[6-(1,3-benzodioxol-5-yl)benzothiophen-2-yl]methyl]-1,2,4-triazol-3-one;

6-[2-[[1-[2-(aminomethyl)-3,3-difluoro-allyl]-5-oxo-1,2,4-triazol-4-yl]methyl]benzothiophen-6-yl]-8-methyl-3,4-dihydro-1H-quinolin-2-one;

6-[2-[[1-[2-(aminomethyl)-3,3-difluoro-allyl]-5-oxo-1,2,4-triazol-4-yl]methyl]benzothiophen-6-yl]-1-methyl-3,4-dihydroquinolin-2-one;

2-[2-(aminomethyl)-3,3-difluoro-allyl]-4-[[6-(1-ethylpyrazol-4-yl)benzothiophen-2-yl]methyl]-1,2,4-triazol-3-one;

2-[2-(aminomethyl)-3,3-difluoro-allyl]-4-[[5-(4-methylsulfonylphenyl)benzothiophen-2-yl]methyl]-1,2,4-triazol-3-one;

2-[2-(aminomethyl)-3,3-difluoro-allyl]-4-[[5-(4-piperazin-1-ylphenyl)benzothiophen-2-yl]methyl]-1,2,4-triazol-3-one;

5-[2-[[1-[2-(aminomethyl)-3,3-difluoro-allyl]-5-oxo-1,2,4-triazol-4-yl]methyl]benzothiophen-5-yl]-1-ethyl-pyridin-2-one;

2-[2-(aminomethyl)-3,3-difluoro-allyl]-4-[[5-[6-(dimethylamino)-3-pyridyl]benzothiophen-2-yl]methyl]-1,2,4-triazol-3-one;

2-[2-(aminomethyl)-3,3-difluoro-allyl]-4-[[5-(1,3-benzodioxol-5-yl)benzothiophen-2-yl]methyl]-1,2,4-triazol-3-one;

6-[2-[[1-[2-(aminomethyl)-3,3-difluoro-allyl]-5-oxo-1,2,4-triazol-4-yl]methyl]benzothiophen-5-yl]-8-methyl-3,4-dihydro-1H-quinolin-2-one;

6-[2-[[1-[2-(aminomethyl)-3,3-difluoro-allyl]-5-oxo-1,2,4-triazol-4-yl]methyl]benzothiophen-5-yl]-1-methyl-3,4-dihydroquinolin-2-one;

2-[2-(aminomethyl)-3,3-difluoro-allyl]-4-[[5-(1-ethylpyrazol-4-yl)benzothiophen-2-yl]methyl]-1,2,4-triazol-3-one;

2-[2-(aminomethyl)-3,3-difluoro-allyl]-4-[6-(6-piperazin-1-yl-3-pyridyl)-2-pyridyl]-1,2,4-triazol-3-one;

2-[2-(aminomethyl)-3,3-difluoro-allyl]-4-[6-[4-(morpholine-4-carbonyl)phenyl]-2-pyridyl]-1,2,4-triazol-3-one;

2-[2-(aminomethyl)-3,3-difluoro-allyl]-4-[6-(6-morpholino-3-pyridyl)-2-pyridyl]-1,2,4-triazol-3-one;

2-[2-(aminomethyl)-3,3-difluoro-allyl]-4-[6-(3-piperazin-1-ylphenyl)-2-pyridyl]-1,2,4-triazol-3-one;

2-[2-(aminomethyl)-3,3-difluoro-allyl]-4-[6-[3-(dimethylamino)-4-fluoro-phenyl]-2-pyridyl]-1,2,4-triazol-3-one;

5-[6-[1-[2-(aminomethyl)-3,3-difluoro-allyl]-5-oxo-1,2,4-triazol-4-yl]-2-pyridyl]-1-ethyl-pyridin-2-one;

7-[6-[1-[2-(aminomethyl)-3,3-difluoro-allyl]-5-oxo-1,2,4-triazol-4-yl]-2-pyridyl]-1,4-dihydro-3,1-benzoxazin-2-one;

2-[2-(aminomethyl)-3,3-difluoro-allyl]-4-[3-methyl-5-(6-piperazin-1-yl-3-pyridyl)-2-pyridyl]-1,2,4-triazol-3-one;

6-[6-[1-[2-(aminomethyl)-3,3-difluoro-allyl]-5-oxo-1,2,4-triazol-4-yl]-5-methyl-3-pyridyl]-4H-1,4-benzoxazin-3-one;

2-[2-(aminomethyl)-3,3-difluoro-allyl]-4-[5-[2-(2-methoxyethylamino)pyrimidin-5-yl]-3-methyl-2-pyridyl]-1,2,4-triazol-3-one;

2-[2-(aminomethyl)-3,3-difluoro-allyl]-4-[3-methyl-5-(4-methyl-2,3-dihydro-1,4-benzoxazin-7-yl)-2-pyridyl]-1,2,4-triazol-3-one;

2-[2-(aminomethyl)-3,3-difluoro-allyl]-4-[3-methyl-5-(3,4,5-trimethoxyphenyl)-2-pyridyl]-1,2,4-triazol-3-one;

2-[2-(aminomethyl)-3,3-difluoro-allyl]-4-[5-(6-methoxy-3-pyridyl)-3-methyl-2-pyridyl]-1,2,4-triazol-3-one;

4-[5-(2-amino-1,3-benzothiazol-5-yl)-3-methyl-2-pyridyl]-2-[2-(aminomethyl)-3,3-difluoro-allyl]-1,2,4-triazol-3-one;

2-[2-(aminomethyl)-3,3-difluoro-allyl]-4-[5-(2,1,3-benzoxadiazol-5-yl)-3-methyl-2-pyridyl]-1,2,4-triazol-3-one;

2-[2-(aminomethyl)-3,3-difluoro-allyl]-4-[3-methyl-5-(1H-pyrrolo[2,3-b]pyridin-5-yl)-2-pyridyl]-1,2,4-triazol-3-one;

2-[2-(aminomethyl)-3,3-difluoro-allyl]-4-[5-(1,3-benzoxazol-5-yl)-3-methyl-2-pyridyl]-1,2,4-triazol-3-one;

2-[2-(aminomethyl)-3,3-difluoro-allyl]-4-[3-methyl-5-[4-(2-oxopyrrolidin-1-yl)phenyl]-2-pyridyl]-1,2,4-triazol-3-one;

4-[5-(5-acetyl-2-thienyl)-3-methyl-2-pyridyl]-2-[2-(aminomethyl)-3,3-difluoro-allyl]-1,2,4-triazol-3-one;

2-[2-(aminomethyl)-3,3-difluoro-allyl]-4-[3-methyl-5-[3-(1H-pyrazol-3-yl)phenyl]-2-pyridyl]-1,2,4-triazol-3-one;

2-[2-(aminomethyl)-3,3-difluoro-allyl]-4-[5-(1H-indazol-6-yl)-3-methyl-2-pyridyl]-1,2,4-triazol-3-one;

2-[2-(aminomethyl)-3,3-difluoro-allyl]-4-[3-methyl-5-(3-methylsulfonylphenyl)-2-pyridyl]-1,2,4-triazol-3-one;

2-[2-(aminomethyl)-3,3-difluoro-allyl]-4-[3-methyl-5-(3-piperazin-1-ylphenyl)-2-pyridyl]-1,2,4-triazol-3-one;

2-[2-(aminomethyl)-3,3-difluoro-allyl]-4-[3-methyl-5-[4-(morpholine-4-carbonyl)phenyl]-2-pyridyl]-1,2,4-triazol-3-one;

2-[2-(aminomethyl)-3,3-difluoro-allyl]-4-[3-methyl-5-(4-morpholinophenyl)-2-pyridyl]-1,2,4-triazol-3-one;

4-[6-[1-[2-(aminomethyl)-3,3-difluoro-allyl]-5-oxo-1,2,4-triazol-4-yl]-5-methyl-3-pyridyl]-N,N-dimethyl-benzenesulfonamide;

2-[2-(aminomethyl)-3,3-difluoro-allyl]-4-[3-methyl-5-[3-(1H-1,2,4-triazol-3-yl)phenyl]-2-pyridyl]-1,2,4-triazol-3-one;

2-[2-(aminomethyl)-3,3-difluoro-allyl]-4-[3-methyl-5-[2-(1-methylpyrazol-4-yl)ethynyl]-2-pyridyl]-1,2,4-triazol-3-one;

2-[2-(aminomethyl)-3,3-difluoro-allyl]-4-[5-[2-[6-(dimethylamino)-3-pyridyl]ethynyl]-3-methyl-2-pyridyl]-1,2,4-triazol-3-one;

2-[2-(aminomethyl)-3,3-difluoro-allyl]-4-[3-methyl-5-[2-(6-morpholino-3-pyridyl)ethynyl]-2-pyridyl]-1,2,4-triazol-3-one;

2-[2-(aminomethyl)-3,3-difluoro-allyl]-4-[5-[2-(3,4-dihydro-2H-1,4-benzoxazin-6-yl)ethynyl]-3-methyl-2-pyridyl]-1,2,4-triazol-3-one;

2-[2-(aminomethyl)-3,3-difluoro-allyl]-4-[5-[2-(2,3-dihydro-1H-pyrido[2,3-b][1,4]oxazin-7-yl)ethynyl]-3-methyl-2-pyridyl]-1,2,4-triazol-3-one;

2-[2-(aminomethyl)-3,3-difluoro-allyl]-4-[5-[2-(3,4-dihydro-2H-pyrido[3,2-b][1,4]oxazin-7-yl)ethynyl]-3-methyl-2-pyridyl]-1,2,4-triazol-3-one;

2-[2-(aminomethyl)-3,3-difluoro-allyl]-4-[5-[2-(2,3-dihydro-1H-pyrido[2,3-b][1,4]oxazin-6-yl)ethynyl]-3-methyl-2-pyridyl]-1,2,4-triazol-3-one;

7-[2-[6-[1-[2-(aminomethyl)-3,3-difluoro-allyl]-5-oxo-1,2,4-triazol-4-yl]-5-methyl-3-pyridyl]ethynyl]-1H-pyrido[2,3-b][1,4]oxazin-2-one;

7-[2-[6-[1-[2-(aminomethyl)-3,3-difluoro-allyl]-5-oxo-1,2,4-triazol-4-yl]-5-methyl-3-pyridyl]ethynyl]-4H-pyrido[3,2-b][1,4]oxazin-3-one;

6-[2-[6-[1-[2-(aminomethyl)-3,3-difluoro-allyl]-5-oxo-1,2,4-triazol-4-yl]-5-methyl-3-pyridyl]ethynyl]-3,4-dihydro-1H-quinolin-2-one;

6-[6-[1-[2-(aminomethyl)-3,3-difluoro-allyl]-5-oxo-1,2,4-triazol-4-yl]-5-methyl-3-pyridyl]-3-methyl-1,4-dihydroquinazolin-2-one;

2-[2-(aminomethyl)-3,3-difluoro-allyl]-4-[5-[1-(difluoromethyl)pyrazol-4-yl]-3-methyl-2-pyridyl]-1,2,4-triazol-3-one;

2-[2-(aminomethyl)-3,3-difluoro-allyl]-4-[5-(1-isopropylpyrazol-4-yl)-3-methyl-2-pyridyl]-1,2,4-triazol-3-one;

2-[2-(aminomethyl)-3,3-difluoro-allyl]-4-[2-methyl-3-(4-methylsulfonylphenyl)phenyl]-1,2,4-triazol-3-one;

2-[2-(aminomethyl)-3,3-difluoro-allyl]-4-[2-methyl-3-(4-piperazin-1-ylphenyl)phenyl]-1,2,4-triazol-3-one;

2-[2-(aminomethyl)-3,3-difluoro-allyl]-4-[2-methyl-3-[6-(trifluoromethyl)-3-pyridyl]phenyl]-1,2,4-triazol-3-one;

2-[2-(aminomethyl)-3,3-difluoro-allyl]-4-[3-[6-(dimethylamino)-3-pyridyl]-2-methyl-phenyl]-1,2,4-triazol-3-one;

2-[2-(aminomethyl)-3,3-difluoro-allyl]-4-[3-(1,3-benzodioxol-5-yl)-2-methyl-phenyl]-1,2,4-triazol-3-one;

6-[3-[1-[2-(aminomethyl)-3,3-difluoro-allyl]-5-oxo-1,2,4-triazol-4-yl]-2-methyl-phenyl]-8-methyl-3,4-dihydro-1H-quinolin-2-one;

6-[3-[1-[2-(aminomethyl)-3,3-difluoro-allyl]-5-oxo-1,2,4-triazol-4-yl]-2-methyl-phenyl]-1-methyl-3,4-dihydroquinolin-2-one;

2-[2-(aminomethyl)-3,3-difluoro-allyl]-4-[3-(1-ethylpyrazol-4-yl)-2-methyl-phenyl]-1,2,4-triazol-3-one;

2-[2-(aminomethyl)-3,3-difluoro-allyl]-4-[3-[1-(difluoromethyl)pyrazol-4-yl]-2-methyl-phenyl]-1,2,4-triazol-3-one;

2-[2-(aminomethyl)-3,3-difluoro-allyl]-4-[3-(1-isopropylpyrazol-4-yl)-2-methyl-phenyl]-1,2,4-triazol-3-one;

2-[2-(aminomethyl)-3,3-difluoro-allyl]-4-[2-methyl-3-[3-(1H-1,2,4-triazol-3-yl)phenyl]phenyl]-1,2,4-triazol-3-one;

2-[2-(aminomethyl)-3,3-difluoro-allyl]-4-[[4-(1-ethylpyrazol-4-yl)phenyl]methyl]-1,2,4-triazol-3-one;

2-[2-(aminomethyl)-3,3-difluoro-allyl]-4-[[4-(4-methylsulfonylphenyl)methyl]-1,2,4-triazol-3-one;

2-[2-(aminomethyl)-3,3-difluoro-allyl]-4-[[4-(4-piperazin-1-ylphenyl)phenyl]methyl]-1,2,4-triazol-3-one;

2-[2-(aminomethyl)-3,3-difluoro-allyl]-4-[[4-[6-(dimethylamino)-3-pyridyl]phenyl]methyl]-1,2,4-triazol-3-one;

2-[2-(aminomethyl)-3,3-difluoro-allyl]-4-[[4-(1,3-benzodioxol-5-yl)phenyl]methyl]-1,2,4-triazol-3-one;

6-[4-[[1-[2-(aminomethyl)-3,3-difluoro-allyl]-5-oxo-1,2,4-triazol-4-yl]methyl]phenyl]-8-methyl-3,4-dihydro-1H-quinolin-2-one;

5-[4-[[1-[2-(aminomethyl)-3,3-difluoro-allyl]-5-oxo-1,2,4-triazol-4-yl]methyl]phenyl]-1-ethyl-pyridin-2-one;

2-[2-(aminomethyl)-3,3-difluoro-allyl]-4-[[3-(1-ethylpyrazol-4-yl)phenyl]methyl]-1,2,4-triazol-3-one;

2-[2-(aminomethyl)-3,3-difluoro-allyl]-4-[[3-(4-methylsulfonylphenyl)phenyl]methyl]-1,2,4-triazol-3-one;

2-[2-(aminomethyl)-3,3-difluoro-allyl]-4-[[3-[6-(dimethylamino)-3-pyridyl]phenyl]methyl]-1,2,4-triazol-3-one;

2-[2-(aminomethyl)-3,3-difluoro-allyl]-4-[[3-(1,3-benzodioxol-5-yl)phenyl]methyl]-1,2,4-triazol-3-one;

6-[3-[[1-[2-(aminomethyl)-3,3-difluoro-allyl]-5-oxo-1,2,4-triazol-4-yl]methyl]phenyl]-8-methyl-3,4-dihydro-1H-quinolin-2-one;

6-[3-[[1-[2-(aminomethyl)-3,3-difluoro-allyl]-5-oxo-1,2,4-triazol-4-yl]methyl]phenyl]-1-methyl-3,4-dihydroquinolin-2-one;

5-[3-[[1-[2-(aminomethyl)-3,3-difluoro-allyl]-5-oxo-1,2,4-triazol-4-yl]methyl]phenyl]-1-ethyl-pyridin-2-one;

2-[2-(aminomethyl)-3,3-difluoro-allyl]-4-[[2-(1-ethylpyrazol-4-yl)phenyl]methyl]-1,2,4-triazol-3-one;

2-[2-(aminomethyl)-3,3-difluoro-allyl]-4-[[2-(4-methylsulfonylphenyl)phenyl]methyl]-1,2,4-triazol-3-one;

2-[2-(aminomethyl)-3,3-difluoro-allyl]-4-[[2-(4-piperazin-1-ylphenyl)phenyl]methyl]-1,2,4-triazol-3-one;

2-[2-(aminomethyl)-3,3-difluoro-allyl]-4-[[2-[6-(dimethylamino)-3-pyridyl]phenyl]methyl]-1,2,4-triazol-3-one;

2-[2-(aminomethyl)-3,3-difluoro-allyl]-4-[[2-(1,3-benzodioxol-5-yl)phenyl]methyl]-1,2,4-triazol-3-one;

6-[2-[[1-[2-(aminomethyl)-3,3-difluoro-allyl]-5-oxo-1,2,4-triazol-4-yl]methyl]phenyl]-8-methyl-3,4-dihydro-1H-quinolin-2-one;

6-[2-[[1-[2-(aminomethyl)-3,3-difluoro-allyl]-5-oxo-1,2,4-triazol-4-yl]methyl]phenyl]-1-methyl-3,4-dihydroquinolin-2-one;

5-[2-[[1-[2-(aminomethyl)-3,3-difluoro-allyl]-5-oxo-1,2,4-triazol-4-yl]methyl]phenyl]-1-ethyl-pyridin-2-one;

2-[2-(aminomethyl)-3,3-difluoro-allyl]-4-[[5-[4-(1-ethylpyrazol-4-yl)phenyl]-2-thienyl]methyl]-1,2,4-triazol-3-one;

2-[2-(aminomethyl)-3,3-difluoro-allyl]-4-[[5-[3-(1-ethylpyrazol-4-yl)phenyl]-2-thienyl]methyl]-1,2,4-triazol-3-one;

2-[2-(aminomethyl)-3,3-difluoro-allyl]-4-[[4-[4-(1-ethylpyrazol-4-yl)phenyl]-2-thienyl]methyl]-1,2,4-triazol-3-one;

2-[2-(aminomethyl)-3,3-difluoro-allyl]-4-[[4-[3-(1-ethylpyrazol-4-yl)phenyl]-2-thienyl]methyl]-1,2,4-triazol-3-one;

2-[2-(aminomethyl)-3,3-difluoro-allyl]-4-[5-[4-(1-ethylpyrazol-4-yl)phenyl]-3-methyl-2-pyridyl]-1,2,4-triazol-3-one;

2-[2-(aminomethyl)-3,3-difluoro-allyl]-4-[5-[3-(1-ethylpyrazol-4-yl)phenyl]-3-methyl-2-pyridyl]-1,2,4-triazol-3-one;

2-[2-(aminomethyl)-3,3-difluoro-allyl]-4-[[5-(1H-pyrazol-4-yl)-2-thienyl]methyl]-1,2,4-triazol-3-one;

2-[2-(aminomethyl)-3,3-difluoro-allyl]-4-[[5-(1-methylsulfonylpyrazol-4-yl)-2-thienyl]methyl]-1,2,4-triazol-3-one;

2-[2-(aminomethyl)-3,3-difluoro-allyl]-4-[[5-(1-cyclopropylsulfonylpyrazol-4-yl)-2-thienyl]methyl]-1,2,4-triazol-3-one;

2-[2-(aminomethyl)-3,3-difluoro-allyl]-4-[[5-[1-(cyclopropylmethyl)pyrazol-4-yl]-2-thienyl]methyl]-1,2,4-triazol-3-one;

2-[2-(aminomethyl)-3,3-difluoro-allyl]-4-[[5-(1-methylpyrazol-4-yl)-2-thienyl]methyl]-1,2,4-triazol-3-one;

2-[2-(aminomethyl)-3,3-difluoro-allyl]-4-[[5-(1-benzylpyrazol-4-yl)-2-thienyl]methyl]-1,2,4-triazol-3-one;

2-[2-(aminomethyl)-3,3-difluoro-allyl]-4-[[3-fluoro-5-(4-piperazin-1-ylphenyl)-2-thienyl]methyl]-1,2,4-triazol-3-one;

5-[5-[[1-[2-(aminomethyl)-3,3-difluoro-allyl]-5-oxo-1,2,4-triazol-4-yl]methyl]-4-fluoro-2-thienyl]-1-ethyl-pyridin-2-one;

2-[2-(aminomethyl)-3,3-difluoro-allyl]-4-[[5-(1,3-benzodioxol-5-yl)-3-fluoro-2-thienyl]methyl]-1,2,4-triazol-3-one;

6-[5-[[1-[2-(aminomethyl)-3,3-difluoro-allyl]-5-oxo-1,2,4-triazol-4-yl]methyl]-4-fluoro-2-thienyl]-1-methyl-3,4-dihydroquinolin-2-one;

2-[2-(aminomethyl)-3,3-difluoro-allyl]-4-[[5-(1-ethylpyrazol-4-yl)-3-fluoro-2-thienyl]methyl]-1,2,4-triazol-3-one;

2-(2-(aminomethyl)-3,3-difluoroallyl)-4-((5-(6-(dimethylamino)pyridin-3-yl)-3-fluorothiophen-2-yl)methyl)-2,4-dihydro-3H-1,2,4-triazol-3-one; and 6-(5-((1-(2-(aminomethyl)-3,3-difluoroallyl)-5-oxo-1,5-dihydro-4H-1,2,4-triazol-4-yl)methyl)-4-fluorothiophen-2-yl)-8-methyl-3,4-dihydroquinolin-2(1H)-one.

As for the compound of Formula 1, or its stereoisomer, or its pharmaceutically acceptable salt, the more preferred compound may be a compound selected from the group consisting of the following compounds or a pharmaceutically acceptable salt thereof:

2-[2-(aminomethyl)-3,3-difluoro-allyl]-4-(4-fluorophenyl)-1,2,4-triazol-3-one; and 2-[2-(aminomethyl)-3,3-difluoro-allyl]-4-(4-bromo-2-fluoro-phenyl)-1,2,4-triazol-3-one.

The compound of Formula 1 of the present technology can be in the form of a pharmaceutically acceptable salt. The term "pharmaceutically acceptable salt," as used herein, represents salts or zwitterionic forms of the compounds of the present technology which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by, for example, reacting the appropriate compound in the form of the free base with a suitable acid. Such salts include conventional acid addition salts, e.g., a salt derived from inorganic acid such as hydrochloric acid, bromic acid, sulfuric acid, sulfamic acid, phosphoric acid, or nitric acid and a salt derived from organic acid such as acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, p-toluenesulfonic acid, oxalic acid or trifluoroacetic acid. Further, said salts include conventional metal salt types, e.g., a salt derived from a metal such as lithium, sodium, potassium, magnesium, or calcium. Said acid addition salt or metal salt can be prepared according to conventional methods.

The compound of Formulas X, Y, or 1, or the stereoisomer thereof, or a salt thereof according to the present technology may be prepared by various methods. For example, the compound of Formula 1, or a stereoisomer thereof, or a salt thereof according to the present technology can be prepared by a preparation process comprising the step of reacting a compound of Formula 2 with a compound of Formula 3a or a compound of Formula 3b to obtain a compound of Formula 1a; and the step of deprotecting said compound of Formula 1a.

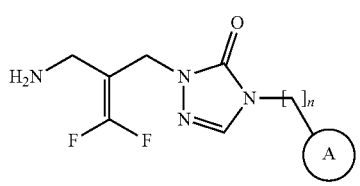

(Formula 1)

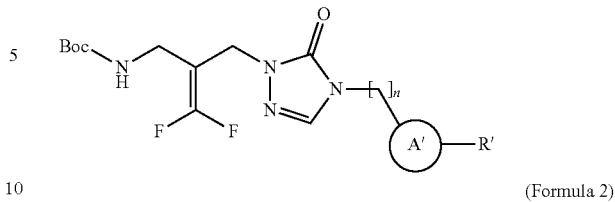

(Formula 1a)

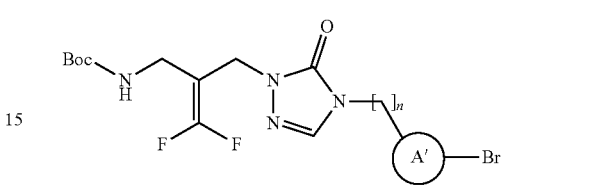

(Formula 2)

Z—R'  (Formula 3a)

HC≡CR  (Formula 3b)

In said Formulae 1, 1a, 2, 3a and 3b, Boc is an amine protecting group (e.g., tert-butoxycarbonyl, 9-fluorenylmethyloxycarbonyl (FMOC), benzyloxycarbonyl (CBZ), triphenylmethyl (trityl), etc.), A' is an aryl or heteroaryl group selected from the group consisting of phenyl, pyridine, pyrazine, and thiophene; Z is a boronic acid $(B(OH)_2)$ or boronic acid pinacol ester, R' is one or two groups chosen from $C_{1-3}$ alkyl, halogen, benzyloxy, —R, —CH=CH—R, or —C≡C—R, and A and R are the same as defined above.

The reaction of the compound of Formula 2 above with a commercially available compound of Formula 3a may be carried out via Suzuki reaction. Said reaction can be carried out by using a palladium catalyst. The palladium catalyst includes palladium diacetate $(Pd(OAc)_2)$, tris(dibenzylideneacetone)dipalladium $(Pd_2(dba)_3)$, tetrakis(triphenylphosphine)palladium $(Pd(PPh_3)_4)$ or palladiumdi[1,1'-bis(diphenylphosphino)ferrocene]dichloride $(PdCl_2(dppf)_2)$, etc. In the reaction carried out under a palladium catalyst, a ligand and a base can be added in addition to the palladium catalyst. Said ligand includes (S)-2,2-bis(diphenylphospino)-1,1-binaphthyl(BINAP), 1,1'-bis(diphenylphospino)ferrocene (dppf), (tri-O-tolyl)phosphine $(P(O-Tol)_3)$, or the like and said base includes an inorganic base such as cesium carbonate $(Cs_2CO_3)$, sodium carbonate $(Na_2CO_3)$, potassium carbonate $(K_2CO_3)$, potassium fluoride (KF), cesium fluoride (CsF), sodium hydroxide (NaOH), potassium phosphonate $(K_3PO_4)$, sodium tert-butoxide (teRT-BuONa), potassium tert-butoxide (tert-BuOK), or the like. The reaction may be carried out in a non-polar organic solvent such as benzene or toluene, or a polar solvent such as dioxane, tetrahydrofuran, acetonitrile, 1,2-dimethoxyethane, N,N-dimethylformamide, or the like, at a temperature ranging from 50° C. to 150° C., preferably from 80° C. to 110° C. Other reaction conditions, including e.g., reaction time, may be determined from the reaction conditions for conventional Suzuki reaction (Barbara Czako and Laszlo Kurti, *STRATEGIC APPLICATIONS of NAMED REACTIONS in ORGANIC SYNTHESIS*, 2005). Further, the reaction of the compound of Formula 2 with a commercially available compound of Formula 3b (i.e., an ethyne derivative) can be carried out via Sonogashira coupling reaction using a palladium reagent such as bis(triphenylphosphine)palladium(II) dichloride, tetrakis(triphenylphosphine)palladium(0), etc., and a copper iodide. The coupling reaction may be carried out at room temperature or a heated temperature, e.g., a temperature ranging from 20° C. to 60° C. In addition, in order to improve reaction rate and reaction yield, said coupling reaction can be carried out in the presence of a base such as a diisopropylamine, a triethylamine, etc., and a ligand such as triphenylphosphine or the like.

Deprotection of the compound of Formula 1a can be carried out according to conventional methods (e.g., Theodora W. Greene and Peter G. M. Wuts, *Protective groups in organic synthesis,* 3rd Ed., 1999). For example, said amine protecting group in an organic solvent such as dichloromethane, dioxane, ethyl acetate, etc., can be removed by using an acid such as trifluoroacetate or hydrochloric acid gas at room temperature.

The compound of Formula 2 can be prepared according to the following Reaction Scheme 1.

The compound of Formula 5 can be converted to a compound of Formula 6 via hydrazinolysis reaction. The hydrazinolysis reaction can be carried out according to known methods (e.g., WO 2005/014583, etc.).

The compound of Formula 6 can be converted to a compound of Formula 10 via cyclization reaction. The cyclization reaction can be carried out at room temperature to 80° C. by using a formamidineacetate and an acetic acid in N,N-dimethylformamide or 1-propanol (Chunquan Sheng; Xiaoying Che; Wenya Wang; Shengzheng Wang; Yongbing Cao; Zhenyuan Miao; Jianzhong Yao; Wannian Zhang, *European Journal of Medicinal Chemistry,* 46, 5276-5282, 2011).

In another method, the compound of Formula 4 can be converted to a compound of Formula 10 via cyclization reaction with a compound of Formula 7. Said cyclization Reaction Scheme 1.

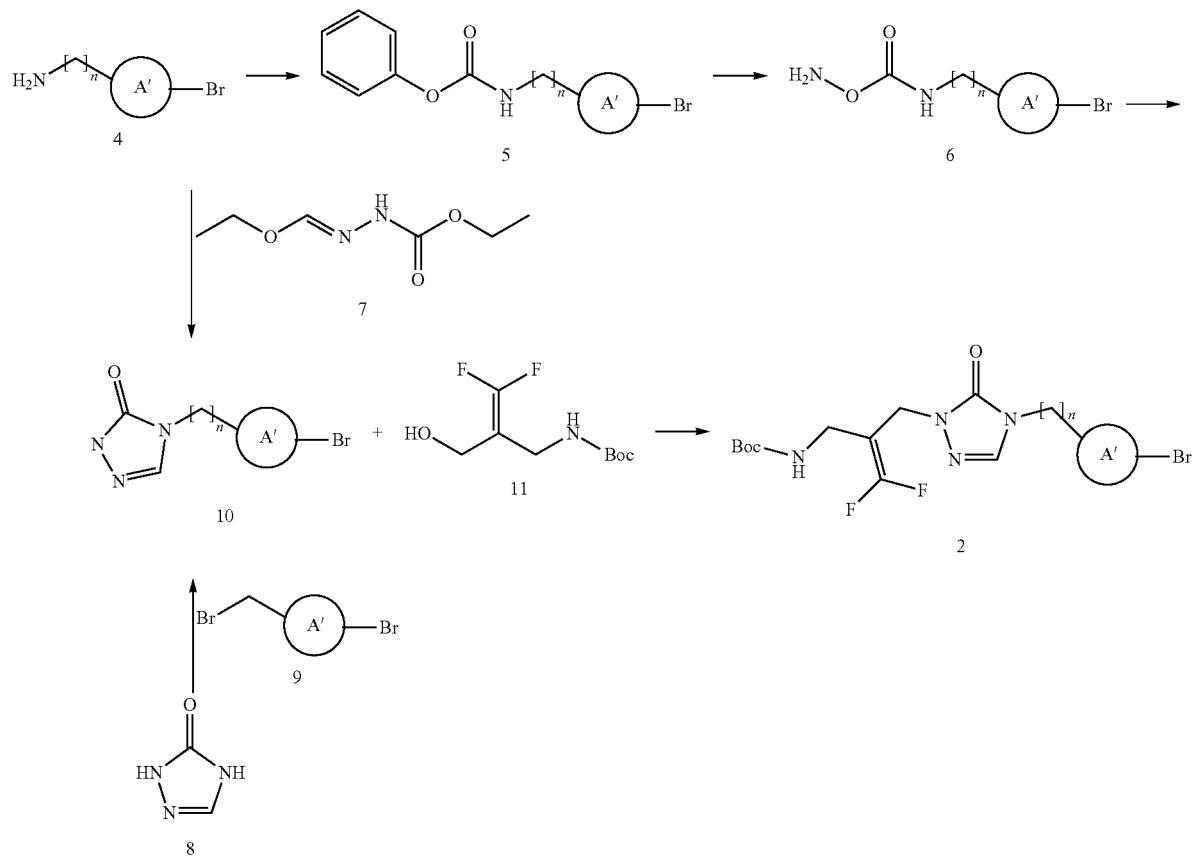

In Reaction Scheme 1, A', n, and Boc are the same as defined in the above.

A compound of Formula 4 is commercially available. The compound of Formula 4 can be converted to a compound of Formula 5 via nucleophilic acylsubstitution reaction. Said nucleophilic acylsubstitution reaction can be carried out at 0° C. to room temperature by using pyridine, triethylamine, or the like in a solvent such as ethyl acetate, tetrahydrofuran, etc. (Chunquan Sheng; Xiaoying Che; Wenya Wang; Shengzheng Wang; Yongbing Cao; Zhenyuan Miao; Jianzhong Yao; Wannian Zhang, *European Journal of Medicinal Chemistry,* 46, 5276-5282, 2011).

reaction can be performed in a solvent such as methanol, N,N-dimethylformamide, or the like, by using sodium methoxide or potassium hydroxide at a temperature between 50° C. to 150° C. The compound of Formula 7 above can be prepared by formylation reaction of a commercially available ethyl carbazate. Said formylation reaction may preferably be orthoester reaction, which can be carried out, for example, by using triethyl orthoformate or trimethyl orthoformate. Said formylation reaction can be performed in a solvent such as methanol, N,N-dimethylformamide, or the like at a temperature between 80° C.-150° C.

In another method, the compound of Formula 8 also can be converted to a compound of Formula 10 via C—N alkylation reaction with a compound of Formula 9. The compound of Formula 8 and Formula 9 are both commercially available. Said alkylation reaction can be performed in organic solvent such as N,N-dimethylformamide or the like, by using sodium hydride or potassium carbonate at a temperature between 20° C. to 60° C.

The reaction of the compound of Formula 10 above with a compound of Formula 11 can be carried out via Mitsunobu reaction. For example, said reaction can be carried out in the presence of triphenylphosphine or trin-butylphosphine using diethyl azodicarboxylate (DEAD) or diisopropyl azodicarboxylate (DIAD). The reaction solvent may be a polar organic solvent such as dichloromethane, dioxane, tetrahydrofuran, dimethylformamide, etc. The reaction may be carried out at 0° C. to room temperature, and can be carried out at a higher temperature on occasion. Other reaction conditions including reaction time may be determined from the reaction conditions for conventional Mitsunobu reaction (Barbara Czako and Laszlo Kurti, *STRATEGIC APPLICATIONS of NAMED REACTIONS in ORGANIC SYNTHESIS*, 2005).

The compound of Formula 11 can be prepared according to the following Reaction Scheme 2.

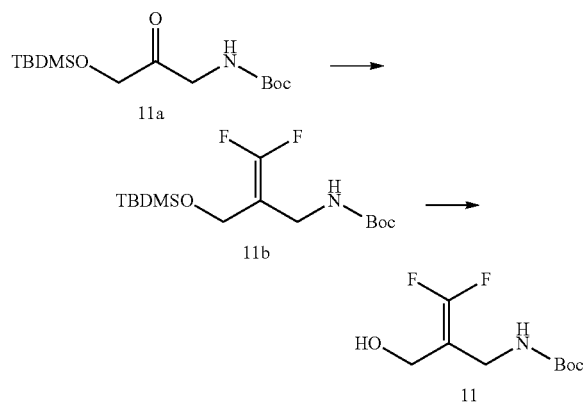

Reaction Scheme 2.

In Reaction Scheme 2, TBDMS is tert-butyldimethylsilyl, which is a hydroxyl protecting group and Boc is the same as defined in the above.

A compound of Formula 11a is commercially available and can be prepared according to known methods (e.g., WO 2013/163675, etc.). The compound of Formula 11a can be converted to a compound of Formula 11b via gem-difluoroolefination reaction. The gem-difluoroolefination reaction can be carried out in the presence of a base such as potassium tert-butoxide (tert-BuOK), lithium bis(trimethylsilyl)amide (LiHMDS), or the like using a fluorinated sulfone such as difluoromethyl 2-pyridyl sulfone. The reaction solvent may be an organic solvent such as dimethylformamide, tetrahydrofuran, or the like and the reaction can be carried out at a temperature between −40° C.-0° C. (Yanchuan Zhao; Weizhou Huang; Lingui Zhu; Jinbo Hu, *Organic Letters*, 12, 1444-1447, 2010), etc.

The compound of Formula 11b can be converted to a compound of Formula 11 via deprotection reaction of a hydroxyl protecting group (TBDMS). The deprotection reaction of a hydroxyl protecting group can be carried out according to known methods (Theodora W. Greene and Peter G. M. Wuts, *Protective groups in organic synthesis*, 3rd Ed., 1999). For example, the deprotection group of a hydroxyl protecting group (TBDMS) can be carried out in a solvent such as dichloromethane, tetrahydrofuran, or the like, using an organic salt such as tetrabutylamoniumfluoride (TBAF), etc., at room temperature.

The 3,3-difhioroallylamines according to the present technology, i.e., a compound of Formulas X, Y, 1, 12, 13, 14, 15, 16, 17, 18, 19, or 20, or a stereoisomer thereof, or a pharmaceutically acceptable salt thereof, have an inhibitory activity on VAP-1, and thus can be usefully applied in the prevention or treatment of a disease mediated by VAP-1. Preferably, the compound of Formulas X, Y, 1, 12, 13, 14, 15, 16, 17, 18, 19, or 20, according to the present technology, or a stereoisomer thereof, or a pharmaceutically acceptable salt thereof can be usefully applied for the prevention of treatment of nonalcoholic steatohepatitis (NASH).

In some embodiments, provided herein is the use of the 3,3-difluoroallylamines according to the present technology, i.e., the compound of Formulas X, Y, 1, 12, 13, 14, 15, 16, 17, 18, 19, or 20, or a stereoisomer thereof, or a pharmaceutically acceptable salt thereof, in the preparation of a medicament for the prophylaxis and/or treatment of lipid and lipoprotein disorders (such as, but not limited to, hypercholesterolemia, hypertriglyceridemia, and atherosclerosis), of conditions and diseases which result from chronic fatty and fibrotic degeneration of organs due to accumulated lipid and specifically triglyceride accumulation and subsequent activation of profibrotic pathways (such as, but not limited to, NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system), of Type I or Type II Diabetes and clinical complications of Type I and Type II Diabetes (such as, but not limited to, Diabetic Nephropathy, Diabetic Retinopathy, Diabetic Neuropathies, or Peripheral Arterial Occlusive Disease (PAOD)), of chronic intrahepatic or some forms of extrahepatic cholestatic conditions, of liver fibrosis, of acute intraheptic cholestatic conditions, of obstructive or chronic inflammatory disorders that arise out of improper bile composition (such as, but not limited to, cholelithiasis also known as cholesterol gallstones), of gastrointestinal conditions with a reduced uptake of dietary fat and fat-soluble dietary vitamins, of inflammatory bowel diseases, of obesity and metabolic syndrome (combined conditions of dyslipidemia, diabetes and abnormally high body-mass index), of persistent infections by intracellular bacteria or parasitic protozoae, of non-malignant hyperproliferative disorders, of malignant hyperproliferative disorders (such as, but not limited to, different forms of cancer, specifically certain forms of breast, liver or colon cancer, or a disorder selected from the group consisting of hepatocellular carcinoma, colon adenoma, and polyposis), of colon adenocarcinoma and hepatocellular carcinoma in particular, of liver steatosis and associated syndromes, of Hepatitis B infection, of Hepatitis C infection and/or of cholestatic and fibrotic effects that are associated with alcohol-induced cirrhosis or with viral-home forms of hepatitis, of liver failure or liver malfunction as an outcome of chronic liver diseases or of surgical liver resection, of acute myocardial infarction, of acute stroke, of thrombosis which occurs as an endpoint of chronic obstructive atherosclerosis, of osteoarthritis, of rheumatoid arthritis, of psoriasis, or of cerebral infarction, individually or of any combination thereof.

In some embodiments, the compounds and/or pharmaceutical compositions disclosed herein are used for prophylaxis and/or treatment of chronic intrahepatic conditions, such as Primary Biliary Cirrhosis (PBC), Primary Sclerosing Cholangitis (PSC), progressive familiar cholestasis (PFIC), alcohol-induced cirrhosis and associated cholestasis, and some forms of extrahepatic cholestatic conditions, or liver fibrosis.

In some embodiments, provided herein is a method to treat chronic intrahepatic conditions and/or some forms of extrahepatic cholestatic conditions in a patient in need thereof, the method comprising, consisting essentially of, or consisting of administering to the patient a therapeutically effective amount of a compound or a composition disclosed herein. In some embodiments, the chronic intrahepatic conditions are selected from PBC, PSC, PFIC, and alcohol-induced cirrhosis and associated cholestasis.

In some embodiments, provided herein is a method to treat liver fibrosis in a patient in need thereof, the method comprising, consisting essentially of, or consisting of administering to the patient a therapeutically effective amount of a compound or a composition disclosed herein.

In some embodiments, provided herein is a method to treat a lipid and lipoprotein disorder in a patient in need thereof, the method comprising, consisting essentially of, or consisting of administering to the patient a therapeutically effective amount of a compound or a composition disclosed herein. In some embodiments, the lipid and lipoprotein disorder is selected from hypercholesterolemia, hypertriglyceridemia, and atherosclerosis.

In some embodiments, provided herein is a method to treat a condition or disease which results from chronic fatty and fibrotic degeneration of organs due to accumulated lipid and specifically triglyceride accumulation and subsequent activation of profibrotic pathways in a patient in need thereof, the method comprising, consisting essentially of, or consisting of administering to the patient a therapeutically effective amount of a compound or a composition disclosed herein. In some embodiments, the condition or disease which results from chronic fatty and fibrotic degeneration of organs due to accumulated lipid and specifically triglyceride accumulation and subsequent activation of profibrotic pathways is selected from NASH and chronic cholestatic conditions in the liver, Glomerulosclerosis and Diabetic Nephropathy in the kidney, Macular Degeneration and Diabetic Retinopathy in the eye, and neurodegenerative diseases. In some further embodiments, neurodegenerative diseases are selected from Alzheimer's Disease in the brain, and Diabetic Neuropathies in the peripheral nervous system.

In some embodiments, provided herein is a method to treat Type I or Type II Diabetes and clinical complications of Type I and Type II Diabetes in a patient in need thereof, the method comprising, consisting essentially of, or consisting of administering to the patient a therapeutically effective amount of a compound or a composition disclosed herein. In some embodiments, provided herein is a method to treat Type I Diabetes in a patient in need thereof, the method comprising, consisting essentially of, or consisting of administering to the patient a therapeutically effective amount of a compound or a composition disclosed herein. In some embodiments, provided herein is a method to treat Type II Diabetes in a patient in need thereof, the method comprising, consisting essentially of, or consisting of administering to the patient a therapeutically effective amount of a compound or a composition disclosed herein. In some embodiments, provided herein is a method to treat one or more clinical complications of Type I and Type II Diabetes in a patient in need thereof, the method comprising, consisting essentially of, or consisting of administering to the patient a therapeutically effective amount of a compound or a composition disclosed herein. In some embodiments, the clinical complications of Type I and Type II Diabetes are selected from Diabetic Nephropathy, Diabetic Retinopathy, Diabetic Neuropathies, and Peripheral Arterial Occlusive Disease (PAOD), or any combination thereof.

In some embodiments, provided herein is a method to treat acute intraheptic cholestatic conditions in a patient in need thereof, the method comprising, consisting essentially of, or consisting of administering to the patient a therapeutically effective amount of a compound or a composition disclosed herein.

In some embodiments, provided herein is a method to treat obstructive or chronic inflammatory disorders that arise out of improper bile composition in a patient in need thereof, the method comprising, consisting essentially of, or consisting of administering to the patient a therapeutically effective amount of a compound or a composition disclosed herein. In some embodiments, the obstructive or chronic inflammatory disorders that arise out of improper bile composition is cholelithiasis also known as cholesterol gallstones.

In some embodiments, provided herein is a method to treat gastrointestinal conditions with a reduced uptake of dietary fat and fat-soluble dietary vitamins in a patient in need thereof, the method comprising, consisting essentially of, or consisting of administering to the patient a therapeutically effective amount of a compound or a composition disclosed herein.

In some embodiments, provided herein is a method to treat inflammatory bowel diseases in a patient in need thereof, the method comprising, consisting essentially of, or consisting of administering to the patient a therapeutically effective amount of a compound or a composition disclosed herein.

In some embodiments, provided herein is a method to treat obesity and metabolic syndrome in a patient in need thereof, the method comprising, consisting essentially of, or consisting of administering to the patient a therapeutically effective amount of a compound or a composition disclosed herein.

In some embodiments, provided herein is a method to treat persistent infections by intracellular bacteria or parasitic protozoae in a patient in need thereof, the method comprising, consisting essentially of, or consisting of administering to the patient a therapeutically effective amount of a compound or a composition disclosed herein.

In some embodiments, provided herein is a method to treat non-malignant hyperproliferative disorders in a patient in need thereof, the method comprising, consisting essentially of, or consisting of administering to the patient a therapeutically effective amount of a compound or a composition disclosed herein.

In some embodiments, provided herein is a method to treat malignant hyperproliferative disorders in a patient in need thereof, the method comprising, consisting essentially of, or consisting of administering to the patient a therapeutically effective amount of a compound or a composition disclosed herein. In some embodiments, malignant hyperproliferative disorders are selected from different forms of cancer, specifically certain forms of breast, liver or colon cancer, or a disorder selected from the group consisting of hepatocellular carcinoma, colon adenoma, and polyposis.

In some embodiments, provided herein is a method to treat colon adenocarcinoma in a patient in need thereof, the method comprising, consisting essentially of, or consisting of administering to the patient a therapeutically effective amount of a compound or a composition disclosed herein.

In some embodiments, provided herein is a method to treat hepatocellular carcinoma in a patient in need thereof, the method comprising, consisting essentially of, or consisting of administering to the patient a therapeutically effective amount of a compound or a composition disclosed herein.

In some embodiments, provided herein is a method to treat liver steatosis and associated syndromes in a patient in need thereof, the method comprising, consisting essentially of, or consisting of administering to the patient a therapeutically effective amount of a compound or a composition disclosed herein.

In some embodiments, provided herein is a method to treat Hepatitis B infection in a patient in need thereof, the method comprising, consisting essentially of, or consisting of administering to the patient a therapeutically effective amount of a compound or a composition disclosed herein.

In some embodiments, provided herein is a method to treat Hepatitis C infection in a patient in need thereof, the method comprising, consisting essentially of, or consisting of administering to the patient a therapeutically effective amount of a compound or a composition disclosed herein.

In some embodiments, provided herein is a method to treat cholestatic and fibrotic effects that are associated with alcohol-induced cirrhosis or with viral-home forms of hepatitis in a patient in need thereof, the method comprising, consisting essentially of, or consisting of administering to the patient a therapeutically effective amount of a compound or a composition disclosed herein.

In some embodiments, provided herein is a method to treat liver failure or liver malfunction as an outcome of chronic liver diseases or of surgical liver resection in a patient in need thereof, the method comprising, consisting essentially of, or consisting of administering to the patient a therapeutically effective amount of a compound or a composition disclosed herein.

In some embodiments, provided herein is a method to treat acute myocardial infarction in a patient in need thereof, the method comprising, consisting essentially of, or consisting of administering to the patient a therapeutically effective amount of a compound or a composition disclosed herein.

In some embodiments, provided herein is a method to treat acute stroke in a patient in need thereof, the method comprising, consisting essentially of, or consisting of administering to the patient a therapeutically effective amount of a compound or a composition disclosed herein.

In some embodiments, provided herein is a method to treat thrombosis which occurs as an endpoint of chronic obstructive atherosclerosis in a patient in need thereof, the method comprising, consisting essentially of, or consisting of administering to the patient a therapeutically effective amount of a compound or a composition disclosed herein.

In some embodiments, provided herein is a method to treat osteoarthritis in a patient in need thereof, the method comprising, consisting essentially of, or consisting of administering to the patient a therapeutically effective amount of a compound or a composition disclosed herein.

In some embodiments, provided herein is a method to treat rheumatoid arthritis in a patient in need thereof, the method comprising, consisting essentially of, or consisting of administering to the patient a therapeutically effective amount of a compound or a composition disclosed herein.

In some embodiments, provided herein is a method to treat psoriasis in a patient in need thereof, the method comprising, consisting essentially of, or consisting of administering to the patient a therapeutically effective amount of a compound or a composition disclosed herein.

In some embodiments, provided herein is a method to treat cerebral infarction in a patient in need thereof, the method comprising, consisting essentially of, or consisting of administering to the patient a therapeutically effective amount of a compound or a composition disclosed herein.

Thus, the present technology includes a pharmaceutical composition for inhibiting vascular adhesion protein-1 (VAP-1), comprising a therapeutically effective amount of a compound of Formula 1, or a stereoisomer thereof, or a pharmaceutically acceptable salt thereof as an active ingredient. In one embodiment, the present technology provides a pharmaceutical composition for preventing or treating nonalcoholic steatohepatitis (NASH), comprising a therapeutically effective amount of a compound of Formula 1, or a stereoisomer thereof, or a pharmaceutically acceptable salt thereof as an active ingredient. In some embodiments, provided herein is a pharmaceutical composition for preventing or treating NASH comprising, consisting essentially of, or consisting of a therapeutically effective amount of a compound of Formula 1, or a stereoisomer thereof, or a pharmaceutically acceptable salt thereof, and at least one pharmaceutically acceptable carrier or excipient.

In another aspect, the present technology provides a pharmaceutical composition for preventing or treating diabetic nephropathy comprising, consisting essentially of, or consisting of a therapeutically effective amount of a compound of Formula 1, or a stereoisomer thereof, or a pharmaceutically acceptable salt thereof, and at least one pharmaceutically acceptable carrier or excipient.

In another aspect, the present technology provides a pharmaceutical composition for preventing or treating primary sclerosing cholangitis comprising, consisting essentially of, or consisting of a therapeutically effective amount of a compound of Formula 1, or a stereoisomer thereof, or a pharmaceutically acceptable salt thereof, and at least one pharmaceutically acceptable carrier or excipient.

In some embodiments, the compounds of the present disclosure may be combined with one or more additional therapies for the prevention or treatment of a disease or condition amenable to treatment by inhibition of VAP-1.

In some embodiments, the compositions disclosed herein contain at least one additional active agent.

Exemplary additional active agents include, but are not limited, one or more of a(n) ACE inhibitor, Acetyl CoA carboxylase inhibitor, Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Apoptosis Signaling Kinase 1 inhibitor, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, intereukin-1 receptor-associated kinase 4 (IRAK4) inhibitor, Jak2 tyrosine kinase inhibitor, ketohexokinase inhibitors, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21 (miR-21) inhibitor, Mitochondrial uncoupler, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator, Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signalling-1 stimulator, Suppressor of cytokine signalling-3 stimulator, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, and YAP/TAZ modulator. Examples of JAK inhibitors include, but are not limited to, filgotonib and tofacitinib. A non-limiting example of an apoptosis signal kinase inhibitor is selonsertib.

The compound of Formula 1, or the stereoisomer thereof, or the pharmaceutically acceptable salt thereof, and at least one additional active agent may be administered in any order or even simultaneously. The multiple active agents may be provided in a single, unified form, or in multiple forms (by way of example only, either as a single pill or as two separate pills). One of the active agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

The pharmaceutical composition of the present technology may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition of the present technology may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition.

Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

The composition of the present technology can be administered orally or parenterally, including inhalation, intravenous, intraperitoneal, subcutaneous, rectal and topical routes of administration. Therefore, the composition of the present technology can be formulated into various forms such as tablets, capsules, aqueous solutions, suspensions, or the like. In the case of tablets for oral administration, carriers such as lactose, corn starch, and lubricating agents, e.g., magnesium stearate, can be conventionally added thereto. In the case of capsules for oral administration, lactose and/or dried corn starch can be used as a diluent. When an aqueous suspension is required for oral administration, the active ingredient can be combined with emulsifying and/or suspending agents. If desired, certain sweetening agents and/or flavoring agents can be added thereto. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present technology may be in the form of an aqueous solution containing pharmaceutically acceptable carriers, e.g., saline having a pH level of 7.4. The solutions may be introduced into a patient's intramuscular blood-stream by local bolus injection.

Said 3,3-difluoroallylamines, i.e., a compound of Formula 1, or a stereoisomer thereof, or its pharmaceutically acceptable salt can be administered to a patient in an effective amount ranging from about 0.001 mg/kg to about 100 mg/kg per day. This includes 0.001, 0.0025, 0.005, 0.0075, 0.01, 0.025, 0.05, 0.075, 0.1, 0.25, 0.5, 0.75, 1, 2, 3, 4, 5, 6, 7, 8, 9, 10, 15, 20, 25, 30, 35, 40, 45, 50, 55, 60, 65, 70, 75, 80, 85, 90, 95, or 100 mg/kg.

Generally, a therapeutically effective amount of the compound of Formula 1, or a stereoisomer thereof, or a pharmaceutically acceptable salt thereof, will range from a total daily dosage of about 0.1 mg/day to 1000 mg/day, about 30-720 mg/day, about 60-600 mg/day, or about 100-480 mg/day, or more. In some embodiments, a therapeutically effective amount of the compound of Formula 1, or a stereoisomer thereof, or a pharmaceutically acceptable salt thereof, will range from about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, multiple dosages include two, three, or four doses per day.

In some embodiments, the therapeutically effective amount of the compound of Formula 1, or a stereoisomer thereof, or a pharmaceutically acceptable salt thereof, is at least 0.1 mg/day, at least 0.5 mg/day, at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, at least 725 mg/day, at least 750 mg/day, at least 775 mg/day, at least 800 mg/day, at least 825 mg/day, at least 850 mg/day, at least 875 mg/day, at least 900 mg/day, at least 925 mg/day, at least 950 mg/day, at least 975 mg/day, or at least 1000 mg/day.

Of course, the dosage may be changed according to the patient's age, weight, susceptibility, symptom, or the efficacy of the compound.

In some embodiments, the present technology provides a method of inhibiting vascular adhesion protein (VAP)-1 in a mammal, comprising administering to the mammal a therapeutically effective amount of a compound of Formula 1, or a stereoisomer thereof, or a pharmaceutically acceptable salt thereof. In one embodiment, the present technology provides a method for treating nonalcoholic hepatosteatosis (NASH), comprising administering to a mammal a therapeutically effective amount of a compound of Formula 1, or a stereoisomer thereof, or a pharmaceutically acceptable salt thereof. In some embodiments, provided herein is a method for treating NASH in a subject in need thereof, the method comprising, consisting essentially of, or consisting of administering to the subject a therapeutically effective amount of a compound of Formula 1, or a stereoisomer thereof, or a pharmaceutically acceptable salt thereof. Mammals include, but are not limited to, mice, rodents, rats, simians, humans, farm animals, dogs, cats, sport animals, and pets.

In some embodiments, the present technology provides a use of the compound of Formula 1 above, or a stereoisomer thereof, or a pharmaceutically acceptable salt thereof for use in the preparation of a medicament for inhibiting a vascular adhesion protein-1 (VAP-1) in mammals.

In one embodiment, the present technology provides a use of the compound of Formula 1 above, or a stereoisomer thereof, or a pharmaceutically acceptable salt thereof for use in the preparation of a medicament for treating or preventing nonalcoholic hepatosteatosis (NASH).

Hereinafter, the present technology is further elaborated through examples and experimental examples. However, the following examples and experimental examples are provided for illustration purposes only, and are not intended to limit the scope of the invention.

As will be apparent to those of skill in the art upon reading this disclosure, each of the individual embodiments described and illustrated herein has discrete components and features which may be readily separated from or combined with the features of any of the other several embodiments without departing from the scope or spirit of the present technology. Any recited method can be carried out in the order of events recited or in any other order which is logically possible.

EXAMPLES

The analyses of the compounds prepared in the following examples were carried out as follows: Nuclear magnetic resonance (NMR) spectrum analysis was carried out using Bruker 400 MHz spectrometer and Agilent 600 MHz spectrometer and chemical shifts thereof were analyzed in ppm. Further, the indicated molecular weights were measured by using liquid chromatography/mass selective detector (MSD) of Agilent 1260 Infinity series equipped with an electrostatic spray interface (by using Single Quadrupole, it indicates a value of m/z in ESI+ (ESI-MS (cation), which is represented by the [M+H]+peak). Column chromatography was carried out on silica gel (Merck, 70-230 mesh). (W. C. Still, J. Org. Chem., 43, 2923, 1978). Further, the abbreviations used in the following examples are as follows: 'methyl' is abbreviated to 'Me'; 'ethyl' is abbreviated to 'Et'; 'phenyl' is abbreviated to 'Ph, tert-butyloxycarbonyl is abbreviated to 'Boc'; and tert-butyl dimethylsilyl is abbreviated to TBDMS. Further, the starting materials in each Example are known compounds, which were synthesized according literatures or obtained from Sigma-Aldrich.

Reference Example 1. tert-butyl N-[3,3-difluoro-2-(hydroxymethyl)alkyl]carbamate Step 1: tert-butyl N-[2-[[tert-butyl(dimethyl)silyl]oxymethyl]-3,3-difluoro-allyl]carbamate Under nitrogen condition, 2.4 g of tert-butyl N-[3-[tert-butyl(dimethyl)silyl]oxy-2-oxo-propyl]carbamate and 1.0 g of 2-(difluoromethylsulfonyl)pyridine were dissolved in 34.5 mL of N,N-dimethylformamide and then cooled to −70° C. To the reaction mixture, 10.4 mL of a tetrahydrofuran solution of 1.0 M lithium bis(trimethylsilyl)amide was slowly added dropwise. The resulting solution was stirred at −70° C. for 30 minutes and then stirred again by slowly increasing the temperature to −10° C. 20 mL of an ammonium chloride solution was added to the reaction mixture, followed by the addition of 20 mL of a 3 N hydrogen chloride solution. The reaction mixture was extracted with ethyl acetate three times. The extracted organic layer was washed with brine, dried over anhydrous magnesium sulfate, and concentrated under reduced pressure to give a yellow liquid residue. The residue was purified with silica gel column chromatography (developing solvent: n-hexane/ethyl acetate=20/1) to give 446.0 mg of the title compound as a yellow liquid (yield: 25.5%). $^1$H-NMR (CDCl$_3$, 400 MHz) δ 4.98 (s, 1H), 4.20 (s, 2H), 3.83 (s, 2H), 1.42 (s, 9H), 0.89 (s, 9H), 0.07 (s, 6H)

Step 2: tert-butyl N-[3,3-difluoro-2-(hydroxymethyl)allyl]carbamate 426 mg of tert-butyl N-[2-[[tert-butyl(dimethyl)silyl]oxymethyl]-3,3-difluoro-allyl]carbamate was dissolved in 2.0 mL of tetrahydrofuran, followed by the addition of 1.5 mL of a tetrahydrofuran solution of 1.0 M tetrabutylamoniumfluoride (TBAF), and then the resulting solution was stirred at room temperature for 2 hours. Ethyl acetate and water were added to the reaction mixture to separate an organic layer. Ethyl acetate was added to the aqueous layer of the reaction mixture to separate an organic layer again. The organic layers thus obtained were combined and washed with an ammonium chloride solution and brine, dried over anhydrous magnesium sulfate, and concentrated under reduced pressure to give a yellow residue. The residue was purified with silica gel column chromatography (developing solvent: n-hexane/ethyl acetate=2/1) to give 285 mg of the title compound as a colorless liquid (yield: 100%). $^1$H-NMR (CDCl$_3$, 400 MHz) δ 4.91 (s, 1H), 4.14 (s, 2H), 3.86 (d, 2H), 3.72 (s, 1H), 1.45 (s, 9H)

Reference Example 2.
4-(4-fluorophenyl)-1H-1,2,4-triazol-5-one

Step 1: (E)-ethyl 2-(ethoxymethylene)hydrazinecarboxylate 30.0 g of ethyl carbazate was dissolved in 240.2 mL of triethyl orthoformate and then stirred overnight at 110° C. The reaction mixture was cooled to room temperature and concentrated under reduced pressure to give 30.3 g of the title compound as a white solid (yield: 65.6%). $^1$H-NMR (DMSO-d$_6$, 400 MHz) δ 10.09 (s, 1H), 7.94 (s, 1H), 4.03 (t, 4H), 1.24-1.16 (m, 6H)

Step 2: 4-(4-fluorophenyl)-1H-1,2,4-triazol-5-one 4.3 g of (E)-ethyl 2-(ethoxymethylene)hydrazinecarboxylate prepared in Step 1 was dissolved in 90 mL of methanol, 3.0 g of 4-fluoroaniline was added thereto, and then the resulting solution was stirred at 80° C. for 5 hours. After the reaction mixture was cooled to room temperature, 7.7 mL of a sodium methoxide solution (<25% in methanol>) was added thereto. The resulting solution was refluxed overnight at 80° C. The reaction mixture was cooled to room temperature and concentrated under reduced pressure. Ethyl acetate was added to the resultant residue and then washed with an ammonium chloride solution. The organic layer thereof was dried over anhydrous magnesium sulfate and concentrated under reduced pressure to give 948 mg of the title compound as a light grey solid (yield: 19.6%). MS (ESI) m/z=180.1 (M+H)+

Reference Example 3.
4-(3-bromophenyl)-1H-1,2,4-triazol-5-one

Step 1: phenyl (3-bromophenyl)carbamate 1.0 g of 3-bromoaniline and 0.98 mL of pyridine were dissolved in 10.0 mL of ethyl acetate. To the resulting solution, 0.77 mL of phenylchloroformate at 0° C. was slowly added, and the solution was stirred at room temperature for 3 hours. To the solution, ethyl acetate was added, and the resulting reaction mixture was washed with 1N hydrochloric acid solution and brine, dried over anhydrous magnesium sulfate, and concentrated under reduced pressure to give 1.4 g of the title compound as a yellow solid (yield: 80.80%).

Step 2: N-(3-bromophenyl)hydrazine carboxamide 1.4 g of phenyl (3-bromophenyl)carbamate prepared in Step 1 and 480.0 mg of hydrazine hydrate were dissolved in 4.0 mL of tetrahydrofuran and 4.0 mL of ethanol, and the resulting solution was stirred overnight at room temperature. The resulting reaction mixture was concentrated and then washed with ethyl acetate to give 890.0 mg of the title compound as a white solid (yield: 80.0%).

Step 3: 4-(3-bromophenyl)-1H-1,2,4-triazol-5-one 890.0 mg of N-(3-bromophenyl)hydrazine carboxamide prepared in Step 2 and 1.6 g of formamidine acetate were dissolved in 8.9 mL of 1-propanol, and the resulting solution was stirred at room temperature for 30 minutes, and then 1.3 mL of acetic acid was added and stirred at 80° C. for 8 hours. The reaction mixture was cooled to room temperature, distilled water was added to the cooled reaction mixture, and then the reaction mixture was stirred overnight. The resulting crystals were filtered and dried to give 742.8 mg of the title compound as a white solid (yield: 80.2%). MS (ESI) m/z=241.2 (M+H)+

Reference Example 4.
4-(3,4-difluorophenyl)-1H-1,2,4-triazol-5-one 492.0 mg of the title compound (yield: 32.2%) was prepared in the same fashion as Reference Example 2, except that 1.0 g of 3,4-difluoroaniline was used in Step 2 instead of 4-fluoroaniline. $^1$H-NMR (MeOD, 400 MHz) δ 8.16 (s, 1H), 7.73 (t, 1H), 7.47-7.42 (m, 2H)

Reference Example 5. 4-(4-bromo-3-fluorophenyl)-1H-1,2,4-triazol-5-one 517.3 mg of the title compound (yield: 38.1%) was prepared in the same fashion as Reference Example 3, except that 1.0 g of 4-bromo-3-fluoroaniline was used in Step 1 instead of 3-bromoaniline. MS (ESI) m/z=259.1 (M+H)+

Reference Example 6. 4-(4-bromo-2-fluorophenyl)-1H-1,2,4-triazol-5-one 443.5 mg of the title compound (yield: 32.7%) was prepared in the same fashion as Reference Example 3, except that 1.0 g of 4-bromo-2-fluoroaniline was used in Step 1 instead of 3-bromoaniline. MS (ESI) m/z=259.2 (M+H)+

Reference Example 7. 4-(4-bromo-2-methylphenyl)-1H-1,2,4-triazol-5-one 450 mg of the title compound (yield: 33.0%) was prepared in the same fashion as Reference Example 3, except that 1.0 g of 4-bromo-3-methylaniline was used in Step 1 instead of 3-bromoaniline. MS (ESI) m/z=255.1 (M+H)+

Reference Example 8. 4-(6-bromo-3-pyridyl)-1H-1,2,4-triazol-5-one 500.7 mg of the title compound (yield: 35.9%) was prepared in the same fashion as Reference Example 3, except that 1.0 g of 3-amino-6-bromopyridine was used in Step 1 instead of 3-bromoaniline. MS (ESI) m/z=242.1 (M+H)+

Reference Example 9. 4-(6-bromo-2-pyridyl)-1H-1,2,4-triazol-5-one 6.0 g of the title compound (yield: 86.1%) was prepared in the same fashion as Reference Example 3, except that 5.0 g of 2-amino-6-bromopyridine was used in Step 1 instead of 3-bromoaniline. $^1$H-NMR (CDCl$_3$, 400 MHz) δ 9.79 (s, 1H), 8.44 (s, 1H), 8.33 (d, 1H), 7.71 (t, 1H), 7.43 (d, 1H)

Reference Example 10. 4-(4-bromo-2-pyridyl)-1H-1,2,4-triazol-5-one 902.2 mg of the title compound (yield: 64.8%) was prepared in the same fashion as Reference Example 3, except that 1.0 g of 2-amino-4-bromopyridine was used in Step 1 instead of 3-bromoaniline. MS (ESI) m/z=242.1 (M+H)+

Reference Example 11. 4-(2-bromo-4-pyridyl)-1H-1,2,4-triazol-5-one 2.0 g of the title compound (yield: 28.7%) was prepared in the same fashion as Reference Example 3, except that 5.0 g of 4-amino-2-bromopyridine was used in Step 1 instead of 3-bromoaniline. $^1$H-NMR (DMSO-d$_6$, 600 MHz) δ 8.65 (s, 1H), 8.45 (d, 1H), 8.17 (s, 1H), 8.12 (d, 1H), 7.97 (dd, 1H)

Reference Example 12. 4-(5-bromo-3-methyl-2-pyridyl)-1H-1,2,4-triazol-5-one 1.9 g of the title compound (yield: 69.6%) was prepared in the same fashion as Reference Example 3, except that 2.0 g of 2-amino-5-bromo-3-methylpyridine was used in Step 1 instead of 3-bromoaniline. $^1$H-NMR (DMSO-d$_6$, 400 MHz) δ 8.55 (d, 1H), 8.21 (s, 1H), 8.13 (s, 1H), 2.27 (s, 3H)

Reference Example 13. 4-(6-bromo-4-methyl-3-pyridyl)-1H-1,2,4-triazol-5-one 4.5 g of the title compound (yield: 66.1, %) was prepared in the same fashion as Reference Example 3, except that 5.0 g of 2-bromo-4-methyl-5-aminopyridine was used in Step 1 instead of 3-bromoaniline. MS (ESI) m/z=256.0 (M+H)+

Reference Example 14. 4-(6-bromo-5-methyl-3-pyridyl)-1H-1,2,4-triazol-5-one 362.1 mg of the title compound (yield: 26.5%) was prepared in the same fashion as Reference Example 3, except that 1.0 g of 5-amino-2-bromo-3-picoline was used in Step 1 instead of 3-bromoaniline. MS (ESI) m/z=256.1 (M+H)+

Reference Example 15. 4-(5-bromo-3-fluoro-2-pyridyl)-1H-1,2,4-triazol-5-one 715.0 mg of the title compound (yield: 52.7%) was prepared in the same fashion as Reference Example 3, except that 1.0 g of 2-amino-5-bromo-3-fluoropyridine was used in Step 1 instead of 3-bromoaniline. MS (ESI) m/z=260.2 (M+H)+

Reference Example 16. 4-(6-bromo-3-methyl-2-pyridyl)-1H-1,2,4-triazol-5-one 1.8 g of the title compound (yield: 65.9%) was prepared in the same fashion as Reference Example 3, except that 2.0 g of 2-amino-6-bromo-3-methylpyridine was used in Step 1 instead of 3-bromoaniline. MS (ESI) m/z=256.1 (M+H)+

Reference Example 17. 4-(5-bromopyrazin-2-yl)-1H-1,2,4-triazol-5-one 4.3 g of the title compound (yield: 61.9%) was prepared in the same fashion as Reference Example 3, except that 5.0 g of 2-amino-5-bromopyrazine was used in Step 1 instead of 3-bromoaniline. MS (ESI) m/z=243.2 (M+H)+

Reference Example 18. 4-[(4-benzyloxyphenyl)methyl]-1H-1,2,4-triazol-5-one 570 mg of the title compound (yield: 43.2%) was prepared in the same fashion as Reference Example 3, except that 1.0 g of (4-(benzyloxy)phenyl)methylamine was used in Step 1 instead of 3-bromoaniline. MS (ESI) m/z=282.2 (M+H)+

Reference Example 19. 4-[(5-bromo-2-thienyl)methyl]-1H-1,2,4-triazol-5-one 742.8 mg of the white solid title compound (yield: 80.3%) was prepared in the same fashion as Reference Example 2, except that 1.0 g of (5-bromothiophen-2-yl)methylamine was used in Step 2 instead of 4-fluoroaniline. $^1$H-NMR (MeOD, 400 MHz) δ 7.83 (s, 1H), 7.01 (s, 1H), 6.94 (s, 1H), 5.04 (s, 2H)

Reference Example 20. 4-[(4-bromo-2-thienyl)methyl]-1H-1,2,4-triazol-5-one 3.9 g of the title compound (yield: 57.6%) was prepared in the same fashion as Reference Example 2, except that 5.0 g of (4-bromothiophen-2-yl)methylamine was used in Step 2 instead of 4-fluoroaniline. $^1$H-NMR (DMSO-d$_6$, 400 MHz) δ 11.74 (s, 1H), 7.97 (s, 1H), 7.61 (s, 1H), 7.10 (s, 1H), 4.92 (s, 2H)

Reference Example 21. 4-[(5-bromo-3-methyl-2-thienyl)methyl]-1H-1,2,4-triazol-5-one 1.4 g of the title compound (yield: 41.2%) was prepared in the same fashion as Reference Example 3, except that 2.6 g of (5-bromo-3-methylthiophen-2-yl)methylamine was used in Step 1 instead of 3-bromoaniline. MS (ESI) m/z=275.1 (M+H)+

Reference Example 22. 4-[2-(2-thienyl)ethyl]-1H-1,2,4-triazol-5-one 569 mg of the white solid title compound (yield: 72.0%) was prepared in the same fashion as Reference Example 3, except that 1.0 g of 2-thiophenethylamine was used in Step 1 instead of 3-bromoaniline. MS (ESI) m/z=196.2 (M+H)+

Reference Example 23. 4-[2-(5-bromo-2-thienyl)ethyl]-1H-1,2,4-triazol-5-one 2.1 g of the title compound (yield: 68.6%) was prepared in the same fashion as Reference Example 2, except that 2.3 g of 2-(5-bromothiophen-2-yl)ethan-1-amine was used in Step 2 instead of 4-fluoroaniline. MS (ESI) m/z=275.2 (M+H)+

Reference Example 24. tert-butyl N-[3,3-difluoro-2-[[4-(4-fluorophenyl)-5-oxo-1,2,4-triazol-1-yl]methyl]allyl]carbamate 321 mg of 4-(4-fluorophenyl)-1H-1,2,4-triazol-5-one prepared in Step 2 of Reference Example 2, 400 mg of tert-butyl N-[3,3-difluoro-2-(hydroxymethyl)allyl]carbamate prepared in Step 2 of Reference Example 1, and 940 mg of triphenylphosphine were dissolved in 4.5 mL of tetrahydrofuran, and the resulting solution was stirred and cooled to 0° C. To the reaction mixture, 706 uL of diisopropyl azodicarboxylate (DIAD) was slowly added dropwise and stirred at room temperature for 6 hours. The reaction mixture was concentrated under reduced pressure to give a yellow liquid residue. The residue was purified with silica gel column chromatography (developing solvent: n-hexane/ethyl acetate=2/1) to give 222 mg of the title compound as a colorless liquid (yield: 32.3%). $^1$H-NMR (CDCl$_3$, 400 MHz) δ 7.68 (s, 1H), 7.52 (s, 2H), 7.19 (t, 2H), 5.37 (s, 1H), 4.54 (s, 2H), 3.79 (s, 2H), 1.41 (s, 9H)

Reference Example 25. tert-butyl N-[2-[[4-(3-bromophenyl)-5-oxo-1,2,4-triazol-1-yl]methyl]-3,3-difluoro-allyl]carbamate 30 mg of the title compound (yield: 10.0%) was prepared in the same fashion as Reference Example 24, except that 161 mg of 4-(3-bromophenyl)-1H-1,2,4-triazol-5-one prepared in Reference Example 3 was used instead of 4-(4-fluorophenyl)-1H-1,2,4-triazol-5-one. MS (ESI) m/z=346.2 (M+H)+

Reference Example 26. tert-butyl N-[2-[[4-(3,4-difluorophenyl)-5-oxo-1,2,4-triazol-1-yl]methyl]-3,3-difluoro-allyl]carbamate 1.8 g of the title compound (yield: 100%) was prepared in the same fashion as Reference Example 24, except that 883 mg of 4-(3,4-difluorophenyl)-1H-1,2,4-triazol-5-one prepared in Reference Example 4 was used instead of 4-(4-fluorophenyl)-1H-1,2,4-triazol-5-one. MS (ESI) m/z=303.1 (M+H)+

Reference Example 27. tert-butyl N-[2-[[4-(4-bromo-3-fluoro-phenyl)-5-oxo-1,2,4-triazol-1-yl]methyl]-3,3-difluoro-allyl]carbamate 19 mg of the title compound (yield: 9.3%) was prepared in the same fashion as Reference Example 24, except that 150 mg of 4-(4-bromo-3-fluorophenyl)-1H-1,2,4-triazol-5-one prepared in Reference Example 5 was used instead of 4-(4-fluorophenyl)-1H-1,2,4-triazol-5-one. MS (ESI) m/z=(M+H)+

Reference Example 28. tert-butyl N-[2-[[4-(4-bromo-2-fluoro-phenyl)-5-oxo-1,2,4-triazol-1-yl]methyl]-3,3-difluoro-allyl]carbamate 448 mg of the title compound (yield: 8.3%) was prepared in the same fashion as Reference Example 24, except that 3.0 g of 4-(4-bromo-2-fluorophenyl)-1H-1,2,4-triazol-5-one prepared in Reference Example 6 was used instead of 4-(4-fluorophenyl)-1H-1,2,4-triazol-5-one. MS (ESI) m/z=364.2 (M+H)+

Reference Example 29. tert-butyl N-[2-[[4-(4-bromo-2-methyl-phenyl)-5-oxo-1,2,4-triazol-1-yl]methyl]-3,3-difluoro-allyl]carbamate 35 mg of the title compound (yield: 24.2%) was prepared in the same fashion as Reference Example 24, except that 80 mg of 4-(4-bromo-2-methylphenyl)-1H-1,2,4-triazol-5-one prepared in Reference Example 7 was used instead of 4-(4-fluorophenyl)-1H-1,2,4-triazol-5-one. MS (ESI) m/z=360.1 (M+H)+

Reference Example 30. tert-butyl N-[2-[[4-(6-bromo-3-pyridyl)-5-oxo-1,2,4-triazol-1-yl]methyl]-3,3-difluoro-allyl]carbamate 1.3 g of the title compound (yield: 41.3%) was prepared in the same fashion as Reference Example 24, except that 1.7 g of 4-(6-bromo-3-pyridyl)-1H-1,2,4-triazol-5-one prepared in Reference Example 8 was used instead of 4-(4-fluorophenyl)-1H-1,2,4-triazol-5-one. MS (ESI) m/z=347.2 (M+H)+

Reference Example 31. tert-butyl N-[2-[[4-(6-bromo-2-pyridyl)-5-oxo-1,2,4-triazol-1-yl]methyl]-3,3-difluoro-allyl]carbamate 1.8 g of the title compound (yield: 100%) was prepared in the same fashion as Reference Example 24, except that 972 mg of 4-(6-bromo-2-pyridyl)-1H-1,2,4-triazol-5-one prepared in Reference Example 9 was used instead of 4-(4-fluorophenyl)-1H-1,2,4-triazol-5-one. $^1$H-NMR (CDCl$_3$, 400 MHz) δ 8.42 (s, 1H), 8.32 (d, 1H), 7.70 (t, 1H), 7.43 (d, 1H), 4.53 (s, 2H), 3.78 (s, 2H), 1.40 (s, 9H)

Reference Example 32. tert-butyl N-[2-[[4-(4-bromo-2-pyridyl)-5-oxo-1,2,4-triazol-1-yl]methyl]-3,3-difluoro-allyl]carbamate 499 mg of the title compound (yield: 49.9%) was prepared in the same fashion as Reference Example 24, except that 540 mg of 4-(4-bromo-2-pyridyl)-1H-1,2,4-triazol-5-one prepared in Reference Example 10 was used instead of 4-(4-fluorophenyl)-1H-1,2,4-triazol-5-one. MS (ESI) m/z=347.2 (M+H)+

Reference Example 33. tert-butyl N-[2-[[4-(2-bromo-4-pyridyl)-5-oxo-1,2,4-triazol-1-yl]methyl]-3,3-difluoro-allyl]carbamate 1.2 g of the title compound (yield: 90.0%) was prepared in the same fashion as Reference Example 24, except that 702 mg of 4-(2-bromo-4-pyridyl)-1H-1,2,4-triazol-5-one prepared in Reference Example 11 was used instead of 4-(4-fluorophenyl)-1H-1,2,4-triazol-5-one. MS (ESI) m/z=347.1 (M+H)+

Reference Example 34. tert-butyl N-[2-[[4-(5-bromo-3-methyl-2-pyridyl)-5-oxo-1,2,4-triazol-1-yl]methyl]-3,3-difluoro-allyl]carbamate 1.8 g of the title compound (yield: 97.0%) was prepared in the same fashion as Reference Example 24, except that 1.0 g of 4-(5-bromo-3-methyl-2-pyridyl)-1H-1,2,4-triazol-5-one prepared in Reference Example 12 was used instead of 4-(4-fluorophenyl)-1H-1,2,4-triazol-5-one. $^1$H-NMR (CDCl$_3$, 400 MHz) δ 8.42 (s, 1H), 7.87 (s, 1H), 7.74 (s, 1H), 5.36 (s, 1H), 4.53 (s, 2H), 3.78 (s, 2H), 2.40 (s, 3H), 1.42 (s, 9H)

Reference Example 35. tert-butyl N-[2-[[4-(6-bromo-4-methyl-3-pyridyl)-5-oxo-1,2,4-triazol-1-yl]methyl]-3,3-difluoro-allyl]carbamate 56 mg of the title compound (yield: 34.4%) was prepared in the same fashion as Reference Example 24, except that 89 mg of 4-(6-bromo-4-methyl-3-pyridyl)-1H-1,2,4-triazol-5-one prepared in Reference Example 13 was used instead of 4-(4-fluorophenyl)-1H-1,2,4-triazol-5-one. MS (ESI) m/z=361.1 (M+H)+

Reference Example 36. tert-butyl N-[2-[[4-(6-bromo-5-methyl-3-pyridyl)-5-oxo-1,2,4-triazol-1-yl]methyl]-3,3-difluoro-allyl]carbamate 405 mg of the title compound (yield: 39.3%) was prepared in the same fashion as Reference Example 24, except that 571 mg of 4-(6-bromo-5-methyl-3-pyridyl)-1H-1,2,4-triazol-5-one prepared in Reference Example 14 was used instead of 4-(4-fluorophenyl)-1H-1,2,4-triazol-5-one. MS (ESI) m/z=361.1 (M+H)+

Reference Example 37. tert-butyl N-[2-[[4-(5-bromo-3-fluoro-2-pyridyl)-5-oxo-1,2,4-triazol-1-yl]methyl]-3,3-difluoro-allyl]carbamate 780 mg of the title compound (yield: 33.5%) was prepared in the same fashion as Reference Example 24, except that 1.3 g of 4-(5-bromo-3-fluoro-2-pyridyl)-1H-1,2,4-triazol-5-one prepared in Reference Example 15 was used instead of 4-(4-fluorophenyl)-1H-1,2,4-triazol-5-one. MS (ESI) m/z=365.2 (M+H)+

Reference Example 38. tert-butyl N-[2-[[4-(6-bromo-3-methyl-2-pyridyl)-5-oxo-1,2,4-triazol-1-yl]methyl]-3,3-difluoro-allyl]carbamate 521 mg of the title compound (yield: 50.5%) was prepared in the same fashion as Reference Example 24, except that 571 mg of 4-(6-bromo-3-methyl-2-pyridyl)-1H-1,2,4-triazol-5-one prepared in Reference Example 14 was used instead of 4-(4-fluorophenyl)-1H-1,2,4-triazol-5-one. MS (ESI) m/z=361.2 (M+H)+

Reference Example 39. tert-butyl N-[2-[[4-(5-bromopyrazin-2-yl)-5-oxo-1,2,4-triazol-1-yl]methyl]-3,3-difluoro-allyl]carbamate 110 mg of the title compound (yield: 43.1%) was prepared in the same fashion as Reference Example 24, except that 138 mg of 4-(5-bromopyrazin-2-yl)-1H-1,2,4-triazol-5-one prepared in Reference Example 17 was used instead of 4-(4-fluorophenyl)-1H-1,2,4-triazol-5-one. MS (ESI) m/z=348.1 (M+H)+

Reference Example 40. tert-butyl N-[2-[[4-[(4-benzyloxyphenyl)methyl]-5-oxo-1,2,4-triazol-1-yl]methyl]-3,3-difluoro-allyl]carbamate 20 mg of the title compound (yield: 4.6%) was prepared in the same fashion as Reference Example 24, except that 126 mg of 4-[(4-benzyloxyphenyl)methyl]-1H-1,2,4-triazol-5-one prepared in Reference Example 18 was used instead of 4-(4-fluorophenyl)-1H-1,2,4-triazol-5-one. MS (ESI) m/z=387.1 (M+H)+

Reference Example 41. tert-butyl N-[2-[[4-(5-bromo-2-thienyl)methyl]-5-oxo-1,2,4-triazol-1-yl]methyl]-3,3-difluoro-allyl]carbamate 3.3 g of the title compound (yield: 87.2%) was prepared in the same fashion as Reference Example 24, except that 2.0 g of 4-[(5-bromo-2-thienyl)methyl]-1H-1,2,4-triazol-5-one prepared in Reference Example 19 was used instead of 4-(4-fluorophenyl)-1H-1,2,4-triazol-5-one. $^1$H-NMR (CDCl$_3$, 400 MHz) δ 7.38 (s, 1H), 6.95 (s, 1H), 6.85 (s, 1H), 5.40 (s, 1H), 4.88 (s, 2H), 4.47 (s, 2H), 3.71 (s, 2H), 1.44 (s, 9H)

Reference Example 42. tert-butyl N-[2-[[4-(4-bromo-2-thienyl)methyl]-5-oxo-1,2,4-triazol-1-yl]methyl]-3,3-difluoro-allyl]carbamate 2.9 g of the title compound (yield: 64.9%) was prepared in the same fashion as Reference Example 24, except that 2.3 g of 4-[(4-bromo-2-thienyl)methyl]-1H-1,2,4-triazol-5-one prepared in Reference Example 20 was used instead of 4-(4-fluorophenyl)-1H-1,2,4-triazol-5-one. $^1$H-NMR (CDCl$_3$, 400 MHz) δ 7.41 (s, 1H), 7.22 (s, 1H), 7.02 (s, 1H), 5.38 (s, 1H), 4.93 (s, 2H), 4.48 (s, 2H), 3.72 (s, 2H), 1.44 (s, 9H)

Reference Example 43. tert-butyl N-[2-[[4-(5-bromo-3-methyl-2-thienyl)methyl]-5-oxo-1,2,4-triazol-1-yl]methyl]-3,3-difluoro-allyl]carbamate 546 mg of the title compound (yield: 33.0%) was prepared in the same fashion as Reference Example 24, except that 946 mg of 4-[(5-bromo-3-methyl-2-thienyl)methyl]-1H-1,2,4-triazol-5-one prepared in Reference Example 21 was used instead of 4-(4-fluorophenyl)-1H-1,2,4-triazol-5-one. MS (ESI) m/z=380.2 (M+H)+

Reference Example 44. tert-butyl N-[3,3-difluoro-2-[[5-oxo-4-[2-(2-thienyl)ethyl]-1,2,4-triazol-1-yl]methyl]allyl]carbamate 44 mg of the title compound (yield: 14.3%) was prepared in the same fashion as Reference Example 24, except that 87 mg of 4-[2-(2-thienyl)ethyl]-1H-1,2,4-triazol-5-one prepared in Reference Example 22 was used instead of 4-(4-fluorophenyl)-1H-1,2,4-triazol-5-one. MS (ESI) m/z=387.2 (M+H)+

Reference Example 45. tert-butyl N-[2-[[4-(5-bromo-2-thienyl)ethyl]-5-oxo-1,2,4-triazol-1-yl]methyl]-3,3-difluoro-allyl]carbamate 780 mg of the title compound (yield: 22.3%) was prepared in the same fashion as Reference Example 24, except that 2.0 g of 4-[2-(5-bromo-2-thienyl)ethyl]-1H-1,2,4-triazol-5-one prepared in Reference Example 23 was used instead of 4-(4-fluorophenyl)-1H-1,2,4-triazol-5-one. MS (ESI) m/z=380.1 (M+H)+

Reference Example 46. 4-(3-bromo-2-methyl-phenyl)-1H-1,2,4-triazol-5-one 528 mg of the title compound (yield: 38.7%) was prepared in the same fashion as Reference Example 3, except that 1.0 g of 3-bromo-2-methylaniline was used in Step 1 instead of 3-bromoaniline. MS (ESI) m/z=255.2 (M+H)+

Reference Example 47. 4-[(4-bromophenyl)methyl]-1H-1,2,4-triazol-5-one 1.0 g of 1,4-dihydro-1,2,4-triazol-5-one and 3.2 g of potassium carbonate were dissolved in 100.0 mL of N,N-dimethylformamide, and the solution was stirred at RT for 10 min. 2.9 g of 4-bromobenzyl bromide was added to the resulting solution, and then the solution was stirred at RT for 16 hours. After addition of distilled water, the reaction mixture was extracted with ethyl acetate three times. The combined organic extracts were dried over anhydrous magnesium sulfate and then concentrated under reduced pressure to give a residue as a yellow liquid. The residue was purified with silica gel column chromatography (developing solvent: n-hexane/ethyl acetate=1/2) to give 715 mg of the title compound as a white solid (yield: 23.9%). $^1$H-NMR (DMSO-$d_6$, 400 MHz) δ 11.7 (s, 1H), 7.96 (s, 1H), 7.56 (d, 2H), 7.24 (d, 2H), 4.73 (s, 2H)

Reference Example 48. 4-[(3-bromophenyl)methyl]-1H-1,2,4-triazol-5-one 944 mg of the title compound (yield: 31.6%) was prepared as a white solid in the same fashion as Reference Example 47, except that 2.9 g of 3-bromobenzyl bromide was used instead of 4-bromobenzyl bromide. $^1$H-NMR (DMSO-$d_6$, 400 MHz) δ 11.8 (s, 1H), 8.00 (s, 1H), 7.51 (d, 2H), 7.35-7.28 (m, 2H), 4.76 (s, 2H)

Reference Example 49. 4-[(2-bromophenyl)methyl]-1H-1,2,4-triazol-5-one 1.4 g of the title compound (yield: 48.4%) was prepared as a white solid in the same fashion as Reference Example 47, except that 2.9 g of 2-bromobenzyl bromide was used instead of 4-bromobenzyl bromide. $^1$H-NMR (DMSO-$d_6$, 400 MHz) δ 11.80 (s, 1H), 7.91 (s, 1H), 7.67 (d, 1H), 7.40 (t, 1H), 7.28 (t, 1H), 7.09 (d, 1H), 4.81 (s, 2H)

Reference Example 50. 4-[(6-bromobenzothiophen-2-yl)methyl]-1H-1,2,4-triazol-5-one 1.5 g of the title compound (yield: 66.8%) was prepared as a pale pink solid in the same fashion as Reference Example 2, except that 1.8 g of (6-bromo-1-benzothiophen-2-yl)methanamine was used in Step 2 instead of 4-fluoroaniline. MS (ESI) m/z=311.2 (M+H)+

Reference Example 51. 4-[(5-bromobenzothiophen-2-yl)methyl]-1H-1,2,4-triazol-5-one 1.5 g of the title compound (yield: 57.5%) was prepared as a pale brown solid in the same fashion as Reference Example 2, except that 2.0 g of (5-bromo-1-benzothiophen-2-yl)methanamine was used in Step 2 instead of 4-fluoroaniline. $^1$H-NMR (DMSO-$d_6$, 400 MHz) δ 11.8 (s, 1H), 8.24 (s, 1H), 8.00 (s, 1H), 7.78 (d, 1H), 7.52 (d, 1H), 7.36 (s, 1H), 5.04 (s, 2H)

Reference Example 52. 4-[(5-bromo-3-fluoro-2-thienyl)methyl]-1H-1,2,4-triazol-5-one 689 mg of the title compound (yield: 66.0%) was prepared as a pale yellow liquid in the same fashion as Reference Example 47, except that 1.1 g of (5-bromo-3-fluoro-2-thienyl)methyl methanesulfonate was used instead of 4-bromobenzyl bromide. $^1$H-NMR (MeOD, 400 MHz) δ 7.84 (s, 1H), 7.02 (s, 1H), 4.93 (s, 2H)

Reference Example 53. tert-butyl N-[2-[[4-(3-bromo-2-methyl-phenyl)-5-oxo-1,2,4-triazol-1-yl]methyl]-3,3-difluoro-allyl]carbamate 4.7 g of the title compound (yield: 86.1%) was prepared in the same fashion as Reference Example 24, except that 3.0 g of 4-(3-bromo-2-methyl-phenyl)-1H-1,2,4-triazol-5-one prepared in Reference Example 46 was used instead of 4-(4-fluorophenyl)-1H-1,2,4-triazol-5-one. $^1$H-NMR (CDCl$_3$, 400 MHz) δ 7.70 (d, 1H), 7.49 (s, 1H), 7.24-7.18 (m, 2H), 5.41 (bs, 1H), 4.57 (s, 2H), 3.81 (d, 2H), 2.33 (s, 3H), 1.44 (s, 9H)

Reference Example 54. tert-butyl N-[2-[[4-[(4-bromophenyl)methyl]-5-oxo-1,2,4-triazol-1-yl]methyl]-3,3-difluoro-allyl]carbamate 624 mg of the title compound (yield: 48.3%) was prepared in the same fashion as Reference Example 24, except that 715 mg of 4-[(4-bromophenyl)methyl]-1H-1,2,4-triazol-5-one prepared in Reference Example 47 was used instead of 4-(4-fluorophenyl)-1H-1,2,4-triazol-5-one. $^1$H-NMR (CDCl$_3$, 400 MHz) δ 7.60 (s, 1H), 7.55 (d, 2H), 7.43 (d, 2H), 5.18 (s, 2H), 4.66 (s, 2H), 4.37 (s, 2H), 1.33 (s, 9H)

Reference Example 55. tert-butyl N-[2-[[4-[(3-bromophenyl)methyl]-5-oxo-1,2,4-triazol-1-yl]methyl]-3,3-difluoro-allyl]carbamate 790 mg of the title compound (yield: 64.0%) was prepared in the same fashion as Reference Example 24, except that 683 mg of 4-[(3-bromophenyl)methyl]-1H-1,2,4-triazol-5-one prepared in Reference Example 48 was used instead of 4-(4-fluorophenyl)-1H-1,2,4-triazol-5-one. MS (ESI) m/z=459.1 (M+H)+

Reference Example 56. tert-butyl N-[2-[[4-[(2-bromophenyl)methyl]-5-oxo-1,2,4-triazol-1-yl]methyl]-3,3-difluoro-allyl]carbamate 692 mg of the title compound (yield: 56.2%) was prepared in the same fashion as Reference Example 24, except that 683 mg of 4-[(2-bromophenyl)methyl]-1H-1,2,4-triazol-5-one prepared in Reference Example 49 was used instead of 4-(4-fluorophenyl)-1H-1,2,4-triazol-5-one. MS (ESI) m/z=460.1 (M+H)+

Reference Example 57. tert-butyl N-[2-[[4-[(6-bromobenzothiophen-2-yl)methyl]-5-oxo-1,2,4-triazol-1-yl]methyl]-3,3-difluoro-allyl]carbamate 368 mg of the title compound (yield: 37.0%) was prepared in the same fashion as Reference Example 24, except that 600 mg of 4-[(6-bromobenzothiophen-2-yl)methyl]-1H-1,2,4-triazol-5-one prepared in Reference Example 50 was used instead of 4-(4-fluorophenyl)-1H-1,2,4-triazol-5-one. ¹H-NMR (CDCl₃, 400 MHz) δ 7.92 (s, 1H), 7.60 (d, 1H), 7.48-7.43 (m, 2H), 7.26 (s, 1H), 5.34 (s, 1H), 5.02 (s, 2H), 4.48 (s, 2H), 3.73 (s, 2H), 1.42 (s, 9H)

Reference Example 58. tert-butyl N-[2-[[4-[(5-bromobenzothiophen-2-yl)methyl]-5-oxo-1,2,4-triazol-1-yl]methyl]-3,3-difluoro-allyl]carbamate 344 mg of the title compound (yield: 44.5%) was prepared in the same fashion as Reference Example 24, except that 464 mg of 4-[(5-bromobenzothiophen-2-yl)methyl]-1H-1,2,4-triazol-5-one prepared in Reference Example 51 was used instead of 4-(4-fluorophenyl)-1H-1,2,4-triazol-5-one. ¹H-NMR (CDCl₃, 400 MHz) δ 7.91 (s, 1H), 7.66 (d, 1H), 7.46 (d, 2H), 7.28 (s, 1H), 5.41 (bs, 1H), 5.06 (s, 2H), 4.51 (s, 2H), 3.75 (s, 2H), 1.45 (s, 9H)

Reference Example 59. tert-butyl N-[2-[[4-[(5-bromo-3-fluoro-2-thienyl)methyl]-5-oxo-1,2,4-triazol-1-yl]methyl]-3,3-difluoro-allyl]carbamate 581 mg of the title compound (yield: 48.6%) was prepared as a yellow liquid in the same fashion as Reference Example 24, except that 689 mg of 4-[(5-bromo-3-fluoro-2-thienyl)methyl]-1H-1,2,4-triazol-5-one prepared in Reference Example 52 was used instead of 4-(4-fluorophenyl)-1H-1,2,4-triazol-5-one. ¹H-NMR (CDCl₃, 400 MHz) δ 7.44 (s, 1H), 6.85 (s, 1H), 6.37 (s, 1H), 4.83 (s, 2H), 4.47 (s, 2H), 3.73 (s, 2H), 1.45 (s, 9H)

Example 1. 2-[2-(aminomethyl)-3,3-difluoro-allyl]-4-(4-fluorophenyl)-1,2,4-triazol-3-one trifluoroacetate 287 mg of tert-butyl N-[3,3-difluoro-2-[[4-(4-fluorophenyl)-5-oxo-1,2,4-triazol-1-yl]methyl]allyl]carbamate prepared in Reference Example 24 was dissolved in 10.0 mL of dichloromethane and 1.1 mL of trifluoroacetic acid was added thereto. The resulting solution was stirred at room temperature for 2.5 hours. The reaction mixture thus obtained was concentrated, followed by the addition of dichloromethane. The solution was concentrated under reduced pressure and then dried in vacuo to obtain a yellow liquid residue. The residue was purified with silica gel column chromatography (developing solvent: dichloromethane/methanol=10/1) to give 262 mg of the title compound as a white solid (yield: 100%). ¹H-NMR (MeOD, 400 MHz) δ 8.23 (s, 1H), 7.65 (s, 2H), 7.27 (t, 2H), 4.64 (s, 2H), 3.73 (s, 2H)

Example 2. 2-[2-(aminomethyl)-3,3-difluoro-allyl]-4-(3-bromophenyl)-1,2,4-triazol-3-one trifluoroacetate 31 mg of the title compound (yield: 40.1%) was prepared in the same fashion as Example 1, except that 96 mg of tert-butyl N-[2-[[4-(3-bromophenyl)-5-oxo-1,2,4-triazol-1-yl]methyl]-3,3-difluoro-allyl]carbamate prepared in Reference Example 25 was used. ¹H-NMR (MeOD, 400 MHz) δ 8.30 (s, 1H), 7.95 (s, 1H), 7.65-7.56 (m, 2H), 7.44 (t, 1H), 4.63 (s, 2H), 3.72 (s, 2H)

Example 3. 2-[2-(aminomethyl)-3,3-difluoro-allyl]-4-(3,4-difluorophenyl)-1,2,4-triazol-3-one trifluoroacetate 143 mg of the title compound as a colorless liquid (yield: 100%) was prepared in the same fashion as Example 1, except that 189 mg of tert-butyl N-[2-[[4-(3,4-difluorophenyl)-5-oxo-1,2,4-triazol-1-yl]methyl]-3,3-difluoro-allyl]carbamate prepared in Reference Example 26 was used. ¹H-NMR (MeOD, 400 MHz) δ 8.29 (s, 1H), 7.74 (t, 3H), 7.48 (s, 1H), 7.42 (t, 1H), 4.65 (s, 2H), 3.75 (s, 2H)

Example 4. 2-[2-(aminomethyl)-3,3-difluoro-allyl]-4-(4-bromo-3-fluoro-phenyl)-1,2,4-triazol-3-one trifluoroacetate 56 mg of the title compound (yield: 58.0%) was prepared in the same fashion as Example 1, except that 123 mg of tert-butyl N-[2-[[4-(4-bromo-3-fluoro-phenyl)-5-oxo-1,2,4-triazol-1-yl]methyl]-3,3-difluoro-allyl]carbamate prepared in Reference Example 27 was used. ¹H-NMR (MeOD, 400 MHz) δ 8.34 (s, 1H), 7.79-7.69 (m, 2H), 7.47 (d, 2H), 4.63 (s, 2H), 3.72 (s, 2H)

Example 5. 2-[2-(aminomethyl)-3,3-difluoro-allyl]-4-(4-bromo-2-fluoro-phenyl)-1,2,4-triazol-3-one trifluoroacetate 51 mg of the title compound (yield: 57.7%) was prepared in the same fashion as Example 1, except that 113 mg of tert-butyl N-[2-[[4-(4-bromo-2-fluoro-phenyl)-5-oxo-1,2,4-triazol-1-yl]methyl]-3,3-difluoro-allyl]carbamate prepared in Reference Example 28 was used. ¹H-NMR (MeOD, 400 MHz) δ 8.11 (s, 1H), 7.65-7.53 (m, 3H), 4.64 (s, 2H), 3.73 (s, 2H)

Example 6. 2-[2-(aminomethyl)-3,3-difluoro-allyl]-4-(4-bromo-2-methyl-phenyl)-1,2,4-triazol-3-one trifluoroacetate 27 mg of the title compound (yield: 69.0%) was prepared in the same fashion as Example 1, except that 50 mg of tert-butyl N-[2-[[4-(4-bromo-2-methyl-phenyl)-5-oxo-1,2,4-triazol-1-yl]methyl]-3,3-difluoro-allyl]carbamate prepared in Reference Example 29 was used. ¹H-NMR (MeOD, 400 MHz) δ 8.02 (s, 1H), 7.58-7.55 (m, 2H), 7.34 (d, 2H), 4.64 (s, 2H), 3.73 (s, 2H), 2.20 (s, 3H)

Example 7. 2-[2-(aminomethyl)-3,3-difluoro-allyl]-4-(6-bromo-3-pyridyl)-1,2,4-triazol-3-one trifluoroacetate 34 mg of the title compound (yield: 87.7%) was prepared in the same fashion as Example 1, except that 50 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used. ¹H-NMR (MeOD, 400 MHz) δ 8.73 (s, 1H), 8.35 (s, 1H), 8.06 (d, 1H), 7.76 (d, 1H), 5.49 (s, 2H), 4.62 (s, 2H), 3.54 (s, 2H)

Example 8. 2-[2-(aminomethyl)-3,3-difluoro-allyl]-4-(6-bromo-2-pyridyl)-1,2,4-triazol-3-one trifluoroacetate 325 mg of the title compound (yield: 98.4%) was prepared in the same fashion as Example 1, except that 369 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used. ¹H-NMR (MeOD, 400 MHz) δ 8.58 (s, 1H), 8.26 (d, 1H), 7.87 (t, 1H), 7.58 (d, 1H), 4.65 (s, 2H), 3.74 (s, 2H)

Example 9. 2-[2-(aminomethyl)-3,3-difluoro-allyl]-4-(4-bromo-2-pyridyl)-1,2,4-triazol-3-one trifluoroacetate 38 mg of the title compound (yield: 98.0%) was prepared in the same fashion as Example 1, except that 50 mg of tert-butyl N-[2-[[4-(4-bromo-2-pyridyl)-5-oxo-1,2,4-triazol-1-yl]methyl]-3,3-difluoro-allyl]carbamate prepared in Reference Example 32 was used. ¹H-NMR (MeOD, 400 MHz) δ 8.62 (s, 1H), 8.48 (s, 1H), 8.32 (d, 1H), 7.56 (d, 1H), 4.66 (s, 2H), 3.75 (s, 2H)

Example 10. 2-[2-(aminomethyl)-3,3-difluoro-allyl]-4-(2-bromo-4-pyridyl)-1,2,4-triazol-3-one trifluoroacetate 34 mg of the title compound (yield: 88.4%) was prepared in the same fashion as Example 1, except that 50 mg of tert-butyl N-[2-[[4-(2-bromo-4-pyridyl)-5-oxo-1,2,4-triazol-1-yl]methyl]-3,3-difluoro-allyl]carbamate prepared in Reference Example 33 was used. ¹H-NMR (MeOD, 400 MHz) δ 8.69 (s, 1H), 8.44 (d, 2H), 8.21 (s, 1H), 7.89 (d, 1H), 4.65 (s, 2H), 3.73 (s, 2H)

Example 11. 2-[2-(aminomethyl)-3,3-difluoro-allyl]-4-(5-bromo-3-methyl-2-pyridyl)-1,2,4-triazol-3-one trifluoroacetate 260 mg of the title compound (yield: 73.0%) was prepared in the same fashion as Example 1, except that 455 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used. ¹H-NMR (MeOD, 400 MHz) δ 8.50 (s, 1H), 8.13 (s, 2H), 4.64 (s, 2H), 3.73 (s, 2H), 2.34 (s, 3H)

Example 12. 2-[2-(aminomethyl)-3,3-difluoro-allyl]-4-(6-bromo-4-methyl-3-pyridyl)-1,2,4-triazol-3-one trifluoroacetate 35 mg of the title compound (yield: 89.2%) was prepared in the same fashion as Example 1, except that 50 mg of tert-butyl N-[2-[[4-(6-bromo-4-methyl-3-pyridyl)-5-oxo-1,2,4-triazol-1-yl]methyl]-3,3-difluoro-allyl]carbamate prepared in Reference Example 35 was used. ¹H-NMR (MeOD, 400 MHz) δ 8.31 (s, 1H), 8.08 (s, 1H), 7.72 (s, 1H), 4.65 (s, 2H), 3.74 (s, 2H), 2.29 (s, 3H)

Example 13. 2-[2-(aminomethyl)-3,3-difluoro-allyl]-4-(6-bromo-5-methyl-3-pyridyl)-1,2,4-triazol-3-one trifluoroacetate 22 mg of the title compound (yield: 56.0%) was prepared in the same fashion as Example 1, except that 50 mg of tert-butyl N-[2-[[4-(6-bromo-5-methyl-3-pyridyl)-5-oxo-1,2,4-triazol-1-yl]methyl]-3,3-difluoro-allyl]carbamate prepared in Reference Example 36 was used. ¹H-NMR (MeOD, 400 MHz) δ 8.57 (s, 1H), 8.35 (s, 1H), 8.06 (d, 1H), 4.64 (s, 2H), 3.67 (s, 2H), 2.46 (s, 3H)

Example 14. 2-[2-(aminomethyl)-3,3-difluoro-allyl]-4-(5-bromo-3-fluoro-2-pyridyl)-1,2,4-triazol-3-one trifluoroacetate 19 mg of the title compound (yield: 48.3%) was prepared in the same fashion as Example 1, except that 50 mg of tert-butyl N-[2-[[4-(5-bromo-3-fluoro-2-pyridyl)-5-oxo-1,2,4-triazol-1-yl]methyl]-3,3-difluoro-allyl]carbamate prepared in Reference Example 37 was used. ¹H-NMR (MeOD, 400 MHz) δ 8.54 (s, 1H), 8.24 (d, 1H), 8.20 (s, 1H), 4.65 (s, 2H), 3.74 (s, 2H)

Example 15. 2-[2-(aminomethyl)-3,3-difluoro-allyl]-4-(6-bromo-3-methyl-2-pyridyl)-1,2,4-triazol-3-one trifluoroacetate 28 mg of the title compound (yield: 71.3%) was prepared in the same fashion as Example 1, except that 50 mg of tert-butyl N-[2-[[4-(6-bromo-3-methyl-2-pyridyl)-5-oxo-1,2,4-triazol-1-yl]methyl]-3,3-difluoro-allyl]carbamate prepared in Reference Example 38 was used. ¹H-NMR (MeOD, 400 MHz) δ 8.15 (s, 1H), 7.79 (d, 1H), 7.66 (d, 1H), 4.65 (s, 2H), 3.72 (s, 2H), 2.31 (s, 3H)

Example 16. 2-[2-(aminomethyl)-3,3-difluoro-allyl]-4-(5-bromopyrazin-2-yl)-1,2,4-triazol-3-one trifluoroacetate 56 mg of the title compound (yield: 65.6%) was prepared in the same fashion as Example 1, except that 110 mg of tert-butyl N-[2-[[4-(5-bromopyrazin-2-yl)-5-oxo-1,2,4-triazol-1-yl]methyl]-3,3-difluoro-allyl]carbamate prepared in Reference Example 39 was used. ¹H-NMR (MeOD, 400 MHz) δ 9.31 (s, 1H), 8.67 (s, 1H), 8.58 (s, 1H), 4.65 (s, 2H), 3.73 (s, 2H)

Example 17. 2-[2-(aminomethyl)-3,3-difluoro-allyl]-4-[3-(4-methylsulfonylphenyl)phenyl]-1,2,4-triazol-3-one trifluoroacetate

Step 1: tert-butyl N-[3,3-difluoro-2-[[4-[3-(4-methylsulfonylphenyl)phenyl]-5-oxo-1,2,4-triazol-1-yl]methyl]allyl]carbamate 70 mg of tert-butyl N-[2-[[4-(3-bromophenyl)-5-oxo-1,2,4-triazol-1-yl]methyl]-3,3-difluoro-allyl]carbamate prepared in Reference Example 25 and 31 mg of 4-(methanesulfonyl)phenylboronic acid were dissolved in 1.0 mL of 1,4-dioxane, followed by the addition of 785 uL of 1 M potassium carbonate and 6 mg of palladiumdi[1,1'-bis(diphenylphospino)ferrocene]dichloride (PdCl₂(dppf)), and the resulting solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 53 mg of the title compound (yield: 64.8%). MS (ESI) m/z=421.1 (M+H)+

Step 2: 2-[2-(aminomethyl)-3,3-difluoro-allyl]-4-[3-(4-methylsulfonylphenyl)phenyl]-1,2,4-triazol-3-one53 mg of tert-butyl N-[3,3-difluoro-2-[[4-[3-(4-methylsulfonylphenyl)phenyl]-5-oxo-1,2,4-triazol-1-yl]methyl]allyl]carbamate prepared in Step 1 was dissolved in 1.0 mL of dichloromethane, followed by the addition of 0.1 mL of trifluoroacetic acid, the resulting solution was stirred at room temperature for 2 hours. The reaction mixture thus obtained was concentrated, followed by the addition of dichloromethane. The solution was concentrated under reduced pressure and then dried in vacuo to obtain a yellow liquid residue. The residue was purified with silica gel column chromatography (developing solvent: dichloromethane/methanol=10/1) to give 40 mg of the title compound as a white solid (yield: 93.1%). $^1$H-NMR (MeOD, 400 MHz) δ 8.36 (s, 1H), 8.07-7.95 (m, 4H), 7.76-7.66 (m, 4H), 4.66 (s, 2H), 3.50 (s, 2H), 2.22 (s, 3H)

Example 18. 2-[2-(aminomethyl)-3,3-difluoro-allyl]-4-[3-(4-piperazin-1-ylphenyl)phenyl]-1,2,4-triazol-3-one ditrifluoroacetate 35 mg of the title compound (yield: 35.6%) was prepared in the same fashion as Example 17, except that in Step 1, 61 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 8.33 (s, 1H), 7.88 (s, 1H), 7.66-7.55 (m, 5H), 7.14 (d, 2H), 4.67 (s, 2H), 3.71 (s, 2H), 3.49-3.46 (m, 4H), 3.40-3.37 (m, 4H)

Example 19. 2-[2-(aminomethyl)-3,3-difluoro-allyl]-4-[3-[6-(trifluoromethyl)-3-pyridyl]phenyl]-1,2,4-triazol-3-one trifluoroacetate 36 mg of the title compound (yield: 44.8%) was prepared in the same fashion as Example 17, except that 43 mg of 2-(trifluoromethyl)pyridine-5-boronic acid pinacol ester was used instead of 4-(methanesulfonyl)phenylboronic acid in Step 1. $^1$H-NMR (MeOD, 400 MHz) δ 9.05 (s, 1H), 8.41 (s, 1H), 8.36 (d, 1H), 8.06 (s, 1H), 7.94 (d, 1H), 7.83-7.72 (m, 3H), 4.68 (s, 2H), 3.74 (s, 2H)

Example 20. 2-[2-(aminomethyl)-3,3-difluoro-allyl]-4-[3-[6-(dimethylamino)-3-pyridyl]phenyl]-1,2,4-triazol-3-one trifluoroacetate 38 mg of the title compound (yield: 49.7%) was prepared in the same fashion as Example 17, except that 39 mg of 6-(dimethylamino)pyridine-3-boronic acid was used instead of 4-(methanesulfonyl)phenylboronic acid in Step 1. $^1$H-NMR (MeOD, 400 MHz) δ 8.37 (s, 1H), 8.28 (d, 2H), 7.93 (s, 1H), 7.70-7.65 (m, 3H), 7.26 (d, 1H), 4.68 (s, 2H), 3.76 (s, 2H), 3.32 (s, 6H)

Example 21. 2-[2-(aminomethyl)-3,3-difluoro-allyl]-4-[3-(1,3-benzodioxol-5-yl)phenyl]-1,2,4-triazol-3-one trifluoroacetate 62 mg of the title compound (yield: 81.2%) was prepared in the same fashion as Example 17, except that 39 mg of 2-(1,3-benzodioxol-5-yl)-4,4,5,5-tetramethyl-1,3,2-dioxaborolane was used instead of 4-(methanesulfonyl)phenylboronic acid in Step 1. $^1$H-NMR (MeOD, 400 MHz) δ 8.33 (s, 1H), 7.83 (s, 1H), 7.57-7.55 (m, 3H), 7.18 (s, 1H), 6.91 (s, 2H), 6.01 (s, 2H), 4.66 (s, 2H), 3.67 (s, 2H)

Example 22. 6-[3-[1-[2-(aminomethyl)-3,3-difluoro-allyl]-5-oxo-1,2,4-triazol-4-yl]phenyl]-8-methyl-3,4-dihydro-1H-quinolin-2-one trifluoroacetate 33 mg of the title compound (yield: 40.0%) was prepared in the same fashion as Example 17, except that 45 mg of 8-methyl-2-oxo-1,2,3,4-tetrahydroquinoline-6-boronic acid pinacol ester was used instead of 4-(methanesulfonyl)phenylboronic acid in Step 1. $^1$H-NMR (MeOD, 400 MHz) δ 8.34 (s, 1H), 7.87 (s, 1H), 7.65 (t, 1H), 7.59-7.56 (m, 2H), 7.39 (s, 2H), 4.66 (s, 2H), 3.64 (s, 2H), 3.02 (t, 2H), 2.60 (t, 2H)

Example 23. 2-[2-(aminomethyl)-3,3-difluoro-allyl]-4-[3-(1-ethylpyrazol-4-yl)phenyl]-1,2,4-triazol-3-one trifluoroacetate 35 mg of the title compound (yield: 48.4%) was prepared in the same fashion as Example 17, except that X mg of 1-ethylpyrazole-4-boronic acid pinacol ester was used instead of 4-(methanesulfonyl)phenylboronic acid in Step 1. $^1$H-NMR (MeOD, 400 MHz) δ 8.32 (s, 1H), 8.11 (s, 1H), 7.91 (s, 1H), 7.83 (s, 1H), 7.62 (d, 1H), 7.54-7.47 (m, 2H), 4.67 (d, 2H), 4.23 (q, 2H), 3.75 (s, 2H), 1.50 (t, 3H)

Example 24. 2-[2-(aminomethyl)-3,3-difluoro-allyl]-4-[3-fluoro-4-(4-methylsulfonylphenyl)phenyl]-1,2,4-triazol-3-one trifluoroacetate 25 mg of the title compound (yield: 52.8%) was prepared in the same fashion as Example 17, except that 50 mg of tert-butyl N-[2-[[4-(4-bromo-3-fluoro-phenyl)-5-oxo-1,2,4-triazol-1-yl]methyl]-3,3-difluoro-allyl]carbamate prepared in Reference Example 27 was used in Step 1, instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.38 (s, 1H), 8.08 (d, 1H), 7.86 (d, 1H), 7.79-7.67 (m, 3H), 4.63 (s, 2H), 3.18 (s, 3H)

Example 25. 2-[2-(aminomethyl)-3,3-difluoro-allyl]-4-[3-fluoro-4-(4-piperazin-1-ylphenyl)phenyl]-1,2,4-triazol-3-one ditrifluoroacetate 21 mg of the title compound (yield: 43.7%) was prepared in the same fashion as Example 17, except that in Step 1, 50 mg of tert-butyl N-[2-[[4-(4-bromo-3-fluoro-phenyl)-5-oxo-1,2,4-triazol-1-yl]methyl]-3,3-difluoro-allyl]carbamate prepared in Reference Example 27 was used instead of tert-butyl N-[2-[[4-(3-bromophenyl)-5-oxo-1,2,4-triazol-1-yl]methyl]-3,3-difluoro-allyl]carbamate prepared in Reference Example 25 and 54 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 8.36 (s, 1H), 7.67-7.53 (m, 5H), 7.14 (d, 2H), 4.66 (s, 2H), 3.71 (s, 2H), 3.51-3.39 (m, 8H)

Example 26. 2-[2-(aminomethyl)-3,3-difluoro-allyl]-4-[3-fluoro-4-[6-(trifluoromethyl)-3-pyridyl]phenyl]-1,2,4-triazol-3-one trifluoroacetate 33 mg of the title compound (yield: 71.2%) was prepared in the same fashion as Example 17, except that in Step 1, 50 mg of tert-butyl N-[2-[[4-(4-bromo-3-fluoro-phenyl)-5-oxo-1,2,4-triazol-1-yl]methyl]-3,3-difluoro-allyl]carbamate prepared in Reference Example 27 was used instead of tert-butyl N-[2-[[4-(3-bromophenyl)-5-oxo-1,2,4-triazol-1-yl]methyl]-3,3-difluoro-allyl]carbamate prepared in Reference Example 25 and 38 mg of 2-(trifluoromethyl)pyridine-5-boronic acid pinacol ester was used instead of 4-(methanesulfonyl)phenylboronic acid. $^1$H-NMR (MeOD, 400 MHz) δ

8.94 (s, 1H), 8.40 (s, 1H), 8.28 (d, 1H), 7.95 (d, 1H), 7.85-7.72 (m, 3H), 4.64 (s, 2H), 3.39 (s, 2H)

Example 27. 2-[2-(aminomethyl)-3,3-difluoro-allyl]-4-[4-[6-(dimethylamino)-3-pyridyl]-3-fluoro-phenyl]-1,2,4-triazol-3-one trifluoroacetate 24 mg of the title compound (yield: 55.0%) was prepared in the same fashion as Example 17, except that in Step 1, 50 mg of tert-butyl N-[2-[[4-(4-bromo-3-fluoro-phenyl)-5-oxo-1,2,4-triazol-1-yl]methyl]-3,3-difluoro-allyl]carbamate prepared in Reference Example 27 was used instead of tert-butyl N-[2-[[4-(3-bromophenyl)-5-oxo-1,2,4-triazol-1-yl]methyl]-3,3-difluoro-allyl]carbamate prepared in Reference Example 25 and 35 mg of 6-(dimethylamino)pyridine-3-boronic acid was used instead of 4-(methanesulfonyl)phenylboronic acid. $^1$H-NMR (MeOD, 400 MHz) δ 8.40 (s, 1H), 8.19 (s, 1H), 8.12 (d, 1H), 7.78-7.64 (m, 3H), 7.21 (d, 1H), 4.67 (s, 2H), 3.75 (s, 2H), 3.32 (s, 6H)

Example 28. 2-[2-(aminomethyl)-3,3-difluoro-allyl]-4-[4-(1,3-benzodioxol-5-yl)-3-fluoro-phenyl]-1,2,4-triazol-3-one trifluoroacetate 31 mg of the title compound (yield: 71.0%) was prepared in the same fashion as Example 17, except that in Step 1, 50 mg of tert-butyl N-[2-[[4-(4-bromo-3-fluoro-phenyl)-5-oxo-1,2,4-triazol-1-yl]methyl]-3,3-difluoro-allyl]carbamate prepared in Reference Example 27 was used instead of tert-butyl N-[2-[[4-(3-bromophenyl)-5-oxo-1,2,4-triazol-1-yl]methyl]-3,3-difluoro-allyl]carbamate prepared in Reference Example 25 and 35 mg pf 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 8.36 (s, 1H), 7.67-7.54 (m, 3H), 7.06 (s, 2H), 6.94 (d, 1H), 6.02 (s, 2H), 4.65 (s, 2H), 3.66 (s, 2H)

Example 29. 6-[4-[1-[2-(aminomethyl)-3,3-difluoro-allyl]-5-oxo-1,2,4-triazol-4-yl]-2-fluoro-phenyl]-8-methyl-3,4-dihydro-1H-quinolin-2-one trifluoroacetate 27 mg of the title compound (yield: 56.4%) was prepared in the same fashion as Example 17, except that in Step 1, 50 mg of tert-butyl N-[2-[[4-(4-bromo-3-fluoro-phenyl)-5-oxo-1,2,4-triazol-1-yl]methyl]-3,3-difluoro-allyl]carbamate prepared in Reference Example 27 was used instead of tert-butyl N-[2-[[4-(3-bromophenyl)-5-oxo-1,2,4-triazol-1-yl]methyl]-3,3-difluoro-allyl]carbamate prepared in Reference Example 25 and 40 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 8.36 (s, 1H), 7.67-7.54 (m, 3H), 7.26 (s, 2H), 4.67 (s, 2H), 3.75 (s, 2H), 3.00 (t, 2H), 2.60 (t, 2H), 2.32 (s, 3H)

Example 30. 2-[2-(aminomethyl)-3,3-difluoro-allyl]-4-[4-(1-ethylpyrazol-4-yl)-3-fluoro-phenyl]-1,2,4-triazol-3-one trifluoroacetate 28 mg of the title compound (yield: 81.4%) was prepared in the same fashion as Example 17, except that in Step 1, 50 mg of tert-butyl N-[2-[[4-(4-bromo-3-fluoro-phenyl)-5-oxo-1,2,4-triazol-1-yl]methyl]-3,3-difluoro-allyl]carbamate prepared in Reference Example 27 was used instead of tert-butyl N-[2-[[4-(3-bromophenyl)-5-oxo-1,2,4-triazol-1-yl]methyl]-3,3-difluoro-allyl]carbamate prepared in Reference Example 25 and 31 mg of 1-ethylpyrazole-4-boronic acid pinacol ester was used instead of 4-(methanesulfonyl)phenylboronic acid. $^1$H-NMR (MeOD, 400 MHz) δ 8.33 (s, 1H), 8.13 (s, 1H), 7.95 (s, 1H), 7.83 (t, 1H), 7.64 (d, 1H), 7.51 (d, 1H), 4.64 (s, 2H), 4.26 (q, 2H), 3.62 (s, 2H), 1.51 (t, 3H)

Example 31. 2-[2-(aminomethyl)-3,3-difluoro-allyl]-4-[2-fluoro-4-(4-methylsulfonylphenyl)phenyl]-1,2,4-triazol-3-one trifluoroacetate 29 mg of the title compound (yield: 61.2%) was prepared in the same fashion as Example 17, except that in Step 1, 50 mg of tert-butyl N-[2-[[4-(4-bromo-2-fluoro-phenyl)-5-oxo-1,2,4-triazol-1-yl]methyl]-3,3-difluoro-allyl]carbamate prepared in Reference Example 28 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.19 (s, 1H), 8.08 (d, 2H), 7.97 (d, 2H), 7.81-7.72 (m, 3H), 4.68 (s, 2H), 3.76 (s, 2H), 3.18 (s, 3H)

Example 32. 2-[2-(aminomethyl)-3,3-difluoro-allyl]-4-[2-fluoro-4-(4-piperazin-1-ylphenyl)phenyl]-1,2,4-triazol-3-one ditrifluoroacetate 22 mg of the title compound (yield: 45.8%) was prepared in the same fashion as Example 17, except that in Step 1, 50 mg of tert-butyl N-[2-[[4-(4-bromo-2-fluoro-phenyl)-5-oxo-1,2,4-triazol-1-yl]methyl]-3,3-difluoro-allyl]carbamate prepared in Reference Example 28 was used instead of tert-butyl N-[2-[[4-(3-bromophenyl)-5-oxo-1,2,4-triazol-1-yl]methyl]-3,3-difluoro-allyl]carbamate prepared in Reference Example 25 and 54 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 8.14 (s, 1H), 7.64-7.60 (m, 5H), 7.14 (d, 2H), 4.67 (s, 2H), 3.73 (s, 2H), 3.50-3.40 (m, 8H)

Example 33. 2-[2-(aminomethyl)-3,3-difluoro-allyl]-4-[2-fluoro-4-[6-(trifluoromethyl)-3-pyridyl]phenyl]-1,2,4-triazol-3-one trifluoroacetate 25 mg of the title compound (yield: 53.9%) was prepared in the same fashion as Example 17, except that in Step 1, 50 mg of tert-butyl N-[2-[[4-(4-bromo-2-fluoro-phenyl)-5-oxo-1,2,4-triazol-1-yl]methyl]-3,3-difluoro-allyl]carbamate prepared in Reference Example 28 was used instead of tert-butyl N-[2-[[4-(3-bromophenyl)-5-oxo-1,2,4-triazol-1-yl]methyl]-3,3-difluoro-allyl]carbamate prepared in Reference Example 25, and 38 mg of 2-(trifluoromethyl)pyridine-5-boronic acid pinacol ester was used instead of 4-(methanesulfonyl)phenylboronic acid. $^1$H-NMR (MeOD, 400 MHz) δ 8.19 (s, 1H), 8.08 (d, 2H), 7.97 (d, 2H), 7.81-7.72 (m, 3H), 4.68 (s, 2H), 3.76 (s, 2H), 3.18 (s, 3H)

Example 34. 2-[2-(aminomethyl)-3,3-difluoro-allyl]-4-[4-[6-(dimethylamino)-3-pyridyl]-2-fluoro-phenyl]-1,2,4-triazol-3-one trifluoroacetate 35 mg of the title compound (yield: 80.1%) was prepared in the same fashion as Example 17, except that in Step 1, 50 mg of tert-butyl N-[2-[[4-(4-bromo-2-fluoro-phenyl)-5-oxo-1,2,4-triazol-1-yl]methyl]-3,3-difluoro-allyl]carbamate prepared in Reference Example 28 was used instead of tert-butyl N-[2-[[4-(3-bromophenyl)-5-oxo-1,2,4-triazol-1-yl]

methyl]-3,3-difluoro-allyl]carbamate prepared in Reference Example 25 and 35 mg of 6-(dimethylamino)pyridine-3-boronic acid was used instead of 4-(methanesulfonyl)phenylboronic acid. $^1$H-NMR (MeOD, 400 MHz) δ 8.30-8.16 (m, 3H), 7.74-7.62 (m, 3H), 7.20 (d, 1H), 4.67 (s, 2H), 3.73 (s, 2H), 1.87 (s, 6H)

Example 35. 2-[2-(aminomethyl)-3,3-difluoro-allyl]-4-[4-(1,3-benzodioxol-5-yl)-2-fluoro-phenyl]-1,2,4-triazol-3-one trifluoroacetate 30 mg of the title compound (yield: 68.7%) was prepared in the same fashion as Example 17, except that in Step 1, 50 mg of tert-butyl N-[2-[[4-(4-bromo-2-fluoro-phenyl)-5-oxo-1,2,4-triazol-1-yl]methyl]-3,3-difluoro-allyl]carbamate prepared in Reference Example 28 was used instead of tert-butyl N-[2-[[4-(3-bromophenyl)-5-oxo-1,2,4-triazol-1-yl]methyl]-3,3-difluoro-allyl]carbamate prepared in Reference Example 25 and 35 mg of 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 8.13 (s, 1H), 7.64-7.53 (m, 3H), 7.18 (s, 2H), 6.94 (s, 1H), 6.02 (d, 2H), 4.67 (s, 2H), 3.73 (s, 2H)

Example 36. 6-[4-[1-[2-(aminomethyl)-3,3-difluoro-allyl]-5-oxo-1,2,4-triazol-4-yl]-3-fluoro-phenyl]-8-methyl-3,4-dihydro-TH-quinolin-2-one trifluoroacetate 33 mg of the title compound (yield: 68.9%) was prepared in the same fashion as Example 17, except that in Step 1, 50 mg of tert-butyl N-[2-[[4-(4-bromo-2-fluoro-phenyl)-5-oxo-1,2,4-triazol-1-yl]methyl]-3,3-difluoro-allyl]carbamate prepared in Reference Example 28 was used instead of tert-butyl N-[2-[[4-(3-bromophenyl)-5-oxo-1,2,4-triazol-1-yl]methyl]-3,3-difluoro-allyl]carbamate prepared in Reference Example 25 and 40 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 9.06 (s, 1H), 8.36 (s, 1H), 8.17 (s, 1H), 7.95-7.76 (m, 4H), 4.65 (s, 2H), 3.49 (s, 2H)

Example 37. 2-[2-(aminomethyl)-3,3-difluoro-allyl]-4-[4-(1-ethylpyrazol-4-yl)-2-fluoro-phenyl]-1,2,4-triazol-3-one trifluoroacetate 21 mg of the title compound (yield: 61.1%) was prepared in the same fashion as Example 17, except that in Step 1, 50 mg of tert-butyl N-[2-[[4-(4-bromo-2-fluoro-phenyl)-5-oxo-1,2,4-triazol-1-yl]methyl]-3,3-difluoro-allyl]carbamate prepared in Reference Example 28 was used instead of tert-butyl N-[2-[[4-(3-bromophenyl)-5-oxo-1,2,4-triazol-1-yl]methyl]-3,3-difluoro-allyl]carbamate prepared in Reference Example 25 and 31 mg of 1-ethylpyrazole-4-boronic acid pinacol ester was used instead of 4-(methanesulfonyl)phenylboronic acid. $^1$H-NMR (MeOD, 400 MHz) δ 8.16 (s, 1H), 8.11 (s, 1H), 7.93 (s, 1H), 7.61-7.56 (m, 3H), 4.65 (s, 2H), 4.23 (q, 2H), 3.63 (s, 2H), 1.50 (t, 3H)

Example 38. 2-[2-(aminomethyl)-3,3-difluoro-allyl]-4-[6-(4-methylsulfonylphenyl)-3-pyridyl]-1,2,4-triazol-3-one trifluoroacetate 25 mg of the title compound (yield: 44.0%) was prepared in the same fashion as Example 17, except that in Step 1, 60 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 9.04 (s, 1H), 8.44 (s, 1H), 8.30 (d, 2H), 8.24 (d, 1H), 8.13 (d, 1H), 8.06 (d, 2H), 4.69 (s, 2H), 3.77 (s, 2H), 3.18 (s, 3H)

Example 39. 2-[2-(aminomethyl)-3,3-difluoro-allyl]-4-[6-(4-piperazin-1-ylphenyl)-3-pyridyl]-1,2,4-triazol-3-one ditrifluoroacetate 32 mg of the title compound (yield: 55.9%) was prepared in the same fashion as Example 17, except that in Step 1, 60 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used instead of tert-butyl N-[2-[[4-(3-bromophenyl)-5-oxo-1,2,4-triazol-1-yl]methyl]-3,3-difluoro-allyl]carbamate prepared in Reference Example 25 and 52 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 8.37 (s, 1H), 8.12 (d, 1H), 8.00-7.95 (m, 3H), 7.14 (d, 2H) 4.67 (s, 2H), 3.73 (s, 2H), 3.53 (t, 4H), 3.39 (t, 4H)

Example 40. 2-[2-(aminomethyl)-3,3-difluoro-allyl]-4-[6-[6-(trifluoromethyl)-3-pyridyl]-3-pyridyl]-1,2,4-triazol-3-one trifluoroacetate 17 mg of the title compound (yield: 29.8%) was prepared in the same fashion as Example 17, except that in Step 1, 60 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used instead of tert-butyl N-[2-[[4-(3-bromophenyl)-5-oxo-1,2,4-triazol-1-yl]methyl]-3,3-difluoro-allyl]carbamate prepared in Reference Example 25 and 37 mg of 2-(trifluoromethyl)pyridine-5-boronic acid pinacol ester was used instead of 4-(methanesulfonyl)phenylboronic acid. $^1$H-NMR (MeOD, 400 MHz) δ 9.41 (s, 1H), 9.10 (s, 1H), 8.71 (d, 1H), 8.46 (s, 1H), 8.31 (d, 1H), 8.23 (d, 1H), 7.96 (d, 1H), 4.69 (s, 2H), 3.77 (s, 2H)

Example 41. 2-[2-(aminomethyl)-3,3-difluoro-allyl]-4-[6-[6-(dimethylamino)-3-pyridyl]-3-pyridyl]-1,2,4-triazol-3-one trifluoroacetate 19 mg of the title compound (yield: 37.3%) was prepared in the same fashion as Example 17, except that in Step 1, 60 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used instead of tert-butyl N-[2-[[4-(3-bromophenyl)-5-oxo-1,2,4-triazol-1-yl]methyl]-3,3-difluoro-allyl]carbamate prepared in Reference Example 25 and 33 mg of 6-(dimethylamino)pyridine-3-boronic acid was used instead of 4-(methanesulfonyl)phenylboronic acid. $^1$H-NMR (MeOD, 400 MHz) δ 9.00 (s, 1H), 8.68 (d, 1H), 8.65 (s, 1H), 8.42 (s, 1H), 8.23 (d, 1H), 8.07 (d, 1H), 7.35 (d, 1H), 4.68 (s, 2H), 3.36 (s, 3H)

Example 42. 2-[2-(aminomethyl)-3,3-difluoro-allyl]-4-[6-(1,3-benzodioxol-5-yl)-3-pyridyl]-1,2,4-triazol-3-one trifluoroacetate 26 mg of the title compound (yield: 50.0%) was prepared in the same fashion as Example 17, except that in Step 1, 60 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used instead of tert-butyl N-[2-[[4-(3-bromophenyl)-5-oxo-1,2,4-triazol-1-yl]methyl]-3,3-difluoro-allyl]carbamate prepared in Reference Example 25 and 33 mg of 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 8.37 (s, 1H), 8.11 (d, 1H), 7.93 (d, 1H), 7.57 (d, 1H), 7.55 (s, 1H), 6.94 (d, 1H), 6.04 (s, 2H), 4.67 (s, 2H), 3.76 (s, 2H)

Example 43. 6-[5-[1-[2-(aminomethyl)-3,3-difluoro-allyl]-5-oxo-1,2,4-triazol-4-yl]-2-pyridyl]-8-methyl-3,4-dihydro-1H-quinolin-2-one trifluoroacetate 17 mg of the title compound (yield: 29.8%) was prepared in the same fashion as Example 17, except that in Step 1, 60 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used instead of tert-butyl N-[2-[[4-(3-bromophenyl)-5-oxo-1,2,4-triazol-1-yl]methyl]-3,3-difluoro-allyl]carbamate prepared in Reference Example 25 and 39 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 8.89 (s, 1H), 8.38 (s, 1H), 8.11 (d, 1H), 7.94 (d, 1H), 7.71 (s, 2H), 4.68 (s, 2H), 3.77 (s, 2H), 3.01 (t, 2H), 2.60 (t, 4H), 2.33 (s, 3H)

Example 44. 6-[5-[1-[2-(aminomethyl)-3,3-difluoro-allyl]-5-oxo-1,2,4-triazol-4-yl]-2-pyridyl]-1-methyl-3,4-dihydroquinolin-2-one trifluoroacetate 22 mg of the title compound (yield: 39.6%) was prepared in the same fashion as Example 17, except that in Step 1, 60 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used instead of tert-butyl N-[2-[[4-(3-bromophenyl)-5-oxo-1,2,4-triazol-1-yl]methyl]-3,3-difluoro-allyl]carbamate prepared in Reference Example 25 and 39 mg of (1-methyl-2-oxo-1,2,3,4-tetrahydroquinolin-6-yl)boronic acid pinacol ester was used instead of 4-(methanesulfonyl)phenylboronic acid. $^1$H-NMR (MeOD, 400 MHz) δ 8.90 (s, 1H), 8.38 (s, 1H), 8.11 (d, 1H), 7.96-7.86 (m, 3H), 7.17 (d, 1H), 4.68 (s, 2H), 3.34 (s, 3H), 2.96 (t, 2H), 2.64 (t, 2H)

Example 45. 2-[2-(aminomethyl)-3,3-difluoro-allyl]-4-[6-(1-ethylpyrazol-4-yl)-3-pyridyl]-1,2,4-triazol-3-one trifluoroacetate 22 mg of the title compound (yield: 45.4%) was prepared in the same fashion as Example 17, except that in Step 1, 60 mg of tert-butyl N-[2-[[4-(6-bromo-3-pyridyl)-5-oxo-1,2,4-triazol-1-yl]methyl]-3,3-difluoro-allyl]carbamate prepared in Reference Example 30 was used instead of tert-butyl N-[2-[[4-(3-bromophenyl)-5-oxo-1,2,4-triazol-1-yl]methyl]-3,3-difluoro-allyl]carbamate prepared in Reference Example 25 and 30 mg of 1-ethylpyrazole-4-boronic acid pinacol ester was used instead of 4-(methanesulfonyl)phenylboronic acid. $^1$H-NMR (MeOD, 400 MHz) δ 8.35 (s, 1H), 8.26 (s, 1H), 8.07 (s, 2H), 7.80 (d, 1H) 4.67 (s, 2H), 4.27 (q, 2H), 3.75 (s, 2H), 1.52 (t, 3H)

Example 46. 2-[2-(aminomethyl)-3,3-difluoro-allyl]-4-[6-(4-methylsulfonylphenyl)-2-pyridyl]-1,2,4-triazol-3-one trifluoroacetate 35 mg of the title compound (yield: 74.2%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.85 (s, 1H), 8.37 (d, 2H), 8.28 (d, 1H), 8.07 (t, 3H), 7.99 (d, 1H), 4.68 (s, 2H), 3.77 (s, 2H), 3.18 (s, 3H)

Example 47. 2-[2-(aminomethyl)-3,3-difluoro-allyl]-4-[6-(4-piperazin-1-ylphenyl)-2-pyridyl]-1,2,4-triazol-3-one ditrifluoroacetate 33 mg of the title compound (yield: 68.9%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 52 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 8.79 (s, 1H), 8.07 (d, 3H), 7.95 (t, 1H), 7.80 (d, 1H), 7.13 (d, 2H), 4.67 (s, 2H), 3.72 (s, 2H), 3.53 (s, 4H), 3.39 (s, 4H)

Example 48. 2-[2-(aminomethyl)-3,3-difluoro-allyl]-4-[6-[6-(trifluoromethyl)-3-pyridyl]-2-pyridyl]-1,2,4-triazol-3-one trifluoroacetate 28 mg of the title compound (yield: 60.6%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 26 mg of 2-(trifluoromethyl)pyridine-5-boronic acid pinacol ester was used instead of 4-(methanesulfonyl)phenylboronic acid. $^1$H-NMR (MeOD, 400 MHz) δ 9.44 (s, 1H), 8.88 (s, 1H), 8.75 (d, 1H), 8.33 (d, 1H), 8.13 (t, 1H), 8.05 (d, 1H), 7.95 (d, 1H), 4.69 (s, 2H), 3.77 (s, 2H)

Example 49. 2-[2-(aminomethyl)-3,3-difluoro-allyl]-4-[6-[6-(dimethylamino)-3-pyridyl]-2-pyridyl]-1,2,4-triazol-3-one trifluoroacetate 25 mg of the title compound (yield: 57.6%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 33 mg of 6-(dimethylamino)pyridine-3-boronic acid was used instead of 4-(methanesulfonyl)phenylboronic acid. $^1$H-NMR (MeOD, 400 MHz) δ 8.83 (s, 1H), 8.70 (s, 1H), 8.63 (d, 1H), 8.21 (d, 1H), 8.05 (t, 1H), 7.86 (d, 1H), 7.24 (d, 1H), 4.68 (s, 2H), 3.76 (s, 2H), 3.34 (s, 6H)

Example 50. 2-[2-(aminomethyl)-3,3-difluoro-allyl]-4-[6-(1,3-benzodioxol-5-yl)-2-pyridyl]-1,2,4-triazol-3-one trifluoroacetate 36 mg of the title compound (yield: 83.0%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 8.76 (s, 1H), 8.07 (d, 1H), 7.93 (t, 1H), 7.73 (d, 1H), 7.61 (d, 2H), 6.90 (d, 1H), 6.02 (s, 2H), 4.66 (s, 2H), 3.75 (s, 2H)

Example 51. 6-[6-[1-[2-(aminomethyl)-3,3-difluoro-allyl]-5-oxo-1,2,4-triazol-4-yl]-2-pyridyl]-8-methyl-3,4-dihydro-1H-quinolin-2-one trifluoroacetate 29 mg of the title compound (yield: 60.7%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 39 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 8.81 (s, 1H), 8.10 (d, 1H), 7.96 (t, 1H), 7.80 (s, 3H), 4.68 (s, 2H), 3.76 (s, 2H), 3.03 (t, 2H), 2.61 (t, 2H), 2.34 (s, 3H)

Example 52. 6-[6-[1-[2-(aminomethyl)-3,3-difluoro-allyl]-5-oxo-1,2,4-triazol-4-yl]-2-pyridyl]-1-methyl-3,4-dihydroquinolin-2-one trifluoroacetate 36 mg of the title compound (yield: 75.4%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 39 mg of (1-methyl-2-oxo-1,2,3,4-tetrahydroquinolin-6-yl)boronic acid pinacol ester was used instead of 4-(methanesulfonyl)phenylboronic acid. $^1$H-NMR (MeOD, 400 MHz) δ 8.82 (s, 1H), 8.12 (d, 1H), 8.01-7.96 (m, 3H), 7.83 (d, 1H), 7.18 (d, 1H), 4.68 (s, 2H), 3.76 (s, 2H), 3.36 (s, 3H), 3.00 (t, 2H), 2.66 (t, 2H)

Example 53. 2-[2-(aminomethyl)-3,3-difluoro-allyl]-4-[6-(1-ethylpyrazol-4-yl)-2-pyridyl]-1,2,4-triazol-3-one trifluoroacetate 24 mg of the title compound (yield: 59.3%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 30 mg of 1-ethylpyrazole-4-boronic acid pinacol ester was used instead of 4-(methanesulfonyl)phenylboronic acid. $^1$H-NMR (MeOD, 400 MHz) δ 8.81 (s, 1H), 8.32 (s, 1H), 8.09 (s, 1H), 8.02 (d, 1H), 7.89 (t, 1H), 7.58 (d, 1H), 4.66 (s, 3H), 4.25 (q, 2H), 3.75 (s, 2H), 1.51 (t, 3H)

Example 54. 2-[2-(aminomethyl)-3,3-difluoro-allyl]-4-[4-(4-methylsulfonylphenyl)-2-pyridyl]-1,2,4-triazol-3-one trifluoroacetate 34 mg of the title compound (yield: 72.0%) was prepared in the same fashion as Example 17, except that in Step 1, 50 mg of tert-butyl N-[2-[[4-(4-bromo-2-pyridyl)-5-oxo-1,2,4-triazol-1-yl]methyl]-3,3-difluoro-allyl]carbamate prepared in Reference Example 32 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.68 (s, 1H), 8.58 (d, 2H), 8.12 (d, 2H), 8.04 (d, 2H), 7.72 (s, 1H), 4.66 (s, 2H), 3.66 (s, 2H), 3.20 (s, 3H)

Example 55. 2-[2-(aminomethyl)-3,3-difluoro-allyl]-4-[4-(4-piperazin-1-ylphenyl)-2-pyridyl]-1,2,4-triazol-3-one ditrifluoroacetate 25 mg of the title compound (yield: 52.2%) was prepared in the same fashion as Example 17, except that in Step 1, 50 mg of tert-butyl N-[2-[[4-(4-bromo-2-pyridyl)-5-oxo-1,2,4-triazol-1-yl]methyl]-3,3-difluoro-allyl]carbamate prepared in Reference Example 32 was used instead of tert-butyl N-[2-[[4-(3-bromophenyl)-5-oxo-1,2,4-triazol-1-yl]methyl]-3,3-difluoro-allyl]carbamate prepared in Reference Example 25 and 52 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 8.65 (s, 1H), 8.47 (d, 2H), 7.76 (d, 2H), 7.62 (s, 1H), 7.16 (d, 2H), 4.67 (s, 2H), 3.67 (s, 2H), 3.51 (d, 4H), 3.36 (d, 4H)

Example 56. 2-[2-(aminomethyl)-3,3-difluoro-allyl]-4-[4-[6-(trifluoromethyl)-3-pyridyl]-2-pyridyl]-1,2,4-triazol-3-one trifluoroacetate 29 mg of the title compound (yield: 62.8%) was prepared in the same fashion as Example 17, except that in Step 1, 50 mg of tert-butyl N-[2-[[4-(4-bromo-2-pyridyl)-5-oxo-1,2,4-triazol-1-yl]methyl]-3,3-difluoro-allyl]carbamate prepared in Reference Example 32 was used instead of tert-butyl N-[2-[[4-(3-bromophenyl)-5-oxo-1,2,4-triazol-1-yl]methyl]-3,3-difluoro-allyl]carbamate prepared in Reference Example 25 and 31 mg of 2-(trifluoromethyl)pyridine-5-boronic acid pinacol ester was used instead of 4-(methanesulfonyl)phenylboronic acid. $^1$H-NMR (MeOD, 400 MHz) δ 9.11 (s, 1H), 8.68 (s, 1H), 8.59 (s, 2H), 8.42 (d, 1H), 7.99 (d, 1H), 7.75 (d, 1H), 4.67 (s, 2H), 3.63 (s, 2H)

Example 57. 2-[2-(aminomethyl)-3,3-difluoro-allyl]-4-[4-[6-(dimethylamino)-3-pyridyl]-2-pyridyl]-1,2,4-triazol-3-one trifluoroacetate 30 mg of the title compound (yield: 69.1%) was prepared in the same fashion as Example 17, except that in Step 1, 50 mg of tert-butyl N-[2-[[4-(4-bromo-2-pyridyl)-5-oxo-1,2,4-triazol-1-yl]methyl]-3,3-difluoro-allyl]carbamate prepared in Reference Example 32 was used instead of tert-butyl N-[2-[[4-(3-bromophenyl)-5-oxo-1,2,4-triazol-1-yl]methyl]-3,3-difluoro-allyl]carbamate prepared in Reference Example 25 and 28 mg of 6-(dimethylamino)pyridine-3-boronic acid was used instead of 4-(methanesulfonyl)phenylboronic acid. $^1$H-NMR (MeOD, 400 MHz) δ 8.68 (s, 1H), 8.52 (s, 1H), 8.46 (d, 2H), 8.25 (d, 1H), 7.65 (s, 1H), 7.19 (d, 1H), 4.69 (s, 2H), 3.76 (s, 2H), 3.31 (s, 3H)

Example 58. 2-[2-(aminomethyl)-3,3-difluoro-allyl]-4-[4-(1,3-benzodioxol-5-yl)-2-pyridyl]-1,2,4-triazol-3-one trifluoroacetate 26 mg of the title compound (yield: 59.9%) was prepared in the same fashion as Example 17, except that in Step 1, 50 mg of tert-butyl N-[2-[[4-(4-bromo-2-pyridyl)-5-oxo-1,2,4-triazol-1-yl]methyl]-3,3-difluoro-allyl]carbamate prepared in Reference Example 32 was used instead of tert-butyl N-[2-[[4-(3-bromophenyl)-5-oxo-1,2,4-triazol-1-yl]methyl]-3,3-difluoro-allyl]carbamate prepared in Reference Example 25 and 28 mg of 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 8.63 (s, 1H), 8.42 (d, 2H), 7.56 (s, 1H), 7.32-7.28 (m, 2H), 6.97 (d, 1H), 6.06 (s, 2H), 4.66 (s, 2H), 3.54 (s, 2H)

Example 59. 6-[2-[1-[2-(aminomethyl)-3,3-difluoro-allyl]-5-oxo-1,2,4-triazol-4-yl]-4-pyridyl]-8-methyl-3,4-dihydro-1H-quinolin-2-one trifluoroacetate 25 mg of the title compound (yield: 52.3%) was prepared in the same fashion as Example 17, except that in Step 1, 50 mg of tert-butyl N-[2-[[4-(4-bromo-2-pyridyl)-5-oxo-1,2,4-triazol-1-yl]methyl]-3,3-difluoro-allyl]carbamate prepared in Reference Example 32 was used instead of tert-butyl N-[2-[[4-(3-bromophenyl)-5-oxo-1,2,4-triazol-1-yl]methyl]-3,3-difluoro-allyl]carbamate prepared in Reference Example 25 and 33 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 8.61 (s, 1H), 8.44 (d, 2H), 7.60 (d, 1H), 7.50 (d, 2H), 4.64 (s, 2H), 3.36 (s, 2H), 3.04 (d, 2H), 2.62 (d, 2H)

Example 60. 2-[2-(aminomethyl)-3,3-difluoro-allyl]-4-[4-(1-ethylpyrazol-4-yl)-2-pyridyl]-1,2,4-triazol-3-one trifluoroacetate 24 mg of the title compound (yield: 59.3%) was prepared in the same fashion as Example 17, except that in Step 1, 50 mg of tert-butyl N-[2-[[4-(4-bromo-2-pyridyl)-5-oxo-1,2,4-triazol-1-yl]methyl]-3,3-difluoro-allyl]carbamate prepared in Reference Example 32 was used instead of tert-butyl N-[2-[[4-(3-bromophenyl)-5-oxo-1,2,4-triazol-1-yl]methyl]-3,3-difluoro-allyl]carbamate prepared in Reference Example 25 and 26 mg of 1-ethylpyrazole-4-boronic acid pinacol ester was used instead of 4-(methanesulfonyl)phenylboronic acid. $^1$H-NMR (MeOD, 400 MHz) δ 8.62 (s, 1H), 8.37-8.29 (m, 3H), 8.02 (s, 1H), 7.53 (s, 1H), 4.68 (s, 2H), 4.26 (q, 2H), 3.76 (s, 2H), 1.52 (t, 3H)

Example 61. 2-[2-(aminomethyl)-3,3-difluoro-allyl]-4-[2-(4-methylsulfonylphenyl)-4-pyridyl]-1,2,4-triazol-3-one trifluoroacetate 45 mg of the title compound (yield: 47.7%) was prepared in the same fashion as Example 17, except that in Step 1, 100 mg of tert-butyl N-[2-[[4-(2-bromo-4-pyridyl)-5-oxo-1,2,4-triazol-1-yl]methyl]-3,3-difluoro-allyl]carbamate prepared in Reference Example 33 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.78 (s, 1H), 8.63 (s, 1H), 8.41 (s, 1H), 8.29 (s, 1H), 8.07 (d, 2H), 7.91 (s, 1H), 4.68 (s, 2H), 3.76 (s, 2H), 3.18 (s, 3H)

Example 62. 2-[2-(aminomethyl)-3,3-difluoro-allyl]-4-[2-(4-piperazin-1-ylphenyl)-4-pyridyl]-1,2,4-triazol-3-one ditrifluoroacetate 50 mg of the title compound (yield: 52.2%) was prepared in the same fashion as Example 17, except that in Step 1, 100 mg of tert-butyl N-[2-[[4-(2-bromo-4-pyridyl)-5-oxo-1,2,4-triazol-1-yl]methyl]-3,3-difluoro-allyl]carbamate prepared in Reference Example 33 was used instead of tert-butyl N-[2-[[4-(3-bromophenyl)-5-oxo-1,2,4-triazol-1-yl]methyl]-3,3-difluoro-allyl]carbamate prepared in Reference Example 25 and 87 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 8.67 (d, 1H), 8.61 (s, 1H), 8.27 (s, 2H), 7.99 (d, 2H), 7.75 (d, 1H), 7.16 (d, 2H), 4.68 (s, 2H), 3.75 (s, 2H), 3.55 (t, 4H), 3.40 (t, 4H)

Example 63. 2-[2-(aminomethyl)-3,3-difluoro-allyl]-4-[2-[6-(dimethylamino)-3-pyridyl]-4-pyridyl]-1,2,4-triazol-3-one trifluoroacetate 40 mg of the title compound (yield: 46.1%) was prepared in the same fashion as Example 17, except that in Step 1, 100 mg of tert-butyl N-[2-[[4-(2-bromo-4-pyridyl)-5-oxo-1,2,4-triazol-1-yl]methyl]-3,3-difluoro-allyl]carbamate prepared in Reference Example 33 was used instead of tert-butyl N-[2-[[4-(3-bromophenyl)-5-oxo-1,2,4-triazol-1-yl]methyl]-3,3-difluoro-allyl]carbamate prepared in Reference Example 25 and 56 mg of 6-(dimethylamino)pyridine-3-boronic acid was used instead of 4-(methanesulfonyl)phenylboronic acid. $^1$H-NMR (MeOD, 400 MHz) δ 8.75 (d, 1H), 8.65 (d, 3H), 8.34 (s, 1H), 7.90 (d, 1H), 7.36 (d, 1H), 4.68 (s, 2H), 3.76 (s, 2H), 3.37 (s, 6H)

Example 64. 2-[2-(aminomethyl)-3,3-difluoro-allyl]-4-[2-(1,3-benzodioxol-5-yl)-4-pyridyl]-1,2,4-triazol-3-one trifluoroacetate 38 mg of the title compound (yield: 43.8%) was prepared in the same fashion as Example 17, except that in Step 1, 100 mg of tert-butyl N-[2-[[4-(2-bromo-4-pyridyl)-5-oxo-1,2,4-triazol-1-yl]methyl]-3,3-difluoro-allyl]carbamate prepared in Reference Example 33 was used instead of tert-butyl N-[2-[[4-(3-bromophenyl)-5-oxo-1,2,4-triazol-1-yl]methyl]-3,3-difluoro-allyl]carbamate prepared in Reference Example 25 and 67 mg of 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 8.63 (d, 1H), 8.59 (s, 1H), 8.19 (s, 1H), 7.78 (d, 1H), 7.52 (d, 1H), 7.49 (s, 1H), 6.93 (d, 1H), 4.67 (s, 2H), 3.75 (s, 2H)

Example 65. 6-[4-[1-[2-(aminomethyl)-3,3-difluoro-allyl]-5-oxo-1,2,4-triazol-4-yl]-2-pyridyl]-8-methyl-3,4-dihydro-1H-quinolin-2-one trifluoroacetate 42 mg of the title compound (yield: 44.0%) was prepared in the same fashion as Example 17, except that in Step 1, 100 mg of tert-butyl N-[2-[[4-(2-bromo-4-pyridyl)-5-oxo-1,2,4-triazol-1-yl]methyl]-3,3-difluoro-allyl]carbamate prepared in Reference Example 33 was used instead of tert-butyl N-[2-[[4-(3-bromophenyl)-5-oxo-1,2,4-triazol-1-yl]methyl]-3,3-difluoro-allyl]carbamate prepared in Reference Example 25 and 64 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 8.66 (d, 1H), 8.64 (s, 1H), 8.27 (s, 1H), 7.82 (d, 1H), 7.71 (s, 2H), 3.03 (t, 2H), 2.61 (t, 2H), 2.29 (s, 3H)

Example 66. 6-[4-[1-[2-(aminomethyl)-3,3-difluoro-allyl]-5-oxo-1,2,4-triazol-4-yl]-2-pyridyl]-1-methyl-3,4-dihydroquinolin-2-one trifluoroacetate 46 mg of the title compound (yield: 48.2%) was prepared in the same fashion as Example 17, except that in Step 1, 100 mg of tert-butyl N-[2-[[4-(2-bromo-4-pyridyl)-5-oxo-1,2,4-triazol-1-yl]methyl]-3,3-difluoro-allyl]carbamate prepared in Reference Example 33 was used instead of tert-butyl N-[2-[[4-(3-bromophenyl)-5-oxo-1,2,4-triazol-1-yl]methyl]-3,3-difluoro-allyl]carbamate prepared in Reference Example 25 and 64 mg of (1-methyl-2-oxo-1,2,3,4-tetrahydroquinolin-6-yl)boronic acid pinacol ester was used instead of 4-(methanesulfonyl)phenylboronic acid. $^1$H-NMR (MeOD, 400 MHz) δ 8.76 (d, 1H), 8.74 (s, 1H), 8.52 (s, 1H), 8.13 (s, 1H), 7.95 (d, 1H), 7.90 (s, 1H), 7.32 (d, 1H), 4.69 (s, 2H), 3.76 (s, 2H), 3.41 (s, 3H), 3.05 (t, 2H), 2.70 (t, 2H)

Example 67. 2-[2-(aminomethyl)-3,3-difluoro-allyl]-4-[2-(1-ethylpyrazol-4-yl)-4-pyridyl]-1,2,4-triazol-3-one trifluoroacetate 42 mg of the title compound (yield: 51.9%) was prepared in the same fashion as Example 17, except that in Step 1, 100 mg of tert-butyl N-[2-[[4-(2-bromo-4-pyridyl)-5-oxo-1,2,4-triazol-1-yl]methyl]-3,3-difluoro-allyl]carbamate prepared in Reference Example 33 was used instead of tert-butyl N-[2-[[4-(3-bromophenyl)-5-oxo-1,2,4-triazol-1-yl]methyl]-3,3-difluoro-allyl]carbamate prepared in Reference Example 25 and 50 mg of 1-ethylpyrazole-4-boronic acid pinacol ester was used instead of 4-(methanesulfonyl)phenylboronic acid. $^1$H-NMR (MeOD, 400 MHz) δ 8.60 (s, 1H), 8.58 (d, 1H), 8.28 (s, 1H), 8.10 (d, 2H), 7.76 (d, 1H), 4.67 (s, 2H), 4.26 (q, 2H), 3.75 (s, 2H), 1.52 (t, 3H)

Example 68. 2-[2-(aminomethyl)-3,3-difluoro-allyl]-4-[3-methyl-5-(4-methylsulfonylphenyl)-2-pyridyl]-1,2,4-triazol-3-one trifluoroacetate 38 mg of the title compound (yield: 80.1%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.74 (s, 1H), 8.25 (s, 1H), 8.21 (s, 1H), 8.09 (d, 2H), 7.99 (d, 2H), 4.69 (s, 2H), 3.77 (s, 2H), 3.19 (s, 3H), 2.45 (s, 3H)

Example 69. 2-[2-(aminomethyl)-3,3-difluoro-allyl]-4-[3-methyl-5-(4-piperazin-1-ylphenyl)-2-pyridyl]-1,2,4-triazol-3-one ditrifluoroacetate 39 mg of the title compound (yield: 81.0%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 51 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 8.63 (s, 1H), 8.16 (s, 1H), 8.11 (s, 1H), 7.68 (d, 2H), 7.17 (d, 2H), 4.68 (s, 2H), 3.73 (s, 2H), 3.51 (s, 4H), 3.40 (s, 4H), 2.40 (s, 3H)

Example 70. 2-[2-(aminomethyl)-3,3-difluoro-allyl]-4-[3-methyl-5-[6-(trifluoromethyl)-3-pyridyl]-2-pyridyl]-1,2,4-triazol-3-one trifluoroacetate 35 mg of the title compound (yield: 75.3%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of 2-(trifluoromethyl)pyridine-5-boronic acid pinacol ester was used instead of 4-(methanesulfonyl)phenylboronic acid. $^1$H-NMR (MeOD, 400 MHz) δ 9.09 (s, 1H), 8.80 (s, 1H), 8.41 (d, 1H), 8.32 (s, 1H), 8.22 (s, 1H), 7.98 (d, 1H), 4.69 (s, 2H), 3.77 (s, 2H), 2.47 (s, 3H)

Example 71. 2-[2-(aminomethyl)-3,3-difluoro-allyl]-4-[5-[6-(dimethylamino)-3-pyridyl]-3-methyl-2-pyridyl]-1,2,4-triazol-3-one trifluoroacetate 30 mg of the title compound (yield: 68.6%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 32 mg of 6-(dimethylamino)pyridine-3-boronic acid was used instead of 4-(methanesulfonyl)phenylboronic acid. $^1$H-NMR (MeOD, 400 MHz) δ 8.68 (s, 1H), 8.35 (s, 1H), 8.24 (d, 1H), 8.18 (s, 2H), 7.21 (d, 1H), 4.68 (s, 2H), 3.76 (s, 2H), 3.31 (s, 6H), 2.43 (s, 3H)

Example 72. 2-[2-(aminomethyl)-3,3-difluoro-allyl]-4-[5-(1,3-benzodioxol-5-yl)-3-methyl-2-pyridyl]-1,2,4-triazol-3-one trifluoroacetate 32 mg of the title compound (yield: 73.1%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of 3,4-(methylenedioxy)phenyl boronic acid was used instead of 4-(methanesulfonyl)phenylboronic acid. $^1$H-NMR (MeOD, 400 MHz) δ 8.59 (s, 1H), 8.16 (s, 1H), 8.07 (s, 1H), 7.21 (s, 1H), 7.20 (d, 1H), 6.96 (d, 1H), 6.03 (s, 2H), 4.68 (s, 2H), 3.76 (s, 2H), 2.40 (s, 3H)

Example 73. 6-[6-[1-[2-(aminomethyl)-3,3-difluoro-allyl]-5-oxo-1,2,4-triazol-4-yl]-5-methyl-3-pyridyl]-8-methyl-3,4-dihydro-1H-quinolin-2-one trifluoroacetate 40 mg of the title compound (yield: 83.3%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 37 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 8.54 (s, 1H), 8.16 (s, 1H), 8.06 (s, 1H), 7.36 (d, 2H), 4.70 (s, 2H), 3.78 (s, 2H), 3.01 (t, 2H), 2.59 (t, 2H), 2.40 (s, 3H), 2.29 (s, 3H)

Example 74. 6-[6-[1-[2-(aminomethyl)-3,3-difluoro-allyl]-5-oxo-1,2,4-triazol-4-yl]-5-methyl-3-pyridyl]-1-methyl-3,4-dihydroquinolin-2-one trifluoroacetate 42 mg of the title compound (yield: 87.5%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 37 mg of (1-methyl-2-oxo-1,2,3,4-tetrahydroquinolin-6-yl)boronic acid pinacol ester was used instead of 4-(methanesulfonyl)phenylboronic acid. $^1$H-NMR (MeOD, 400 MHz) δ 8.65 (s, 1H), 8.16 (d, 2H), 7.64 (d, 1H), 7.60 (s, 1H), 7.25 (d, 1H), 4.69 (s, 2H), 3.77 (s, 2H), 3.39 (s, 3H), 3.01 (t, 2H), 2.67 (t, 2H), 2.42 (s, 3H)

Example 75. 2-[2-(aminomethyl)-3,3-difluoro-allyl]-4-[5-(1-ethylpyrazol-4-yl)-3-methyl-2-pyridyl]-1,2,4-triazol-3-one trifluoroacetate 32 mg of the title compound (yield: 78.2%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 29 mg of 1-ethylpyrazole-4-boronic acid pinacol ester was used instead of 4-(methanesulfonyl)phenylboronic acid. $^1$H-NMR (MeOD, 400 MHz) δ 8.63 (s, 1H), 8.23 (s, 1H), 8.15 (s, 1H), 8.09 (s, 1H), 7.99 (s, 1H), 4.68 (s, 2H), 4.25 (q, 2H), 3.75 (s, 2H), 2.36 (s, 3H), 1.51 (t, 3H)

Example 76. 2-[2-(aminomethyl)-3,3-difluoro-allyl]-4-[5-methyl-6-(4-methylsulfonylphenyl)-3-pyridyl]-1,2,4-triazol-3-one trifluoroacetate 25 mg of the title compound (yield: 52.3%) was prepared in the same fashion as Example 17, except that in Step 1, 50 mg of tert-butyl N-[2-[[4-(6-bromo-5-methyl-3-pyridyl)-5-oxo-1,2,4-triazol-1-yl]methyl]-3,3-difluoro-allyl]carbamate prepared in Reference Example 36 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.87 (s, 1H), 8.43 (s, 1H), 8.15-8.08 (m, 3H), 7.81 (d, 2H), 4.69 (s, 2H), 3.77 (s, 2H), 3.20 (s, 3H), 2.44 (s, 3H)

Example 77. 2-[2-(aminomethyl)-3,3-difluoro-allyl]-4-[5-methyl-6-[6-(trifluoromethyl)-3-pyridyl]-3-pyridyl]-1,2,4-triazol-3-one trifluoroacetate 17 mg of the title compound (yield: 35.8%) was prepared in the same fashion as Example 17, except that in Step 1, 50 mg of tert-butyl N-[2-[[4-(6-bromo-5-methyl-3-pyridyl)-5-oxo-1,2,4-triazol-1-yl]methyl]-3,3-difluoro-allyl]carbamate prepared in Reference Example 36 was used instead of tert-butyl N-[2-[[4-(3-bromophenyl)-5-oxo-1,2,4-triazol-1-yl]methyl]-3,3-difluoro-allyl]carbamate prepared in Reference Example 25 and 30 mg of 2-(trifluoromethyl)pyridine-5-boronic acid pinacol ester was used instead of 4-(methanesulfonyl)phenylboronic acid. $^1$H-NMR (MeOD, 400 MHz) δ 8.93 (s, 2H), 8.45 (s, 1H), 8.27 (s, 1H), 8.19 (s, 1H), 7.97 (s, 1H), 4.68 (s, 2H), 3.77 (s, 2H), 2.49 (s, 3H)

Example 78. 2-[2-(aminomethyl)-3,3-difluoro-allyl]-4-[6-[6-(dimethylamino)-3-pyridyl]-5-methyl-3-pyridyl]-1,2,4-triazol-3-one trifluoroacetate 19 mg of the title compound (yield: 44.0%) was prepared in the same fashion as Example 17, except that in Step 1, 50 mg of tert-butyl N-[2-[[4-(6-bromo-5-methyl-3-pyridyl)-5-oxo-1,2,4-triazol-1-yl]methyl]-3,3-difluoro-allyl]carbamate prepared in Reference Example 36 was used instead of tert-butyl N-[2-[[4-(3-bromophenyl)-5-oxo-1,2,4-triazol-1-yl]methyl]-3,3-difluoro-allyl]carbamate prepared in Reference Example 25 and 27 mg of 6-(dimethylamino)pyridine-3-boronic acid was used instead of 4-(methanesulfonyl)phenylboronic acid. $^1$H-NMR (MeOD, 400 MHz) δ 8.83 (s, 1H), 8.40 (s, 1H), 8.23 (s, 1H), 8.10 (s, 1H), 8.02 (s, 1H), 7.06 (s, 1H), 4.68 (s, 2H), 3.76 (s, 2H), 3.26 (s, 6H), 2.50 (s, 3H)

Example 79. 2-[2-(aminomethyl)-3,3-difluoro-allyl]-4-[6-(1,3-benzodioxol-5-yl)-5-methyl-3-pyridyl]-1,2,4-triazol-3-one trifluoroacetate 26 mg of the title compound (yield: 59.6%) was prepared in the same fashion as Example 17, except that in Step 1, 50 mg of tert-butyl N-[2-[[4-(6-bromo-5-methyl-3-pyridyl)-5-oxo-1,2,4-triazol-1-yl]methyl]-3,3-difluoro-allyl]carbamate prepared in Reference Example 36 was used instead of tert-butyl N-[2-[[4-(3-bromophenyl)-5-oxo-1,2,4-triazol-1-yl]methyl]-3,3-difluoro-allyl]carbamate prepared in Reference Example 25 and 27 mg of 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 8.76 (s, 1H), 8.39 (s, 1H), 8.07 (s, 1H), 7.01-6.96 (m, 3H), 6.04 (s, 2H), 4.67 (s, 2H), 3.76 (s, 2H), 2.43 (s, 3H)

Example 80. 6-[5-[1-[2-(aminomethyl)-3,3-difluoro-allyl]-5-oxo-1,2,4-triazol-4-yl]-3-methyl-2-pyridyl]-8-methyl-3,4-dihydro-1H-quinolin-2-one trifluoroacetate 17 mg of the title compound (yield: 35.8%) was prepared in the same fashion as Example 17, except that in Step 1, 50 mg of tert-butyl N-[2-[[4-(6-bromo-5-methyl-3-pyridyl)-5-oxo-1,2,4-triazol-1-yl]methyl]-3,3-difluoro-allyl]carbamate prepared in Reference Example 36 was used instead of tert-butyl N-[2-[[4-(3-bromophenyl)-5-oxo-1,2,4-triazol-1-yl]methyl]-3,3-difluoro-allyl]carbamate prepared in Reference Example 25 and 32 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 8.77 (s, 1H), 8.40 (s, 1H), 8.07 (s, 1H), 7.23 (s, 2H), 4.68 (s, 2H), 3.77 (s, 2H), 3.02 (t, 2H), 2.62 (t, 2H), 2.44 (s, 3H), 2.34 (s, 3H)

Example 81. 6-[5-[1-[2-(aminomethyl)-3,3-difluoro-allyl]-5-oxo-1,2,4-triazol-4-yl]-3-methyl-2-pyridyl]-1-methyl-3,4-dihydroquinolin-2-one trifluoroacetate 22 mg of the title compound (yield: 46.8%) was prepared in the same fashion as Example 17, except that in Step 1, 50 mg of tert-butyl N-[2-[[4-(6-bromo-5-methyl-3-pyridyl)-5-oxo-1,2,4-triazol-1-yl]methyl]-3,3-difluoro-allyl]carbamate prepared in Reference Example 36 was used instead of tert-butyl N-[2-[[4-(3-bromophenyl)-5-oxo-1,2,4-triazol-1-yl]methyl]-3,3-difluoro-allyl]carbamate prepared in Reference Example 25 and 32 mg of (1-methyl-2-oxo-1,2,3,4-tetrahydroquinolin-6-yl)boronic acid pinacol ester was used instead of 4-(methanesulfonyl)phenylboronic acid. $^{1}$H-NMR (MeOD, 400 MHz) δ 8.80 (s, 1H), 8.41 (s, 1H), 8.09 (s, 1H), 7.46 (d, 1H), 7.42 (s, 1H), 7.25 (d, 1H), 4.68 (s, 2H), 3.77 (s, 2H), 3.42 (s, 3H), 3.01 (t, 2H), 2.69 (t, 2H), 2.45 (s, 3H)

Example 82. 2-[2-(aminomethyl)-3,3-difluoro-allyl]-4-[3-fluoro-5-(4-methylsulfonylphenyl)-2-pyridyl]-1,2,4-triazol-3-one trifluoroacetate 23 mg of the title compound (yield: 48.1%) was prepared in the same fashion as Example 17, except that in Step 1, 50 mg of tert-butyl N-[2-[[4-(5-bromo-3-fluoro-2-pyridyl)-5-oxo-1,2,4-triazol-1-yl]methyl]-3,3-difluoro-allyl]carbamate prepared in Reference Example 37 was used instead of tert-butyl N-[2-[[4-(3-bromophenyl)-5-oxo-1,2,4-triazol-1-yl]methyl]-3,3-difluoro-allyl]carbamate prepared in Reference Example 25. $^{1}$H-NMR (MeOD, 400 MHz) δ 8.77 (s, 1H), 8.31 (s, 1H), 8.28 (s, 1H), 8.11 (d, 2H), 8.02 (d, 2H), 4.69 (s, 2H), 3.77 (s, 2H), 3.19 (s, 3H)

Example 83. 2-[2-(aminomethyl)-3,3-difluoro-allyl]-4-[3-fluoro-5-(4-piperazin-1-ylphenyl)-2-pyridyl]-1,2,4-triazol-3-one ditrifluoroacetate 18 mg of the title compound (yield: 38.9%) was prepared in the same fashion as Example 17, except that in Step 1, 50 mg of tert-butyl N-[2-[[4-(5-bromo-3-fluoro-2-pyridyl)-5-oxo-1,2,4-triazol-1-yl]methyl]-3,3-difluoro-allyl]carbamate prepared in Reference Example 37 was used instead of tert-butyl N-[2-[[4-(3-bromophenyl)-5-oxo-1,2,4-triazol-1-yl]methyl]-3,3-difluoro-allyl]carbamate prepared in Reference Example 25 and 42 mg of tert-butyl 4-[4-(tetramethyl-1,3,2-dioxaborolan-2-yl)phenyl]piperazine-1-carboxylate was used instead of 4-(methanesulfonyl)phenylboronic acid. $^{1}$H-NMR (MeOD, 400 MHz) δ 8.67 (s, 1H), 8.24 (s, 1H), 8.12 (d, 1H), 7.72 (d, 2H), 7.18 (d, 2H), 4.68 (s, 2H), 3.76 (s, 2H), 3.54 (t, 4H), 3.41 (t, 4H)

Example 84. 2-[2-(aminomethyl)-3,3-difluoro-allyl]-4-[3-fluoro-5-[6-(trifluoromethyl)-3-pyridyl]-2-pyridyl]-1,2,4-triazol-3-one trifluoroacetate 21 mg of the title compound (yield: 44.4%) was prepared in the same fashion as Example 17, except that in Step 1, 50 mg of tert-butyl N-[2-[[4-(5-bromo-3-fluoro-2-pyridyl)-5-oxo-1,2,4-triazol-1-yl]methyl]-3,3-difluoro-allyl]carbamate prepared in Reference Example 37 was used instead of tert-butyl N-[2-[[4-(3-bromophenyl)-5-oxo-1,2,4-triazol-1-yl]methyl]-3,3-difluoro-allyl]carbamate prepared in Reference Example 25 and 29 mg of 2-(trifluoromethyl)pyridine-5-boronic acid pinacol ester was used instead of 4-(methanesulfonyl)phenylboronic acid. $^{1}$H-NMR (MeOD, 400 MHz) δ 9.13 (s, 1H), 8.83 (s, 1H), 8.44 (d, 2H), 8.29 (s, 1H), 8.00 (s, 1H), 4.69 (s, 2H), 3.77 (s, 2H)

Example 85. 2-[2-(aminomethyl)-3,3-difluoro-allyl]-4-[5-(1,3-benzodioxol-5-yl)-3-fluoro-2-pyridyl]-1,2,4-triazol-3-one trifluoroacetate 32 mg of the title compound (yield: 74.1%) was prepared in the same fashion as Example 17, except that in Step 1, 50 mg of tert-butyl N-[2-[[4-(5-bromo-3-fluoro-2-pyridyl)-5-oxo-1,2,4-triazol-1-yl]methyl]-3,3-difluoro-allyl]carbamate prepared in Reference Example 37 was used instead of tert-butyl N-[2-[[4-(3-bromophenyl)-5-oxo-1,2,4-triazol-1-yl]methyl]-3,3-difluoro-allyl]carbamate prepared in Reference Example 25 and 27 mg of 2-(1,3-benzodioxol-5-yl)-4,4,5,5-tetramethyl-1,3,2-dioxaborolane was used instead of 4-(methanesulfonyl)phenylboronic acid. $^{1}$H-NMR (MeOD, 400 MHz) δ 8.60 (s, 1H), 8.22 (s, 1H), 8.07 (d, 1H), 7.24 (s, 1H), 7.22 (s, 1H), 6.96 (d, 1H), 6.04 (s, 2H), 4.68 (s, 2H), 3.74 (s, 2H)

Example 86. 6-[6-[1-[2-(aminomethyl)-3,3-difluoro-allyl]-5-oxo-1,2,4-triazol-4-yl]-5-fluoro-3-pyridyl]-8-methyl-3,4-dihydro-1H-quinolin-2-one trifluoroacetate 17 mg of the title compound (yield: 35.2%) was prepared in the same fashion as Example 17, except that in Step 1, 50 mg of tert-butyl N-[2-[[4-(5-bromo-3-fluoro-2-pyridyl)-5-oxo-1,2,4-triazol-1-yl]methyl]-3,3-difluoro-allyl]carbamate prepared in Reference Example 37 was used instead of tert-butyl N-[2-[[4-(3-bromophenyl)-5-oxo-1,2,4-triazol-1-yl]methyl]-3,3-difluoro-allyl]carbamate prepared in Reference Example 25 and 31 mg of 8-methyl-2-oxo-1,2,3,4-tetrahydroquinoline-6-boronic acid pinacol ester was used instead of 4-(methanesulfonyl)phenylboronic acid. $^{1}$H-NMR (MeOD, 400 MHz) δ 8.58 (s, 1H), 8.23 (s, 1H), 8.07 (d, 1H), 7.41 (s, 1H), 4.69 (s, 2H), 3.78 (s, 2H), 3.01 (t, 2H), 2.59 (t, 2H), 2.31 (s, 3H)

Example 87. 6-[6-[1-[2-(aminomethyl)-3,3-difluoro-allyl]-5-oxo-1,2,4-triazol-4-yl]-5-fluoro-3-pyridyl]-1-methyl-3,4-dihydroquinolin-2-one trifluoroacetate 18 mg of the title compound (yield: 38.9%) was prepared in the same fashion as Example 17, except that in Step 1, 50 mg of tert-butyl N-[2-[[4-(5-bromo-3-fluoro-2-pyridyl)-5-oxo-1,2,4-triazol-1-yl]methyl]-3,3-difluoro-allyl]carbamate prepared in Reference Example 37 was used instead of tert-butyl N-[2-[[4-(3-bromophenyl)-5-oxo-1,2,4-triazol-1-yl]methyl]-3,3-difluoro-allyl]carbamate prepared in Reference Example 25 and 31 mg of (1-methyl-2-oxo-1,2,3,4-tetrahydroquinolin-6-yl)boronic acid pinacol ester was used instead of 4-(methanesulfonyl)phenylboronic acid. $^{1}$H-NMR (MeOD, 400 MHz) δ 8.68 (s, 1H), 8.25 (s, 1H), 8.17 (d, 1H), 7.68 (d, 1H), 7.64 (s, 1H), 7.27 (d, 1H), 4.68 (s, 2H), 3.77 (s, 2H), 3.39 (s, 3H), 3.02 (t, 2H), 2.66 (t, 2H)

Example 88. 2-[2-(aminomethyl)-3,3-difluoro-allyl]-4-[5-(1-ethylpyrazol-4-yl)-3-fluoro-2-pyridyl]-1,2,4-triazol-3-one trifluoroacetate 18 mg of the title compound (yield: 45.4%) was prepared in the same fashion as Example 17, except that in Step 1, 50 mg of tert-butyl N-[2-[[4-(5-bromo-3-fluoro-2-pyridyl)-5-oxo-1,2,4-triazol-1-yl]methyl]-3,3-difluoro-allyl]carbamate prepared in Reference Example 37 was used instead of tert-butyl N-[2-[[4-(3-bromophenyl)-5-oxo-1,2,4-triazol-1-yl]methyl]-3,3-difluoro-allyl]carbamate prepared in Reference Example 25 and 37 mg of 1-ethylpyrazole-4-boronic acid pinacol ester was used instead of 4-(methanesulfonyl)phenylboronic acid. $^1$H-NMR (MeOD, 400 MHz) δ 8.65 (s, 1H), 8.28 (s, 1H), 8.21 (s, 1H), 8.10 (d, 1H), 8.03 (s, 1H), 4.67 (s, 2H), 4.26 (q, 2H), 3.75 (s, 2H), 1.50 (t, 3H)

Example 89. 2-[2-(aminomethyl)-3,3-difluoro-allyl]-4-[5-(4-methylsulfonylphenyl)-pyrazin-2-yl]-1,2,4-triazol-3-one trifluoroacetate 38 mg of the title compound (yield: 57.3%) was prepared in the same fashion as Example 17, except that in Step 1, 70 mg of tert-butyl N-[2-[[4-(5-bromopyrazin-2-yl)-5-oxo-1,2,4-triazol-1-yl]methyl]-3,3-difluoro-allyl]carbamate prepared in Reference Example 39 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 9.53 (s, 1H), 9.04 (s, 1H), 8.63 (s, 1H), 8.30 (d, 2H), 8.03 (d, 2H), 4.69 (s, 2H), 3.78 (s, 2H), 3.17 (s, 3H)

Example 90. 2-[2-(aminomethyl)-3,3-difluoro-allyl]-4-[5-(4-piperazin-1-ylphenyl)pyrazin-2-yl]-1,2,4-triazol-3-one ditrifluoroacetate 30 mg of the title compound (yield: 44.6%) was prepared in the same fashion as Example 17, except that in Step 1, 70 mg of tert-butyl N-[2-[[4-(5-bromopyrazin-2-yl)-5-oxo-1,2,4-triazol-1-yl]methyl]-3,3-difluoro-allyl]carbamate prepared in Reference Example 39 was used instead of tert-butyl N-[2-[[4-(3-bromophenyl)-5-oxo-1,2,4-triazol-1-yl]methyl]-3,3-difluoro-allyl]carbamate prepared in Reference Example 25 and 61 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 9.45 (s, 1H), 8.98 (s, 1H), 8.63 (s, 1H), 8.07 (d, 2H), 7.18 (d, 2H), 4.68 (s, 2H), 3.76 (s, 2H), 3.56 (t, 4H), 3.41 (t, 4H)

Example 91. 2-[2-(aminomethyl)-3,3-difluoro-allyl]-4-[5-[6-(trifluoromethyl)-3-pyridyl]pyrazin-2-yl]-1,2,4-triazol-3-one trifluoroacetate 32 mg of the title compound (yield: 49.3%) was prepared in the same fashion as Example 17, except that in Step 1, 70 mg of tert-butyl N-[2-[[4-(5-bromopyrazin-2-yl)-5-oxo-1,2,4-triazol-1-yl]methyl]-3,3-difluoro-allyl]carbamate prepared in Reference Example 39 was used instead of tert-butyl N-[2-[[4-(3-bromophenyl)-5-oxo-1,2,4-triazol-1-yl]methyl]-3,3-difluoro-allyl]carbamate prepared in Reference Example 25 and 43 mg of 2-(trifluoromethyl)pyridine-5-boronic acid pinacol ester was used instead of 4-(methanesulfonyl)phenylboronic acid. $^1$H-NMR (MeOD, 400 MHz) δ 9.64 (s, 1H), 9.43 (s, 1H), 9.20 (s, 1H), 8.75 (d, 1H), 8.68 (s, 2H), 7.98 (d, 1H), 4.69 (s, 2H), 3.78 (s, 2H)

Example 92. 2-[2-(aminomethyl)-3,3-difluoro-allyl]-4-[5-[6-(dimethylamino)-3-pyridyl]pyrazin-2-yl]-1,2,4-triazol-3-one trifluoroacetate 29 mg of the title compound (yield: 47.6%) was prepared in the same fashion as Example 17, except that in Step 1, 70 mg of tert-butyl N-[2-[[4-(5-bromopyrazin-2-yl)-5-oxo-1,2,4-triazol-1-yl]methyl]-3,3-difluoro-allyl]carbamate prepared in Reference Example 39 was used instead of tert-butyl N-[2-[[4-(3-bromophenyl)-5-oxo-1,2,4-triazol-1-yl]methyl]-3,3-difluoro-allyl]carbamate prepared in Reference Example 25 and 39 mg of 6-(dimethylamino)pyridine-3-boronic acid was used instead of 4-(methanesulfonyl)phenylboronic acid. $^1$H-NMR (MeOD, 400 MHz) δ 9.48 (s, 1H), 8.97 (s, 1H), 8.76 (s, 1H), 8.63 (s, 1H), 8.44 (d, 1H), 7.05 (d, 1H), 4.68 (s, 2H), 3.76 (s, 2H), 3.32 (s, 6H)

Example 93. 2-[2-(aminomethyl)-3,3-difluoro-allyl]-4-[5-(1,3-benzodioxol-5-yl)pyrazin-2-yl]-1,2,4-triazol-3-one trifluoroacetate 35 mg of the title compound (yield: 57.4%) was prepared in the same fashion as Example 17, except that in Step 1, 70 mg of tert-butyl N-[2-[[4-(5-bromopyrazin-2-yl)-5-oxo-1,2,4-triazol-1-yl]methyl]-3,3-difluoro-allyl]carbamate prepared in Reference Example 39 was used instead of tert-butyl N-[2-[[4-(3-bromophenyl)-5-oxo-1,2,4-triazol-1-yl]methyl]-3,3-difluoro-allyl]carbamate prepared in Reference Example 25 and 39 mg of 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 9.44 (s, 1H), 8.91 (s, 1H), 8.61 (s, 1H), 7.64 (d, 1H), 7.60 (s, 1H), 6.96 (d, 1H), 6.05 (s, 2H), 4.67 (s, 2H), 3.69 (s, 2H)

Example 94. 6-[5-[1-[2-(aminomethyl)-3,3-difluoro-allyl]-5-oxo-1,2,4-triazol-4-yl]pyrazin-2-yl]-1-methyl-3,4-dihydro-TH-quinolin-2-one trifluoroacetate 41 mg of the title compound (yield: 61.1%) was prepared in the same fashion as Example 17, except that in Step 1, 70 mg of tert-butyl N-[2-[[4-(5-bromopyrazin-2-yl)-5-oxo-1,2,4-triazol-1-yl]methyl]-3,3-difluoro-allyl]carbamate prepared in Reference Example 39 was used instead of tert-butyl N-[2-[[4-(3-bromophenyl)-5-oxo-1,2,4-triazol-1-yl]methyl]-3,3-difluoro-allyl]carbamate prepared in Reference Example 25 and 45 mg of (1-methyl-2-oxo-1,2,3,4-tetrahydroquinolin-6-yl)boronic acid pinacol ester was used instead of 4-(methanesulfonyl)phenylboronic acid. $^1$H-NMR (MeOD, 400 MHz) δ 9.47 (s, 1H), 8.98 (s, 1H), 8.64 (s, 1H), 8.03 (d, 1H), 7.99 (s, 1H), 7.25 (d, 1H), 4.68 (s, 2H), 3.77 (s, 2H), 3.39 (s, 3H), 3.03 (t, 2H), 2.68 (t, 2H)

Example 95. 2-[2-(aminomethyl)-3,3-difluoro-allyl]-4-[5-(1-ethylpyrazol-4-yl)pyrazin-2-yl]-1,2,4-triazol-3-one trifluoroacetate 39 mg of the title compound (yield: 68.6%) was prepared in the same fashion as Example 17, except that in Step 1, 70 mg of tert-butyl N-[2-[[4-(5-bromopyrazin-2-yl)-5-oxo-1,2,4-triazol-1-yl]methyl]-3,3-difluoro-allyl]carbamate prepared in Reference Example 39 was used instead of tert-butyl N-[2-[[4-(3-bromophenyl)-5-oxo-1,2,4-triazol-1-yl]methyl]-3,3-difluoro-allyl]carbamate prepared in Reference Example 25 and 35 mg of 1-ethylpyrazole-4-boronic acid pinacol ester was used instead of 4-(methanesulfonyl)phenylboronic acid. $^1$H-NMR (MeOD, 400 MHz) δ 9.37 (s, 1H), 8.79 (s, 1H), 8.60 (s, 1H), 8.34 (s, 1H), 8.12 (s, 1H), 4.67 (s, 1H), 4.27 (q, 2H), 3.92 (s, 2H), 1.52 (t, 3H)

Example 96. 2-[2-(aminomethyl)-3,3-difluoro-allyl]-4-[(4-benzyloxyphenyl)methyl]-1,2,4-triazol-3-one trifluoroacetate 17 mg of the title compound (yield: 8.5%) as a colorless liquid was prepared in the same fashion as Example 1, except that 126 mg of tert-butyl N-[2-[[4-[(4-benzyloxyphenyl)methyl]-5-oxo-1,2,4-triazol-1-yl]methyl]-3,3-difluoro-allyl]carbamate prepared in Reference Example 40 was used. $^1$H-NMR (MeOD, 400 MHz) δ 7.88 (s, 1H), 7.41-7.36 (m, 4H), 7.29 (d, 3H), 6.99 (d, 2H), 5.08 (s, 2H), 4.79 (s, 2H), 4.57 (s, 2H), 3.66 (s, 2H)

Example 97. 2-[2-(aminomethyl)-3,3-difluoro-allyl]-4-[(5-bromo-2-thienyl)methyl]-1,2,4-triazol-3-one trifluoroacetate 92 mg of the title compound (yield: 1.0%) was prepared in the same fashion as Example 1, except that 116 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used. $^1$H-NMR (MeOD, 400 MHz) δ 7.96 (s, 1H), 6.98 (d, 2H), 5.00 (s, 2H), 4.58 (s, 2H), 3.67 (s, 2H)

Example 98. 2-[2-(aminomethyl)-3,3-difluoro-allyl]-4-[(4-bromo-2-thienyl)methyl]-1,2,4-triazol-3-one trifluoroacetate 34 mg of the title compound (yield: 76.0%) was prepared in the same fashion as Example 1, except that 57 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used. $^1$H-NMR (MeOD, 400 MHz) δ 7.97 (s, 1H), 7.40 (s, 1H), 7.12 (s, 1H), 5.04 (s, 2H), 4.57 (s, 2H), 3.66 (s, 2H)

Example 99. 2-[2-(aminomethyl)-3,3-difluoro-allyl]-4-[(5-bromo-3-methyl-2-thienyl)methyl]-1,2,4-triazol-3-one trifluoroacetate 16 mg of the title compound (yield: 3.7%) was prepared in the same fashion as Example 1, except that 546 mg of tert-butyl N-[2-[[4-(5-bromo-3-methyl-2-thienyl)methyl]-5-oxo-1,2,4-triazol-1-yl]methyl]-3,3-difluoro-allyl]carbamate prepared in Reference Example 43 was used. $^1$H-NMR (MeOD, 400 MHz) δ 7.90 (s, 1H), 6.90 (s, 1H), 4.94 (s, 2H), 4.57 (s, 2H), 3.67 (s, 2H), 2.27 (s, 3H)

Example 100. 4-[[5-(4-acetylphenyl)-2-thienyl]methyl]-2-[2-(aminomethyl)-3,3-difluoro-allyl]-1,2,4-triazol-3-one trifluoroacetate Step 1: tert-butyl N-[2-[[4-[[5-(4-acetylphenyl)-2-thienyl]methyl]-5-oxo-1,2,4-triazol-1-yl]methyl]-3,3-difluoro-allyl]carbamate 80 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 28 m of 4-acetylphenylboronicacid 28 were dissolved in 1.6 mL of 1,4-dioxane, followed by the addition of 0.9 mL of 1 M potassium carbonate and 7 mg of palladiumdi[1,1'-bis(diphenylphospino)ferrocene]dichloride (PdCl$_2$(dppf)), and the resulting solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 47 mg of the title compound (yield: 54.2%). MS (ESI) m/z=405.2 (M+H)+

Step 2: 4-[[5-(4-acetylphenyl)-2-thienyl]methyl]-2-[2-(aminomethyl)-3,3-difluoro-allyl]-1,2,4-triazol-3-one 47 mg of tert-butyl N-[2-[[4-[[5-(4-acetylphenyl)-2-thienyl]methyl]-5-oxo-1,2,4-triazol-1-yl]methyl]-3,3-difluoro-allyl]carbamate prepared in Step 1 was dissolved in 1.0 mL of dichloromethane, followed by the addition of 0.1 mL of trifluoroacetic acid, and the resulting solution was stirred at room temperature for 2 hours. The reaction mixture thus obtained was concentrated, followed by the addition of dichloromethane. The solution was concentrated under reduced pressure and then dried in vacuo to obtain a yellow liquid residue. The residue was purified with silica gel column chromatography (developing solvent: dichloromethane/methanol=10/1) to give 4 mg of the title compound as a white solid (yield: 12.0%). $^1$H-NMR (MeOD, 400 MHz) δ 8.00 (s, 1H), 7.99 (d, 2H), 7.72 (d, 2H), 7.43 (s, 1H), 7.18 (s, 1H), 5.09 (s, 2H), 4.60 (s, 2H), 3.69 (s, 2H), 2.60 (s, 3H)

Example 101. 2-[2-(aminomethyl)-3,3-difluoro-allyl]-4-[[5-(4-methylsulfonylphenyl)-2-thienyl]methyl]-1,2,4-triazol-3-one trifluoroacetate 42 mg of the title compound (yield: 82.2%) was prepared in the same fashion as Example 100, except that in Step 1, 26 mg of 4-(methanesulfonyl)phenylboronic acid was used instead of 4-acetylphenylboronicacid. $^1$H-NMR (MeOD, 400 MHz) δ 8.01 (s, 1H), 7.94 (d, 2H), 7.84 (d, 2H), 7.48 (s, 1H), 7.19 (s, 1H), 5.10 (s, 2H), 4.59 (s, 2H), 3.68 (s, 2H), 3.14 (s, 3H)

Example 102. 2-[2-(aminomethyl)-3,3-difluoro-allyl]-4-[[5-(3-methylsulfonylphenyl)-2-thienyl]methyl]-1,2,4-triazol-3-one trifluoroacetate 8 mg of the title compound (yield: 11.0%) was prepared in the same fashion as Example 100, except that in Step 1, 34 mg of 3-(methanesulfonyl)phenylboronic acid was used instead of 4-acetylphenylboronicacid. $^1$H-NMR (MeOD, 400 MHz) δ 8.11 (s, 1H), 8.00 (s, 1H), 7.92-7.86 (m, 2H), 7.64 (t, 1H), 7.42 (s, 1H), 7.17 (s, 1H), 5.09 (s, 2H), 4.60 (s, 2H), 3.69 (s, 2H), 3.17 (s, 3H)

Example 103. 3-[5-[[1-[2-(aminomethyl)-3,3-difluoro-allyl]-5-oxo-1,2,4-triazol-4-yl]methyl]-2-thienyl]-N,N-dimethyl-benzenesulfonamide trifluoroacetate 16 mg of the title compound (yield: 17.6%) was prepared in the same fashion as Example 100, except that in Step 1, 54 mg of 3-(N,N-dimethylaminosulfonyl)phenylboronic acid pinacol ester was used instead of 4-acetylphenylboronicacid. $^1$H-NMR (MeOD, 400 MHz) δ 8.00 (s, 1H), 7.92 (s, 2H), 7.72-7.63 (m, 2H), 7.42 (s, 1H), 7.19 (s, 1H), 5.10 (s, 2H), 4.60 (s, 2H), 3.68 (s, 2H), 2.72 (s, 6H)

Example 104. 4-[5-[[1-[2-(aminomethyl)-3,3-difluoro-allyl]-5-oxo-1,2,4-triazol-4-yl]methyl]-2-thienyl]-N-methyl-benzamide trifluoroacetate 22 mg of the title compound (yield: 29.4%) was prepared in the same fashion as Example 100, except that in Step 1, 36 mg of (4-(methylcarbamoyl)phenyl)boronic acid was used instead of 4-acetylphenylboronicacid. ¹H-NMR (MeOD, 400 MHz) δ 8.00 (s, 1H), 7.83 (d, 2H), 7.69 (d, 2H), 7.39 (s, 1H), 7.16 (s, 1H), 5.08 (s, 2H), 4.59 (s, 2H), 3.68 (s, 2H), 2.93 (s, 3H)

Example 105. 2-[2-(aminomethyl)-3,3-difluoro-allyl]-4-[[5-(3,4,5-trimethoxyphenyl)-2-thienyl]methyl]-1,2,4-triazol-3-one trifluoroacetate 22 mg of the title compound (yield: 45.4%) was prepared in the same fashion as Example 100, except that in Step 1, 23 mg of 3,4,5-trimethoxyphenylboronicacid was used instead of 4-acetylphenylboronicacid. ¹H-NMR (MeOD, 400 MHz) δ 7.98 (s, 1H), 7.24 (s, 1H), 7.12 (s, 1H), 6.85 (s, 2H), 5.05 (s, 2H), 4.59 (s, 2H), 3.88 (s, 6H), 3.78 (s, 3H), 3.67 (s, 2H)

Example 106. 2-[2-(aminomethyl)-3,3-difluoro-allyl]-4-[[5-(4-piperazin-1-ylphenyl)-2-thienyl]methyl]-1,2,4-triazol-3-one ditrifluoroacetate 40 mg of the title compound (yield: 81.8%) was prepared in the same fashion as Example 100, except that in Step 1, 50 mg of tert-butyl 4-[4-(tetramethyl-1,3,2-dioxaborolan-2-yl)phenyl]piperazine-1-carboxylate was used instead of 4-acetylphenylboronicacid. ¹H-NMR (MeOD, 400 MHz) δ 7.97 (s, 1H), 7.52 (d, 2H), 7.15 (s, 1H), 7.09 (s, 1H), 7.03 (d, 2H), 5.04 (s, 2H), 4.59 (s, 2H), 3.66 (s, 2H), 3.45 (s, 4H), 3.38 (s, 4H)

Example 107. 2-[2-(aminomethyl)-3,3-difluoro-allyl]-4-[[5-(3-piperazin-1-ylphenyl)-2-thienyl]methyl]-1,2,4-triazol-3-one ditrifluoroacetate 11 mg of the title compound (yield: 18.2%) was prepared in the same fashion as Example 100, except that in Step 1, 51 mg of tert-butyl 4-(3-(4,4,5,5-tetramethyl-1,3,2-dioxaborolan-2-yl)phenyl)piperazine-1-carboxylate was used instead of 4-acetylphenylboronicacid. ¹H-NMR (MeOD, 400 MHz) δ 7.98 (s, 1H), 7.33-7.29 (m, 2H), 7.22 (s, 1H), 7.18-7.13 (m, 2H), 6.99 (d, 1H), 5.06 (s, 2H), 4.59 (s, 2H), 3.64 (s, 2H), 3.45 (t, 4H), 3.38 (t, 4H)

Example 108. 4-[[5-[4-(4-acetylpiperazin-1-yl)phenyl]-2-thienyl]methyl]-2-[2-(aminomethyl)-3,3-difluoro-allyl]-1,2,4-triazol-3-one trifluoroacetate 695 mg of the title compound (yield: 66.0%) was prepared in the same fashion as Example 100, except that in Step 1, 923 mg of 4-(4-acetyl-1-piperazinyl)phenylboronic acid pinacol ester was used instead of 4-acetylphenylboronicacid. ¹H-NMR (MeOD, 400 MHz) δ 7.97 (s, 1H), 7.49 (d, 2H), 7.14 (d, 1H), 7.09 (d, 1H), 7.00 (d, 2H), 5.03 (s, 2H), 4.59 (s, 2H), 3.74 (t, 2H), 3.71 (t, 2H), 3.66 (s, 2H), 3.26 (t, 2H), 3.21 (t, 2H), 2.16 (s, 3H)

Example 109. 2-[2-(aminomethyl)-3,3-difluoro-allyl]-4-[[5-(4-morpholine-4-carbonyl)phenyl]-2-thienyl]methyl]-1,2,4-triazol-3-one trifluoroacetate 23 mg of the title compound (yield: 29.4%) was prepared in the same fashion as Example 100, except that in Step 1, 54 mg of 4-(morpholine-4-carbonyl)phenylboronic acid pinacol ester was used instead of 4-acetylphenylboronicacid. ¹H-NMR (MeOD, 400 MHz) δ 8.00 (s, 1H), 7.71 (d, 2H), 7.47 (d, 2H), 7.38 (s, 1H), 7.16 (s, 1H), 5.08 (s, 2H), 4.59 (s, 2H), 3.75-3.50 (m, 8H), 3.68 (s, 2H)

Example 110. 2-[2-(aminomethyl)-3,3-difluoro-allyl]-4-[[5-[3-(1H-pyrazol-3-yl)phenyl]-2-thienyl]methyl]-1,2,4-triazol-3-one trifluoroacetate 6 mg of the title compound (yield: 5.9%) was prepared in the same fashion as Example 100, except that in Step 1, 32 mg of [3-(1H-pyrazol-3-yl)phenyl]boronic acid was used instead of 4-acetylphenylboronicacid. ¹H-NMR (MeOD, 400 MHz) δ 8.04 (s, 1H), 8.00 (s, 1H), 7.70 (s, 2H), 7.56 (d, 1H), 7.46 (t, 1H), 7.37 (s, 1H), 7.17 (s, 1H), 6.73 (s, 1H), 5.09 (s, 2H), 4.60 (s, 2H), 3.65 (s, 2H)

Example 111. 2-[2-(aminomethyl)-3,3-difluoro-allyl]-4-[[5-[6-(trifluoromethyl)-3-pyridyl]-2-thienyl]methyl]-1,2,4-triazol-3-one trifluoroacetate 7 mg of the title compound (yield: 9.1%) was prepared in the same fashion as Example 100, except that in Step 1, 25 mg of 2-(trifluoromethyl)pyridine-5-boronic acid pinacol ester was used instead of 4-acetylphenylboronicacid. ¹H-NMR (MeOD, 400 MHz) δ 8.97 (s, 1H), 8.24 (d, 1H), 8.02 (s, 1H), 7.84 (d, 1H), 7.57 (s, 1H), 7.24 (s, 1H), 5.12 (s, 2H), 4.59 (s, 2H), 3.67 (s, 2H)

Example 112. 2-[2-(aminomethyl)-3,3-difluoro-allyl]-4-[[5-[6-(dimethylamino)-3-pyridyl]-2-thienyl]methyl]-1,2,4-triazol-3-one trifluoroacetate 45 mg of the title compound (yield: 1.0%) was prepared in the same fashion as Example 100, except that in Step 1, 32 mg of 6-(dimethylamino)pyridine-3-boronic acid was used instead of 4-acetylphenylboronicacid. ¹H-NMR (MeOD, 400 MHz) δ 8.11 (d, 2H), 7.99 (s, 1H), 7.28 (s, 1H), 7.17 (s, 2H), 5.08 (s, 2H), 4.59 (s, 2H), 3.68 (s, 2H), 3.28 (s, 6H)

Example 113. 2-[2-(aminomethyl)-3,3-difluoro-allyl]-4-[[5-(6-methoxy-3-pyridyl)-2-thienyl]methyl]-1,2,4-triazol-3-one trifluoroacetate 29 mg of the title compound (yield: 41.2%) was prepared in the same fashion as Example 100, except that in Step 1, 40 mg of 2-methoxy-5-(4,4,5,5-tetramethyl-1,3,2-dioxaborolan-2-yl)pyridine was used instead of 4-acetylphenylboronicacid. ¹H-NMR (MeOD, 400 MHz) δ 8.34 (s, 1H), 7.99 (s, 1H), 7.88 (d, 1H), 7.21 (s, 1H), 7.14 (s, 1H), 6.83 (d, 1H), 5.06 (s, 2H), 4.59 (s, 2H), 3.93 (s, 3H), 3.68 (s, 2H)

Example 114. 2-[2-(aminomethyl)-3,3-difluoro-allyl]-4-[[5-(6-piperazin-1-yl-3-pyridyl)-2-thienyl]methyl]-1,2,4-triazol-3-one ditrifluoroacetate 35 mg of the title compound (yield: 72.7%) was prepared in the same fashion as Example 100, except that in Step 1, 54 mg of tert-butyl 4-[5-(4,4,5,5-tetramethyl-1,3,2-dioxaborolan-2-yl)-2-pyridyl]piperazine-1-carboxylate was used instead of 4-acetylphenylboronicacid. ¹H-NMR (MeOD, 400 MHz) δ 8.41 (s, 1H), 7.98 (s, 1H), 7.83 (d, 1H), 7.15 (d, 2H), 6.96 (d, 1H), 5.06 (s, 2H), 4.59 (s, 2H), 3.85 (s, 4H), 3.68 (s, 2H), 3.32 (s, 4H)

Example 115. 2-[2-(aminomethyl)-3,3-difluoro-allyl]-4-[[5-[6-(dimethylamino)-5-fluoro-3-pyridyl]-2-thienyl]methyl]-1,2,4-triazol-3-one trifluoroacetate 26 mg of the title compound (yield: 35.3%) was prepared in the same fashion as Example 100, except that in Step 1, 46 mg of 3-fluoro-N,N-dimethyl-5-(4,4,5,5-tetramethyl-1,3,2-dioxaborolan-2-yl)pyridine-2-amine was used instead of 4-acetylphenylboronicacid. $^1$H-NMR (MeOD, 400 MHz) δ 8.13 (s, 1H), 7.98 (s, 1H), 7.54 (d, 1H), 7.17 (s, 1H), 7.11 (s, 1H), 5.05 (s, 2H), 4.59 (s, 2H), 3.68 (s, 2H), 3.11 (s, 6H)

Example 116. 2-[2-(aminomethyl)-3,3-difluoro-allyl]-4-[[5-(2-aminopyrimidin-5-yl)-2-thienyl]methyl]-1,2,4-triazol-3-one trifluoroacetate 25 mg of the title compound (yield: 41.2%) was prepared in the same fashion as Example 100, except that in Step 1, 55 mg of 2-(tert-butoxycarbonylamino)pyrimidine-5-boronic acid pinacol ester was used instead of 4-acetylphenyl-boronicacid. $^1$H-NMR (MeOD, 400 MHz) δ 8.47 (s, 2H), 7.98 (s, 1H), 7.15 (d, 2H), 5.06 (s, 2H), 4.59 (s, 2H), 3.66 (s, 2H)

Example 117. 2-[2-(aminomethyl)-3,3-difluoro-allyl]-4-[[5-(2-ethoxypyrimidin-5-yl)-2-thienyl]methyl]-1,2,4-triazol-3-one trifluoroacetate 21 mg of the title compound (yield: 29.4%) was prepared in the same fashion as Example 100, except that in Step 1, 29 mg of 2-ethoxypyrimidin-5-boronic acid was used instead of 4-acetylphenylboronicacid. $^1$H-NMR (MeOD, 400 MHz) δ 8.76 (s, 2H), 8.00 (s, 1H), 7.33 (s, 1H), 7.19 (s, 1H), 5.09 (s, 2H), 4.59 (s, 2H), 4.48 (q, 2H), 3.68 (s, 2H), 1.42 (t, 3H)

Example 118. 2-[2-(aminomethyl)-3,3-difluoro-allyl]-4-[[5-[2-(2-methoxyethylamino)pyrimidin-5-yl]-2-thienyl]methyl]-1,2,4-triazol-3-one trifluoroacetate 21 mg of the title compound (yield: 43.6%) was prepared in the same fashion as Example 100, except that in Step 1, 30 mg of N-(2-methoxyethyl)-5-(tetramethyl-1,3,2-dioxaborolan-2-yl)pyrimidine-2-amine was used instead of 4-acetylphenylboronicacid. $^1$H-NMR (MeOD, 400 MHz) δ 8.49 (s, 2H), 7.94 (s, 1H), 7.14 (d, 1H), 5.50 (s, 4H), 5.05 (s, 2H), 4.55 (s, 2H), 3.38-3.28 (m, 7H)

Example 119. 2-[2-(aminomethyl)-3,3-difluoro-allyl]-4-[[5-(1-ethylpyrazol-4-yl)-2-thienyl]methyl]-1,2,4-triazol-3-one trifluoroacetate 48 mg of the title compound (yield: 51.6%) was prepared in the same fashion as Example 100, except that in Step 1, 62 mg of 1-ethylpyrazole-4-boronic acid pinacol ester was used instead of 4-acetylphenylboronicacid. $^1$H-NMR (MeOD, 400 MHz) δ 7.96 (s, 1H), 7.89 (s, 1H), 7.66 (s, 1H), 7.06 (s, 1H), 7.01 (s, 1H), 5.02 (s, 2H), 4.58 (s, 2H), 4.18 (q, 2H), 3.67 (s, 2H), 1.47 (t, 3H)

Example 120. 2-[2-(aminomethyl)-3,3-difluoro-allyl]-4-[[5-(2-chloro-3-methyl-imidazol-4-yl)-2-thienyl]methyl]-1,2,4-triazol-3-one trifluoroacetate 17 mg of the title compound (yield: 24.9%) was prepared in the same fashion as Example 100, except that in Step 1, 42 mg of 2-chloro-1-methyl-5-(4,4,5,5-tetramethyl-1,3,2-dioxaborolan-2-yl)-1H-imidazole was used instead of 4-acetylphenylboronicacid. $^1$H-NMR (MeOD, 400 MHz) δ 7.98 (s, 1H), 7.20 (S, 1H), 7.14 (d, 1H), 7.05 (s, 1H), 5.09 (s, 2H), 4.57 (s, 2H), 3.68 (s, 2H), 3.65 (s, 3H)

Example 121. 5-[5-[[1-[2-(aminomethyl)-3,3-difluoro-allyl]-5-oxo-1,2,4-triazol-4-yl]methyl]-2-thienyl]-1-methyl-pyridin-2-one trifluoroacetate 8 mg of the title compound (yield: 11.8%) was prepared in the same fashion as Example 100, except that in Step 1, 40 mg of 1-methyl-5-(4,4,5,5-tetramethyl-[1,3,2]dioxaborolan-2-yl)-1H-pyridin-2-one was used instead of 4-acetylphenylboronicacid. $^1$H-NMR (MeOD, 400 MHz) δ 7.97 (s, 2H), 7.77 (d, 1H), 7.12 (d, 2H), 6.58 (d, 1H), 5.04 (s, 2H), 4.59 (s, 2H), 3.68 (s, 2H), 3.60 (s, 3H)

Example 122. 5-[5-[[1-[2-(aminomethyl)-3,3-difluoro-allyl]-5-oxo-1,2,4-triazol-4-yl]methyl]-2-thienyl]-1-ethyl-pyridin-2-one trifluoroacetate 46 mg of the title compound (yield: 52.4%) was prepared in the same fashion as Example 100, except that in Step 1, 70 mg of 1-ethyl-6-oxo-1,6-dihydropyridine-3-boronic acid pinacol ester was used instead of 4-acetylphenylboronicacid. $^1$H-NMR (MeOD, 400 MHz) δ 7.98 (s, 2H), 7.77 (d, 1H), 7.13 (d, 2H), 6.59 (d, 1H), 5.05 (s, 2H), 4.59 (s, 2H), 4.08 (q, 2H), 3.68 (s, 2H), 1.36 (t, 3H)

Example 123. 5-[5-[[1-[2-(aminomethyl)-3,3-difluoro-allyl]-5-oxo-1,2,4-triazol-4-yl]methyl]-2-thienyl]-1-isopropyl-pyridin-2-one trifluoroacetate 14 mg of the title compound (yield: 33.3%) was prepared in the same fashion as Example 100, except that in Step 1, 27 mg of 1-isopropyl-6-oxo-1,6-dihydropyridine-3-boronic acid pinacol ester was used instead of 4-acetylphenylboronicacid. $^1$H-NMR (MeOD, 400 MHz) δ 7.98 (s, 1H), 7.86 (s, 1H), 7.74 (d, 1H), 7.15 (d, 2H), 6.60 (d, 1H), 5.20 (m, 1H), 5.06 (s, 2H), 4.59 (s, 2H), 3.67 (s, 2H), 1.44 (d, 6H)

Example 124. 2-[2-(aminomethyl)-3,3-difluoro-allyl]-4-[[5-(1-methyl-3,6-dihydro-2H-pyridin-4-yl)-2-thienyl]methyl]-1,2,4-triazol-3-one trifluoroacetate 14 mg of the title compound (yield: 27.3%) was prepared in the same fashion as Example 100, except that in Step 1, 31 mg of 1-methyl-4-(tetramethyl-1,3,2-dioxaborolan-2-yl)-1,2,3,6-tetrahydropyridine was used instead of 4-acetylphenylboronicacid. $^1$H-NMR (MeOD, 400 MHz) δ 7.95 (s, 1H), 7.06 (s, 2H), 6.08 (s, 1H), 5.02 (s, 2H), 4.58 (s, 2H), 3.85 (s, 2H), 3.67 (s, 2H), 3.59 (s, 2H), 2.96 (s, 3H), 2.86 (s, 2H)

Example 125. 2-[2-(aminomethyl)-3,3-difluoro-allyl]-4-[[5-(1-acetyl-3,6-dihydro-2H-pyridin-4-yl)-2-thienyl]methyl]-1,2,4-triazol-3-one trifluoroacetate 11 mg of the title compound (yield: 18.2%) was prepared in the same fashion as Example 100, except that in Step 1, 35 mg of 1-(4-(4,4,5,5-tetramethyl-1,3,2-dioxaborolan-2-yl)-5,6-dihydropyridine-1(2H)-yl)ethanone was used instead of 4-acetylphenylboronicacid. $^1$H-NMR (MeOD, 400 MHz) δ 7.94 (s, 1H), 7.03 (s, 1H), 6.95 (d, 1H), 6.09 (s, 1H), 5.00 (s, 2H), 4.58 (s, 2H), 4.16 (d, 2H), 3.75 (d, 2H), 3.66 (s, 2H), 2.56 (d, 2H), 2.15 (s, 3H)

Example 126. 2-[2-(aminomethyl)-3,3-difluoro-allyl]-4-[[5-(1,3-benzodioxol-5-yl)-2-thienyl]methyl]-1,2,4-triazol-3-one trifluoroacetate 42 mg of the title compound (yield: 90.9%) was prepared in the same fashion as Example 100, except that in Step 1, 21 mg of 3,4-(methylenedioxy)phenyl boronic acid was used instead of 4-acetylphenylboronicacid. $^1$H-NMR (MeOD, 400 MHz) δ 7.96 (s, 1H), 7.11 (s, 1H), 7.06 (s, 3H), 6.81 (d, 1H), 5.97 (s, 2H), 5.02 (s, 2H), 4.58 (s, 2H), 3.67 (s, 2H)

Example 127. 2-[2-(aminomethyl)-3,3-difluoro-allyl]-4-[[5-(1H-indazol-6-yl)-2-thienyl]methyl]-1,2,4-triazol-3-one trifluoroacetate 27 mg of the title compound (yield: 63.6%) was prepared in the same fashion as Example 100, except that in Step 1, 34 mg of 1H-indazole-6-boronic acid pinacol ester was used instead of 4-acetylphenylboronicacid. $^1$H-NMR (MeOD, 400 MHz) δ 8.02 (d, 2H), 7.78 (d, 1H), 7.73 (s, 1H), 7.42 (d, 1H), 7.36 (s, 1H), 7.16 (s, 1H), 5.08 (s, 2H), 4.60 (s, 2H), 3.68 (s, 2H)

Example 128. 2-[2-(aminomethyl)-3,3-difluoro-allyl]-4-[[5-([1,2,4]triazolo[1,5-a]pyridin-7-yl)-2-thienyl]methyl]-1,2,4-triazol-3-one trifluoroacetate 40 mg of the title compound (yield: 90.9%) was prepared in the same fashion as Example 100, except that in Step 1, 34 mg of 7-(4,4,5,5-tetramethyl-[1,3,2]dioxaborolan-2-yl)-[1,2,4]triazolo[1,5-a]pyridine was used instead of 4-acetylphenylboronicacid. $^1$H-NMR (MeOD, 400 MHz) δ 8.74 (d, 1H), 8.40 (s, 1H), 8.03 (s, 1H), 7.87 (s, 1H), 7.57 (s, 1H), 7.47 (d, 1H), 7.21 (s, 1H), 5.12 (s, 2H), 4.60 (s, 2H), 3.69 (s, 2H)

Example 129. 2-[2-(aminomethyl)-3,3-difluoro-allyl]-4-[[5-(2,1,3-benzoxadiazol-5-yl)-2-thienyl]methyl]-1,2,4-triazol-3-one trifluoroacetate 34 mg of the title compound (yield: 72.7%) was prepared in the same fashion as Example 100, except that in Step 1, 26 mg of benzo[c][1,2,5]oxadiazole-5-boronic acid pinacol ester was used instead of 4-acetylphenylboronicacid. $^1$H-NMR (MeOD, 400 MHz) δ 8.02 (d, 2H), 7.94 (d, 1H), 7.86 (d, 1H), 7.57 (d, 1H), 7.21 (d, 1H), 5.12 (s, 2H), 4.60 (s, 2H), 3.67 (s, 2H)

Example 130. 5-[5-[[1-[2-(aminomethyl)-3,3-difluoro-allyl]-5-oxo-1,2,4-triazol-4-yl]methyl]-2-thienyl]-7-fluoro-indolin-2-one trifluoroacetate 14 mg of the title compound (yield: 27.3%) was prepared in the same fashion as Example 100, except that in Step 1, 7-fluoro-5-(4,4,5,5-tetramethyl-1,3,2-dioxaborolan-2-yl)indolin-2-one 39 mg was used instead of 4-acetylphenylboronicacid. $^1$H-NMR (MeOD, 400 MHz) δ 7.98 (s, 1H), 7.35 (s, 1H), 7.29 (d, 1H), 7.22 (s, 1H), 7.11 (s, 1H), 5.05 (s, 2H), 4.58 (s, 2H), 3.65 (d, 2H), 3.59 (s, 2H)

Example 131. N-[6-[5-[[1-[2-(aminomethyl)-3,3-difluoro-allyl]-5-oxo-1,2,4-triazol-4-yl]methyl]-2-thienyl]-1,3-benzothiazol-2-yl]acetamide trifluoroacetate 28 mg of the title compound (yield: 54.5%) was prepared in the same fashion as Example 100, except that in Step 1, 44 mg of N-(6-(4,4,5,5-tetramethyl-1,3,2-dioxaborolan-2-yl)benzo[d]thiazol-2-yl)acetamide was used instead of 4-acetylphenylboronicacid. $^1$H-NMR (MeOD, 400 MHz) δ 8.07 (s, 1H), 8.00 (s, 1H), 7.71 (d, 1H), 7.64 (d, 1H), 7.30 (d, 1H), 7.14 (d, 1H), 5.07 (s, 2H), 4.60 (s, 2H), 3.68 (s, 2H), 2.27 (s, 3H)

Example 132. 7-[5-[[1-[2-(aminomethyl)-3,3-difluoro-allyl]-5-oxo-1,2,4-triazol-4-yl]methyl]-2-thienyl]-3,4-dihydro-2H-isoquinolin-1-one trifluoroacetate 33 mg of the title compound (yield: 63.6%) was prepared in the same fashion as Example 100, except that in Step 1, 38 mg of (1-oxo-1,2,3,4-tetrahydroisoquinolin-7-yl)boronic acid pinacol ester was used instead of 4-acetylphenylboronicacid. $^1$H-NMR (MeOD, 400 MHz) δ 8.14 (s, 1H), 8.00 (s, 1H), 7.74 (d, 1H), 7.35 (d, 1H), 7.34 (s, 1H), 7.15 (s, 1H), 5.08 (s, 2H), 4.59 (s, 2H), 3.65 (s, 2H), 3.53 (t, 2H), 3.01 (t, 2H)

Example 133. 6-[5-[[1-[2-(aminomethyl)-3,3-difluoro-allyl]-5-oxo-1,2,4-triazol-4-yl]methyl]-2-thienyl]-3,4-dihydro-1H-quinolin-2-one trifluoroacetate 26 mg of the title compound (yield: 54.5%) was prepared in the same fashion as Example 100, except that in Step 1, 38 mg of 6-(4,4,5,5-tetramethyl-1,3,2-dioxaborolan-2-yl)-3,4-dihydroquinolin-2(1H)-one was used instead of 4-acetylphenylboronicacid. $^1$H-NMR (MeOD, 400 MHz) δ 7.98 (s, 1H), 7.43 (s, 1H), 7.40 (d, 1H), 7.20 (d, 1H), 7.10 (d, 1H), 6.87 (d, 1H), 5.05 (s, 2H), 4.59 (s, 2H), 3.68 (s, 2H), 2.98 (t, 2H), 2.58 (t, 2H)

Example 134. 6-[5-[[1-[2-(aminomethyl)-3,3-difluoro-allyl]-5-oxo-1,2,4-triazol-4-yl]methyl]-2-thienyl]-8-methyl-3,4-dihydro-1H-quinolin-2-one trifluoroacetate 34 mg of the title compound (yield: 63.6%) was prepared in the same fashion as Example 100, except that in Step 1, 37 mg of 8-methyl-2-oxo-1,2,3,4-tetrahydroquinoline-6-boronic acid pinacol ester was used instead of 4-acetylphenylboronicacid. $^1$H-NMR (MeOD, 400 MHz) δ 7.98 (s, 1H), 7.26 (s, 2H), 7.17 (s, 1H), 7.09 (s, 1H), 5.04 (s, 2H), 4.59 (s, 2H), 3.68 (s, 2H), 2.94 (t, 2H), 2.55 (t, 2H), 2.27 (s, 3H)

Example 135. 6-[5-[[1-[2-(aminomethyl)-3,3-difluoro-allyl]-5-oxo-1,2,4-triazol-4-yl]methyl]-2-thienyl]-8-methyl-1H-quinolin-2-one trifluoroacetate 33 mg of the title compound (yield: 63.6%) was prepared in the same fashion as Example 100, except that in Step 1, 40 mg of 8-methyl-6-(4,4,5,5-tetramethyl-1,3,2-dioxaborolan-2-yl)-1H-quinolin-2-one was used instead of 4-acetylphenylboronicacid. $^1$H-NMR (MeOD, 400 MHz) δ 8.01 (s, 1H), 7.90 (d, 1H), 7.61 (d, 2H), 7.25 (s, 1H), 7.12 (s, 1H), 6.59 (d, 1H), 5.07 (s, 2H), 4.60 (s, 2H), 3.69 (s, 2H), 2.47 (s, 3H)

Example 136. 6-[5-[[1-[2-(aminomethyl)-3,3-difluoro-allyl]-5-oxo-1,2,4-triazol-4-yl]methyl]-2-thienyl]-8-fluoro-3,4-dihydro-TH-quinolin-2-one trifluoroacetate 29 mg of the title compound (yield: 54.5%) was prepared in the same fashion as Example 100, except that in Step 1, 41 mg of 8-fluoro-6-(4,4,5,5-tetramethyl-1,3,2-dioxaborolan-2-yl)-3,4-dihydro-1H-quinolin-2-one was used instead of 4-acetylphenylboronicacid. $^1$H-NMR (MeOD, 400 MHz)

δ 7.98 (s, 1H), 7.26-7.24 (m, 3H), 7.11 (s, 1H), 5.05 (s, 2H), 4.59 (s, 2H), 3.68 (s, 2H), 3.01 (t, 2H), 2.60 (t, 2H)

Example 137. 6-[5-[[1-[2-(aminomethyl)-3,3-difluoro-allyl]-5-oxo-1,2,4-triazol-4-yl]methyl]-2-thienyl]-8-fluoro-TH-quinolin-2-one trifluoroacetate 30 mg of the title compound (yield: 54.5%) was prepared in the same fashion as Example 100, except that in Step 1, 40 mg of 8-fluoro-6-(4,4,5,5-tetramethyl-1,3,2-dioxaborolan-2-yl)-1H-quinolin-2-one was used instead of 4-acetylphenylboronicacid. ¹H-NMR (MeOD, 400 MHz) δ 8.01 (s, 1H), 7.95 (d, 1H), 7.65 (s, 1H), 7.60 (d, 1H), 7.31 (s, 1H), 7.13 (s, 1H), 6.65 (d, 1H), 5.08 (s, 2H), 4.60 (s, 2H), 3.68 (s, 2H)

Example 138. 6-[5-[[1-[2-(aminomethyl)-3,3-difluoro-allyl]-5-oxo-1,2,4-triazol-4-yl]methyl]-2-thienyl]-1-methyl-3,4-dihydroquinolin-2-one trifluoroacetate 41 mg of the title compound (yield: 81.8%) was prepared in the same fashion as Example 100, except that in Step 1, 37 mg of (1-methyl-2-oxo-1,2,3,4-tetrahydroquinolin-6-yl) boronic acid pinacol ester was used instead of 4-acetylphenylboronicacid. ¹H-NMR (MeOD, 400 MHz) δ 7.99 (s, 1H), 7.48 (d, 1H), 7.44 (s, 1H), 7.22 (s, 1H), 7.12 (s, 2H), 5.05 (s, 2H), 4.59 (s, 2H), 3.68 (s, 2H), 3.34 (s, 3H), 2.93 (t, 2H), 2.62 (t, 2H)

Example 139. 2-[2-(aminomethyl)-3,3-difluoro-allyl]-4-[[5-(5-methyl-3,4-dihydro-2H-1,4-benzoxazin-6-yl)-2-thienyl]methyl]-1,2,4-triazol-3-one trifluoroacetate 32 mg of the title compound (yield: 63.6%) was prepared in the same fashion as Example 100, except that in Step 1, 38 mg of (5-methyl-3,4-dihydro-2H-benzo[b][1,4]oxazin-6-yl)boronic acid pinacol ester was used instead of 4-acetylphenylboronicacid. ¹H-NMR (MeOD, 400 MHz) δ 7.98 (s, 1H), 7.09 (d, 1H), 6.78 (d, 1H), 6.58 (s, 2H), 5.05 (s, 2H), 4.59 (s, 2H), 4.17 (t, 2H), 3.68 (s, 2H), 3.43 (t, 2H), 2.10 (s, 3H)

Example 140. 2-[2-(aminomethyl)-3,3-difluoro-allyl]-4-[[5-(4-methyl-2,3-dihydro-1,4-benzoxazin-7-yl)-2-thienyl]methyl]-1,2,4-triazol-3-one trifluoroacetate 27 mg of the title compound (yield: 54.5%) was prepared in the same fashion as Example 100, except that in Step 1, 38 mg of 4-methyl-7-(4,4,5,5-tetramethyl-1,3,2-dioxaborolan-2-yl)-3,4-dihydro-2H-1,4-benzoxazine was used instead of 4-acetylphenylboronicacid. ¹H-NMR (MeOD, 400 MHz) δ 7.95 (s, 1H), 7.04 (s, 3H), 6.91 (s, 1H), 6.68 (d, 1H), 5.01 (s, 2H), 4.58 (s, 2H), 4.27 (s, 2H), 3.66 (s, 2H), 3.36-3.27 (m, 6H), 2.90 (s, 3H)

Example 141. 6-[5-[[1-[2-(aminomethyl)-3,3-difluoro-allyl]-5-oxo-1,2,4-triazol-4-yl]methyl]-2-thienyl]-4H-1,4-benzoxazin-3-one trifluoroacetate 11 mg of the title compound (yield: 27.3%) was prepared in the same fashion as Example 100, except that in Step 1, 30 mg of 6-(4,4,5,5-tetramethyl-1,3,2-dioxaborolan-2-yl)-2H-benzo[b][1,4]oxazine-3(4H)-ones was used instead of 4-acetylphenylboronicacid. ¹H-NMR (MeOD, 400 MHz) δ 7.97 (s, 1H), 7.21-7.12 (m, 4H), 6.96 (d, 1H), 5.05 (s, 2H), 4.59 (d, 4H), 3.59 (s, 2H)

Example 142. 7-[5-[[1-[2-(aminomethyl)-3,3-difluoro-allyl]-5-oxo-1,2,4-triazol-4-yl]methyl]-2-thienyl]-1,4-dihydro-3,1-benzoxazin-2-one trifluoroacetate 35 mg of the title compound (yield: 72.7%) was prepared in the same fashion as Example 100, except that in Step 1, 41 mg of 7-(4,4,5,5-tetramethyl-1,3,2-dioxaborolan-2-yl)-1,4-dihydro-2H-benzo[d][1,3]oxazin-2-one was used instead of 4-acetylphenylboronicacid. ¹H-NMR (MeOD, 400 MHz) δ 7.99 (s, 1H), 7.28 (s, 1H), 7.26 (d, 1H), 7.18 (d, 1H), 7.13 (d, 1H), 7.09 (s, 1H), 5.31 (s, 2H), 5.06 (s, 2H), 4.59 (s, 2H), 3.68 (s, 2H)

Example 143. 6-[5-[[1-[2-(aminomethyl)-3,3-difluoro-allyl]-5-oxo-1,2,4-triazol-4-yl]methyl]-2-thienyl]-1,4-dihydro-3,1-benzoxazin-2-one trifluoroacetate 31 mg of the title compound (yield: 63.6%) was prepared in the same fashion as Example 100, except that in Step 1, 38 mg of 6-(4,4,5,5-tetramethyl-1,3,2-dioxaborolan-2-yl)-1,4-dihydro-2H-benzo[d][1,3]oxazin-2-one was used instead of 4-acetylphenylboronicacid. ¹H-NMR (MeOD, 400 MHz) δ 7.98 (s, 1H), 7.49 (d, 1H), 7.43 (s, 1H), 7.21 (d, 1H), 7.11 (d, 1H), 6.89 (d, 1H), 5.33 (s, 2H), 5.05 (s, 2H), 4.59 (s, 2H), 3.68 (s, 2H)

Example 144. 7-[5-[[1-[2-(aminomethyl)-3,3-difluoro-allyl]-5-oxo-1,2,4-triazol-4-yl]methyl]-2-thienyl]-4-methyl-1,4-benzoxazin-3-one trifluoroacetate 34 mg of the title compound (yield: 63.6%) was prepared in the same fashion as Example 100, except that in Step 1, 43 mg of 4-methyl-3-oxo-3,4-dihydro-2H-1,4-benzo[b][1,4]oxazine-7-boronic acid pinacol ester was used instead of 4-acetylphenylboronicacid. ¹H-NMR (MeOD, 400 MHz) δ 7.98 (s, 1H), 7.28 (d, 1H), 7.20 (d, 2H), 7.12 (d, 2H), 5.05 (s, 2H), 4.62 (s, 2H), 4.59 (s, 2H), 3.68 (s, 2H), 3.34 (s, 3H)

Example 145. 2-[2-(aminomethyl)-3,3-difluoro-allyl]-4-[[5-(5,6,7,8-tetrahydro-1,8-naphthyridin-3-yl)-2-thienyl]methyl]-1,2,4-triazol-3-one ditrifluoroacetate 6 mg of the title compound (yield: 18.2%) was prepared in the same fashion as Example 100, except that in Step 1, 36 mg of (5,6,7,8-tetrahydro-1,8-naphthyridin-3-yl)boronic acid pinacol ester was used instead of 4-acetylphenylboronicacid. ¹H-NMR (MeOD, 400 MHz) δ 7.97 (s, 1H), 7.92 (s, 1H), 7.69 (s, 1H), 7.17 (s, 1H), 7.12 (s, 1H), 5.05 (s, 2H), 4.58 (s, 2H), 3.67 (s, 2H), 3.50 (d, 2H), 2.86 (m, 2H), 1.95 (m, 2H)

Example 146. 2-[2-(aminomethyl)-3,3-difluoro-allyl]-4-[[4-(4-methylsulfonylphenyl)-2-thienyl]methyl]-1,2,4-triazol-3-one trifluoroacetate 83 mg of the title compound (yield: 87.0%) was prepared in the same fashion as Example 100, except that in Step 1, 100 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 60 mg of 4-(methanesulfonyl)phenylboronic acid was used instead of 4-acetylphenylboronicacid. $^1$H-NMR (MeOD, 400 MHz) δ 8.02-7.97 (m, 3H), 7.92-7.86 (m, 3H), 7.62 (s, 1H), 5.12 (s, 2H), 4.59 (s, 2H), 3.68 (s, 2H), 3.15 (s, 3H)

Example 147. 2-[2-(aminomethyl)-3,3-difluoro-allyl]-4-[[4-(4-piperazin-1-ylphenyl)-2-thienyl]methyl]-1,2,4-triazol-3-one ditrifluoroacetate 45 mg of the title compound (yield: 56.3%) was prepared in the same fashion as Example 100, except that in Step 1, 100 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 83 mg of tert-butyl 4-[4-(tetramethyl-1,3,2-dioxaborolan-2-yl)phenyl]piperazine-1-carboxylate was used instead of 4-acetylphenylboronicacid. $^1$H-NMR (MeOD, 400 MHz) δ 7.99 (s, 1H), 7.58-7.48 (m, 4H), 7.06 (d, 2H), 5.08 (s, 2H), 4.59 (s, 2H), 3.67 (s, 2H), 3.45-3.32 (m, 8H)

Example 148. 2-[2-(aminomethyl)-3,3-difluoro-allyl]-4-[[4-[6-(trifluoromethyl)-3-pyridyl]-2-thienyl]methyl]-1,2,4-triazol-3-one trifluoroacetate 33 mg of the title compound (yield: 35.6%) was prepared in the same fashion as Example 100, except that in Step 1, 100 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 59 mg of 2-(trifluoromethyl)pyridine-5-boronic acid pinacol ester was used instead of 4-acetylphenylboronicacid. $^1$H-NMR (MeOD, 400 MHz) δ 9.01 (s, 1H), 8.29 (d, 1H), 8.02 (s, 1H), 7.97 (s, 1H), 7.85 (d, 1H), 7.66 (s, 1H), 5.13 (s, 2H), 4.59 (s, 2H), 3.67 (s, 2H)

Example 149. 2-[2-(aminomethyl)-3,3-difluoro-allyl]-4-[[4-[6-(dimethylamino)-3-pyridyl]-2-thienyl]methyl]-1,2,4-triazol-3-one trifluoroacetate 35 mg of the title compound (yield: 40.0%) was prepared in the same fashion as Example 100, except that in Step 1, X mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 53 mg of 6-(dimethylamino)pyridine-3-boronic acid was used instead of 4-acetylphenylboronicacid. $^1$H-NMR (MeOD, 400 MHz) δ 8.20-8.17 (m, 2H), 8.00 (s, 1H), 7.68 (s, 1H), 7.51 (s, 1H), 7.16 (d, 1H), 5.10 (s, 2H), 4.59 (s, 2H), 3.72 (s, 2H), 3.27 (s, 6H)

Example 150. 2-[2-(aminomethyl)-3,3-difluoro-allyl]-4-[[4-(1,3-benzodioxol-5-yl)-2-thienyl]methyl]-1,2,4-triazol-3-one trifluoroacetate 40 mg of the title compound (yield: 45.8%) was prepared in the same fashion as Example 100, except that in Step 1, 100 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 44 mg of 3,4-(methylenedioxy)phenyl boronic acid was used instead of 4-acetylphenylboronicacid. $^1$H-NMR (MeOD, 400 MHz) δ 7.98 (s, 1H), 7.45 (d, 2H), 7.11 (d, 2H), 6.93 (s, 1H), 6.84 (d, 1H), 5.96 (s, 2H), 5.07 (s, 2H), 4.58 (s, 2H), 3.66 (s, 2H)

Example 151. 6-[5-[[1-[2-(aminomethyl)-3,3-difluoro-allyl]-5-oxo-1,2,4-triazol-4-yl]methyl]-3-thienyl]-8-methyl-3,4-dihydro-TH-quinolin-2-one trifluoroacetate 36 mg of the title compound (yield: 37.6%) was prepared in the same fashion as Example 100, except that in Step 1, 100 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 62 mg of 8-methyl-2-oxo-1,2,3,4-tetrahydroquinoline-6-boronic acid pinacol ester was used instead of 4-acetylphenylboronicacid. MS (ESI) m/z=444.1 (M+H)+

Example 152. 6-[5-[[1-[2-(aminomethyl)-3,3-difluoro-allyl]-5-oxo-1,2,4-triazol-4-yl]methyl]-3-thienyl]-1-methyl-3,4-dihydroquinolin-2-one trifluoroacetate 40 mg of the title compound (yield: 41.8%) was prepared in the same fashion as Example 100, except that in Step 1, 100 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 62 mg of (1-methyl-2-oxo-1,2,3,4-tetrahydroquinolin-6-yl)boronic acid pinacol ester was used instead of 4-acetylphenylboronicacid. $^1$H-NMR (MeOD, 400 MHz) δ 8.00 (s, 1H), 7.57-7.50 (m, 4H), 7.14 (d, 1H), 5.09 (s, 2H), 4.59 (s, 2H), 3.68 (s, 2H), 3.35 (s, 3H), 2.95 (t, 2H), 2.63 (t, 2H)

Example 153. 2-[2-(aminomethyl)-3,3-difluoro-allyl]-4-[[4-(1-ethylpyrazol-4-yl)-2-thienyl]methyl]-1,2,4-triazol-3-one trifluoroacetate 37 mg of the title compound (yield: 45.2%) was prepared in the same fashion as Example 100, except that in Step 1, 100 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 48 mg of 1-ethylpyrazole-4-boronic acid pinacol ester was used instead of 4-acetylphenylboronicacid. $^1$H-NMR (MeOD, 400 MHz) δ 7.97 (s, 1H), 7.91 (s, 1H), 7.73 (s, 1H), 7.36 (d, 2H), 5.05 (s, 2H), 4.58 (s, 2H), 4.18 (q, 2H), 3.67 (s, 2H), 1.47 (t, 3H)

Example 154. 2-[2-(aminomethyl)-3,3-difluoro-allyl]-4-[[3-methyl-5-(4-methylsulfonylphenyl)-2-thienyl]methyl]-1,2,4-triazol-3-one trifluoroacetate 21 mg of the title compound (yield: 43.3%) was prepared in the same fashion as Example 100, except that in Step 1, 50 mg of tert-butyl N-[2-[[4-(5-bromo-3-methyl-2-thienyl)methyl]-5-oxo-1,2,4-triazol-1-yl]methyl]-3,3-difluoro-allyl]carbamate prepared in Reference Example 43 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 21 mg of 4-(methanesulfonyl)phenylboronic acid was used instead of 4-acetylphenylboronicacid. $^1$H-NMR (MeOD, 400 MHz) δ 7.99-7.92 (m, 3H), 7.81 (d, 2H), 7.38 (s, 1H), 5.03 (s, 2H), 4.59 (s, 2H), 3.68 (s, 2H), 3.12 (s, 3H), 2.34 (s, 3H)

Example 155. 2-[2-(aminomethyl)-3,3-difluoro-allyl]-4-[[3-methyl-5-(4-piperazin-1-ylphenyl)-2-thienyl]methyl]-1,2,4-triazol-3-one ditrifluoroacetate 6 mg of the title compound (yield: 13.5%) was prepared in the same fashion as Example 100, except that in Step 1, 50 mg of tert-butyl N-[2-[[4-(5-bromo-3-methyl-2-thienyl)methyl]-5-oxo-1,2,4-triazol-1-yl]methyl]-3,3-difluoro-allyl]carbamate prepared in Reference Example 43 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 40 mg of tert-butyl 4-[4-(tetramethyl-1,3,2-dioxaborolan-2-yl)phenyl]piperazine-1-carboxylate was used instead of 4-acetylphenylboronicacid. $^1$H-NMR (MeOD, 400 MHz) δ 7.90 (s, 1H), 7.51 (d, 2H), 7.06-7.02 (m, 3H), 4.98 (s, 2H), 4.58 (s, 2H), 3.67 (s, 2H), 3.45 (t, 4H), 3.38 (t, 4H), 2.30 (s, 3H)

Example 156. 2-[2-(aminomethyl)-3,3-difluoro-allyl]-4-[[3-methyl-5-[6-(trifluoromethyl)-3-pyridyl]-2-thienyl]methyl]-1,2,4-triazol-3-one trifluoroacetate 14 mg of the title compound (yield: 30.8%) was prepared in the same fashion as Example 100, except that in Step 1, 50 mg of tert-butyl N-[2-[[4-(5-bromo-3-methyl-2-thienyl)methyl]-5-oxo-1,2,4-triazol-1-yl]methyl]-3,3-difluoro-allyl]carbamate prepared in Reference Example 43 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 28 mg of 2-(trifluoromethyl)pyridine-5-boronic acid pinacol ester was used instead of 4-acetylphenylboronicacid. $^1$H-NMR (MeOD, 400 MHz) δ 8.92 (s, 1H), 8.19 (d, 1H), 7.97 (s, 1H), 7.81 (d, 1H), 7.45 (s, 1H), 5.06 (s, 2H), 4.59 (s, 2H), 3.68 (s, 2H), 2.35 (s, 3H)

Example 157. 2-[2-(aminomethyl)-3,3-difluoro-allyl]-4-[[5-[6-(dimethylamino)-3-pyridyl]-3-methyl-2-thienyl]methyl]-1,2,4-triazol-3-one trifluoroacetate 17 mg of the title compound (yield: 38.5%) was prepared in the same fashion as Example 100, except that in Step 1, 50 mg of tert-butyl N-[2-[[4-(5-bromo-3-methyl-2-thienyl)methyl]-5-oxo-1,2,4-triazol-1-yl]methyl]-3,3-difluoro-allyl]carbamate prepared in Reference Example 43 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 26 mg of 6-(dimethylamino)pyridine-3-boronic acid was used instead of 4-acetylphenylboronicacid. $^1$H-NMR (MeOD, 400 MHz) δ 8.11-8.07 (m, 2H), 7.92 (s, 1H), 7.18-7.14 (m, 2H), 5.10 (s, 2H), 4.58 (s, 2H), 3.68 (s, 2H), 3.27 (s, 6H), 2.32 (s, 3H)

Example 158. 2-[2-(aminomethyl)-3,3-difluoro-allyl]-4-[[5-(1,3-benzodioxol-5-yl)-3-methyl-2-thienyl]methyl]-1,2,4-triazol-3-one trifluoroacetate 28 mg of the title compound (yield: 62.5%) was prepared in the same fashion as Example 100, except that in Step 1, 50 mg of tert-butyl N-[2-[[4-(5-bromo-3-methyl-2-thienyl)methyl]-5-oxo-1,2,4-triazol-1-yl]methyl]-3,3-difluoro-allyl]carbamate prepared in Reference Example 43 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 26 mg of 2-(1,3-benzodioxol-5-yl)-4,4,5,5-tetramethyl-1,3,2-dioxaborolane was used instead of 4-acetylphenylboronicacid. $^1$H-NMR (MeOD, 400 MHz) δ 7.89 (s, 1H), 7.05-7.00 (m, 2H), 6.80 (d, 1H), 5.95 (s, 2H), 4.96 (s, 2H), 4.58 (s, 2H), 3.67 (s, 2H), 2.29 (s, 3H)

Example 159. 2-[2-(aminomethyl)-3,3-difluoro-allyl]-4-[[5-(1-ethylpyrazol-4-yl)-3-methyl-2-thienyl]methyl]-1,2,4-triazol-3-one trifluoroacetate 10 mg of the title compound (yield: 24.0%) was prepared in the same fashion as Example 100, except that in Step 1, 50 mg of tert-butyl N-[2-[[4-(5-bromo-3-methyl-2-thienyl)methyl]-5-oxo-1,2,4-triazol-1-yl]methyl]-3,3-difluoro-allyl]carbamate prepared in Reference Example 43 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 23 mg of 1-ethylpyrazole-4-boronic acid pinacol ester was used instead of 4-acetylphenylboronicacid. $^1$H-NMR (MeOD, 400 MHz) δ 7.88 (s, 1H), 7.86 (s, 1H), 7.64 (s, 1H), 6.91 (s, 1H), 4.96 (s, 2H), 4.58 (s, 2H), 4.18 (q, 2H), 3.67 (s, 2H), 2.28 (s, 3H), 1.46 (t, 3H)

Example 160. 2-[2-(aminomethyl)-3,3-difluoro-allyl]-4-[6-[2-(1-methylpyrazol-4-yl)ethynyl]-2-pyridyl]-1,2,4-triazol-3-one trifluoroacetate Step 1: tert-butyl N-[3,3-difluoro-2-[[4-[6-[2-(1-methylpyrazol-4-yl)ethynyl]-2-pyridyl]-5-oxo-1,2,4-triazol-1-yl]methyl]allyl]carbamate 60 mg of tert-butyl N-[2-[[4-(6-bromo-2-pyridyl)-5-oxo-1,2,4-triazol-1-yl]methyl]-3,3-difluoro-allyl]carbamate prepared in Reference Example 31, 10 mg of 4-ethynyl-1-methyl-1H-pyrazole, 8 mg of tetrakis(triphenylphosphine)palladium (Pd(PPh$_3$)$_4$), and 3 mg of copper(I) iodide (CuI) were dissolved in 1 mL of N,N-dimethylformamide, followed by the addition of 56.0 uL of triethylamine, and the resulting solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=2/1) to give 51.7 mg of the title compound as a yellow liquid (yield: 82.1%). MS (ESI) m/z=372.0 (M+H)+

Step 2: 2-[2-(aminomethyl)-3,3-difluoro-allyl]-4-[6-[2-(1-methylpyrazol-4-yl)ethynyl]-2-pyridyl]-1,2,4-triazol-3-one 51.7 mg of tert-butyl N-[3,3-difluoro-2-[[4-[6-[2-(1-methylpyrazol-4-yl)ethynyl]-2-pyridyl]-5-oxo-1,2,4-triazol- 1-yl]methyl]allyl]carbamate prepared in Step 1 was dissolved in 1.0 mL of dichloromethane, followed by the addition of 0.1 mL of trifluoroacetic acid, and the resulting solution was stirred at room temperature for 2 hours. The reaction mixture thus obtained was concentrated, followed by the addition of dichloromethane. The solution was concentrated under reduced pressure and then dried in vacuo to obtain a yellow liquid residue. The residue was purified with silica gel column chromatography (developing solvent: dichloromethane/methanol=10/1) to give 10 mg of the title compound as a white solid (yield: 24.5%). $^1$H-NMR (MeOD, 400 MHz) δ 8.62 (s, 1H), 8.19 (d, 1H), 7.94 (s, 2H), 7.70 (s, 1H), 7.48 (d, 1H), 4.61 (s, 2H), 3.92 (s, 3H), 3.40 (s, 2H)

Example 161. 7-[(E)-2-[5-[[1-[2-(aminomethyl)-3,3-difluoro-allyl]-5-oxo-1,2,4-triazol-4-yl]methyl]-2-thienyl]vinyl]-1H-pyrido[2,3-b][1,4]oxazin-2-one trifluoroacetate 17 mg of the title compound (yield: 36.4%) was prepared in the same fashion as Example 100, except that in Step 1, 42 mg of 7-[(E)-2-(tetramethyl-1,3,2-dioxaborolan-2-yl)ethenyl]-1H,2H,3H-pyrido[2,3,b][1,4]oxazin-2-one was used instead of 4-acetylphenylboronicacid. $^1$H-NMR (MeOD, 400 MHz) δ 7.97 (s, 1H), 7.87 (s, 1H), 7.44 (s, 1H), 7.23 (d, 1H), 7.04 (d, 2H), 6.85 (d, 1H), 5.04 (s, 2H), 4.84 (s, 2H), 4.58 (s, 2H), 3.60 (s, 2H)

Example 162. 2-[2-(aminomethyl)-3,3-difluoro-allyl]-4-[[5-[2-[6-(dimethylamino)-3-pyridyl]ethynyl]-2-thienyl]methyl]-1,2,4-triazol-3-one trifluoroacetate 29 mg of the title compound (yield: 54.5%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31 and 39 mg of 5-ethynyl-N,N-dimethylpyridine-2-amine was used instead of 4-ethynyl-1-methyl-1H-pyrazole. $^1$H-NMR (MeOD, 400 MHz) δ 8.15 (s, 1H), 7.98 (s, 1H), 7.73 (d, 1H), 7.17 (s, 1H), 7.08 (s, 1H), 6.90 (d, 1H), 5.05 (s, 2H), 4.59 (s, 2H), 3.68 (s, 2H), 3.20 (s, 6H)

Example 163. 2-[2-(aminomethyl)-3,3-difluoro-allyl]-4-[[5-[2-(6-morpholino-3-pyridyl)ethynyl]-2-thienyl]methyl]-1,2,4-triazol-3-one trifluoroacetate 42 mg of the title compound (yield: 81.8%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31 and 51 mg of 4-(5-ethynylpyridin-2-yl)morpholine was used instead of 4-ethynyl-1-methyl-1H-pyrazole. $^1$H-NMR (MeOD, 400 MHz) δ 8.23 (s, 1H), 7.98 (s, 1H), 7.61 (d, 1H), 7.13 (s, 1H), 7.07 (s, 1H), 6.79 (d, 1H), 5.04 (s, 2H), 4.59 (s, 2H), 3.78 (s, 4H), 3.67 (s, 2H), 3.56 (s, 4H)

Example 164. 2-[2-(aminomethyl)-3,3-difluoro-allyl]-4-[[5-[2-(3,4-dihydro-2H-1,4-benzoxazin-6-yl)ethynyl]-2-thienyl]methyl]-1,2,4-triazol-3-one ditrifluoroacetate 26 mg of the title compound (yield: 81.8%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31 and 70 mg of tert-butyl-6-ethynyl-2H-benzo[b][1,4]oxazine-4(3H)-carboxylate was used instead of 4-ethynyl-1-methyl-1H-pyrazole. $^1$H-NMR (MeOD, 400 MHz) δ 7.97 (s, 1H), 7.07 (d, 2H), 6.72 (s, 1H), 6.67 (t, 2H), 5.03 (s, 2H), 4.58 (s, 2H), 4.21 (s, 2H), 3.67 (s, 2H), 3.34-3.31 (s, 2H)

Example 165. 6-[2-[5-[[1-[2-(aminomethyl)-3,3-difluoro-allyl]-5-oxo-1,2,4-triazol-4-yl]methyl]-2-thienyl]ethynyl]-3,4-dihydro-TH-quinolin-2-one trifluoroacetate 38 mg of the title compound (yield: 72.7%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31 and 46 mg of 6-ethynyl-1,2,3,4-tetrahydroquinolin-2-one was used instead of 4-ethynyl-1-methyl-1H-pyrazole. $^1$H-NMR (MeOD, 400 MHz) δ 7.98 (s, 1H), 7.30 (d, 2H), 7.14 (s, 1H), 7.07 (s, 1H), 6.86 (d, 1H), 5.04 (s, 2H), 4.59 (s, 2H), 3.67 (s, 2H), 2.96 (t, 2H), 2.58 (t, 2H)

Example 166. 2-[2-(aminomethyl)-3,3-difluoro-allyl]-4-[[5-[2-(2,3-dihydro-TH-pyrido[2,3-b][1,4]oxazin-7-yl)ethynyl]-2-thienyl]methyl]-1,2,4-triazol-3-one ditrifluoroacetate 38 mg of the title compound (yield: 81.8%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31 and 43 mg of 7-ethynyl-2,3-dihydro-TH-pyrido[2,3-b][1,4]oxazine was used instead of 4-ethynyl-1-methyl-1H-pyrazole. $^1$H-NMR (MeOD, 400 MHz) δ 7.98 (s, 1H), 7.52 (s, 1H), 7.16 (s, 1H), 7.07 (s, 1H), 7.01 (s, 1H), 5.05 (s, 2H), 4.59 (s, 2H), 4.39 (s, 2H), 3.67 (s, 2H), 3.38 (s, 2H)

Example 167. 2-[2-(aminomethyl)-3,3-difluoro-allyl]-4-[[5-[2-(3,4-dihydro-2H-pyrido[3,2-b][1,4]oxazin-7-yl)ethynyl]-2-thienyl]methyl]-1,2,4-triazol-3-one ditrifluoroacetate 39 mg of the title compound (yield: 72.7%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate was used instead of tert-butyl N-[2-[[4-(6-bromo-2-pyridyl)-

5-oxo-1,2,4-triazol-1-yl]methyl]-3,3-difluoro-allyl]carbamate prepared in Reference Example 31 and 43 mg of 7-ethynyl-2H,3H,4H-pyrido[3,2-b][1,4]oxazine was used instead of 4-ethynyl-1-methyl-1H-pyrazole. $^1$H-NMR (MeOD, 400 MHz) δ 7.97 (s, 1H), 7.69 (s, 1H), 7.12 (s, 1H), 7.05 (d, 2H), 5.04 (s, 2H), 4.58 (s, 2H), 4.18 (s, 2H), 3.67 (s, 2H), 3.55 (s, 2H)

Example 168. 2-[2-(aminomethyl)-3,3-difluoro-allyl]-4-[[5-[2-(2,3-dihydro-1H-pyrido[2,3-b][1,4]oxazin-6-yl)ethynyl]-2-thienyl]methyl]-1,2,4-triazol-3-one ditrifluoroacetate 26 mg of the title compound (yield: 54.5%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31 and 43 mg of 6-ethynyl-2,3-dihydro-1H-pyrido[2,3-b][1,4]oxazine was used instead of 4-ethynyl-1-methyl-1H-pyrazole. $^1$H-NMR (MeOD, 400 MHz) δ 7.97 (s, 1H), 7.16 (s, 1H), 7.07 (s, 1H), 7.01 (d, 1H), 6.91 (d, 1H), 5.04 (s, 2H), 4.58 (s, 2H), 4.36 (s, 2H), 3.66 (s, 2H), 3.41 (s, 2H)

Example 169. 7-[2-[5-[[1-[2-(aminomethyl)-3,3-difluoro-allyl]-5-oxo-1,2,4-triazol-4-yl]methyl]-2-thienyl]ethynyl]-1H-pyrido[2,3-b][1,4]oxazin-2-one trifluoroacetate 32 mg of the title compound (yield: 63.6%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31 and 47 mg of 7-ethynyl-1H,2H,3H-pyrido[2,3-b][1,4]oxazin-2-one was used instead of 4-ethynyl-1-methyl-1H-pyrazole. $^1$H-NMR (MeOD, 400 MHz) δ 7.98 (s, 1H), 7.93 (s, 1H), 7.32 (s, 1H), 7.21 (s, 1H), 7.10 (s, 1H), 5.06 (s, 2H), 4.87 (s, 2H), 4.59 (s, 2H), 3.67 (s, 2H)

Example 170. 7-[2-[5-[[1-[2-(aminomethyl)-3,3-difluoro-allyl]-5-oxo-1,2,4-triazol-4-yl]methyl]-2-thienyl]ethynyl]-4H-pyrido[3,2-b][1,4]oxazin-3-one trifluoroacetate 34 mg of the title compound (yield: 63.6%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31 and 47 mg of 7-ethynyl-2H,3H,4H-pyrido[3,2-b][1,4]oxazin-3-one was used instead of 4-ethynyl-1-methyl-1H-pyrazole. $^1$H-NMR (MeOD, 400 MHz) δ 8.03 (s, 1H), 7.98 (s, 1H), 7.37 (s, 1H), 7.20 (s, 1H), 7.09 (s, 1H), 5.06 (s, 2H), 4.68 (s, 2H), 4.59 (s, 2H), 3.67 (s, 2H)

Example 171. 2-[2-(aminomethyl)-3,3-difluoro-allyl]-4-[[5-[2-(1-methylpyrazol-4-yl)ethynyl]-2-thienyl]methyl]-1,2,4-triazol-3-one trifluoroacetate 32 mg of the title compound (yield: 72.7%) was prepared in the same fashion as Example 160, except that in Step 1, 50 mg of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 was used instead of tert-butyl N-[2-[[4-(6-bromo-2-pyridyl)-5-oxo-1,2,4-triazol-1-yl]methyl]-3,3-difluoro-allyl]carbamate prepared in Reference Example 31. $^1$H-NMR (MeOD, 400 MHz) δ 7.97 (s, 1H), 7.84 (s, 1H), 7.61 (s, 1H), 7.08 (d, 2H), 5.04 (s, 2H), 4.58 (s, 2H), 3.90 (s, 3H), 3.67 (s, 2H)

Example 172. 2-[2-(aminomethyl)-3,3-difluoro-allyl]-4-[2-(2-thienyl)ethyl]-1,2,4-triazol-3-one trifluoroacetate 43 mg of tert-butyl N-[3,3-difluoro-2-[[5-oxo-4-[2-(2-thienyl)ethyl]-1,2,4-triazol-1-yl]methyl]allyl]carbamate prepared in Reference Example 44 was dissolved in 5.0 mL of dichloromethane, followed by the addition of 0.5 mL of trifluoroacetate, and the resulting solution was stirred at room temperature for 3 hours. The reaction mixture thus obtained was concentrated, followed by the addition of dichloromethane. The concentrated reaction mixture was washed with an aqueous solution of sodium hydrogen carbonate, then dried over anhydrous magnesium sulfate, and concentrated under reduced pressure to obtain a yellow liquid residue. The residue was purified with silica gel column chromatography (developing solvent: dichloromethane/methanol=10/1) to give 34 mg of the title compound as a white solid (yield: 100%). $^1$H-NMR (MeOD, 400 MHz) δ 7.67 (s, 1H), 7.25 (s, 1H), 6.94 (s, 1H), 6.86 (s, 1H), 4.55 (s, 2H), 3.96 (t, 2H), 3.63 (s, 2H), 3.27 (t, 2H)

Example 173. 2-[2-(aminomethyl)-3,3-difluoro-allyl]-4-[2-[5-(4-methylsulfonylphenyl)-2-thienyl]ethyl]-1,2,4-triazol-3-one trifluoroacetate Step 1: tert-butyl N-[3,3-difluoro-2-[[4-[2-[5-(4-methylsulfonylphenyl)-2-thienyl]ethyl]-5-oxo-1,2,4-triazol-1-yl]methyl]allyl]carbamate 60 mg of tert-butyl N-[2-[[4-(5-bromo-2-thienyl)ethyl]-5-oxo-1,2,4-triazol-1-yl]methyl]-3,3-difluoro-allyl]carbamate prepared in Reference Example 45 and 32 mg of 4-(methanesulfonyl)phenylboronic acid were dissolved in 1.6 mL of 1,4-dioxane, followed by the addition of 0.4 mL of 1 M potassium carbonate and 3 mg of palladiumdi[1,1'-bis(diphenylphospino)ferrocene]dichloride (PdCl$_2$(dppf)), and the resulting solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/2) to give 48 mg of the title compound (yield: 69.2%). MS (ESI) m/z=455.2 (M+H)+

Step 2: 2-[2-(aminomethyl)-3,3-difluoro-allyl]-4-[2-[5-(4-methylsulfonylphenyl)-2-thienyl]ethyl]-1,2,4-triazol-3-one 48 mg of tert-butyl N-[3,3-difluoro-2-[[4-[2-[5-(4-methylsulfonylphenyl)-2-thienyl]ethyl]-5-oxo-1,2,4-triazol-1-yl]methyl]allyl]carbamate prepared in Step 1 was dissolved in 1.0 mL of dichloromethane, followed by the addition of 0.1 mL of trifluoroacetic acid, and the resulting solution was stirred at room temperature for 2 hours. The reaction mixture thus obtained was concentrated, followed by the addition of dichloromethane. The solution was concentrated under reduced pressure and then dried in vacuo to obtain a yellow liquid residue. The residue was purified with silica gel column chromatography (developing solvent: dichloromethane/methanol=10/1) to give 34 mg of the title compound (yield: 59.2%). $^1$H-NMR (MeOD, 400 MHz) δ 7.94-7.92 (m, 2H), 7.82-7.77 (m, 3H), 7.44 (s, 1H), 6.92 (s, 1H), 4.56 (s, 2H), 3.99 (t, 2H), 3.65 (s, 2H), 3.36 (s, 3H), 3.31 (t, 2H)

Example 174. 2-[2-(aminomethyl)-3,3-difluoro-allyl]-4-[2-[5-(4-piperazin-1-ylphenyl)-2-thienyl]ethyl]-1,2,4-triazol-3-one ditrifluoroacetate 9 mg of the title compound (yield: 16.0%) was prepared in the same fashion as Example 173, except that in Step 1, 49 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 7.74 (s, 1H), 7.50 (d, 1H), 7.10 (s, 1H), 7.03 (d, 1H), 6.80 (s, 1H), 4.56 (s, 2H), 3.98 (t, 2H), 3.59 (s, 2H), 3.44 (t, 4H), 3.37 (t, 4H), 3.24 (t, 2H)

Example 175. 2-[2-(aminomethyl)-3,3-difluoro-allyl]-4-[2-[5-[6-(trifluoromethyl)-3-pyridyl]-2-thienyl]ethyl]-1,2,4-triazol-3-one trifluoroacetate 21 mg of the title compound (yield: 37.6%) was prepared in the same fashion as Example 173, except that in Step 1, 34 mg of 2-(trifluoromethyl)pyridine-5-boronic acid pinacol ester was used instead of 4-(methanesulfonyl)phenylboronic acid. $^1$H-NMR (MeOD, 400 MHz) δ 8.92 (s, 1H), 8.19 (d, 1H), 7.82 (d, 1H), 7.79 (s, 1H), 7.51 (s, 1H), 6.97 (s, 1H), 4.56 (s, 2H), 4.01 (t, 2H), 3.65 (s, 2H), 3.36 (s, 3H), 3.32 (t, 2H)

Example 176. 2-[2-(aminomethyl)-3,3-difluoro-allyl]-4-[2-[5-[6-(dimethylamino)-3-pyridyl]-2-thienyl]ethyl]-1,2,4-triazol-3-one trifluoroacetate 29 mg of the title compound (yield: 35.2%) was prepared in the same fashion as Example 173, except that in Step 1, 31 mg of 6-(dimethylamino)pyridine-3-boronic acid was used instead of 4-(methanesulfonyl)phenylboronic acid. $^1$H-NMR (MeOD, 400 MHz) δ 8.10 (s, 1H), 8.06 (d, 1H), 7.76 (s, 1H), 7.22 (s, 1H), 7.13 (d, 1H), 6.87 (s, 1H), 4.56 (s, 2H), 3.99 (t, 2H), 3.65 (s, 2H), 3.36 (t, 2H), 3.27 (s, 6H)

Example 177. 2-[2-(aminomethyl)-3,3-difluoro-allyl]-4-[2-[5-(1,3-benzodioxol-5-yl)-2-thienyl]ethyl]-1,2,4-triazol-3-one trifluoroacetate 29 mg of the title compound (yield: 55.2%) was prepared in the same fashion as Example 173, except that in Step 1, 34 mg of 2-(1,3-benzodioxol-5-yl)-4,4,5,5-tetramethyl-1,3,2-dioxaborolane was used instead of 4-(methanesulfonyl)phenylboronic acid. $^1$H-NMR (MeOD, 400 MHz) δ 7.73 (s, 1H), 7.06-7.02 (m, 3H), 6.82-6.77 (m, 2H), 5.97 (s, 2H), 4.59 (s, 2H), 3.97 (t, 2H), 3.63 (s, 2H), 3.23 (t, 2H)

Example 178. 6-[5-[2-[1-[2-(aminomethyl)-3,3-difluoro-allyl]-5-oxo-1,2,4-triazol-4-yl]ethyl]-2-thienyl]-8-methyl-3,4-dihydro-TH-quinolin-2-one trifluoroacetate 21 mg of the title compound (yield: 36.0%) was prepared in the same fashion as Example 173, except that in Step 1, 36 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 7.75 (s, 1H), 7.24 (d, 1H), 7.13 (d, 1H), 6.80 (d, 1H), 4.56 (s, 2H), 3.97 (t, 2H), 3.63 (s, 2H), 3.24 (t, 2H), 2.94 (t, 2H), 2.57 (t, 2H), 2.27 (s, 3H)

Example 179. 6-[5-[2-[1-[2-(aminomethyl)-3,3-difluoro-allyl]-5-oxo-1,2,4-triazol-4-yl]ethyl]-2-thienyl]-1-methyl-3,4-dihydroquinolin-2-one trifluoroacetate 17 mg of the title compound (yield: 30.4%) was prepared in the same fashion as Example 173, except that in Step 1, 36 mg of (1-methyl-2-oxo-1,2,3,4-tetrahydroquinolin-6-yl)boronic acid pinacol ester was used instead of 4-(methanesulfonyl)phenylboronic acid. $^1$H-NMR (MeOD, 400 MHz) δ 7.75 (s, 1H), 7.47 (d, 1H), 7.43 (s, 1H), 7.18 (s, 1H), 7.12 (d, 1H), 6.83 (s, 1H), 4.56 (s, 2H), 3.99 (t, 2H), 3.64 (s, 2H), 3.32 (s, 3H), 3.26 (t, 2H), 2.94 (t, 2H), 2.64 (t, 2H)

Example 180. 2-[2-(aminomethyl)-3,3-difluoro-allyl]-4-[2-[5-(1-ethylpyrazol-4-yl)-2-thienyl]ethyl]-1,2,4-triazol-3-one trifluoroacetate 21 mg of the title compound (yield: 42.4%) was prepared in the same fashion as Example 173, except that in Step 1, 28 mg of 1-ethylpyrazole-4-boronic acid pinacol ester was used instead of 4-(methanesulfonyl)phenylboronic acid. $^1$H-NMR (MeOD, 400 MHz) δ 7.84 (s, 1H), 7.72 (s, 1H), 7.63 (s, 1H), 6.95 (s, 1H), 6.75 (s, 1H), 4.56 (s, 2H), 4.19 (q, 2H), 3.96 (t, 2H), 3.63 (s, 2H), 3.22 (t, 2H), 1.47 (t, 3H)

Example 181. 3-[5-[[1-[2-(aminomethyl)-3,3-difluoro-allyl]-5-oxo-1,2,4-triazol-4-yl]methyl]-2-thienyl]-N,N-dimethyl-benzamide trifluoroacetate 925 mg of the title compound (yield: 99.3%) was prepared in the same fashion as Example 100, except that in Step 1, 539 mg of 3-(dimethylcarbamoyl)phenylboronic acid was used instead of 4-acetylphenylboronicacid. $^1$H-NMR (MeOD, 400 MHz) δ 8.00 (s, 1H), 7.70 (d, 1H), 7.65 (s, 1H), 7.49 (t, 1H), 7.36 (d, 2H), 7.16 (d, 1H), 5.08 (s, 2H), 4.59 (s, 2H), 3.67 (s, 2H), 3.13 (s, 3H), 3.03 (s, 3H)

Example 182. 6-[5-[[1-[2-(aminomethyl)-3,3-difluoro-allyl]-5-oxo-1,2,4-triazol-4-yl]methyl]-2-thienyl]-3-methyl-1,4-dihydroquinazolin-2-one trifluoroacetate 26 mg of the title compound (yield: 46.4%) was prepared in the same fashion as Example 100, except that in Step 1, 40 mg of 3-methyl-6-(4,4,5,5-tetramethyl-1,3,2-dioxaborolan-2-yl)-1,4-dihydroquinazolin-2-one was used instead of 4-acetylphenylboronicacid. $^1$H-NMR (MeOD, 400 MHz) δ 7.98 (s, 1H), 7.37 (d, 1H), 7.32 (s, 1H), 7.15 (d, 1H), 7.09 (d, 1H), 6.78 (d, 1H), 5.04 (s, 2H), 4.59 (s, 2H), 4.48 (s, 2H), 3.67 (s, 2H), 2.98 (s, 3H)

Example 183. 2-[2-(aminomethyl)-3,3-difluoro-allyl]-4-[[5-[1-(difluoromethyl)pyrazol-4-yl]-2-thienyl]methyl]-1,2,4-triazol-3-one trifluoroacetate 26 mg of the title compound (yield: 60.7%) was prepared in the same fashion as Example 100, except that in Step 1, 26 mg of 1-difluoromethyl-4-(4,4,5,5-tetramethyl-1,3,2-dioxaborolan-2-yl)pyrazole was used instead of 4-acetylphenylboronicacid. ¹H-NMR (MeOD, 400 MHz) δ 8.31 (s, 1H), 7.95 (d, 2H), 7.49 (t, 1H), 7.13 (d, 2H), 5.05 (s, 2H), 4.58 (s, 2H), 3.67 (s, 2H)

Example 184. 2-[2-(aminomethyl)-3,3-difluoro-allyl]-4-[[5-(1-isopropylpyrazol-4-yl)-2-thienyl]methyl]-1,2,4-triazol-3-one trifluoroacetate 36 mg of the title compound (yield: 81.8%) was prepared in the same fashion as Example 100, except that in Step 1, 17 mg of (1-isopropylpyrazole-4-yl)boronic acid was used instead of 4-acetylphenylboronicacid. ¹H-NMR (MeOD, 400 MHz) δ 7.94 (d, 2H), 7.67 (s, 1H), 7.04 (m, 2H), 5.03 (s, 2H), 4.55 (m, 3H), 3.68 (s, 2H), 1.51 (d, 6H)

Example 185. 2-[2-(aminomethyl)-3,3-difluoro-allyl]-4-[[5-[3-(1H-1,2,4-triazol-3-yl)phenyl]-2-thienyl]methyl]-1,2,4-triazol-3-one trifluoroacetate 19 mg of the title compound (yield: 37.5%) was prepared in the same fashion as Example 100, except that in Step 1, 50 mg of trimethyl-[2-[[3-[3-(4,4,5,5-tetramethyl-1,3,2-dioxaborolan-2-yl)phenyl]-1,2,4-triazole-1-yl]methoxy]ethyl]silane was used instead of 4-acetylphenylboronicacid. ¹H-NMR (MeOD, 400 MHz) δ 8.41 (bs, 1H), 8.21 (s, 1H), 8.02 (s, 1H), 7.96 (d, 1H), 7.70 (d, 1H), 7.52 (t, 1H), 7.39 (d, 1H), 7.18 (d, 1H), 5.10 (s, 2H), 4.60 (s, 2H), 3.68 (s, 2H)

Example 186. 6-[5-[[1-[2-(aminomethyl)-3,3-difluoro-allyl]-5-oxo-1,2,4-triazol-4-yl]methyl]-3-thienyl]-3-methyl-1,4-dihydroquinazolin-2-one trifluoroacetate 19 mg of the title compound (yield: 30.4%) was prepared in the same fashion as Example 100, except that in Step 1, 58 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 40 mg of 3-methyl-6-(4,4,5,5-tetramethyl-1,3,2-dioxaborolan-2-yl)-1,4-dihydroquinazolin-2-one was used instead of 4-acetylphenylboronic acid. ¹H-NMR (MeOD, 400 MHz) δ 7.99 (s, 1H), 7.47 (d, 2H), 7.42 (d, 1H), 7.37 (s, 1H), 6.80 (d, 1H), 5.07 (s, 2H), 4.59 (s, 2H), 4.50 (s, 2H), 3.67 (s, 2H), 2.83 (s, 3H)

Example 187. 5-[5-[[1-[2-(aminomethyl)-3,3-difluoro-allyl]-5-oxo-1,2,4-triazol-4-yl]methyl]-3-thienyl]-1-isopropyl-pyridin-2-one trifluoroacetate 36 mg of the title compound (yield: 80.4%) was prepared in the same fashion as Example 100, except that in Step 1, 50 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 28 mg of 1-isopropyl-5-(4,4,5,5-tetramethyl-1,3,2-dioxaborolan-2-yl)pyridin-2(1H)-one was used instead of 4-acetylphenylboronic acid. ¹H-NMR (MeOD, 400 MHz) δ 8.01 (s, 1H), 7.94 (d, 1H), 7.83 (dd, 1H), 7.56 (d, 1H), 7.48 (s, 1H), 6.61 (d, 1H), 5.24 (m, 1H), 5.09 (s, 2H), 4.60 (s, 2H), 3.69 (s, 2H), 1.46 (d, 6H)

Example 188. 4-[[4-[4-(4-acetylpiperazin-1-yl)phenyl]-2-thienyl]methyl]-2-[2-(aminomethyl)-3,3-difluoro-allyl]-1,2,4-triazol-3-one trifluoroacetate 28 mg of the title compound (yield: 53.3%) was prepared in the same fashion as Example 100, except that in Step 1, 50 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 27 mg of 4-(4-acetyl-1-piperazinyl)phenylboronic acid was used instead of 4-acetylphenylboronic acid. ¹H-NMR (MeOD, 400 MHz) δ 7.99 (s, 1H), 7.54 (d, 2H), 7.46 (d, 2H), 7.00 (d, 2H), 5.08 (s, 2H), 4.59 (s, 2H), 3.74 (t, 2H), 3.68 (d, 4H), 3.24 (d, 2H), 3.18 (d, 2H), 2.15 (s, 3H)

Example 189. 6-[5-[[1-[2-(aminomethyl)-3,3-difluoro-allyl]-5-oxo-1,2,4-triazol-4-yl]methyl]-3-thienyl]-8-fluoro-1H-quinolin-2-one trifluoroacetate 35 mg of the title compound (yield: 73.8%) was prepared in the same fashion as Example 100, except that in Step 1, 50 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 31 mg of 8-fluoro-6-(4,4,5,5-tetramethyl-1,3,2-dioxaborolan-2-yl)-1H-quinolin-2-one was used instead of 4-acetylphenylboronic acid. ¹H-NMR (MeOD, 400 MHz) δ 8.04 (s, 1H), 7.94 (d, 1H), 7.65 (m, 3H), 7.53 (s, 1H), 6.64 (d, 1H), 5.11 (s, 2H), 4.61 (s, 2H), 3.70 (s, 2H)

Example 190. 5-[5-[[1-[2-(aminomethyl)-3,3-difluoro-allyl]-5-oxo-1,2,4-triazol-4-yl]methyl]-3-thienyl]-1-methyl-pyridin-2-one trifluoroacetate 39 mg of the title compound (yield: 93.4%) was prepared in the same fashion as Example 100, except that in Step 1, 50 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 25 mg of (1-methyl-6-oxo-1,6-dihydropyridin-3-yl)boronic acid pinacol ester was used instead of 4-acetylphenylboronic acid. ¹H-NMR (MeOD, 400 MHz) δ 8.02 (m, 2H), 7.87 (dd, 1H), 7.52 (d, 1H), 7.42 (s, 1H), 6.60 (d, 1H) 5.08 (s, 2H), 4.60 (s, 2H), 3.68 (s, 2H), 3.62 (s, 3H)

Example 191. 6-[5-[[1-[2-(aminomethyl)-3,3-difluoro-allyl]-5-oxo-1,2,4-triazol-4-yl]methyl]-3-thienyl]-1,4-dihydro-3,1-benzoxazin-2-one trifluoroacetate 43 mg of the title compound (yield: 92.5%) was prepared in the same fashion as Example 100, except that in Step 1, 50 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 30 mg of 1,4-dihydro- 6-(4,4,5,5-tetramethyl-1,3,2-dioxaborolan-2-yl)-2H-3,1-benzoxazin-2-one was used instead of 4-acetylphenylboronic acid. $^1$H-NMR (MeOD, 400 MHz) δ 8.01 (s, 1H), 7.59 (d, 1H), 7.48 (s, 1H), 7.31 (dd, 1H), 7.19 (d, 1H), 7.10 (s, 1H), 5.31 (s, 2H), 5.09 (s, 2H), 4.60 (s, 2H), 3.69 (s, 2H)

Example 192. 6-[5-[[1-[2-(aminomethyl)-3,3-difluoro-allyl]-5-oxo-1,2,4-triazol-4-yl]methyl]-3-thienyl]-3,4-dihydro-TH-quinolin-2-one trifluoroacetate 25 mg of the title compound (yield: 54.2%) was prepared in the same fashion as Example 100, except that in Step 1, 50 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 29 mg of 6-(4,4,5,5-tetramethyl-1,3,2-dioxaborolan-2-yl)-3,4-dihydroquinolin-2(1H)-one was used instead of 4-acetylphenylboronic acid. $^1$H-NMR (MeOD, 400 MHz) δ 8.00 (s, 1H), 7.53 (d, 1H), 7.46 (m, 3H), 6.89 (d, 1H), 5.08 (s, 2H), 4.60 (s, 2H), 3.68 (s, 2H), 2.99 (t, 2H), 2.59 (t, 2H)

Example 193. 5-[5-[[1-[2-(aminomethyl)-3,3-difluoro-allyl]-5-oxo-1,2,4-triazol-4-yl]methyl]-3-thienyl]-1-ethyl-pyridin-2-one trifluoroacetate 23 mg of the title compound (yield: 53.3%) was prepared in the same fashion as Example 100, except that in Step 1, 50 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 27 mg of 1-ethyl-6-oxo-1,6-dihydropyridin-3-boronic acid pinacol ester was used instead of 4-acetylphenylboronic acid. $^1$H-NMR (MeOD, 400 MHz) δ 8.03 (m, 2H), 7.87 (dd, 1H), 7.54 (d, 1H), 7.44 (s, 1H), 6.61 (d, 1H), 5.09 (s, 2H), 4.60 (s, 2H), 4.11 (q, 2H), 3.68 (s, 2H), 1.38 (t, 3H)

Example 194. 2-[2-(aminomethyl)-3,3-difluoro-allyl]-4-[[4-[1-(difluoromethyl)pyrazol-4-yl]-2-thienyl]methyl]-1,2,4-triazol-3-one trifluoroacetate 24 mg of the title compound (yield: 56.1%) was prepared in the same fashion as Example 100, except that in Step 1, 50 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 17 mg of 1-(difluoromethyl)-4-(4,4,5,5-tetramethyl-1,3,2-dioxaborolan-2-yl)pyrazole was used instead of 4-acetylphenylboronic acid. $^1$H-NMR (MeOD, 400 MHz) δ 8.34 (s, 1H), 8.00 (d, 2H), 7.50 (m, 3H), 5.08 (s, 2H), 4.59 (s, 2H), 3.68 (s, 2H)

Example 195. 2-[2-(aminomethyl)-3,3-difluoro-allyl]-4-[[4-(1-isopropylpyrazol-4-yl)-2-thienyl]methyl]-1,2,4-triazol-3-one trifluoroacetate 38 mg of the title compound (yield: 87.3%) was prepared in the same fashion as Example 100, except that in Step 1, 51 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 17 mg of (1-isopropylpyrazol-4-yl)boronic acid was used instead of 4-acetylphenylboronic acid. $^1$H-NMR (MeOD, 400 MHz) δ 7.97 (d, 2H), 7.74 (s, 1H), 7.37 (d, 2H), 5.06 (s, 2H), 4.56 (m, 3H), 3.68 (s, 2H), 1.52 (d, 6H)

Example 196. 2-[2-(aminomethyl)-3,3-difluoro-allyl]-4-[[4-[3-(1H-1,2,4-triazol-3-yl)phenyl]-2-thienyl]methyl]-1,2,4-triazol-3-one trifluoroacetate 8 mg of the title compound (yield: 15.2%) was prepared in the same fashion as Example 100, except that in Step 1, 52 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 50 mg of trimethyl-[2-[[3-[3-(4,4,5,5-tetramethyl-1,3,2-dioxaborolan-2-yl)phenyl]-1,2,4-triazole-1-yl]methoxy]ethyl]silane was used instead of 4-acetylphenylboronic acid. $^1$H-NMR (MeOD, 400 MHz) δ 8.43 (bs, 1H), 8.24 (s, 1H), 8.04 (s, 1H), 7.95 (d, 1H), 7.76 (d, 1H), 7.73 (s, 1H), 7.65 (s, 1H), 7.57 (t, 1H), 5.13 (s, 2H), 4.60 (s, 2H), 3.68 (s, 2H)

Example 197. 2-[2-(aminomethyl)-3,3-difluoro-allyl]-4-[[6-(4-methylsulfonylphenyl)benzothiophen-2-yl]methyl]-1,2,4-triazol-3-one trifluoroacetate Step 1: tert-butyl N-[3,3-difluoro-2-[[4-[[6-(4-methylsulfonylphenyl)benzothiophen-2-yl]methyl]-5-oxo-1,2,4-triazol-1-yl]methyl]allyl]carbamate 40 mg of tert-butyl N-[2-[[4-[(6-bromobenzothiophen-2-yl)methyl]-5-oxo-1,2,4-triazol-1-yl]methyl]-3,3-difluoro-allyl]carbamate prepared in Reference Example 57 and 22 mg of 4,4,5,5-tetramethyl-2-(4-methylsulfonylphenyl)-1,3,2-dioxaborolan were dissolved in 1.5 mL of 1,4-dioxane, followed by the addition of 0.2 mL of 1 M potassium carbonate and 2 mg of palladiumdi[1,1'-bis(diphenylphosphino)ferrocene]dichloride (PdCl$_2$(dppf)), and the resulting solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 38 mg of the title compound (yield: 83.8%). MS (ESI) m/z=491.2 (M+H)+

Step 2: 2-[2-(aminomethyl)-3,3-difluoro-allyl]-4-[[6-(4-methylsulfonylphenyl)benzothiophen-2-yl]methyl]-1,2,4-triazol-3-one 47 mg of tert-butyl N-[3,3-difluoro-2-[[4-[[6-(4-methylsulfonylphenyl)benzothiophen-2-yl]methyl]-5-oxo-1,2,4-triazol-1-yl]methyl]allyl]carbamate prepared in Step 1 was dissolved in 1.0 mL of dichloromethane, followed by the addition of 0.1 mL of trifluoroacetic acid, and the resulting solution was stirred at room temperature for 2 hours. The reaction mixture thus obtained was concentrated, followed by the addition of dichloromethane. Dichloromethane was added to the concentrated reaction mixture, and it was concentrated under reduced pressure to obtain a yellow liquid residue. The residue was purified with silica gel column chromatography (developing solvent: dichloromethane/methanol=10/1) to give 4 mg of the title compound as a white solid (yield: 12.0%). $^1$H-NMR (DMSO-$d_6$, 400 MHz) δ 8.40 (s, 1H), 8.22 (s, 1H), 8.02 (s, 4H), 7.97 (d, 1H), 7.79 (dd, 1H), 7.46 (s, 1H), 5.15 (s, 2H), 4.53 (s, 2H), 3.49 (s, 2H), 3.27 (s, 3H)

Example 198. 2-[2-(aminomethyl)-3,3-difluoro-allyl]-4-[[6-(4-piperazin-1-ylphenyl)benzothiophen-2-yl]methyl]-1,2,4-triazol-3-one ditrifluoroacetate 30 mg of the title compound (yield: 76.9%) was prepared in the same fashion as Example 197, except that in Step 1, 30 mg of tert-butyl 4-[4-(tetramethyl-1,3,2-dioxaborolan-2-yl)phenyl]piperazine-1-carboxylate was used instead of 4,4,5,5-tetramethyl-2-(4-methylsulfonylphenyl)-1,3,2-dioxaborolan. $^1$H-NMR (MeOD, 400 MHz) δ 8.03 (d, 2H), 7.82 (d, 1H), 7.62 (m, 3H), 7.39 (s, 1H), 7.12 (d, 2H), 5.17 (s, 2H), 4.61 (s, 2H), 3.68 (s, 2H), 3.49 (t, 4H), 3.40 (t, 4H)

Example 199. 2-[2-(aminomethyl)-3,3-difluoro-allyl]-4-[[6-[6-(trifluoromethyl)-3-pyridyl]benzothiophen-2-yl]methyl]-1,2,4-triazol-3-one trifluoroacetate 37 mg of the title compound (yield: 98.5%) was prepared in the same fashion as Example 197, except that in Step 1, 21 mg of 2-(trifluoromethyl)pyridine-5-boronic acid pinacol ester was used instead of 4,4,5,5-tetramethyl-2-(4-methylsulfonylphenyl)-1,3,2-dioxaborolan. $^1$H-NMR (MeOD, 400 MHz) δ 9.02 (s, 1H), 8.33 (dd, 1H), 8.24 (s, 1H), 8.05 (s, 1H), 7.91 (dd, 2H), 7.73 (dd, 1H), 7.46 (s, 1H), 5.21 (s, 2H), 4.62 (s, 2H), 3.70 (s, 2H)

Example 200. 2-[2-(aminomethyl)-3,3-difluoro-allyl]-4-[[6-[6-(dimethylamino)-3-pyridyl]benzothiophen-2-yl]methyl]-1,2,4-triazol-3-one trifluoroacetate 24 mg of the title compound (yield: 65.8%) was prepared in the same fashion as Example 197, except that in Step 1, 13 mg of (6-(dimethylamino)pyridin-3-yl)boronic acid was used instead of 4,4,5,5-tetramethyl-2-(4-methylsulfonylphenyl)-1,3,2-dioxaborolan. $^1$H-NMR (MeOD, 400 MHz) δ 8.24 (d, 2H), 8.11 (s, 1H), 8.04 (s, 1H), 7.89 (d, 1H), 7.62 (dd, 1H), 7.43 (s, 1H), 7.18 (d, 1H), 5.20 (s, 2H), 4.61 (s, 2H), 3.69 (s, 2H), 3.29 (s, 6H)

Example 201. 2-[2-(aminomethyl)-3,3-difluoro-allyl]-4-[[6-(1,3-benzodioxol-5-yl)benzothiophen-2-yl]methyl]-1,2,4-triazol-3-one trifluoroacetate 30 mg of the title compound (yield: 83.5%) was prepared in the same fashion as Example 197, except that in Step 1, 20 mg of 2-(1,3-benzodioxol-5-yl)-4,4,5,5-tetramethyl-1,3,2-dioxaborolane was used instead of 4,4,5,5-tetramethyl-2-(4-methylsulfonylphenyl)-1,3,2-dioxaborolan. $^1$H-NMR (DMSO-$d_6$, 400 MHz) δ 8.19 (d, 2H), 8.01 (bs, 1H), 7.85 (d, 1H), 7.64 (dd, 1H), 7.40 (s, 1H), 7.32 (d, 1H), 7.21 (dd, 1H), 7.02 (d, 1H), 6.07 (s, 2H), 5.12 (s, 2H), 4.52 (s, 2H), 3.48 (s, 2H)

Example 202. 6-[2-[[1-[2-(aminomethyl)-3,3-difluoro-allyl]-5-oxo-1,2,4-triazol-4-yl]methyl]benzothiophen-6-yl]-8-methyl-3,4-dihydro-1H-quinolin-2-one trifluoroacetate 36 mg of the title compound (yield: 92.4%) was prepared in the same fashion as Example 197, except that in Step 1, 23 mg of 8-methyl-2-oxo-1,2,3,4-tetrahydroquinoline-6-boronic acid pinacol ester was used instead of 4,4,5,5-tetramethyl-2-(4-methylsulfonylphenyl)-1,3,2-dioxaborolan. $^1$H-NMR (MeOD, 400 MHz) δ 8.03 (s, 1H), 7.98 (s, 1H), 7.79 (d, 1H), 7.57 (dd, 1H), 7.38 (s, 1H), 7.32 (d, 2H), 5.17 (s, 2H), 4.62 (s, 2H), 3.69 (s, 2H), 2.96 (t, 2H), 2.56 (t, 2H), 2.31 (s, 3H)

Example 203. 6-[2-[[1-[2-(aminomethyl)-3,3-difluoro-allyl]-5-oxo-1,2,4-triazol-4-yl]methyl]benzothiophen-6-yl]-1-methyl-3,4-dihydroquinolin-2-one trifluoroacetate 30 mg of the title compound (yield: 75.9%) was prepared in the same fashion as Example 197, except that in Step 1, 23 mg of (1-methyl-2-oxo-1,2,3,4-tetrahydroquinoline-6-yl)boronic acid pinacol ester was used instead of 4,4,5,5-tetramethyl-2-(4-methylsulfonylphenyl)-1,3,2-dioxaborolan. $^1$H-NMR (MeOD, 400 MHz) δ 8.03 (d, 1H), 7.81 (d, 1H), 7.61 (dd, 1H), 7.56 (dd, 1H), 7.51 (s, 1H), 7.40 (s, 1H), 7.15 (d, 1H), 5.17 (s, 2H), 4.62 (s, 2H), 3.69 (s, 2H), 3.33 (m, 3H), 2.95 (t, 2H), 2.62 (t, 2H)

Example 204. 2-[2-(aminomethyl)-3,3-difluoro-allyl]-4-[[6-(1-ethylpyrazol-4-yl)benzothiophen-2-yl]methyl]-1,2,4-triazol-3-one trifluoroacetate 27 mg of the title compound (yield: 78.5%) was prepared in the same fashion as Example 197, except that in Step 1, 18 mg of 1-ethyl-4-(4,4,5,5-tetramethyl-1,3,2-dioxaborolan-2-yl)-1H-pyrazole was used instead of 4,4,5,5-tetramethyl-2-(4-methylsulfonylphenyl)-1,3,2-dioxaborolan. $^1$H-NMR (MeOD, 400 MHz) δ 8.07 (s, 1H), 8.02 (d, 2H), 7.89 (s, 1H), 7.76 (d, 1H), 7.58 (dd, 1H), 7.36 (s, 1H), 5.15 (s, 2H), 4.61 (s, 2H), 4.23 (q, 2H), 3.68 (s, 2H), 1.50 (t, 3H)

Example 205. 2-[2-(aminomethyl)-3,3-difluoro-allyl]-4-[[5-(4-methylsulfonylphenyl)benzothiophen-2-yl]methyl]-1,2,4-triazol-3-one trifluoroacetate 36 mg of the title compound (yield: 91.4%) was prepared in the same fashion as Example 197, except that in Step 1, 42 mg of tert-butyl N-[2-[[4-[(5-bromobenzothiophen-2-yl)methyl]-5-oxo-1,2,4-triazol-1-yl]methyl]-3,3-difluoro-allyl]carbamate prepared in Reference Example 58 was used instead of tert-butyl N-[2-[[4-[(6-bromobenzothiophen-2-yl)methyl]-5-oxo-1,2,4-triazol-1-yl]methyl]-3,3-difluoro-allyl]carbamate prepared in Reference Example 57. $^1$H-NMR (MeOD, 400 MHz) δ 8.10 (s, 1H), 8.03 (d, 3H), 7.93 (m, 3H), 7.68 (d, 1H), 7.48 (s, 1H), 5.20 (s, 2H), 4.62 (s, 2H), 3.69 (s, 2H), 3.17 (s, 3H)

Example 206. 2-[2-(aminomethyl)-3,3-difluoro-allyl]-4-[[5-(4-piperazin-1-ylphenyl)benzothiophen-2-yl]methyl]-1,2,4-triazol-3-one ditrifluoroacetate 18 mg of the title compound (yield: 44.4%) was prepared in the same fashion as Example 197, except that in Step 1, 42 mg of tert-butyl N-[2-[[4-[(5-bromobenzothiophen-2-yl)methyl]-5-oxo-1,2,4-triazol-1-yl]methyl]-3,3-difluoro-allyl]

carbamate prepared in Reference Example 58 was used instead of tert-butyl N-[2-[[4-[(6-bromobenzothiophen-2-yl)methyl]-5-oxo-1,2,4-triazol-1-yl]methyl]-3,3-difluoro-allyl] carbamate prepared in Reference Example 57 and 31 mg of tert-butyl 4-[4-(tetramethyl-1,3,2-dioxaborolan-2-yl)phenyl]piperazine-1-carboxylate was used instead of 4,4,5,5-tetramethyl-2-(4-methylsulfonylphenyl)-1,3,2-dioxaborolan. $^1$H-NMR (MeOD, 400 MHz) δ 7.99 (d, 2H), 7.87 (d, 1H), 7.62 (m, 3H), 7.44 (s, 1H), 7.14 (s, 1H), 5.19 (s, 2H), 4.61 (s, 2H), 3.68 (s, 2H), 3.48 (d, 4H), 3.42 (d, 4H), 3.32 (s, 3H)

Example 207. 5-[2-[[1-[2-(aminomethyl)-3,3-difluoro-allyl]-5-oxo-1,2,4-triazol-4-yl]methyl]benzothiophen-5-yl]-1-ethyl-pyridin-2-one trifluoroacetate 32 mg of the title compound (yield: 86.4%) was prepared in the same fashion as Example 197, except that in Step 1, 42 mg of tert-butyl N-[2-[[4-[(5-bromobenzothiophen-2-yl)methyl]-5-oxo-1,2,4-triazol-1-yl]methyl]-3,3-difluoro-allyl] carbamate prepared in Reference Example 58 was used instead of tert-butyl N-[2-[[4-[(6-bromobenzothiophen-2-yl)methyl]-5-oxo-1,2,4-triazol-1-yl]methyl]-3,3-difluoro-allyl] carbamate prepared in Reference Example 57 and 20 mg of 1-ethyl-6-oxo-1,6-dihydropyridine-3-boronic acid pinacol ester was used instead of 4,4,5,5-tetramethyl-2-(4-methylsulfonylphenyl)-1,3,2-dioxaborolan. $^1$H-NMR (MeOD, 400 MHz) δ 8.03 (d, 2H), 7.91 (m, 3H), 7.54 (d, 1H), 7.44 (s, 1H), 6.66 (d, 1H), 5.19 (s, 2H), 4.61 (s, 2H), 4.13 (q, 2H), 3.69 (s, 2H), 1.40 (t, 3H)

Example 208. 2-[2-(aminomethyl)-3,3-difluoro-allyl]-4-[[5-[6-(dimethylamino)-3-pyridyl]benzothiophen-2-yl]methyl]-1,2,4-triazol-3-one trifluoroacetate 35 mg of the title compound (yield: 94.6%) was prepared in the same fashion as Example 197, except that in Step 1, 42 mg of tert-butyl N-[2-[[4-[(5-bromobenzothiophen-2-yl)methyl]-5-oxo-1,2,4-triazol-1-yl]methyl]-3,3-difluoro-allyl] carbamate prepared in Reference Example 58 was used instead of tert-butyl N-[2-[[4-[(6-bromobenzothiophen-2-yl)methyl]-5-oxo-1,2,4-triazol-1-yl]methyl]-3,3-difluoro-allyl] carbamate prepared in Reference Example 57 and 20 mg of 6-(dimethylamino)pyridine-3-boronic acid pinacol ester was used instead of 4,4,5,5-tetramethyl-2-(4-methylsulfonylphenyl)-1,3,2-dioxaborolan. $^1$H-NMR (MeOD, 400 MHz) δ 8.30 (d, 1H), 8.21 (s, 1H), 8.04 (s, 2H), 7.96 (d, 1H), 7.60 (d, 1H), 7.48 (s, 1H), 7.27 (d, 1H), 5.20 (s, 2H), 4.61 (s, 2H), 3.70 (s, 2H), 3.32 (s, 6H)

Example 209. 2-[2-(aminomethyl)-3,3-difluoro-allyl]-4-[[5-(1,3-benzodioxol-5-yl)benzothiophen-2-yl]methyl]-1,2,4-triazol-3-one trifluoroacetate 31 mg of the title compound (yield: 82.7%) was prepared in the same fashion as Example 197, except that in Step 1, 42 mg of tert-butyl N-[2-[[4-[(5-bromobenzothiophen-2-yl)methyl]-5-oxo-1,2,4-triazol-1-yl]methyl]-3,3-difluoro-allyl] carbamate prepared in Reference Example 58 was used instead of tert-butyl N-[2-[[4-[(6-bromobenzothiophen-2-yl)methyl]-5-oxo-1,2,4-triazol-1-yl]methyl]-3,3-difluoro-allyl] carbamate prepared in Reference Example 57 and 20 mg of 2-(1,3-benzodioxol-5-yl)-4,4,5,5-tetramethyl-1,3,2-dioxaborolane was used instead of 4,4,5,5-tetramethyl-2-(4-methylsulfonylphenyl)-1,3,2-dioxaborolan. $^1$H-NMR (MeOD, 400 MHz) δ 8.02 (s, 1H), 7.92 (s, 1H), 7.84 (d, 1H), 7.54 (d, 1H), 7.42 (s, 1H), 7.14 (d, 2H), 7.91 (d, 1H), 6.00 (s, 2H), 5.17 (s, 2H), 4.61 (s, 2H), 3.68 (s, 2H)

Example 210. 6-[2-[[1-[2-(aminomethyl)-3,3-difluoro-allyl]-5-oxo-1,2,4-triazol-4-yl]methyl]benzothiophen-5-yl]-8-methyl-3,4-dihydro-TH-quinolin-2-one trifluoroacetate 29 mg of the title compound (yield: 71.6%) was prepared in the same fashion as Example 197, except that in Step 1, 42 mg of tert-butyl N-[2-[[4-[(5-bromobenzothiophen-2-yl)methyl]-5-oxo-1,2,4-triazol-1-yl]methyl]-3,3-difluoro-allyl] carbamate prepared in Reference Example 58 was used instead of tert-butyl N-[2-[[4-[(6-bromobenzothiophen-2-yl)methyl]-5-oxo-1,2,4-triazol-1-yl]methyl]-3,3-difluoro-allyl] carbamate prepared in Reference Example 57 and 23 mg of 8-methyl-2-oxo-1,2,3,4-tetrahydroquinoline-6-boronic acid pinacol ester was used instead of 4,4,5,5-tetramethyl-2-(4-methylsulfonylphenyl)-1,3,2-dioxaborolan. $^1$H-NMR (MeOD, 400 MHz) δ 8.03 (s, 1H), 7.94 (s, 1H), 7.85 (d, 1H), 7.57 (d, 1H), 7.42 (s, 1H), 7.34 (d, 2H), 5.18 (s, 2H), 4.61 (s, 2H), 3.69 (s, 2H), 2.98 (t, 2H), 2.58 (t, 2H), 2.33 (s, 3H)

Example 211. 6-[2-[[1-[2-(aminomethyl)-3,3-difluoro-allyl]-5-oxo-1,2,4-triazol-4-yl]methyl]benzothiophen-5-yl]-1-methyl-3,4-dihydroquinolin-2-one trifluoroacetate 27 mg of the title compound (yield: 66.7%) was prepared in the same fashion as Example 197, except that in Step 1, 42 mg of tert-butyl N-[2-[[4-[(5-bromobenzothiophen-2-yl)methyl]-5-oxo-1,2,4-triazol-1-yl]methyl]-3,3-difluoro-allyl] carbamate prepared in Reference Example 58 was used instead of tert-butyl N-[2-[[4-[(6-bromobenzothiophen-2-yl)methyl]-5-oxo-1,2,4-triazol-1-yl]methyl]-3,3-difluoro-allyl] carbamate prepared in Reference Example 57 and 23 mg of (1-methyl-2-oxo-1,2,3,4-tetrahydroquinoline-6-yl)boronic acid pinacol ester was used instead of 4,4,5,5-tetramethyl-2-(4-methylsulfonylphenyl)-1,3,2-dioxaborolan. $^1$H-NMR (MeOD, 400 MHz) δ 8.02 (d, 2H), 7.87 (d, 1H), 7.58 (m, 3H), 7.44 (s, 1H), 7.19 (d, 1H), 5.18 (s, 2H), 4.62 (s, 2H), 3.69 (s, 2H), 3.38 (s, 3H), 2.98 (t, 2H), 2.65 (t, 2H)

Example 212. 2-[2-(aminomethyl)-3,3-difluoro-allyl]-4-[[5-(1-ethylpyrazol-4-yl)benzothiophen-2-yl]methyl]-1,2,4-triazol-3-one trifluoroacetate 25 mg of the title compound (yield: 72.8%) was prepared in the same fashion as Example 197, except that in Step 1, 42 mg of tert-butyl N-[2-[[4-[(5-bromobenzothiophen-2-yl)methyl]-5-oxo-1,2,4-triazol-1-yl]methyl]-3,3-difluoro-allyl] carbamate prepared in Reference Example 58 was used instead of tert-butyl N-[2-[[4-[(6-bromobenzothiophen-2-yl)methyl]-5-oxo-1,2,4-triazol-1-yl]methyl]-3,3-difluoro-allyl] carbamate prepared in Reference Example 57 and 18 mg of 1-ethyl-4-(4,4,5,5-tetramethyl-1,3,2-dioxaborolan-2-yl)-1H-pyrazole was used instead of 4,4,5,5-tetramethyl-2-(4-methylsulfonylphenyl)-1,3,2-dioxaborolan. $^1$H-NMR (MeOD, 400 MHz) δ 8.04 (d, 2H), 7.97 (s, 1H), 7.88 (s, 1H), 7.81 (d, 1H), 7.57 (d, 1H), 7.39 (s, 1H), 5.17 (s, 2H), 4.61 (s, 2H), 4.24 (q, 2H), 3.68 (s, 2H), 1.51 (t, 3H)

Example 213. 2-[2-(aminomethyl)-3,3-difluoro-allyl]-4-[6-(6-piperazin-1-yl-3-pyridyl)-2-pyridyl]-1,2,4-triazol-3-one ditrifluoroacetate 28 mg of the title compound (yield: 56.2%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 57 mg of tert-butyl 4-[5-(4,4,5,5-tetramethyl-1,3,2-dioxaborolan-2-yl)-2-pyridyl]piperazine-1-carboxylate was used instead of 4-(methanesulfonyl)phenylboronic acid. $^1$H-NMR (MeOD, 400 MHz) δ 8.93 (s, 1H), 8.80 (s, 1H), 8.35 (d, 1H), 8.12 (d, 1H), 7.98 (t, 1H), 7.81 (d, 1H), 7.03 (d, 1H), 4.68 (s, 2H), 3.93 (s, 4H), 3.75 (s, 2H), 3.36 (s, 4H)

Example 214. 2-[2-(aminomethyl)-3,3-difluoro-allyl]-4-[6-[4-(morpholine-4-carbonyl)phenyl]-2-pyridyl]-1,2,4-triazol-3-one trifluoroacetate 28 mg of the title compound (yield: 53.6%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 46 mg of 4-(morpholine-4-carbonyl)phenylboronic acid pinacol ester was used instead of 4-(methanesulfonyl)phenylboronic acid. $^1$H-NMR (MeOD, 400 MHz) δ 8.84 (s, 1H), 8.23 (t, 3H), 8.06 (t, 1H), 7.94 (d, 1H), 7.57 (d, 2H), 4.68 (s, 2H), 3.76-3.66 (m, 8H), 3.51 (bs, 2H)

Example 215. 2-[2-(aminomethyl)-3,3-difluoro-allyl]-4-[6-(6-morpholino-3-pyridyl)-2-pyridyl]-1,2,4-triazol-3-one trifluoroacetate 34 mg of the title compound (yield: 70.5%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 42 mg of 6-(morpholin-4-yl)pyridine-3-boronic acid pinacol ester was used instead of 4-(methanesulfonyl)phenylboronic acid. $^1$H-NMR (MeOD, 400 MHz) δ 8.81 (d, 2H), 8.40 (d, 1H), 8.13 (d, 1H), 7.99 (t, 1H), 7.79 (d, 1H), 7.05 (d, 1H), 4.68 (s, 2H), 3.84 (s, 4H), 3.76 (s, 2H), 3.64 (s, 4H)

Example 216. 2-[2-(aminomethyl)-3,3-difluoro-allyl]-4-[6-(3-piperazin-1-ylphenyl)-2-pyridyl]-1,2,4-triazol-3-one ditrifluoroacetate 36 mg of the title compound (yield: 74.1%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 56 mg of 3-[4-N-Boc-piperazin-1-yl]phenylboronic acid pinacol ester was used instead of 4-(methanesulfonyl)phenylboronic acid. $^1$H-NMR (MeOD, 400 MHz) δ 8.81 (s, 1H), 8.17 (d, 1H), 8.02 (t, 1H), 7.88 (d, 1H), 7.75 (s, 1H), 7.66 (d, 1H), 7.43 (t, 1H), 7.14 (d, 1H), 4.68 (s, 2H), 3.76 (s, 2H), 3.52 (d, 4H), 3.43 (d, 4H)

Example 217. 2-[2-(aminomethyl)-3,3-difluoro-allyl]-4-[6-[3-(dimethylamino)-4-fluoro-phenyl]-2-pyridyl]-1,2,4-triazol-3-one trifluoroacetate 30 mg of the title compound (yield: 62.5%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 27 mg of (3-(dimethylamino)-4-fluorophenyl)boronic acid was used instead of 4-(methanesulfonyl)phenylboronic acid. $^1$H-NMR (MeOD, 400 MHz) δ 8.75 (s, 1H), 8.13 (d, 1H), 7.99 (t, 1H), 7.83 (d, 1H), 7.70 (d, 1H), 7.66-7.64 (m, 1H), 7.15 (dd, 1H), 4.68 (s, 2H), 3.76 (s, 2H), 2.92 (s, 6H)

Example 218. 5-[6-[1-[2-(aminomethyl)-3,3-difluoro-allyl]-5-oxo-1,2,4-triazol-4-yl]-2-pyridyl]-1-ethyl-pyridin-2-one trifluoroacetate 33 mg of the title compound (yield: 74.1%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 36 mg of 1-ethyl-6-oxo-1,6-dihydropyridine-3-boronic acid pinacol ester was used instead of 4-(methanesulfonyl)phenylboronic acid. $^1$H-NMR (MeOD, 400 MHz) δ 8.88 (s, 1H), 8.55 (d, 1H), 8.26 (dd, 1H), 8.13 (d, 1H), 7.97 (t, 1H), 7.72 (d, 1H), 6.62 (d, 1H), 4.68 (s, 2H), 4.15 (q, 2H), 3.77 (s, 2H), 1.41 (t, 3H)

Example 219. 7-[6-[1-[2-(aminomethyl)-3,3-difluoro-allyl]-5-oxo-1,2,4-triazol-4-yl]-2-pyridyl]-1,4-dihydro-3,1-benzoxazin-2-one trifluoroacetate 20 mg of the title compound (yield: 36.6%) was prepared in the same fashion as Example 17, except that in Step 1, 50 mg of tert-butyl N-[2-[[4-(6-bromo-2-pyridyl)-5-oxo-1,2,4-triazol-1-yl]methyl]-3,3-difluoro-allyl]carbamate prepared in Reference Example 31 was used instead of tert-butyl N-[2-[[4-(3-bromophenyl)-5-oxo-1,2,4-triazol-1-yl]methyl]-3,3-difluoro-allyl]carbamate prepared in Reference Example 25 and 40 mg of 7-(4,4,5,5-tetramethyl-1,3,2-dioxaborolan-2-yl)-1,4,4a,8a-tetrahydro-2H-benzo[d][1,3]oxazin-2-one was used instead of 4-(methanesulfonyl)phenylboronic acid. $^1$H-NMR (DMSO-d$_6$, 400 MHz) δ 10.22 (s, 1H), 8.81 (s, 1H), 8.13 (s, 2H), 7.89 (t, 1H), 7.84 (d, 1H), 7.71 (s, 1H), 7.34 (d, 1H), 5.36 (s, 2H), 4.62 (s, 2H), 3.56 (s, 2H)

Example 220. 2-[2-(aminomethyl)-3,3-difluoro-allyl]-4-[3-methyl-5-(6-piperazin-1-yl-3-pyridyl)-2-pyridyl]-1,2,4-triazol-3-one ditrifluoroacetate 38 mg of the title compound (yield: 70.6%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 55 mg of tert-butyl 4-[5-(4,4,5,5- tetramethyl-1,3,2-dioxaborolan-2-yl)-2-pyridyl]piperazine-1-carboxylate was used instead of 4-(methanesulfonyl)phenylboronic acid. $^1$H-NMR (MeOD, 400 MHz) δ 8.64 (s, 1H), 8.55 (S, 1H), 8.14 (d, 2H), 8.01 (s, 1H), 7.06 (s, 1H), 4.68 (s, 2H), 3.91 (s, 4H), 3.76 (s, 2H), 3.35 (s, 4H), 2.40 (s, 3H)

Example 221. 6-[6-[1-[2-(aminomethyl)-3,3-difluoro-allyl]-5-oxo-1,2,4-triazol-4-yl]-5-methyl-3-pyridyl]-4H-1,4-benzoxazin-3-one trifluoroacetate 33 mg of the title compound (yield: 35.5%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 60 mg of 6-(4,4,5,5-tetramethyl-1,3,2-dioxaborolan-2-yl)-2H-Benzo[b][1,4]oxazin-3(4H)-one was used instead of 4-(methanesulfonyl)phenylboronic acid. $^1$H-NMR (MeOD, 400 MHz) δ 8.57 (s, 1H), 8.17 (s, 1H), 8.06 (s, 1H), 7.30 (d, 1H), 7.19 (s, 1H), 7.08 (d, 1H), 4.69 (s, 2H), 4.64 (s, 2H), 3.77 (s, 2H), 2.41 (s, 3H)

Example 222. 2-[2-(aminomethyl)-3,3-difluoro-allyl]-4-[5-[2-(2-methoxyethylamino)pyrimidin-5-yl]-3-methyl-2-pyridyl]-1,2,4-triazol-3-one trifluoroacetate 377 mg of the title compound (yield: 40.0%) was prepared in the same fashion as Example 17, except that in Step 1, 1000 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 788 mg of N-(2-methoxyethyl)-5-(tetramethyl-1,3,2-dioxaborolan-2-yl)pyrimidin-2-amine was used instead of 4-(methanesulfonyl)phenylboronic acid. $^1$H-NMR (MeOD, 400 MHz) δ 8.66 (d, 3H), 8.16 (d, 2H), 4.68 (s, 2H), 3.75 (s, 2H), 3.62 (dd, 4H), 3.40 (s, 3H), 2.41 (s, 3H)

Example 223. 2-[2-(aminomethyl)-3,3-difluoro-allyl]-4-[3-methyl-5-(4-methyl-2,3-dihydro-1,4-benzoxazin-7-yl)-2-pyridyl]-1,2,4-triazol-3-one trifluoroacetate 38 mg of the title compound (yield: 41.0%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 60 mg of 4-methyl-7-(4,4,5,5-tetramethyl-1,3,2-dioxaborolan-2-yl)-3,4-dihydro-2H-1,4-benzoxazine was used instead of 4-(methanesulfonyl)phenylboronic acid. $^1$H-NMR (MeOD, 400 MHz) δ 8.56 (s, 1H), 8.14 (s, 1H), 8.03 (s, 1H), 7.19 (d, 1H), 7.07 (s, 1H), 6.81 (d, 1H), 4.68 (s, 2H), 4.30 (t, 2H), 3.76 (s, 2H), 3.32 (t, 2H) 2.95 (s, 3H), 2.37 (s, 3H)

Example 224. 2-[2-(aminomethyl)-3,3-difluoro-allyl]-4-[3-methyl-5-(3,4,5-trimethoxyphenyl)-2-pyridyl]-1,2,4-triazol-3-one trifluoroacetate 487 mg of the title compound (yield: 50.0%) was prepared in the same fashion as Example 17, except that in Step 1, 1000 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 599 mg of 3,4,5-trimethoxyphenylboronic acid was used instead of 4-(methanesulfonyl)phenylboronic acid. $^1$H-NMR (MeOD, 400 MHz) δ 8.68 (s, 1H), 8.18 (d, 2H), 6.99 (s, 2H), 4.69 (s, 2H), 3.94 (s, 6H), 3.83 (s, 3H), 3.76 (s, 2H), 2.43 (s, 3H)

Example 225. 2-[2-(aminomethyl)-3,3-difluoro-allyl]-4-[5-(6-methoxy-3-pyridyl)-3-methyl-2-pyridyl]-1,2,4-triazol-3-one trifluoroacetate 46 mg of the title compound (yield: 54.4%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 33 mg of 6-methoxy-3-pyridinylboronic acid was used instead of 4-(methanesulfonyl)phenylboronic acid. $^1$H-NMR (MeOD, 400 MHz) δ 8.64 (s, 1H), 8.48 (s, 1H), 8.17 (d, 1H), 8.14 (d, 1H), 8.03 (s, 1H), 6.95 (s, 1H), 4.68 (s, 2H), 3.97 (s, 3H), 3.76 (s, 2H), 2.41 (s, 3H)

Example 226. 4-[5-(2-amino-1,3-benzothiazol-5-yl)-3-methyl-2-pyridyl]-2-[2-(aminomethyl)-3,3-difluoro-allyl]-1,2,4-triazol-3-one trifluoroacetate 23 mg of the title compound (yield: 24.9%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 75 mg of N-[6-(4,4,5,5-tetramethyl-1,3,2-dioxaborolan-2-yl)benzo[d]thiazol-2-yl]acetamide was used instead of 4-(methanesulfonyl)phenylboronic acid. $^1$H-NMR (MeOD, 400 MHz) δ 8.68 (s, 1H), 8.18 (s, 2H), 7.75-7.68 (m, 2H), 7.42 (s, 1H), 4.68 (s, 2H), 3.74 (s, 2H), 2.43 (s, 3H)

Example 227. 2-[2-(aminomethyl)-3,3-difluoro-allyl]-4-[5-(2,1,3-benzoxadiazol-5-yl)-3-methyl-2-pyridyl]-1,2,4-triazol-3-one trifluoroacetate 40 mg of the title compound (yield: 46.1%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 53 mg of benzo[c][1,2,5]oxadiazol-5-boronic acid pinacol ester was used instead of 4-(methanesulfonyl)phenylboronic acid. $^1$H-NMR (MeOD, 400 MHz) δ 8.81 (s, 1H), 8.29 (d, 2H), 8.21 (s, 1H), 8.07 (s, 1H), 7.92 (s, 1H), 4.69 (s, 2H), 3.78 (s, 2H), 2.47 (s, 3H)

Example 228. 2-[2-(aminomethyl)-3,3-difluoro-allyl]-4-[3-methyl-5-(1H-pyrrolo[2,3-b]pyridin-5-yl)-2-pyridyl]-1,2,4-triazol-3-one trifluoroacetate 33 mg of the title compound (yield: 38.2%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 53 mg of 7-azaindol-5-boronic acid pinacol ester was used instead of 4-(methanesulfonyl)phenylboronic acid. $^1$H-NMR (MeOD, 400 MHz) δ 8.70 (s, 1H), 8.51 (s, 1H), 8.32 (s, 1H), 8.19 (s, 2H), 7.48 (s, 1H), 6.60 (d, 1H), 4.69 (s, 2H), 3.77 (s, 2H), 2.43 (s, 3H)

Example 229. 2-[2-(aminomethyl)-3,3-difluoro-allyl]-4-[5-(1,3-benzoxazol-5-yl)-3-methyl-2-pyridyl]-1,2,4-triazol-3-one trifluoroacetate 29 mg of the title compound (yield: 48.0%) was prepared in the same fashion as Example 17, except that in Step 1, 70 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of benzo[d]oxazol-5-yl boronic acid pinacol ester was used instead of 4-(methanesulfonyl)phenylboronic acid. $^1$H-NMR (MeOD, 400 MHz) δ 8.61 (s, 1H), 8.50 (s, 1H), 8.38 (s, 1H), 8.18 (s, 1H), 8.10 (s, 1H), 7.36 (s, 1H), 7.01 (s, 1H), 4.68 (s, 2H), 3.75 (s, 2H), 2.40 (s, 3H)

Example 230. 2-[2-(aminomethyl)-3,3-difluoro-allyl]-4-[3-methyl-5-[4-(2-oxopyrrolidin-1-yl)phenyl]-2-pyridyl]-1,2,4-triazol-3-one trifluoroacetate 395 mg of the title compound (yield: 40.6%) was prepared in the same fashion as Example 17, except that in Step 1, 1000 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 811 mg of 1-(4-(4,4,5,5-tetramethyl-1,3,2-dioxaborolan-2-yl)phenyl)pyrrolidin-2-one was used instead of 4-(methanesulfonyl)phenylboronic acid. $^1$H-NMR (MeOD, 400 MHz) δ 8.69 (s, 1H), 8.19 (s, 2H), 7.82 (d, 2H), 7.77 (d, 2H), 4.69 (s, 2H), 4.00 (t, 2H), 3.76 (s, 2H), 2.65 (t, 2H), 2.43 (s, 3H), 2.23 (p, 2H)

Example 231. 4-[5-(5-acetyl-2-thienyl)-3-methyl-2-pyridyl]-2-[2-(aminomethyl)-3,3-difluoro-allyl]-1,2,4-triazol-3-one trifluoroacetate 35 mg of the title compound (yield: 56.6%) was prepared in the same fashion as Example 17, except that in Step 1, 70 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 40 mg of 5-acetyl-2-thiopheneboronic acid was used instead of 4-(methanesulfonyl)phenylboronic acid. $^1$H-NMR (MeOD, 400 MHz) δ 8.75 (s, 1H), 8.23-8.17 (m, 2H), 7.90 (s, 1H), 7.67 (s, 1H), 4.67 (s, 2H), 3.75 (s, 2H), 2.60 (s, 3H), 2.42 (s, 3H)

Example 232. 2-[2-(aminomethyl)-3,3-difluoro-allyl]-4-[3-methyl-5-[3-(1H-pyrazol-3-yl)phenyl]-2-pyridyl]-1,2,4-triazol-3-one trifluoroacetate 50 mg of the title compound (yield: 54.4%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 41 mg of [3-(1H-pyrazol-3-yl)phenyl]boronic acid was used instead of 4-(methanesulfonyl)phenylboronic acid. MS (ESI) m/z=424.2 (M+H)+

Example 233. 2-[2-(aminomethyl)-3,3-difluoro-allyl]-4-[5-(1H-indazol-6-yl)-3-methyl-2-pyridyl]-1,2,4-triazol-3-one trifluoroacetate 35 mg of the title compound (yield: 40.6%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 76 mg of 1H-indazole-6-boronic acid was used instead of 4-(methanesulfonyl)phenylboronic acid. MS (ESI) m/z=398.2 (M+H)+

Example 234. 2-[2-(aminomethyl)-3,3-difluoro-allyl]-4-[3-methyl-5-(3-methylsulfonylphenyl)-2-pyridyl]-1,2,4-triazol-3-one trifluoroacetate 34 mg of the title compound (yield: 51.3%) was prepared in the same fashion as Example 17, except that in Step 1, 70 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 30 mg of 3-(methanesulfonyl)phenylboronic acid was used instead of 4-(methanesulfonyl)phenylboronic acid. $^1$H-NMR (MeOD, 400 MHz) δ 8.74 (s, 1H), 8.28-8.19 (m, 3H), 8.07 (s, 2H), 7.80 (s, 1H), 4.69 (s, 2H), 3.77 (s, 2H), 3.21 (s, 3H), 2.45 (s, 3H)

Example 235. 2-[2-(aminomethyl)-3,3-difluoro-allyl]-4-[3-methyl-5-(3-piperazin-1-ylphenyl)-2-pyridyl]-1,2,4-triazol-3-one ditrifluoroacetate 40 mg of the title compound (yield: 59.9%) was prepared in the same fashion as Example 17, except that in Step 1, 70 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 59 mg of tert-butyl 4-(3-(4,4,5,5-tetramethyl-1,3,2-dioxaborolan-2-yl)phenyl)piperazine-1-carboxylate was used instead of 4-(methanesulfonyl)phenylboronic acid. $^1$H-NMR (MeOD, 400 MHz) δ 8.66 (s, 1H), 8.17 (s, 2H), 7.45 (s, 1H), 7.33 (s, 1H), 7.27 (s, 1H), 7.13 (s, 1H), 4.68 (s, 2H), 3.74 (s, 2H), 3.51-3.31 (m, 8H), 2.42 (s, 3H)

Example 236. 2-[2-(aminomethyl)-3,3-difluoro-allyl]-4-[3-methyl-5-[4-(morpholine-4-carbonyl)phenyl]-2-pyridyl]-1,2,4-triazol-3-one trifluoroacetate 33 mg of the title compound (yield: 46.0%) was prepared in the same fashion as Example 17, except that in Step 1, 70 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 36 mg of [4-(morpholine-4-carbonyl)phenyl]boronic acid was used instead of 4-(methanesulfonyl)phenylboronic acid. $^1$H-NMR (MeOD, 400 MHz) δ 8.72 (s, 1H), 8.20 (d, 2H), 7.84 (s, 2H), 7.60 (d, 2H), 4.68 (s, 2H), 3.76-3.31 (m, 10H), 2.44 (s, 3H)

Example 237. 2-[2-(aminomethyl)-3,3-difluoro-allyl]-4-[3-methyl-5-(4-morpholinophenyl)-2-pyridyl]-1,2,4-triazol-3-one trifluoroacetate 50 mg of the title compound (yield: 52.1%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 63 mg of 4-morpholinophenylboronic acid pinacol ester was used instead of 4-(methanesulfonyl)phenylboronic acid. $^1$H-NMR (MeOD, 400 MHz) δ 8.62 (s, 1H), 8.16 (s, 1H), 8.10 (s, 1H), 7.64 (d, 2H), 7.10 (d, 2H), 4.68 (s, 2H), 3.86 (m, 4H), 3.76 (s, 2H), 3.23 (m, 4H), 2.40 (s, 3H)

Example 238. 4-[6-[1-[2-(aminomethyl)-3,3-difluoro-allyl]-5-oxo-1,2,4-triazol-4-yl]-5-methyl-3-pyridyl]-N,N-dimethyl-benzenesulfonamide trifluoroacetate 55 mg of the title compound (yield: 54.4%) was prepared in the same fashion as Example 17, except that in Step 1, 100 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 68 mg of N,N-dimethyl-4-(4,4,5,5-tetramethyl-1,3,2-dioxaborolan-2-yl)benzenesulfonamide was used instead of 4-(methanesulfonyl)phenylboronic acid. $^1$H-NMR (MeOD, 400 MHz) δ 8.74 (s, 1H), 8.25 (s, 1H), 8.20 (s, 1H), 7.95 (d, 4H), 4.68 (s, 2H), 3.75 (s, 2H), 2.73 (s, 6H), 2.45 (s, 3H)

Example 239. 2-[2-(aminomethyl)-3,3-difluoro-allyl]-4-[3-methyl-5-[3-(1H-1,2,4-triazol-3-yl)phenyl]-2-pyridyl]-1,2,4-triazol-3-one trifluoroacetate 8 mg of the title compound (yield: 12.8%) was prepared in the same fashion as Example 17, except that in Step 1, 52 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 50 mg of trimethyl-[2-[[3-[3-(4,4,5,5-tetramethyl-1,3,2-dioxaborolan-2-yl)phenyl]-1,2,4-triazol-1-yl]methoxy]ethyl]silane was used instead of 4-(methanesulfonyl)phenylboronic acid. $^1$H-NMR (MeOD, 400 MHz) δ 9.09 (d, 1H), 8.77 (s, 1H), 8.48-8.44 (m, 2H), 8.41 (s, 1H), 8.26 (s, 1H), 8.22 (s, 1H), 7.83 (d, 1H), 6.24 (s, 1H), 4.91 (s, 2H), 3.74 (s, 2H), 2.46 (s, 3H)

Example 240. 2-[2-(aminomethyl)-3,3-difluoro-allyl]-4-[3-methyl-5-[2-(1-methylpyrazol-4-yl)ethynyl]-2-pyridyl]-1,2,4-triazol-3-one trifluoroacetate Step 1: tert-butyl N-[3,3-difluoro-2-[[4-[3-methyl-5-[2-(1-methylpyrazol-4-yl)ethynyl]-2-pyridyl]-5-oxo-1,2,4-triazol-1-yl]methyl]allyl]carbamate 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34, 29 mg of 4-ethynyl-1-methyl-1H-pyrazole, 6 mg of tetrakis(triphenylphosphine)palladium (Pd(PPh$_3$)$_4$), and 2 mg of copper (I) iodide (CuI) were dissolved in 1.0 mL of N,N-dimethylformamide. To the resulting solution, 45 uL of triethylamine was added and then the solution was stirred overnight at 90° C. The resulting reaction mixture was filtered through a celite pad and concentrated under reduced pressure to give a residue. The residue thus obtained was dissolved in ethylacetate, washed with distilled water, dried over anhydrous magnesium sulfate, and concentrated under reduced pressure to give a yellow liquid residue. The residue was purified with silica gel column chromatography (developing solvent: n-hexane/ethyl acetate=1/1) to give 30 mg of the title compound as a yellow solid (yield: 27.6%). MS (ESI) m/z=386.1 (M+H)+

Step 2: 2-[2-(aminomethyl)-3,3-difluoro-allyl]-4-[3-methyl-5-[2-(1-methylpyrazol-4-yl)ethynyl]-2-pyridyl]-1,2,4-triazol-3-one 30 mg of tert-butyl N-[3,3-difluoro-2-[[4-[3-methyl-5-[2-(1-methylpyrazol-4-yl)ethynyl]-2-pyridyl]-5-oxo-1,2,4-triazol-1-yl]methyl]allyl]carbamate prepared in Step 1 was dissolved in 1.0 mL of dichloromethane, and 150 uL of trifluoroacetic acid was added thereto. The solution was stirred at room temperature for 2 hours. The reaction mixture thus obtained was concentrated, followed by the addition of dichloromethane. Dichloromethane was added to the concentrated reaction mixture, and it was concentrated under reduced pressure to obtain a yellow liquid residue. The residue was purified with silica gel column chromatography (developing solvent: dichloromethane/methanol=10/1) to give 19 mg of the title compound as a pale yellow solid (yield: 80.2%). $^1$H-NMR (MeOD, 400 MHz) δ 8.47 (s, 1H), 8.16 (s, 1H), 7.96 (s, 1H), 7.92 (s, 1H), 7.69 (s, 1H), 4.67 (S, 2H), 3.93 (s, 3H), 3.75 (s, 2H), 2.36 (s, 3H)

Example 241. 2-[2-(aminomethyl)-3,3-difluoro-allyl]-4-[5-[2-[6-(dimethylamino)-3-pyridyl]ethynyl]-3-methyl-2-pyridyl]-1,2,4-triazol-3-one trifluoroacetate 22 mg of the title compound (yield: 45.0%) was prepared in the same fashion as Example 240 except that in Step 1, 40 mg of 5-ethynyl-N,N-dimethylpyridin-2-amine was used instead of 4-ethynyl-1-methyl-1H-pyrazole. $^1$H-NMR (MeOD, 400 MHz) δ 8.51 (s, 1H), 8.26 (s, 1H), 8.17 (s, 1H), 8.01 (s, 1H), 7.78 (d, 1H), 6.88 (d, 1H), 4.67 (s, 2H), 3.75 (s, 2H), 3.32 (s, 3H), 3.20 (s, 6H), 2.37 (s, 3H)

Example 242. 2-[2-(aminomethyl)-3,3-difluoro-allyl]-4-[3-methyl-5-[2-(6-morpholino-3-pyridyl)ethynyl]-2-pyridyl]-1,2,4-triazol-3-one trifluoroacetate 25 mg of the title compound (yield: 48.6%) was prepared in the same fashion as Example 240 except that in Step 1, 51 mg of 4-(5-ethynylpyridin-2-yl)morpholine was used instead of 4-ethynyl-1-methyl-1H-pyrazole. $^1$H-NMR (MeOD, 400 MHz) δ 8.50 (s, 1H), 8.33 (s, 1H), 8.16 (s, 1H), 7.99 (s, 1H), 7.70 (d, 1H), 6.84 (d, 1H), 4.67 (s, 2H), 3.79 (t, 4H), 3.75 (s, 2H), 3.59 (t, 4H), 2.37 (s, 3H)

Example 243. 2-[2-(aminomethyl)-3,3-difluoro-allyl]-4-[5-[2-(3,4-dihydro-2H-1,4-benzoxazin-6-yl)ethynyl]-3-methyl-2-pyridyl]-1,2,4-triazol-3-one ditrifluoroacetate 27 mg of the title compound (yield: 55.0%) was prepared in the same fashion as Example 240 except that in Step 1, 70 mg of tert-butyl 6-ethynyl-2H-benzo[b][1,4]oxazine-4(3H)-carboxylate was used instead of 4-ethynyl-1-methyl-1H-pyrazole. $^1$H-NMR (MeOD, 400 MHz) δ 8.46 (s, 1H), 8.15 (s, 1H), 7.95 (s, 1H), 6.79 (d, 2H), 6.69 (d, 1H), 4.67 (s, 2H), 4.22 (t, 2H), 3.75 (s, 2H), 3.36 (t, 2H), 2.35 (s, 3H)

Example 244. 2-[2-(aminomethyl)-3,3-difluoro-allyl]-4-[5-[2-(2,3-dihydro-1H-pyrido[2,3-b][1,4]oxazin-7-yl)ethynyl]-3-methyl-2-pyridyl]-1,2,4-triazol-3-one ditrifluoroacetate 22 mg of the title compound (yield: 45.9%) was prepared in the same fashion as Example 240 except that in Step 1, 44 mg of 7-ethynyl-2,3-dihydro-1H-pyrido[2,3-b][1,4]oxazine was used instead of 4-ethynyl-1-methyl-1H-pyrazole. $^1$H-NMR (MeOD, 400 MHz) δ 8.51 (s, 1H), 8.17 (s, 1H), 8.01 (s, 1H), 7.62 (s, 1H), 7.10 (s, 1H), 4.67 (s, 2H), 4.41 (t, 2H), 3.75 (s, 2H), 3.40 (t, 2H), 2.37 (s, 3H)

Example 245. 2-[2-(aminomethyl)-3,3-difluoro-allyl]-4-[5-[2-(3,4-dihydro-2H-pyrido[3,2-b][1,4]oxazin-7-yl)ethynyl]-3-methyl-2-pyridyl]-1,2,4-triazol-3-one ditrifluoroacetate 24 mg of the title compound (yield: 47.7%) was prepared in the same fashion as Example 240 except that in Step 1, 44 mg of 7-ethynyl-2H,3H,4H-pyrido[3,2-b][1,4]oxazine was used instead of 4-ethynyl-1-methyl-1H-pyrazole. $^1$H-NMR (MeOD, 400 MHz) δ 8.49 (s, 1H), 8.16 (s, 1H), 7.98 (s, 1H), 7.80 (s, 1H), 7.14 (s, 1H), 4.67 (s, 2H), 4.20 (t, 2H), 3.75 (s, 2H), 3.57 (t, 2H), 2.36 (s, 3H)

Example 246. 2-[2-(aminomethyl)-3,3-difluoro-allyl]-4-[5-[2-(2,3-dihydro-1H-pyrido[2,3-b][1,4]oxazin-6-yl)ethynyl]-3-methyl-2-pyridyl]-1,2,4-triazol-3-one ditrifluoroacetate 24 mg of the title compound (yield: 49.5%) was prepared in the same fashion as Example 240 except that in Step 1, 44 mg of 6-ethynyl-2,3-dihydro-1H-pyrido[2,3-b][1,4]oxazine was used instead of 4-ethynyl-1-methyl-1H-pyrazole. $^1$H-NMR (MeOD, 400 MHz) δ 8.51 (s, 1H), 8.16 (s, 1H), 8.01 (s, 1H), 7.11 (d, 1H), 6.94 (d, 1H), 4.67 (s, 2H), 4.38 (t, 2H), 3.75 (s, 2H), 3.43 (t, 2H), 2.36 (s, 3H)

Example 247. 7-[2-[6-[1-[2-(aminomethyl)-3,3-difluoro-allyl]-5-oxo-1,2,4-triazol-4-yl]-5-methyl-3-pyridyl]ethynyl]-1H-pyrido[2,3-b][1,4]oxazin-2-one trifluoroacetate 22 mg of the title compound (yield: 44.0%) was prepared in the same fashion as Example 240 except that in Step 1, 47 mg of 7-ethynyl-1H,2H,3H-pyrido[2,3-b][1,4]oxazin-2-one was used instead of 4-ethynyl-1-methyl-1H-pyrazole. $^1$H-NMR (MeOD, 400 MHz) δ 8.54 (s, 1H), 8.18 (s, 1H), 8.03 (t, 2H), 7.40 (d, 1H), 4.89 (s, 2H), 4.68 (s, 2H), 3.76 (s, 2H), 2.38 (s, 3H)

Example 248. 7-[2-[6-[1-[2-(aminomethyl)-3,3-difluoro-allyl]-5-oxo-1,2,4-triazol-4-yl]-5-methyl-3-pyridyl]ethynyl]-4H-pyrido[3,2-b][1,4]oxazin-3-one trifluoroacetate 16 mg of the title compound (yield: 32.1%) was prepared in the same fashion as Example 240 except that in Step 1, 47 mg of 7-ethynyl-2H,3H,4H-pyrido[3,2-b][1,4]oxazin-3-one was used instead of 4-ethynyl-1-methyl-1H-pyrazole. $^1$H-NMR (MeOD, 400 MHz) δ 8.55 (s, 1H), 8.17 (s, 1H), 8.14 (s, 1H), 8.05 (s, 1H), 7.49 (s, 1H), 4.71 (s, 2H), 4.66 (s, 2H), 3.65 (s, 2H), 2.38 (s, 3H)

Example 249. 6-[2-[6-[1-[2-(aminomethyl)-3,3-difluoro-allyl]-5-oxo-1,2,4-triazol-4-yl]-5-methyl-3-pyridyl]ethynyl]-3,4-dihydro-1H-quinolin-2-one trifluoroacetate 25 mg of the title compound (yield: 47.7%) was prepared in the same fashion as Example 240 except that in Step 1, 46 mg of 6-ethynyl-1,2,3,4-tetrahydroquinolin-2-one was used instead of 4-ethynyl-1-methyl-1H-pyrazole. $^1$H-NMR (MeOD, 400 MHz) δ 8.52 (s, 1H), 8.18 (s, 1H), 8.02 (s, 1H), 7.43 (s, 1H), 7.40 (d, 1H), 6.90 (d, 1H), 4.67 (s, 2H), 3.75 (s, 2H), 3.00 (t, 2H), 2.61 (t, 2H), 2.38 (s, 3H)

Example 250. 6-[6-[1-[2-(aminomethyl)-3,3-difluoro-allyl]-5-oxo-1,2,4-triazol-4-yl]-5-methyl-3-pyridyl]-3-methyl-1,4-dihydroquinazolin-2-one trifluoroacetate 20 mg of the title compound (yield: 33.6%) was prepared in the same fashion as Example 17, except that in Step 1, 58 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 40 mg of 3-methyl-6-(4,4,5,5-tetramethyl-1,3,2-dioxaborolan-2-yl)-1,4-dihydroquinazolin-2-one was used instead of 4-(methanesulfonyl)phenylboronic acid. $^1$H-NMR (MeOD, 400 MHz) δ 8.60 (s, 1H), 8.17 (s, 1H), 8.08 (s, 1H), 7.51 (d, 1H), 7.47 (s, 1H), 6.88 (d, 1H), 4.69 (s, 2H), 4.56 (s, 2H), 3.76 (s, 2H), 3.01 (s, 3H), 2.40 (s, 3H)

Example 251. 2-[2-(aminomethyl)-3,3-difluoro-allyl]-4-[5-[1-(difluoromethyl)pyrazol-4-yl]-3-methyl-2-pyridyl]-1,2,4-triazol-3-one trifluoroacetate 22 mg of the title compound (yield: 51.4%) was prepared in the same fashion as Example 17, except that in Step 1, 49 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 26 mg of 1-(difluoromethyl)-4-(4,4,5,5-tetramethyl-1,3,2-dioxaborolan-2-yl)pyrazole was used instead of 4-(methanesulfonyl)phenylboronic acid.

¹H-NMR (MeOD, 400 MHz) δ 8.70 (d, 2H), 8.21 (m, 3H), 7.57 (t, 1H), 4.69 (s, 2H), 3.61 (s, 2H), 2.40 (s, 3H)

Example 252. 2-[2-(aminomethyl)-3,3-difluoro-allyl]-4-[5-(1-isopropylpyrazol-4-yl)-3-methyl-2-pyridyl]-1,2,4-triazol-3-one trifluoroacetate 32 mg of the title compound (yield: 75.4%) was prepared in the same fashion as Example 17, except that in Step 1, 51 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 17 mg of (1-isopropylpyrazole-4-yl) boronic acid was used instead of 4-(methanesulfonyl)phenylboronic acid. ¹H-NMR (MeOD, 400 MHz) δ 8.64 (s, 1H), 8.10 (m, 4H), 4.64 (m, 3H), 3.76 (s, 2H), 2.37 (s, 3H), 1.56 (d, 6H)

Example 253. 2-[2-(aminomethyl)-3,3-difluoro-allyl]-4-[2-methyl-3-(4-methylsulfonylphenyl)phenyl]-1,2,4-triazol-3-one trifluoroacetate 37 mg of the title compound (yield: 98.8%) was prepared in the same fashion as Example 17, except that in Step 1, 40 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25. ¹H-NMR (MeOD, 400 MHz) δ 8.08 (m, 3H), 7.65 (d, 2H), 7.46 (m, 3H), 4.69 (s, 2H), 3.77 (s, 2H), 3.20 (s, 2H), 2.11 (s, 3H)

Example 254. 2-[2-(aminomethyl)-3,3-difluoro-allyl]-4-[2-methyl-3-(4-piperazin-1-ylphenyl)phenyl]-1,2,4-triazol-3-one ditrifluoroacetate 28 mg of the title compound (yield: 73.6%) was prepared in the same fashion as Example 17, except that in Step 1, 40 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 34 mg of tert-butyl 4-[4-(tetramethyl-1,3,2-dioxaborolan-2-yl)phenyl]piperazine-1-carboxylate was used instead of 4-(methanesulfonyl)phenylboronic acid. ¹H-NMR (MeOD, 400 MHz) δ 8.06 (d, 2H), 7.39 (m, 2H), 7.32 (m, 3H), 7.13 (d, 2H), 4.69 (s, 2H), 3.76 (s, 2H), 3.49 (t, 4H), 3.41 (t, 4H), 2.11 (s, 3H)

Example 255. 2-[2-(aminomethyl)-3,3-difluoro-allyl]-4-[2-methyl-3-[6-(trifluoromethyl)-3-pyridyl]phenyl]-1,2,4-triazol-3-one trifluoroacetate 32 mg of the title compound (yield: 86.2%) was prepared in the same fashion as Example 17, except that in Step 1, 40 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 24 mg of 2-(trifluoromethyl)pyridin-5-boronic acid pinacol ester was used instead of 4-(methanesulfonyl)phenylboronic acid. ¹H-NMR (MeOD, 400 MHz) δ 8.75 (s, 1H), 8.09 (t, 2H), 7.96 (d, 1H), 7.51 (m, 3H), 4.69 (s, 2H), 3.77 (s, 2H), 2.13 (s, 3H)

Example 256. 2-[2-(aminomethyl)-3,3-difluoro-allyl]-4-[3-[6-(dimethylamino)-3-pyridyl]-2-methyl-phenyl]-1,2,4-triazol-3-one trifluoroacetate 35 mg of the title compound (yield: 100%) was prepared in the same fashion as Example 17, except that in Step 1, 40 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of 6-(dimethylamino)pyridin-3-boronic acid pinacol ester was used instead of 4-(methanesulfonyl)phenylboronic acid. ¹H-NMR (MeOD, 400 MHz) δ 8.07 (s, 1H), 7.96 (m, 2H), 7.46 (m, 3H), 7.25 (d, 1H), 4.69 (s, 2H), 3.77 (s, 2H), 3.33 (s, 6H), 2.16 (s, 3H)

Example 257. 2-[2-(aminomethyl)-3,3-difluoro-allyl]-4-[3-(1,3-benzodioxol-5-yl)-2-methyl-phenyl]-1,2,4-triazol-3-one trifluoroacetate 29 mg of the title compound (yield: 82.8%) was prepared in the same fashion as Example 17, except that in Step 1, 40 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of 2-(1,3-benzodioxol-5-yl)-4,4,5,5-tetramethyl-1,3,2-dioxaborolane was used instead of 4-(methanesulfonyl)phenylboronic acid. ¹H-NMR (MeOD, 400 MHz) δ 8.06 (s, 1H), 7.39 (t, 2H), 7.32 (m, 1H), 6.91 (d, 1H), 6.80 (m, 2H), 6.01 (s, 2H), 4.68 (d, 2H), 3.76 (d, 2H), 2.06 (d, 3H)

Example 258. 6-[3-[1-[2-(aminomethyl)-3,3-difluoro-allyl]-5-oxo-1,2,4-triazol-4-yl]-2-methyl-phenyl]-8-methyl-3,4-dihydro-1H-quinolin-2-one trifluoroacetate 31 mg of the title compound (yield: 81.6%) was prepared in the same fashion as Example 17, except that in Step 1, 40 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of 8-methyl-2-oxo-1,2,3,4-tetrahydroquinoline-6-boronic acid pinacol ester was used instead of 4-(methanesulfonyl)phenylboronic acid. ¹H-NMR (MeOD, 400 MHz) δ 8.06 (s, 1H), 7.86 (m, 3H), 7.04 (s, 2H), 4.69 (s, 2H), 3.77 (s, 2H), 2.99 (t, 2H), 2.61 (t, 2H), 2.31 (s, 3H), 2.11 (s, 3H)

Example 259. 6-[3-[1-[2-(aminomethyl)-3,3-difluoro-allyl]-5-oxo-1,2,4-triazol-4-yl]-2-methyl-phenyl]-1-methyl-3,4-dihydroquinolin-2-one trifluoroacetate 29 mg of the title compound (yield: 77.0%) was prepared in the same fashion as Example 17, except that in Step 1, 40 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of (1-methyl-2-oxo-1,2,3,4-tetrahydroquinoline-6-yl)boronic acid pinacol ester was used instead of 4-(methanesulfonyl)phenylboronic acid. $^1$H-NMR (MeOD, 400 MHz) δ 8.07 (s, 1H), 7.41 (t, 2H), 7.35 (m, 1H), 7.27 (m, 1H), 7.23 (d, 2H), 4.69 (s, 2H), 3.77 (s, 2H), 3.41 (s, 3H), 2.99 (t, 2H), 2.68 (t, 2H), 2.12 (s, 3H)

Example 260. 2-[2-(aminomethyl)-3,3-difluoro-allyl]-4-[3-(1-ethylpyrazol-4-yl)-2-methyl-phenyl]-1,2,4-triazol-3-one trifluoroacetate 24 mg of the title compound (yield: 73.6%) was prepared in the same fashion as Example 17, except that in Step 1, 40 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 19 mg of 1-ethylpyrazol-4-boronic acid pinacol ester was used instead of 4-(methanesulfonyl)phenylboronic acid. $^1$H-NMR (MeOD, 400 MHz) δ 8.05 (s, 1H), 7.88 (s, 1H), 7.67 (s, 1H), 7.52 (d, 1H), 7.38 (t, 1H), 7.27 (d, 1H), 4.69 (s, 2H), 4.26 (q, 2H), 3.77 (s, 2H), 2.24 (s, 3H), 1.52 (t, 3H)

Example 261. 2-[2-(aminomethyl)-3,3-difluoro-allyl]-4-[3-[1-(difluoromethyl)pyrazol-4-yl]-2-methyl-phenyl]-1,2,4-triazol-3-one trifluoroacetate 22 mg of the title compound (yield: 52.3%) was prepared in the same fashion as Example 17, except that in Step 1, 49 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 26 mg of 1-(difluoromethyl)-4-(4,4,5,5-tetramethyl-1,3,2-dioxaborolan-2-yl)pyrazole was used instead of 4-(methanesulfonyl)phenylboronic acid. $^1$H-NMR (MeOD, 400 MHz) δ 8.27 (s, 1H), 8.06 (s, 1H), 7.92 (s, 1H), 7.70 (d, 2H), 7.39 (m, 2H), 4.69 (s, 2H), 3.77 (s, 2H), 2.24 (s, 3H)

Example 262. 2-[2-(aminomethyl)-3,3-difluoro-allyl]-4-[3-(1-isopropylpyrazol-4-yl)-2-methyl-phenyl]-1,2,4-triazol-3-one trifluoroacetate 40 mg of the title compound (yield: 92.7%) was prepared in the same fashion as Example 17, except that in Step 1, 51 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 17 mg of (1-isopropylpyrazole-4-yl)boronic acid was used instead of 4-(methanesulfonyl)phenylboronic acid. $^1$H-NMR (MeOD, 400 MHz) δ 7.97 (d, 2H), 7.67 (s, 1H), 7.40 (m, 3H), 4.62 (m, 3H), 3.77 (s, 2H), 2.24 (s, 3H), 1.56 (d, 6H)

Example 263. 2-[2-(aminomethyl)-3,3-difluoro-allyl]-4-[2-methyl-3-[3-(1H-1,2,4-triazol-3-yl)phenyl]phenyl]-1,2,4-triazol-3-one trifluoroacetate 8 mg of the title compound (yield: 13.6%) was prepared in the same fashion as Example 17, except that in Step 1, 57 mg of tert-butyl N-[2-[[4-(3-bromo-2-methyl-phenyl)-5-oxo-1,2,4-triazol-1-yl]methyl]-3,3-difluoro-allyl]carbamate prepared in Reference Example 53 was used instead of tert-butyl N-[2-[[4-(3-bromophenyl)-5-oxo-1,2,4-triazol-1-yl]methyl]-3,3-difluoro-allyl]carbamate prepared in Reference Example 25 and 50 mg of trimethyl-[2-[[3-[3-(4,4,5,5-tetramethyl-1,3,2-dioxaborolan-2-yl)phenyl]-1,2,4-triazole-1-yl]methoxy]ethyl]silane was used instead of 4-(methanesulfonyl)phenylboronic acid. $^1$H-NMR (MeOD, 400 MHz) δ 8.67 (s, 1H), 8.65-8.63 (m, 1H), 8.12-8.10 (m, 2H), 8.08-8.06 (m, 2H), 7.59 (t, 1H), 7.48 (d, 1H), 7.47-7.38 (m, 2H), 5.60 (bs, 1H), 4.69 (s, 2H), 3.73 (s, 2H), 2.15 (s, 3H)

Example 264. 2-[2-(aminomethyl)-3,3-difluoro-allyl]-4-[[4-(1-ethylpyrazol-4-yl)phenyl]methyl]-1,2,4-triazol-3-one trifluoroacetate 23 mg of the title compound (yield: 28.0%) was prepared in the same fashion as Example 17, except that in Step 1, 100 mg of tert-butyl N-[2-[[4-[(4-bromophenyl)methyl]-5-oxo-1,2,4-triazol-1-yl]methyl]-3,3-difluoro-allyl]carbamate prepared in Reference Example 54 was used instead of tert-butyl N-[2-[[4-(3-bromophenyl)-5-oxo-1,2,4-triazol-1-yl]methyl]-3,3-difluoro-allyl]carbamate prepared in Reference Example 25 and 48 mg of 1-ethylpyrazol-4-boronic acid pinacol ester was used instead of 4-(methanesulfonyl)phenylboronic acid. $^1$H-NMR (MeOD, 400 MHz) δ 8.02 (s, 1H), 7.94 (s, 1H), 7.83 (s, 1H), 7.57 (d, 2H), 7.35 (d, 2H), 4.86 (s, 2H), 4.60 (s, 2H), 4.21 (q, 2H), 3.68 (s, 2H), 1.49 (t, 3H)

Example 265. 2-[2-(aminomethyl)-3,3-difluoro-allyl]-4-[[4-(4-methylsulfonylphenyl)phenyl]methyl]-1,2,4-triazol-3-one trifluoroacetate 7 mg of the title compound (yield: 10.5%) was prepared in the same fashion as Example 17, except that in Step 1, 70 mg of tert-butyl N-[2-[[4-[(4-bromophenyl)methyl]-5-oxo-1,2,4-triazol-1-yl]methyl]-3,3-difluoro-allyl]carbamate prepared in Reference Example 54 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.04 (d, 2H), 7.99 (s, 1H), 7.89 (d, 2H), 7.74 (d, 2H), 7.50 (d, 2H), 4.96 (s, 2H), 4.61 (s, 2H), 3.69 (s, 2H), 3.17 (s, 3H)

Example 266. 2-[2-(aminomethyl)-3,3-difluoro-allyl]-4-[[4-(4-piperazin-1-ylphenyl)phenyl]methyl]-1,2,4-triazol-3-one ditrifluoroacetate 9 mg of the title compound (yield: 11.8%) was prepared in the same fashion as Example 17, except that in Step 1, 70 mg of tert-butyl N-[2-[[4-[(4-bromophenyl)methyl]-5-oxo-1,2,4-triazol-1-yl]methyl]-3,3-difluoro-allyl]carbamate prepared in Reference Example 54 was used instead of tert-butyl N-[2-[[4-(3-bromophenyl)-5-oxo-1,2,4-triazol-1-yl]methyl]-3,3-difluoro-allyl]carbamate prepared in Reference Example 25 and 59 mg of tert-butyl 4-[4-(tetramethyl-1,3,2-dioxaborolan-2-yl)phenyl]piperazine-1-carboxylate was used instead of 4-(methanesulfonyl)phenylboronic acid. $^1$H-NMR (MeOD, 400 MHz) δ 7.95 (s, 1H), 7.61 (d, 2H), 7.58 (d, 2H), 7.41 (d, 2H), 7.11 (d, 2H), 4.90 (s, 2H), 4.60 (s, 2H), 3.66 (s, 2H), 3.47 (d, 4H), 3.39 (d, 4H)

Example 267. 2-[2-(aminomethyl)-3,3-difluoro-allyl]-4-[[4-[6-(dimethylamino)-3-pyridyl]phenyl]methyl]-1,2,4-triazol-3-one trifluoroacetate 12 mg of the title compound (yield: 18.4%) was prepared in the same fashion as Example 17, except that in Step 1, 70 mg of tert-butyl N-[2-[[4-[(4-bromophenyl)methyl]-5-oxo-1,2,4-triazol-1-yl]methyl]-3,3-difluoro-allyl]carbamate prepared in Reference Example 54 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of (6-(dimethylamino)pyridine-3-yl)boronic acid was used instead of 4-(methanesulfonyl)phenylboronic acid. $^1$H-NMR (MeOD, 400 MHz) δ 8.19 (s, 1H), 8.18 (d, 1H), 7.97 (s, 1H), 7.64 (d, 2H), 7.47 (d, 2H), 7.19 (d, 1H), 4.93 (s, 2H), 4.60 (s, 2H), 3.69 (s, 2H), 3.29 (s, 6H)

Example 268. 2-[2-(aminomethyl)-3,3-difluoro-allyl]-4-[[4-(1,3-benzodioxol-5-yl)phenyl]methyl]-1,2,4-triazol-3-one trifluoroacetate 12 mg of the title compound (yield: 19.7%) was prepared in the same fashion as Example 17, except that in Step 1, 70 mg of tert-butyl N-[2-[[4-[(4-bromophenyl)methyl]-5-oxo-1,2,4-triazol-1-yl]methyl]-3,3-difluoro-allyl]carbamate prepared in Reference Example 54 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of 3,4-(methylenedioxy)phenylboronic acid was used instead of 4-(methanesulfonyl)phenylboronic acid. $^1$H-NMR (MeOD, 400 MHz) δ 7.95 (s, 1H), 7.56 (d, 2H), 7.39 (d, 2H), 7.09 (d, 2H), 6.89 (d, 1H), 5.99 (s, 2H), 4.90 (s, 2H), 4.60 (s, 2H), 3.68 (s, 2H)

Example 269. 6-[4-[[1-[2-(aminomethyl)-3,3-difluoro-allyl]-5-oxo-1,2,4-triazol-4-yl]methyl]phenyl]-8-methyl-3,4-dihydro-TH-quinolin-2-one trifluoroacetate 7 mg of the title compound (yield: 9.9%) was prepared in the same fashion as Example 17, except that in Step 1, 70 mg of tert-butyl N-[2-[[4-[(4-bromophenyl)methyl]-5-oxo-1,2,4-triazol-1-yl]methyl]-3,3-difluoro-allyl]carbamate prepared in Reference Example 54 was used instead of tert-butyl N-[2-[[4-(3-bromophenyl)-5-oxo-1,2,4-triazol-1-yl]methyl]-3,3-difluoro-allyl]carbamate prepared in Reference Example 25 and 44 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 7.96 (s, 1H), 7.61 (d, 2H), 7.40 (d, 2H), 7.32 (s, 2H), 4.90 (s, 2H), 4.60 (s, 2H), 3.69 (s, 2H), 3.01 (t, 2H), 2.60 (t, 2H), 2.33 (s, 3H)

Example 270. 5-[4-[[1-[2-(aminomethyl)-3,3-difluoro-allyl]-5-oxo-1,2,4-triazol-4-yl]methyl]phenyl]-1-ethyl-pyridin-2-one trifluoroacetate 8 mg of the title compound (yield: 12.5%) was prepared in the same fashion as Example 17, except that in Step 1, 70 mg of tert-butyl N-[2-[[4-[(4-bromophenyl)methyl]-5-oxo-1,2,4-triazol-1-yl]methyl]-3,3-difluoro-allyl]carbamate prepared in Reference Example 54 was used instead of tert-butyl N-[2-[[4-(3-bromophenyl)-5-oxo-1,2,4-triazol-1-yl]methyl]-3,3-difluoro-allyl]carbamate prepared in Reference Example 25 and 38 mg of 1-ethyl-6-oxo-1,6-dihydropyridine-3-boronic acid pinacol ester was used instead of 4-(methanesulfonyl)phenylboronic acid. $^1$H-NMR (MeOD, 400 MHz) δ 8.01 (d, 1H), 7.96 (s, 1H), 7.87 (dd, 1H), 7.58 (d, 2H), 7.43 (d, 2H), 6.65 (d, 1H), 4.90 (s, 2H), 4.60 (s, 2H), 4.13 (q, 2H), 3.69 (s, 2H), 1.39 (t, 3H)

Example 271. 2-[2-(aminomethyl)-3,3-difluoro-allyl]-4-[[3-(1-ethylpyrazol-4-yl)phenyl]methyl]-1,2,4-triazol-3-one trifluoroacetate 25 mg of the title compound (yield: 75.9%) was prepared in the same fashion as Example 17, except that in Step 1, 40 mg of tert-butyl N-[2-[[4-[(3-bromophenyl)methyl]-5-oxo-1,2,4-triazol-1-yl]methyl]-3,3-difluoro-allyl]carbamate prepared in Reference Example 55 was used instead of tert-butyl N-[2-[[4-(3-bromophenyl)-5-oxo-1,2,4-triazol-1-yl]methyl]-3,3-difluoro-allyl]carbamate prepared in Reference Example 25 and 19 mg of 1-ethylpyrazol-4-boronic acid pinacol ester was used instead of 4-(methanesulfonyl)phenylboronic acid. $^1$H-NMR (MeOD, 400 MHz) δ 8.04 (s, 1H), 7.97 (s, 1H), 7.84 (s, 1H), 7.55 (t, 2H), 7.38 (t, 1H), 7.20 (d, 1H), 4.89 (s, 2H), 4.60 (s, 2H), 4.23 (dd, 2H), 3.68 (s, 2H), 1.50 (t, 3H)

Example 272. 2-[2-(aminomethyl)-3,3-difluoro-allyl]-4-[[3-(4-methylsulfonylphenyl)phenyl]methyl]-1,2,4-triazol-3-one trifluoroacetate 33 mg of the title compound (yield: 87.4%) was prepared in the same fashion as Example 17, except that in Step 1, 40 mg of tert-butyl N-[2-[[4-[(3-bromophenyl)methyl]-5-oxo-1,2,4-triazol-1-yl]methyl]-3,3-difluoro-allyl]carbamate prepared in Reference Example 55 was used instead of tert-butyl N-[2-[[4-(3-bromophenyl)-5-oxo-1,2,4-triazol-1-yl]methyl]-3,3-difluoro-allyl]carbamate prepared in Reference Example 25. $^1$H-NMR (MeOD, 400 MHz) δ 8.03 (t, 3H), 7.90 (d, 2H), 7.71 (m, 2H), 7.54 (t, 1H), 7.44 (d, 1H), 4.98 (s, 2H), 4.60 (s, 2H), 3.69 (s, 2H), 3.17 (s, 3H)

Example 273. 2-[2-(aminomethyl)-3,3-difluoro-allyl]-4-[[3-[6-(dimethylamino)-3-pyridyl]phenyl]methyl]-1,2,4-triazol-3-one trifluoroacetate 34 mg of the title compound (yield: 98.8%) was prepared in the same fashion as Example 17, except that in Step 1, 40 mg of tert-butyl N-[2-[[4-[(3-bromophenyl)methyl]-5-oxo-1,2,4-triazol-1-yl]methyl]-3,3-difluoro-allyl]carbamate prepared in Reference Example 55 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of (6-(dimethylamino)pyridine-3-yl)boronic acid was used instead of 4-(methanesulfonyl)phenylboronic acid. $^1$H-NMR (MeOD, 400 MHz) δ 8.25 (dd, 1H), 8.19 (d, 1H), 8.00 (s, 1H), 7.66 (s, 1H), 7.62 (d, 1H), 7.52 (t, 1H), 7.40 (d, 1H), 7.27 (d, 1H), 4.96 (s, 2H), 4.60 (s, 2H), 3.69 (s, 2H), 3.33 (s, 6H)

Example 274. 2-[2-(aminomethyl)-3,3-difluoro-allyl]-4-[[3-(1,3-benzodioxol-5-yl)phenyl]methyl]-1,2,4-triazol-3-one trifluoroacetate 33 mg of the title compound (yield: 94.2%) was prepared in the same fashion as Example 17, except that in Step 1, 40 mg of tert-butyl N-[2-[[4-[(3-bromophenyl)methyl]-5-oxo-1,2,4-triazol-1-yl]methyl]-3,3-difluoro-allyl]carbamate prepared in Reference Example 55 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of 3,4-(methylenedioxy)phenylboronic acid was used instead of 4-(methanesulfonyl)phenylboronic acid. $^{1}$H-NMR (MeOD, 400 MHz) δ 7.98 (s, 2H), 7.53 (d, 2H), 7.42 (t, 1H), 7.29 (d, 1H), 7.09 (t, 2H), 6.90 (d, 1H), 5.99 (s, 2H), 4.92 (s, 2H), 4.60 (s, 2H), 3.68 (s, 2H)

Example 275. 6-[3-[[1-[2-(aminomethyl)-3,3-difluoro-allyl]-5-oxo-1,2,4-triazol-4-yl]methyl]phenyl]-8-methyl-3,4-dihydro-1H-quinolin-2-one trifluoroacetate 26 mg of the title compound (yield: 66.7%) was prepared in the same fashion as Example 17, except that in Step 1, 40 mg of tert-butyl N-[2-[[4-[(3-bromophenyl)methyl]-5-oxo-1,2,4-triazol-1-yl]methyl]-3,3-difluoro-allyl]carbamate prepared in Reference Example 55 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of 8-methyl-2-oxo-1,2,3,4-tetrahydroquinoline-6-boronic acid pinacol ester was used instead of 4-(methanesulfonyl)phenylboronic acid. $^{1}$H-NMR (MeOD, 400 MHz) δ 7.99 (s, 1H), 7.58 (m, 2H), 7.43 (t, 1H), 7.30 (m, 3H), 4.93 (s, 2H), 4.60 (s, 2H), 3.68 (s, 2H), 3.01 (t, 2H), 2.59 (t, 2H), 2.33 (s, 3H)

Example 276. 6-[3-[[1-[2-(aminomethyl)-3,3-difluoro-allyl]-5-oxo-1,2,4-triazol-4-yl]methyl]phenyl]-1-methyl-3,4-dihydroquinolin-2-one trifluoroacetate 28 mg of the title compound (yield: 73.6%) was prepared in the same fashion as Example 17, except that in Step 1, 40 mg of tert-butyl N-[2-[[4-[(3-bromophenyl)methyl]-5-oxo-1,2,4-triazol-1-yl]methyl]-3,3-difluoro-allyl]carbamate prepared in Reference Example 55 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of (1-methyl-2-oxo-1,2,3,4-tetrahydroquinoline-6-yl)boronic acid pinacol ester was used instead of 4-(methanesulfonyl)phenylboronic acid. $^{1}$H-NMR (MeOD, 400 MHz) δ 7.99 (s, 1H), 7.62 (m, 2H), 7.56 (t, 1H), 7.51 (s, 1H), 7.46 (t, 1H), 7.32 (d, 1H), 7.21 (d, 1H), 4.94 (s, 2H), 4.60 (s, 2H), 3.68 (s, 2H), 3.40 (s, 3H), 3.00 (t, 2H), 2.67 (t, 2H)

Example 277. 5-[3-[[1-[2-(aminomethyl)-3,3-difluoro-allyl]-5-oxo-1,2,4-triazol-4-yl]methyl]phenyl]-1-ethyl-pyridin-2-one trifluoroacetate 30 mg of the title compound (yield: 86.2%) was prepared in the same fashion as Example 17, except that in Step 1, 40 mg of tert-butyl N-[2-[[4-[(3-bromophenyl)methyl]-5-oxo-1,2,4-triazol-1-yl]methyl]-3,3-difluoro-allyl]carbamate prepared in Reference Example 55 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of 1-ethyl-6-oxo-1,6-dihydropyridine-3-boronic acid pinacol ester was used instead of 4-(methanesulfonyl)phenylboronic acid. $^{1}$H-NMR (MeOD, 400 MHz) δ 8.02 (d, 2H), 7.88 (m, 1H), 7.56 (m, 2H), 7.46 (t, 1H), 7.33 (d, 1H), 6.65 (d, 1H), 4.93 (s, 2H), 4.60 (s, 2H), 4.14 (q, 2H), 3.69 (s, 2H), 1.40 (t, 3H)

Example 278. 2-[2-(aminomethyl)-3,3-difluoro-allyl]-4-[[2-(1-ethylpyrazol-4-yl)phenyl]methyl]-1,2,4-triazol-3-one trifluoroacetate 26 mg of the title compound (yield: 78.2%) was prepared in the same fashion as Example 17, except that in Step 1, 40 mg of tert-butyl N-[2-[[4-[(2-bromophenyl)methyl]-5-oxo-1,2,4-triazol-1-yl]methyl]-3,3-difluoro-allyl]carbamate prepared in Reference Example 56 was used instead of tert-butyl N-[2-[[4-(3-bromophenyl)-5-oxo-1,2,4-triazol-1-yl]methyl]-3,3-difluoro-allyl]carbamate prepared in Reference Example 25 and 19 mg of 1-ethylpyrazol-4-boronic acid pinacol ester was used instead of 4-(methanesulfonyl)phenylboronic acid. $^{1}$H-NMR (MeOD, 400 MHz) δ 7.81 (s, 1H), 7.55 (d, 2H), 7.35 (m, 3H), 7.27 (d, 1H), 4.98 (s, 2H), 4.55 (s, 2H), 4.26 (q, 2H), 3.66 (s, 2H), 1.52 (t, 3H)

Example 279. 2-[2-(aminomethyl)-3,3-difluoro-allyl]-4-[[2-(4-methylsulfonylphenyl)phenyl]methyl]-1,2,4-triazol-3-one trifluoroacetate 30 mg of the title compound (yield: 78.2%) was prepared in the same fashion as Example 17, except that in Step 1, 40 mg of tert-butyl N-[2-[[4-[(2-bromophenyl)methyl]-5-oxo-1,2,4-triazol-1-yl]methyl]-3,3-difluoro-allyl]carbamate prepared in Reference Example 56 was used instead of tert-butyl N-[2-[[4-(3-bromophenyl)-5-oxo-1,2,4-triazol-1-yl]methyl]-3,3-difluoro-allyl]carbamate prepared in Reference Example 25. $^{1}$H-NMR (MeOD, 400 MHz) δ 8.03 (d, 2H), 7.60 (d, 2H), 7.49 (m, 3H), 7.41 (m, 1H), 7.32 (m, 1H), 4.87 (s, 2H), 4.46 (s, 2H), 3.61 (s, 2H), 3.20 (s, 3H)

Example 280. 2-[2-(aminomethyl)-3,3-difluoro-allyl]-4-[[2-(4-piperazin-1-ylphenyl)phenyl]methyl]-1,2,4-triazol-3-one ditrifluoroacetate 27 mg of the title compound (yield: 69.0%) was prepared in the same fashion as Example 17, except that in Step 1, 40 mg of tert-butyl N-[2-[[4-[(2-bromophenyl)methyl]-5-oxo-1,2,4-triazol-1-yl]methyl]-3,3-difluoro-allyl]carbamate prepared in Reference Example 56 was used instead of tert-butyl N-[2-[[4-(3-bromophenyl)-5-oxo-1,2,4-triazol-1-yl]methyl]-3,3-difluoro-allyl]carbamate prepared in Reference Example 25 and 34 mg of tert-butyl 4-[4-(tetramethyl-1,3,2-dioxaborolan-2-yl)phenyl]piperazine-1-carboxylate was used instead of 4-(methanesulfonyl)phenylboronic acid. $^{1}$H-NMR (MeOD, 400 MHz) δ 7.47 (m, 3H), 7.28 (m, 4H), 7.12 (d, 2H), 4.88 (s, 2H), 4.51 (s, 2H), 3.64 (s, 2H), 3.50 (t, 4H), 3.41 (t, 4H), 3.33 (m, 2H)

Example 281. 2-[2-(aminomethyl)-3,3-difluoro-allyl]-4-[[2-[6-(dimethylamino)-3-pyridyl]phenyl]methyl]-1,2,4-triazol-3-one trifluoroacetate 35 mg of the title compound (yield: 100%) was prepared in the same fashion as Example 17, except that in Step 1, 40 mg of tert-butyl N-[2-[[4-[(2-bromophenyl)methyl]-5-oxo-1,2,4-triazol-1-yl]methyl]-3,3-difluoro-allyl]carbamate prepared in Reference Example 56 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of (6-(dimethylamino)pyridine-3-yl)boronic acid was used instead of 4-(methanesulfonyl)phenylboronic acid. $^{1}$H-NMR (MeOD, 400 MHz) δ 7.94 (m, 2H), 7.75 (s, 1H), 7.48 (m, 2H), 7.39 (m, 1H), 7.33 (m, 1H), 7.24 (d, 1H), 4.88 (s, 2H), 4.52 (s, 2H), 3.67 (d, 2H), 3.32 (s, 6H)

Example 282. 2-[2-(aminomethyl)-3,3-difluoro-allyl]-4-[[2-(1,3-benzodioxol-5-yl)phenyl]methyl]-1,2,4-triazol-3-one trifluoroacetate 35 mg of the title compound (yield: 100%) was prepared in the same fashion as Example 17, except that in Step 1, 40 mg of tert-butyl N-[2-[[4-[(2-bromophenyl)methyl]-5-oxo-1,2,4-triazol-1-yl]methyl]-3,3-difluoro-allyl]carbamate prepared in Reference Example 56 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of 3,4-(methylenedioxy)phenylboronic acid was used instead of 4-(methanesulfonyl)phenylboronic acid. $^1$H-NMR (MeOD, 400 MHz) δ 7.39 (m, 3H), 7.32 (t, 1H), 7.23 (m, 1H), 6.89 (d, 1H), 6.75 (m, 2H), 6.01 (s, 2H), 4.86 (s, 2H), 4.50 (s, 2H), 3.64 (s, 2H)

Example 283. 6-[2-[[1-[2-(aminomethyl)-3,3-difluoro-allyl]-5-oxo-1,2,4-triazol-4-yl]methyl]phenyl]-8-methyl-3,4-dihydro-1H-quinolin-2-one trifluoroacetate 25 mg of the title compound (yield: 65.5%) was prepared in the same fashion as Example 17, except that in Step 1, 40 mg of tert-butyl N-[2-[[4-[(2-bromophenyl)methyl]-5-oxo-1,2,4-triazol-1-yl]methyl]-3,3-difluoro-allyl]carbamate prepared in Reference Example 56 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of 8-methyl-2-oxo-1,2,3,4-tetrahydroquinoline-6-boronic acid pinacol ester was used instead of 4-(methanesulfonyl)phenylboronic acid. $^1$H-NMR (MeOD, 400 MHz) δ 7.39 (m, 3H), 7.31 (t, 1H), 7.27 (m, 1H), 6.99 (d, 2H), 4.87 (s, 2H), 4.94 (s, 2H), 3.64 (s, 2H), 2.99 (t, 2H), 2.61 (t, 2H), 2.31 (s, 3H)

Example 284. 6-[2-[[1-[2-(aminomethyl)-3,3-difluoro-allyl]-5-oxo-1,2,4-triazol-4-yl]methyl]phenyl]-1-methyl-3,4-dihydroquinolin-2-one trifluoroacetate 28 mg of the title compound (yield: 72.4%) was prepared in the same fashion as Example 17, except that in Step 1, 40 mg of tert-butyl N-[2-[[4-[(2-bromophenyl)methyl]-5-oxo-1,2,4-triazol-1-yl]methyl]-3,3-difluoro-allyl]carbamate prepared in Reference Example 56 was used instead of tert-butyl N-[2-[[4-(3-bromophenyl)-5-oxo-1,2,4-triazol-1-yl]methyl]-3,3-difluoro-allyl]carbamate prepared in Reference Example 25 and 25 mg of (1-methyl-2-oxo-1,2,3,4-tetrahydroquinoline-6-yl)boronic acid pinacol ester was used instead of 4-(methanesulfonyl)phenylboronic acid. $^1$H-NMR (MeOD, 400 MHz) δ 7.40 (d, 3H), 7.34 (d, 1H), 7.30 (t, 1H), 7.21 (t, 3H), 4.88 (s, 2H), 4.49 (s, 2H), 3.64 (s, 2H), 3.41 (s, 3H), 2.97 (t, 2H), 2.68 (t, 2H)

Example 285. 5-[2-[[1-[2-(aminomethyl)-3,3-difluoro-allyl]-5-oxo-1,2,4-triazol-4-yl]methyl]phenyl]-1-ethyl-pyridin-2-one trifluoroacetate 17 mg of the title compound (yield: 49.4%) was prepared in the same fashion as Example 17, except that in Step 1, 40 mg of tert-butyl N-[2-[[4-[(2-bromophenyl)methyl]-5-oxo-1,2,4-triazol-1-yl]methyl]-3,3-difluoro-allyl]carbamate prepared in Reference Example 56 was used instead of tert-butyl N-[2-[[4-(3-bromophenyl)-5-oxo-1,2,4-triazol-1-yl]methyl]-3,3-difluoro-allyl]carbamate prepared in Reference Example 25 and 22 mg of 1-ethyl-6-oxo-1,6-dihydropyridine-3-boronic acid pinacol ester was used instead of 4-(methanesulfonyl)phenylboronic acid. $^1$H-NMR (MeOD, 400 MHz) δ 7.76 (d, 1H), 7.62 (s, 1H), 7.46 (m, 3H), 7.38 (t, 1H), 7.32 (m, 1H), 6.58 (d, 1H), 4.90 (s, 2H), 4.49 (s, 2H), 4.10 (q, 2H), 3.64 (s, 2H), 1.40 (t, 3H)

Example 286. 2-[2-(aminomethyl)-3,3-difluoro-allyl]-4-[[5-[4-(1-ethylpyrazol-4-yl)phenyl]-2-thienyl]methyl]-1,2,4-triazol-3-one trifluoroacetate 37 mg of the title compound (yield: 75.7%) was prepared in the same fashion as Example 100, except that in Step 1, 48 mg of 1-ethyl-4-[4-(4,4,5,5-tetramethyl-1,3,2-dioxaborolan-2-yl)phenyl]pyrazole was used instead of 4-acetylphenylboronic acid. $^1$H-NMR (MeOD, 400 MHz) δ 8.01 (d, 2H), 7.85 (s, 1H), 7.58 (s, 4H), 7.27 (d, 1H), 7.13 (d, 1H), 5.06 (s, 2H), 4.60 (s, 2H), 4.22 (dd, 2H), 3.68 (s, 2H), 1.50 (t, 3H)

Example 287. 2-[2-(aminomethyl)-3,3-difluoro-allyl]-4-[[5-[3-(1-ethylpyrazol-4-yl)phenyl]-2-thienyl]methyl]-1,2,4-triazol-3-one trifluoroacetate 29 mg of the title compound (yield: 58.9%) was prepared in the same fashion as Example 100, except that in Step 1, 48 mg of 1-ethyl-4-[3-(4,4,5,5-tetramethyl-1,3,2-dioxaborolan-2-yl)phenyl]pyrazole was used instead of 4-acetylphenylboronic acid. $^1$H-NMR (MeOD, 400 MHz) δ 8.07 (s, 1H), 8.00 (s, 1H), 7.88 (s, 1H), 7.77 (s, 1H), 7.50 (d, 1H), 7.43 (d, 1H), 7.37 (m, 2H), 7.15 (d, 1H), 5.08 (s, 2H), 4.60 (s, 2H), 4.24 (q, 2H), 3.68 (s, 2H), 1.51 (t, 3H)

Example 288. 2-[2-(aminomethyl)-3,3-difluoro-allyl]-4-[[4-[4-(1-ethylpyrazol-4-yl)phenyl]-2-thienyl]methyl]-1,2,4-triazol-3-one trifluoroacetate 27 mg of the title compound (yield: 51.8%) was prepared in the same fashion as Example 100, except that in Step 1, 52 mg of tert-butyl N-[2-[[4-(4-bromo-2-thienyl)methyl]-5-oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 50 mg of 1-ethyl-4-[4-(4,4,5,5-tetramethyl-1,3,2-dioxaborolan-2-yl)phenyl]pyrazole was used instead of 4-acetylphenylboronic acid. $^1$H-NMR (MeOD, 400 MHz) δ 8.01 (d, 2H), 7.85 (s, 1H), 7.59 (m, 6H), 5.10 (s, 2H), 4.60 (s, 2H), 4.22 (q, 2H), 3.68 (s, 2H), 1.50 (t, 3H)

Example 289. 2-[2-(aminomethyl)-3,3-difluoro-allyl]-4-[[4-[3-(1-ethylpyrazol-4-yl)phenyl]-2-thienyl]methyl]-1,2,4-triazol-3-one trifluoroacetate 29 mg of the title compound (yield: 57.1%) was prepared in the same fashion as Example 100, except that in Step 1, 52 mg of tert-butyl N-[2-[[4-(4-bromo-2-thienyl)methyl]-5- oxo-1,2,4-triazol-1-yl]methyl]-3,3-difluoro-allyl]carbamate prepared in Reference Example 42 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 50 mg of 1-ethyl-4-[3-(4,4,5,5-tetramethyl-1,3,2-dioxaborolan-2-yl)phenyl]pyrazole was used instead of 4-acetylphenylboronic acid. $^{1}$H-NMR (MeOD, 400 MHz) δ 8.04 (d, 2H), 7.86 (d, 2H), 7.68 (d, 1H), 7.59 (s, 1H), 7.49 (d, 2H), 7.38 (t, 1H), 5.11 (s, 2H), 4.60 (s, 2H), 4.24 (dd, 2H), 3.68 (s, 2H), 1.51 (t, 3H)

Example 290. 2-[2-(aminomethyl)-3,3-difluoro-allyl]-4-[5-[4-(1-ethylpyrazol-4-yl)phenyl]-3-methyl-2-pyridyl]-1,2,4-triazol-3-one trifluoroacetate 15 mg of the title compound (yield: 30.3%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 48 mg of 1-ethyl-4-[4-(4,4,5,5-tetramethyl-1,3,2-dioxaborolan-2-yl)phenyl]pyrazole was used instead of 4-(methanesulfonyl)phenylboronic acid. $^{1}$H-NMR (MeOD, 400 MHz) δ 8.70 (s, 1H), 8.19 (s, 2H), 8.11 (s, 1H), 7.91 (s, 1H), 7.73 (s, 4H), 4.70 (s, 2H), 4.25 (q, 2H), 3.77 (s, 2H), 2.43 (s, 3H), 1.50 (t, 3H)

Example 291. 2-[2-(aminomethyl)-3,3-difluoro-allyl]-4-[5-[3-(1-ethylpyrazol-4-yl)phenyl]-3-methyl-2-pyridyl]-1,2,4-triazol-3-one trifluoroacetate 27 mg of the title compound (yield: 56.0%) was prepared in the same fashion as Example 17, except that in Step 1, 50 mg of tert-butyl N-[2-[[4-(5-bromo-3-methyl-2-pyridyl)-5-oxo-1,2,4-triazol-1-yl]methyl]-3,3-difluoro-allyl]carbamate prepared in Reference Example 34 was used instead of tert-butyl N-[2-[[4-(3-bromophenyl)-5-oxo-1,2,4-triazol-1-yl]methyl]-3,3-difluoro-allyl]carbamate prepared in Reference Example 25 and 48 mg of 1-ethyl-4-[3-(4,4,5,5-tetramethyl-1,3,2-dioxaborolan-2-yl)phenyl]pyrazole was used instead of 4-(methanesulfonyl)phenylboronic acid. $^{1}$H-NMR (MeOD, 400 MHz) δ 8.71 (s, 1H), 8.20 (s, 1H), 8.14 (s, 1H), 7.95 (s, 1H), 7.90 (s, 1H), 7.66 (d, 1H), 7.54 (m, 2H), 4.70 (s, 2H), 4.25 (q, 2H), 3.78 (s, 2H), 2.44 (s, 3H), 1.52 (t, 3H)

Example 292. 2-[2-(aminomethyl)-3,3-difluoro-allyl]-4-[[5-(1H-pyrazol-4-yl)-2-thienyl]methyl]-1,2,4-triazol-3-one trifluoroacetate 22 mg of the title compound (yield: 57.0%) was prepared in the same fashion as Example 100, except that in Step 1, 25 mg of 1-[4-(4,4,5,5-tetramethyl-1,3,2-dioxaborolan-2-yl)pyrazol-1-yl]ethanone was used instead of 4-acetylphenylboronic acid. $^{1}$H-NMR (MeOD, 400 MHz) δ 7.97 (s, 1H), 7.83 (s, 2H), 7.55 (m, 2H), 5.03 (s, 2H), 4.59 (s, 2H), 3.68 (s, 2H)

Example 293. 2-[2-(aminomethyl)-3,3-difluoro-allyl]-4-[[5-(1-methylsulfonylpyrazol-4-yl)-2-thienyl]methyl]-1,2,4-triazol-3-one trifluoroacetate 13 mg of the title compound (yield: 28.0%) was prepared in the same fashion as Example 100, except that in Step 1, 20 mg of (1-methylsulfonylpyrazol-4-yl)boronic acid was used instead of 4-acetylphenylboronic acid. $^{1}$H-NMR (MeOD, 400 MHz) δ 8.42 (s, 1H), 8.12 (s, 1H), 7.98 (s, 1H), 7.22 (d, 1H), 7.13 (d, 1H), 5.06 (s, 2H), 4.59 (s, 2H), 3.68 (s, 2H), 3.45 (s, 3H)

Example 294. 2-[2-(aminomethyl)-3,3-difluoro-allyl]-4-[[5-(1-cyclopropylsulfonylpyrazol-4-yl)-2-thienyl]methyl]-1,2,4-triazol-3-one trifluoroacetate 38 mg of the title compound (yield: 77.6%) was prepared in the same fashion as Example 100, except that in Step 1, 32 mg of 1-cyclopropylsulfonyl-4-(4,4,5,5-tetramethyl-1,3,2-dioxaborolan-2-yl)pyrazole was used instead of 4-acetylphenylboronic acid. $^{1}$H-NMR (MeOD, 400 MHz) δ 8.40 (s, 1H), 8.10 (s, 1H), 7.98 (s, 1H), 7.21 (d, 1H), 7.12 (d, 1H), 5.06 (s, 2H), 4.59 (s, 2H), 3.69 (s, 2H), 2.97 (m, 1H), 1.41 (m, 2H), 1.23 (m, 2H)

Example 295. 2-[2-(aminomethyl)-3,3-difluoro-allyl]-4-[[5-[1-(cyclopropylmethyl)pyrazol-4-yl]-2-thienyl]methyl]-1,2,4-triazol-3-one trifluoroacetate 31 mg of the title compound (yield: 72.0%) was prepared in the same fashion as Example 100, except that in Step 1, 27 mg of 1-(cyclopropylmethyl)-4-(4,4,5,5-tetramethyl-1,3,2-dioxaborolan-2-yl)pyrazole was used instead of 4-acetylphenylboronic acid. $^{1}$H-NMR (MeOD, 400 MHz) δ 7.95 (d, 2H), 7.67 (s, 1H), 7.05 (dd, 2H), 5.03 (s, 2H), 4.59 (s, 2H), 4.00 (d, 2H), 3.68 (s, 2H), 1.30 (m, 1H), 0.63 (m, 2H), 0.42 (m, 2H)

Example 296. 2-[2-(aminomethyl)-3,3-difluoro-allyl]-4-[[5-(1-methylpyrazol-4-yl)-2-thienyl]methyl]-1,2,4-triazol-3-one trifluoroacetate 12 mg of the title compound (yield: 29.0%) was prepared in the same fashion as Example 100, except that in Step 1, 22 mg of 1-methyl-4-(4,4,5,5-tetramethyl-1,3,2-dioxaborolan-2-yl)-1H-pyrazole was used instead of 4-acetylphenylboronic acid. $^{1}$H-NMR (MeOD, 400 MHz) δ 7.96 (s, 2H), 7.85 (s, 1H), 7.66 (s, 1H), 7.06 (d, 1H), 7.01 (d, 1H), 5.03 (s, 2H), 4.59 (s, 2H), 3.90 (s, 3H), 3.67 (s, 2H)

Example 297. 2-[2-(aminomethyl)-3,3-difluoro-allyl]-4-[[5-(1-benzylpyrazol-4-yl)-2-thienyl]methyl]-1,2,4-triazol-3-one trifluoroacetate 23 mg of the title compound (yield: 48.6%) was prepared in the same fashion as Example 100, except that in Step 1, 30 mg of 1-benzyl-4-(4,4,5,5-tetramethyl-1,3,2-dioxaborolan-2-yl)pyrazole was used instead of 4-acetylphenylboronic acid. $^{1}$H-NMR (MeOD, 400 MHz) δ 7.94 (d, 2H), 7.71 (s, 1H), 7.34 (m, 3H), 7.27 (m, 2H), 7.04 (dd, 2H), 5.34 (s, 2H), 5.02 (s, 2H), 4.58 (s, 2H), 3.67 (s, 2H)

Example 298. 2-[2-(aminomethyl)-3,3-difluoro-allyl]-4-[[3-fluoro-5-(4-piperazin-1-ylphenyl)-2-thienyl]methyl]-1,2,4-triazol-3-one ditrifluoroacetate 17 mg of the title compound (yield: 35.9%) was prepared in the same fashion as Example 100, except that in Step 1, 50 mg of tert-butyl N-[2-[[4-[(5-bromo-3-fluoro-2-thienyl)methyl]-5-oxo-1,2,4-triazol-1-yl]methyl]-3,3-difluoro-allyl]carbamate prepared in Reference Example 59 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 40 mg of tert-butyl 4-[4-(tetramethyl-1,3,2-dioxaborolan-2-yl)phenyl]piperazine-1-carboxylate was used instead of 4-acetylphenylboronic acid. $^1$H-NMR (MeOD, 400 MHz) δ 7.97 (s, 1H), 7.54 (d, 2H), 7.07 (t, 3H), 5.01 (s, 2H), 4.59 (s, 2H), 3.67 (s, 2H), 3.49 (t, 4H), 3.39 (m, 4H)

Example 299. 5-[5-[[1-[2-(aminomethyl)-3,3-difluoro-allyl]-5-oxo-1,2,4-triazol-4-yl]methyl]-4-fluoro-2-thienyl]-1-ethyl-pyridin-2-one trifluoroacetate 28 mg of the title compound (yield: 65.0%) was prepared in the same fashion as Example 100, except that in Step 1, 50 mg of tert-butyl N-[2-[[4-[(5-bromo-3-fluoro-2-thienyl)methyl]-5-oxo-1,2,4-triazol-1-yl]methyl]-3,3-difluoro-allyl]carbamate prepared in Reference Example 59 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 26 mg of 1-ethyl-6-oxo-1,6-dihydropyridine-3-boronic acid pinacol ester was used instead of 4-acetylphenylboronic acid. $^1$H-NMR (MeOD, 400 MHz) δ 8.05 (d, 2H), 7.75 (q, 1H), 7.11 (s, 1H), 5.02 (s, 2H), 4.59 (s, 2H), 4.08 (q, 2H), 3.69 (s, 2H), 1.37 (t, 3H)

Example 300. 2-[2-(aminomethyl)-3,3-difluoro-allyl]-4-[[5-(1,3-benzodioxol-5-yl)-3-fluoro-2-thienyl]methyl]-1,2,4-triazol-3-one trifluoroacetate 26 mg of the title compound (yield: 59.2%) was prepared in the same fashion as Example 100, except that in Step 1, 50 mg of tert-butyl N-[2-[[4-[(5-bromo-3-fluoro-2-thienyl)methyl]-5-oxo-1,2,4-triazol-1-yl]methyl]-3,3-difluoro-allyl]carbamate prepared in Reference Example 59 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 26 mg of 2-(1,3-benzodioxol-5-yl)-4,4,5,5-tetramethyl-1,3,2-dioxaborolane was used instead of 4-acetylphenylboronic acid. $^1$H-NMR (MeOD, 400 MHz) δ 7.97 (s, 1H), 7.08 (m, 3H), 6.85 (d, 1H), 6.01 (s, 2H), 5.00 (s, 2H), 4.59 (s, 2H), 3.68 (s, 2H)

Example 301. 6-[5-[[1-[2-(aminomethyl)-3,3-difluoro-allyl]-5-oxo-1,2,4-triazol-4-yl]methyl]-4-fluoro-2-thienyl]-1-methyl-3,4-dihydroquinolin-2-one trifluoroacetate 25 mg of the title compound (yield: 52.4%) was prepared in the same fashion as Example 100, except that in Step 1, 50 mg of tert-butyl N-[2-[[4-[(5-bromo-3-fluoro-2-thienyl)methyl]-5-oxo-1,2,4-triazol-1-yl]methyl]-3,3-difluoro-allyl]carbamate prepared in Reference Example 59 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 30 mg of (1-methyl-2-oxo-1,2,3,4-tetrahydroquinolin-6-yl)boronic acid pinacol ester was used instead of 4-acetylphenylboronic acid. $^1$H-NMR (MeOD, 400 MHz) δ 7.98 (s, 1H), 7.49 (m, 2H), 7.16 (t, 2H), 5.02 (s, 2H), 4.59 (s, 2H), 3.68 (s, 2H), 3.36 (s, 3H), 2.96 (t, 2H), 2.64 (t, 2H)

Example 302. 2-[2-(aminomethyl)-3,3-difluoro-allyl]-4-[[5-(1-ethylpyrazol-4-yl)-3-fluoro-2-thienyl]methyl]-1,2,4-triazol-3-one trifluoroacetate 21 mg of the title compound (yield: 51.4%) was prepared in the same fashion as Example 100, except that in Step 1, 50 mg of tert-butyl N-[2-[[4-[(5-bromo-3-fluoro-2-thienyl)methyl]-5-oxo-1,2,4-triazol-1-yl]methyl]-3,3-difluoro-allyl]carbamate prepared in Reference Example 59 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 23 mg of 1-ethyl-4-(4,4,5,5-tetramethyl-1,3,2-dioxaborolan-2-yl)-1H-pyrazole was used instead of 4-acetylphenylboronic acid. $^1$H-NMR (MeOD, 400 MHz) δ 7.96 (s, 2H), 7.70 (s, 1H), 6.95 (s, 1H), 4.98 (s, 2H), 4.58 (s, 2H), 4.20 (q, 2H), 3.67 (s, 2H), 1.47 (t, 3H), Example 303. 2-(2-(aminomethyl)-3,3-difluoroallyl)-4-((5-(6-(dimethylamino)pyridin-3-yl)-3-fluoro-thiophen-2-yl)methyl)-2,4-dihydro-3H-1,2,4-triazol-3-one trifluoroacetate 2 mg of the title compound (yield: 3.9%) was prepared in the same fashion as Example 100, except that in Step 1, 50 mg of tert-butyl N-[2-[[4-[(5-bromo-3-fluoro-2-thienyl)methyl]-5-oxo-1,2,4-triazol-1-yl]methyl]-3,3-difluoro-allyl]carbamate prepared in Reference Example 59 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 26 mg of 6-(dimethylamino)pyridine-3-boronic acid pinacol ester was used instead of 4-acetylphenylboronic acid. $^1$H-NMR (MeOD, 400 MHz) δ 8.29 (d, 1H), 7.95 (s, 1H), 7.74 (m, 1H), 7.05 (s, 1H), 6.71 (d, 1H), 5.00 (s, 2H), 4.57 (s, 2H), 3.47 (s, 2H), 3.13 (s, 6H)

Example 304. 6-(5-((1-(2-(aminomethyl)-3,3-difluoroallyl)-5-oxo-1,5-dihydro-4H-1,2,4-triazol-4-yl)methyl)-4-fluorothiophen-2-yl)-8-methyl-3,4-dihydroquinolin-2(1H)-one trifluoroacetate 2 mg of the title compound (yield: 4.8%) was prepared in the same fashion as Example 100, except that in Step 1, 50 mg of tert-butyl N-[2-[[4-[(5-bromo-3-fluoro-2-thienyl)methyl]-5-oxo-1,2,4-triazol-1-yl]methyl]-3,3-difluoro-allyl]carbamate prepared in Reference Example 59 was used instead of tert-butyl N-[2-[[4-(5-bromo-2-thienyl)methyl]-5-oxo-1,2,4-triazol-1-yl]methyl]-3,3-difluoro-allyl]carbamate prepared in Reference Example 41 and 30 mg of 8-methyl-2-oxo-1,2,3,4-tetrahydroquinoline-6-boronic acid pinacol ester was used instead of 4-acetylphenylboronic acid. $^1$H-NMR (MeOD, 400 MHz) δ 7.96 (s, 1H), 7.31 (s, 2H), 7.15 (s, 1H), 5.01 (s, 2H), 4.58 (s, 2H), 3.65 (s, 2H), 2.99 (t, 2H), 2.59 (t, 2H), 2.30 (s, 3H)

Compounds from the Examples are shown in Table 1.

TABLE 1*

| Ex No | Structure | Chemical Name |
|---|---|---|
| 1 | 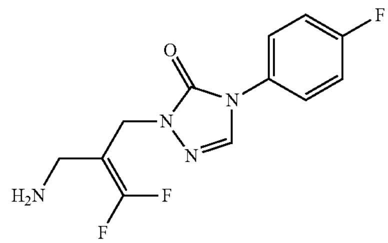 [SMILES: NCC(Cn1ncn(-c2ccc(F)cc2)c1=O)=C(F)F] | 2-[2-(aminomethyl)-3,3-difluoro-allyl]-4-(4-fluorophenyl)-1,2,4-triazol-3-one |
| 2 | 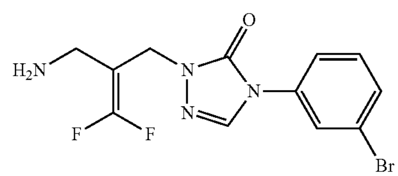 | 2-[2-(aminomethyl)-3,3-difluoro-allyl]-4-(3-bromophenyl)-1,2,4-triazol-3-one |
| 3 | 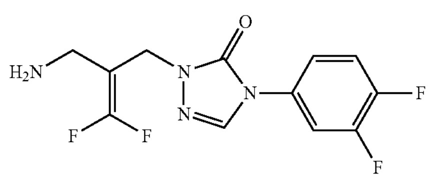 [SMILES: NCC(Cn1ncn(-c2ccc(F)c(F)c2)c1=O)=C(F)F] | 2-[2-(aminomethyl)-3,3-difluoro-allyl]-4-(3,4-difluorophenyl)-1,2,4-triazol-3-one |
| 4 | 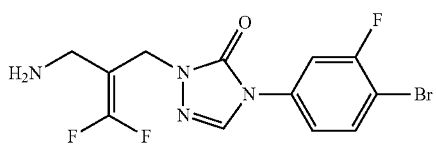 [SMILES: NCC(Cn1ncn(-c2ccc(Br)c(F)c2)c1=O)=C(F)F] | 2-[2-(aminomethyl)-3,3-difluoro-allyl]-4-(4-bromo-3-fluoro-phenyl)-1,2,4-triazol-3-one |
| 5 | 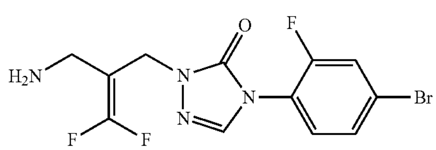 [SMILES: NCC(Cn1ncn(-c2ccc(Br)cc2F)c1=O)=C(F)F] | 2-[2-(aminomethyl)-3,3-difluoro-allyl]-4-(4-bromo-2-fluoro-phenyl)-1,2,4-triazol-3-one |
| 6 | 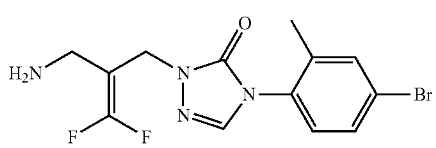 [SMILES: Cc1cc(Br)ccc1-n1cnn(CC(CN)=C(F)F)c1=O] | 2-[2-(aminomethyl)-3,3-difluoro-allyl]-4-(4-bromo-2-methyl-phenyl)-1,2,4-triazol-3-one |
| 7 | 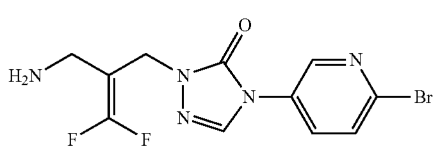 [SMILES: NCC(Cn1ncn(-c2ccc(Br)nc2)c1=O)=C(F)F] | 2-[2-(aminomethyl)-3,3-difluoro-allyl]-4-(6-bromo-3-pyridyl)-1,2,4-triazol-3-one |
| 8 | 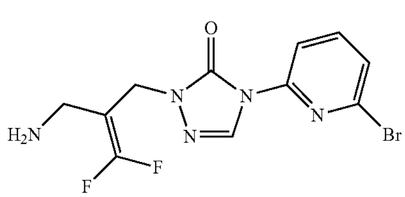 [SMILES: NCC(Cn1ncn(-c2cccc(Br)n2)c1=O)=C(F)F] | 2-[2-(aminomethyl)-3,3-difluoro-allyl]-4-(6-bromo-2-pyridyl)-1,2,4-triazol-3-one |

TABLE 1*-continued

| Ex No | Structure | Chemical Name |
|---|---|---|
| 9 | 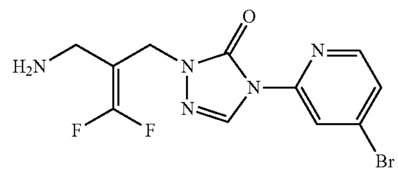 [SMILES: NCC(Cn1ncn(-c2cc(Br)ccn2)c1=O)=C(F)F] | 2-[2-(aminomethyl)-3,3-difluoro-allyl]-4-(4-bromo-2-pyridyl)-1,2,4-triazol-3-one |
| 10 | 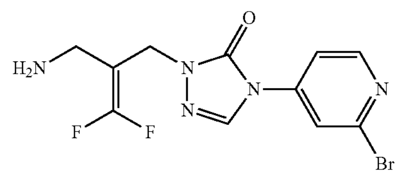 [SMILES: NCC(Cn1ncn(-c2ccnc(Br)c2)c1=O)=C(F)F] | 2-[2-(aminomethyl)-3,3-difluoro-allyl]-4-(2-bromo-4-pyridyl)-1,2,4-triazol-3-one |
| 11 | 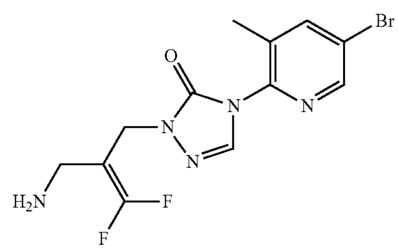 [SMILES: Cc1cc(Br)cnc1-n1cnn(CC(CN)=C(F)F)c1=O] | 2-[2-(aminomethyl)-3,3-difluoro-allyl]-4-(5-bromo-3-methyl-2-pyridyl)-1,2,4-triazol-3-one |
| 12 | 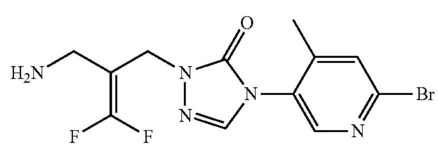 [SMILES: Cc1cc(Br)ncc1-n1cnn(CC(CN)=C(F)F)c1=O] | 2-[2-(aminomethyl)-3,3-difluoro-allyl]-4-(6-bromo-4-methyl-3-pyridyl)-1,2,4-triazol-3-one |
| 13 | 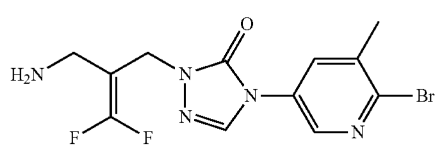 [SMILES: Cc1cc(-n2cnn(CC(CN)=C(F)F)c2=O)cnc1Br] | 2-[2-(aminomethyl)-3,3-difluoro-allyl]-4-(6-bromo-5-methyl-3-pyridyl)-1,2,4-triazol-3-one |
| 14 | 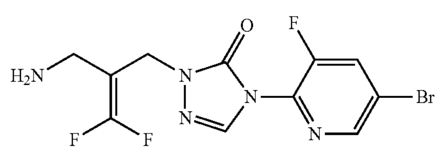 [SMILES: NCC(Cn1ncn(-c2ncc(Br)cc2F)c1=O)=C(F)F] | 2-[2-(aminomethyl)-3,3-difluoro-allyl]-4-(5-bromo-3-fluoro-2-pyridyl)-1,2,4-triazol-3-one |
| 15 | 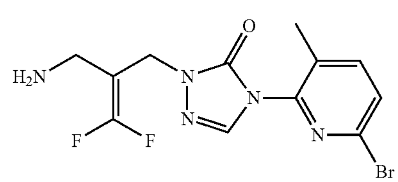 | 2-[2-(aminomethyl)-3,3-difluoro-allyl]-4-(6-bromo-3-methyl-2-pyridyl)-1,2,4-triazol-3-one |
| 16 | 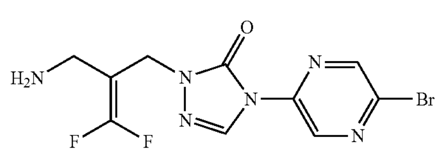 [SMILES: NCC(Cn1ncn(-c2cnc(Br)cn2)c1=O)=C(F)F] | 2-[2-(aminomethyl)-3,3-difluoro-allyl]-4-(5-bromopyrazin-2-yl)-1,2,4-triazol-3-one |

TABLE 1*-continued

| Ex No | Structure | Chemical Name |
|---|---|---|
| 17 | 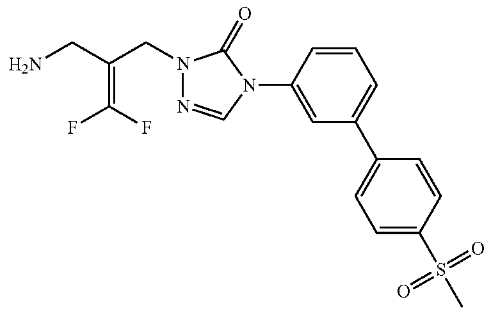 [SMILES: CS(=O)(=O)c1ccc(-c2cccc(-n3cnn(CC(CN)=C(F)F)c3=O)c2)cc1] | 2-[2-(aminomethyl)-3,3-difluoro-allyl]-4-[3-(4-methylsulfonylphenyl)phenyl]-1,2,4-triazol-3-one |
| 18 | 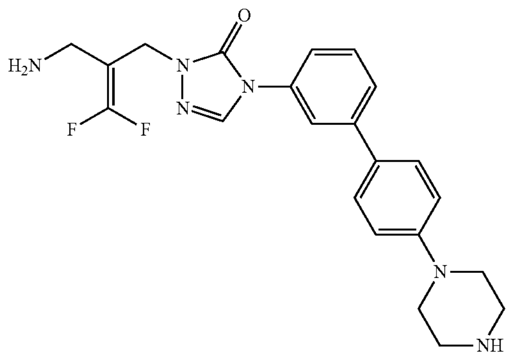 [SMILES: NCC(Cn1ncn(-c2cccc(-c3ccc(N4CCNCC4)cc3)c2)c1=O)=C(F)F] | 2-[2-(aminomethyl)-3,3-difluoro-allyl]-4-[3-(4-piperazin-1-ylphenyl)phenyl]-1,2,4-triazol-3-one |
| 19 | 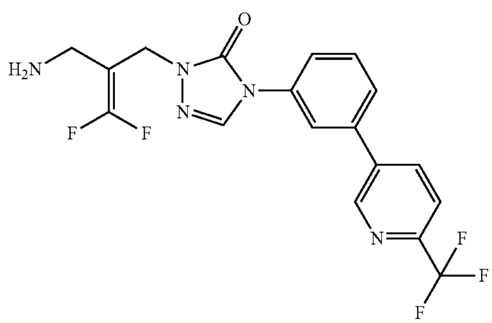 [SMILES: NCC(Cn1ncn(-c2cccc(-c3ccc(C(F)(F)F)nc3)c2)c1=O)=C(F)F] | 2-[2-(aminomethyl)-3,3-difluoro-allyl]-4-[3-[6-(trifluoromethyl)-3-pyridyl]phenyl]-1,2,4-triazol-3-one |
| 20 | 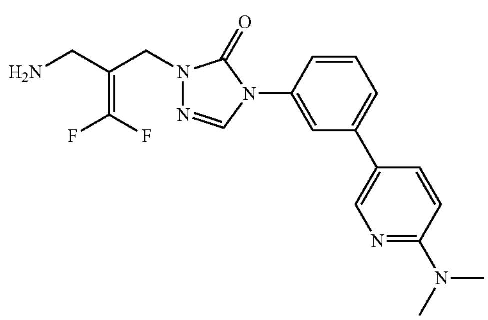 [SMILES: CN(C)c1ccc(-c2cccc(-n3cnn(CC(CN)=C(F)F)c3=O)c2)cn1] | 2-[2-(aminomethyl)-3,3-difluoro-allyl]-4-[3-[6-(dimethylamino)-3-pyridyl]phenyl]-1,2,4-triazol-3-one |
| 21 | 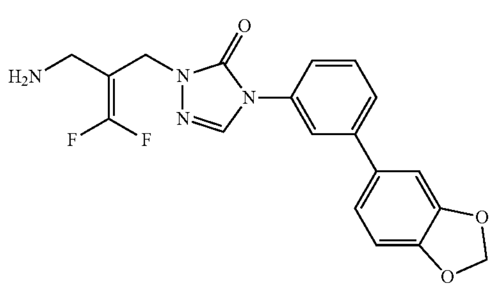 | 2-[2-(aminomethyl)-3,3-difluoro-allyl]-4-[3-(1,3-benzodioxol-5-yl)phenyl]-1,2,4-triazol-3-one |

TABLE 1*-continued

| Ex No | Structure | Chemical Name |
|---|---|---|
| 22 | 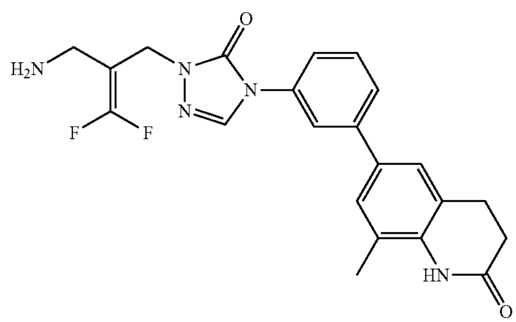 | 6-[3-[1-[2-(aminomethyl)-3,3-difluoro-allyl]-5-oxo-1,2,4-triazol-4-yl]phenyl]-8-methyl-3,4-dihydro-1H-quinolin-2-one |
| 23 | 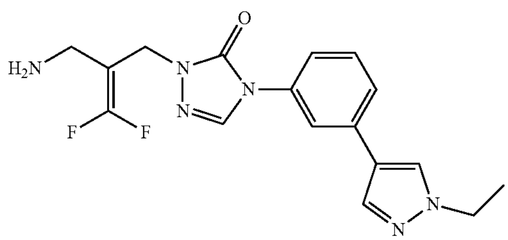 [SMILES: CCn1cc(-c2cccc(-n3cnn(CC(CN)=C(F)F)c3=O)c2)cn1] | 2-[2-(aminomethyl)-3,3-difluoro-allyl]-4-[3-(1-ethylpyrazol-4-yl)phenyl]-1,2,4-triazol-3-one |
| 24 | 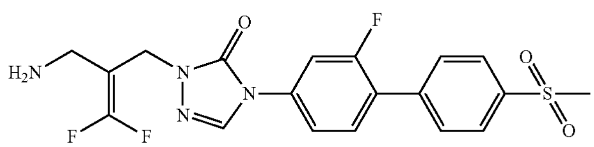 [SMILES: CS(=O)(=O)c1ccc(-c2ccc(-n3cnn(CC(CN)=C(F)F)c3=O)cc2F)cc1] | 2-[2-(aminomethyl)-3,3-difluoro-allyl]-4-[3-fluoro-4-(4-methylsulfonylphenyl)phenyl]-1,2,4-triazol-3-one |
| 25 | 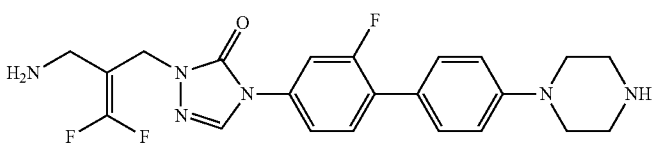 [SMILES: NCC(Cn1ncn(-c2ccc(-c3ccc(N4CCNCC4)cc3)c(F)c2)c1=O)=C(F)F] | 2-[2-(aminomethyl)-3,3-difluoro-allyl]-4-[3-fluoro-4-(4-piperazin-1-ylphenyl)phenyl]-1,2,4-triazol-3-one |
| 26 | 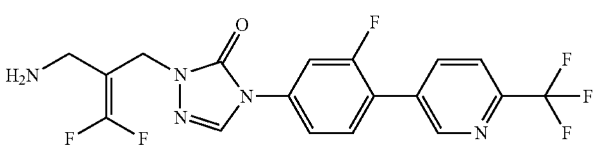 [SMILES: NCC(Cn1ncn(-c2ccc(-c3ccc(C(F)(F)F)nc3)c(F)c2)c1=O)=C(F)F] | 2-[2-(aminomethyl)-3,3-difluoro-allyl]-4-[3-fluoro-4-[6-(trifluoromethyl)-3-pyridyl]phenyl]-1,2,4-triazol-3-one |
| 27 | 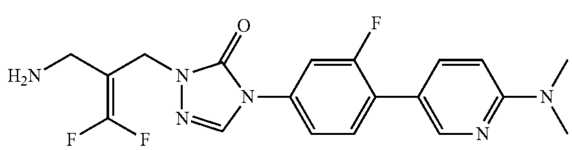 [SMILES: CN(C)c1ccc(-c2ccc(-n3cnn(CC(CN)=C(F)F)c3=O)cc2F)cn1] | 2-[2-(aminomethyl)-3,3-difluoro-allyl]-4-[4-[6-(dimethylamino)-3-pyridyl]-3-fluoro-phenyl]-1,2,4-triazol-3-one |
| 28 | 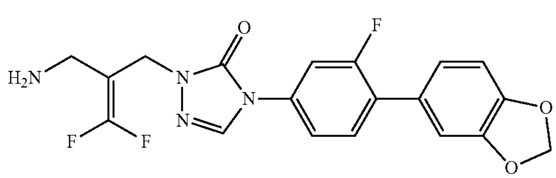 [SMILES: NCC(Cn1ncn(-c2ccc(-c3ccc4c(c3)OCO4)c(F)c2)c1=O)=C(F)F] | 2-[2-(aminomethyl)-3,3-difluoro-allyl]-4-[4-(1,3-benzodioxol-5-yl)-3-fluoro-phenyl]-1,2,4-triazol-3-one |
| 29 | 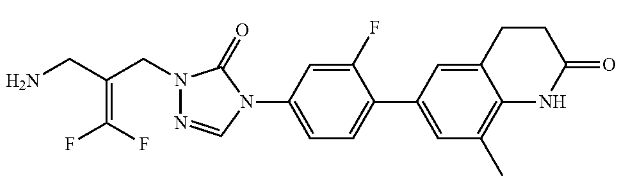 [SMILES: Cc1cc(-c2ccc(-n3cnn(CC(CN)=C(F)F)c3=O)cc2F)cc2c1NC(=O)CC2] | 6-[4-[1-[2-(aminomethyl)-3,3-difluoro-allyl]-5-oxo-1,2,4-triazol-4-yl]-2-fluoro-phenyl]-8-methyl-3,4-dihydro-1H-quinolin-2-one |

TABLE 1*-continued

| Ex No | Structure | Chemical Name |
|---|---|---|
| 30 | 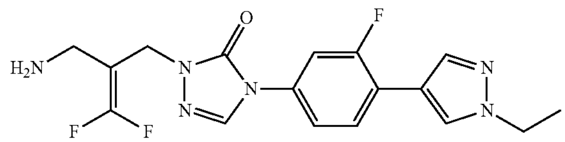 [SMILES: CCn1cc(-c2ccc(-n3cnn(CC(CN)=C(F)F)c3=O)cc2F)cn1] | 2-[2-(aminomethyl)-3,3-difluoro-allyl]-4-[4-(1-ethylpyrazol-4-yl)-3-fluoro-phenyl]-1,2,4-triazol-3-one |
| 31 | 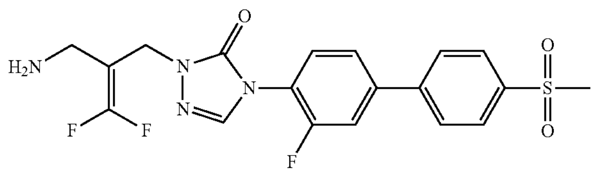 [SMILES: CS(=O)(=O)c1ccc(-c2ccc(-n3cnn(CC(CN)=C(F)F)c3=O)c(F)c2)cc1] | 2-[2-(aminomethyl)-3,3-difluoro-allyl]-4-[2-fluoro-4-(4-methylsulfonylphenyl)phenyl]-1,2,4-triazol-3-one |
| 32 | 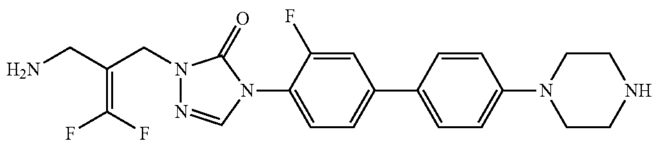 [SMILES: NCC(Cn1ncn(-c2ccc(-c3ccc(N4CCNCC4)cc3)cc2F)c1=O)=C(F)F] | 2-[2-(aminomethyl)-3,3-difluoro-allyl]-4-[2-fluoro-4-(4-piperazin-1-ylphenyl)phenyl]-1,2,4-triazol-3-one |
| 33 | 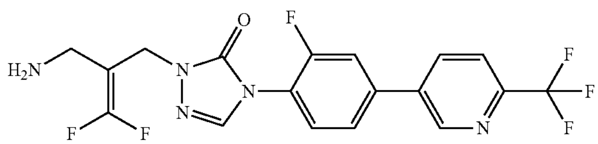 [SMILES: NCC(Cn1ncn(-c2ccc(-c3ccc(C(F)(F)F)nc3)cc2F)c1=O)=C(F)F] | 2-[2-(aminomethyl)-3,3-difluoro-allyl]-4-[2-fluoro-4-[6-(trifluoromethyl)-3-pyridyl]phenyl]-1,2,4-triazol-3-one |
| 34 | 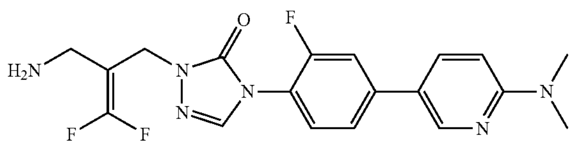 [SMILES: CN(C)c1ccc(-c2ccc(-n3cnn(CC(CN)=C(F)F)c3=O)c(F)c2)cn1] | 2-[2-(aminomethyl)-3,3-difluoro-allyl]-4-[4-[6-(dimethylamino)-3-pyridyl]-2-fluoro-phenyl]-1,2,4-triazol-3-one |
| 35 | 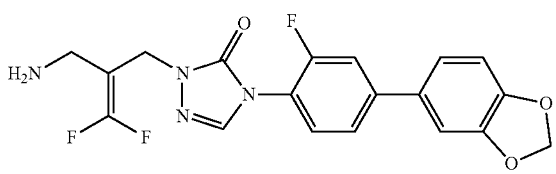 | 2-[2-(aminomethyl)-3,3-difluoro-allyl]-4-[4-(1,3-benzodioxol-5-yl)-2-fluoro-phenyl]-1,2,4-triazol-3-one |
| 36 | 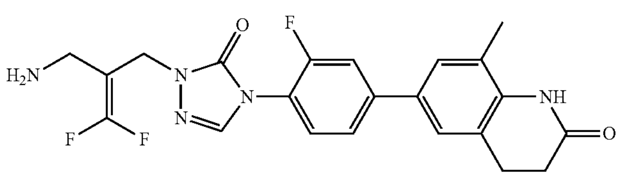 | 6-[4-[1-[2-(aminomethyl)-3,3-difluoro-allyl]-5-oxo-1,2,4-triazol-4-yl]-3-fluoro-phenyl]-8-methyl-3,4-dihydro-1H-quinolin-2-one |
| 37 | 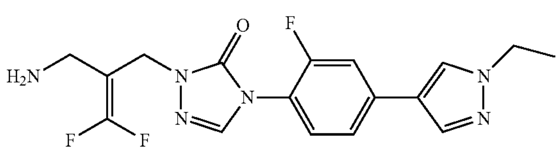 [SMILES: CCn1cc(-c2ccc(-n3cnn(CC(CN)=C(F)F)c3=O)c(F)c2)cn1] | 2-[2-(aminomethyl)-3,3-difluoro-allyl]-4-[4-(1-ethylpyrazol-4-yl)-2-fluoro-phenyl]-1,2,4-triazol-3-one |
| 38 | 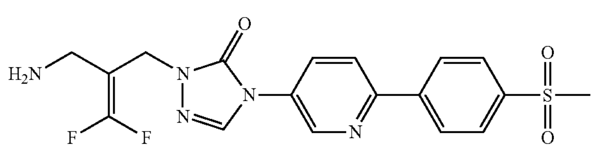 [SMILES: CS(=O)(=O)c1ccc(-c2ccc(-n3cnn(CC(CN)=C(F)F)c3=O)cn2)cc1] | 2-(2-(aminomethyl)-3,3-difluoro-allyl)-4-[6-(4-methylsulfonylphenyl)-3-pyridyl]-1,2,4-triazol-3-one |
| 39 | 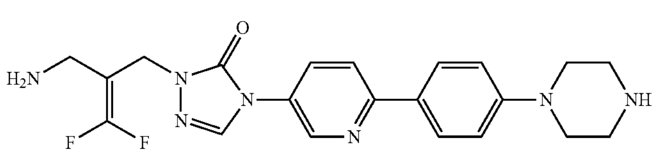 | 2-[2-(aminomethyl)-3,3-difluoro-allyl]-4-[6-(4-piperazin-1-ylphenyl)-3-pyridyl]-1,2,4-triazol-3-one |

TABLE 1*-continued

| Ex No | Structure | Chemical Name |
|---|---|---|
| 40 | 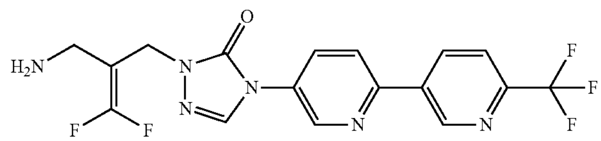 [SMILES: NCC(Cn1ncn(-c2ccc(-c3ccc(C(F)(F)F)nc3)nc2)c1=O)=C(F)F] | 2-[2-(aminomethyl)-3,3-difluoro-allyl]-4-[6-[6-(trifluoromethyl)-3-pyridyl]-3-pyridyl]-1,2,4-triazol-3-one |
| 41 | 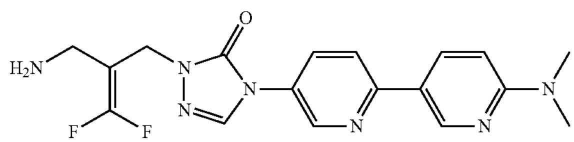 | 2-[2-(aminomethyl)-3,3-difluoro-allyl]-4-[6-[6-(dimethylamino)-3-pyridyl]-3-pyridyl]-1,2,4-triazol-3-one |
| 42 | 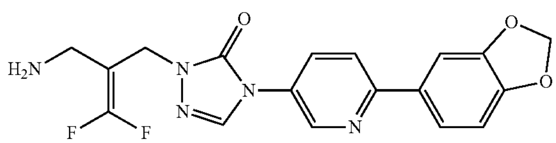 | 2-[2-(aminomethyl)-3,3-difluoro-allyl]-4-[6-(1,3-benzodioxol-5-yl)-3-pyridyl]-1,2,4-triazol-3-one |
| 43 | 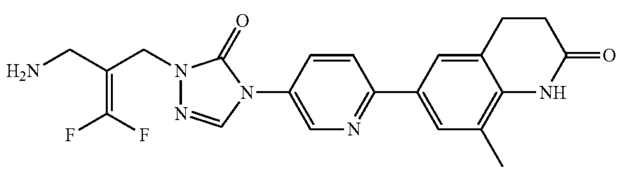 [SMILES: Cc1cc(-c2ccc(-n3cnn(CC(CN)=C(F)F)c3=O)cn2)cc2c1NC(=O)CC2] | 6-[5-[1-[2-(aminomethyl)-3,3-difluoro-allyl]-5-oxo-1,2,4-triazol-4-yl]-2-pyridyl]-8-methyl-3,4-dihydro-1H-quinolin-2-one |
| 44 | 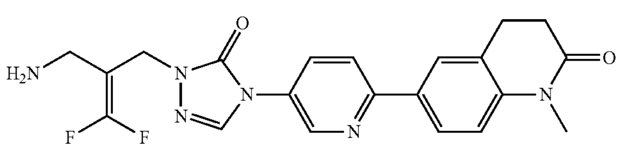 [SMILES: CN1C(=O)CCc2cc(-c3ccc(-n4cnn(CC(CN)=C(F)F)c4=O)cn3)ccc21] | 6-[5-[1-[2-(aminomethyl)-3,3-difluoro-allyl]-5-oxo-1,2,4-triazol-4-yl]-2-pyridyl]-1-methyl-3,4-dihydroquinolin-2-one |
| 45 | 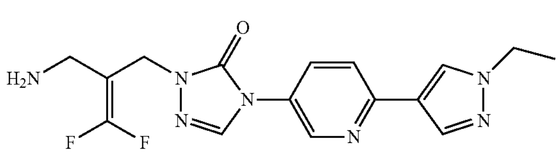 | 2-[2-(aminomethyl)-3,3-difluoro-allyl]-4-[6-(1-ethylpyrazol-4-yl)-3-pyridyl]-1,2,4 triazol-3-one |
| 46 | 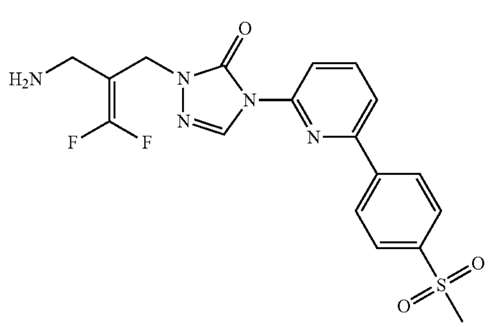 | 2-[2-(aminomethyl)-3,3-difluoro-allyl]-4-[6-(4-methylsulfonylphenyl)-2-pyridyl]-1,2,4-triazol-3-one |

TABLE 1*-continued

| Ex No | Structure | Chemical Name |
|---|---|---|
| 47 | 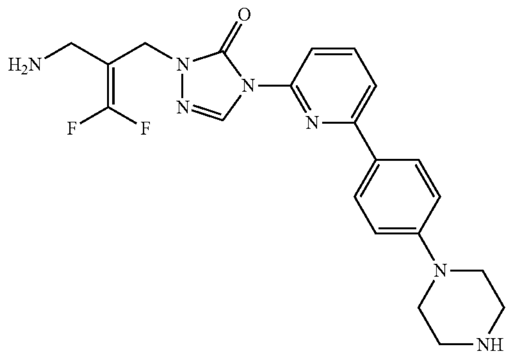 | 2-[2-(aminomethyl)-3,3-difluoro-allyl]-4-[6-(4-piperazin-1-ylphenyl)-2-pyridyl]-1,2,4-triazol-3-one |
| 48 | 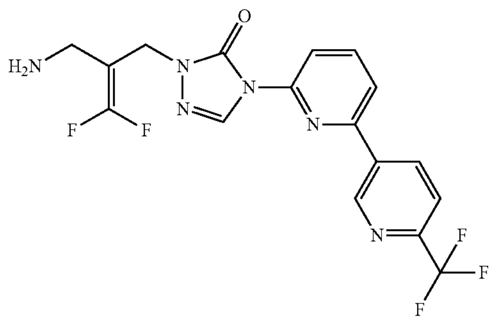 | 2-[2-(aminomethyl)-3,3-difluoro-allyl]-4-[6-[6-(trifluoromethyl)-3-pyridyl]-2-pyridyl]-1,2,4-triazol-3-one |
| 49 | 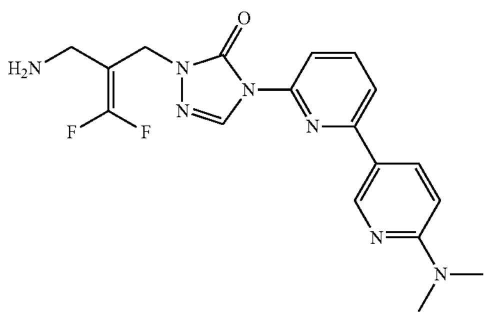 | 2-[2-(aminomethyl)-3,3-difluoro-allyl]-4-[6-[6-(dimethylamino)-3-pyridyl]-2-pyridyl]-1,2,4-triazol-3-one |
| 50 | 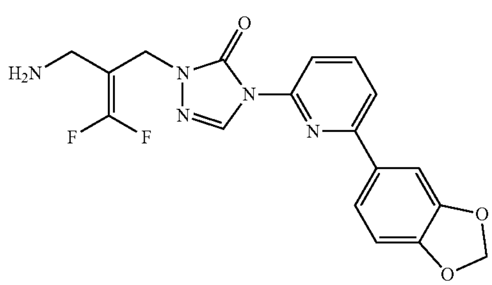 [SMILES: NCC(Cn1ncn(-c2cccc(-c3ccc4c(c3)OCO4)n2)c1=O)=C(F)F] | 2-[2-(aminomethyl)-3,3-difluoro-allyl]-4-[6-(1,3-benzodioxol-5-yl)-2-pyridyl]-1,2,4-triazol-3-one |
| 51 | 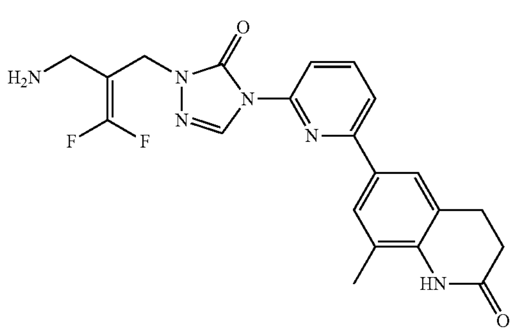 [SMILES: Cc1cc(-c2cccc(-n3cnn(CC(CN)=C(F)F)c3=O)n2)cc2c1NC(=O)CC2] | 6-[6-[1-[2-(aminomethyl)-3,3-difluoro-allyl]-5-oxo-1,2,4-triazol-4-yl]-2-pyridyl]-8-methyl-3,4-dihydro-1H-quinolin-2-one |

TABLE 1*-continued

| Ex No | Structure | Chemical Name |
|---|---|---|
| 52 | 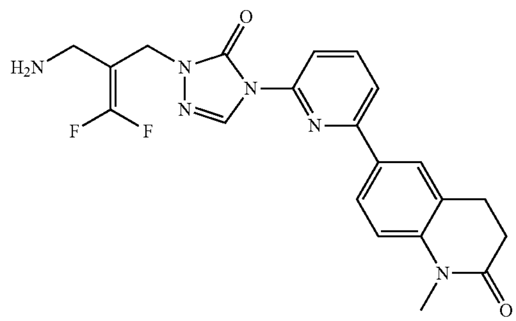 [SMILES: CN1C(=O)CCc2cc(-c3cccc(-n4cnn(CC(CN)=C(F)F)c4=O)n3)ccc21] | 6-[6-[1-[2-(aminomethyl)-3,3-difluoro-allyl]-5-oxo-1,2,4-triazol-4-yl]-2-pyridyl]-1-methyl-3,4-dihydroquinolin-2-one |
| 53 | 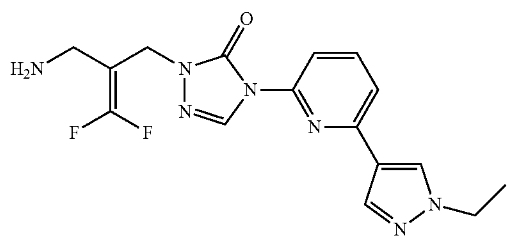 | 2-[2-(aminomethyl)-3,3-difluoro-allyl]-4-[6-(1-ethylpyrazol-4-yl)-2-pyridyl]-1,2,4-triazol-3-one |
| 54 | 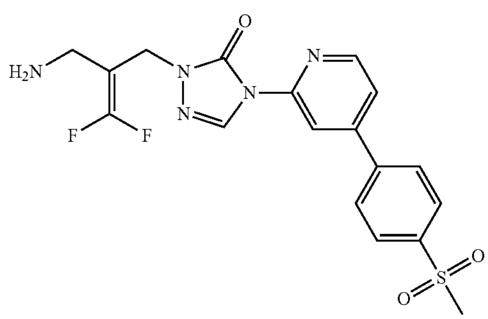 [SMILES: CS(=O)(=O)c1ccc(-c2ccnc(-n3cnn(CC(CN)=C(F)F)c3=O)c2)cc1] | 2-[2-(aminomethyl)-3,3-difluoro-allyl]-4-[4-(4-methylsulfonylphenyl)-2-pyridyl]-1,2,4-triazol-3-one |
| 55 | 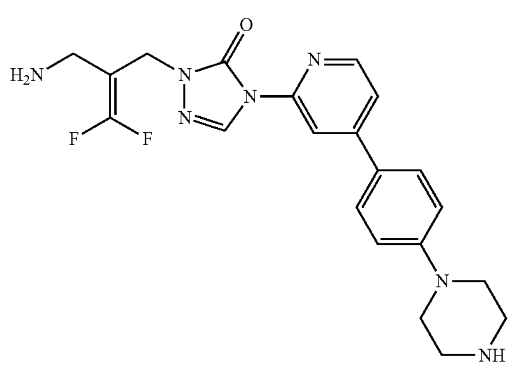 | 2-[2-(aminomethyl)-3,3-difluoro-allyl]-4-[4-(4-piperazin-1-ylphenyl)-2-pyridyl]-1,2,4-triazol-3-one |
| 56 | 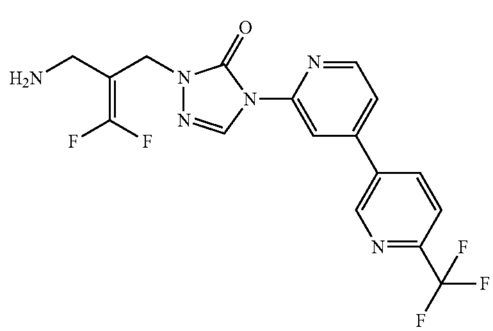 | 2-[2-(aminomethyl)-3,3-difluoro-allyl]-4-[4-[6-(trifluoromethyl)-3-pyridyl]-2-pyridyl]-1,2,4-triazol-3-one |

TABLE 1*-continued

| Ex No | Structure | Chemical Name |
|---|---|---|
| 57 | 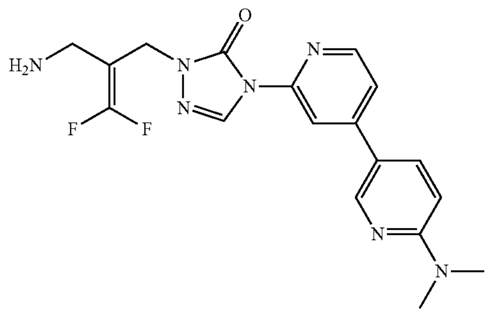 [SMILES: CN(C)c1ccc(-c2ccnc(-n3cnn(CC(CN)=C(F)F)c3=O)c2)cn1] | 2-[2-(aminomethyl)-3,3-difluoro-allyl]-4-[4-[6-(dimethylamino)-3-pyridyl]-2-pyridyl]-1,2,4-triazol-3-one |
| 58 | 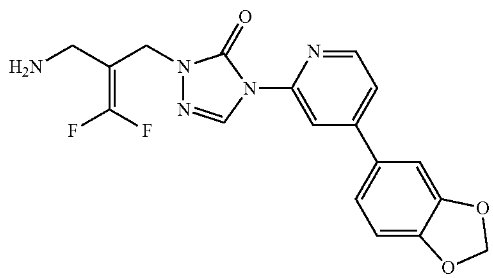 | 2-[2-(aminomethyl)-3,3-difluoro-allyl]-4-[4-(1,3-benzodioxol-5-yl)-2-pyridyl]-1,2,4-triazol-3-one |
| 59 | 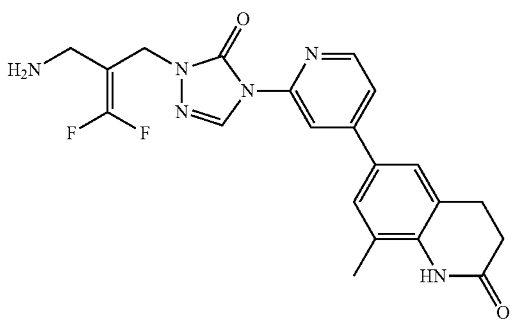 [SMILES: Cc1cc(-c2ccnc(-n3cnn(CC(CN)=C(F)F)c3=O)c2)cc2c1NC(=O)CC2] | 6-[2-[1-[2-(aminomethyl)-3,3-difluoro-allyl]-5-oxo-1,2,4-triazol-4-yl]-4-pyridyl]-8-methyl-3,4-dihydro-1H-quinolin-2-one |
| 60 | 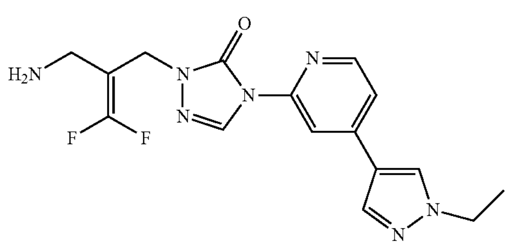 [SMILES: CCn1cc(-c2ccnc(-n3cnn(CC(CN)=C(F)F)c3=O)c2)cn1] | 2-[2-(aminomethyl)-3,3-difluoro-allyl]-4-[4-(1-ethylpyrazol-4-yl)-2-pyridyl]-1,2,4-triazol-3-one |
| 61 | 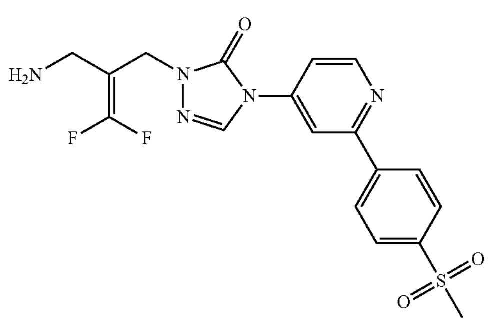 [SMILES: CS(=O)(=O)c1ccc(-c2cc(-n3cnn(CC(CN)=C(F)F)c3=O)ccn2)cc1] | 2-[2-(aminomethyl)-3,3-difluoro-allyl]-4-[2-(4-methylsulfonylphenyl)-4-pyridyl]-1,2,4-triazol-3-one |

TABLE 1*-continued

| Ex No | Structure | Chemical Name |
|---|---|---|
| 62 | 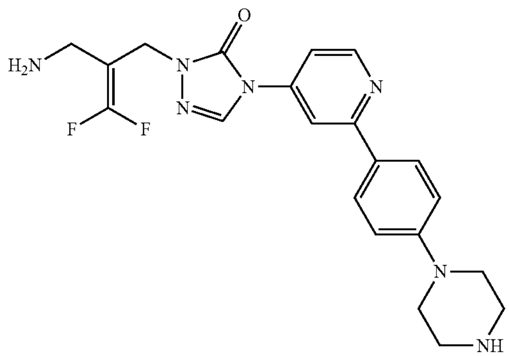 [SMILES: NCC(Cn1ncn(-c2ccnc(-c3ccc(N4CCNCC4)cc3)c2)c1=O)=C(F)F] | 2-[2-(aminomethyl)-3,3-difluoro-allyl]-4-[2-(4-piperazin-1-ylphenyl)-4-pyridyl]-1,2,4-triazol-3-one |
| 63 | 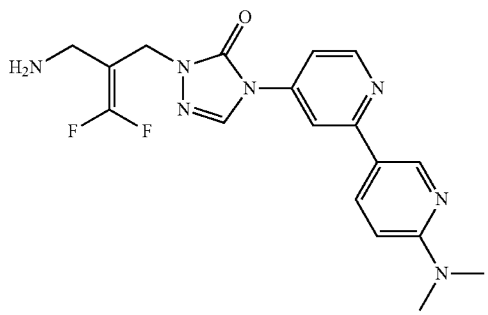 [SMILES: CN(C)c1ccc(-c2cc(-n3cnn(CC(CN)=C(F)F)c3=O)ccn2)cn1] | 2-[2-(aminomethyl)-3,3-difluoro-allyl]-4-[2-[6-(dimethylamino)-3-pyridyl]-4-pyridyl]-1,2,4-triazol-3-one |
| 64 | 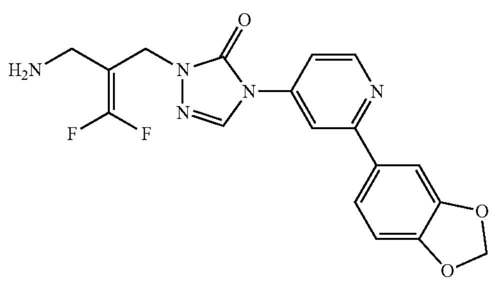 [SMILES: NCC(Cn1ncn(-c2ccnc(-c3ccc4c(c3)OCO4)c2)c1=O)=C(F)F] | 2-[2-(aminomethyl)-3,3-difluoro-allyl]-4-[2-(1,3-benzodioxol-5-yl)-4-pyridyl]-1,2,4-triazol-3-one |
| 65 | 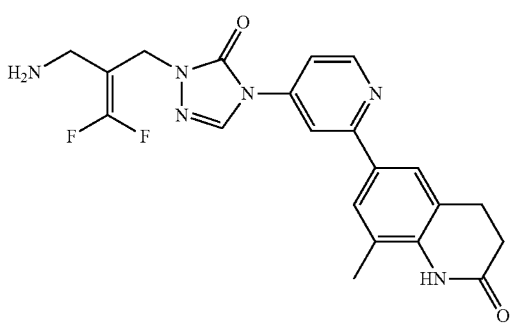 [SMILES: Cc1cc(-c2cc(-n3cnn(CC(CN)=C(F)F)c3=O)ccn2)cc2c1NC(=O)CC2] | 6-[4-[1-[2-(aminomethyl)-3,3-difluoro-allyl]-5-oxo-1,2,4-triazol-4-yl]-2-pyridyl]-8-methyl-3,4-dihydro-1H-quinolin-2-one |
| 66 | 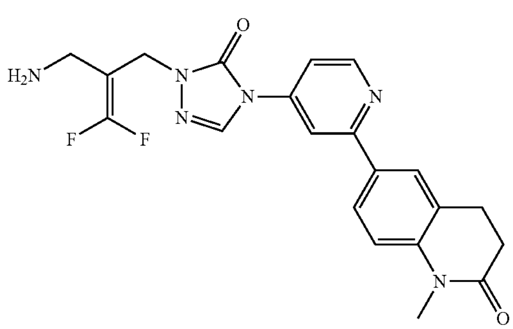 [SMILES: CN1C(=O)CCc2cc(-c3cc(-n4cnn(CC(CN)=C(F)F)c4=O)ccn3)ccc21] | 6-[4-[1-[2-(aminomethyl)-3,3-difluoro-allyl]-5-oxo-1,2,4-triazol-4-yl]-2-pyridyl]-1-methyl-3,4-dihydroquinolin-2-one |

TABLE 1*-continued

| Ex No | Structure | Chemical Name |
|---|---|---|
| 67 | 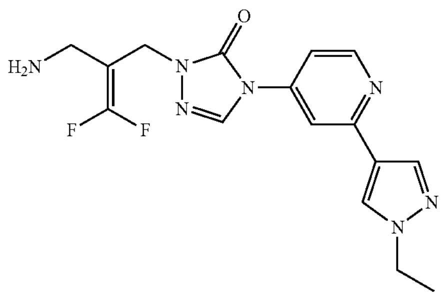 [SMILES: CCn1cc(-c2cc(-n3cnn(CC(CN)=C(F)F)c3=O)ccn2)cn1] | 2-[2-(aminomethyl)-3,3-difluoro-allyl]-4-[2-(1-ethylpyrazol-4-yl)-4-pyridyl]-1,2,4-triazol-3-one |
| 68 | 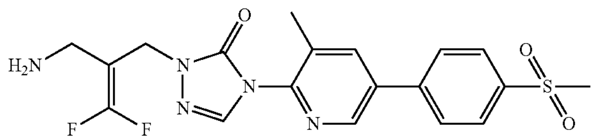 [SMILES: Cc1cc(-c2ccc(S(C)(=O)=O)cc2)cnc1-n1cnn(CC(CN)=C(F)F)c1=O] | 2-[2-(aminomethyl)-3,3-difluoro-allyl]-4-[3-methyl-5-(4-methylsulfonylphenyl)-2-pyridyl]-1,2,4-triazol-3-one |
| 69 | 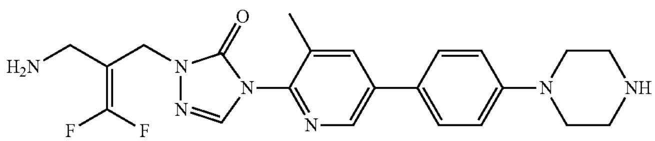 [SMILES: Cc1cc(-c2ccc(N3CCNCC3)cc2)cnc1-n1cnn(CC(CN)=C(F)F)c1=O] | 2-[2-(aminomethyl)-3,3-difluoro-allyl]-4-[3-methyl-5-(4-piperazin-1-ylphenyl)-2-pyridyl]-1,2,4-triazol-3-one |
| 70 | 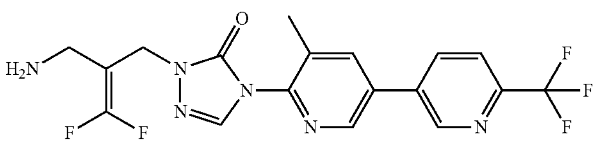 [SMILES: Cc1cc(-c2ccc(C(F)(F)F)nc2)cnc1-n1cnn(CC(CN)=C(F)F)c1=O] | 2-[2-(aminomethyl)-3,3-difluoro-allyl]-4-[3-methyl-5-[6-(trifluoromethyl)-3-pyridyl]-2-pyridyl]-1,2,4-triazol-3-one |
| 71 | 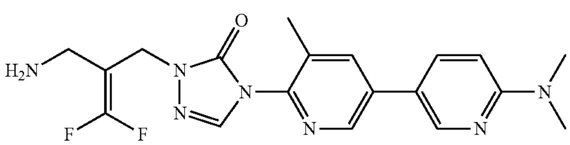 | 2-[2-(aminomethyl)-3,3-difluoro-allyl]-4-[5-[6-(dimethylamino)-3-pyridyl]-3 methyl-2-pyridyl]-1,2,4-triazol-3-one |
| 72 | 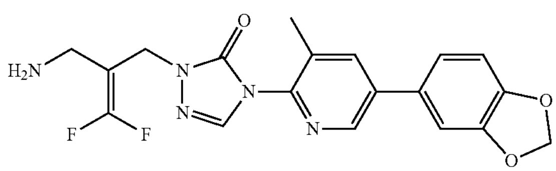 [SMILES: Cc1cc(-c2ccc3c(c2)OCO3)cnc1-n1cnn(CC(CN)=C(F)F)c1=O] | 2-[2-(aminomethyl)-3,3-difluoro-allyl]-4-[5-(1,3-benzodioxol-5-yl)-3-methyl-2-pyridyl]-1,2,4-triazol-3-one |
| 73 | 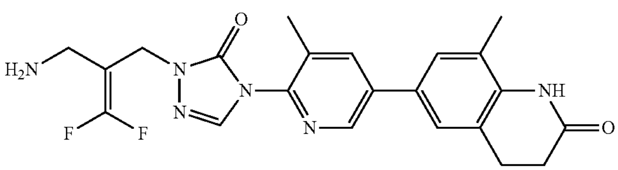 [SMILES: Cc1cc(-c2cc(C)c3c(c2)CCC(=O)N3)cnc1-n1cnn(CC(CN)=C(F)F)c1=O] | 6-[6-[1-[2-(aminomethyl)-3,3-difluoro-allyl]-5-oxo-1,2,4-triazol-4-yl]-5-methyl-3-pyridyl]-8-methyl-3,4-dihydro-1H-quinolin-2-one |
| 74 | 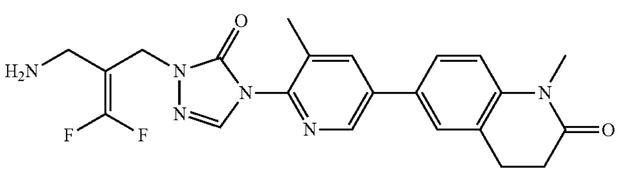 [SMILES: Cc1cc(-c2ccc3c(c2)CCC(=O)N3C)cnc1-n1cnn(CC(CN)=C(F)F)c1=O] | 6-[6-[1-[2-(aminomethyl)-3,3-difluoro-allyl]-5-oxo-1,2,4-triazol-4-yl]-5-methyl-3-pyridyl]-1-methyl-3,4-dihydroquinolin-2-one |
| 75 | 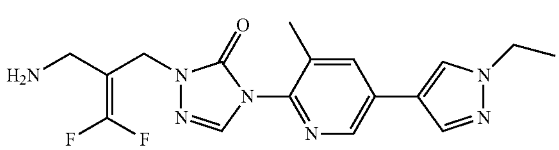 [SMILES: CCn1cc(-c2cnc(-n3cnn(CC(CN)=C(F)F)c3=O)c(C)c2)cn1] | 2-[2-(aminomethyl)-3,3-difluoro-allyl]-4-[5-(1-ethylpyrazol-4-yl)-3-methyl-2-pyridyl]-1,2,4-triazol-3-one |

TABLE 1*-continued

| Ex No | Structure | Chemical Name |
|---|---|---|
| 76 | 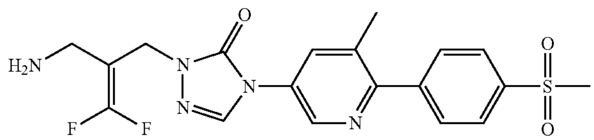 [SMILES: Cc1cc(-n2cnn(CC(CN)=C(F)F)c2=O)cnc1-c1ccc(S(C)(=O)=O)cc1] | 2-[2-(aminomethyl)-3,3-difluoro-allyl]-4-[5-methyl-6-(4-methylsulfonylphenyl)-3-pyridyl]-1,2,4-triazol-3-one |
| 77 | 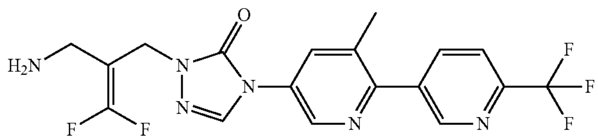 | 2-[2-(aminomethyl)-3,3-difluoro-allyl]-4-[5-methyl-6-[6-(trifluoromethyl)-3-pyridyl]-3-pyridyl]-1,2,4-triazol-3-one |
| 78 | 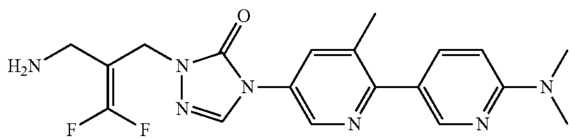 [SMILES: Cc1cc(-n2cnn(CC(CN)=C(F)F)c2=O)cnc1-c1ccc(N(C)C)nc1] | 2-[2-(aminomethyl)-3,3-difluoro-allyl]-4-[6-[6-(dimethylamino)-3-pyridyl]-5-methyl-3-pyridyl]-1,2,4-triazol-3-one |
| 79 | 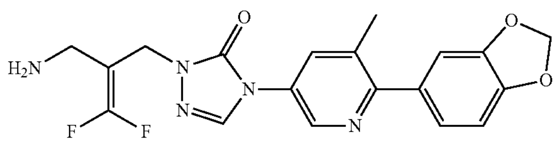 [SMILES: Cc1cc(-n2cnn(CC(CN)=C(F)F)c2=O)cnc1-c1ccc2c(c1)OCO2] | 2-[2-(aminomethyl)-3,3-difluoro-allyl]-4-[6-(1,3-benzodioxol-5-yl)-5-methyl-3-pyridyl]-1,2,4-triazol-3-one |
| 80 | 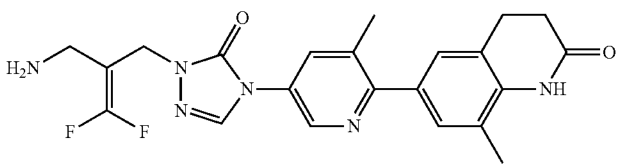 [SMILES: Cc1cc(-n2cnn(CC(CN)=C(F)F)c2=O)cnc1-c1cc(C)c2c(c1)CCC(=O)N2] | 6-[5-[1-[2-(aminomethyl)-3,3-difluoro-allyl]-5-oxo-1,2,4-triazol-4-yl]-3-methyl-2-pyridyl]-8-methyl-3,4-dihydro-1H-quinolin-2-one |
| 81 | 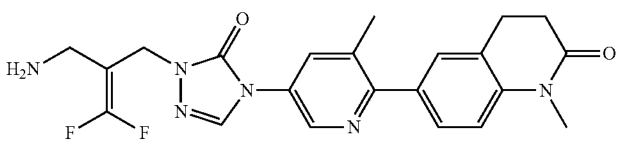 | 6-[5-[1-[2-(aminomethyl)-3,3-difluoro-allyl]-5-oxo-1,2,4-triazol-4-yl]-3-methyl-2-pyridyl]-1-methyl-3,4-dihydroquinolin-2-one |
| 82 | 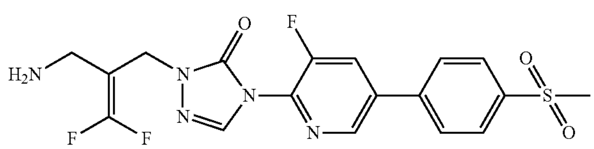 [SMILES: CS(=O)(=O)c1ccc(-c2cnc(-n3cnn(CC(CN)=C(F)F)c3=O)c(F)c2)cc1] | 2-[2-(aminomethyl)-3,3-difluoro-allyl]-4-[3-fluoro-5-(4-methylsulfonylphenyl)-2-pyridyl]-1,2,4-triazol-3-one |
| 83 | 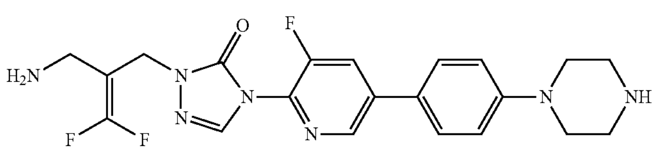 | 2-[2-(aminomethyl)-3,3-difluoro-allyl]-4-[3-fluoro-5-(4-piperazin-1-ylphenyl)-2-pyridyl]-1,2,4-triazol-3-one |
| 84 | 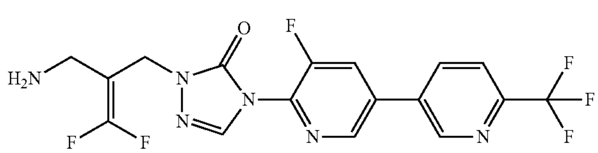 [SMILES: NCC(Cn1ncn(-c2ncc(-c3ccc(C(F)(F)F)nc3)cc2F)c1=O)=C(F)F] | 2-[2-(aminomethyl)-3,3-difluoro-allyl]-4-[3-fluoro-5-[6-(trifluoromethyl)-3-pyridyl]-2-pyridyl]-1,2,4-triazol-3-one |
| 85 | 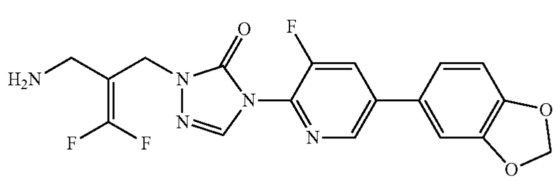 [SMILES: NCC(Cn1ncn(-c2ncc(-c3ccc4c(c3)OCO4)cc2F)c1=O)=C(F)F] | 2-[2-(aminomethyl)-3,3-difluoro-allyl]-4-[5-(1,3-benzodioxol-5-yl)-3-fluoro-2-pyridyl]-1,2,4-triazol-3-one |

TABLE 1*-continued

| Ex No | Structure | Chemical Name |
|---|---|---|
| 86 | 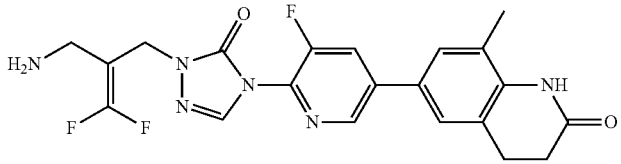 [SMILES: Cc1cc(-c2cnc(-n3cnn(CC(CN)=C(F)F)c3=O)c(F)c2)cc2c1NC(=O)CC2] | 6-[6-[1-[2-(aminomethyl)-3,3-difluoro-allyl]-5-oxo-1,2,4-triazol-4-yl]-5-fluoro-3-pyridyl]-8-methyl-3,4-dihydro-1H-quinolin-2-one |
| 87 | 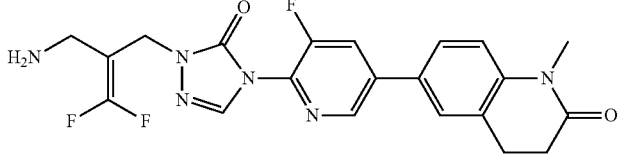 | 6-[6-[1-[2-(aminomethyl)-3,3-difluoro-allyl]-5-oxo-1,2,4-triazol-4-yl]-5-fluoro-3-pyridyl]-1-methyl-3,4-dihydroquinolin-2-one |
| 88 | 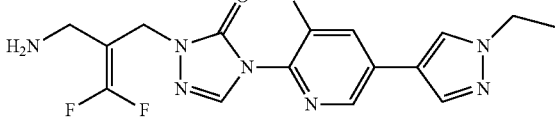 | 2-[2-(aminomethyl)-3,3-difluoro-allyl]-4-[5-(1-ethylpyrazol-4-yl)-3-fluoro-2-pyridyl]-1,2,4-triazol-3-one |
| 89 | 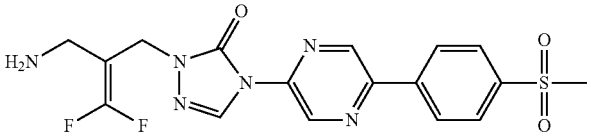 | 2-[2-(aminomethyl)-3,3-difluoro-allyl]-4-[5-(4-methylsulfonylphenyl)pyrazin-2-yl]-1,2,4-triazol-3-one |
| 90 | 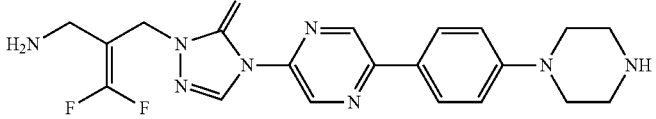 | 2-[2-(aminomethyl)-3,3-difluoro-allyl]-4-[5-(4-piperazin-1-ylphenyl)pyrazin-2-yl]-1,2,4-triazol-3-one |
| 91 | 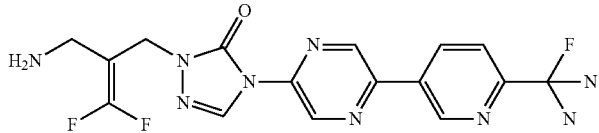 [SMILES: NCC(Cn1ncn(-c2cnc(-c3ccc(C(N)(N)F)nc3)cn2)c1=O)=C(F)F] | 2-[2-(aminomethyl)-3,3-difluoro-allyl]-4-[5-[6-(trifluoromethyl)-3-pyridyl]pyrazin-2-yl]-1,2,4-triazol-3-one |
| 92 | 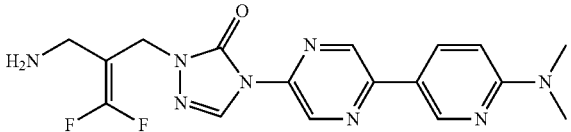 [SMILES: CN(C)c1ccc(-c2cnc(-n3cnn(CC(CN)=C(F)F)c3=O)cn2)cn1] | 2-[2-(aminomethyl)-3,3-difluoro-allyl]-4-[5-[6-(dimethylamino)-3-pyridyl]pyrazin-2-yl]-1,2,4-triazol-3-one |
| 93 | 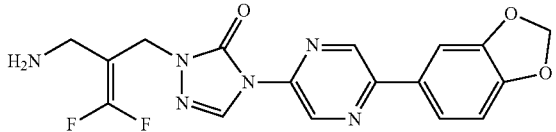 [SMILES: NCC(Cn1ncn(-c2cnc(-c3ccc4c(c3)OCO4)cn2)c1=O)=C(F)F] | 2-[2-(aminomethyl)-3,3-difluoro-allyl]-4-[5-(1,3-benzodioxol-5-yl)pyrazin-2-yl]-1,2,4-triazol-3-one |
| 94 | 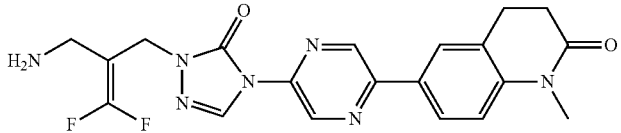 [SMILES: CN1C(=O)CCc2cc(-c3cnc(-n4cnn(CC(CN)=C(F)F)c4=O)cn3)ccc21] | 6-[5-[1-[2-(aminomethyl)-3,3-difluoro-allyl]-5-oxo-1,2,4-triazol-4-yl]pyrazin-2-yl]-1-methyl-3,4-dihydro-1H-quinolin-2-one |
| 95 | 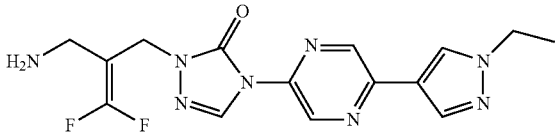 | 2-[2-(aminomethyl)-3,3-difluoro-allyl]-4-[5-(1-ethylpyrazol-4-yl)pyrazin-2-yl]-1,2,4-triazol-3-one |

TABLE 1*-continued

| Ex No | Structure | Chemical Name |
|---|---|---|
| 96 | 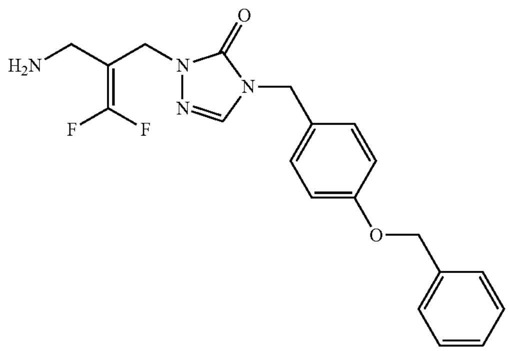 [SMILES: NCC(Cn1ncn(Cc2ccc(OCc3ccccc3)cc2)c1=O)=C(F)F] | 2-[2-(aminomethyl)-3,3-difluoro-allyl]-4-[(4-benzyloxyphenyl)methyl]-1,2,4-triazol-3-one |
| 97 | 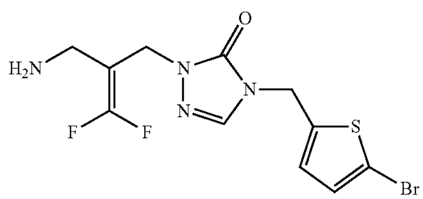 [SMILES: NCC(Cn1ncn(Cc2ccc(Br)s2)c1=O)=C(F)F] | 2-[2-(aminomethyl)-3,3-difluoro-allyl]-4-[(5-bromo-2-thienyl)methyl]-1,2,4-triazol-3-one |
| 98 | 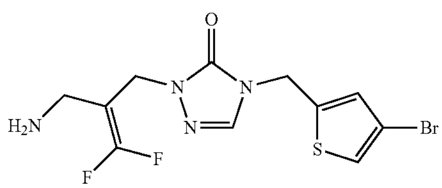 [SMILES: NCC(Cn1ncn(Cc2cc(Br)cs2)c1=O)=C(F)F] | 2-[2-(aminomethyl)-3,3-difluoro-allyl]-4-[(4-bromo-2-thienyl)methyl]-1,2,4-triazol-3-one |
| 99 | 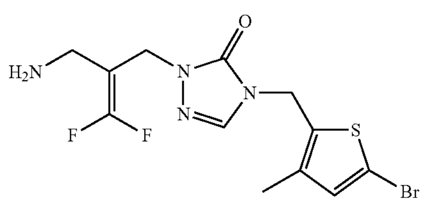 [SMILES: Cc1cc(Br)sc1Cn1cnn(CC(CN)=C(F)F)c1=O] | 2-[2-(aminomethyl)-3,3-difluoro-allyl]-4-[(5-bromo-3-methyl-2-thienyl)methyl]-1,2,4-triazol-3-one |
| 100 | 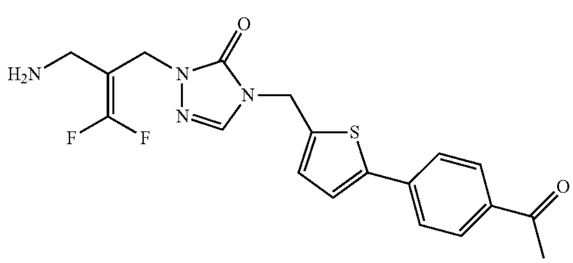 [SMILES: CC(=O)c1ccc(-c2ccc(Cn3cnn(CC(CN)=C(F)F)c3=O)s2)cc1] | 4-[[5-(4-acetylphenyl)-2-thienyl]methyl]-2-[2-(aminomethyl)-3,3-difluoro-allyl]-1,2,4-triazol-3-one |
| 101 | 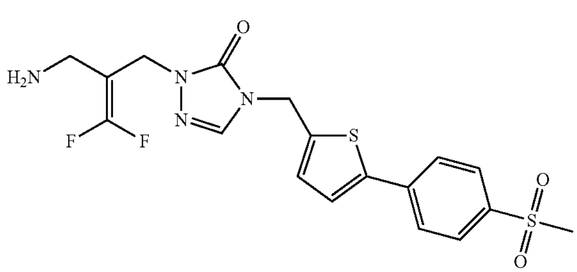 [SMILES: CS(=O)(=O)c1ccc(-c2ccc(Cn3cnn(CC(CN)=C(F)F)c3=O)s2)cc1] | 2-[2-(aminomethyl)-3,3-difluoro-allyl]-4-[[5-(4-methylsulfonylphenyl)-2-thienyl]methyl]-1,2,4-triazol-3-one |

TABLE 1*-continued

| Ex No | Structure | Chemical Name |
|---|---|---|
| 102 | 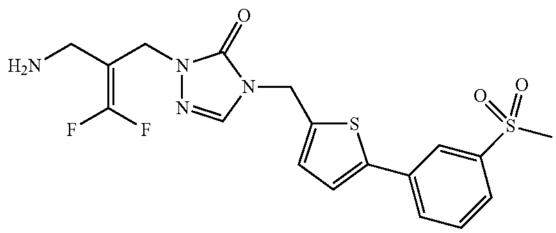 [SMILES: CS(=O)(=O)c1cccc(-c2ccc(Cn3cnn(CC(CN)=C(F)F)c3=O)s2)c1] | 2-[2-(aminomethyl)-3,3-difluoro-allyl]-4-[[5-(3-methylsulfonylphenyl)-2-thienyl]methyl]-1,2,4-triazol-3-one |
| 103 | 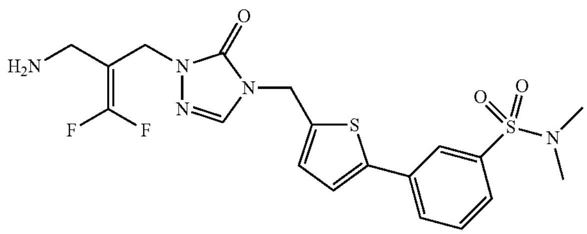 [SMILES: CN(C)S(=O)(=O)c1cccc(-c2ccc(Cn3cnn(CC(CN)=C(F)F)c3=O)s2)c1] | 3-[5-[[1-[2-(aminomethyl)-3,3-difluoro-allyl]-5-oxo-1,2,4-triazol-4-yl]methyl]-2-thienyl]-N,N-dimethyl-benzenesulfonamide |
| 104 | 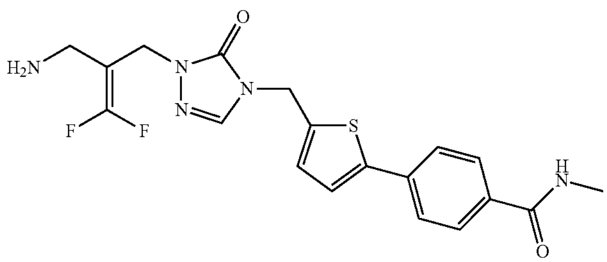 [SMILES: CNC(=O)c1ccc(-c2ccc(Cn3cnn(CC(CN)=C(F)F)c3=O)s2)cc1] | 4-[5-[[1-[2-(aminomethyl)-3,3-difluoro-allyl]-5-oxo-1,2,4-triazol-4-yl]methyl]-2-thienyl]-N-methyl-benzamide |
| 105 | 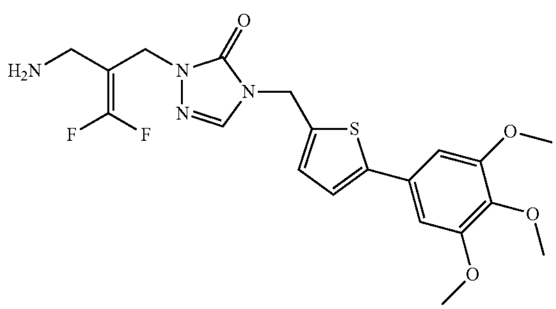 [SMILES: COc1cc(-c2ccc(Cn3cnn(CC(CN)=C(F)F)c3=O)s2)cc(OC)c1OC] | 2-[2-(aminomethyl)-3,3-difluoro-allyl]-4-[[5-(3,4,5-trimethoxyphenyl)-2-thienyl]methyl]-1,2,4-triazol-3-one |
| 106 | 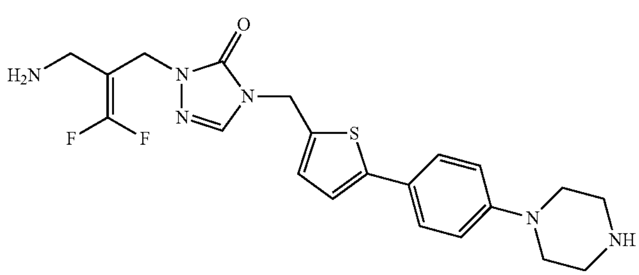 | 2-[2-(aminomethyl)-3,3-difluoro-allyl]-4-[[5-(4-piperazin-1-ylphenyl)-2-thienyl]methyl]-1,2,4-triazol-3-one |
| 107 | 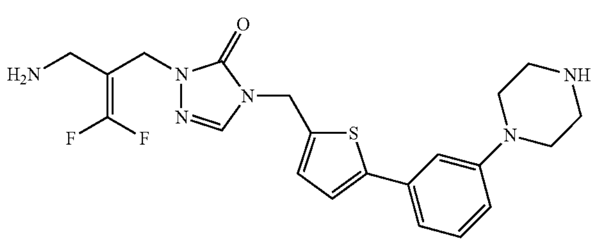 [SMILES: NCC(Cn1ncn(Cc2ccc(-c3cccc(N4CCNCC4)c3)s2)c1=O)=C(F)F] | 2-[2-(aminomethyl)-3,3-difluoro-allyl]-4-[[5-(3-piperazin-1-ylphenyl)-2-thienyl]methyl]-1,2,4-triazol-3-one |

TABLE 1*-continued

| Ex No | Structure | Chemical Name |
|---|---|---|
| 108 | 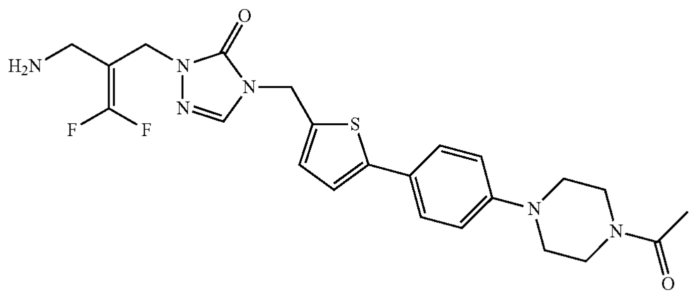 [SMILES: CC(=O)N1CCN(c2ccc(-c3ccc(Cn4cnn(CC(CN)=C(F)F)c4=O)s3)cc2)CC1] | 4-[[5-[4-(4-acetylpiperazin-1-yl)phenyl]-2-thienyl]methyl]-2-[2-(aminomethyl)-3,3-difluoro-allyl]-1,2,4-triazol-3-one |
| 109 | 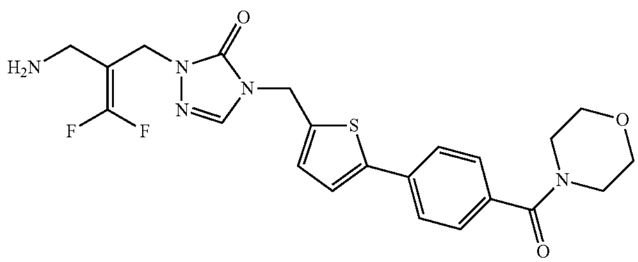 [SMILES: NCC(Cn1ncn(Cc2ccc(-c3ccc(C(=O)N4CCOCC4)cc3)s2)c1=O)=C(F)F] | 2-[2-(aminomethyl)-3,3-difluoro-allyl]-4-[[5-[4-(morpholine-4-carbonyl)phenyl]-2-thienyl]methyl]-1,2,4-triazol-3-one |
| 110 | 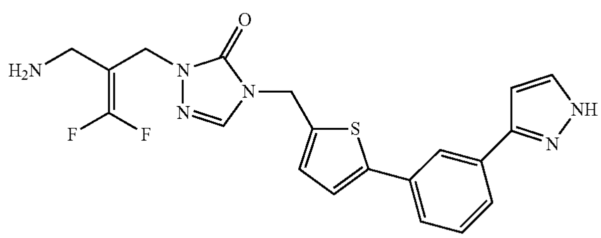 [SMILES: NCC(Cn1ncn(Cc2ccc(-c3cccc(-c4cc[nH]n4)c3)s2)c1=O)=C(F)F] | 2-[2-(aminomethyl)-3,3-difluoro-allyl]-4-[[5-[3-(1H-pyrazol-3-yl)phenyl]-2-thienyl]methyl]-1,2,4-triazol-3-one |
| 111 | 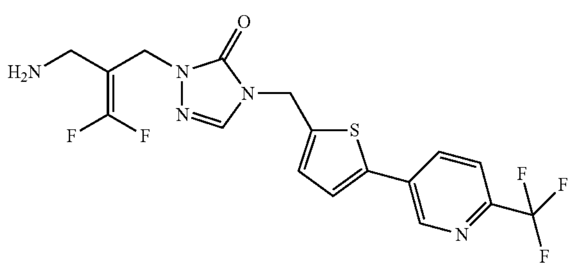 [SMILES: NCC(Cn1ncn(Cc2ccc(-c3ccc(C(F)(F)F)nc3)s2)c1=O)=C(F)F] | 2-[2-(aminomethyl)-3,3-difluoro-allyl]-4-[[5-[6-(trifluoromethyl)-3-pyridyl]-2-thienyl]methyl]-1,2,4-triazol-3-one |
| 112 | 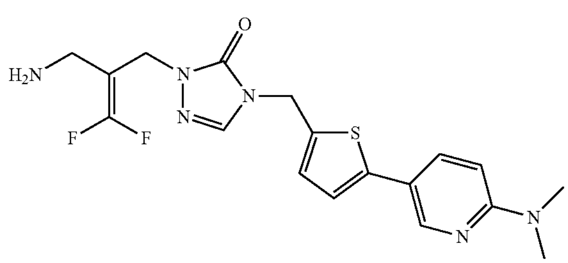 [SMILES: CN(C)c1ccc(-c2ccc(Cn3cnn(CC(CN)=C(F)F)c3=O)s2)cn1] | 2-[2-(aminomethyl)-3,3-difluoro-allyl]-4-[[5-[6-(dimethylamino)-3-pyridyl]-2-thienyl]methyl]-1,2,4-triazol-3-one |
| 113 | 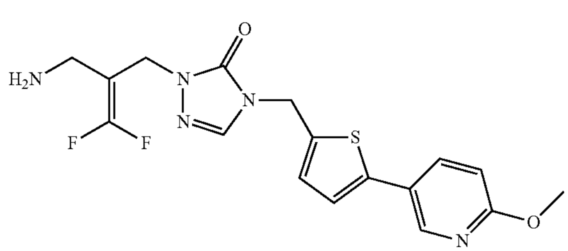 [SMILES: COc1ccc(-c2ccc(Cn3cnn(CC(CN)=C(F)F)c3=O)s2)cn1] | 2-[2-(aminomethyl)-3,3-difluoro-allyl]-4-[[5-(6-methoxy-3-pyridyl)-2-thienyl]methyl]-1,2,4-triazol-3-one |

TABLE 1*-continued

| Ex No | Structure | Chemical Name |
|---|---|---|
| 114 | 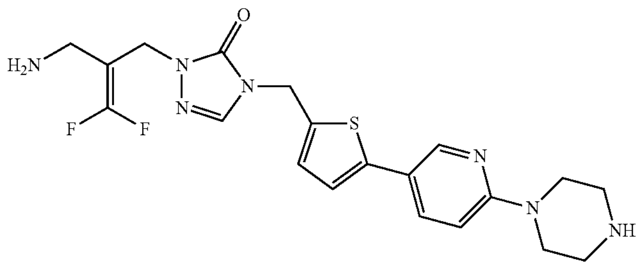 [SMILES: NCC(Cn1ncn(Cc2ccc(-c3ccc(N4CCNCC4)nc3)s2)c1=O)=C(F)F] | 2-[2-(aminomethyl)-3,3-difluoro-allyl]-4-[[5-(6-piperazin-1-yl-3-pyridyl)-2-thienyl]methyl]-1,2,4-triazol-3-one |
| 115 | 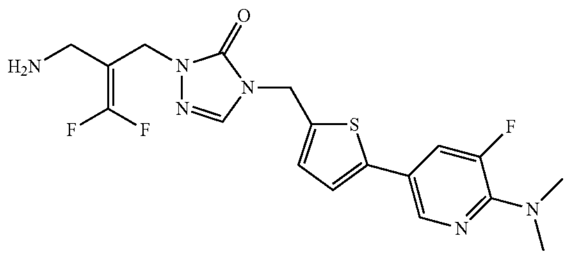 [SMILES: CN(C)c1ncc(-c2ccc(Cn3cnn(CC(CN)=C(F)F)c3=O)s2)cc1F] | 2-[2-(aminomethyl)-3,3-difluoro-allyl]-4-[[5-[6-(dimethylamino)-5-fluoro-3-pyridyl]-2-thienyl]methyl]-1,2,4-triazol-3-one |
| 116 | 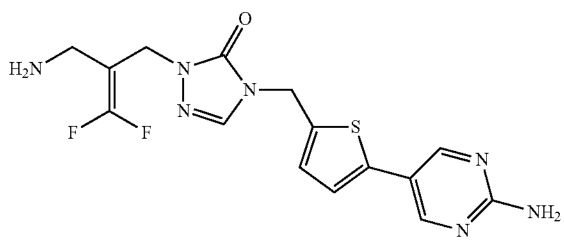 [SMILES: NCC(Cn1ncn(Cc2ccc(-c3cnc(N)nc3)s2)c1=O)=C(F)F] | 2-[2-(aminomethyl)-3,3-difluoro-allyl]-4-[[5-(2-aminopyrimidin-5-yl)-2-thienyl]methyl]-1,2,4-triazol-3-one |
| 117 | 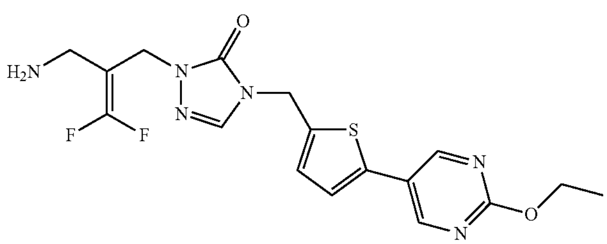 [SMILES: CCOc1ncc(-c2ccc(Cn3cnn(CC(CN)=C(F)F)c3=O)s2)cn1] | 2-[2-(aminomethyl)-3,3-difluoro-allyl]-4-[[5-(2-ethoxypyrimidin-5-yl)-2-thienyl]methyl]-1,2,4-triazol-3-one |
| 118 | 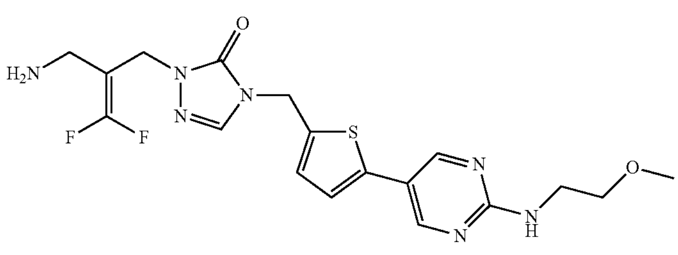 [SMILES: COCCNc1ncc(-c2ccc(Cn3cnn(CC(CN)=C(F)F)c3=O)s2)cn1] | 2-[2-(aminomethyl)-3,3-difluoro-allyl]-4-[[5-[2-(2-methoxyethylamino)pyrimidin-5-yl]-2-thienyl]methyl]-1,2,4-triazol-3-one |
| 119 | 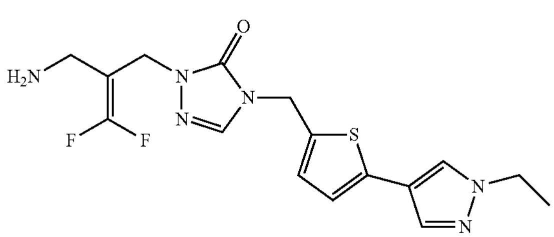 [SMILES: CCn1cc(-c2ccc(Cn3cnn(CC(CN)=C(F)F)c3=O)s2)cn1] | 2-[2-(aminomethyl)-3,3-difluoro-allyl]-4-[[5-(1-ethylpyrazol-4-yl)-2-thienyl]methyl]-1,2,4-triazol-3-one |

TABLE 1*-continued

| Ex No | Structure | Chemical Name |
|---|---|---|
| 120 | 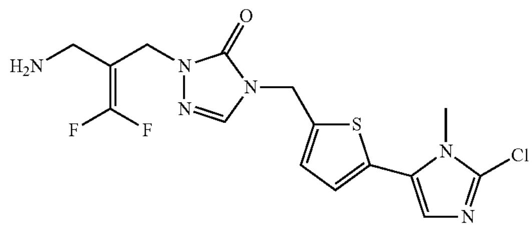 [SMILES: Cn1c(-c2ccc(Cn3cnn(CC(CN)=C(F)F)c3=O)s2)cnc1Cl] | 2-[2-(aminomethyl)-3,3-difluoro-allyl]-4-[[5-(2-chloro-3-methyl-imidazol-4-yl)-2-thienyl]methyl]-1,2,4-triazol-3-one |
| 121 | 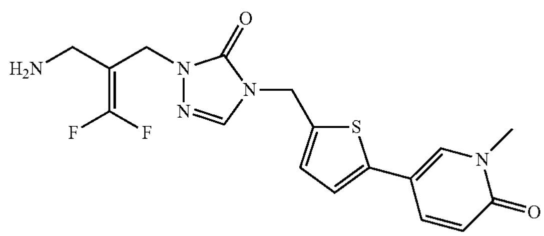 [SMILES: Cn1cc(-c2ccc(Cn3cnn(CC(CN)=C(F)F)c3=O)s2)ccc1=O] | 5-[5-[[1-[2-(aminomethyl)-3,3-difluoro-allyl]-5-oxo-1,2,4-triazol-4-yl]methyl]-2-thienyl]-1-methyl-pyridin-2-one |
| 122 | 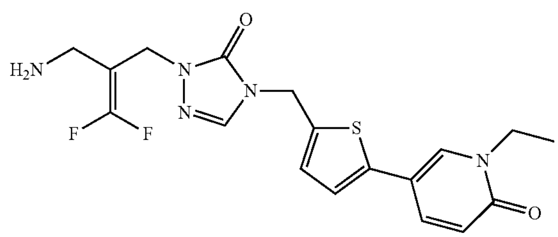 [SMILES: CCn1cc(-c2ccc(Cn3cnn(CC(CN)=C(F)F)c3=O)s2)ccc1=O] | 5-[5-[[1-[2-(aminomethyl)-3,3-difluoro-allyl]-5-oxo-1,2,4-triazol-4-yl]methyl]-2-thienyl]-1-ethyl-pyridin-2-one |
| 123 | 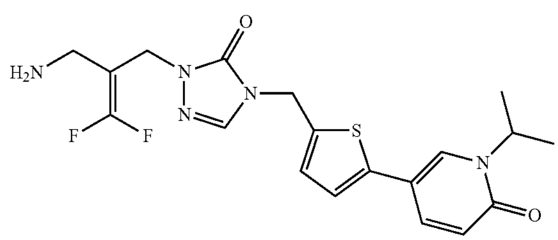 [SMILES: CC(C)n1cc(-c2ccc(Cn3cnn(CC(CN)=C(F)F)c3=O)s2)ccc1=O] | 5-[5-[[1-[2-(aminomethyl)-3,3-difluoro-allyl]-5-oxo-1,2,4-triazol-4-yl]methyl]-2-thienyl]-1-isopropyl-pyridin-2-one |
| 124 | 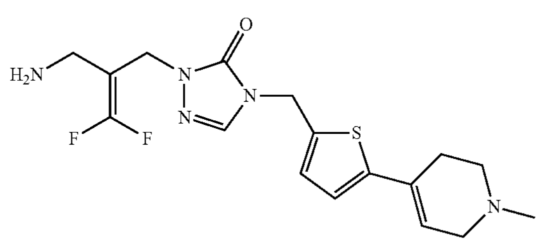 [SMILES: CN1CC=C(c2ccc(Cn3cnn(CC(CN)=C(F)F)c3=O)s2)CC1] | 2-[2-(aminomethyl)-3,3-difluoro-allyl]-4-[[5-(1-methyl-3,6-dihydro-2H-pyridin-4-yl)-2-thienyl]methyl]-1,2,4-triazol-3-one |
| 125 | 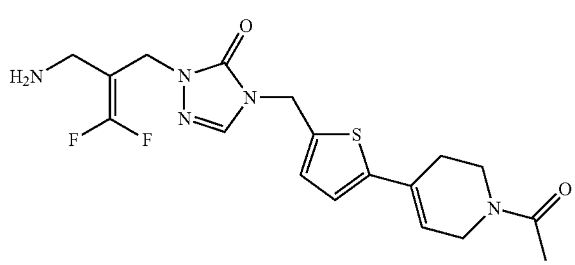 [SMILES: CC(=O)N1CC=C(c2ccc(Cn3cnn(CC(CN)=C(F)F)c3=O)s2)CC1] | 4-[[5-(1-acetyl-3,6-dihydro-2H-pyridin-4-yl)-2-thienyl]methyl]-2-[2-(aminomethyl)-3,3-difluoro-allyl]-1,2,4-triazol-3-one |

TABLE 1*-continued

| Ex No | Structure | Chemical Name |
|---|---|---|
| 126 | 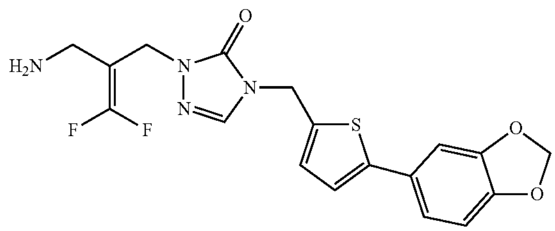 [SMILES: NCC(Cn1ncn(Cc2ccc(-c3ccc4c(c3)OCO4)s2)c1=O)=C(F)F] | 2-[2-(aminomethyl)-3,3-difluoro-allyl]-4-[[5-(1,3-benzodioxol-5-yl)-2-thienyl]methyl]-1,2,4-triazol-3-one |
| 127 | 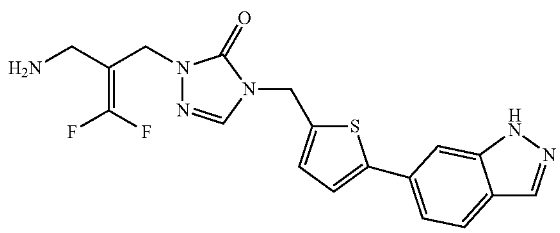 [SMILES: NCC(Cn1ncn(Cc2ccc(-c3ccc4cn[nH]c4c3)s2)c1=O)=C(F)F] | 2-[2-(aminomethyl)-3,3-difluoro-allyl]-4-[[5-(1H-indazol-6-yl)-2-thienyl]methyl]-1,2,4-triazol-3-one |
| 128 | 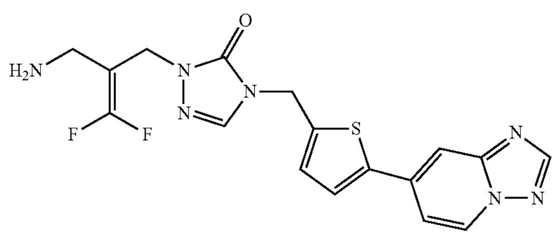 [SMILES: NCC(Cn1ncn(Cc2ccc(-c3ccn4ncnc4c3)s2)c1=O)=C(F)F] | 2-[2-(aminomethyl)-3,3-difluoro-allyl]-4-[[5-([1,2,4]triazolo[1,5-a]pyridin-7-yl)-2-thienyl]methyl]-1,2,4-triazol-3-one |
| 129 | 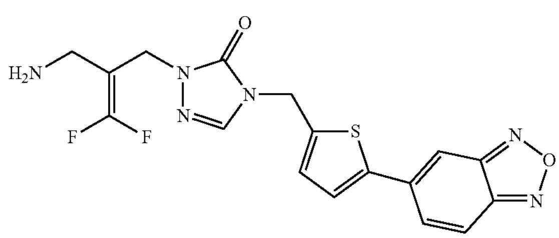 [SMILES: NCC(Cn1ncn(Cc2ccc(-c3ccc4nonc4c3)s2)c1=O)=C(F)F] | 2-[2-(aminomethyl)-3,3-difluoro-allyl]-4-[[5-(2,1,3-benzoxadiazol-5-yl)-2-thienyl]methyl]-1,2,4-triazol-3-one |
| 130 | 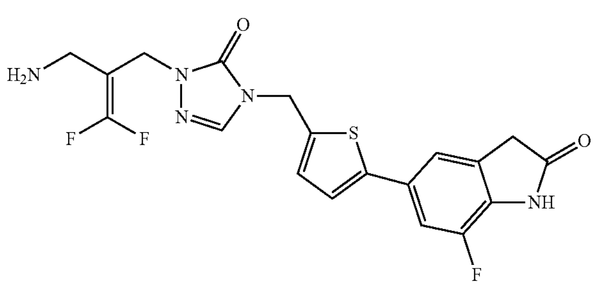 [SMILES: NCC(Cn1ncn(Cc2ccc(-c3cc(F)c4c(c3)CC(=O)N4)s2)c1=O)=C(F)F] | 5-[5-[[1-[2-(aminomethyl)-3,3-difluoro-allyl]-5-oxo-1,2,4-triazol-4-yl]methyl]-2-thienyl]-7-fluoro-indolin-2-one |
| 131 | 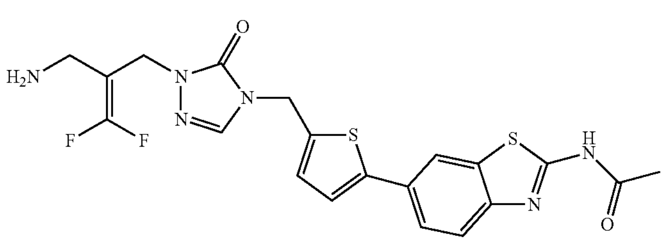 [SMILES: CC(=O)Nc1nc2ccc(-c3ccc(Cn4cnn(CC(CN)=C(F)F)c4=O)s3)cc2s1] | N-[6-[5-[[1-[2-(aminomethyl)-3,3-difluoro-allyl]-5-oxo-1,2,4-triazol-4-yl]methyl]-2-thienyl]-1,3-benzothiazol-2-yl]acetamide |

TABLE 1*-continued

| Ex No | Structure | Chemical Name |
|---|---|---|
| 132 | 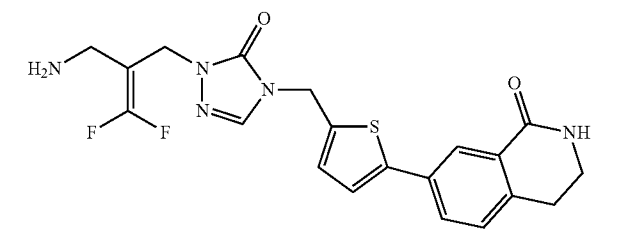 [SMILES: NCC(Cn1ncn(Cc2ccc(-c3ccc4c(c3)C(=O)NCC4)s2)c1=O)=C(F)F] | 7-[5-[[1-[2-(aminomethyl)-3,3-difluoro-allyl]-5-oxo-1,2,4-triazol-4-yl]methyl]-2-thienyl]-3,4-dihydro-2H-isoquinolin-1-one |
| 133 | 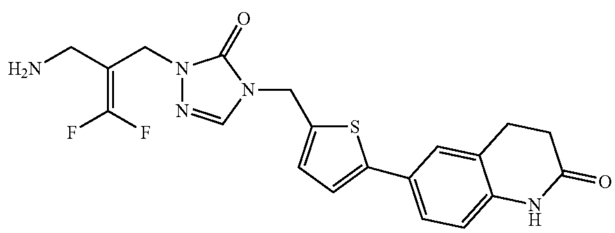 | 6-[5-[[1-[2-(aminomethyl)-3,3-difluoro-allyl]-5-oxo-1,2,4-triazol-4-yl]methyl]-2-thienyl]-3,4-dihydro-1H-quinolin-2-one |
| 134 | 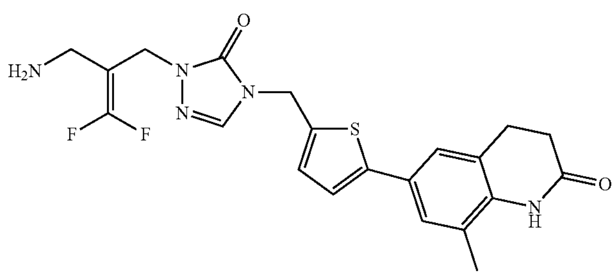 [SMILES: Cc1cc(-c2ccc(Cn3cnn(CC(CN)=C(F)F)c3=O)s2)cc2c1NC(=O)CC2] | 6-[5-[[1-[2-(aminomethyl)-3,3-difluoro-allyl]-5-oxo-1,2,4-triazol-4-yl]methyl]-2-thienyl]-8-methyl-3,4-dihydro-1H-quinolin-2-one |
| 135 | 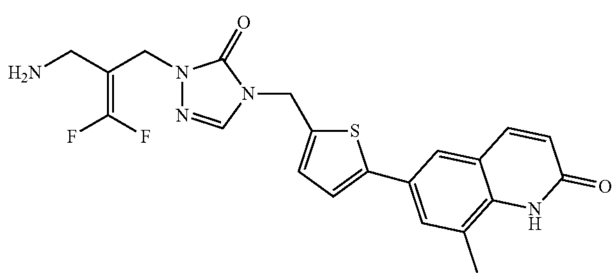 [SMILES: Cc1cc(-c2ccc(Cn3cnn(CC(CN)=C(F)F)c3=O)s2)cc2ccc(=O)[nH]c12] | 6-[5-[[1-[2-(aminomethyl)-3,3-difluoro-allyl]-5-oxo-1,2,4-triazol-4-yl]methyl]-2-thienyl]-8-methyl-1H-quinolin-2-one |
| 136 | 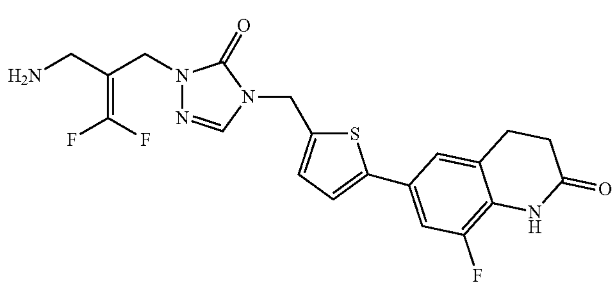 [SMILES: NCC(Cn1ncn(Cc2ccc(-c3cc(F)c4c(c3)CCC(=O)N4)s2)c1=O)=C(F)F] | 6-[5-[[1-[2-(aminomethyl)-3,3-difluoro-allyl]-5-oxo-1,2,4-triazol-4-yl]methyl]-2-thienyl]-8-fluoro-3,4-dihydro-1H-quinolin-2-one |
| 137 | 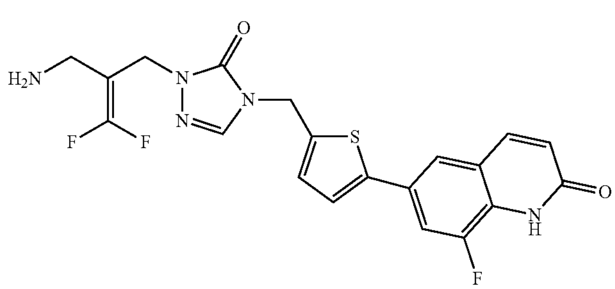 [SMILES: NCC(Cn1ncn(Cc2ccc(-c3cc(F)c4[nH]c(=O)ccc4c3)s2)c1=O)=C(F)F] | 6-[5-[[1-[2-(aminomethyl)-3,3-difluoro-allyl]-5-oxo-1,2,4-triazol-4-yl]methyl]-2-thienyl]-8-fluoro-1H-quinolin-2-one |

TABLE 1*-continued

| Ex No | Structure | Chemical Name |
|---|---|---|
| 138 | 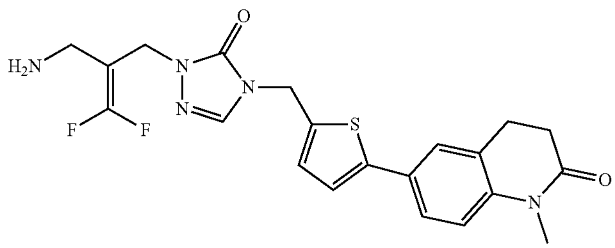 [SMILES: CN1C(=O)CCc2cc(-c3ccc(Cn4cnn(CC(CN)=C(F)F)c4=O)s3)ccc21] | 6-[5-[[1-[2-(aminomethyl)-3,3-difluoro-allyl]-5-oxo-1,2,4-triazol-4-yl]methyl]-2-thienyl]-1-methyl-3,4-dihydroquinolin-2-one |
| 139 | 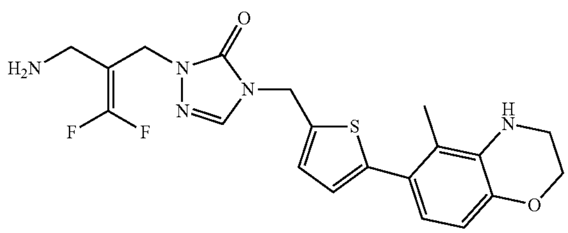 [SMILES: Cc1c(-c2ccc(Cn3cnn(CC(CN)=C(F)F)c3=O)s2)ccc2c1NCCO2] | 2-[2-(aminomethyl)-3,3-difluoro-allyl]-4-[[5-(5-methyl-3,4-dihydro-2H-1,4-benzoxazin-6-yl)-2-thienyl]methyl]-1,2,4-triazol-3-one |
| 140 | 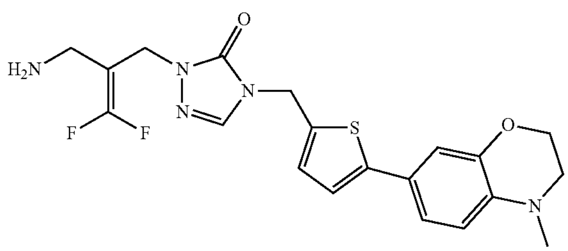 [SMILES: CN1CCOc2cc(-c3ccc(Cn4cnn(CC(CN)=C(F)F)c4=O)s3)ccc21] | 2-[2-(aminomethyl)-3,3-difluoro-allyl]-4-[[5-(4-methyl-2,3-dihydro-1,4-benzoxazin-7-yl)-2-thienyl]methyl]-1,2,4-triazol-3-one |
| 141 | 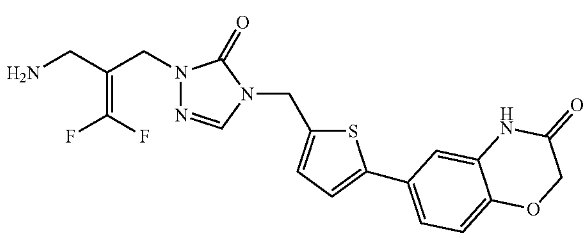 [SMILES: NCC(Cn1ncn(Cc2ccc(-c3ccc4c(c3)NC(=O)CO4)s2)c1=O)=C(F)F] | 6-[5-[[1-[2-(aminomethyl)-3,3-difluoro-allyl]-5-oxo-1,2,4-triazol-4-yl]methyl]-2-thienyl]-4H-1,4-benzoxazin-3-one |
| 142 | 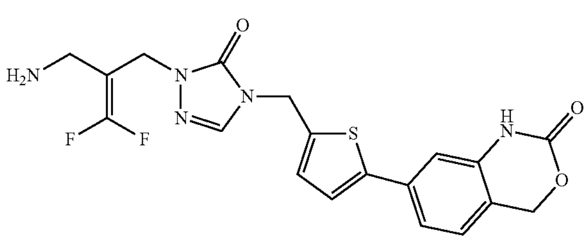 [SMILES: NCC(Cn1ncn(Cc2ccc(-c3ccc4c(c3)NC(=O)OC4)s2)c1=O)=C(F)F] | 7-[5-[[1-[2-(aminomethyl)-3,3-difluoro-allyl]-5-oxo-1,2,4-triazol-4-yl]methyl]-2-thienyl]-1,4-dihydro-3,1-benzoxazin-2-one |
| 143 | 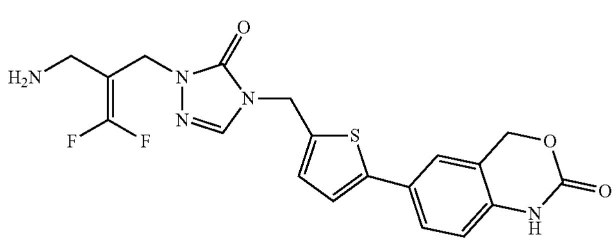 | 6-[5-[[1-[2-(aminomethyl)-3,3-difluoro-allyl]-5-oxo-1,2,4-triazol-4-yl]methyl]-2-thienyl]-1,4-dihydro-3,1-benzoxazin-2-one |

TABLE 1*-continued

| Ex No | Structure | Chemical Name |
|---|---|---|
| 144 | 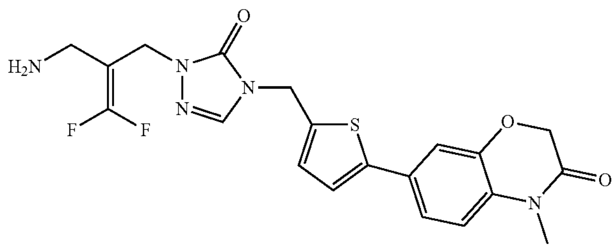 [SMILES: CN1C(=O)COc2cc(-c3ccc(Cn4cnn(CC(CN)=C(F)F)c4=O)s3)ccc21] | 7-[5-[[1-[2-(aminomethyl)-3,3-difluoro-allyl]-5-oxo-1,2,4-triazol-4-yl]methyl]-2-thienyl]-4-methyl-1,4-benzoxazin-3-one |
| 145 | 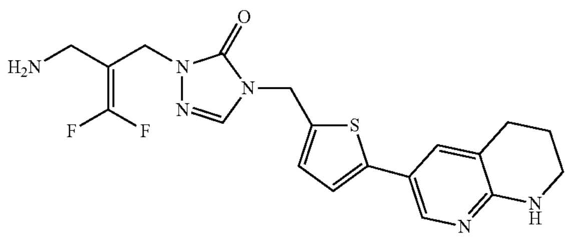 [SMILES: NCC(Cn1ncn(Cc2ccc(-c3cnc4c(c3)CCCN4)s2)c1=O)=C(F)F] | 2-[2-(aminomethyl)-3,3-difluoro-allyl]-4-[[5-(5,6,7,8-tetrahydro-1,8-naphthyridin-3-yl)-2-thienyl]methyl]-1,2,4-triazol-3-one |
| 146 | 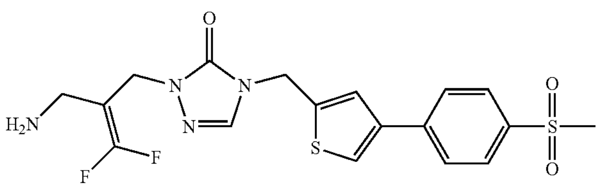 [SMILES: CS(=O)(=O)c1ccc(-c2csc(Cn3cnn(CC(CN)=C(F)F)c3=O)c2)cc1] | 2-[2-(aminomethyl)-3,3-difluoro-allyl]-4-[[4-(4-methylsulfonylphenyl)-2-thienyl]methyl]-1,2,4-triazol-3-one |
| 147 | 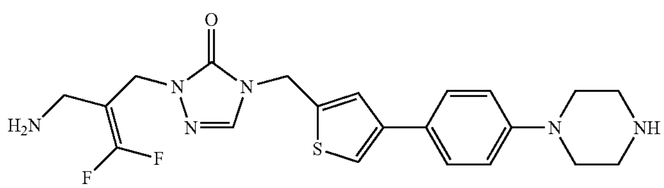 [SMILES: NCC(Cn1ncn(Cc2cc(-c3ccc(N4CCNCC4)cc3)cs2)c1=O)=C(F)F] | 2-[2-(aminomethyl)-3,3-difluoro-allyl]-4-[[4-(4-piperazin-1-ylphenyl)-2-thienyl]methyl]-1,2,4-triazol-3-one |
| 148 | 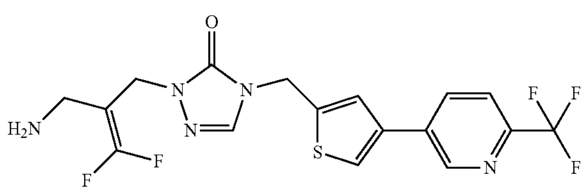 [SMILES: NCC(Cn1ncn(Cc2cc(-c3ccc(C(F)(F)F)nc3)cs2)c1=O)=C(F)F] | 2-[2-(aminomethyl)-3,3-difluoro-allyl]-4-[[4-[6-(trifluoromethyl)-3-pyridyl]-2-thienyl]methyl]-1,2,4-triazol-3-one |
| 149 | 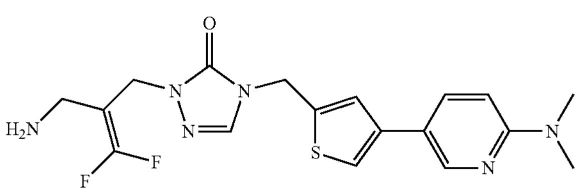 [SMILES: CN(C)c1ccc(-c2csc(Cn3cnn(CC(CN)=C(F)F)c3=O)c2)cn1] | 2-[2-(aminomethyl)-3,3-difluoro-allyl]-4-[[4-[6-(dimethylamino)-3-pyridyl]-2-thienyl]methyl]-1,2,4-triazol-3-one |
| 150 | 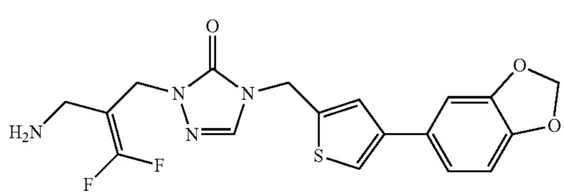 [SMILES: NCC(Cn1ncn(Cc2cc(-c3ccc4c(c3)OCO4)cs2)c1=O)=C(F)F] | 2-[2-(aminomethyl)-3,3-difluoro-allyl]-4-[[4-(1,3-benzodioxol-5-yl)-2-thienyl]methyl]-1,2,4-triazol-3-one |

TABLE 1*-continued

| Ex No | Structure | Chemical Name |
|---|---|---|
| 151 | 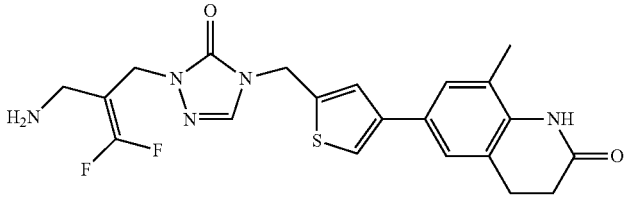 [SMILES: Cc1cc(-c2csc(Cn3cnn(CC(CN)=C(F)F)c3=O)c2)cc2c1NC(=O)CC2] | 6-[5-[[1-[2-(aminomethyl)-3,3-difluoro-allyl]-5-oxo-1,2,4-triazol-4-yl]methyl]-3-thienyl]-8-methyl-3,4-dihydro-1H-quinolin-2-one |
| 152 | 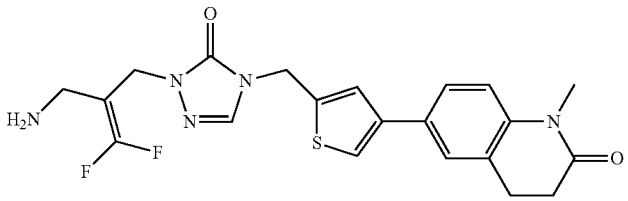 [SMILES: CN1C(=O)CCc2cc(-c3csc(Cn4cnn(CC(CN)=C(F)F)c4=O)c3)ccc21] | 6-[5-[[1-[2-(aminomethyl)-3,3-difluoro-allyl]-5-oxo-1,2,4-triazol-4-yl]methyl]-3-thienyl]-1-methyl-3,4-dihydroquinolin-2-one |
| 153 | 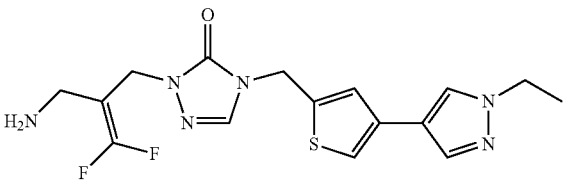 [SMILES: CCn1cc(-c2csc(Cn3cnn(CC(CN)=C(F)F)c3=O)c2)cn1] | 2-[2-(aminomethyl)-3,3-difluoro-allyl]-4-[[4-(1-ethylpyrazol-4-yl)-2-thienyl]methyl]-1,2,4-triazol-3-one |
| 154 | 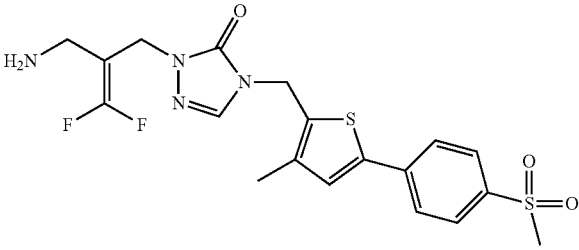 [SMILES: Cc1cc(-c2ccc(S(C)(=O)=O)cc2)sc1Cn1cnn(CC(CN)=C(F)F)c1=O] | 2-[2-(aminomethyl)-3,3-difluoro-allyl]-4-[[3-methyl-5-(4-methylsulfonylphenyl)-2-thienyl]methyl]-1,2,4-triazol-3-one |
| 155 | 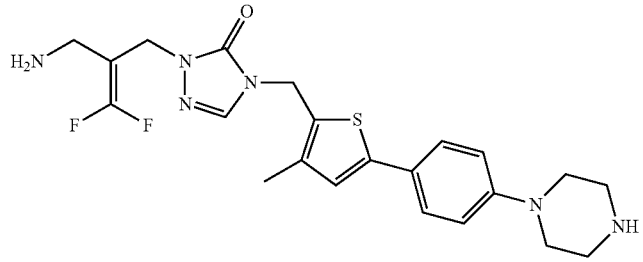 [SMILES: Cc1cc(-c2ccc(N3CCNCC3)cc2)sc1Cn1cnn(CC(CN)=C(F)F)c1=O] | 2-[2-(aminomethyl)-3,3-difluoro-allyl]-4-[[3-methyl-5-(4-piperazin-1-ylphenyl)-2-thienyl]methyl]-1,2,4-triazol-3-one |
| 156 | 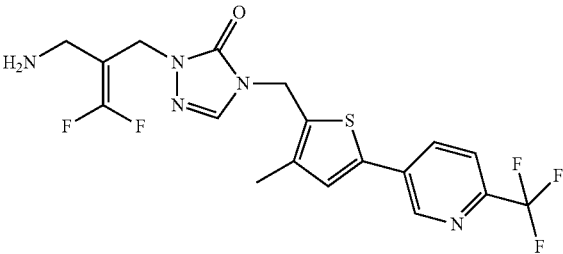 [SMILES: Cc1cc(-c2ccc(C(F)(F)F)nc2)sc1Cn1cnn(CC(CN)=C(F)F)c1=O] | 2-[2-(aminomethyl)-3,3-difluoro-allyl]-4-[[3-methyl-5-[6-(trifluoromethyl)-3-pyridyl]-2-thienyl]methyl]-1,2,4-triazol-3-one |

TABLE 1*-continued

| Ex No | Structure | Chemical Name |
|---|---|---|
| 157 | 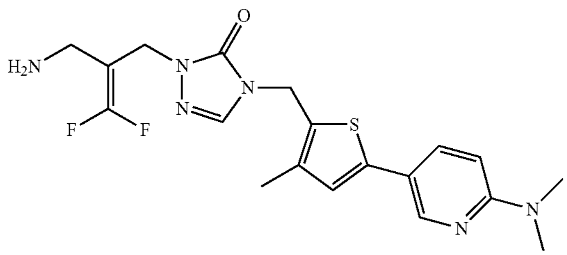 [SMILES: Cc1cc(-c2ccc(N(C)C)nc2)sc1Cn1cnn(CC(CN)=C(F)F)c1=O] | 2-[2-(aminomethyl)-3,3-difluoro-allyl]-4-[[5-[6-(dimethylamino)-3-pyridyl]-3-methyl-2-thienyl]methyl]-1,2,4-triazol-3-one |
| 158 | 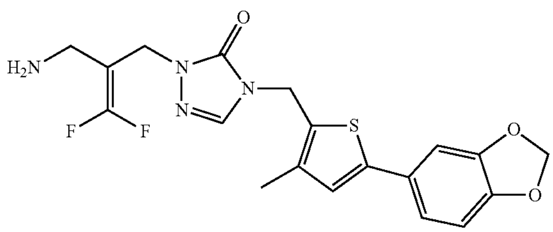 [SMILES: Cc1cc(-c2ccc3c(c2)OCO3)sc1Cn1cnn(CC(CN)=C(F)F)c1=O] | 2-[2-(aminomethyl)-3,3-difluoro-allyl]-4-[[5-(1,3-benzodioxol-5-yl)-3-methyl-2-thienyl]methyl]-1,2,4-triazol-3-one |
| 159 | 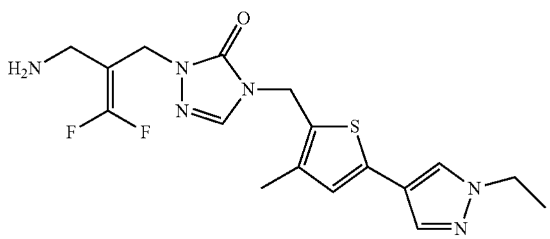 [SMILES: CCn1cc(-c2cc(C)c(Cn3cnn(CC(CN)=C(F)F)c3=O)s2)cn1] | 2-[2-(aminomethyl)-3,3-difluoro-allyl]-4-[[5-(1-ethylpyrazol-4-yl)-3-methyl-2-thienyl]methyl]-1,2,4-triazol-3-one |
| 160 | 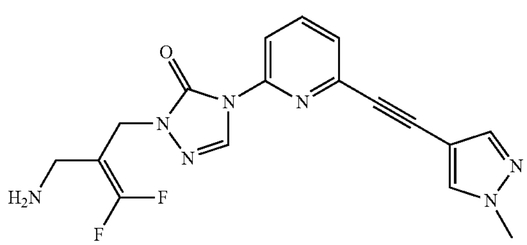 [SMILES: Cn1cc(C#Cc2cccc(-n3cnn(CC(CN)=C(F)F)c3=O)n2)cn1] | 2-[2-(aminomethyl)-3,3-difluoro-allyl]-4-[6-[2-(1-methylpyrazol-4-yl)ethynyl]-2-pyridyl]-1,2,4-triazol-3-one |
| 161 | 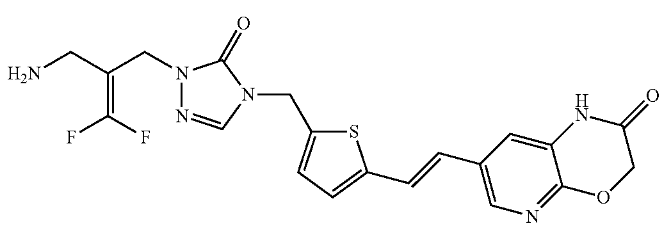 [SMILES: NCC(Cn1ncn(Cc2ccc(/C=C/c3cnc4c(c3)NC(=O)CO4)s2)c1=O)=C(F)F] | 7-[(E)-2-[5-[[1-[2-(aminomethyl)-3,3-difluoro-allyl]-5-oxo-1,2,4-triazol-4-yl]methyl]-2-thienyl]vinyl]-1H-pyrido[2,3-b][1,4]oxazin-2-one |
| 162 | 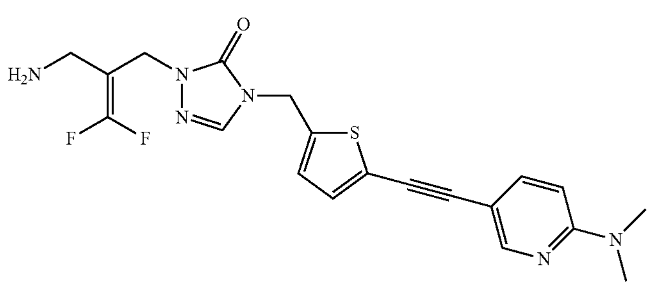 [SMILES: CN(C)c1ccc(C#Cc2ccc(Cn3cnn(CC(CN)=C(F)F)c3=O)s2)cn1] | 2-[2-(aminomethyl)-3,3-difluoro-allyl]-4-[[5-[2-[6-(dimethylamino)-3-pyridyl]ethynyl]-2-thienyl]methyl]-1,2,4-triazol-3-one |

TABLE 1*-continued

| Ex No | Structure | Chemical Name |
|---|---|---|
| 163 | 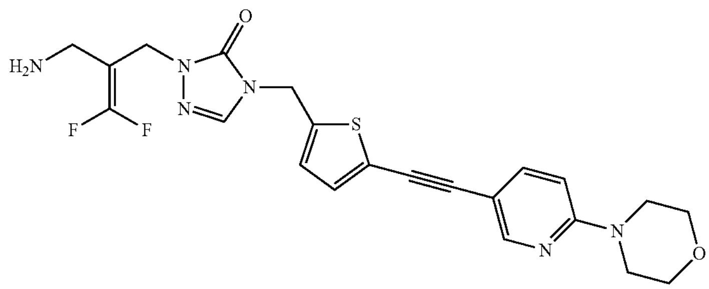 [SMILES: NCC(Cn1ncn(Cc2ccc(C#Cc3ccc(N4CCOCC4)nc3)s2)c1=O)=C(F)F] | 2-[2-(aminomethyl)-3,3-difluoro-allyl]-4-[[5-[2-(6-morpholino-3-pyridyl)ethynyl]-2-thienyl]methyl]-1,2,4-triazol-3-one |
| 164 | 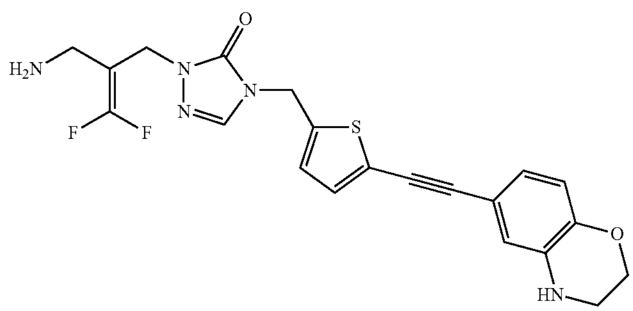 [SMILES: NCC(Cn1ncn(Cc2ccc(C#Cc3ccc4c(c3)NCCO4)s2)c1=O)=C(F)F] | 2-[2-(aminomethyl)-3,3-difluoro-allyl]-4-[[5-[2-(3,4-dihydro-2H-1,4-benzoxazin-6-yl)ethynyl]-2-thienyl]methyl]-1,2,4-triazol-3-one |
| 165 | 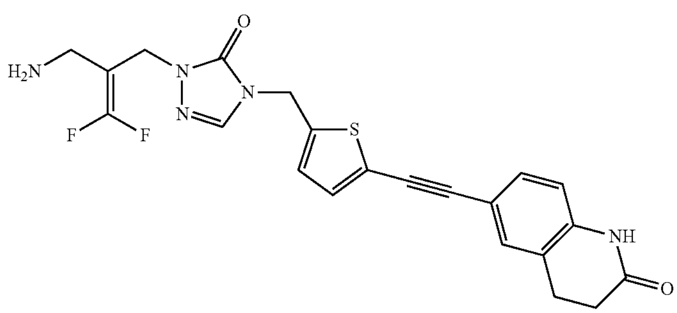 [SMILES: NCC(Cn1ncn(Cc2ccc(C#Cc3ccc4c(c3)CCC(=O)N4)s2)c1=O)=C(F)F] | 6-[2-[5-[[1-[2-(aminomethyl)-3,3-difluoro-allyl]-5-oxo-1,2,4-triazol-4-yl]methyl]-2-thienyl]ethynyl]-3,4-dihydro-1H-quinolin-2-one |
| 166 | 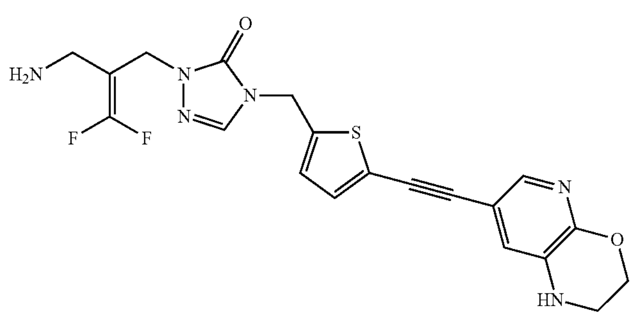 | 2-[2-(aminomethyl)-3,3-difluoro-allyl]-4-[[5-[2-(2,3-dihydro-1H-pyrido[2,3-b][1,4]oxazin-7-yl)ethynyl]-2-thienyl]methyl]-1,2,4-triazol-3-one |
| 167 | 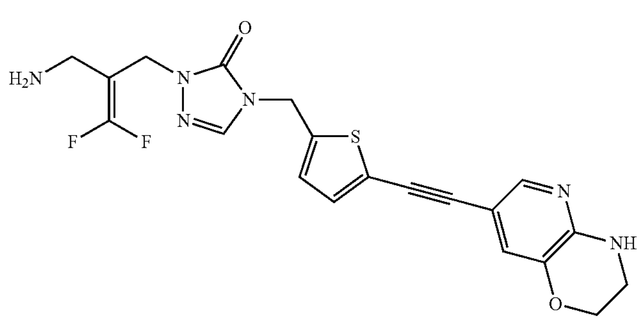 [SMILES: NCC(Cn1ncn(Cc2ccc(C#Cc3cnc4c(c3)OCCN4)s2)c1=O)=C(F)F] | 2-[2-(aminomethyl)-3,3-difluoro-allyl]-4-[[5-[2-(3,4-dihydro-2H-pyrido[3,2-b][1,4]oxazin-7-yl)ethynyl]-2-thienyl]methyl]-1,2,4-triazol-3-one |

TABLE 1*-continued

| Ex No | Structure | Chemical Name |
|---|---|---|
| 168 | 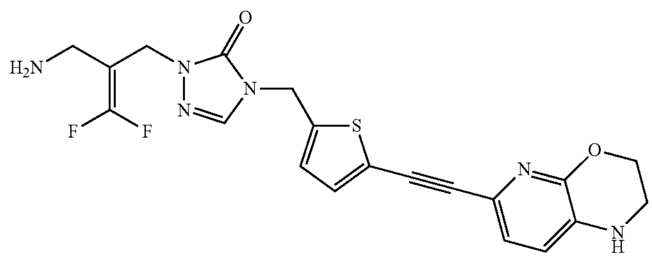 [SMILES: NCC(Cn1ncn(Cc2ccc(C#Cc3ccc4c(n3)OCCN4)s2)c1=O)=C(F)F] | 2-[2-(aminomethyl)-3,3-difluoro-allyl]-4-[[5-[2-(2,3-dihydro-1H-pyrido[2,3-b][1,4]oxazin-6-yl)ethynyl]-2-thienyl]methyl]-1,2,4-triazol-3-one |
| 169 | 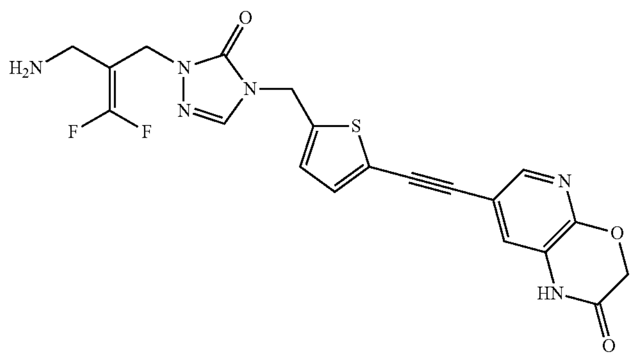 [SMILES: NCC(Cn1ncn(Cc2ccc(C#Cc3cnc4c(c3)NC(=O)CO4)s2)c1=O)=C(F)F] | 7-[2-[5-[[1-[2-(aminomethyl)-3,3-difluoro-allyl]-5-oxo-1,2,4-triazol-4-yl]methyl]-2-thienyl]ethynyl]-1H-pyrido[2,3-b][1,4]oxazin-2-one |
| 170 | 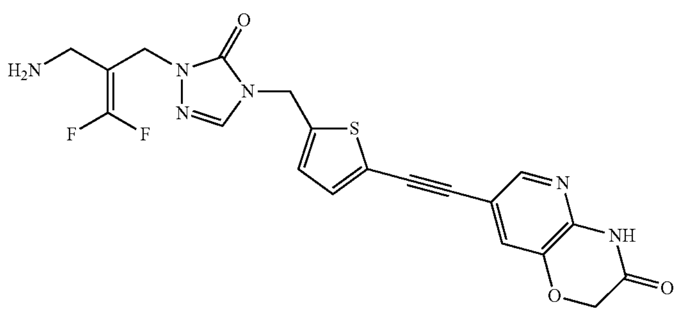 [SMILES: NCC(Cn1ncn(Cc2ccc(C#Cc3cnc4c(c3)OCC(=O)N4)s2)c1=O)=C(F)F] | 7-[2-[5-[[1-[2-(aminomethyl)-3,3-difluoro-allyl]-5-oxo-1,2,4-triazol-4-yl]methyl]-2-thienyl]ethynyl]-4H-pyrido[3,2-b][1,4]oxazin-3-one |
| 171 | 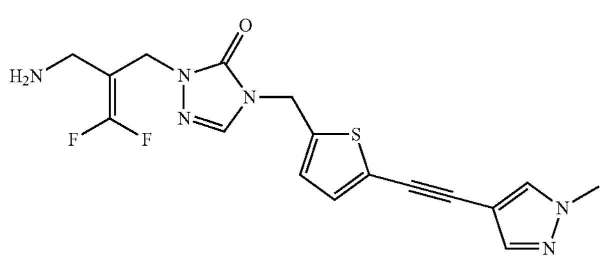 [SMILES: Cn1cc(C#Cc2ccc(Cn3cnn(CC(CN)=C(F)F)c3=O)s2)cn1] | 2-[2-(aminomethyl)-3,3-difluoro-allyl]-4-[[5-[2-(1-methylpyrazol-4-yl)ethynyl]-2-thienyl]methyl]-1,2,4-triazol-3-one |
| 172 | 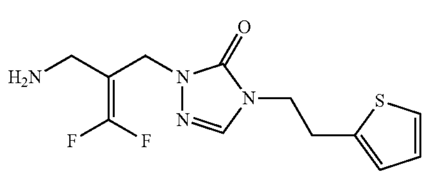 [SMILES: NCC(Cn1ncn(CCc2cccs2)c1=O)=C(F)F] | 2-[2-(aminomethyl)-3,3-difluoro-allyl]-4-[2-(2-thienyl)ethyl]-1,2,4-triazol-3-one |

TABLE 1*-continued

| Ex No | Structure | Chemical Name |
|---|---|---|
| 173 | 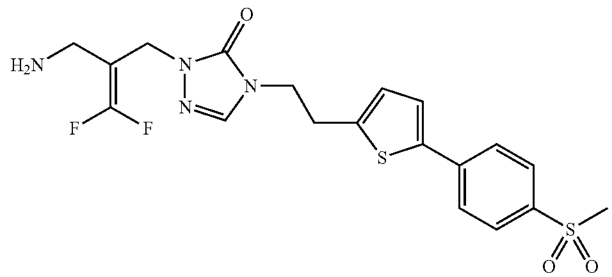 [SMILES: CS(=O)(=O)c1ccc(-c2ccc(CCn3cnn(CC(CN)=C(F)F)c3=O)s2)cc1] | 2-[2-(aminomethyl)-3,3-difluoro-allyl]-4-[2-[5-(4-methylsulfonylphenyl)-2-thienyl]ethyl]-1,2,4-triazol-3-one |
| 174 | 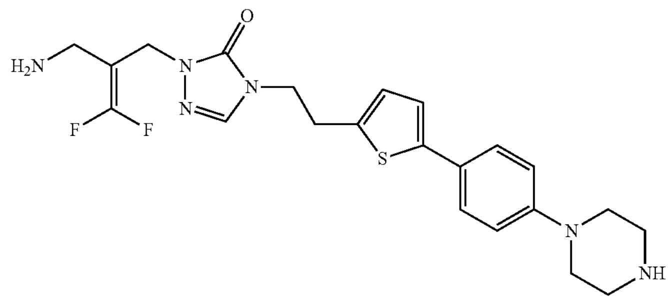 [SMILES: NCC(Cn1ncn(CCc2ccc(-c3ccc(N4CCNCC4)cc3)s2)c1=O)=C(F)F] | 2-[2-(aminomethyl)-3,3-difluoro-allyl]-4-[2-[5-(4-piperazin-1-ylphenyl)-2-thienyl]ethyl]-1,2,4-triazol-3-one |
| 175 | 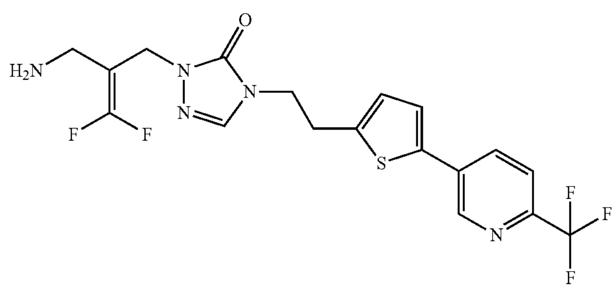 [SMILES: NCC(Cn1ncn(CCc2ccc(-c3ccc(C(F)(F)F)nc3)s2)c1=O)=C(F)F] | 2-[2-(aminomethyl)-3,3-difluoro-allyl]-4-[2-[5-[6-(trifluoromethyl)-3-pyridyl]-2-thienyl]ethyl]-1,2,4-triazol-3-one |
| 176 | 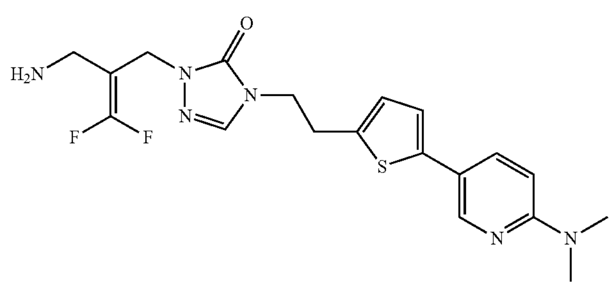 [SMILES: CN(C)c1ccc(-c2ccc(CCn3cnn(CC(CN)=C(F)F)c3=O)s2)cn1] | 2-[2-(aminomethyl)-3,3-difluoro-allyl]-4-[2-[5-[6-(dimethylamino)-3-pyridyl]-2-thienyl]ethyl]-1,2,4-triazol-3-one |
| 177 | 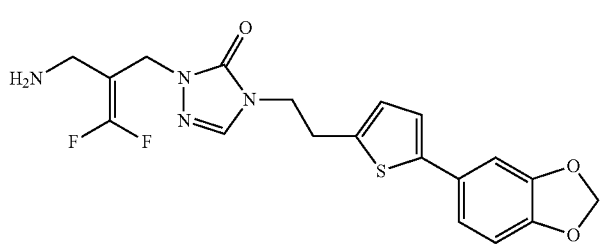 [SMILES: NCC(Cn1ncn(CCc2ccc(-c3ccc4c(c3)OCO4)s2)c1=O)=C(F)F] | 2-[2-(aminomethyl)-3,3-difluoro-allyl]-4-[2-[5-(1,3-benzodioxol-5-yl)-2-thienyl]ethyl]-1,2,4-triazol-3-one |

TABLE 1*-continued

| Ex No | Structure | Chemical Name |
|---|---|---|
| 178 | 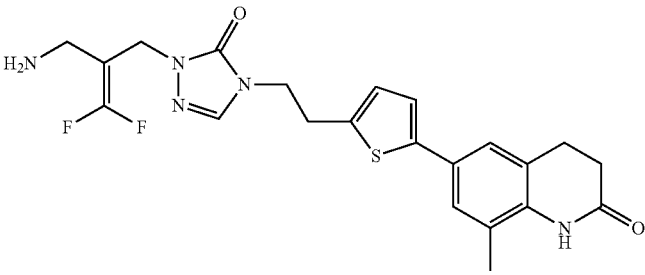 [SMILES: Cc1cc(-c2ccc(CCn3cnn(CC(CN)=C(F)F)c3=O)s2)cc2c1NC(=O)CC2] | 6-[5-[2-[1-[2-(aminomethyl)-3,3-difluoro-allyl]-5-oxo-1,2,4-triazol-4-yl]ethyl]-2-thienyl]-8-methyl-3,4-dihydro-1H-quinolin-2-one |
| 179 | 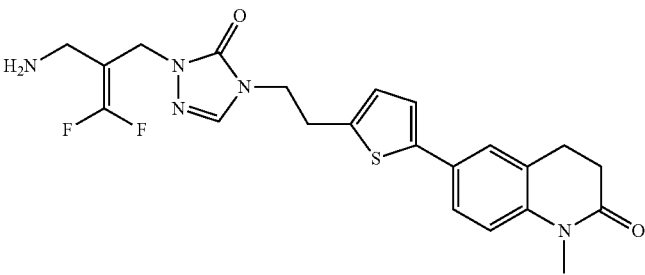 [SMILES: CN1C(=O)CCc2cc(-c3ccc(CCn4cnn(CC(CN)=C(F)F)c4=O)s3)ccc21] | 6-[5-[2-[1-[2-(aminomethyl)-3,3-difluoro-allyl]-5-oxo-1,2,4-triazol-4-yl]ethyl]-2-thienyl]-1-methyl-3,4-dihydroquinolin-2-one |
| 180 | 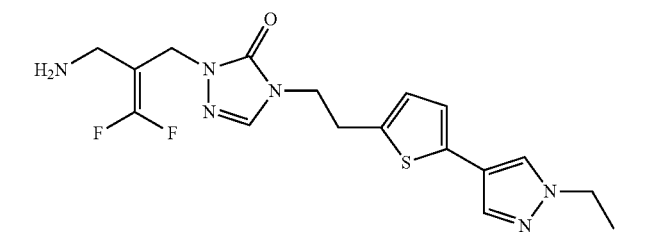 [SMILES: CCn1cc(-c2ccc(CCn3cnn(CC(CN)=C(F)F)c3=O)s2)cn1] | 2-[2-(aminomethyl)-3,3-difluoro-allyl]-4-[2-[5-(1-ethylpyrazol-4-yl)-2-thienyl]ethyl]-1,2,4-triazol-3-one |
| 181 | 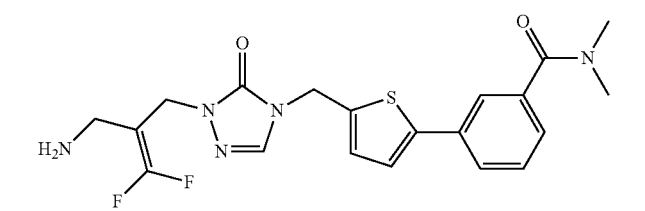 [SMILES: CN(C)C(=O)c1cccc(-c2ccc(Cn3cnn(CC(CN)=C(F)F)c3=O)s2)c1] | 3-[5-[[1-[2-(aminomethyl)-3,3-difluoro-allyl]-5-oxo-1,2,4-triazol-4-yl]methyl]-2-thienyl]-N,N-dimethyl-benzamide |
| 182 | 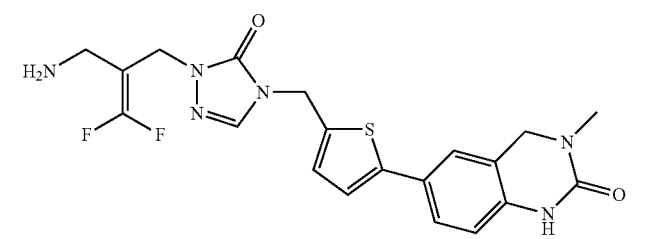 [SMILES: CN1Cc2cc(-c3ccc(Cn4cnn(CC(CN)=C(F)F)c4=O)s3)ccc2NC1=O] | 6-[5-[[1-[2-(aminomethyl)-3,3-difluoro-allyl]-5-oxo-1,2,4-triazol-4-yl]methyl]-2-thienyl]-3-methyl-1,4-dihydroquinazolin-2-one |
| 183 | 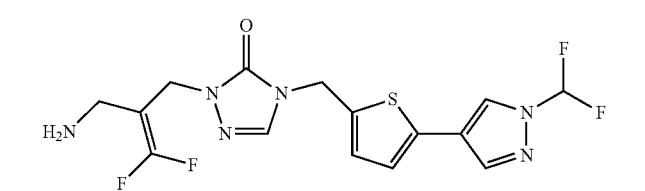 [SMILES: NCC(Cn1ncn(Cc2ccc(-c3cnn(C(F)F)c3)s2)c1=O)=C(F)F] | 2-[2-(aminomethyl)-3,3-difluoro-allyl]-4-[[5-[1-(difluoromethyl)pyrazol-4-yl]-2-thienyl]methyl]-1,2,4-triazol-3-one |

TABLE 1*-continued

| Ex No | Structure | Chemical Name |
|---|---|---|
| 184 | 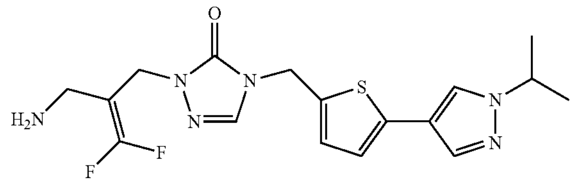 [SMILES: CC(C)n1cc(-c2ccc(Cn3cnn(CC(CN)=C(F)F)c3=O)s2)cn1] | 2-[2-(aminomethyl)-3,3-difluoro-allyl]-4-[[5-(1-isopropylpyrazol-4-yl)-2-thienyl]methyl]-1,2,4-triazol-3-one |
| 185 | 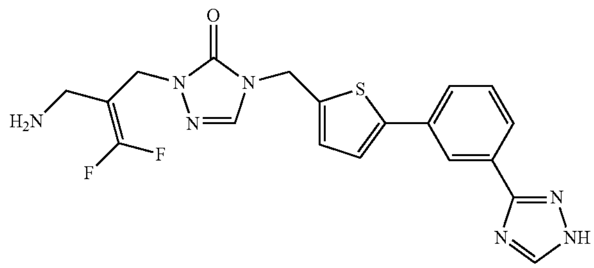 [SMILES: NCC(Cn1ncn(Cc2ccc(-c3cccc(-c4nc[nH]n4)c3)s2)c1=O)=C(F)F] | 2-[2-(aminomethyl)-3,3-difluoro-allyl]-4-[[5-[3-(1H-1,2,4-triazol-3-yl)phenyl]-2-thienyl]methyl]-1,2,4-triazol-3-one |
| 186 | 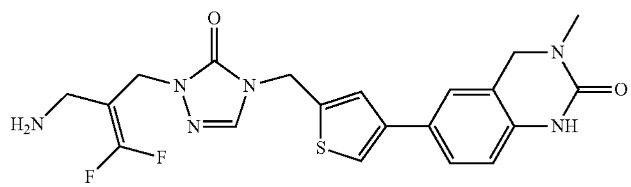 [SMILES: CN1Cc2cc(-c3csc(Cn4cnn(CC(CN)=C(F)F)c4=O)c3)ccc2NC1=O] | 6-[5-[[1-[2-(aminomethyl)-3,3-difluoro-allyl]-5-oxo-1,2,4-triazol-4-yl]methyl]-3-thienyl]-3-methyl-1,4-dihydroquinazolin-2-one |
| 187 | 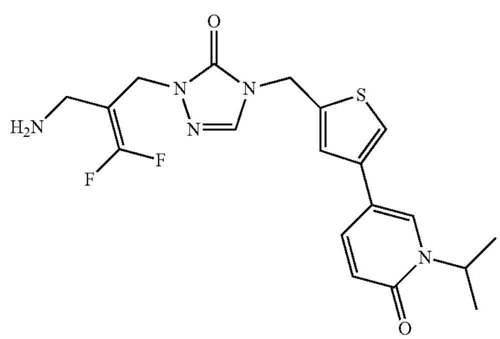 [SMILES: CC(C)n1cc(-c2csc(Cn3cnn(CC(CN)=C(F)F)c3=O)c2)ccc1=O] | 5-[5-[[1-[2-(aminomethyl)-3,3-difluoro-allyl]-5-oxo-1,2,4-triazol-4-yl]methyl]-3-thienyl]-1-isopropyl-pyridin-2-one |
| 188 | 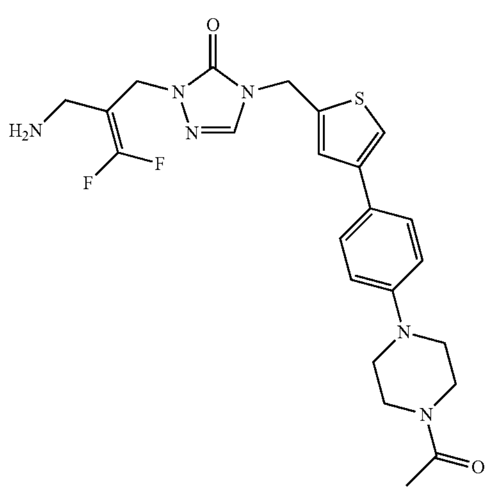 [SMILES: CC(=O)N1CCN(c2ccc(-c3csc(Cn4cnn(CC(CN)=C(F)F)c4=O)c3)cc2)CC1] | 4-[[4-[4-(4-acetylpiperazin-1-yl)phenyl]-2-thienyl]methyl]-2-[2-(aminomethyl)-3,3-difluoro-allyl]-1,2,4-triazol-3-one |

TABLE 1*-continued

| Ex No | Structure | Chemical Name |
|---|---|---|
| 189 | 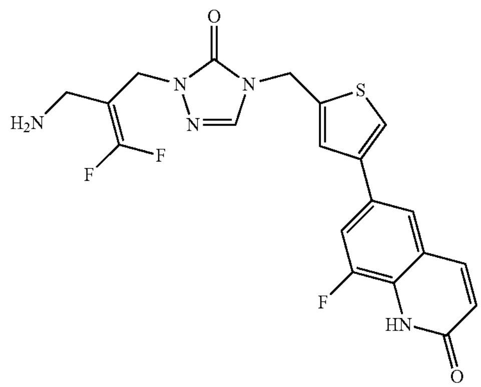 [SMILES: NCC(Cn1ncn(Cc2cc(-c3cc(F)c4[nH]c(=O)ccc4c3)cs2)c1=O)=C(F)F] | 6-[5-[[1-[2-(aminomethyl)-3,3-difluoro-allyl]-5-oxo-1,2,4-triazol-4-yl]methyl]-3-thienyl]-8-fluoro-1H-quinolin-2-one |
| 190 | 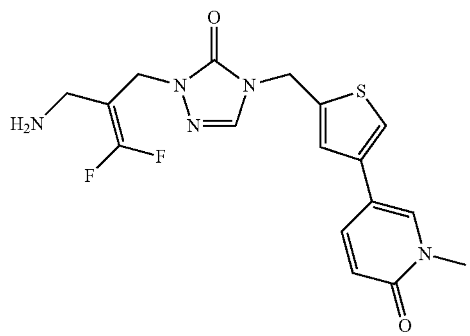 [SMILES: Cn1cc(-c2csc(Cn3cnn(CC(CN)=C(F)F)c3=O)c2)ccc1=O] | 5-[5-[[1-[2-(aminomethyl)-3,3-difluoro-allyl]-5-oxo-1,2,4-triazol-4-yl]methyl]-3-thienyl]-1-methyl-pyridin-2-one |
| 191 | 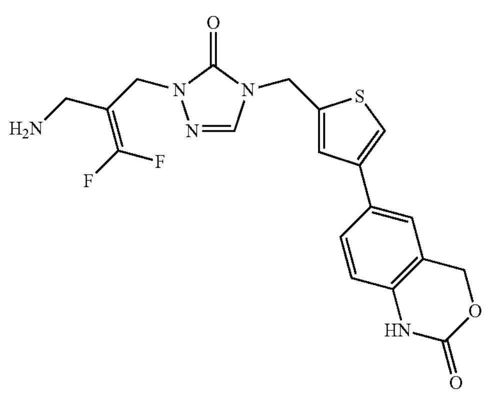 [SMILES: NCC(Cn1ncn(Cc2cc(-c3ccc4c(c3)COC(=O)N4)cs2)c1=O)=C(F)F] | 6-[5-[[1-[2-(aminomethyl)-3,3-difluoro-allyl]-5-oxo-1,2,4-triazol-4-yl]methyl]-3-thienyl]-1,4-dihydro-3,1-benzoxazin-2-one |
| 192 | 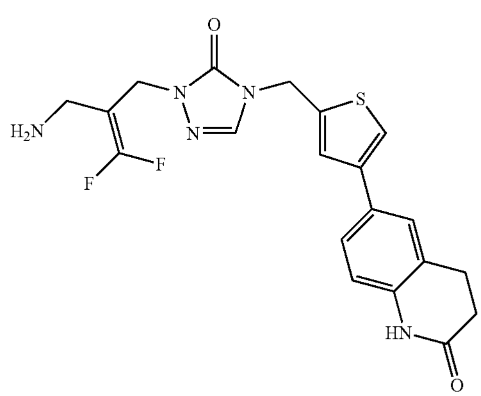 [SMILES: NCC(Cn1ncn(Cc2cc(-c3ccc4c(c3)CCC(=O)N4)cs2)c1=O)=C(F)F] | 6-[5-[[1-[2-(aminomethyl)-3,3-difluoro-allyl]-5-oxo-1,2,4-triazol-4-yl]methyl]-3-thienyl]-3,4-dihydro-1H-quinolin-2-one |

TABLE 1*-continued

| Ex No | Structure | Chemical Name |
|---|---|---|
| 193 | 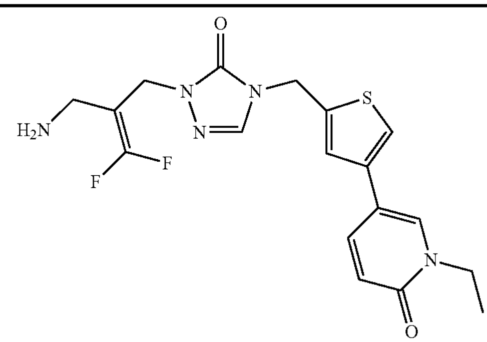 | 5-[5-[[1-[2-(aminomethyl)-3,3-difluoro-allyl]-5-oxo-1,2,4-triazol-4-yl]methyl]-3-thienyl]-1-ethyl-pyridin-2-one |
| 194 | 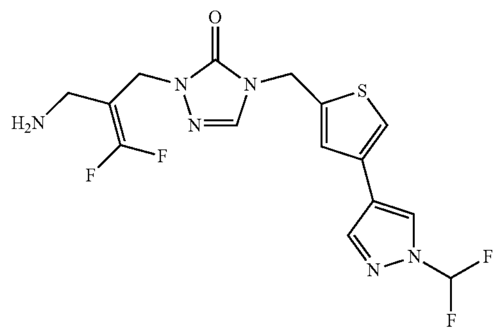 [SMILES: NCC(Cn1ncn(Cc2cc(-c3cnn(C(F)F)c3)cs2)c1=O)=C(F)F] | 2-[2-(aminomethyl)-3,3-difluoro-allyl]-4-[[4-[1-(difluoromethyl)pyrazol-4-yl]-2-thienyl]methyl]-1,2,4-triazol-3-one |
| 195 | 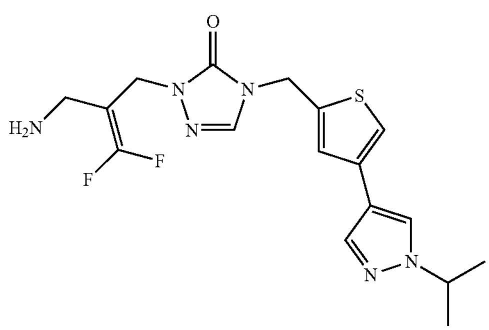 [SMILES: CC(C)n1cc(-c2csc(Cn3cnn(CC(CN)=C(F)F)c3=O)c2)cn1] | 2-[2-(aminomethyl)-3,3-difluoro-allyl]-4-[[4-(1-isopropylpyrazol-4-yl)-2-thienyl]methyl]-1,2,4-triazol-3-one |
| 196 | 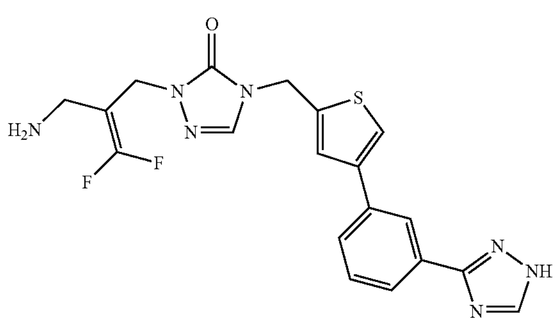 [SMILES: NCC(Cn1ncn(Cc2cc(-c3cccc(-c4nc[nH]n4)c3)cs2)c1=O)=C(F)F] | 2-[2-(aminomethyl)-3,3-difluoro-allyl]-4-[[4-[3-(1H-1,2,4-triazol-3-yl)phenyl]-2-thienyl]methyl]-1,2,4-triazol-3-one |
| 197 | 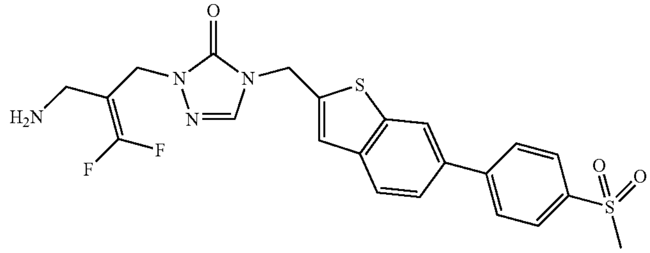 [SMILES: CS(=O)(=O)c1ccc(-c2ccc3cc(Cn4cnn(CC(CN)=C(F)F)c4=O)sc3c2)cc1] | 2-[2-(aminomethyl)-3,3-difluoro-allyl]-4-[[6-(4-methylsulfonylphenyl)benzothiophen-2-yl]methyl]-1,2,4-triazol-3-one |

TABLE 1*-continued

| Ex No | Structure | Chemical Name |
|---|---|---|
| 198 | 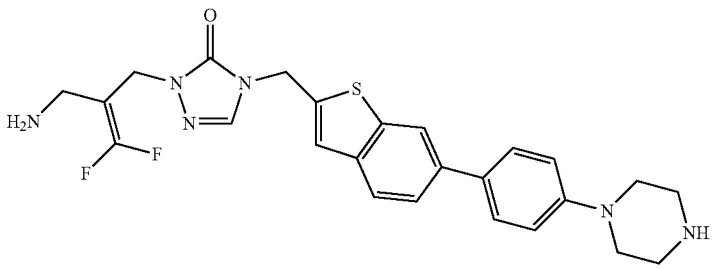 [SMILES: NCC(Cn1ncn(Cc2cc3ccc(-c4ccc(N5CCNCC5)cc4)cc3s2)c1=O)=C(F)F] | 2-[2-(aminomethyl)-3,3-difluoro-allyl]-4-[[6-(4-piperazin-1-ylphenyl)benzothiophen-2-yl]methyl]-1,2,4-triazol-3-one |
| 199 | 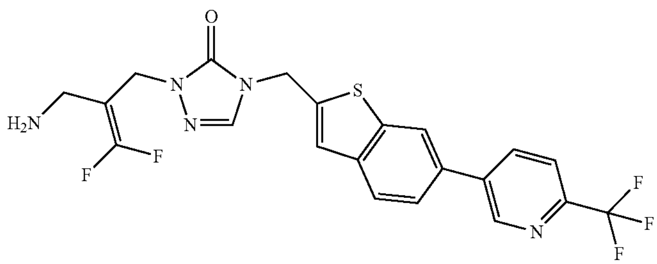 [SMILES: NCC(Cn1ncn(Cc2cc3ccc(-c4ccc(C(F)(F)F)nc4)cc3s2)c1=O)=C(F)F] | 2-[2-(aminomethyl)-3,3-difluoro-allyl]-4-[[6-[6-(trifluoromethyl)-3-pyridyl]benzothiophen-2-yl]methyl]-1,2,4-triazol-3-one |
| 200 | 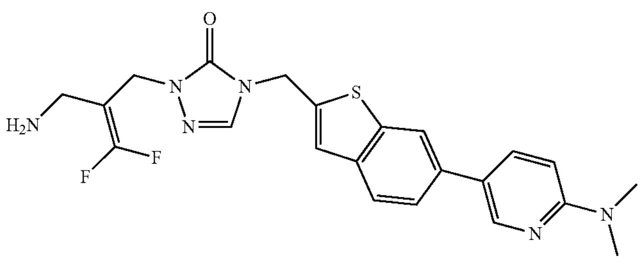 [SMILES: CN(C)c1ccc(-c2ccc3cc(Cn4cnn(CC(CN)=C(F)F)c4=O)sc3c2)cn1] | 2-[2-(aminomethyl)-3,3-difluoro-allyl]-4-[[6-[6-(dimethylamino)-3-pyridyl]benzothiophen-2-yl]methyl]-1,2,4-triazol-3-one |
| 201 | 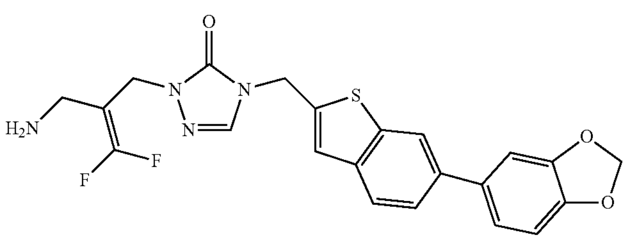 [SMILES: NCC(Cn1ncn(Cc2cc3ccc(-c4ccc5c(c4)OCO5)cc3s2)c1=O)=C(F)F] | 2-[2-(aminomethyl)-3,3-difluoro-allyl]-4-[[6-(1,3-benzodioxol-5-yl)benzothiophen-2-yl]methyl]-1,2,4-triazol-3-one |
| 202 | 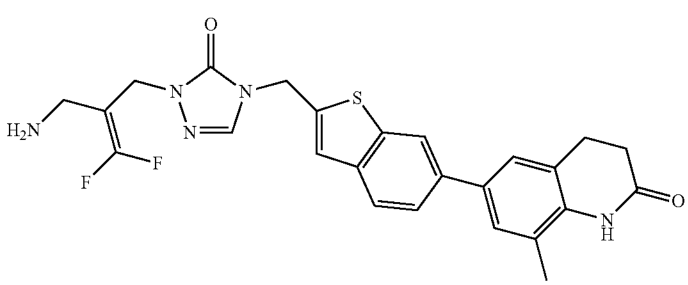 [SMILES: Cc1cc(-c2ccc3cc(Cn4cnn(CC(CN)=C(F)F)c4=O)sc3c2)cc2c1NC(=O)CC2] | 6-[2-[[1-[2-(aminomethyl)-3,3-difluoro-allyl]-5-oxo-1,2,4-triazol-4-yl]methyl]benzothiophen-6-yl]-8-methyl-3,4-dihydro-1H-quinolin-2-one |
| 203 | 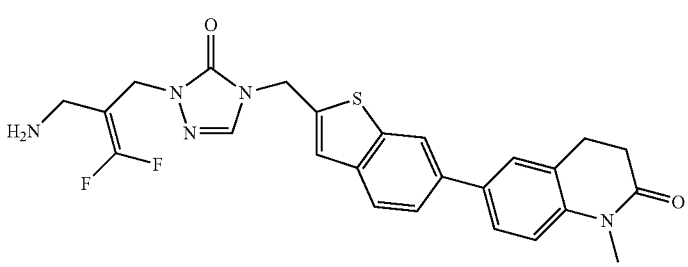 [SMILES: CN1C(=O)CCc2cc(-c3ccc4cc(Cn5cnn(CC(CN)=C(F)F)c5=O)sc4c3)ccc21] | 6-[2-[[1-[2-(aminomethyl)-3,3-difluoro-allyl]-5-oxo-1,2,4-triazol-4-yl]methyl]benzothiophen-6-yl]-1-methyl-3,4-dihydroquinolin-2-one |

TABLE 1*-continued

| Ex No | Structure | Chemical Name |
|---|---|---|
| 204 | 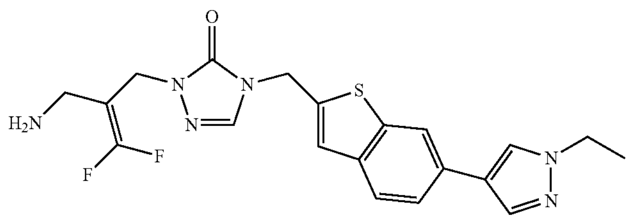 [SMILES: CCn1cc(-c2ccc3cc(Cn4cnn(CC(CN)=C(F)F)c4=O)sc3c2)cn1] | 2-[2-(aminomethyl)-3,3-difluoro-allyl]-4-[[6-(1-ethylpyrazol-4-yl)benzothiophen-2-yl]methyl]-1,2,4-triazol-3-one |
| 205 | 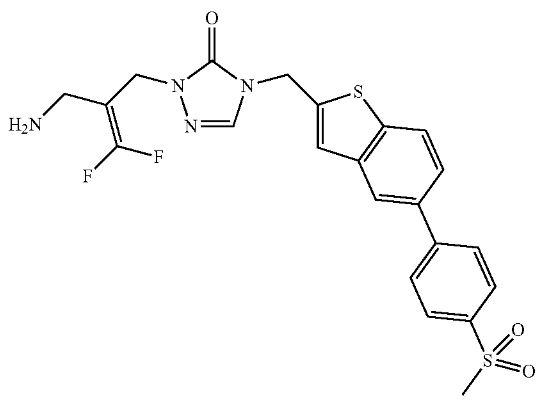 [SMILES: CS(=O)(=O)c1ccc(-c2ccc3sc(Cn4cnn(CC(CN)=C(F)F)c4=O)cc3c2)cc1] | 2-[2-(aminomethyl)-3,3-difluoro-allyl]-4-[[5-(4-methylsulfonylphenyl)benzothiophen-2-yl]methyl]-1,2,4-triazol-3-one |
| 206 | 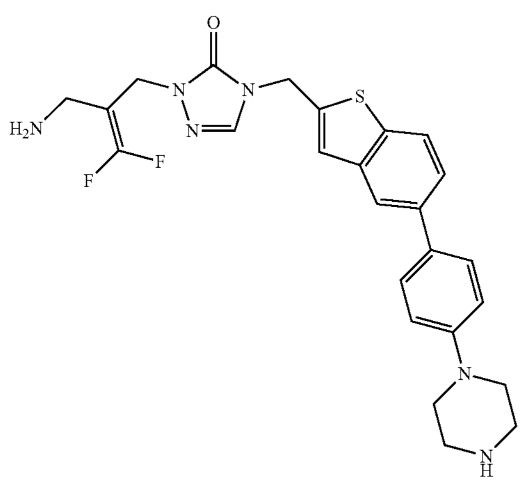 [SMILES: NCC(Cn1ncn(Cc2cc3cc(-c4ccc(N5CCNCC5)cc4)ccc3s2)c1=O)=C(F)F] | 2-[2-(aminomethyl)-3,3-difluoro-allyl]-4-[[5-(4-piperazin-1-ylphenyl)benzothiophen-2-yl]methyl]-1,2,4-triazol-3-one |
| 207 | 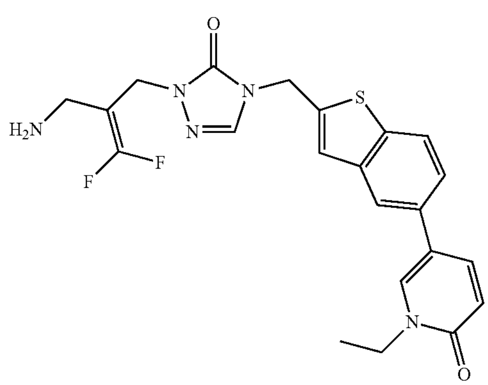 [SMILES: CCn1cc(-c2ccc3sc(Cn4cnn(CC(CN)=C(F)F)c4=O)cc3c2)ccc1=O] | 5-[2-[[1-[2-(aminomethyl)-3,3-difluoro-allyl]-5-oxo-1,2,4-triazol-4-yl]methyl]benzothiophen-5-yl]-1-ethyl-pyridin-2-one |

TABLE 1*-continued

| Ex No | Structure | Chemical Name |
|---|---|---|
| 208 | 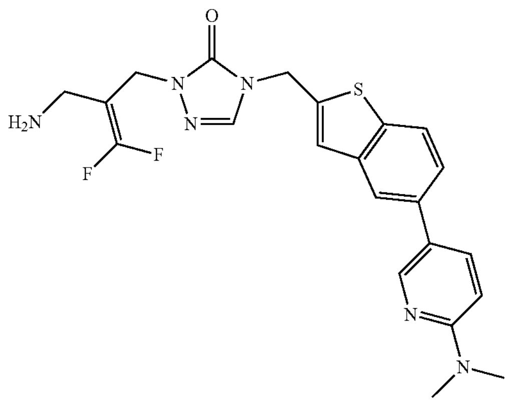 [SMILES: CN(C)c1ccc(-c2ccc3sc(Cn4cnn(CC(CN)=C(F)F)c4=O)cc3c2)cn1] | 2-[2-(aminomethyl)-3,3-difluoro-allyl]-4-[[5-[6-(dimethylamino)-3-pyridyl]benzothiophen-2-yl]methyl]-1,2,4-triazol-3-one |
| 209 | 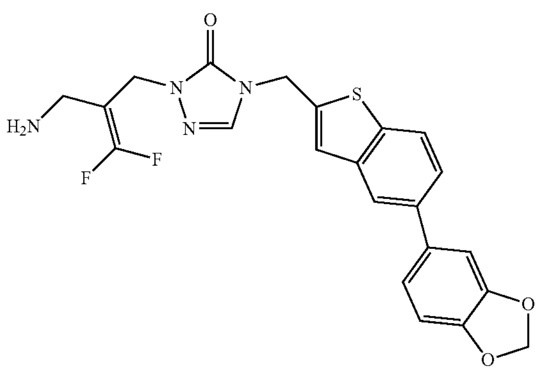 [SMILES: NCC(Cn1ncn(Cc2cc3cc(-c4ccc5c(c4)OCO5)ccc3s2)c1=O)=C(F)F] | 2-[2-(aminomethyl)-3,3-difluoro-allyl]-4-[[5-(1,3-benzodioxol-5-yl)benzothiophen-2-yl]methyl]-1,2,4-triazol-3-one |
| 210 | 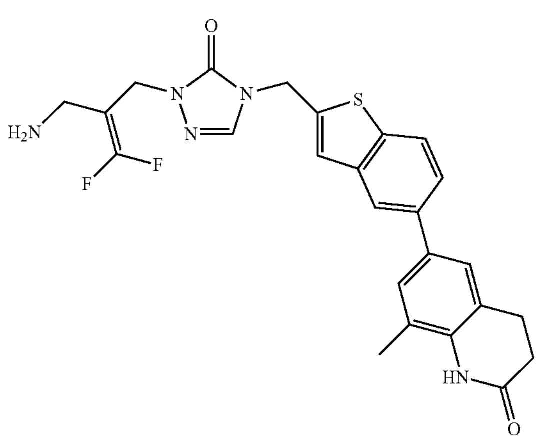 [SMILES: Cc1cc(-c2ccc3sc(Cn4cnn(CC(CN)=C(F)F)c4=O)cc3c2)cc2c1NC(=O)CC2] | 6-[2-[[1-[2-(aminomethyl)-3,3-difluoro-allyl]-5-oxo-1,2,4-triazol-4-yl]methyl]benzothiophen-5-yl]-8-methyl-3,4-dihydro-1H-quinolin-2-one |

TABLE 1*-continued

| Ex No | Structure | Chemical Name |
|---|---|---|
| 211 | 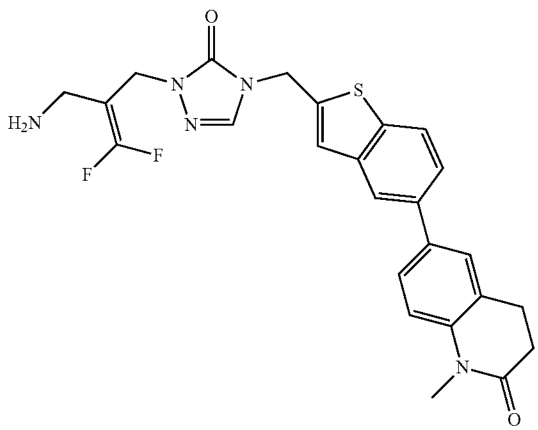 [SMILES: CN1C(=O)CCc2cc(-c3ccc4sc(Cn5cnn(CC(CN)=C(F)F)c5=O)cc4c3)ccc21] | 6-[2-[[1-[2-(aminomethyl)-3,3-difluoro-allyl]-5-oxo-1,2,4-triazol-4-yl]methyl]benzothiophen-5-yl]-1-methyl-3,4-dihydroquinolin-2-one |
| 212 | 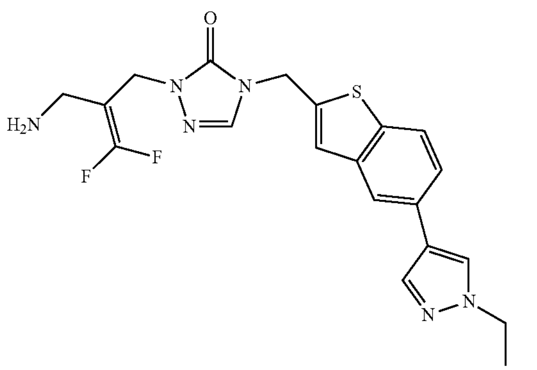 [SMILES: CCn1cc(-c2ccc3sc(Cn4cnn(CC(CN)=C(F)F)c4=O)cc3c2)cn1] | 2-[2-(aminomethyl)-3,3-difluoro-allyl]-4-[[5-(1-ethylpyrazol-4-yl)benzothiophen-2-yl]methyl]-1,2,4-triazol-3-one |
| 213 | 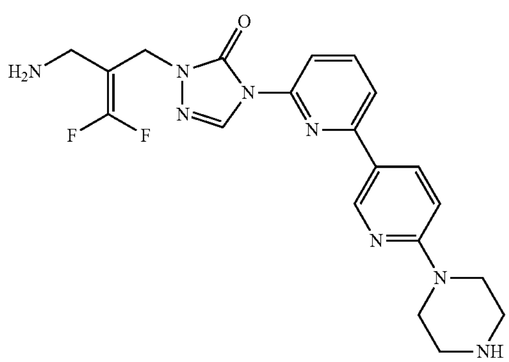 [SMILES: NCC(Cn1ncn(-c2cccc(-c3ccc(N4CCNCC4)nc3)n2)c1=O)=C(F)F] | 2-[2-(aminomethyl)-3,3-difluoro-allyl]-4-[6-(6-piperazin-1-yl-3-pyridyl)-2-pyridyl]-1,2,4-triazol-3-one |
| 214 | 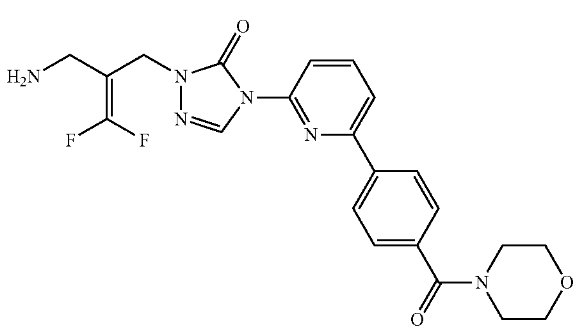 [SMILES: NCC(Cn1ncn(-c2cccc(-c3ccc(C(=O)N4CCOCC4)cc3)n2)c1=O)=C(F)F] | 2-[2-(aminomethyl)-3,3-difluoro-allyl]-4-[6-[4-(morpholine-4-carbonyl)phenyl]-2-pyridyl]-1,2,4-triazol-3-one |

TABLE 1*-continued

| Ex No | Structure | Chemical Name |
|---|---|---|
| 215 | 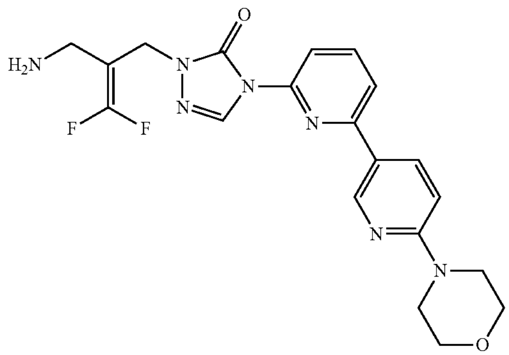 [SMILES: NCC(Cn1ncn(-c2cccc(-c3ccc(N4CCOCC4)nc3)n2)c1=O)=C(F)F] | 2-[2-(aminomethyl)-3,3-difluoro-allyl]-4-[6-(6-morpholino-3-pyridyl)-2-pyridyl]-1,2,4-triazol-3-one |
| 216 | 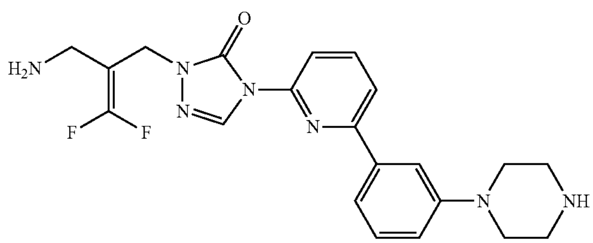 [SMILES: NCC(Cn1ncn(-c2cccc(-c3cccc(N4CCNCC4)c3)n2)c1=O)=C(F)F] | 2-[2-(aminomethyl)-3,3-difluoro-allyl]-4-[6-(3-piperazin-1-ylphenyl)-2-pyridyl]-1,2,4-triazol-3-one |
| 217 | 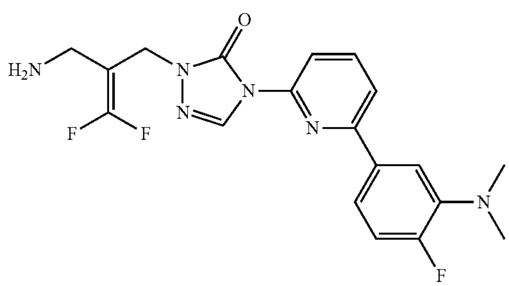 [SMILES: CN(C)c1cc(-c2cccc(-n3cnn(CC(CN)=C(F)F)c3=O)n2)ccc1F] | 2-[2-(aminomethyl)-3,3-difluoro-allyl]-4-[6-[3-(dimethylamino)-4-fluoro-phenyl]-2-pyridyl]-1,2,4-triazol-3-one |
| 218 | 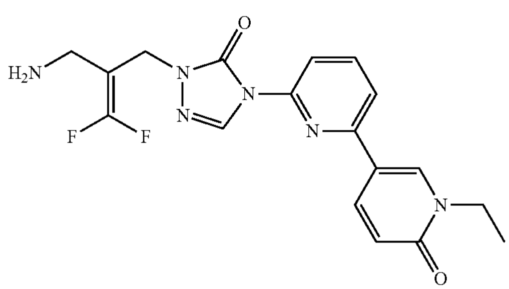 [SMILES: CCn1cc(-c2cccc(-n3cnn(CC(CN)=C(F)F)c3=O)n2)ccc1=O] | 5-[6-[1-[2-(aminomethyl)-3,3-difluoro-allyl]-5-oxo-1,2,4-triazol-4-yl]-2-pyridyl]-1-ethyl-pyridin-2-one |
| 219 | 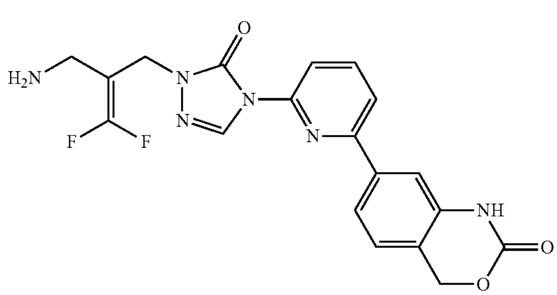 [SMILES: NCC(Cn1ncn(-c2cccc(-c3ccc4c(c3)NC(=O)OC4)n2)c1=O)=C(F)F] | 7-[6-[1-[2-(aminomethyl)-3,3-difluoro-allyl]-5-oxo-1,2,4-triazol-4-yl]-2-pyridyl]-1,4-dihydro-3,1-benzoxazin-2-one |

TABLE 1*-continued

| Ex No | Structure | Chemical Name |
|---|---|---|
| 220 | 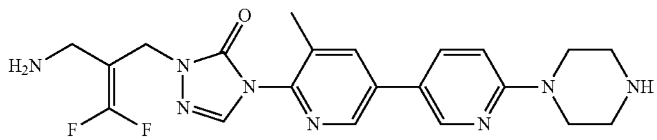 | 2-[2-(aminomethyl)-3,3-difluoro-allyl]-4-[3-methyl-5-(6-piperazin-1-yl-3-pyridyl)-2-pyridyl]-1,2,4-triazol-3-one |
| 221 | 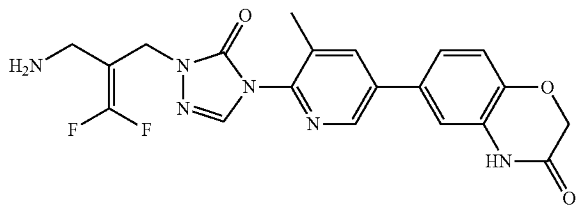 [SMILES: Cc1cc(-c2ccc3c(c2)NC(=O)CO3)cnc1-n1cnn(CC(CN)=C(F)F)c1=O] | 6-[6-[1-[2-(aminomethyl)-3,3-difluoro-allyl]-5-oxo-1,2,4-triazol-4-yl]-5-methyl-3-pyridyl]-4H-1,4-benzoxazin-3-one |
| 222 | 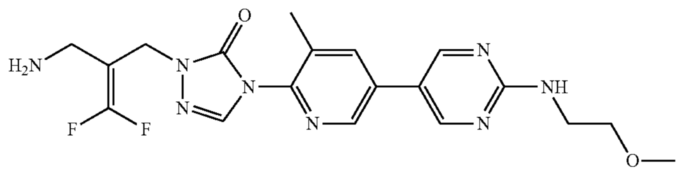 [SMILES: COCCNc1ncc(-c2cnc(-n3cnn(CC(CN)=C(F)F)c3=O)c(C)c2)cn1] | 2-[2-(aminomethyl)-3,3-difluoro-allyl]-4-[5-[2-(2-methoxyethylamino)pyrimidin-5-yl]-3-methyl-2-pyridyl]-1,2,4-triazol-3-one |
| 223 | 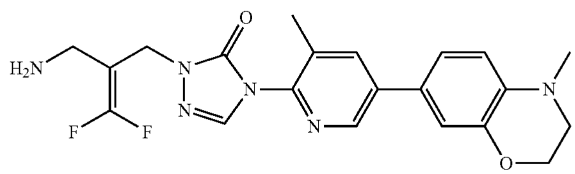 [SMILES: Cc1cc(-c2ccc3c(c2)OCCN3C)cnc1-n1cnn(CC(CN)=C(F)F)c1=O] | 2-[2-(aminomethyl)-3,3-difluoro-allyl]-4-[3-methyl-5-(4-methyl-2,3-dihydro-1,4-benzoxazin-7-yl)-2-pyridyl]-1,2,4-triazol-3-one |
| 224 | 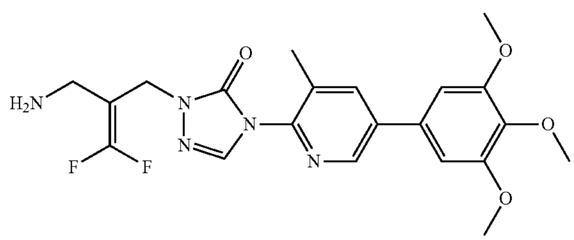 [SMILES: COc1cc(-c2cnc(-n3cnn(CC(CN)=C(F)F)c3=O)c(C)c2)cc(OC)c1OC] | 2-[2-(aminomethyl)-3,3-difluoro-allyl]-4-[3-methyl-5-(3,4,5-trimethoxyphenyl)-2-pyridyl]-1,2,4-triazol-3-one |
| 225 | 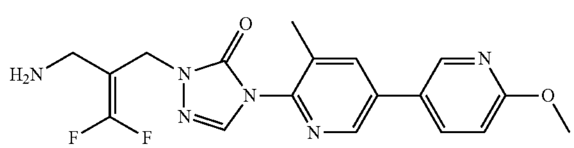 [SMILES: COc1ccc(-c2cnc(-n3cnn(CC(CN)=C(F)F)c3=O)c(C)c2)cn1] | 2-[2-(aminomethyl)-3,3-difluoro-allyl]-4-[5-(6-methoxy-3-pyridyl)-3-methyl-2-pyridyl]-1,2,4-triazol-3-one |
| 226 | 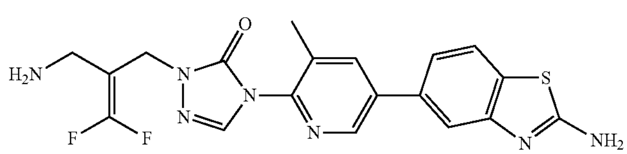 [SMILES: Cc1cc(-c2ccc3sc(N)nc3c2)cnc1-n1cnn(CC(CN)=C(F)F)c1=O] | 4-[5-(2-amino-1,3-benzothiazol-5-yl)-3-methyl-2-pyridyl]-2-[2-(aminomethyl)-3,3-difluoro-allyl]-1,2,4-triazol-3-one |
| 227 | 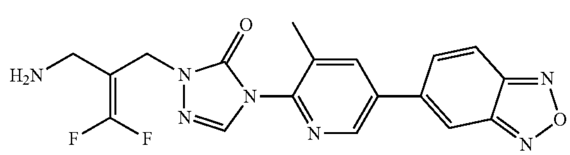 [SMILES: Cc1cc(-c2ccc3nonc3c2)cnc1-n1cnn(CC(CN)=C(F)F)c1=O] | 2-[2-(aminomethyl)-3,3-difluoro-allyl]-4-[5-(2,1,3-benzoxadiazol-5-yl)-3-methyl-2-pyridyl]-1,2,4-triazol-3-one |
| 228 | 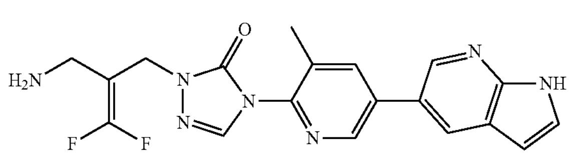 [SMILES: Cc1cc(-c2cnc3[nH]ccc3c2)cnc1-n1cnn(CC(CN)=C(F)F)c1=O] | 2-[2-(aminomethyl)-3,3-difluoro-allyl]-4-[3-methyl-5-(1H-pyrrolo[2,3-b]pyridin-5-yl)-2-pyridyl]-1,2,4-triazol-3-one |

TABLE 1*-continued

| Ex No | Structure | Chemical Name |
|---|---|---|
| 229 | 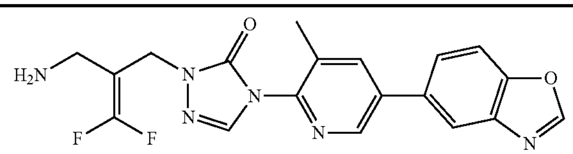 | 2-[2-(aminomethyl)-3,3-difluoro-allyl]-4-[5-(1,3-benzoxazol-5-yl)-3-methyl-2-pyridyl]-1,2,4-triazol-3-one |
| 230 | 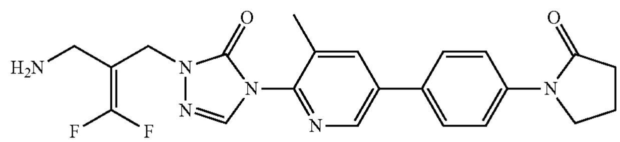 [SMILES: Cc1cc(-c2ccc(N3CCCC3=O)cc2)cnc1-n1cnn(CC(CN)=C(F)F)c1=O] | 2-[2-(aminomethyl)-3,3-difluoro-allyl]-4-[3-methyl-5-[4-(2-oxopyrrolidin-1-yl)phenyl]-2-pyridyl]-1,2,4-triazol-3-one |
| 231 | 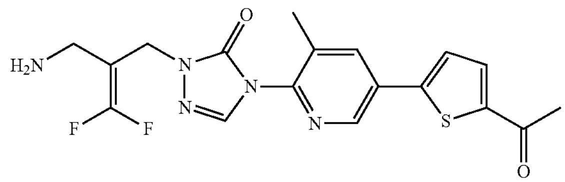 [SMILES: CC(=O)c1ccc(-c2cnc(-n3cnn(CC(CN)=C(F)F)c3=O)c(C)c2)s1] | 4-[5-(5-acetyl-2-thienyl)-3-methyl-2-pyridyl]-2-[2-(aminomethyl)-3,3-difluoro-allyl]-1,2,4-triazol-3-one |
| 232 | 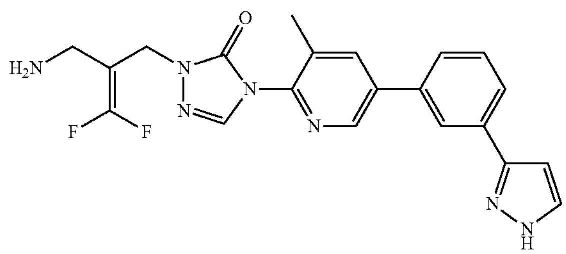 [SMILES: Cc1cc(-c2cccc(-c3cc[nH]n3)c2)cnc1-n1cnn(CC(CN)=C(F)F)c1=O] | 2-[2-(aminomethyl)-3,3-difluoro-allyl]-4-[3-methyl-5-[3-(1H-pyrazol-3-yl)phenyl]-2-pyridyl]-1,2,4-triazol-3-one |
| 233 | 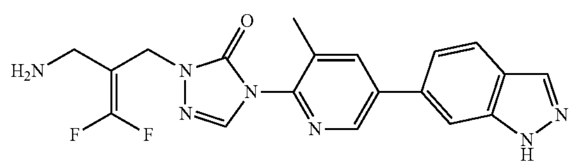 [SMILES: Cc1cc(-c2ccc3cn[nH]c3c2)cnc1-n1cnn(CC(CN)=C(F)F)c1=O] | 2-[2-(aminomethyl)-3,3-difluoro-allyl]-4-[5-(1H-indazol-6-yl)-3-methyl-2-pyridyl]-1,2,4-triazol-3-one |
| 234 | 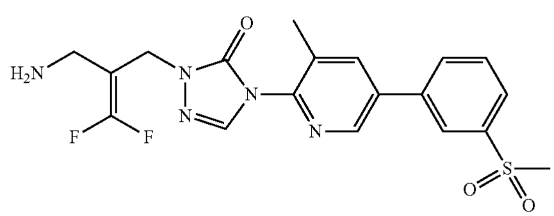 [SMILES: Cc1cc(-c2cccc(S(C)(=O)=O)c2)cnc1-n1cnn(CC(CN)=C(F)F)c1=O] | 2-[2-(aminomethyl)-3,3-difluoro-allyl]-4-[3-methyl-5-(3-methylsulfonylphenyl)-2-pyridyl]-1,2,4-triazol-3-one |
| 235 | 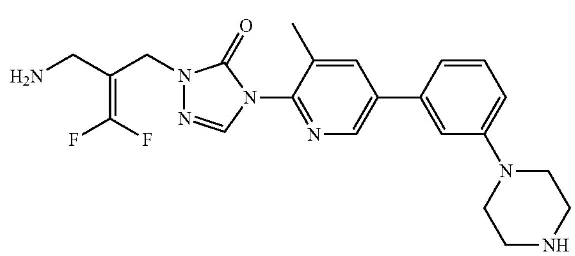 [SMILES: Cc1cc(-c2cccc(N3CCNCC3)c2)cnc1-n1cnn(CC(CN)=C(F)F)c1=O] | 2-[2-(aminomethyl)-3,3-difluoro-allyl]-4-[3-methyl-5-(3-piperazin-1-ylphenyl)-2-pyridyl]-1,2,4-triazol-3-one |
| 236 | 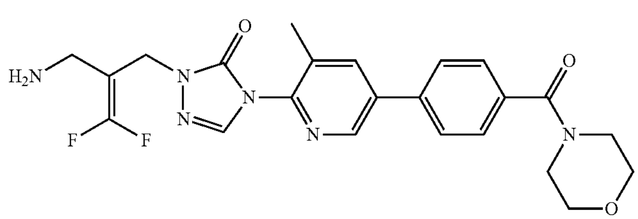 [SMILES: Cc1cc(-c2ccc(C(=O)N3CCOCC3)cc2)cnc1-n1cnn(CC(CN)=C(F)F)c1=O] | 2-[2-(aminomethyl)-3,3-difluoro-allyl]-4-[3-methyl-5-[4-(morpholine-4-carbonyl)phenyl]-2-pyridyl]-1,2,4-triazol-3-one |

| Ex No | Structure | Chemical Name |
|---|---|---|
| 237 | 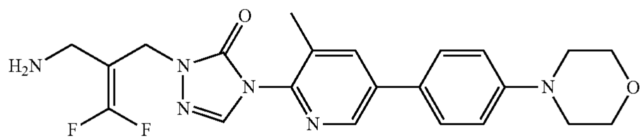 [SMILES: Cc1cc(-c2ccc(N3CCOCC3)cc2)cnc1-n1cnn(CC(CN)=C(F)F)c1=O] | 2-[2-(aminomethyl)-3,3-difluoro-allyl]-4-[3-methyl-5-(4-morpholinophenyl)-2-pyridyl]-1,2,4-triazol-3-one |
| 238 | 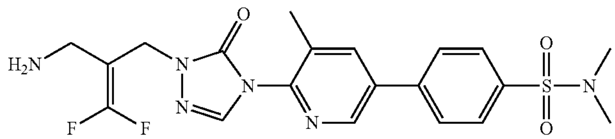 [SMILES: Cc1cc(-c2ccc(S(=O)(=O)N(C)C)cc2)cnc1-n1cnn(CC(CN)=C(F)F)c1=O] | 4-[6-[1-[2-(aminomethyl)-3,3-difluoro-allyl]-5-oxo-1,2,4-triazol-4-yl]-5-methyl-3-pyridyl]-N,N-dimethyl-benzenesulfonamide |
| 239 | 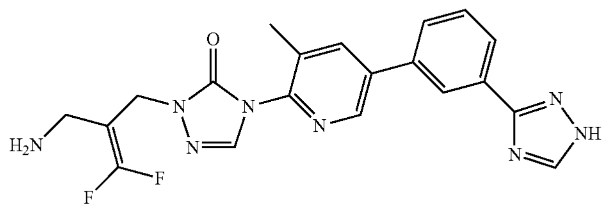 [SMILES: Cc1cc(-c2cccc(-c3nc[nH]n3)c2)cnc1-n1cnn(CC(CN)=C(F)F)c1=O] | 2-[2-(aminomethyl)-3,3-difluoro-allyl]-4-[3-methyl-5-[3-(1H-1,2,4-triazol-3-yl)phenyl]-2-pyridyl]-1,2,4-triazol-3-one |
| 240 | 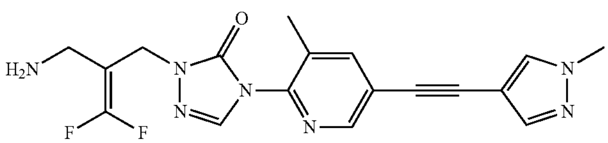 [SMILES: Cc1cc(C#Cc2cnn(C)c2)cnc1-n1cnn(CC(CN)=C(F)F)c1=O] | 2-[2-(aminomethyl)-3,3-difluoro-allyl]-4-[3-methyl-5-[2-(1-methylpyrazol-4-yl)ethynyl]-2-pyridyl]-1,2,4-triazol-3-one |
| 241 | 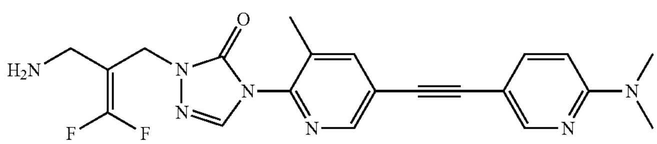 [SMILES: Cc1cc(C#Cc2ccc(N(C)C)nc2)cnc1-n1cnn(CC(CN)=C(F)F)c1=O] | 2-[2-(aminomethyl)-3,3-difluoro-allyl]-4-[5-[2-[6-(dimethylamino)-3-pyridyl]ethynyl]-3-methyl-2-pyridyl]-1,2,4-triazol-3-one |
| 242 | 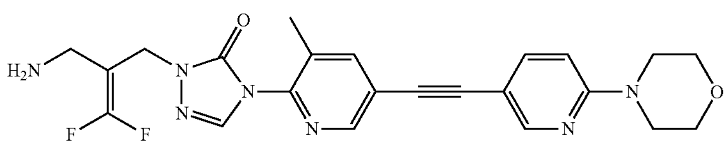 [SMILES: Cc1cc(C#Cc2ccc(N3CCOCC3)nc2)cnc1-n1cnn(CC(CN)=C(F)F)c1=O] | 2-[2-(aminomethyl)-3,3-difluoro-allyl]-4-[3-methyl-5-[2-(6-morpholino-3-pyridyl)ethynyl]-2-pyridyl]-1,2,4-triazol-3-one |
| 243 | 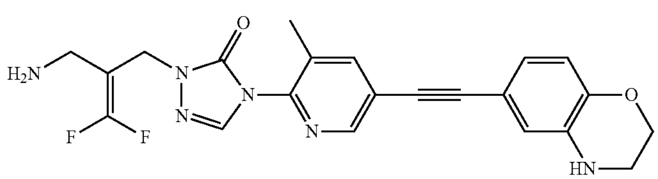 [SMILES: Cc1cc(C#Cc2cnc3c(c2)NCCO3)cnc1-n1cnn(CC(CN)=C(F)F)c1=O] | 2-[2-(aminomethyl)-3,3-difluoro-allyl]-4-[5-[2-(3,4-dihydro-2H-1,4-benzoxazin-6-yl)ethynyl]-3-methyl-2-pyridyl]-1,2,4-triazol-3-one |
| 244 | 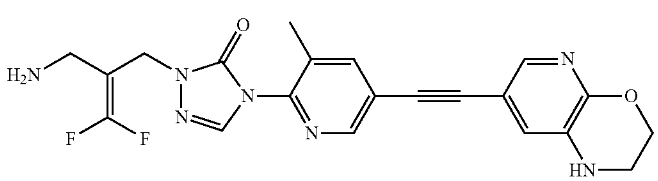 | 2-[2-(aminomethyl)-3,3-difluoro-allyl]-4-[5-[2-(2,3-dihydro-1H-pyrido[2,3-b][1,4]oxazin-7-yl)ethynyl]-3-methyl-2-pyridyl]-1,2,4-triazol-3-one |
| 245 | 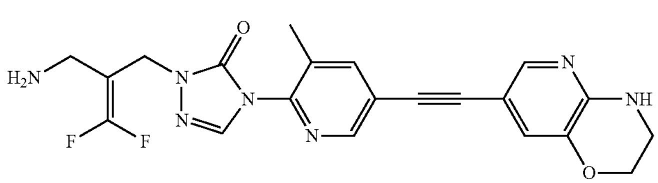 | 2-[2-(aminomethyl)-3,3-difluoro-allyl]-4-[5-[2-(3,4-dihydro-2H-pyrido[3,2-b][1,4]oxazin-7-yl)ethynyl]-3-methyl-2-pyridyl]-1,2,4-triazol-3-one |

TABLE 1*-continued

| Ex No | Structure | Chemical Name |
|---|---|---|
| 246 | 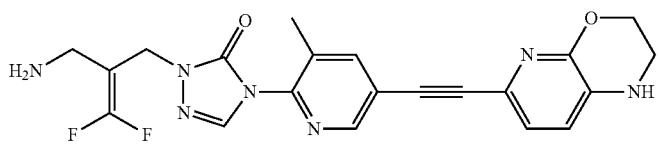 [SMILES: Cc1cc(C#Cc2ccc3c(n2)OCCN3)cnc1-n1cnn(CC(CN)=C(F)F)c1=O] | 2-[2-(aminomethyl)-3,3-difluoro-allyl]-4-[5-[2-(2,3-dihydro-1H-pyrido[2,3-b][1,4]oxazin-6-yl)ethynyl]-3-methyl-2-pyridyl]-1,2,4-triazol-3-one |
| 247 | 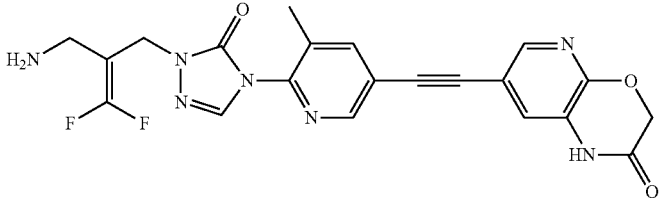 [SMILES: Cc1cc(C#Cc2cnc3c(c2)NC(=O)CO3)cnc1-n1cnn(CC(CN)=C(F)F)c1=O] | 7-[2-[6-[1-[2-(aminomethyl)-3,3-difluoro-allyl]-5-oxo-1,2,4-triazol-4-yl]-5-methyl-3-pyridyl]ethynyl]-1H-pyrido[2,3-b][1,4]oxazin-2-one |
| 248 | 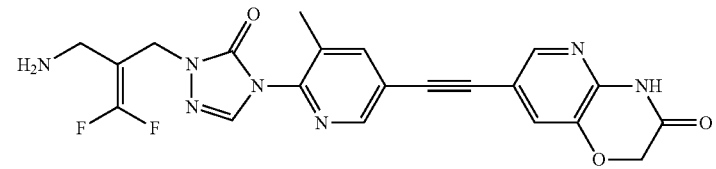 [SMILES: Cc1cc(C#Cc2cnc3c(c2)OCC(=O)N3)cnc1-n1cnn(CC(CN)=C(F)F)c1=O] | 7-[2-[6-[1-[2-(aminomethyl)-3,3-difluoro-allyl]-5-oxo-1,2,4-triazol-4-yl]-5-methyl-3-pyridyl]ethynyl]-4H-pyrido[3,2-b][1,4]oxazin-3-one |
| 249 | 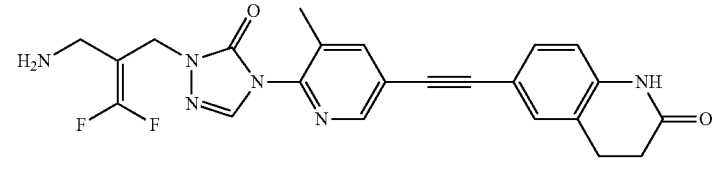 [SMILES: Cc1cc(C#Cc2ccc3c(c2)CCC(=O)N3)cnc1-n1cnn(CC(CN)=C(F)F)c1=O] | 6-[2-[6-[1-[2-(aminomethyl)-3,3-difluoro-allyl]-5-oxo-1,2,4-triazol-4-yl]-5-methyl-3-pyridyl]ethynyl]-3,4-dihydro-1H-quinolin-2-one |
| 250 | 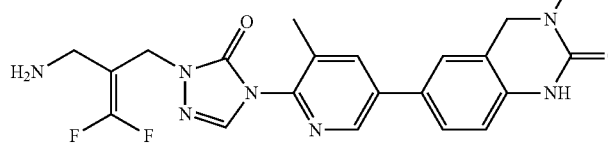 | 6-[6-[1-[2-(aminomethyl)-3,3-difluoro-allyl]-5-oxo-1,2,4-triazol-4-yl]-5-methyl-3-pyridyl]-3-methyl-1,4-dihydroquinazolin-2-one |
| 251 | 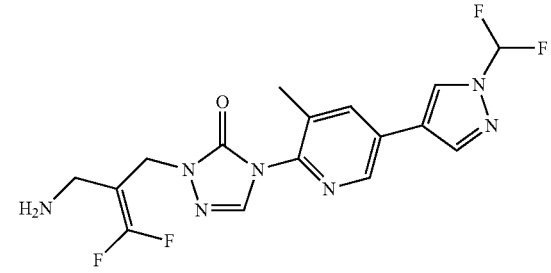 [SMILES: Cc1cc(-c2cnn(C(F)F)c2)cnc1-n1cnn(CC(CN)=C(F)F)c1=O] | 2-[2-(aminomethyl)-3,3-difluoro-allyl]-4-[5-[1-(difluoromethyl)pyrazol-4-yl]-3-methyl-2-pyridyl]-1,2,4-triazol-3-one |
| 252 | 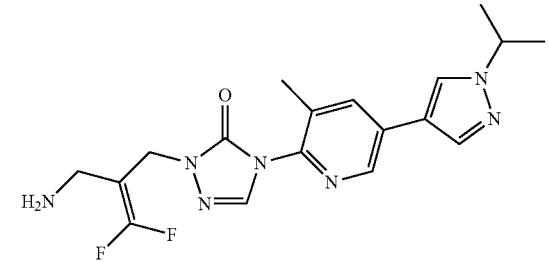 [SMILES: Cc1cc(-c2cnn(C(C)C)c2)cnc1-n1cnn(CC(CN)=C(F)F)c1=O] | 2-[2-(aminomethyl)-3,3-difluoro-allyl]-4-[5-(1-isopropylpyrazol-4-yl)-3-methyl-2-pyridyl]-1,2,4-triazol-3-one |

TABLE 1*-continued

| Ex No | Structure | Chemical Name |
|---|---|---|
| 253 | 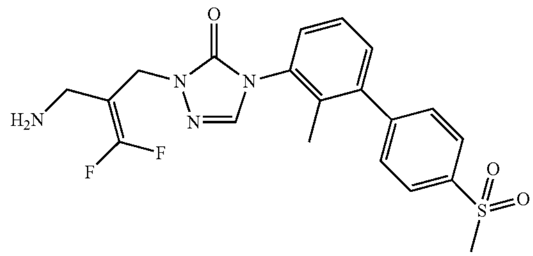 [SMILES: Cc1c(-c2ccc(S(C)(=O)=O)cc2)cccc1-n1cnn(CC(CN)=C(F)F)c1=O] | 2-[2-(aminomethyl)-3,3-difluoro-allyl]-4-[2-methyl-3-(4-methylsulfonylphenyl)phenyl]-1,2,4-triazol-3-one |
| 254 | 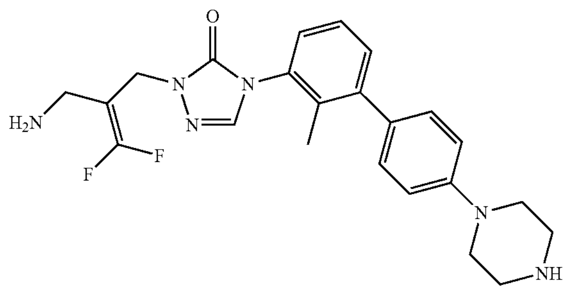 [SMILES: Cc1c(-c2ccc(N3CCNCC3)cc2)cccc1-n1cnn(CC(CN)=C(F)F)c1=O] | 2-[2-(aminomethyl)-3,3-difluoro-allyl]-4-[2-methyl-3-(4-piperazin-1-ylphenyl)phenyl]-1,2,4-triazol-3-one |
| 255 | 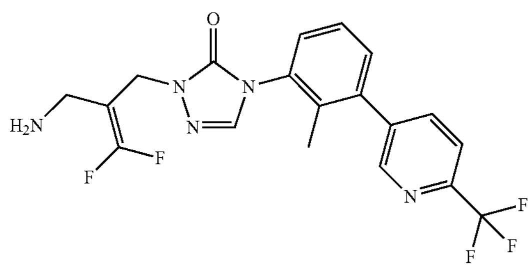 [SMILES: Cc1c(-c2ccc(C(F)(F)F)nc2)cccc1-n1cnn(CC(CN)=C(F)F)c1=O] | 2-[2-(aminomethyl)-3,3-difluoro-allyl]-4-[2-methyl-3-[6-(trifluoromethyl)-3-pyridyl]phenyl]-1,2,4-triazol-3-one |
| 256 | 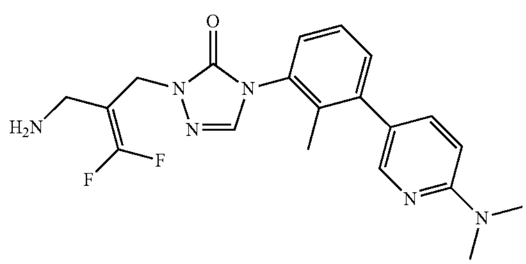 [SMILES: Cc1c(-c2ccc(N(C)C)nc2)cccc1-n1cnn(CC(CN)=C(F)F)c1=O] | 2-[2-(aminomethyl)-3,3-difluoro-allyl]-4-[3-[6-(dimethylamino)-3-pyridyl]-2-methyl-phenyl]-1,2,4-triazol-3-one |
| 257 | 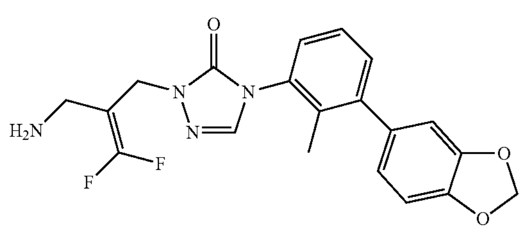 [SMILES: Cc1c(-c2ccc3c(c2)OCO3)cccc1-n1cnn(CC(CN)=C(F)F)c1=O] | 2-[2-(aminomethyl)-3,3-difluoro-allyl]-4-[3-(1,3-benzodioxol-5-yl)-2-methyl-phenyl]-1,2,4-triazol-3-one |
| 258 | 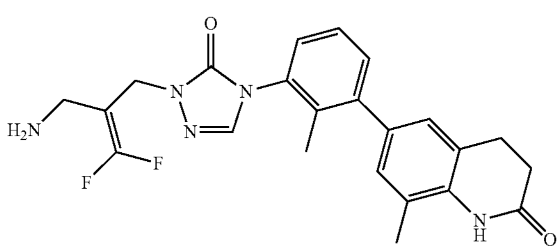 [SMILES: Cc1cc(-c2cccc(-n3cnn(CC(CN)=C(F)F)c3=O)c2C)cc2c1NC(=O)CC2] | 6-[3-[1-[2-(aminomethyl)-3,3-difluoro-allyl]-5-oxo-1,2,4-triazol-4-yl]-2-methyl-phenyl]-8-methyl-3,4-dihydro-1H-quinolin-2-one |

TABLE 1*-continued

| Ex No | Structure | Chemical Name |
|---|---|---|
| 259 | 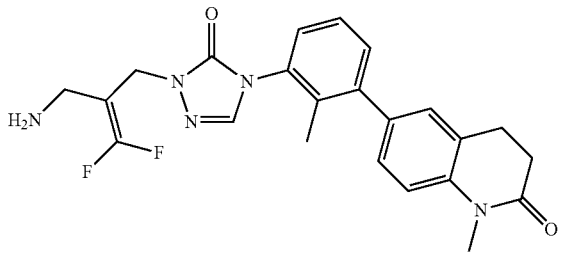 [SMILES: Cc1c(-c2ccc3c(c2)CCC(=O)N3C)cccc1-n1cnn(CC(CN)=C(F)F)c1=O] | 6-[3-[1-[2-(aminomethyl)-3,3-difluoro-allyl]-5-oxo-1,2,4-triazol-4-yl]-2-methyl-phenyl]-1-methyl-3,4-dihydroquinolin-2-one |
| 260 | 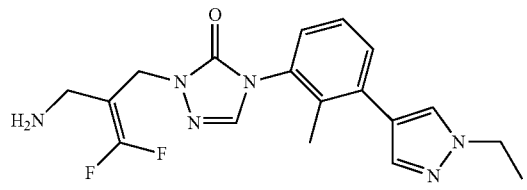 [SMILES: CCn1cc(-c2cccc(-n3cnn(CC(CN)=C(F)F)c3=O)c2C)cn1] | 2-[2-(aminomethyl)-3,3-difluoro-allyl]-4-[3-(1-ethylpyrazol-4-yl)-2-methyl-phenyl]-1,2,4-triazol-3-one |
| 261 | 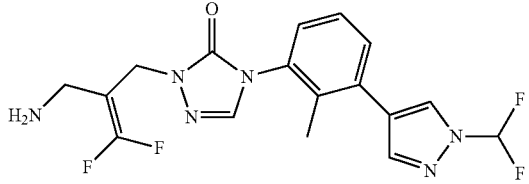 [SMILES: Cc1c(-c2cnn(C(F)F)c2)cccc1-n1cnn(CC(CN)=C(F)F)c1=O] | 2-[2-(aminomethyl)-3,3-difluoro-allyl]-4-[3-[1-(difluoromethyl)pyrazol-4-yl]-2-methyl-phenyl]-1,2,4-triazol-3-one |
| 262 | 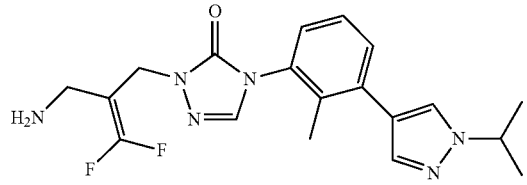 [SMILES: Cc1c(-c2cnn(C(C)C)c2)cccc1-n1cnn(CC(CN)=C(F)F)c1=O] | 2-[2-(aminomethyl)-3,3-difluoro-allyl]-4-[3-(1-isopropylpyrazol-4-yl)-2-methyl-phenyl]-1,2,4-triazol-3-one |
| 263 | 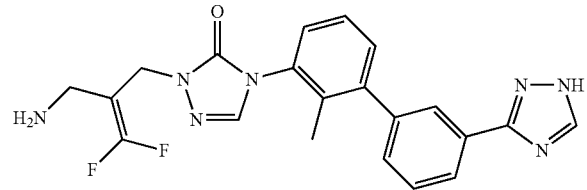 [SMILES: Cc1c(-c2cccc(-c3nc[nH]n3)c2)cccc1-n1cnn(CC(CN)=C(F)F)c1=O] | 2-[2-(aminomethyl)-3,3-difluoro-allyl]-4-[2-methyl-3-[3-(1H-1,2,4-triazol-3-yl)phenyl]phenyl]-1,2,4-triazol-3-one |
| 264 | 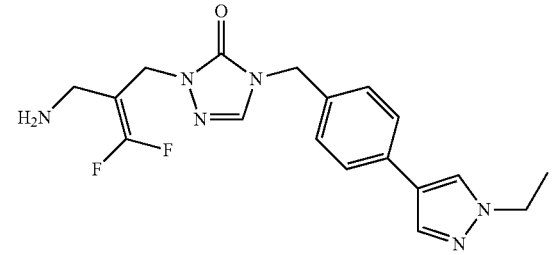 [SMILES: CCn1cc(-c2ccc(Cn3cnn(CC(CN)=C(F)F)c3=O)cc2)cn1] | 2-[2-(aminomethyl)-3,3-difluoro-allyl]-4-[[4-(1-ethylpyrazol-4-yl)phenyl]methyl]-1,2,4-triazol-3-one |

TABLE 1*-continued

| Ex No | Structure | Chemical Name |
|---|---|---|
| 265 | 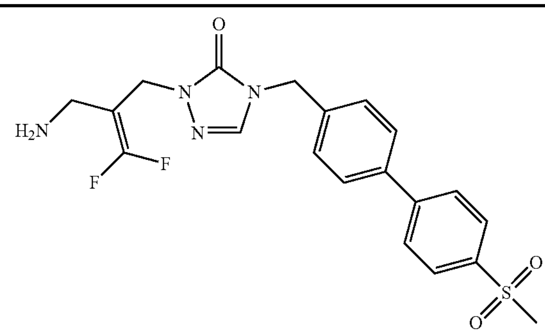 | 2-[2-(aminomethyl)-3,3-difluoro-allyl]-4-[[4-(4-methylsulfonylphenyl)phenyl]methyl]-1,2,4-triazol-3-one |
| 266 | 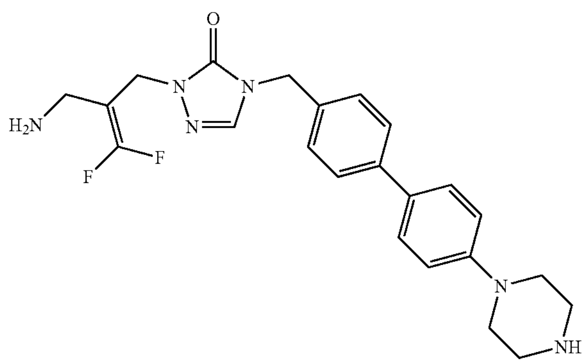 [SMILES: NCC(Cn1ncn(Cc2ccc(-c3ccc(N4CCNCC4)cc3)cc2)c1=O)=C(F)F] | 2-[2-(aminomethyl)-3,3-difluoro-allyl]-4-[[4-(4-piperazin-1-ylphenyl)phenyl]methyl]-1,2,4-triazol-3-one |
| 267 | 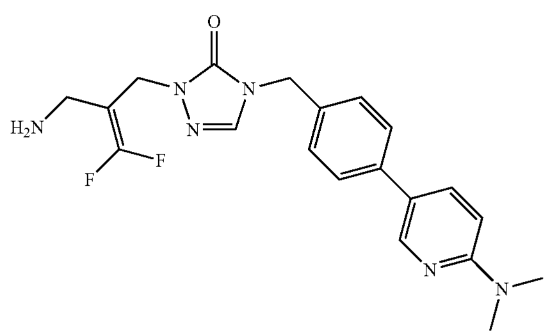 [SMILES: CN(C)c1ccc(-c2ccc(Cn3cnn(CC(CN)=C(F)F)c3=O)cc2)cn1] | 2-[2-(aminomethyl)-3,3-difluoro-allyl]-4-[[4-[6-(dimethylamino)-3-pyridyl]phenyl]methyl]-1,2,4-triazol-3-one |
| 268 | 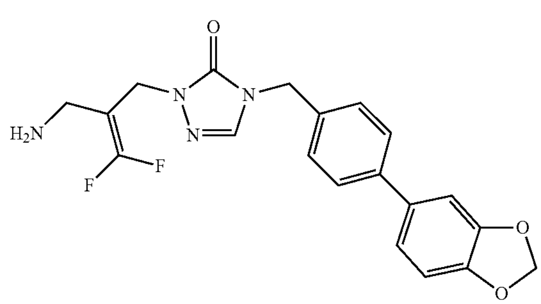 [SMILES: NCC(Cn1ncn(Cc2ccc(-c3ccc4c(c3)OCO4)cc2)c1=O)=C(F)F] | 2-[2-(aminomethyl)-3,3-difluoro-allyl]-4-[[4-(1,3-benzodioxol-5-yl)phenyl]methyl]-1,2,4-triazol-3-one |

TABLE 1*-continued

| Ex No | Structure | Chemical Name |
|---|---|---|
| 269 | 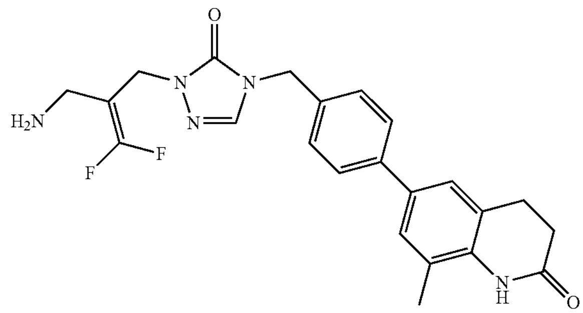 [SMILES: Cc1cc(-c2ccc(Cn3cnn(CC(CN)=C(F)F)c3=O)cc2)cc2c1NC(=O)CC2] | 6-[4-[[1-[2-(aminomethyl)-3,3-difluoro-allyl]-5-oxo-1,2,4-triazol-4-yl]methyl]phenyl]-8-methyl-3,4-dihydro-1H-quinolin-2-one |
| 270 | 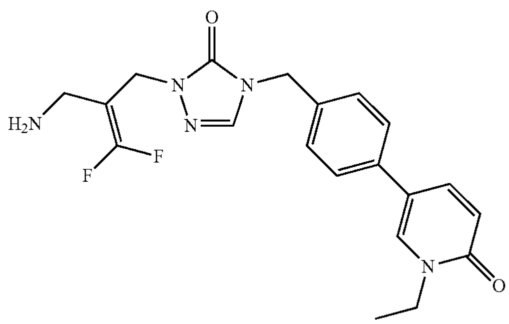 [SMILES: CCn1cc(-c2ccc(Cn3cnn(CC(CN)=C(F)F)c3=O)cc2)ccc1=O] | 5-[4-[[1-[2-(aminomethyl)-3,3-difluoro-allyl]-5-oxo-1,2,4-triazol-4-yl]methyl]phenyl]-1-ethyl-pyridin-2-one |
| 271 | 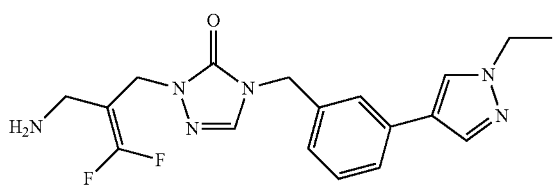 [SMILES: CCn1cc(-c2cccc(Cn3cnn(CC(CN)=C(F)F)c3=O)c2)cn1] | 2-[2-(aminomethyl)-3,3-difluoro-allyl]-4-[[3-(1-ethylpyrazol-4-yl)phenyl]methyl]-1,2,4-triazol-3-one |
| 272 | 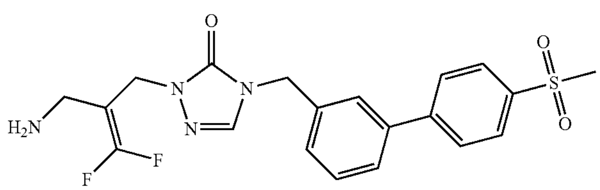 [SMILES: CS(=O)(=O)c1ccc(-c2cccc(Cn3cnn(CC(CN)=C(F)F)c3=O)c2)cc1] | 2-[2-(aminomethyl)-3,3-difluoro-allyl]-4-[[3-(4-methylsulfonylphenyl)phenyl]methyl]-1,2,4-triazol-3-one |
| 273 | 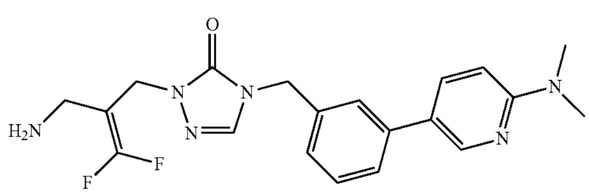 [SMILES: CN(C)c1ccc(-c2cccc(Cn3cnn(CC(CN)=C(F)F)c3=O)c2)cn1] | 2-[2-(aminomethyl)-3,3-difluoro-allyl]-4-[[3-[6-(dimethylamino)-3-pyridyl]phenyl]methyl]-1,2,4-triazol-3-one |
| 274 | 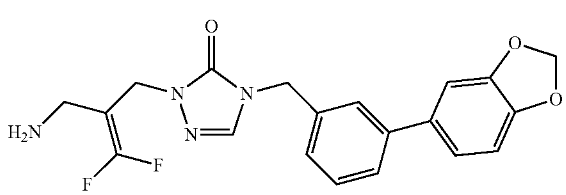 [SMILES: NCC(Cn1ncn(Cc2cccc(-c3ccc4c(c3)OCO4)c2)c1=O)=C(F)F] | 2-[2-(aminomethyl)-3,3-difluoro-allyl]-4-[[3-(1,3-benzodioxol-5-yl)phenyl]methyl]-1,2,4-triazol-3-one |

TABLE 1*-continued

| Ex No | Structure | Chemical Name |
|---|---|---|
| 275 | 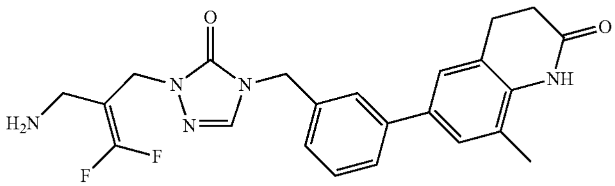 [SMILES: Cc1cc(-c2cccc(Cn3cnn(CC(CN)=C(F)F)c3=O)c2)cc2c1NC(=O)CC2] | 6-[3-[[1-[2-(aminomethyl)-3,3-difluoro-allyl]-5-oxo-1,2,4-triazol-4-yl]methyl]phenyl]-8-methyl-3,4-dihydro-1H-quinolin-2-one |
| 276 | 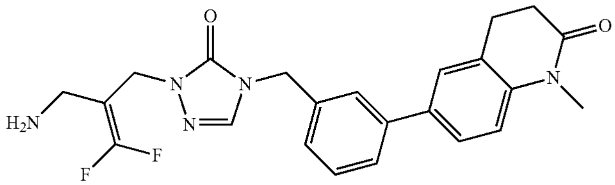 [SMILES: CN1C(=O)CCc2cc(-c3cccc(Cn4cnn(CC(CN)=C(F)F)c4=O)c3)ccc21] | 6-[3-[[1-[2-(aminomethyl)-3,3-difluoro-allyl]-5-oxo-1,2,4-triazol-4-yl]methyl]phenyl]-1-methyl-3,4-dihydroquinolin-2-one |
| 277 | 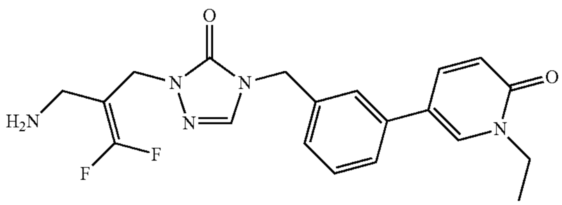 [SMILES: CCn1cc(-c2cccc(Cn3cnn(CC(CN)=C(F)F)c3=O)c2)ccc1=O] | 5-[3-[[1-[2-(aminomethyl)-3,3-difluoro-allyl]-5-oxo-1,2,4-triazol-4-yl]methyl]phenyl]-1-ethyl-pyridin-2-one |
| 278 | 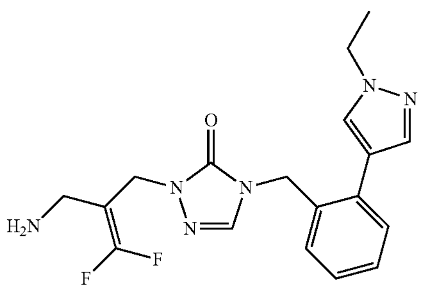 [SMILES: CCn1cc(-c2ccccc2Cn2cnn(CC(CN)=C(F)F)c2=O)cn1] | 2-[2-(aminomethyl)-3,3-difluoro-allyl]-4-[[2-(1-ethylpyrazol-4-yl)phenyl]methyl]-1,2,4-triazol-3-one |
| 279 | 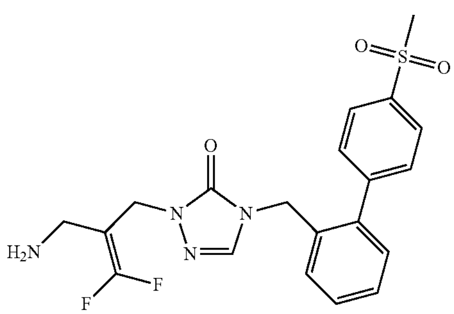 [SMILES: CS(=O)(=O)c1ccc(-c2ccccc2Cn2cnn(CC(CN)=C(F)F)c2=O)cc1] | 2-[2-(aminomethyl)-3,3-difluoro-allyl]-4-[[2-(4-methylsulfonylphenyl)phenyl]methyl]-1,2,4-triazol-3-one |
| 280 | 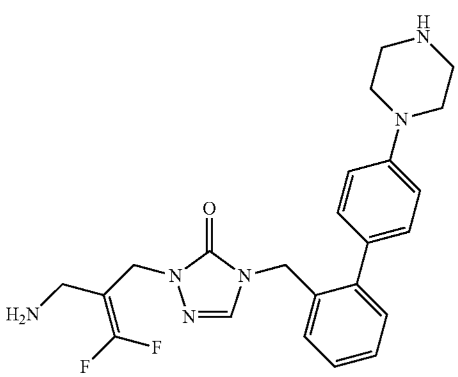 [SMILES: NCC(Cn1ncn(Cc2ccccc2-c2ccc(N3CCNCC3)cc2)c1=O)=C(F)F] | 2-[2-(aminomethyl)-3,3-difluoro-allyl]-4-[[2-(4-piperazin-1-ylphenyl)phenyl]methyl]-1,2,4-triazol-3-one |

TABLE 1*-continued

| Ex No | Structure | Chemical Name |
|---|---|---|
| 281 | 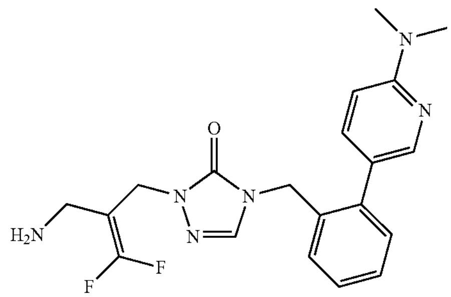 [SMILES: CN(C)c1ccc(-c2ccccc2Cn2cnn(CC(CN)=C(F)F)c2=O)cn1] | 2-[2-(aminomethyl)-3,3-difluoro-allyl]-4-[[2-[6-(dimethylamino)-3-pyridyl]phenyl]methyl]-1,2,4-triazol-3-one |
| 282 | 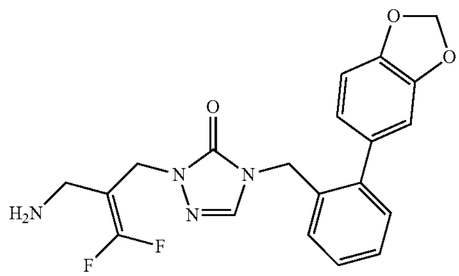 [SMILES: NCC(Cn1ncn(Cc2ccccc2-c2ccc3c(c2)OCO3)c1=O)=C(F)F] | 2-[2-(aminomethyl)-3,3-difluoro-allyl]-4-[[2-(1,3-benzodioxol-5-yl)phenyl]methyl]-1,2,4-triazol-3-one |
| 283 | 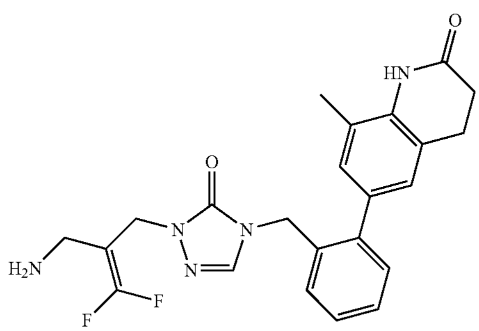 [SMILES: Cc1cc(-c2ccccc2Cn2cnn(CC(CN)=C(F)F)c2=O)cc2c1NC(=O)CC2] | 6-[2-[[1-[2-(aminomethyl)-3,3-difluoro-allyl]-5-oxo-1,2,4-triazol-4-yl]methyl]phenyl]-8-methyl-3,4-dihydro-1H-quinolin-2-one |
| 284 | 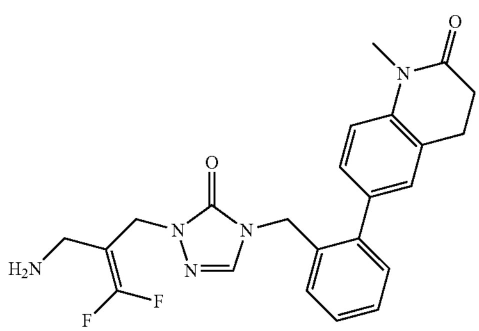 [SMILES: CN1C(=O)CCc2cc(-c3ccccc3Cn3cnn(CC(CN)=C(F)F)c3=O)ccc21] | 6-[2-[[1-[2-(aminomethyl)-3,3-difluoro-allyl]-5-oxo-1,2,4-triazol-4-yl]methyl]phenyl]-1-methyl-3,4-dihydroquinolin-2-one |
| 285 | 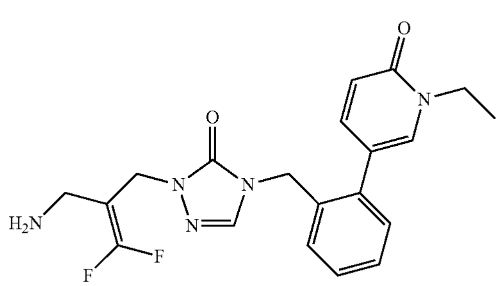 [SMILES: CCn1cc(-c2ccccc2Cn2cnn(CC(CN)=C(F)F)c2=O)ccc1=O] | 5-[2-[[1-[2-(aminomethyl)-3,3-difluoro-allyl]-5-oxo-1,2,4-triazol-4-yl]methyl]phenyl]-1-ethyl-pyridin-2-one |

TABLE 1*-continued

| Ex No | Structure | Chemical Name |
|---|---|---|
| 286 | 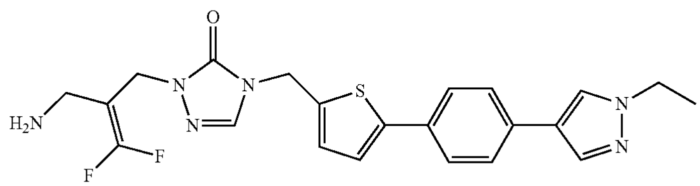 [SMILES: CCn1cc(-c2ccc(-c3ccc(Cn4cnn(CC(CN)=C(F)F)c4=O)s3)cc2)cn1] | 2-[2-(aminomethyl)-3,3-difluoro-allyl]-4-[[5-[4-(1-ethylpyrazol-4-yl)phenyl]-2-thienyl]methyl]-1,2,4-triazol-3-one |
| 287 | 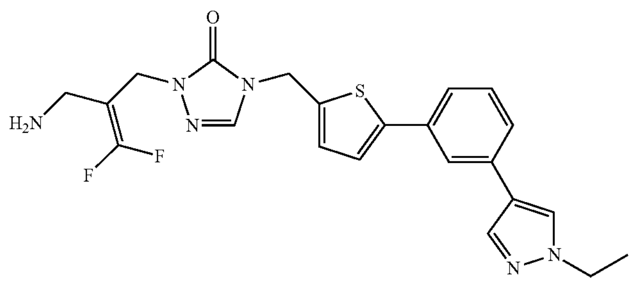 [SMILES: CCn1cc(-c2cccc(-c3ccc(Cn4cnn(CC(CN)=C(F)F)c4=O)s3)c2)cn1] | 2-[2-(aminomethyl)-3,3-difluoro-allyl]-4-[[5-[3-(1-ethylpyrazol-4-yl)phenyl]-2-thienyl]methyl]-1,2,4-triazol-3-one |
| 288 | 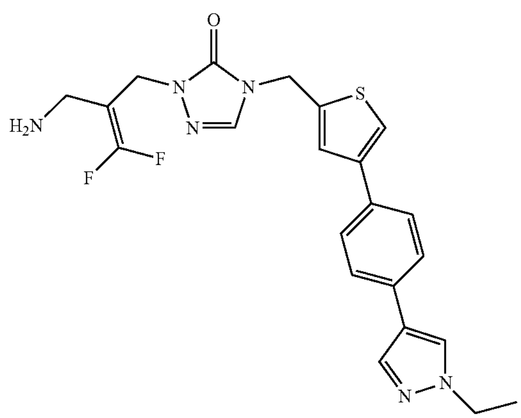 [SMILES: CCn1cc(-c2ccc(-c3csc(Cn4cnn(CC(CN)=C(F)F)c4=O)c3)cc2)cn1] | 2-[2-(aminomethyl)-3,3-difluoro-allyl]-4-[[4-[4-(1-ethylpyrazol-4-yl)phenyl]-2-thienyl]methyl]-1,2,4-triazol-3-one |
| 289 | 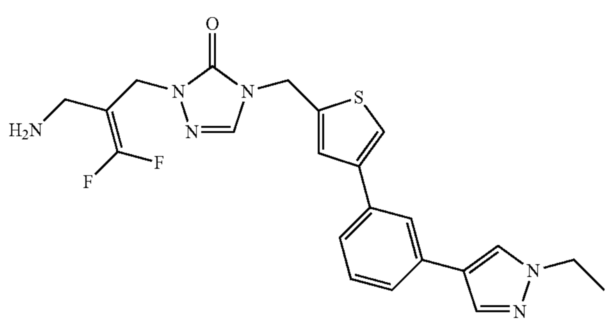 [SMILES: CCn1cc(-c2cccc(-c3csc(Cn4cnn(CC(CN)=C(F)F)c4=O)c3)c2)cn1] | 2-[2-(aminomethyl)-3,3-difluoro-allyl]-4-[[4-[3-(1-ethylpyrazol-4-yl)phenyl]-2-thienyl]methyl]-1,2,4-triazol-3-one |
| 290 | 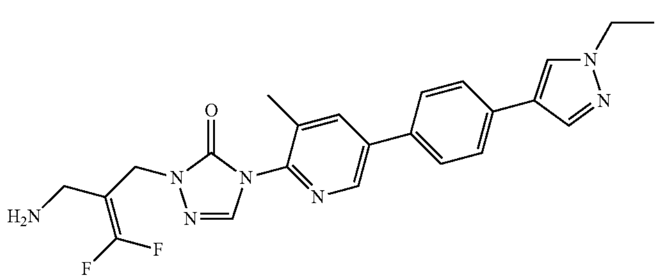 [SMILES: CCn1cc(-c2ccc(-c3cnc(-n4cnn(CC(CN)=C(F)F)c4=O)c(C)c3)cc2)cn1] | 2-[2-(aminomethyl)-3,3-difluoro-allyl]-4-[5-[4-(1-ethylpyrazol-4-yl)phenyl]-3-methyl-2-pyridyl]-1,2,4-triazol-3-one |

//TABLE 1*-continued

| Ex No | Structure | Chemical Name |
|---|---|---|
| 291 | 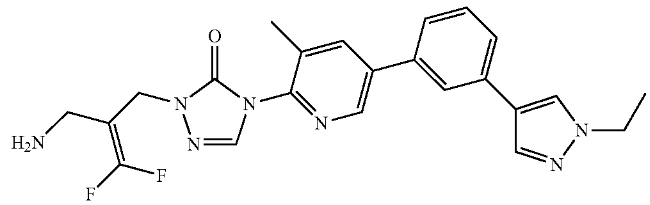 [SMILES: CCn1cc(-c2cccc(-c3cnc(-n4cnn(CC(CN)=C(F)F)c4=O)c(C)c3)c2)cn1] | 2-[2-(aminomethyl)-3,3-difluoro-allyl]-4-[5-[3-(1-ethylpyrazol-4-yl)phenyl]-3-methyl-2-pyridyl]-1,2,4-triazol-3-one |
| 292 | 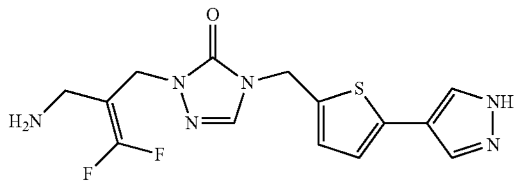 [SMILES: NCC(Cn1ncn(Cc2ccc(-c3cn[nH]c3)s2)c1=O)=C(F)F] | 2-[2-(aminomethyl)-3,3-difluoro-allyl]-4-[[5-(1H-pyrazol-4-yl)-2-thienyl]methyl]-1,2,4-triazol-3-one |
| 293 | 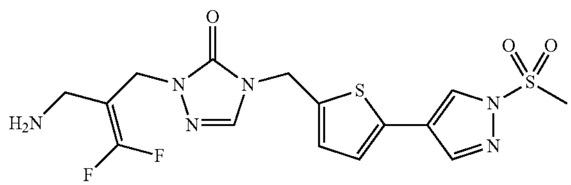 [SMILES: CS(=O)(=O)n1cc(-c2ccc(Cn3cnn(CC(CN)=C(F)F)c3=O)s2)cn1] | 2-[2-(aminomethyl)-3,3-difluoro-allyl]-4-[[5-(1-methylsulfonylpyrazol-4-yl)-2-thienyl]methyl]-1,2,4-triazol-3-one |
| 294 | 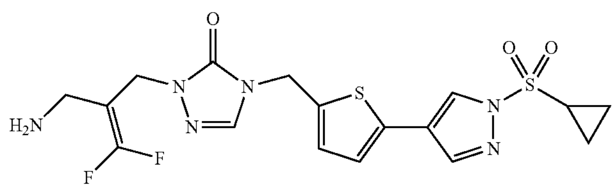 [SMILES: NCC(Cn1ncn(Cc2ccc(-c3cnn(S(=O)(=O)C4CC4)c3)s2)c1=O)=C(F)F] | 2-[2-(aminomethyl)-3,3-difluoro-allyl]-4-[[5-(1-cyclopropylsulfonylpyrazol-4-yl)-2-thienyl]methyl]-1,2,4-triazol-3-one |
| 295 | 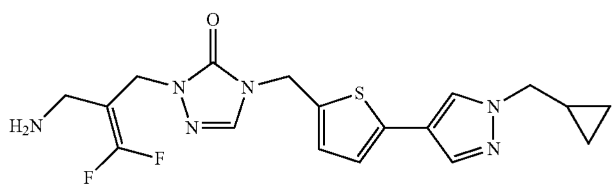 [SMILES: NCC(Cn1ncn(Cc2ccc(-c3cnn(CC4CC4)c3)s2)c1=O)=C(F)F] | 2-[2-(aminomethyl)-3,3-difluoro-allyl]-4-[[5-[1-(cyclopropylmethyl)pyrazol-4-yl]-2-thienyl]methyl]-1,2,4-triazol-3-one |
| 296 | 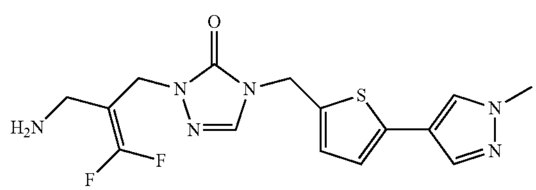 [SMILES: Cn1cc(-c2ccc(Cn3cnn(CC(CN)=C(F)F)c3=O)s2)cn1] | 2-[2-(aminomethyl)-3,3-difluoro-allyl]-4-[[5-(1-methylpyrazol-4-yl)-2-thienyl]methyl]-1,2,4-triazol-3-one |
| 297 | 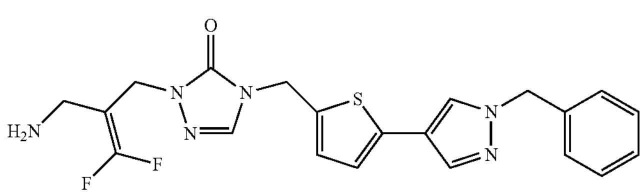 [SMILES: NCC(Cn1ncn(Cc2ccc(-c3cnn(Cc4ccccc4)c3)s2)c1=O)=C(F)F] | 2-[2-(aminomethyl)-3,3-difluoro-allyl]-4-[[5-(1-benzylpyrazol-4-yl)-2-thienyl]methyl]-1,2,4-triazol-3-one |
| 298 | 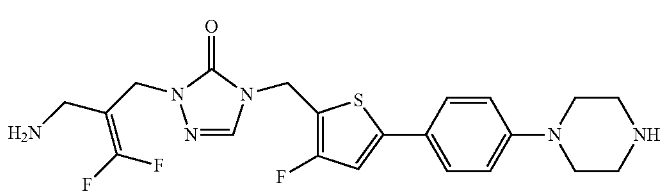 [SMILES: NCC(Cn1ncn(Cc2sc(-c3ccc(N4CCNCC4)cc3)cc2F)c1=O)=C(F)F] | 2-[2-(aminomethyl)-3,3-difluoro-allyl]-4-[[3-fluoro-5-(4-piperazin-1-ylphenyl)-2-thienyl]methyl]-1,2,4-triazol-3-one |

TABLE 1*-continued

| Ex No | Structure | Chemical Name |
|---|---|---|
| 299 | 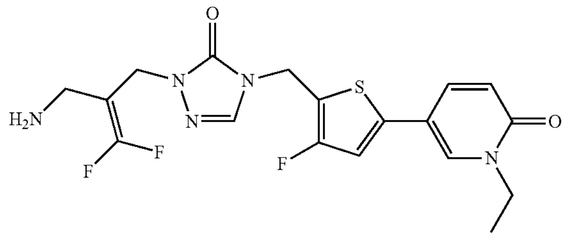 [SMILES: CCn1cc(-c2cc(F)c(Cn3cnn(CC(CN)=C(F)F)c3=O)s2)ccc1=O] | 5-[5-[[1-[2-(aminomethyl)-3,3-difluoro-allyl]-5-oxo-1,2,4-triazol-4-yl]methyl]-4-fluoro-2-thienyl]-1-ethyl-pyridin-2-one |
| 300 | 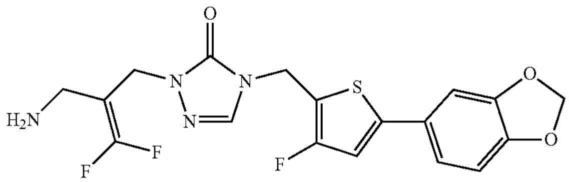 [SMILES: NCC(Cn1ncn(Cc2sc(-c3ccc4c(c3)OCO4)cc2F)c1=O)=C(F)F] | 2-[2-(aminomethyl)-3,3-difluoro-allyl]-4-[[5-(1,3-benzodioxol-5-yl)-3-fluoro-2-thienyl]methyl]-1,2,4-triazol-3-one |
| 301 | 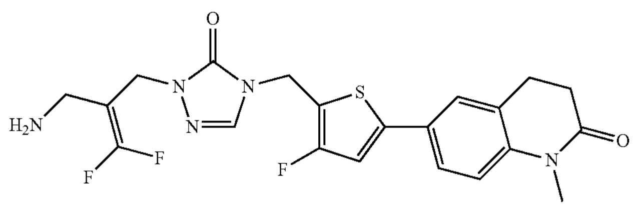 [SMILES: CN1C(=O)CCc2cc(-c3cc(F)c(Cn4cnn(CC(CN)=C(F)F)c4=O)s3)ccc21] | 6-[5-[[1-[2-(aminomethyl)-3,3-difluoro-allyl]-5-oxo-1,2,4-triazol-4-yl]methyl]-4-fluoro-2-thienyl]-1-methyl-3,4-dihydroquinolin-2-one |
| 302 | 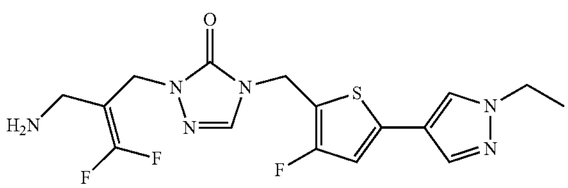 [SMILES: CCn1cc(-c2cc(F)c(Cn3cnn(CC(CN)=C(F)F)c3=O)s2)cn1] | 2-[2-(aminomethyl)-3,3-difluoro-allyl]-4-[[5-(1-ethylpyrazol-4-yl)-3-fluoro-2-thienyl]methyl]-1,2,4-triazol-3-one |
| 303 | 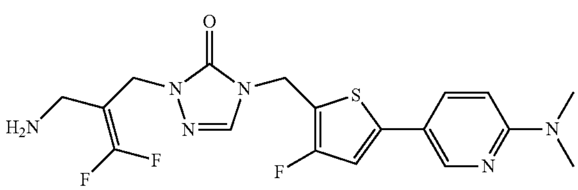 [SMILES: CN(C)c1ccc(-c2cc(F)c(Cn3cnn(CC(CN)=C(F)F)c3=O)s2)cn1] | 2-(2-(aminomethyl)-3,3-difluoroallyl)-4-((5-(6-(dimethylamino)pyridin-3-yl)-3-fluorothiophen-2-yl)methyl)-2,4-dihydro-3H-1,2,4-triazol-3-one |
| 304 | 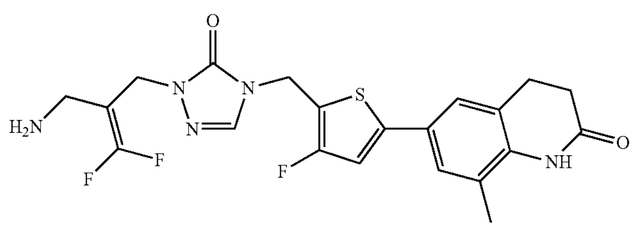 [SMILES: Cc1cc(-c2cc(F)c(Cn3cnn(CC(CN)=C(F)F)c3=O)s2)cc2c1NC(=O)CC2] | 6-(5-((1-(2-(aminomethyl)-3,3-difluoroallyl)-5-oxo-1,5-dihydro-4H-1,2,4-triazol-4-yl)methyl)-4-fluorothiophen-2-yl)-8-methyl-3,4-dihydroquinolin-2(1H)-one |

*Compounds were isolated as trifluoroacetate or ditrifluoroacetate salts as indicated in the Examples.

Experimental Example 1: Activity Evaluation with Respect to Amine Oxidases

The compounds according to the present technology were evaluated in terms of activity on recombinant human VAP-1 (R&D systems) by measuring the level of hydrogen peroxide in horseradish peroxidase (HRP)-coupled reaction using Amplex Red Hydrogen Peroxide Assay Kit (Molecular Probes, Invitrogen, USA). The experiment was carried out at room temperature using benzylamine as a substrate. In the HRP-coupled reaction, hydrogen peroxide oxidation of 10-acetyl-3,7-dihydroxyphenoxazine (Amplex Red reagent) produces resorufin, which is a highly fluorescent compound. Briefly, the test compound was dissolved in dimethyl sulfoxide (DMSO) at a concentration of 20 mM. The dose-response assessment was made by 1:3 serial dilution in DMSO, thereby creating a 8 point curve. The concentration of the upper part was controlled according to the efficacy of the compounds, followed by the dilution with a reaction buffer solution to obtain a final DMSO concentration of less than 1%. To each well of a 96 black well plate, human VAP-1 purified in 50 mM sodium phosphate buffer solution (pH7.4) was added. The test compounds dissolved in DMSO were incubated with the human VAP-1 enzymes at 37° C. for 30 minutes. After 30-minute incubation, each well was added with a reaction mixture containing 200 uM Amplex Red reagent prepared from 50 mM sodium phosphate buffer solution (pH 7.4), 1 mM benzylamine, and 1 U/mL HRP. Fluorescence intensity was measured at several time points during 1-2 hours using a microplate reader (Flexstation3, Molecular Devices) under the wavelength condition exciting at 544 nm and reading the emission at 590 nm. The inhibitory effect of the compounds was measured as a decrease (%) in the signal rate as compared to the control group without any inhibitor (only diluted DMSO). Data was fixed to a logistic model with four variables and $IC_{50}$ value was calculated using GraphPad Prism program.

In addition, the compounds according to the present technology were evaluated in terms of activity on a recombinant human MAO-A (monoamine oxidase-A, Sigma-Aldrich) and a recombinant human MAO-B (monoamine oxidase-B, Sigma-Aldrich) by using as substrates, 0.5 mM tyramine and 1 mM benzylamine, respectively, with a method similar to the activity evaluation method for recombinant human VAP-1. The compounds according to the present technology were also evaluated in terms of activity on a recombinant human DAO (diamine oxidase, R&D systems) by using as a substrate 1 mM putrescine with a method similar to the activity evaluation method for recombinant human VAP-1.

The results obtained by evaluating the activity against the enzymes as above are shown in Tables 2-5 below.

TABLE 2

| Example | Inhibitory Activity ($IC_{50}$, nM) | | | |
|---|---|---|---|---|
| | human VAP-1 | MAO-A | MAO-B | DAO |
| 1 | 2.0 | >100,000 | 39,000 | >10,000 |
| 2 | 6.2 | >100,000 | >100,000 | 46,000 |
| 3 | 4.0 | >100,000 | 25,000 | 19,000 |
| 4 | 4.2 | >100,000 | 2,300 | 58,000 |
| 5 | 2.5 | >100,000 | 4,900 | 67,000 |
| 6 | 9.4 | >100,000 | >100,000 | >100,000 |
| 7 | 9.4 | >100,000 | 6,100 | 10,000 |
| 8 | 2.2 | >100,000 | >100,000 | 10,500 |
| 9 | 3.5 | >100,000 | >100,000 | 7,100 |
| 10 | 7.7 | >100,000 | >100,000 | 1,200 |
| 11 | 1.1 | >100,000 | 57,000 | >100,000 |
| 12 | 43 | >100,000 | >10,000 | 55,000 |
| 13 | 3.6 | >100,000 | 3,600 | 910 |
| 14 | 1.4 | >100,000 | 40,000 | 4,100 |
| 15 | 3.0 | >100,000 | >100,000 | >100,000 |
| 16 | 4.6 | >100,000 | 38,000 | 1,100 |
| 17 | 12 | >100,000 | >10,000 | 1,300 |
| 18 | 15 | >100,000 | >100,000 | 13,000 |
| 19 | 5.3 | >100,000 | >10,000 | 240 |
| 20 | 2.1 | >100,000 | >100,000 | 350 |
| 21 | 2.5 | 36,200 | 18,000 | 6,300 |
| 22 | 0.8 | >100,000 | >100,000 | >10,000 |
| 23 | 3.1 | >100,000 | >100,000 | 8,400 |
| 24 | 2.7 | >100,000 | 3,300 | 600 |
| 25 | 1.7 | 6,280 | >10,000 | 1,300 |
| 26 | 0.7 | >100,000 | 180 | 71 |
| 27 | 0.4 | >100,000 | 350 | 380 |
| 28 | 1.2 | >100,000 | 85 | 1,600 |
| 29 | 0.2 | >100,000 | 150 | 200 |
| 30 | 0.6 | >100,000 | 300 | 890 |
| 31 | 0.2 | >100,000 | 870 | 59 |
| 32 | 1.3 | >100,000 | 17,000 | 670 |
| 33 | 0.3 | 11,000 | 190 | 17 |
| 34 | 0.3 | 27,000 | 770 | 250 |
| 35 | 0.3 | >100,000 | 33 | 540 |
| 36 | 0.1 | >100,000 | 160 | 97 |
| 37 | 0.5 | >100,000 | 880 | 860 |

TABLE 2-continued

| Example | Inhibitory Activity ($IC_{50}$, nM) | | | |
|---|---|---|---|---|
| | human VAP-1 | MAO-A | MAO-B | DAO |
| 38 | 0.4 | >100,000 | 450 | 24 |
| 39 | 1.2 | >100,000 | 46,000 | 310 |
| 40 | 0.3 | >100,000 | 200 | 12 |
| 41 | 0.2 | >100,000 | 470 | 120 |
| 42 | 0.3 | >100,000 | 34 | 250 |
| 43 | 0.2 | >100,000 | 100 | 22 |
| 44 | 0.3 | >100,000 | 110 | 14 |
| 45 | 0.2 | >100,000 | 410 | 200 |
| 46 | 0.9 | >100,000 | >100,000 | 190 |
| 47 | 3.5 | >100,000 | >100,000 | 1,900 |
| 48 | 1 | >100,000 | 31,000 | 61 |
| 49 | 1.6 | >100,000 | >100,000 | 490 |
| 50 | 1.5 | >100,000 | 13,000 | 1,200 |
| 51 | 0.6 | >100,000 | 28,000 | 520 |
| 52 | 0.9 | >100,000 | 23,000 | 300 |
| 53 | 1.3 | >100,000 | >100,000 | 1,710 |
| 54 | 4.9 | >100,000 | >100,000 | 480 |
| 55 | 6.6 | >100,000 | >100,000 | 620 |
| 56 | 1.6 | >100,000 | 79,600 | 75 |
| 57 | 0.9 | >100,000 | 56,400 | 30 |
| 58 | 2.2 | >100,000 | >100,000 | 1,700 |
| 59 | 0.5 | >100,000 | >100,000 | 84 |
| 60 | 1.3 | >100,000 | >100,000 | 810 |
| 61 | 0.7 | >100,000 | 14,000 | 19 |
| 62 | 1.5 | >100,000 | >100,000 | 160 |
| 63 | 0.7 | >100,000 | 16,000 | 110 |
| 64 | 0.4 | >100,000 | 480 | 270 |
| 65 | 0.3 | >100,000 | 12,000 | 290 |
| 66 | 0.6 | >100,000 | 4,800 | 250 |
| 67 | 0.9 | >100,000 | 8,300 | 490 |
| 68 | 0.5 | >100,000 | 55,000 | 2,100 |
| 69 | 1.2 | >100,000 | >100,000 | >100,000 |
| 70 | 0.7 | >100,000 | 5,800 | 1,500 |
| 71 | 0.8 | >100,000 | >100,000 | >100,000 |
| 72 | 0.5 | >100,000 | 1,500 | 57,000 |
| 73 | 0.3 | >100,000 | 7,200 | 6,100 |
| 74 | 0.3 | >100,000 | 7,500 | 6,500 |
| 75 | 0.7 | >100,000 | >100,000 | 20,000 |
| 76 | 1.1 | >100,000 | 44,000 | 32 |
| 77 | 1 | >100,000 | 1,600 | 10 |
| 78 | 0.6 | >100,000 | 9,800 | 57 |
| 79 | 0.9 | >100,000 | 910 | 200 |
| 80 | 0.4 | >100,000 | 5,300 | 36 |
| 81 | 0.4 | >100,000 | 3,500 | 27 |
| 82 | 0.1 | >100,000 | 3,700 | 13 |
| 83 | 0.4 | >100,000 | >10,000 | 250 |
| 84 | 0.2 | >100,000 | 900 | 7 |
| 85 | 0.2 | >100,000 | 130 | 180 |
| 86 | 0.1 | >100,000 | 640 | 33 |
| 87 | 0.1 | >100,000 | 1,100 | 22 |
| 88 | 0.3 | >100,000 | 8,200 | 230 |
| 89 | 0.6 | >100,000 | 1900 | 2 |
| 90 | 1.3 | >100,000 | >100,000 | 30 |
| 91 | 0.5 | >100,000 | 200 | 1 |
| 92 | 0.2 | >100,000 | 6,200 | 8 |
| 93 | 0.3 | >100,000 | 50 | 21 |
| 94 | 0.2 | >100,000 | 860 | 4 |
| 95 | 0.6 | >100,000 | 1,300 | 19 |
| 96 | 13 | >100,000 | 220 | >100,000 |
| 97 | 1.3 | >100,000 | 20,000 | >10,000 |
| 98 | 23 | >100,000 | 13,900 | 18,600 |
| 99 | 9.3 | >100,000 | 21,000 | >100,000 |
| 100 | 0.5 | >100,000 | 11,000 | >10,000 |

TABLE 3

| Example | Inhibitory Activity ($IC_{50}$, nM) | | | |
|---|---|---|---|---|
| | human VAP-1 | MAO-A | MAO-B | DAO |
| 101 | 0.3 | >100,000 | 67,000 | 21,000 |
| 102 | 0.4 | >100,000 | 5,400 | >10,000 |
| 103 | 0.9 | >100,000 | 4,200 | 22,000 |

TABLE 3-continued

Inhibitory Activity (IC$_{50}$, nM)

| Example | human VAP-1 | MAO-A | MAO-B | DAO |
|---|---|---|---|---|
| 104 | 0.5 | >100,000 | >10,000 | 31,000 |
| 105 | 1.5 | >100,000 | 6,500 | >10,000 |
| 106 | 4.7 | >100,000 | >100,000 | 860 |
| 107 | 3.5 | >100,000 | 46,000 | 12,000 |
| 108 | 2.0 | >10,000 | >10,000 | 42,000 |
| 109 | 1.4 | >100,000 | >100,000 | 84,000 |
| 110 | 1.3 | >10,000 | 8,700 | >100,000 |
| 111 | 0.4 | >100,000 | 9,400 | 7,200 |
| 112 | 0.2 | >100,000 | 26,000 | >100,000 |
| 113 | 0.6 | >100,000 | 2,700 | 19,000 |
| 114 | 4.9 | >100,000 | >100,000 | 970 |
| 115 | 0.8 | >100,000 | 10,000 | 11,000 |
| 116 | 1.4 | >100,000 | >10,000 | >100,000 |
| 117 | 1.1 | >100,000 | >100,000 | 7,100 |
| 118 | 3.5 | >100,000 | >100,000 | 40,000 |
| 119 | 0.5 | >100,000 | 30,000 | >10,000 |
| 120 | 6 | >100,000 | >100,000 | >100,000 |
| 121 | 0.9 | >100,000 | 40,000 | >10,000 |
| 122 | 0.4 | >100,000 | 25,000 | 54,000 |
| 123 | 0.9 | >100,000 | 56,000 | 59,000 |
| 124 | 11 | >100,000 | >100,000 | >100,000 |
| 125 | 2.5 | >100,000 | >100,000 | >100,000 |
| 126 | 0.5 | >100,000 | 760 | >100,000 |
| 127 | 0.6 | >100,000 | 1,070 | >100,000 |
| 128 | 0.7 | >100,000 | >100,000 | 97,000 |
| 129 | 0.7 | >100,000 | 311 | 21,000 |
| 130 | 0.7 | >100,000 | >100,000 | >100,000 |
| 131 | 0.4 | 7,800 | 12,000 | >100,000 |
| 132 | 0.2 | >100,000 | >100,000 | >100,000 |
| 133 | 0.2 | >100,000 | >100,000 | >10,000 |
| 134 | 0.3 | >100,000 | 22,000 | >100,000 |
| 135 | 0.4 | >100,000 | >100,000 | 79,000 |
| 136 | 0.4 | >100,000 | >100,000 | >100,000 |
| 137 | 0.3 | >100,000 | >100,000 | >100,000 |
| 138 | 0.1 | >100,000 | 15,000 | 13,000 |
| 139 | 1.0 | 21,000 | 21,000 | 73,000 |
| 140 | 0.8 | 6,600 | 8,000 | 6,800 |

TABLE 4

Inhibitory Activity (IC$_{50}$, nM)

| Example | human VAP-1 | MAO-A | MAO-B | DAO |
|---|---|---|---|---|
| 141 | 0.6 | 8,100 | 20,000 | 16,000 |
| 142 | 0.2 | >100,000 | 32,000 | 16,000 |
| 143 | 0.2 | >100,000 | 6,400 | >10,000 |
| 144 | 0.7 | >100,000 | >100,000 | >10,000 |
| 145 | 0.8 | >100,000 | >100,000 | >100,000 |
| 146 | 1.1 | >100,000 | 33,000 | 9,200 |
| 147 | 11 | >100,000 | >100,000 | 2,600 |
| 148 | 0.7 | >100,000 | 8,700 | 6,300 |
| 149 | 0.6 | >100,000 | >100,000 | >10,000 |
| 150 | 2.9 | >100,000 | 2,800 | >10,000 |
| 151 | 0.3 | >100,000 | 26,100 | 6,600 |
| 152 | 0.2 | >100,000 | 13,400 | 3,500 |
| 153 | 1.3 | >100,000 | 29,000 | 36,000 |
| 154 | 4.0 | >100,000 | >100,000 | 21,000 |
| 155 | 56 | >100,000 | >100,000 | 50,000 |
| 156 | 3.2 | >100,000 | 17,000 | 9,100 |
| 157 | 2.3 | >100,000 | >100,000 | >100,000 |
| 158 | 7 | >100,000 | 3,800 | >100,000 |
| 159 | 5.2 | >100,000 | >100,000 | 52,000 |
| 160 | 1.5 | >100,000 | 15,600 | 5,090 |
| 161 | 0.2 | >100,000 | >100,000 | 54,000 |
| 162 | 0.7 | >10,000 | 10,000 | >10,000 |
| 163 | 0.4 | >100,000 | 31,000 | 8,400 |
| 164 | 2.5 | 4,000 | 34,000 | >10,000 |
| 165 | 0.5 | >100,000 | 5,900 | >10,000 |
| 166 | 0.9 | >10,000 | >10,000 | >10,000 |
| 167 | 2.1 | >100,000 | 41,000 | >10,000 |
| 168 | 1.0 | >10,000 | 45,000 | >100,000 |
| 169 | 0.2 | >100,000 | >100,000 | >100,000 |

TABLE 4-continued

Inhibitory Activity (IC$_{50}$, nM)

| Example | human VAP-1 | MAO-A | MAO-B | DAO |
|---|---|---|---|---|
| 170 | 0.8 | >100,000 | 14,000 | >10,000 |
| 171 | 1.8 | >100,000 | 50,000 | >100,000 |
| 172 | 13 | >100,000 | 61,000 | >100,000 |
| 173 | 0.3 | >100,000 | 69,000 | 260 |
| 174 | 1.3 | >100,000 | >100,000 | 29 |
| 175 | 0.4 | >100,000 | 14,000 | 250 |
| 176 | 0.5 | >100,000 | >100,000 | 1,100 |
| 177 | 1.2 | >100,000 | 700 | 2,500 |
| 178 | 0.6 | >100,000 | >100,000 | 350 |
| 179 | 0.3 | >100,000 | >100,000 | 290 |
| 180 | 0.6 | >100,000 | 61,000 | 1,900 |

TABLE 5

Inhibitory Activity (IC$_{50}$, nM)

| Example | human VAP-1 | MAO-A | MAO-B | DAO |
|---|---|---|---|---|
| 181 | 2.3 | >100,000 | >100,000 | >10,000 |
| 182 | 0.2 | >100,000 | >100,000 | >100,000 |
| 183 | 1.4 | >100,000 | 2,100 | >100,000 |
| 184 | 2.6 | >100,000 | 26,000 | 72,000 |
| 185 | 1.3 | >100,000 | 28,000 | >100,000 |
| 186 | 0.5 | >100,000 | >100,000 | 25,000 |
| 187 | 1.1 | >100,000 | >100,000 | 8,900 |
| 188 | 3.4 | >100,000 | >100,000 | 7,400 |
| 189 | 0.5 | >100,000 | >100,000 | 23,000 |
| 190 | 1.4 | >100,000 | >100,000 | 63,000 |
| 191 | 0.3 | >100,000 | 44,000 | 4,200 |
| 192 | 0.4 | >100,000 | 56,000 | 22,000 |
| 193 | 1.3 | >100,000 | >100,000 | 8,700 |
| 194 | 2.9 | >100,000 | 9,200 | 64,000 |
| 195 | 2 | >100,000 | 38,000 | 31,000 |
| 196 | 1.4 | >100,000 | 2,900 | 1,900 |
| 197 | 0.8 | >100,000 | 18,000 | 2,400 |
| 198 | 4.6 | >100,000 | 23,000 | 880 |
| 199 | 1.7 | >100,000 | 1,100 | 15,000 |
| 200 | 1.9 | >100,000 | 740 | >100,000 |
| 201 | 2.8 | 90800 | 2,000 | 27,000 |
| 202 | 2 | >100,000 | >100,000 | 5,600 |
| 203 | 1.5 | >100,000 | 780 | 4,000 |
| 204 | 0.5 | >100,000 | 89,900 | 41,200 |
| 205 | 0.8 | >100,000 | >100,000 | 7,674 |
| 206 | 2.3 | >100,000 | 14,570 | 639 |
| 207 | 0.7 | >100,000 | >100,000 | >100,000 |
| 208 | 2.5 | 89,940 | 42,390 | >100,000 |
| 209 | 4.3 | >100,000 | 5,185 | 93,690 |
| 210 | 1.5 | >100,000 | >100,000 | 1,227 |
| 211 | 1.1 | 38,860 | 42,730 | 1,861 |
| 212 | 1.5 | 79140 | >100,000 | 4,319 |
| 213 | 2.5 | >100,000 | >100,000 | 1,300 |
| 214 | 1.7 | >100,000 | >100,000 | 940 |
| 215 | 0.7 | >100,000 | >100,000 | 280 |
| 216 | 1.3 | >100,000 | >100,000 | 63 |
| 217 | 1.1 | >100,000 | 13,700 | 1,500 |
| 218 | 0.8 | >100,000 | >100,000 | 130 |
| 219 | 0.2 | >100,000 | 68,500 | 47 |
| 220 | 1.1 | >100,000 | >100,000 | 11,000 |
| 221 | 0.3 | 20,000 | 9,000 | 2,700 |
| 222 | 1 | >100,000 | >100,000 | 4,000 |
| 223 | 1.5 | >10,000 | 38,000 | 37,000 |
| 224 | 0.8 | >100,000 | 1,900 | 5,500 |
| 225 | 0.5 | >100,000 | 1,600 | 14,000 |
| 226 | 0.5 | >100,000 | 11,000 | >100,000 |
| 227 | 0.7 | >100,000 | 340 | 4,800 |
| 228 | 0.6 | >100,000 | 3,300 | 7,700 |
| 229 | 0.6 | >10,000 | 4,100 | 97,000 |
| 230 | 0.7 | >100,000 | 77,000 | 24,000 |
| 231 | 0.2 | 40,400 | 1,950 | 3,910 |
| 232 | 0.5 | >100,000 | 1,100 | 15,000 |
| 233 | 0.2 | >100,000 | 200 | 36,000 |
| 234 | 0.4 | >100,000 | 1,800 | 7,500 |
| 235 | 1.4 | >100,000 | 840 | >100,000 |

TABLE 5-continued

| | Inhibitory Activity (IC$_{50}$, nM) | | | |
|---|---|---|---|---|
| Example | human VAP-1 | MAO-A | MAO-B | DAO |
| 236 | 0.8 | >100,000 | >100,000 | 6,700 |
| 237 | 0.42 | >100,000 | 84,000 | 6,100 |
| 238 | 0.14 | >100,000 | 1,800 | 310 |
| 239 | 2.7 | >100,000 | 14,000 | 11,000 |
| 240 | 1 | >100,000 | 15,000 | 30,000 |
| 241 | 1.3 | >100,000 | 6,300 | 25,000 |
| 242 | 1 | >100,000 | 29,000 | 4,200 |
| 243 | 0.9 | 32,700 | 2,200 | 4,600 |
| 244 | 0.8 | >100,000 | 37,000 | 9,000 |
| 245 | 2.7 | >100,000 | 15,000 | 14,000 |
| 246 | 2.3 | >100,000 | 120,000 | 59,000 |
| 247 | 0.3 | >100,000 | >100,000 | 43,000 |
| 248 | 2.7 | >100,000 | 14,000 | >100,000 |
| 249 | 0.9 | >100,000 | 3,100 | 3,900 |
| 250 | 0.2 | >100,000 | >100,000 | 4,300 |
| 251 | 1.5 | >100,000 | 18,000 | 19,000 |
| 252 | 1 | >100,000 | 35,000 | 17,000 |
| 253 | 2.8 | >100,000 | >100,000 | 8,700 |
| 254 | 8 | >100,000 | >100,000 | >100,000 |
| 255 | 2.3 | >100,000 | >100,000 | 35,000 |
| 256 | 2.5 | >100,000 | >100,000 | >100,000 |
| 257 | 2.4 | >100,000 | 101,000 | >100,000 |
| 258 | 2.5 | >100,000 | >100,000 | >100,000 |
| 259 | 1.3 | >100,000 | >100,000 | >100,000 |
| 260 | 3.7 | >100,000 | >100,000 | >100,000 |
| 261 | 6.5 | >100,000 | >100,000 | >100,000 |
| 262 | 7.4 | >100,000 | >100,000 | >100,000 |
| 263 | 29 | >100,000 | >100,000 | >100,000 |
| 264 | 1.3 | >100,000 | >100,000 | >100,000 |
| 265 | 1.4 | >100,000 | >100,000 | >100,000 |
| 266 | 9.1 | >100,000 | >100,000 | 330 |
| 267 | 1.1 | >100,000 | >100,000 | >100,000 |
| 268 | 2.1 | >100,000 | 1,870 | >100,000 |
| 269 | 1 | >100,000 | >100,000 | 71,000 |
| 270 | 0.6 | >100,000 | >100,000 | >100,000 |
| 271 | 2.2 | >100,000 | 1,592 | >100,000 |
| 272 | 3.2 | >100,000 | 23,780 | 4,326 |
| 273 | 1.8 | >100,000 | 2,897 | 39,270 |
| 274 | 3.1 | >100,000 | 125 | 54,080 |
| 275 | 0.9 | >100,000 | 25,420 | 5,158 |
| 276 | 0.5 | >100,000 | 2,251 | 3,084 |
| 277 | 2.5 | >100,000 | 68,620 | 1,811 |
| 278 | 17 | >100,000 | >100,000 | >100,000 |
| 279 | >100 | >100,000 | >100,000 | >100,000 |
| 280 | 2,376 | >100,000 | >100,000 | >100,000 |
| 281 | 307 | >100,000 | >100,000 | 4,858 |
| 282 | 28 | >100,000 | >100,000 | >100,000 |
| 283 | 154 | >100,000 | >100,000 | >100,000 |
| 284 | 148 | >100,000 | >100,000 | 66,360 |
| 285 | >100 | >100,000 | >100,000 | >100,000 |
| 286 | 1.4 | 2,619 | 3,231 | 2,476 |
| 287 | 0.7 | >100,000 | 12,150 | 13,940 |
| 288 | 2.6 | 2,909 | 3,227 | 3,777 |
| 289 | 0.6 | >100,000 | 11,950 | 14,530 |
| 290 | 0.7 | >100,000 | 1,188 | 2,377 |
| 291 | 0.6 | >100,000 | 3,447 | 6,158 |
| 292 | 2.7 | 86,170 | >100,000 | >100,000 |
| 293 | 2.4 | >100,000 | >100,000 | 25,300 |
| 294 | 2.9 | >100,000 | >100,000 | 5,379 |
| 295 | 0.3 | >100,000 | >100,000 | >100,000 |
| 296 | 1 | >100,000 | >100,000 | >100,000 |
| 297 | 1.9 | >100,000 | >100,000 | 14,810 |
| 298 | 12 | >100,000 | >100,000 | 0.2 |
| 299 | 1.4 | >100,000 | >100,000 | 9,679 |
| 300 | 1.7 | >100,000 | 11,080 | 25,340 |
| 301 | 0.5 | >100,000 | >100,000 | 2,682 |
| 302 | 1.1 | >100,000 | >100,000 | 19,470 |
| 303 | 0.8 | >100,000 | >100,000 | >100,000 |
| 304 | 0.7 | >100,000 | >100,000 | 12,570 |

From the results of Tables 2-5 above, it can be seen that the compounds according to the present technology have excellent inhibitory activity on VAP-1 among various amine oxidases.

Para. A. A compound of Formula X

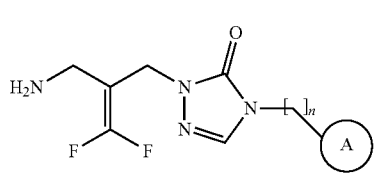

(Formula X)

or a stereoisomer thereof or a pharmaceutically acceptable salt thereof;
wherein
n is 0, 1 or 2; and
A is an aryl group or a heterocyclic group, wherein said heterocyclic group has 1 to 5 heteroatom ring members chosen from O, N, or S, and said heterocyclic group is aromatic or non-aromatic; and wherein said aryl group or said heterocyclic group is optionally substituted with one or two substituents selected from the group consisting of $C_{1-3}$ alkyl, halogen, benzyloxy, —R, —CH=CH—R, and —C≡C—R; and
R is a substituted or unsubstituted cyclic ring, optionally containing 1 to 5 heteroatom ring members chosen from O, N, or S, and said cyclic ring is aromatic or non-aromatic.

Para. B. The compound, or a stereoisomer thereof or a pharmaceutically acceptable salt thereof, of Para. A, wherein A is aryl optionally substituted with one or two substituents selected from the group consisting of $C_{1-3}$ alkyl, halogen, benzyloxy, —R, —CH=CH—R, and —C≡C—R.

Para. C. The compound, or a stereoisomer thereof or a pharmaceutically acceptable salt thereof, of Para. B, wherein A is phenyl substituted with one or two substituents selected from the group consisting of $C_{1-3}$ alkyl, halogen, benzyloxy, —R, —CH=CH—R, and —C≡C—R.

Para. D. The compound, or a stereoisomer thereof or a pharmaceutically acceptable salt thereof, of Para. A, wherein A is a heterocyclic group having 1 to 5 heteroatom ring members chosen from O, N, or S; said heterocyclic group is aromatic or non-aromatic; and said heterocyclic group is optionally substituted with one or two substituents selected from the group consisting of $C_{1-3}$ alkyl, halogen, benzyloxy, —R, —CH=CH—R, and —C≡C—R.

Para. E. The compound, or a stereoisomer thereof or a pharmaceutically acceptable salt thereof, of Para. D, wherein A is a heteroaryl group having 1 to 5 heteroatom ring members chosen from O, N, or S; and said heteroaryl group is optionally substituted with one or two substituents selected from the group consisting of $C_{1-3}$ alkyl, halogen, benzyloxy, —R, —CH=CH—R, and —C≡C—R.

Para. F. The compound, or a stereoisomer thereof or a pharmaceutically acceptable salt thereof, of Para. E, wherein A is pyridine, pyrazine, or thiophene, wherein A is optionally substituted with one or two substituents selected from the group consisting of $C_{1-3}$ alkyl, halogen, benzyloxy, —R, —CH=CH—R, and —C≡C—R.

Para. G. The compound, or a stereoisomer thereof or a pharmaceutically acceptable salt thereof, of any one of Paras. A-F, wherein R is a cyclic ring optionally containing 1-5 heteroatom ring members, and said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, C$_{1-6}$ alkylcarbonyl, morpholinylcarbonyl, piperazinyl, acetylpiperazinyl, morpholinyl, pyrazolyl, C$_{1-6}$ alkylpyrazolyl, triazolyl, pyrrolidinonyl, and pyrrolidinyl.

Para. H. The compound, or a stereoisomer thereof or a pharmaceutically acceptable salt thereof, of any one of Paras. A-G, wherein n is 0.

Para. I. The compound, or a stereoisomer thereof or a pharmaceutically acceptable salt thereof, of any one of Paras. A-G, wherein n is 1.

Para. J. The compound, or a stereoisomer thereof or a pharmaceutically acceptable salt thereof, of any one of Paras. A-G, wherein n is 2.

Para. K. A compound of Formula Y

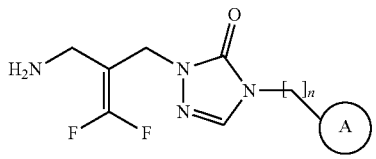

(Formula Y)

or a stereoisomer thereof or a pharmaceutically acceptable salt thereof;
wherein
n is 0, 1 or 2;
A is an aryl or heteroaryl group selected from the group consisting of phenyl, pyridine, pyrazine, thiophene, and benzothiophene;
wherein said aryl or heteroaryl group is optionally substituted with one or two substituents selected from the group consisting of C$_{1-3}$ alkyl, halogen, benzyloxy, —R, —CH═CH—R, and —C≡C—R;
wherein said R is a cyclic ring selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 3,4-dihydro-1,4-benzoxazine, 2,3-dihydro-1,4-benzoxazine, 1,4-benzoxazin-3-one, 1,4-dihydro-3,1-benzoxazin-2-one, 5,6,7,8-tetrahydronaphthyridine, triazolo[1,5-a]pyridine, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, 1,4-dihydroquinazolin-2-one, 1H-pyrrolo[2,3-b]pyridine, benzoxazole, and thiophene;
wherein said cyclic ring is optionally substituted with one to three substituents selected from the group consisting of halogen, C$_{1-6}$ alkyl, difluoromethyl, trifluoromethyl, (cycloalkyl)alkyl, benzyl, C$_{1-6}$ alkoxy, amino, mono- or di-C$_{1-6}$ alkylamino, C$_{1-6}$ alkoxy-C$_{1-6}$ alkylamino, C$_{1-6}$ alkylcarbonylamino, mono- or di-C$_{1-6}$ alkylaminocarbonyl, mono- or di-C$_{1-6}$ alkylaminosulfonyl, C$_{1-6}$ alkylsulfonyl, cycloalkylsulfonyl, C$_{1-6}$ alkylcarbonyl, morpholinylcarbonyl, piperazinyl, acetylpiperazinyl, morpholinyl, pyrazolyl, C$_{1-6}$ alkylpyrazolyl, triazolyl, pyrrolidinonyl, and pyrrolidinyl.

Para. L. The compound, or a stereoisomer thereof or a pharmaceutically acceptable salt thereof, of Para. K, wherein n is 0 or 1, and A is phenyl, pyridine or thiophene, optionally substituted with one or two substituents selected from the group consisting of C$_{1-3}$ alkyl, halogen, benzyloxy, —R, —CH═CH—R, and —C≡C—R.

Para. M. The compound, or a stereoisomer thereof or a pharmaceutically acceptable salt thereof, of Para. K, wherein said aryl or heteroaryl group is substituted with one or two substituents selected from the group consisting of C$_{1-3}$ alkyl, halogen, and —R.

Para. N. The compound, or a stereoisomer thereof or a pharmaceutically acceptable salt thereof, of Para. M, wherein said R is a cyclic ring selected from the group consisting of benzene, pyridine, pyridin-2-one, pyrazole and 3,4-dihydroquinolin-2-one, said cyclic ring is optionally substituted with one to three substituents selected from the group consisting of halogen, C$_{1-6}$ alkyl, difluoromethyl, trifluoromethyl, C$_{1-6}$ alkoxy, amino, mono- or di-C$_{1-6}$ alkylamino, C$_{1-6}$ alkoxy-C$_{1-6}$ alkylamino, C$_{1-6}$ alkylcarbonylamino, mono- or di-C$_{1-6}$ alkylaminocarbonyl, mono- or di-C$_{1-6}$ alkylaminosulfonyl, C$_{1-6}$ alkylsulfonyl, C$_{1-6}$ alkylcarbonyl, morpholinylcarbonyl, piperazinyl, acetylpiperazinyl, morpholinyl, pyrazolyl, triazolyl, and pyrrolidinyl.

Para. O. The compound, or a stereoisomer thereof or a pharmaceutically acceptable salt thereof, of Para. N, wherein said cyclic ring is substituted with a substituent selected from the group consisting of C$_{1-6}$ alkyl, C$_{1-6}$ alkylsulfonyl, di-C$_{1-6}$ alkylamino, and piperazinyl.

Para. P. The compound or a stereoisomer thereof or a pharmaceutically acceptable salt thereof, of Para. K,
wherein n is 0;
A is phenyl;
wherein said phenyl is substituted with one or two substituents selected from the group consisting of halogen and —R;
wherein said R is a cyclic ring selected from the group consisting of benzene, pyridine, 3,4-dihydroquinolin-2-one and pyrazole; and
wherein said cyclic ring is substituted with a substituent selected from the group consisting of C$_{1-6}$ alkyl, C$_{1-6}$ alkylsulfonyl, di-C$_{1-6}$ alkylamino, and piperazinyl.

Para. Q. The compound, or a stereoisomer thereof or a pharmaceutically acceptable salt thereof, of Para. K,
wherein
n is 0;
A is pyridine;
wherein said pyridine is substituted with one or two substituents selected from the group consisting of C$_{1-3}$ alkyl, halogen, and —R;
wherein said R is a cyclic ring selected from the group consisting of benzene, pyridine, 3,4-dihydroquinolin-2-one and pyrazole; and
wherein said cyclic ring is substituted with a substituent selected from the group consisting of C$_{1-6}$ alkyl, C$_{1-6}$ alkylsulfonyl, di-C$_{1-6}$ alkylamino, and piperazinyl.

Para. R. The compound, or a stereoisomer thereof or a pharmaceutically acceptable salt thereof, of Para. K,
wherein
n is 0;
A is thiophene;
wherein said thiophene is substituted with one or two cyclic rings selected from the group consisting of benzene, pyridine, pyridin-2-one, 3,4-dihydroquinolin-2-one and pyrazole; and
wherein said cyclic ring is substituted with a substituent selected from the group consisting of C$_{1-6}$ alkyl, C$_{1-6}$ alkylsulfonyl, di-C$_{1-6}$ alkylamino, and piperazinyl.

Para. S. The compound, or a stereoisomer thereof or a pharmaceutically acceptable salt thereof, of Para. K, wherein A is phenyl optionally substituted with one or two substituents selected from the group consisting of C$_{1-3}$ alkyl, halogen, benzyloxy, —R, —CH═CH—R, and —C≡C—R.

Para. T. The compound, or a stereoisomer thereof or a pharmaceutically acceptable salt thereof, of Para. S, wherein A is phenyl substituted with —R.

Para. U. The compound, or a stereoisomer thereof or a pharmaceutically acceptable salt thereof, of Para. T, wherein —R is a cyclic ring selected from the group consisting of benzene, pyridine, pyridin-2-one, pyrazole, benzodioxole, and 3,4-dihydroquinolin-2-one;

wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinonyl.

Para. V. The compound, or a stereoisomer thereof or a pharmaceutically acceptable salt thereof, of Para. K, wherein A is pyridine substituted with —R.

Para. W. The compound, or a stereoisomer thereof or a pharmaceutically acceptable salt thereof, of Para. V, wherein —R is a cyclic ring selected from the group consisting of benzene, pyridine, pyridin-2-one, pyrimidine, pyrazole, benzodioxole, benzoxadiazole, benzothiazole, indazole, 2,3-dihydro-1,4-benzoxazine, 1,4-benzoxazin-3-one, 1,4-dihydro-3,1-benzoxazin-2-one, 1,4-dihydroquinazolin-2-one, 1H-pyrrolo[2,3-b]pyridine, benzoxazole, and thiophene.

wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinonyl.

Para. X. The compound, or a stereoisomer thereof or a pharmaceutically acceptable salt thereof, of Para. K, wherein A is thiophene substituted with —R.

Para. Y. The compound, or a stereoisomer thereof or a pharmaceutically acceptable salt thereof, of Para. X, wherein —R is a cyclic ring selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 2,3-dihydro-1,4-benzoxazine, 1,4-dihydro-3,1-benzoxazin-2-one, 5,6,7,8-tetrahydronaphthyridine, triazolo[1,5-a]pyridine, pyrido[2,3-b][1,4]oxazin-2-one, and 1,4-dihydroquinazolin-2-one;

wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

Para. Z. The compound, or a stereoisomer thereof or a pharmaceutically acceptable salt thereof, of Para. K, wherein A is benzothiophene substituted with —R.

Para. AA. The compound, or a stereoisomer thereof or a pharmaceutically acceptable salt thereof, of Para. Z, wherein —R is a cyclic ring selected from the group consisting of benzene, pyridine, pyridin-2-one, pyrazole, benzodioxole, and 3,4-dihydroquinolin-2-one, wherein said cyclic ring is optionally substituted with one to three substituents selected from the group consisting of halogen, $C_{1-6}$ alkyl, difluoromethyl, trifluoromethyl, (cycloalkyl)alkyl, benzyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, cycloalkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

Para. AB. The compound, or a stereoisomer thereof or a pharmaceutically acceptable salt thereof, of any one of Paras. S-AA, wherein n is 0.

Para. AC. The compound, or a stereoisomer thereof or a pharmaceutically acceptable salt thereof, of any one of Paras. S-AA, wherein n is 1.

Para. AD. The compound, or a stereoisomer thereof or a pharmaceutically acceptable salt thereof, of any one of Paras. S-AA, wherein n is 2.

Para. AE. A compound of Formula 12

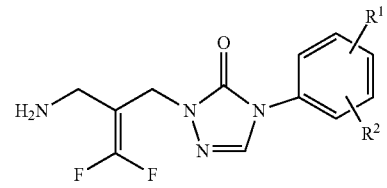

(Formula 12)

or a stereoisomer thereof or a pharmaceutically acceptable salt thereof;

wherein $R^1$ is hydrogen, halogen, or $C_{1-6}$ alkyl; and $R^2$ is a substituted or unsubstituted aryl group or a substituted or unsubstituted heteroaryl group, wherein said heteroaryl group has 1 to 5 heteroatom ring members chosen from O, N, or S.

Para. AF. The compound, or a stereoisomer thereof or a pharmaceutically acceptable salt thereof, of Para. AE, wherein $R^1$ is hydrogen.

Para. AG. The compound, or a stereoisomer thereof or a pharmaceutically acceptable salt thereof, of Para. AE, wherein $R^1$ is halogen.

Para. AH. The compound, or a stereoisomer thereof or a pharmaceutically acceptable salt thereof, of Para. AE, wherein $R^1$ is $C_{1-6}$ alkyl.

Para. AI. The compound, or a stereoisomer thereof or a pharmaceutically acceptable salt thereof, of any one of Paras. AE-AH, wherein $R^2$ is a substituted or unsubstituted aryl group.

Para. AJ. The compound, or a stereoisomer thereof or a pharmaceutically acceptable salt thereof, of Para. AI, wherein $R^2$ is substituted or unsubstituted phenyl.

Para. AK. The compound, or a stereoisomer thereof or a pharmaceutically acceptable salt thereof, of Para. AI, wherein $R^2$ is phenyl substituted with triazolyl, $C_{1-6}$ alkylsulfonyl, or piperazinyl.

Para. AL. The compound, or a stereoisomer thereof or a pharmaceutically acceptable salt thereof, of Para. AI, wherein R² is benzodioxole or 3,4-dihydroquinolin-2-one, wherein said 3,4-dihydroquinolin-2-one is optionally substituted with $C_{1-6}$ alkyl.

Para. AM. The compound, or a stereoisomer thereof or a pharmaceutically acceptable salt thereof, of any one of Paras. AE-AH, wherein R² is a substituted or unsubstituted heteroaryl group, wherein said heteroaryl group has 1 to 5 heteroatom ring members chosen from O, N, or S.

Para. AN. The compound, or a stereoisomer thereof or a pharmaceutically acceptable salt thereof, of Para. AM, wherein R² is substituted or unsubstituted pyridine.

Para. AO. The compound, or a stereoisomer thereof or a pharmaceutically acceptable salt thereof, of Para. AN, wherein R² is pyridine substituted with trifluoromethyl or mono- or di-$C_{1-6}$ alkylamino.

Para. AP. The compound, or a stereoisomer thereof or a pharmaceutically acceptable salt thereof, of Para. AM, wherein R² is substituted or unsubstituted pyrazole.

Para. AQ. The compound, or a stereoisomer thereof or a pharmaceutically acceptable salt thereof, of Para. AP, wherein R² is pyrazole substituted with $C_{1-6}$ alkyl or difluoromethyl.

Para. AR. A compound of Formula 13

(Formula 13)

or a stereoisomer thereof or a pharmaceutically acceptable salt thereof;
wherein
R¹ is hydrogen, halogen, or $C_{1-6}$ alkyl; and
R² is a substituted or unsubstituted aralkoxy group, a substituted or unsubstituted aryl group, or a substituted or unsubstituted heterocyclic group, wherein said heterocyclic group has 1 to 5 heteroatom ring members chosen from O, N, or S, and said heterocyclic group is aromatic or non-aromatic.

Para. AS. The compound, or a stereoisomer thereof or a pharmaceutically acceptable salt thereof, of Para. AR, wherein R¹ is hydrogen.

Para. AT. The compound, or a stereoisomer thereof or a pharmaceutically acceptable salt thereof, of Para. AR, wherein R¹ is halogen.

Para. AU. The compound, or a stereoisomer thereof or a pharmaceutically acceptable salt thereof, of Para. AR, wherein R¹ is $C_{1-6}$ alkyl.

Para. AV. The compound, or a stereoisomer thereof or a pharmaceutically acceptable salt thereof, of any one of Paras. AR-AU, wherein R² is a substituted or unsubstituted aryl group.

Para. AW. The compound, or a stereoisomer thereof or a pharmaceutically acceptable salt thereof, of Para. AV, wherein R² is substituted or unsubstituted phenyl.

Para. AX. The compound, or a stereoisomer thereof or a pharmaceutically acceptable salt thereof, of Para. AW, wherein R² is phenyl substituted with $C_{1-6}$ alkylsulfonyl or piperazinyl.

Para. AY. The compound, or a stereoisomer thereof or a pharmaceutically acceptable salt thereof, of Para. AV, wherein R² is benzodioxole or 3,4-dihydroquinolin-2-one, wherein said 3,4-dihydroquinolin-2-one is optionally substituted with $C_{1-6}$ alkyl.

Para. AZ. The compound, or a stereoisomer thereof or a pharmaceutically acceptable salt thereof, of any one of Paras. AR-AU, wherein R² is a substituted or unsubstituted heteroaryl group, wherein said heteroaryl group has 1 to 5 heteroatom ring members chosen from O, N, or S.

Para. BA. The compound, or a stereoisomer thereof or a pharmaceutically acceptable salt thereof, of Para. AZ, wherein R² is substituted or unsubstituted pyridine.

Para. BB. The compound, or a stereoisomer thereof or a pharmaceutically acceptable salt thereof, of Para. BA, wherein R² is pyridine substituted with mono- or di-$C_{1-6}$ alkylamino.

Para. BC. The compound, or a stereoisomer thereof or a pharmaceutically acceptable salt thereof, of Para. AZ, wherein R² is substituted or unsubstituted pyrazole.

Para. BD. The compound, or a stereoisomer thereof or a pharmaceutically acceptable salt thereof, of Para. BC, wherein R² is pyrazole substituted with $C_{1-6}$ alkyl.

Para. BE. The compound, or a stereoisomer thereof or a pharmaceutically acceptable salt thereof, of any one of Paras. AR-AU, wherein R² is substituted or unsubstituted pyridin-2-one.

Para. BF. The compound, or a stereoisomer thereof or a pharmaceutically acceptable salt thereof, of Para. BE, wherein R² is pyridin-2-one substituted with $C_{1-6}$ alkyl.

Para. BG. The compound, or a stereoisomer thereof or a pharmaceutically acceptable salt thereof, of any one of Paras. AR-AU, wherein R² is substituted or unsubstituted aralkoxy group.

Para. BH. The compound, or a stereoisomer thereof or a pharmaceutically acceptable salt thereof, of Para. BG, wherein R² is substituted or unsubstituted benzyloxy.

Para. BI. A compound of Formula 14

(Formula 14)

or a stereoisomer thereof or a pharmaceutically acceptable salt thereof;
wherein
R¹ is hydrogen, halogen, or $C_{1-6}$ alkyl; and
R² is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

Para. BJ. The compound of Para. BI of Formula 14a (Formula 14a)

Para. BK. The compound of Para. BI of Formula 14b

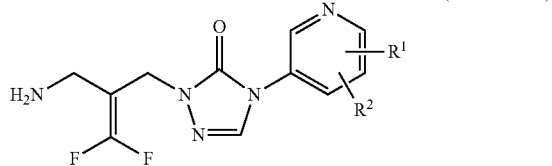
(Formula 14b)

or a stereoisomer thereof or a pharmaceutically acceptable salt thereof.

Para. BL. The compound of Para. BI of Formula 14c

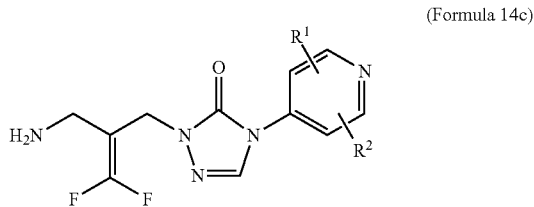
(Formula 14c)

or a stereoisomer thereof or a pharmaceutically acceptable salt thereof.

Para. BM. The compound, or a stereoisomer thereof or a pharmaceutically acceptable salt thereof, of any one of Paras. BI-BL, wherein $R^1$ is hydrogen.

Para. BN. The compound, or a stereoisomer thereof or a pharmaceutically acceptable salt thereof, of any one of Paras. BI-BL, wherein $R^1$ is halogen.

Para. BO. The compound, or a stereoisomer thereof or a pharmaceutically acceptable salt thereof, of any one of Paras. BI-BL, wherein $R^1$ is $C_{1-6}$ alkyl.

Para. BP. The compound, or a stereoisomer thereof or a pharmaceutically acceptable salt thereof, of any one of Paras. BI-BL, wherein $R^2$ is a substituted or unsubstituted aryl group.

Para. BQ. The compound, or a stereoisomer thereof or a pharmaceutically acceptable salt thereof, of Para. BP, wherein $R^2$ is substituted or unsubstituted phenyl.

Para. BR. The compound, or a stereoisomer thereof or a pharmaceutically acceptable salt thereof, of Para. BQ, wherein $R^2$ is phenyl substituted with one to three substituents selected from the group consisting of with halogen, $C_{1-6}$ alkoxy, mono- or di-$C_{1-6}$ alkylamino, mono- or di-$C_{1-6}$ alkylaminosulfonyl, $C_{1-6}$ alkylsulfonyl, morpholinylcarbonyl, piperazinyl, morpholinyl, pyrazolyl, $C_{1-6}$ alkylpyrazolyl, triazolyl, and pyrrolidinonyl.

Para. BS. The compound, or a stereoisomer thereof or a pharmaceutically acceptable salt thereof, of Para. BP, wherein $R^2$ is benzodioxole, benzoxadiazole, benzothiazole, indazole, 2,3-dihydro-1,4-benzoxazine, 1,4-benzoxazin-3-one, 1,4-dihydro-3,1-benzoxazin-2-one, 1,4-dihydroquinazolin-2-one, 3,4-dihydroquinolin-2-one, or benzoxazole, wherein $R^2$ is optionally substituted with $C_{1-6}$ alkyl or amino.

Para. BT. The compound, or a stereoisomer thereof or a pharmaceutically acceptable salt thereof, of any one of Paras. BI-BO, wherein $R^2$ is a substituted or unsubstituted heteroaryl group, wherein said heteroaryl group has 1 to 5 heteroatom ring members chosen from O, N, or S.

Para. BU. The compound, or a stereoisomer thereof or a pharmaceutically acceptable salt thereof, of Para. BT, wherein $R^2$ is substituted or unsubstituted pyridine.

Para. BV. The compound, or a stereoisomer thereof or a pharmaceutically acceptable salt thereof, of Para. BU, wherein $R^2$ is pyridine substituted with $C_{1-6}$ alkoxy, trifluoromethyl, piperazinyl, morpholinyl, or mono- or di-$C_{1-6}$ alkylamino.

Para. BW. The compound, or a stereoisomer thereof or a pharmaceutically acceptable salt thereof, of Para. BT, wherein $R^2$ is pyrimidine, 1H-pyrrolo[2,3-b]pyridine, pyrazole, or thiophene, wherein $R^2$ is optionally substituted with $C_{1-6}$ alkyl, difluoromethyl, $C_{1-6}$ alkoxy-$C_{1-6}$ alkylamino, or $C_{1-6}$ alkylcarbonyl.

Para. BX. The compound, or a stereoisomer thereof or a pharmaceutically acceptable salt thereof, of any one of Paras. BI-BO, wherein $R^2$ is substituted or unsubstituted pyridin-2-one.

Para. BY The compound, or a stereoisomer thereof or a pharmaceutically acceptable salt thereof, of Para. BX, wherein $R^2$ is pyridin-2-one substituted with $C_{1-6}$ alkyl.

Para. BZ. A compound of Formula 15

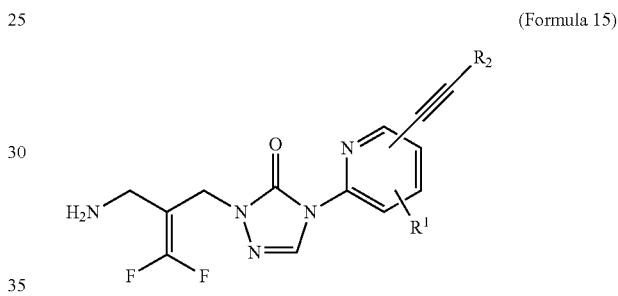
(Formula 15)

or a stereoisomer thereof or a pharmaceutically acceptable salt thereof;
wherein
$R^1$ is hydrogen or $C_{1-6}$ alkyl; and
$R^2$ is a substituted or unsubstituted aryl or a substituted or unsubstituted heteroaryl, wherein said heteroaryl group has 1 to 5 heteroatom ring members chosen from O, N, or S group.

Para. CA. The compound, or a stereoisomer thereof or a pharmaceutically acceptable salt thereof, of Para. BZ, wherein $R^1$ is hydrogen.

Para. CB. The compound, or a stereoisomer thereof or a pharmaceutically acceptable salt thereof, of Para. BZ, wherein $R^1$ is $C_{1-6}$ alkyl.

Para. CC. The compound, or a stereoisomer thereof or a pharmaceutically acceptable salt thereof, of any one of Paras. BZ-CB, wherein $R^2$ is a substituted or unsubstituted aryl group.

Para. CD. The compound, or a stereoisomer thereof or a pharmaceutically acceptable salt thereof, of Para. CC, wherein $R^2$ is substituted or unsubstituted phenyl.

Para. CE. The compound, or a stereoisomer thereof or a pharmaceutically acceptable salt thereof, of Para. CC, wherein $R^2$ is 2,3-dihydro-1,4-benzoxazine or 3,4-dihydroquinolin-2-one, wherein said 3,4-dihydroquinolin-2-one is optionally substituted with $C_{1-6}$ alkyl.

Para. CF. The compound, or a stereoisomer thereof or a pharmaceutically acceptable salt thereof, of any one of Paras. BZ-CB, wherein $R^2$ is a substituted or unsubstituted heteroaryl group, wherein said heteroaryl group has 1 to 5 heteroatom ring members chosen from O, N, or S.

Para. CG. The compound, or a stereoisomer thereof or a pharmaceutically acceptable salt thereof, of Para. CF, wherein $R^2$ is substituted or unsubstituted pyridine.

Para. CH. The compound, or a stereoisomer thereof or a pharmaceutically acceptable salt thereof, of Para. CG, wherein $R^2$ is pyridine substituted with morpholinyl or mono- or di-$C_{1-6}$ alkylamino.

Para. CI. The compound, or a stereoisomer thereof or a pharmaceutically acceptable salt thereof, of Para. CF, wherein $R^2$ is 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, or pyrazole, wherein said pyrazole is optionally substituted with $C_{1-6}$ alkyl.

Para. CJ. A compound of Formula 16

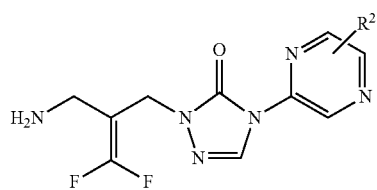

(Formula 16)

or a stereoisomer thereof or a pharmaceutically acceptable salt thereof;

wherein $R^2$ is a substituted or unsubstituted aryl or a substituted or unsubstituted heteroaryl group, wherein said heteroaryl group has 1 to 5 heteroatom ring members chosen from O, N, or S.

Para. CK. The compound, or a stereoisomer thereof or a pharmaceutically acceptable salt thereof, of Para. CJ, wherein $R^2$ is a substituted or unsubstituted aryl group.

Para. CL. The compound, or a stereoisomer thereof or a pharmaceutically acceptable salt thereof, of Para. CK, wherein $R^2$ is substituted or unsubstituted phenyl.

Para. CM. The compound, or a stereoisomer thereof or a pharmaceutically acceptable salt thereof, of Para. CL, wherein $R^2$ is phenyl substituted with $C_{1-6}$ alkylsulfonyl or piperazinyl.

Para. CN. The compound, or a stereoisomer thereof or a pharmaceutically acceptable salt thereof, of Para. CK, wherein $R^2$ is benzodioxole or 3,4-dihydroquinolin-2-one, wherein said 3,4-dihydroquinolin-2-one is optionally substituted with $C_{1-6}$ alkyl.

Para. CO. The compound, or a stereoisomer thereof or a pharmaceutically acceptable salt thereof, of Para. CJ, wherein $R^2$ is a substituted or unsubstituted heteroaryl group, wherein said heteroaryl group has 1 to 5 heteroatom ring members chosen from O, N, or S.

Para. CP. The compound, or a stereoisomer thereof or a pharmaceutically acceptable salt thereof, of Para. CO, wherein $R^2$ is substituted or unsubstituted pyridine.

Para. CQ. The compound, or a stereoisomer thereof or a pharmaceutically acceptable salt thereof, of Para. CQ, wherein $R^2$ is pyridine substituted with trifluoromethyl or mono- or di-$C_{1-6}$ alkylamino.

Para. CR. The compound, or a stereoisomer thereof or a pharmaceutically acceptable salt thereof, of Para. CO, wherein $R^2$ is substituted or unsubstituted pyrazole.

Para. CS. The compound, or a stereoisomer thereof or a pharmaceutically acceptable salt thereof, of Para. CR, wherein $R^2$ is pyrazole substituted with $C_{1-6}$ alkyl.

Para. CT. A compound of Formula 17

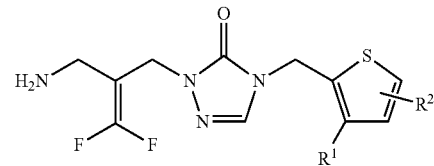

(Formula 17)

or a stereoisomer thereof or a pharmaceutically acceptable salt thereof;

wherein $R^1$ is hydrogen, halogen, or $C_{1-6}$ alkyl; and $R^2$ is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

Para. CU. The compound, or a stereoisomer thereof or a pharmaceutically acceptable salt thereof, of Para. CT, wherein $R^1$ is hydrogen.

Para. CV. The compound, or a stereoisomer thereof or a pharmaceutically acceptable salt thereof, of Para. CT, wherein $R^1$ is halogen.

Para. CW. The compound, or a stereoisomer thereof or a pharmaceutically acceptable salt thereof, of Para. CT, wherein $R^1$ is $C_{1-6}$ alkyl.

Para. CX. The compound, or a stereoisomer thereof or a pharmaceutically acceptable salt thereof, of any one of Paras. CT-CW, wherein $R^2$ is a substituted or unsubstituted aryl group.

Para. CY The compound, or a stereoisomer thereof or a pharmaceutically acceptable salt thereof, of Para. CX, wherein $R^2$ is substituted or unsubstituted phenyl.

Para. CZ. The compound, or a stereoisomer thereof or a pharmaceutically acceptable salt thereof, of Para. CY, wherein $R^2$ is phenyl substituted with one to three substituents selected from the group consisting of $C_{1-6}$ alkoxy, $C_{1-6}$ alkylcarbonyl, $C_{1-6}$ alkylsulfonyl, mono- or di-$C_{1-6}$ alkylaminosulfonyl, mono- or di-$C_{1-6}$ alkylaminocarbonyl, morpholinylcarbonyl, pyrazolyl, $C_{1-6}$ alkylpyrazolyl, triazolyl, piperazinyl, and acetylpiperazinyl.

Para. DA. The compound, or a stereoisomer thereof or a pharmaceutically acceptable salt thereof, of Para. CX, wherein $R^2$ is 3,4-dihydroisoquinolin-1-one, quinolin-2-one, 2,3-dihydro-1,4-benzoxazine, 1,4-benzoxazin-3-one, 1,4-dihydro-3,1-benzoxazin-2-one, 1,4-dihydroquinazolin-2-one, benzothiazole, benzoxadiazole, indazole, benzodioxole, 1,3-dihydroindol-2-one, or 3,4-dihydroquinolin-2-one; wherein $R^2$ is optionally substituted with $C_{1-6}$ alkyl, $C_{1-6}$ alkylcarbonylamino, or halogen.

Para. DB. The compound, or a stereoisomer thereof or a pharmaceutically acceptable salt thereof, of any one of Paras. CT-CW, wherein $R^2$ is a substituted or unsubstituted heteroaryl group, wherein said heteroaryl group has 1 to 5 heteroatom ring members chosen from O, N, or S.

Para. DC. The compound, or a stereoisomer thereof or a pharmaceutically acceptable salt thereof, of Para. DB, wherein $R^2$ is substituted or unsubstituted pyridine.

Para. DD. The compound, or a stereoisomer thereof or a pharmaceutically acceptable salt thereof, of Para. DC, wherein $R^2$ is pyridine substituted with one to three substituents selected from the group consisting of halogen, trifluoromethyl, $C_{1-6}$ alkoxy, piperazinyl and mono- or di-$C_{1-6}$ alkylamino.

Para. DE. The compound, or a stereoisomer thereof or a pharmaceutically acceptable salt thereof, of Para. DB, wherein $R^2$ is substituted or unsubstituted pyrazole.

Para. DF. The compound, or a stereoisomer thereof or a pharmaceutically acceptable salt thereof, of Para. DE, wherein $R^2$ is pyrazole substituted with $C_{1-6}$ alkyl, difluoromethyl, benzyl, (cycloalkyl)alkyl, alkylsulfonyl, or cycloalkylsulfonyl.

Para. DG. The compound, or a stereoisomer thereof or a pharmaceutically acceptable salt thereof, of Para. DB, wherein $R^2$ is 5,6,7,8-tetrahydronaphthyridine, pyrimidine, imidazole, or triazolo[1,5-a]pyridine; wherein $R^2$ is optionally substituted with one to three substituents selected from the group consisting of halogen, $C_{1-6}$ alkyl, $C_{1-6}$ alkoxy, amino, and $C_{1-6}$ alkoxy-$C_{1-6}$ alkylamino.

Para. DH. The compound, or a stereoisomer thereof or a pharmaceutically acceptable salt thereof, of Para. DG, wherein $R^2$ is [1,2,4]triazolo[1,5-a]pyridine.

Para. DI. The compound, or a stereoisomer thereof or a pharmaceutically acceptable salt thereof, of any one of Paras. CT-CW, wherein $R^2$ is tetrahydropyridine or pyridin-2-one, wherein said tetrahydropyridine and said pyridin-2-one are optionally substituted with $C_{1-6}$ alkyl or $C_{1-6}$ alkylcarbonyl.

Para. DJ. A compound of Formula 18

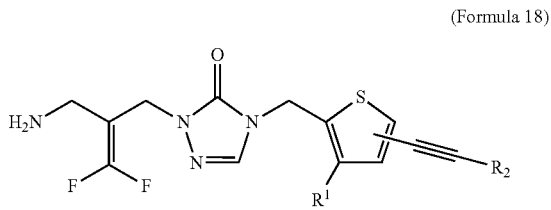

(Formula 18)

or a stereoisomer thereof or a pharmaceutically acceptable salt thereof;

wherein $R^1$ is hydrogen, halogen, or $C_{1-6}$ alkyl; and $R^2$ is a substituted or unsubstituted aryl or a substituted or unsubstituted heteroaryl group, wherein said heteroaryl group has 1 to 5 heteroatom ring members chosen from O, N, or S.

Para. DK. The compound, or a stereoisomer thereof or a pharmaceutically acceptable salt thereof, of Para. DJ, wherein $R^1$ is hydrogen.

Para. DL. The compound, or a stereoisomer thereof or a pharmaceutically acceptable salt thereof, of Para. DJ, wherein $R^1$ is halogen.

Para. DM. The compound, or a stereoisomer thereof or a pharmaceutically acceptable salt thereof, of Para. DJ, wherein $R^1$ is $C_{1-6}$ alkyl.

Para. DN. The compound, or a stereoisomer thereof or a pharmaceutically acceptable salt thereof, of any one of Paras. DJ-DM, wherein $R^2$ is a substituted or unsubstituted aryl group.

Para. DO. The compound, or a stereoisomer thereof or a pharmaceutically acceptable salt thereof, of Para. DM, wherein $R^2$ is substituted or unsubstituted phenyl.

Para. DP. The compound, or a stereoisomer thereof or a pharmaceutically acceptable salt thereof, of Para. DM, wherein $R^2$ is 2,3-dihydro-1,4-benzoxazine or 3,4-dihydroquinolin-2-one.

Para. DQ. The compound, or a stereoisomer thereof or a pharmaceutically acceptable salt thereof, of any one of Paras. DJ-DM, wherein $R^2$ is a substituted or unsubstituted heteroaryl group, wherein said heteroaryl group has 1 to 5 heteroatom ring members chosen from O, N, or S.

Para. DR. The compound, or a stereoisomer thereof or a pharmaceutically acceptable salt thereof, of Para. DQ, wherein $R^2$ is substituted or unsubstituted pyridine.

Para. DS. The compound, or a stereoisomer thereof or a pharmaceutically acceptable salt thereof, of Para. DR, wherein $R^2$ is pyridine substituted with morpholinyl or mono- or di-$C_{1-6}$ alkylamino.

Para. DT. The compound, or a stereoisomer thereof or a pharmaceutically acceptable salt thereof, of Para. DQ, wherein $R^2$ is substituted or unsubstituted pyrazole.

Para. DU. The compound, or a stereoisomer thereof or a pharmaceutically acceptable salt thereof, of Para. DT, wherein $R^2$ is pyrazole substituted with $C_{1-6}$ alkyl.

Para. DV. The compound, or a stereoisomer thereof or a pharmaceutically acceptable salt thereof, of Para. DQ, wherein $R^2$ is 2,3-dihydro-pyrido[2,3-b][1,4]oxazine, 3,4-dihydro-pyrido[3,2-b][1,4]oxazine, pyrido[2,3-b][1,4]oxazin-2-one, or pyrido[3,2-b][1,4]oxazin-3-one.

Para. DW. A compound of Formula 19

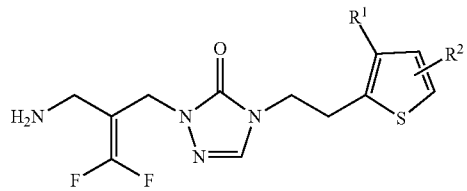

(Formula 19)

or a stereoisomer thereof or a pharmaceutically acceptable salt thereof;

wherein $R^1$ is hydrogen, halogen, or $C_{1-6}$ alkyl; and $R^2$ is a substituted or unsubstituted aryl or a substituted or unsubstituted heteroaryl group, wherein said heteroaryl group has 1 to 5 heteroatom ring members chosen from O, N, or S.

Para. DX. The compound, or a stereoisomer thereof or a pharmaceutically acceptable salt thereof, of Para. DW, wherein $R^1$ is hydrogen.

Para. DY. The compound, or a stereoisomer thereof or a pharmaceutically acceptable salt thereof, of Para. DW, wherein $R^1$ is halogen.

Para. DZ. The compound, or a stereoisomer thereof or a pharmaceutically acceptable salt thereof, of Para. DW, wherein $R^1$ is $C_{1-6}$ alkyl.

Para. EA. The compound, or a stereoisomer thereof or a pharmaceutically acceptable salt thereof, of any one of Paras. DW-DZ, wherein $R^2$ is a substituted or unsubstituted aryl group.

Para. EB. The compound, or a stereoisomer thereof or a pharmaceutically acceptable salt thereof, of Para. EA, wherein $R^2$ is substituted or unsubstituted phenyl.

Para. EC. The compound, or a stereoisomer thereof or a pharmaceutically acceptable salt thereof, of Para. EB, wherein $R^2$ is phenyl substituted with $C_{1-6}$ alkylsulfonyl or piperazinyl.

Para. ED. The compound, or a stereoisomer thereof or a pharmaceutically acceptable salt thereof, of Para. EA, wherein $R^2$ is benzodioxole or 3,4-dihydroquinolin-2-one; wherein $R^2$ is optionally substituted with $C_{1-6}$ alkyl.

Para. EE. The compound, or a stereoisomer thereof or a pharmaceutically acceptable salt thereof, of any one of Paras. DW-DZ, wherein $R^2$ is a substituted or unsubstituted heteroaryl group, wherein said heteroaryl group has 1 to 5 heteroatom ring members chosen from O, N, or S.

Para. EF. The compound, or a stereoisomer thereof or a pharmaceutically acceptable salt thereof, of Para. EE, wherein $R^2$ is substituted or unsubstituted pyridine.

Para. EG. The compound, or a stereoisomer thereof or a pharmaceutically acceptable salt thereof, of Para. EF, wherein $R^2$ is pyridine substituted with trifluoromethyl or mono- or di-$C_{1-6}$ alkylamino.

Para. EH. The compound, or a stereoisomer thereof or a pharmaceutically acceptable salt thereof, of Para. EE, wherein $R^2$ is substituted or unsubstituted pyrazole.

Para. EI. The compound, or a stereoisomer thereof or a pharmaceutically acceptable salt thereof, of Para. EH, wherein $R^2$ is pyrazole substituted with $C_{1-6}$ alkyl.

Para. EJ. A compound of Formula 20

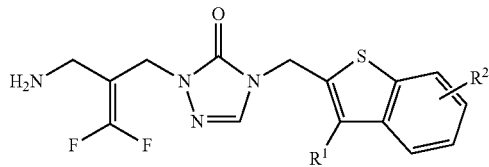

(Formula 20)

or a stereoisomer thereof or a pharmaceutically acceptable salt thereof;
wherein
$R^1$ is hydrogen, halogen, or $C_{1-6}$ alkyl; and
$R^2$ is a substituted or unsubstituted aryl or a substituted or unsubstituted heterocyclic group, wherein said heterocyclic group has 1 to 5 heteroatom ring members chosen from O, N, or S, and said heterocyclic group is aromatic or non-aromatic.

Para. EK. The compound, or a stereoisomer thereof or a pharmaceutically acceptable salt thereof, of Para. EJ, wherein $R^1$ is hydrogen.

Para. EL. The compound, or a stereoisomer thereof or a pharmaceutically acceptable salt thereof, of Para. EJ, wherein $R^1$ is halogen.

Para. EM. The compound, or a stereoisomer thereof or a pharmaceutically acceptable salt thereof, of Para. EJ, wherein $R^1$ is $C_{1-6}$ alkyl.

Para. EN. The compound, or a stereoisomer thereof or a pharmaceutically acceptable salt thereof, of any one of Paras. EJ-EM, wherein $R^2$ is a substituted or unsubstituted aryl group.

Para. EO. The compound, or a stereoisomer thereof or a pharmaceutically acceptable salt thereof, of Para. EN, wherein $R^2$ is substituted or unsubstituted phenyl.

Para. EP. The compound, or a stereoisomer thereof or a pharmaceutically acceptable salt thereof, of Para. EO, wherein $R^2$ is phenyl substituted with $C_{1-6}$ alkylsulfonyl or piperazinyl.

Para. EQ. The compound, or a stereoisomer thereof or a pharmaceutically acceptable salt thereof, of Para. EN, wherein $R^2$ is benzodioxole or 3,4-dihydroquinolin-2-one; wherein $R^2$ is optionally substituted with $C_{1-6}$ alkyl.

Para. ER. The compound, or a stereoisomer thereof or a pharmaceutically acceptable salt thereof, of any one of Paras. EJ-EM, wherein $R^2$ is substituted or unsubstituted heteroaryl group, wherein said heteroaryl group has 1 to 5 heteroatom ring members chosen from O, N, or S.

Para. ES. The compound, or a stereoisomer thereof or a pharmaceutically acceptable salt thereof, of Para. ER, wherein $R^2$ is substituted or unsubstituted pyridine.

Para. ET. The compound, or a stereoisomer thereof or a pharmaceutically acceptable salt thereof, of Para. ES, wherein $R^2$ is pyridine substituted with trifluoromethyl or mono- or di-$C_{1-6}$ alkylamino.

Para. EU. The compound, or a stereoisomer thereof or a pharmaceutically acceptable salt thereof, of Para. ER, wherein $R^2$ is substituted or unsubstituted pyrazole.

Para. EV. The compound, or a stereoisomer thereof or a pharmaceutically acceptable salt thereof, of Para. EU, wherein $R^2$ is pyrazole substituted with $C_{1-6}$ alkyl.

Para. EW. The compound, or a stereoisomer thereof or a pharmaceutically acceptable salt thereof, of any one of Paras. EJ-EM, wherein $R^2$ is a substituted or unsubstituted pyridine-2-one.

Para. EX. The compound, or a stereoisomer thereof or a pharmaceutically acceptable salt thereof, of Para. EW, wherein $R^2$ is pyridine-2-one substituted with $C_{1-6}$ alkyl.

Para. EY. The compound, or a stereoisomer thereof or a pharmaceutically acceptable salt thereof, of Para. A, which is selected from the group consisting of.

2-[2-(aminomethyl)-3,3-difluoro-allyl]-4-(4-fluorophenyl)-1,2,4-triazol-3-one;
2-[2-(aminomethyl)-3,3-difluoro-allyl]-4-(3-bromophenyl)-1,2,4-triazol-3-one;
2-[2-(aminomethyl)-3,3-difluoro-allyl]-4-(3,4-difluorophenyl)-1,2,4-triazol-3-one;
2-[2-(aminomethyl)-3,3-difluoro-allyl]-4-(4-bromo-3-fluoro-phenyl)-1,2,4-triazol-3-one;
2-[2-(aminomethyl)-3,3-difluoro-allyl]-4-(4-bromo-2-fluoro-phenyl)-1,2,4-triazol-3-one;
2-[2-(aminomethyl)-3,3-difluoro-allyl]-4-(4-bromo-2-methyl-phenyl)-1,2,4-triazol-3-one;
2-[2-(aminomethyl)-3,3-difluoro-allyl]-4-(6-bromo-3-pyridyl)-1,2,4-triazol-3-one;
2-[2-(aminomethyl)-3,3-difluoro-allyl]-4-(6-bromo-2-pyridyl)-1,2,4-triazol-3-one;
2-[2-(aminomethyl)-3,3-difluoro-allyl]-4-(4-bromo-2-pyridyl)-1,2,4-triazol-3-one;
2-[2-(aminomethyl)-3,3-difluoro-allyl]-4-(2-bromo-4-pyridyl)-1,2,4-triazol-3-one;
2-[2-(aminomethyl)-3,3-difluoro-allyl]-4-(5-bromo-3-methyl-2-pyridyl)-1,2,4-triazol-3-one;
2-[2-(aminomethyl)-3,3-difluoro-allyl]-4-(6-bromo-4-methyl-3-pyridyl)-1,2,4-triazol-3-one;
2-[2-(aminomethyl)-3,3-difluoro-allyl]-4-(6-bromo-5-methyl-3-pyridyl)-1,2,4-triazol-3-one;
2-[2-(aminomethyl)-3,3-difluoro-allyl]-4-(5-bromo-3-fluoro-2-pyridyl)-1,2,4-triazol-3-one;
2-[2-(aminomethyl)-3,3-difluoro-allyl]-4-(6-bromo-3-methyl-2-pyridyl)-1,2,4-triazol-3-one;
2-[2-(aminomethyl)-3,3-difluoro-allyl]-4-(5-bromopyrazin-2-yl)-1,2,4-triazol-3-one;
2-[2-(aminomethyl)-3,3-difluoro-allyl]-4-[3-(4-methylsulfonylphenyl)phenyl]-1,2,4-triazol-3-one;
2-[2-(aminomethyl)-3,3-difluoro-allyl]-4-[3-(4-piperazin-1-ylphenyl)phenyl]-1,2,4-triazol-3-one;
2-[2-(aminomethyl)-3,3-difluoro-allyl]-4-[3-[6-(trifluoromethyl)-3-pyridyl]phenyl]-1,2,4-triazol-3-one;
2-[2-(aminomethyl)-3,3-difluoro-allyl]-4-[3-[6-(dimethylamino)-3-pyridyl]phenyl]-1,2,4-triazol-3-one;
2-[2-(aminomethyl)-3,3-difluoro-allyl]-4-[3-(1,3-benzodioxol-5-yl)phenyl]-1,2,4-triazol-3-one;

6-[3-[1-[2-(aminomethyl)-3,3-difluoro-allyl]-5-oxo-1,2,4-triazol-4-yl]phenyl]-8-methyl-3,4-dihydro-1H-quinolin-2-one;
2-[2-(aminomethyl)-3,3-difluoro-allyl]-4-[3-(1-ethylpyrazol-4-yl)phenyl]-1,2,4-triazol-3-one;
2-[2-(aminomethyl)-3,3-difluoro-allyl]-4-[3-fluoro-4-(4-methylsulfonylphenyl)phenyl]-1,2,4-triazol-3-one;
2-[2-(aminomethyl)-3,3-difluoro-allyl]-4-[3-fluoro-4-(4-piperazin-1-ylphenyl)phenyl]-1,2,4-triazol-3-one;
2-[2-(aminomethyl)-3,3-difluoro-allyl]-4-[3-fluoro-4-[6-(trifluoromethyl)-3-pyridyl]phenyl]-1,2,4-triazol-3-one;
2-[2-(aminomethyl)-3,3-difluoro-allyl]-4-[4-[6-(dimethylamino)-3-pyridyl]-3-fluoro-phenyl]-1,2,4-triazol-3-one;
2-[2-(aminomethyl)-3,3-difluoro-allyl]-4-[4-(1,3-benzodioxol-5-yl)-3-fluoro-phenyl]-1,2,4-triazol-3-one;
6-[4-[1-[2-(aminomethyl)-3,3-difluoro-allyl]-5-oxo-1,2,4-triazol-4-yl]-2-fluoro-phenyl]-8-methyl-3,4-dihydro-1H-quinolin-2-one;
2-[2-(aminomethyl)-3,3-difluoro-allyl]-4-[4-(1-ethylpyrazol-4-yl)-3-fluoro-phenyl]-1,2,4-triazol-3-one;
2-[2-(aminomethyl)-3,3-difluoro-allyl]-4-[2-fluoro-4-(4-methylsulfonylphenyl)phenyl]-1,2,4-triazol-3-one;
2-[2-(aminomethyl)-3,3-difluoro-allyl]-4-[2-fluoro-4-(4-piperazin-1-ylphenyl)phenyl]-1,2,4-triazol-3-one;
2-[2-(aminomethyl)-3,3-difluoro-allyl]-4-[2-fluoro-4-[6-(trifluoromethyl)-3-pyridyl]phenyl]-1,2,4-triazol-3-one;
2-[2-(aminomethyl)-3,3-difluoro-allyl]-4-[4-[6-(dimethylamino)-3-pyridyl]-2-fluoro-phenyl]-1,2,4-triazol-3-one;
2-[2-(aminomethyl)-3,3-difluoro-allyl]-4-[4-(1,3-benzodioxol-5-yl)-2-fluoro-phenyl]-1,2,4-triazol-3-one;
6-[4-[1-[2-(aminomethyl)-3,3-difluoro-allyl]-5-oxo-1,2,4-triazol-4-yl]-3-fluoro-phenyl]-8-methyl-3,4-dihydro-1H-quinolin-2-one;
2-[2-(aminomethyl)-3,3-difluoro-allyl]-4-[4-(1-ethylpyrazol-4-yl)-2-fluoro-phenyl]-1,2,4-triazol-3-one;
2-[2-(aminomethyl)-3,3-difluoro-allyl]-4-[6-(4-methylsulfonylphenyl)-3-pyridyl]-1,2,4-triazol-3-one;
2-[2-(aminomethyl)-3,3-difluoro-allyl]-4-[6-(4-piperazin-1-ylphenyl)-3-pyridyl]-1,2,4-triazol-3-one;
2-[2-(aminomethyl)-3,3-difluoro-allyl]-4-[6-[6-(trifluoromethyl)-3-pyridyl]-3-pyridyl]-1,2,4-triazol-3-one;
2-[2-(aminomethyl)-3,3-difluoro-allyl]-4-[6-[6-(dimethylamino)-3-pyridyl]-3-pyridyl]-1,2,4-triazol-3-one;
2-[2-(aminomethyl)-3,3-difluoro-allyl]-4-[6-(1,3-benzodioxol-5-yl)-3-pyridyl]-1,2,4-triazol-3-one;
6-[5-[1-[2-(aminomethyl)-3,3-difluoro-allyl]-5-oxo-1,2,4-triazol-4-yl]-2-pyridyl]-8-methyl-3,4-dihydro-1H-quinolin-2-one;
6-[5-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[6-(1-ethylpyrazol-4-yl)-3-pyridyl]-1,2,4-triazol-3-one;
2-[2-(aminomethyl)-3,3-difluoro-allyl]-4-[6-(4-methylsulfonylphenyl)-2-pyridyl]-1,2,4-triazol-3-one;
2-[2-(aminomethyl)-3,3-difluoro-allyl]-4-[6-(4-piperazin-1-ylphenyl)-2-pyridyl]-1,2,4-triazol-3-one;
2-[2-(aminomethyl)-3,3-difluoro-allyl]-4-[6-[6-(trifluoromethyl)-3-pyridyl]-2-pyridyl]-1,2,4-triazol-3-one;
2-[2-(aminomethyl)-3,3-difluoro-allyl]-4-[6-[6-(dimethylamino)-3-pyridyl]-2-pyridyl]-1,2,4-triazol-3-one;
2-[2-(aminomethyl)-3,3-difluoro-allyl]-4-[6-(1,3-benzodioxol-5-yl)-2-pyridyl]-1,2,4-triazol-3-one;
6-[6-[1-[2-(aminomethyl)-3,3-difluoro-allyl]-5-oxo-1,2,4-triazol-4-yl]-2-pyridyl]-8-methyl-3,4-dihydro-1H-quinolin-2-one;
6-[6-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[6-(1-ethylpyrazol-4-yl)-2-pyridyl]-1,2,4-triazol-3-one;
2-[2-(aminomethyl)-3,3-difluoro-allyl]-4-[4-(4-methylsulfonylphenyl)-2-pyridyl]-1,2,4-triazol-3-one;
2-[2-(aminomethyl)-3,3-difluoro-allyl]-4-[4-(4-piperazin-1-ylphenyl)-2-pyridyl]-1,2,4-triazol-3-one;
2-[2-(aminomethyl)-3,3-difluoro-allyl]-4-[4-[6-(trifluoromethyl)-3-pyridyl]-2-pyridyl]-1,2,4-triazol-3-one;
2-[2-(aminomethyl)-3,3-difluoro-allyl]-4-[4-[6-(dimethylamino)-3-pyridyl]-2-pyridyl]-1,2,4-triazol-3-one;
2-[2-(aminomethyl)-3,3-difluoro-allyl]-4-[4-(1,3-benzodioxol-5-yl)-2-pyridyl]-1,2,4-triazol-3-one;
6-[2-[1-[2-(aminomethyl)-3,3-difluoro-allyl]-5-oxo-1,2,4-triazol-4-yl]-4-pyridyl]-8-methyl-3,4-dihydro-1H-quinolin-2-one;
2-[2-(aminomethyl)-3,3-difluoro-allyl]-4-[4-(1-ethylpyrazol-4-yl)-2-pyridyl]-1,2,4-triazol-3-one;
2-[2-(aminomethyl)-3,3-difluoro-allyl]-4-[2-(4-methylsulfonylphenyl)-4-pyridyl]-1,2,4-triazol-3-one;
2-[2-(aminomethyl)-3,3-difluoro-allyl]-4-[2-(4-piperazin-1-ylphenyl)-4-pyridyl]-1,2,4-triazol-3-one;
2-[2-(aminomethyl)-3,3-difluoro-allyl]-4-[2-[6-(dimethylamino)-3-pyridyl]-4-pyridyl]-1,2,4-triazol-3-one;
2-[2-(aminomethyl)-3,3-difluoro-allyl]-4-[2-(1,3-benzodioxol-5-yl)-4-pyridyl]-1,2,4-triazol-3-one;
6-[4-[1-[2-(aminomethyl)-3,3-difluoro-allyl]-5-oxo-1,2,4-triazol-4-yl]-2-pyridyl]-8-methyl-3,4-dihydro-1H-quinolin-2-one;
6-[4-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[2-(1-ethylpyrazol-4-yl)-4-pyridyl]-1,2,4-triazol-3-one;
2-[2-(aminomethyl)-3,3-difluoro-allyl]-4-[3-methyl-5-(4-methylsulfonylphenyl)-2-pyridyl]-1,2,4-triazol-3-one;
2-[2-(aminomethyl)-3,3-difluoro-allyl]-4-[3-methyl-5-(4-piperazin-1-ylphenyl)-2-pyridyl]-1,2,4-triazol-3-one;
2-[2-(aminomethyl)-3,3-difluoro-allyl]-4-[3-methyl-5-[6-(trifluoromethyl)-3-pyridyl]-2-pyridyl]-1,2,4-triazol-3-one;
2-[2-(aminomethyl)-3,3-difluoro-allyl]-4-[5-[6-(dimethylamino)-3-pyridyl]-3-methyl-2-pyridyl]-1,2,4-triazol-3-one;
2-[2-(aminomethyl)-3,3-difluoro-allyl]-4-[5-(1,3-benzodioxol-5-yl)-3-methyl-2-pyridyl]-1,2,4-triazol-3-one;
6-[6-[1-[2-(aminomethyl)-3,3-difluoro-allyl]-5-oxo-1,2,4-triazol-4-yl]-5-methyl-3-pyridyl]-8-methyl-3,4-dihydro-1H-quinolin-2-one;
6-[6-[1-[2-(aminomethyl)-3,3-difluoro-allyl]-5-oxo-1,2,4-triazol-4-yl]-5-methyl-3-pyridyl]-1-methyl-3,4-dihydroquinolin-2-one;
2-[2-(aminomethyl)-3,3-difluoro-allyl]-4-[5-(1-ethylpyrazol-4-yl)-3-methyl-2-pyridyl]-1,2,4-triazol-3-one;
2-[2-(aminomethyl)-3,3-difluoro-allyl]-4-[5-methyl-6-(4-methylsulfonylphenyl)-3-pyridyl]-1,2,4-triazol-3-one;
2-[2-(aminomethyl)-3,3-difluoro-allyl]-4-[5-methyl-6-[6-(trifluoromethyl)-3-pyridyl]-3-pyridyl]-1,2,4-triazol-3-one;
2-[2-(aminomethyl)-3,3-difluoro-allyl]-4-[6-[6-(dimethylamino)-3-pyridyl]-5-methyl-3-pyridyl]-1,2,4-triazol-3-one;
2-[2-(aminomethyl)-3,3-difluoro-allyl]-4-[6-(1,3-benzodioxol-5-yl)-5-methyl-3-pyridyl]-1,2,4-triazol-3-one;

6-[5-[1-[2-(aminomethyl)-3,3-difluoro-allyl]-5-oxo-1,2,4-triazol-4-yl]-3-methyl-2-pyridyl]-8-methyl-3,4-dihydro-1H-quinolin-2-one;

6-[5-[1-[2-(aminomethyl)-3,3-difluoro-allyl]-5-oxo-1,2,4-triazol-4-yl]-3-methyl-2-pyridyl]-1-methyl-3,4-dihydroquinolin-2-one;

2-[2-(aminomethyl)-3,3-difluoro-allyl]-4-[3-fluoro-5-(4-methylsulfonylphenyl)-2-pyridyl]-1,2,4-triazol-3-one;

2-[2-(aminomethyl)-3,3-difluoro-allyl]-4-[3-fluoro-5-(4-piperazin-1-ylphenyl)-2-pyridyl]-1,2,4-triazol-3-one;

2-[2-(aminomethyl)-3,3-difluoro-allyl]-4-[3-fluoro-5-[6-(trifluoromethyl)-3-pyridyl]-2-pyridyl]-1,2,4-triazol-3-one;

2-[2-(aminomethyl)-3,3-difluoro-allyl]-4-[5-(1,3-benzodioxol-5-yl)-3-fluoro-2-pyridyl]-1,2,4-triazol-3-one;

6-[6-[1-[2-(aminomethyl)-3,3-difluoro-allyl]-5-oxo-1,2,4-triazol-4-yl]-5-fluoro-3-pyridyl]-8-methyl-3,4-dihydro-1H-quinolin-2-one;

6-[6-[1-[2-(aminomethyl)-3,3-difluoro-allyl]-5-oxo-1,2,4-triazol-4-yl]-5-fluoro-3-pyridyl]-1-methyl-3,4-dihydroquinolin-2-one;

2-[2-(aminomethyl)-3,3-difluoro-allyl]-4-[5-(1-ethylpyrazol-4-yl)-3-fluoro-2-pyridyl]-1,2,4-triazol-3-one;

2-[2-(aminomethyl)-3,3-difluoro-allyl]-4-[5-(4-methylsulfonylphenyl)-pyrazin-2-yl]-1,2,4-triazol-3-one;

2-[2-(aminomethyl)-3,3-difluoro-allyl]-4-[5-(4-piperazin-1-ylphenyl)pyrazin-2-yl]-1,2,4-triazol-3-one;

2-[2-(aminomethyl)-3,3-difluoro-allyl]-4-[5-[6-(trifluoromethyl)-3-pyridyl]pyrazin-2-yl]-1,2,4-triazol-3-one;

2-[2-(aminomethyl)-3,3-difluoro-allyl]-4-[5-[6-(dimethylamino)-3-pyridyl]pyrazin-2-yl]-1,2,4-triazol-3-one;

2-[2-(aminomethyl)-3,3-difluoro-allyl]-4-[5-(1,3-benzodioxol-5-yl)pyrazin-2-yl]-1,2,4-triazol-3-one;

6-[5-[1-[2-(aminomethyl)-3,3-difluoro-allyl]-5-oxo-1,2,4-triazol-4-yl]pyrazin-2-yl]-1-methyl-3,4-dihydro-1H-quinolin-2-one;

2-[2-(aminomethyl)-3,3-difluoro-allyl]-4-[5-(1-ethylpyrazol-4-yl)pyrazin-2-yl]-1,2,4-triazol-3-one;

2-[2-(aminomethyl)-3,3-difluoro-allyl]-4-[(4-benzyloxyphenyl)methyl]-1,2,4-triazol-3-one;

2-[2-(aminomethyl)-3,3-difluoro-allyl]-4-[(5-bromo-2-thienyl)methyl]-1,2,4-triazol-3-one;

2-[2-(aminomethyl)-3,3-difluoro-allyl]-4-[(4-bromo-2-thienyl)methyl]-1,2,4-triazol-3-one;

2-[2-(aminomethyl)-3,3-difluoro-allyl]-4-[(5-bromo-3-methyl-2-thienyl)methyl]-1,2,4-triazol-3-one;

4-[[5-(4-acetylphenyl)-2-thienyl]methyl]-2-[2-(aminomethyl)-3,3-difluoro-allyl]-1,2,4-triazol-3-one;

2-[2-(aminomethyl)-3,3-difluoro-allyl]-4-[[5-(4-methylsulfonylphenyl)-2-thienyl]methyl]-1,2,4-triazol-3-one;

2-[2-(aminomethyl)-3,3-difluoro-allyl]-4-[[5-(3-methylsulfonylphenyl)-2-thienyl]methyl]-1,2,4-triazol-3-one;

3-[5-[[1-[2-(aminomethyl)-3,3-difluoro-allyl]-5-oxo-1,2,4-triazol-4-yl]methyl]-2-thienyl]-N,N-dimethyl-benzenesulfonamide;

4-[5-[[1-[2-(aminomethyl)-3,3-difluoro-allyl]-5-oxo-1,2,4-triazol-4-yl]methyl]-2-thienyl]-N-methyl-benzamide;

2-[2-(aminomethyl)-3,3-difluoro-allyl]-4-[[5-(3,4,5-trimethoxyphenyl)-2-thienyl]methyl]-1,2,4-triazol-3-one;

2-[2-(aminomethyl)-3,3-difluoro-allyl]-4-[[5-(4-piperazin-1-ylphenyl)-2-thienyl]methyl]-1,2,4-triazol-3-one;

2-[2-(aminomethyl)-3,3-difluoro-allyl]-4-[[5-(3-piperazin-1-ylphenyl)-2-thienyl]methyl]-1,2,4-triazol-3-one;

4-[[5-[4-(4-acetylpiperazin-1-yl)phenyl]-2-thienyl]methyl]-2-[2-(aminomethyl)-3,3-difluoro-allyl]-1,2,4-triazol-3-one;

2-[2-(aminomethyl)-3,3-difluoro-allyl]-4-[[5-(4-morpholine-4-carbonyl)phenyl]-2-thienyl]methyl]-1,2,4-triazol-3-one;

2-[2-(aminomethyl)-3,3-difluoro-allyl]-4-[[5-3-(1H-pyrazol-3-yl)phenyl]-2-thienyl]methyl]-1,2,4-triazol-3-one;

2-[2-(aminomethyl)-3,3-difluoro-allyl]-4-[[5-[6-(trifluoromethyl)-3-pyridyl]-2-thienyl]methyl]-1,2,4-triazol-3-one;

2-[2-(aminomethyl)-3,3-difluoro-allyl]-4-[[5-[6-(dimethylamino)-3-pyridyl]-2-thienyl]methyl]-1,2,4-triazol-3-one;

2-[2-(aminomethyl)-3,3-difluoro-allyl]-4-[[5-(6-methoxy-3-pyridyl)-2-thienyl]methyl]-1,2,4-triazol-3-one;

2-[2-(aminomethyl)-3,3-difluoro-allyl]-4-[[5-(6-piperazin-1-yl-3-pyridyl)-2-thienyl]methyl]-1,2,4-triazol-3-one;

2-[2-(aminomethyl)-3,3-difluoro-allyl]-4-[[5-[6-(dimethylamino)-5-fluoro-3-pyridyl]-2-thienyl]methyl]-1,2,4-triazol-3-one;

2-[2-(aminomethyl)-3,3-difluoro-allyl]-4-[[5-(2-aminopyrimidin-5-yl)-2-thienyl]methyl]-1,2,4-triazol-3-one;

2-[2-(aminomethyl)-3,3-difluoro-allyl]-4-[[5-(2-ethoxypyrimidin-5-yl)-2-thienyl]methyl]-1,2,4-triazol-3-one;

2-[2-(aminomethyl)-3,3-difluoro-allyl]-4-[[5-[2-(2-methoxyethylamino)pyrimidin-5-yl]-2-thienyl]methyl]-1,2,4-triazol-3-one;

2-[2-(aminomethyl)-3,3-difluoro-allyl]-4-[[5-(1-ethylpyrazol-4-yl)-2-thienyl]methyl]-1,2,4-triazol-3-one;

2-[2-(aminomethyl)-3,3-difluoro-allyl]-4-[[5-(2-chloro-3-methyl-imidazol-4-yl)-2-thienyl]methyl]-1,2,4-triazol-3-one;

5-[5-[[1-[2-(aminomethyl)-3,3-difluoro-allyl]-5-oxo-1,2,4-triazol-4-yl]methyl]-2-thienyl]-1-methyl-pyridin-2-one;

5-[5-[[1-[2-(aminomethyl)-3,3-difluoro-allyl]-5-oxo-1,2,4-triazol-4-yl]methyl]-2-thienyl]-1-ethyl-pyridin-2-one;

5-[5-[[1-[2-(aminomethyl)-3,3-difluoro-allyl]-5-oxo-1,2,4-triazol-4-yl]methyl]-2-thienyl]-1-isopropyl-pyridin-2-one;

2-[2-(aminomethyl)-3,3-difluoro-allyl]-4-[[5-(1-methyl-3,6-dihydro-2H-pyridin-4-yl)-2-thienyl]methyl]-1,2,4-triazol-3-one;

2-[2-(aminomethyl)-3,3-difluoro-allyl]-4-[[5-(1-acetyl-3,6-dihydro-2H-pyridin-4-yl)-2-thienyl]methyl]-1,2,4-triazol-3-one;

2-[2-(aminomethyl)-3,3-difluoro-allyl]-4-[[5-(1,3-benzodioxol-5-yl)-2-thienyl]methyl]-1,2,4-triazol-3-one;

2-[2-(aminomethyl)-3,3-difluoro-allyl]-4-[[5-(1H-indazol-6-yl)-2-thienyl]methyl]-1,2,4-triazol-3-one;

2-[2-(aminomethyl)-3,3-difluoro-allyl]-4-[[5-([1,2,4]triazolo[1,5-a]pyridin-7-yl)-2-thienyl]methyl]-1,2,4-triazol-3-one;

2-[2-(aminomethyl)-3,3-difluoro-allyl]-4-[[5-(2,1,3-benzoxadiazol-5-yl)-2-thienyl]methyl]-1,2,4-triazol-3-one;

5-[5-[[1-[2-(aminomethyl)-3,3-difluoro-allyl]-5-oxo-1,2,4-triazol-4-yl]methyl]-2-thienyl]-7-fluoro-indolin-2-one;

N-[6-[5-[[1-[2-(aminomethyl)-3,3-difluoro-allyl]-5-oxo-1,2,4-triazol-4-yl]methyl]-2-thienyl]-1,3-benzothiazol-2-yl]acetamide;

7-[5-[[1-[2-(aminomethyl)-3,3-difluoro-allyl]-5-oxo-1,2,4-triazol-4-yl]methyl]-2-thienyl]-3,4-dihydro-2H-isoquinolin-1-one;

6-[5-[[1-[2-(aminomethyl)-3,3-difluoro-allyl]-5-oxo-1,2,4-triazol-4-yl]methyl]-2-thienyl]-3,4-dihydro-TH-quinolin-2-one;

6-[5-[[1-[2-(aminomethyl)-3,3-difluoro-allyl]-5-oxo-1,2,4-triazol-4-yl]methyl]-2-thienyl]-8-methyl-3,4-dihydro-1H-quinolin-2-one;

6-[5-[[1-[2-(aminomethyl)-3,3-difluoro-allyl]-5-oxo-1,2,4-triazol-4-yl]methyl]-2-thienyl]-8-methyl-TH-quinolin-2-one;

6-[5-[[1-[2-(aminomethyl)-3,3-difluoro-allyl]-5-oxo-1,2,4-triazol-4-yl]methyl]-2-thienyl]-8-fluoro-3,4-dihydro-1H-quinolin-2-one;

6-[5-[[1-[2-(aminomethyl)-3,3-difluoro-allyl]-5-oxo-1,2,4-triazol-4-yl]methyl]-2-thienyl]-8-fluoro-1H-quinolin-2-one;

6-[5-[[1-[2-(aminomethyl)-3,3-difluoro-allyl]-5-oxo-1,2,4-triazol-4-yl]methyl]-2-thienyl]-1-methyl-3,4-dihydroquinolin-2-one;

2-[2-(aminomethyl)-3,3-difluoro-allyl]-4-[[5-(5-methyl-3,4-dihydro-2H-1,4-benzoxazin-6-yl)-2-thienyl]methyl]-1,2,4-triazol-3-one;

2-[2-(aminomethyl)-3,3-difluoro-allyl]-4-[[5-(4-methyl-2,3-dihydro-1,4-benzoxazin-7-yl)-2-thienyl]methyl]-1,2,4-triazol-3-one;

6-[5-[[1-[2-(aminomethyl)-3,3-difluoro-allyl]-5-oxo-1,2,4-triazol-4-yl]methyl]-2-thienyl]-4H-1,4-benzoxazin-3-one;

7-[5-[[1-[2-(aminomethyl)-3,3-difluoro-allyl]-5-oxo-1,2,4-triazol-4-yl]methyl]-2-thienyl]-1,4-dihydro-3,1-benzoxazin-2-one;

6-[5-[[1-[2-(aminomethyl)-3,3-difluoro-allyl]-5-oxo-1,2,4-triazol-4-yl]methyl]-2-thienyl]-1,4-dihydro-3,1-benzoxazin-2-one;

7-[5-[[1-[2-(aminomethyl)-3,3-difluoro-allyl]-5-oxo-1,2,4-triazol-4-yl]methyl]-2-thienyl]-4-methyl-1,4-benzoxazin-3-one;

2-[2-(aminomethyl)-3,3-difluoro-allyl]-4-[[5-(5,6,7,8-tetrahydro-1,8-naphthyridin-3-yl)-2-thienyl]methyl]-1,2,4-triazol-3-one;

2-[2-(aminomethyl)-3,3-difluoro-allyl]-4-[[4-(4-methylsulfonylphenyl)-2-thienyl]methyl]-1,2,4-triazol-3-one;

2-[2-(aminomethyl)-3,3-difluoro-allyl]-4-[[4-(4-piperazin-1-ylphenyl)-2-thienyl]methyl]-1,2,4-triazol-3-one;

2-[2-(aminomethyl)-3,3-difluoro-allyl]-4-[[4-[6-(trifluoromethyl)-3-pyridyl]-2-thienyl]methyl]-1,2,4-triazol-3-one;

2-[2-(aminomethyl)-3,3-difluoro-allyl]-4-[[4-[6-(dimethylamino)-3-pyridyl]-2-thienyl]methyl]-1,2,4-triazol-3-one;

2-[2-(aminomethyl)-3,3-difluoro-allyl]-4-[[4-(1,3-benzodioxol-5-yl)-2-thienyl]methyl]-1,2,4-triazol-3-one;

6-[5-[[1-[2-(aminomethyl)-3,3-difluoro-allyl]-5-oxo-1,2,4-triazol-4-yl]methyl]-3-thienyl]-8-methyl-3,4-dihydro-1H-quinolin-2-one;

6-[5-[[1-[2-(aminomethyl)-3,3-difluoro-allyl]-5-oxo-1,2,4-triazol-4-yl]methyl]-3-thienyl]-1-methyl-3,4-dihydroquinolin-2-one;

2-[2-(aminomethyl)-3,3-difluoro-allyl]-4-[[4-(1-ethylpyrazol-4-yl)-2-thienyl]methyl]-1,2,4-triazol-3-one;

2-[2-(aminomethyl)-3,3-difluoro-allyl]-4-[[3-methyl-5-(4-methylsulfonylphenyl)-2-thienyl]methyl]-1,2,4-triazol-3-one;

2-[2-(aminomethyl)-3,3-difluoro-allyl]-4-[[3-methyl-5-(4-piperazin-1-ylphenyl)-2-thienyl]methyl]-1,2,4-triazol-3-one;

2-[2-(aminomethyl)-3,3-difluoro-allyl]-4-[[3-methyl-5-[6-(trifluoromethyl)-3-pyridyl]-2-thienyl]methyl]-1,2,4-triazol-3-one;

2-[2-(aminomethyl)-3,3-difluoro-allyl]-4-[[5-[6-(dimethylamino)-3-pyridyl]-3-methyl-2-thienyl]methyl]-1,2,4-triazol-3-one;

2-[2-(aminomethyl)-3,3-difluoro-allyl]-4-[[5-(1,3-benzodioxol-5-yl)-3-methyl-2-thienyl]methyl]-1,2,4-triazol-3-one;

2-[2-(aminomethyl)-3,3-difluoro-allyl]-4-[[5-(1-ethylpyrazol-4-yl)-3-methyl-2-thienyl]methyl]-1,2,4-triazol-3-one;

2-[2-(aminomethyl)-3,3-difluoro-allyl]-4-[6-[2-(1-methylpyrazol-4-yl)ethynyl]-2-pyridyl]-1,2,4-triazol-3-one;

7-[(E)-2-[5-[[1-[2-(aminomethyl)-3,3-difluoro-allyl]-5-oxo-1,2,4-triazol-4-yl]methyl]-2-thienyl]vinyl]-1H-pyrido[2,3-b][1,4]oxazin-2-one;

2-[2-(aminomethyl)-3,3-difluoro-allyl]-4-[[5-[2-[6-(dimethylamino)-3-pyridyl]ethynyl]-2-thienyl]methyl]-1,2,4-triazol-3-one;

2-[2-(aminomethyl)-3,3-difluoro-allyl]-4-[[5-[2-(6-morpholino-3-pyridyl)ethynyl]-2-thienyl]methyl]-1,2,4-triazol-3-one;

2-[2-(aminomethyl)-3,3-difluoro-allyl]-4-[[5-[2-(3,4-dihydro-2H-1,4-benzoxazin-6-yl)ethynyl]-2-thienyl]methyl]-1,2,4-triazol-3-one;

6-[2-[5-[[1-[2-(aminomethyl)-3,3-difluoro-allyl]-5-oxo-1,2,4-triazol-4-yl]methyl]-2-thienyl]ethynyl]-3,4-dihydro-1H-quinolin-2-one;

2-[2-(aminomethyl)-3,3-difluoro-allyl]-4-[[5-[2-(2,3-dihydro-1H-pyrido[2,3-b][1,4]oxazin-7-yl)ethynyl]-2-thienyl]methyl]-1,2,4-triazol-3-one;

2-[2-(aminomethyl)-3,3-difluoro-allyl]-4-[[5-[2-(3,4-dihydro-2H-pyrido[3,2-b][1,4]oxazin-7-yl)ethynyl]-2-thienyl]methyl]-1,2,4-triazol-3-one;

2-[2-(aminomethyl)-3,3-difluoro-allyl]-4-[[5-[2-(2,3-dihydro-1H-pyrido[2,3-b][1,4]oxazin-6-yl)ethynyl]-2-thienyl]methyl]-1,2,4-triazol-3-one;

7-[2-[5-[[1-[2-(aminomethyl)-3,3-difluoro-allyl]-5-oxo-1,2,4-triazol-4-yl]methyl]-2-thienyl]ethynyl]-1H-pyrido[2,3-b][1,4]oxazin-2-one;

7-[2-[5-[[1-[2-(aminomethyl)-3,3-difluoro-allyl]-5-oxo-1,2,4-triazol-4-yl]methyl]-2-thienyl]ethynyl]-4H-pyrido[3,2-b][1,4]oxazin-3-one;

2-[2-(aminomethyl)-3,3-difluoro-allyl]-4-[[5-[2-(1-methylpyrazol-4-yl)ethynyl]-2-thienyl]methyl]-1,2,4-triazol-3-one;

2-[2-(aminomethyl)-3,3-difluoro-allyl]-4-[2-(2-thienyl)ethyl]-1,2,4-triazol-3-one;

2-[2-(aminomethyl)-3,3-difluoro-allyl]-4-[2-[5-(4-methylsulfonylphenyl)-2-thienyl]ethyl]-1,2,4-triazol-3-one;

2-[2-(aminomethyl)-3,3-difluoro-allyl]-4-[2-[5-(4-piperazin-1-ylphenyl)-2-thienyl]ethyl]-1,2,4-triazol-3-one;

2-[2-(aminomethyl)-3,3-difluoro-allyl]-4-[2-[5-[6-(trifluoromethyl)-3-pyridyl]-2-thienyl]ethyl]-1,2,4-triazol-3-one;

2-[2-(aminomethyl)-3,3-difluoro-allyl]-4-[2-[5-[6-(dimethylamino)-3-pyridyl]-2-thienyl]ethyl]-1,2,4-triazol-3-one;

2-[2-(aminomethyl)-3,3-difluoro-allyl]-4-[2-[5-(1,3-benzodioxol-5-yl)-2-thienyl]ethyl]-1,2,4-triazol-3-one;

6-[5-[2-[1-[2-(aminomethyl)-3,3-difluoro-allyl]-5-oxo-1,2,4-triazol-4-yl]ethyl]-2-thienyl]-8-methyl-3,4-dihydro-1H-quinolin-2-one;

6-[5-[2-[1-[2-(aminomethyl)-3,3-difluoro-allyl]-5-oxo-1,2,4-triazol-4-yl]ethyl]-2-thienyl]-1-methyl-3,4-dihydroquinolin-2-one;

2-[2-(aminomethyl)-3,3-difluoro-allyl]-4-[2-[5-(1-ethylpyrazol-4-yl)-2-thienyl]ethyl]-1,2,4-triazol-3-one;

3-[5-[[1-[2-(aminomethyl)-3,3-difluoro-allyl]-5-oxo-1,2,4-triazol-4-yl]methyl]-2-thienyl]-N,N-dimethyl-benzamide;

6-[5-[[1-[2-(aminomethyl)-3,3-difluoro-allyl]-5-oxo-1,2,4-triazol-4-yl]methyl]-2-thienyl]-3-methyl-1,4-dihydroquinazolin-2-one;

2-[2-(aminomethyl)-3,3-difluoro-allyl]-4-[[5-[1-(difluoromethyl)pyrazol-4-yl]-2-thienyl]methyl]-1,2,4-triazol-3-one;

2-[2-(aminomethyl)-3,3-difluoro-allyl]-4-[[5-(1-isopropylpyrazol-4-yl)-2-thienyl]methyl]-1,2,4-triazol-3-one;

2-[2-(aminomethyl)-3,3-difluoro-allyl]-4-[[5-[3-(1H-1,2,4-triazol-3-yl)phenyl]-2-thienyl]methyl]-1,2,4-triazol-3-one;

6-[5-[[1-[2-(aminomethyl)-3,3-difluoro-allyl]-5-oxo-1,2,4-triazol-4-yl]methyl]-3-thienyl]-3-methyl-1,4-dihydroquinazolin-2-one;

5-[5-[[1-[2-(aminomethyl)-3,3-difluoro-allyl]-5-oxo-1,2,4-triazol-4-yl]methyl]-3-thienyl]-1-isopropyl-pyridin-2-one;

4-[[4-[4-(4-acetylpiperazin-1-yl)phenyl]-2-thienyl]methyl]-2-[2-(aminomethyl)-3,3-difluoro-allyl]-1,2,4-triazol-3-one;

6-[5-[[1-[2-(aminomethyl)-3,3-difluoro-allyl]-5-oxo-1,2,4-triazol-4-yl]methyl]-3-thienyl]-8-fluoro-1H-quinolin-2-one;

5-[5-[[1-[2-(aminomethyl)-3,3-difluoro-allyl]-5-oxo-1,2,4-triazol-4-yl]methyl]-3-thienyl]-1-methyl-pyridin-2-one;

6-[5-[[1-[2-(aminomethyl)-3,3-difluoro-allyl]-5-oxo-1,2,4-triazol-4-yl]methyl]-3-thienyl]-1,4-dihydro-3,1-benzoxazin-2-one;

6-[5-[[1-[2-(aminomethyl)-3,3-difluoro-allyl]-5-oxo-1,2,4-triazol-4-yl]methyl]-3-thienyl]-3,4-dihydro-TH-quinolin-2-one;

5-[5-[[1-[2-(aminomethyl)-3,3-difluoro-allyl]-5-oxo-1,2,4-triazol-4-yl]methyl]-3-thienyl]-1-ethyl-pyridin-2-one;

2-[2-(aminomethyl)-3,3-difluoro-allyl]-4-[[4-[1-(difluoromethyl)pyrazol-4-yl]-2-thienyl]methyl]-1,2,4-triazol-3-one;

2-[2-(aminomethyl)-3,3-difluoro-allyl]-4-[[4-(1-isopropylpyrazol-4-yl)-2-thienyl]methyl]-1,2,4-triazol-3-one;

2-[2-(aminomethyl)-3,3-difluoro-allyl]-4-[[4-[3-(1H-1,2,4-triazol-3-yl)phenyl]-2-thienyl]methyl]-1,2,4-triazol-3-one;

2-[2-(aminomethyl)-3,3-difluoro-allyl]-4-[[6-(4-methylsulfonylphenyl)benzothiophen-2-yl]methyl]-1,2,4-triazol-3-one;

2-[2-(aminomethyl)-3,3-difluoro-allyl]-4-[[6-(4-piperazin-1-ylphenyl)benzothiophen-2-yl]methyl]-1,2,4-triazol-3-one;

2-[2-(aminomethyl)-3,3-difluoro-allyl]-4-[[6-[6-(trifluoromethyl)-3-pyridyl]benzothiophen-2-yl]methyl]-1,2,4-triazol-3-one;

2-[2-(aminomethyl)-3,3-difluoro-allyl]-4-[[6-[6-(dimethylamino)-3-pyridyl]benzothiophen-2-yl]methyl]-1,2,4-triazol-3-one;

2-[2-(aminomethyl)-3,3-difluoro-allyl]-4-[[6-(1,3-benzodioxol-5-yl)benzothiophen-2-yl]methyl]-1,2,4-triazol-3-one;

6-[2-[[1-[2-(aminomethyl)-3,3-difluoro-allyl]-5-oxo-1,2,4-triazol-4-yl]methyl]benzothiophen-6-yl]-8-methyl-3,4-dihydro-1H-quinolin-2-one;

6-[2-[[1-[2-(aminomethyl)-3,3-difluoro-allyl]-5-oxo-1,2,4-triazol-4-yl]methyl]benzothiophen-6-yl]-1-methyl-3,4-dihydroquinolin-2-one;

2-[2-(aminomethyl)-3,3-difluoro-allyl]-4-[[6-(1-ethylpyrazol-4-yl)benzothiophen-2-yl]methyl]-1,2,4-triazol-3-one;

2-[2-(aminomethyl)-3,3-difluoro-allyl]-4-[[5-(4-methylsulfonylphenyl)benzothiophen-2-yl]methyl]-1,2,4-triazol-3-one;

2-[2-(aminomethyl)-3,3-difluoro-allyl]-4-[[5-(4-piperazin-1-ylphenyl)benzothiophen-2-yl]methyl]-1,2,4-triazol-3-one;

5-[2-[[1-[2-(aminomethyl)-3,3-difluoro-allyl]-5-oxo-1,2,4-triazol-4-yl]methyl]benzothiophen-5-yl]-1-ethyl-pyridin-2-one;

2-[2-(aminomethyl)-3,3-difluoro-allyl]-4-[[5-[6-(dimethylamino)-3-pyridyl]benzothiophen-2-yl]methyl]-1,2,4-triazol-3-one;

2-[2-(aminomethyl)-3,3-difluoro-allyl]-4-[[5-(1,3-benzodioxol-5-yl)benzothiophen-2-yl]methyl]-1,2,4-triazol-3-one;

6-[2-[[1-[2-(aminomethyl)-3,3-difluoro-allyl]-5-oxo-1,2,4-triazol-4-yl]methyl]benzothiophen-5-yl]-8-methyl-3,4-dihydro-1H-quinolin-2-one;

6-[2-[[1-[2-(aminomethyl)-3,3-difluoro-allyl]-5-oxo-1,2,4-triazol-4-yl]methyl]benzothiophen-5-yl]-1-methyl-3,4-dihydroquinolin-2-one;

2-[2-(aminomethyl)-3,3-difluoro-allyl]-4-[[5-(1-ethylpyrazol-4-yl)benzothiophen-2-yl]methyl]-1,2,4-triazol-3-one;

2-[2-(aminomethyl)-3,3-difluoro-allyl]-4-[6-(6-piperazin-1-yl-3-pyridyl)-2-pyridyl]-1,2,4-triazol-3-one;

2-[2-(aminomethyl)-3,3-difluoro-allyl]-4-[6-[4-(morpholine-4-carbonyl)phenyl]-2-pyridyl]-1,2,4-triazol-3-one;

2-[2-(aminomethyl)-3,3-difluoro-allyl]-4-[6-(6-morpholino-3-pyridyl)-2-pyridyl]-1,2,4-triazol-3-one;

2-[2-(aminomethyl)-3,3-difluoro-allyl]-4-[6-(3-piperazin-1-ylphenyl)-2-pyridyl]-1,2,4-triazol-3-one;

2-[2-(aminomethyl)-3,3-difluoro-allyl]-4-[6-[3-(dimethylamino)-4-fluoro-phenyl]-2-pyridyl]-1,2,4-triazol-3-one;

5-[6-[1-[2-(aminomethyl)-3,3-difluoro-allyl]-5-oxo-1,2,4-triazol-4-yl]-2-pyridyl]-1-ethyl-pyridin-2-one;

7-[6-[1-[2-(aminomethyl)-3,3-difluoro-allyl]-5-oxo-1,2,4-triazol-4-yl]-2-pyridyl]-1,4-dihydro-3,1-benzoxazin-2-one;

2-[2-(aminomethyl)-3,3-difluoro-allyl]-4-[3-methyl-5-(6-piperazin-1-yl-3-pyridyl)-2-pyridyl]-1,2,4-triazol-3-one;

6-[6-[1-[2-(aminomethyl)-3,3-difluoro-allyl]-5-oxo-1,2,4-triazol-4-yl]-5-methyl-3-pyridyl]-4H-1,4-benzoxazin-3-one;

2-[2-(aminomethyl)-3,3-difluoro-allyl]-4-[5-[2-(2-methoxyethylamino)pyrimidin-5-yl]-3-methyl-2-pyridyl]-1,2,4-triazol-3-one;

2-[2-(aminomethyl)-3,3-difluoro-allyl]-4-[3-methyl-5-(4-methyl-2,3-dihydro-1,4-benzoxazin-7-yl)-2-pyridyl]-1,2,4-triazol-3-one;

2-[2-(aminomethyl)-3,3-difluoro-allyl]-4-[3-methyl-5-(3,4,5-trimethoxyphenyl)-2-pyridyl]-1,2,4-triazol-3-one;

2-[2-(aminomethyl)-3,3-difluoro-allyl]-4-[5-(6-methoxy-3-pyridyl)-3-methyl-2-pyridyl]-1,2,4-triazol-3-one;

4-[5-(2-amino-1,3-benzothiazol-5-yl)-3-methyl-2-pyridyl]-2-[2-(aminomethyl)-3,3-difluoro-allyl]-1,2,4-triazol-3-one;

2-[2-(aminomethyl)-3,3-difluoro-allyl]-4-[5-(2,1,3-benzoxadiazol-5-yl)-3-methyl-2-pyridyl]-1,2,4-triazol-3-one;

2-[2-(aminomethyl)-3,3-difluoro-allyl]-4-[3-methyl-5-(1H-pyrrolo[2,3-b]pyridin-5-yl)-2-pyridyl]-1,2,4-triazol-3-one;

2-[2-(aminomethyl)-3,3-difluoro-allyl]-4-[5-(1,3-benzoxazol-5-yl)-3-methyl-2-pyridyl]-1,2,4-triazol-3-one;

2-[2-(aminomethyl)-3,3-difluoro-allyl]-4-[3-methyl-5-[4-(2-oxopyrrolidin-1-yl)phenyl]-2-pyridyl]-1,2,4-triazol-3-one;

4-[5-(5-acetyl-2-thienyl)-3-methyl-2-pyridyl]-2-[2-(aminomethyl)-3,3-difluoro-allyl]-1,2,4-triazol-3-one;

2-[2-(aminomethyl)-3,3-difluoro-allyl]-4-[3-methyl-5-[3-(1H-pyrazol-3-yl)phenyl]-2-pyridyl]-1,2,4-triazol-3-one;

2-[2-(aminomethyl)-3,3-difluoro-allyl]-4-[5-(1H-indazol-6-yl)-3-methyl-2-pyridyl]-1,2,4-triazol-3-one;

2-[2-(aminomethyl)-3,3-difluoro-allyl]-4-[3-methyl-5-(3-methylsulfonylphenyl)-2-pyridyl]-1,2,4-triazol-3-one;

2-[2-(aminomethyl)-3,3-difluoro-allyl]-4-[3-methyl-5-(3-piperazin-1-ylphenyl)-2-pyridyl]-1,2,4-triazol-3-one;

2-[2-(aminomethyl)-3,3-difluoro-allyl]-4-[3-methyl-5-[4-(morpholine-4-carbonyl)phenyl]-2-pyridyl]-1,2,4-triazol-3-one;
2-[2-(aminomethyl)-3,3-difluoro-allyl]-4-[3-methyl-5-(4-morpholinophenyl)-2-pyridyl]-1,2,4-triazol-3-one;
4-[6-[1-[2-(aminomethyl)-3,3-difluoro-allyl]-5-oxo-1,2,4-triazol-4-yl]-5-methyl-3-pyridyl]-N,N-dimethyl-benzenesulfonamide;
2-[2-(aminomethyl)-3,3-difluoro-allyl]-4-[3-methyl-5-[3-(1H-1,2,4-triazol-3-yl)phenyl]-2-pyridyl]-1,2,4-triazol-3-one;
2-[2-(aminomethyl)-3,3-difluoro-allyl]-4-[3-methyl-5-[2-(1-methylpyrazol-4-yl)ethynyl]-2-pyridyl]-1,2,4-triazol-3-one;
2-[2-(aminomethyl)-3,3-difluoro-allyl]-4-[5-[2-[6-(dimethylamino)-3-pyridyl]ethynyl]-3-methyl-2-pyridyl]-1,2,4-triazol-3-one;
2-[2-(aminomethyl)-3,3-difluoro-allyl]-4-[3-methyl-5-[2-(6-morpholino-3-pyridyl)ethynyl]-2-pyridyl]-1,2,4-triazol-3-one;
2-[2-(aminomethyl)-3,3-difluoro-allyl]-4-[5-[2-(3,4-dihydro-2H-1,4-benzoxazin-6-yl)ethynyl]-3-methyl-2-pyridyl]-1,2,4-triazol-3-one;
2-[2-(aminomethyl)-3,3-difluoro-allyl]-4-[5-[2-(2,3-dihydro-1H-pyrido[2,3-b][1,4]oxazin-7-yl)ethynyl]-3-methyl-2-pyridyl]-1,2,4-triazol-3-one;
2-[2-(aminomethyl)-3,3-difluoro-allyl]-4-[5-[2-(3,4-dihydro-2H-pyrido[3,2-b][1,4]oxazin-7-yl)ethynyl]-3-methyl-2-pyridyl]-1,2,4-triazol-3-one;
2-[2-(aminomethyl)-3,3-difluoro-allyl]-4-[5-[2-(2,3-dihydro-1H-pyrido[2,3-b][1,4]oxazin-6-yl)ethynyl]-3-methyl-2-pyridyl]-1,2,4-triazol-3-one;
7-[2-[6-[1-[2-(aminomethyl)-3,3-difluoro-allyl]-5-oxo-1,2,4-triazol-4-yl]-5-methyl-3-pyridyl]ethynyl]-1H-pyrido[2,3-b][1,4]oxazin-2-one;
7-[2-[6-[1-[2-(aminomethyl)-3,3-difluoro-allyl]-5-oxo-1,2,4-triazol-4-yl]-5-methyl-3-pyridyl]ethynyl]-4H-pyrido[3,2-b][1,4]oxazin-3-one;
6-[2-[6-[1-[2-(aminomethyl)-3,3-difluoro-allyl]-5-oxo-1,2,4-triazol-4-yl]-5-methyl-3-pyridyl]ethynyl]-3,4-dihydro-TH-quinolin-2-one;
6-[6-[1-[2-(aminomethyl)-3,3-difluoro-allyl]-5-oxo-1,2,4-triazol-4-yl]-5-methyl-3-pyridyl]-3-methyl-1,4-dihydroquinazolin-2-one;
2-[2-(aminomethyl)-3,3-difluoro-allyl]-4-[5-[1-(difluoromethyl)pyrazol-4-yl]-3-methyl-2-pyridyl]-1,2,4-triazol-3-one;
2-[2-(aminomethyl)-3,3-difluoro-allyl]-4-[5-(1-isopropylpyrazol-4-yl)-3-methyl-2-pyridyl]-1,2,4-triazol-3-one;
2-[2-(aminomethyl)-3,3-difluoro-allyl]-4-[2-methyl-3-(4-methylsulfonylphenyl)phenyl]-1,2,4-triazol-3-one;
2-[2-(aminomethyl)-3,3-difluoro-allyl]-4-[2-methyl-3-(4-piperazin-1-ylphenyl)phenyl]-1,2,4-triazol-3-one;
2-[2-(aminomethyl)-3,3-difluoro-allyl]-4-[2-methyl-3-[6-(trifluoromethyl)-3-pyridyl]phenyl]-1,2,4-triazol-3-one;
2-[2-(aminomethyl)-3,3-difluoro-allyl]-4-[3-[6-(dimethylamino)-3-pyridyl]-2-methyl-phenyl]-1,2,4-triazol-3-one;
2-[2-(aminomethyl)-3,3-difluoro-allyl]-4-[3-(1,3-benzodioxol-5-yl)-2-methyl-phenyl]-1,2,4-triazol-3-one;
6-[3-[1-[2-(aminomethyl)-3,3-difluoro-allyl]-5-oxo-1,2,4-triazol-4-yl]-2-methyl-phenyl]-8-methyl-3,4-dihydro-1H-quinolin-2-one;
6-[3-[1-[2-(aminomethyl)-3,3-difluoro-allyl]-5-oxo-1,2,4-triazol-4-yl]-2-methyl-phenyl]-1-methyl-3,4-dihydroquinolin-2-one;
2-[2-(aminomethyl)-3,3-difluoro-allyl]-4-[3-(1-ethylpyrazol-4-yl)-2-methyl-phenyl]-1,2,4-triazol-3-one;
2-[2-(aminomethyl)-3,3-difluoro-allyl]-4-[3-[1-(difluoromethyl)pyrazol-4-yl]-2-methyl-phenyl]-1,2,4-triazol-3-one;
2-[2-(aminomethyl)-3,3-difluoro-allyl]-4-[3-(1-isopropylpyrazol-4-yl)-2-methyl-phenyl]-1,2,4-triazol-3-one;
2-[2-(aminomethyl)-3,3-difluoro-allyl]-4-[2-methyl-3-[3-(1H-1,2,4-triazol-3-yl)phenyl]phenyl]-1,2,4-triazol-3-one;
2-[2-(aminomethyl)-3,3-difluoro-allyl]-4-[[4-(1-ethylpyrazol-4-yl)phenyl]methyl]-1,2,4-triazol-3-one;
2-[2-(aminomethyl)-3,3-difluoro-allyl]-4-[[4-(4-methylsulfonylphenyl)phenyl]methyl]-1,2,4-triazol-3-one;
2-[2-(aminomethyl)-3,3-difluoro-allyl]-4-[[4-(4-piperazin-1-ylphenyl)phenyl]methyl]-1,2,4-triazol-3-one;
2-[2-(aminomethyl)-3,3-difluoro-allyl]-4-[[4-[6-(dimethylamino)-3-pyridyl]phenyl]methyl]-1,2,4-triazol-3-one;
2-[2-(aminomethyl)-3,3-difluoro-allyl]-4-[[4-(1,3-benzodioxol-5-yl)phenyl]methyl]-1,2,4-triazol-3-one;
6-[4-[[1-[2-(aminomethyl)-3,3-difluoro-allyl]-5-oxo-1,2,4-triazol-4-yl]methyl]phenyl]-8-methyl-3,4-dihydro-1H-quinolin-2-one;
5-[4-[[1-[2-(aminomethyl)-3,3-difluoro-allyl]-5-oxo-1,2,4-triazol-4-yl]methyl]phenyl]-1-ethyl-pyridin-2-one;
2-[2-(aminomethyl)-3,3-difluoro-allyl]-4-[[3-(1-ethylpyrazol-4-yl)phenyl]methyl]-1,2,4-triazol-3-one;
2-[2-(aminomethyl)-3,3-difluoro-allyl]-4-[[3-(4-methylsulfonylphenyl)phenyl]methyl]-1,2,4-triazol-3-one;
2-[2-(aminomethyl)-3,3-difluoro-allyl]-4-[[3-[6-(dimethylamino)-3-pyridyl]phenyl]methyl]-1,2,4-triazol-3-one;
2-[2-(aminomethyl)-3,3-difluoro-allyl]-4-[[3-(1,3-benzodioxol-5-yl)phenyl]methyl]-1,2,4-triazol-3-one;
6-[3-[[1-[2-(aminomethyl)-3,3-difluoro-allyl]-5-oxo-1,2,4-triazol-4-yl]methyl]phenyl]-8-methyl-3,4-dihydro-1H-quinolin-2-one;
6-[3-[[1-[2-(aminomethyl)-3,3-difluoro-allyl]-5-oxo-1,2,4-triazol-4-yl]methyl]phenyl]-1-methyl-3,4-dihydroquinolin-2-one;
5-[3-[[1-[2-(aminomethyl)-3,3-difluoro-allyl]-5-oxo-1,2,4-triazol-4-yl]methyl]phenyl]-1-ethyl-pyridin-2-one;
2-[2-(aminomethyl)-3,3-difluoro-allyl]-4-[[2-(1-ethylpyrazol-4-yl)phenyl]methyl]-1,2,4-triazol-3-one;
2-[2-(aminomethyl)-3,3-difluoro-allyl]-4-[[2-(4-methylsulfonylphenyl)phenyl]methyl]-1,2,4-triazol-3-one;
2-[2-(aminomethyl)-3,3-difluoro-allyl]-4-[[2-(4-piperazin-1-ylphenyl)phenyl]methyl]-1,2,4-triazol-3-one;
2-[2-(aminomethyl)-3,3-difluoro-allyl]-4-[[2-[6-(dimethylamino)-3-pyridyl]phenyl]methyl]-1,2,4-triazol-3-one;
2-[2-(aminomethyl)-3,3-difluoro-allyl]-4-[[2-(1,3-benzodioxol-5-yl)phenyl]methyl]-1,2,4-triazol-3-one;
6-[2-[[1-[2-(aminomethyl)-3,3-difluoro-allyl]-5-oxo-1,2,4-triazol-4-yl]methyl]phenyl]-8-methyl-3,4-dihydro-1H-quinolin-2-one;
6-[2-[[1-[2-(aminomethyl)-3,3-difluoro-allyl]-5-oxo-1,2,4-triazol-4-yl]methyl]phenyl]-1-methyl-3,4-dihydroquinolin-2-one;
5-[2-[[1-[2-(aminomethyl)-3,3-difluoro-allyl]-5-oxo-1,2,4-triazol-4-yl]methyl]phenyl]-1-ethyl-pyridin-2-one;
2-[2-(aminomethyl)-3,3-difluoro-allyl]-4-[[5-[4-(1-ethylpyrazol-4-yl)phenyl]-2-thienyl]methyl]-1,2,4-triazol-3-one;
2-[2-(aminomethyl)-3,3-difluoro-allyl]-4-[[5-[3-(1-ethylpyrazol-4-yl)phenyl]-2-thienyl]methyl]-1,2,4-triazol-3-one;
2-[2-(aminomethyl)-3,3-difluoro-allyl]-4-[[4-[4-(1-ethylpyrazol-4-yl)phenyl]-2-thienyl]methyl]-1,2,4-triazol-3-one;

2-[2-(aminomethyl)-3,3-difluoro-allyl]-4-[[4-[3-(1-ethylpyrazol-4-yl)phenyl]-2-thienyl]methyl]-1,2,4-triazol-3-one;

2-[2-(aminomethyl)-3,3-difluoro-allyl]-4-[5-[4-(1-ethylpyrazol-4-yl)phenyl]-3-methyl-2-pyridyl]-1,2,4-triazol-3-one;

2-[2-(aminomethyl)-3,3-difluoro-allyl]-4-[5-[3-(1-ethylpyrazol-4-yl)phenyl]-3-methyl-2-pyridyl]-1,2,4-triazol-3-one;

2-[2-(aminomethyl)-3,3-difluoro-allyl]-4-[[5-(1H-pyrazol-4-yl)-2-thienyl]methyl]-1,2,4-triazol-3-one;

2-[2-(aminomethyl)-3,3-difluoro-allyl]-4-[[5-(1-methylsulfonylpyrazol-4-yl)-2-thienyl]methyl]-1,2,4-triazol-3-one;

2-[2-(aminomethyl)-3,3-difluoro-allyl]-4-[[5-(1-cyclopropylsulfonylpyrazol-4-yl)-2-thienyl]methyl]-1,2,4-triazol-3-one;

2-[2-(aminomethyl)-3,3-difluoro-allyl]-4-[[5-[1-(cyclopropylmethyl)pyrazol-4-yl]-2-thienyl]methyl]-1,2,4-triazol-3-one;

2-[2-(aminomethyl)-3,3-difluoro-allyl]-4-[[5-(1-methylpyrazol-4-yl)-2-thienyl]methyl]-1,2,4-triazol-3-one;

2-[2-(aminomethyl)-3,3-difluoro-allyl]-4-[[5-(1-benzylpyrazol-4-yl)-2-thienyl]methyl]-1,2,4-triazol-3-one;

2-[2-(aminomethyl)-3,3-difluoro-allyl]-4-[[3-fluoro-5-(4-piperazin-1-ylphenyl)-2-thienyl]methyl]-1,2,4-triazol-3-one;

5-[5-[[1-[2-(aminomethyl)-3,3-difluoro-allyl]-5-oxo-1,2,4-triazol-4-yl]methyl]-4-fluoro-2-thienyl]-1-ethyl-pyridin-2-one;

2-[2-(aminomethyl)-3,3-difluoro-allyl]-4-[[5-(1,3-benzodioxol-5-yl)-3-fluoro-2-thienyl]methyl]-1,2,4-triazol-3-one;

6-[5-[[1-[2-(aminomethyl)-3,3-difluoro-allyl]-5-oxo-1,2,4-triazol-4-yl]methyl]-4-fluoro-2-thienyl]-1-methyl-3,4-dihydroquinolin-2-one;

2-[2-(aminomethyl)-3,3-difluoro-allyl]-4-[[5-(1-ethylpyrazol-4-yl)-3-fluoro-2-thienyl]methyl]-1,2,4-triazol-3-one;

2-(2-(aminomethyl)-3,3-difluoroallyl)-4-((5-(6-(dimethylamino)pyridin-3-yl)-3-fluorothiophen-2-yl)methyl)-2,4-dihydro-3H-1,2,4-triazol-3-one; and 6-(5-((1-(2-(aminomethyl)-3,3-difluoroallyl)-5-oxo-1,5-dihydro-4H-1,2,4-triazol-4-yl)methyl)-4-fluorothiophen-2-yl)-8-methyl-3,4-dihydroquinolin-2(1H)-one;

or a stereoisomer thereof or a pharmaceutically acceptable salt thereof.

Para. EZ. A pharmaceutical composition comprising the compound according to any one of Paras. A-EY, or a stereoisomer thereof, or a pharmaceutically acceptable salt thereof, and at least one pharmaceutically acceptable excipient Para. FA. A method of inhibiting vascular adhesion protein (VAP-1), comprising administering to a mammal, a therapeutically effective amount of the compound, or a stereoisomer thereof, or a pharmaceutically acceptable salt thereof according to any one of Paras. A-EY.

Para. FB. A method of treating NASH in a subject in need thereof, the method comprising administering to the subject a therapeutically effective amount of the compound according to any one of Paras. A-EY, or a stereoisomer thereof, or a pharmaceutically acceptable salt thereof, or a therapeutically effective amount of the pharmaceutical composition according to Para. EZ.

Para. FC. Use of the compound according to any one of Paras. A-EY, or a stereoisomer thereof, or a pharmaceutically acceptable salt thereof, for the manufacture of a medicament for the treatment of NASH.

Para. FD. A compound according to any one of Paras. A-EY, or a stereoisomer thereof, or a pharmaceutically acceptable salt thereof, for use in treating NASH.

Para. FE. A compound according to any one of Paras. A-EY, or a stereoisomer thereof, or a pharmaceutically acceptable salt thereof, for use as a medicament for the treatment of NASH.

Para. FF. A composition according to Para. EZ for use in treating NASH.

Para. FG. A compound according to any one of Paras. A-EY, or a stereoisomer thereof, or a pharmaceutically acceptable salt thereof, for use in inhibiting VAP-1.

Para. FH. A compound according to any one of Paras. A-EY, or a stereoisomer thereof, or a pharmaceutically acceptable salt thereof, for use as a medicament for the inhibition of VAP-1.

Para. FL. A composition according to Para. EZ for use in inhibiting VAP-1.

Para. FJ. A method of treating a disease mediated by VAP-1 in a subject in need thereof, the method comprising administering to the subject a therapeutically effective amount of the compound according to any one of Paras. A-EY, or a stereoisomer thereof, or a pharmaceutically acceptable salt thereof, or a therapeutically effective amount of the pharmaceutical composition according to Para. EZ.

Para. FK. The method of Para. FJ, wherein the disease mediated by VAP-1 is selected from the group consisting of lipid and lipoprotein disorders, conditions and diseases which result from chronic fatty and fibrotic degeneration of organs due to accumulated lipid and specifically triglyceride accumulation and subsequent activation of profibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

Para. FL. A compound according to any one of Paras. A-EY, or a stereoisomer thereof, or a pharmaceutically acceptable salt thereof, for use in treating a disease mediated by VAP-1.

Para. FM. A compound according to any one of Paras. A-EY, or a stereoisomer thereof, or a pharmaceutically acceptable salt thereof, for use as a medicament for the treatment of a disease mediated by VAP-1.

Para. FN. The compound for use of Para. FL or Para. FM, wherein the disease mediated by VAP-1 is selected from the group consisting of lipid and lipoprotein disorders, conditions and diseases which result from chronic fatty and fibrotic degeneration of organs due to accumulated lipid and specifically triglyceride accumulation and subsequent activation of profibrotic pathways, Type I or Type II Diabetes and clinical complications of Type I and Type II Diabetes, chronic intrahepatic or some forms of extrahepatic cholestatic conditions, liver fibrosis, acute intraheptic cholestatic conditions, obstructive or chronic inflammatory disorders that arise out of improper bile composition, gastrointestinal conditions with a reduced uptake of dietary fat and fat-soluble dietary vitamins, inflammatory bowel diseases, obesity and metabolic syndrome (combined conditions of dyslipidemia, diabetes and abnormally high body-mass index), persistent infections by intracellular bacteria or parasitic protozoae, non-malignant hyperproliferative disorders, malignant hyperproliferative disorders, colon adenocarcinoma and hepatocellular carcinoma in particular, liver steatosis and associated syndromes, Hepatitis B infection, Hepatitis C infection and/or of cholestatic and fibrotic effects that are associated with alcohol-induced cirrhosis or with viral-borne forms of hepatitis, liver failure or liver malfunction as an outcome of chronic liver diseases or of surgical liver resection, acute myocardial infarction, acute stroke, thrombosis which occurs as an endpoint of chronic obstructive atherosclerosis, osteoarthritis, rheumatoid arthritis, psoriasis, and cerebral infarction, individually or any combination thereof.

Para. FO. A method of preparing a compound of Formula 1aa, or a stereoisomer thereof, or a pharmaceutically acceptable salt thereof,

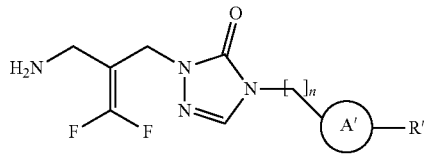

(Formula 1aa)

the method comprising (a) reacting a compound of Formula 2 with a compound of Formula 3a or a compound of Formula 3b to obtain a compound of Formula 1a

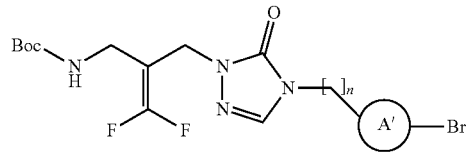

(Formula 2)

Z—R'   (Formula 3a)

HC≡CR   (Formula 3b)

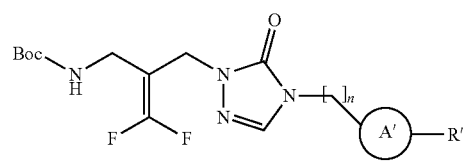

(Formula 1a)

wherein

Boc is an amine protecting group;

n is 0, 1, or 2;

A' is aryl or heteroaryl group selected from the group consisting of phenyl, pyridine, pyrazine, thiophene, and benzothiophene; wherein said aryl or heteroaryl group is optionally substituted with $C_{1-3}$ alkyl or halogen;

Z is boronic acid ($B(OH)_2$) or boronic acid pinacol ester;

R' is —R, —CH=CH—R, or —C≡C—R; and

R is a substituted or unsubstituted cyclic ring, optionally containing 1 to 5 heteroatom ring members chosen from O, N, or S, and said cyclic ring is aromatic or non-aromatic; and (b) removing Boc from the compound of Formula 1a under reaction conditions to obtain the compound of Formula 1aa, or the stereoisomer thereof, or the pharmaceutically acceptable salt thereof.

Para. FP. The method of Para. FO, wherein the cyclic ring is selected from the group consisting of benzene, pyridine, tetrahydropyridine, pyridin-2-one, pyrimidine, imidazole, pyrazole, benzodioxole, benzoxadiazole, benzothiazole, indazole, 1,3-dihydroindol-2-one, quinolin-2-one, 3,4-dihydroisoquinolin-1-one, 3,4-dihydroquinolin-2-one, 3,4-dihydro-1,4-benzoxazine, 2,3-dihydro-1,4-benzoxazine, 1,4-benzoxazin-3-one, 1,4-dihydro-3,1-benzoxazin-2-one, 5,6,7,8-tetrahydronaphthyridine, triazolo[1,5-a]pyridine, 2,3-dihydro-pyrido[2,3-b][1,4]oxazine, 3,4-dihydro-pyrido[3,2-b][1,4]oxazine, pyrido[2,3-b][1,4]oxazin-2-one, pyrido[3,2-b][1,4]oxazin-3-one, 1,4-dihydroquinazolin-2-one, 1H-pyrrolo[2,3-b]pyridine, benzoxazole, and thiophene; wherein said cyclic ring is optionally substituted with one to three substituents selected from the group consisting of halogen, $C_{1-6}$ alkyl, difluoromethyl, trifluoromethyl, $C_{1-6}$ alkoxy, amino, mono- or di-$C_{1-6}$ alkylamino, $C_{1-6}$ alkoxy-$C_{1-6}$ alkylamino, $C_{1-6}$ alkylcarbonylamino, mono- or di-$C_{1-6}$ alkylaminocarbonyl, mono- or di-$C_{1-6}$ alkylaminosulfonyl, $C_{1-6}$ alkylsulfonyl, $C_{1-6}$ alkylcarbonyl, morpholinylcarbonyl, piperazinyl, acetylpiperazinyl, morpholinyl, pyrazolyl, triazolyl, and pyrrolidinyl.

The invention claimed is:

1. A compound selected from the group consisting of:
2-[2-(aminomethyl)-3,3-difluoro-allyl]-4-(4-fluorophenyl)-1,2,4-triazol-3-one;
2-[2-(aminomethyl)-3,3-difluoro-allyl]-4-(3-bromophenyl)-1,2,4-triazol-3-one;
2-[2-(aminomethyl)-3,3-difluoro-allyl]-4-(3,4-difluorophenyl)-1,2,4-triazol-3-one;
2-[2-(aminomethyl)-3,3-difluoro-allyl]-4-(4-bromo-3-fluoro-phenyl)-1,2,4-triazol-3-one;
2-[2-(aminomethyl)-3,3-difluoro-allyl]-4-(4-bromo-2-fluoro-phenyl)-1,2,4-triazol-3-one;
2-[2-(aminomethyl)-3,3-difluoro-allyl]-4-(4-bromo-2-methyl-phenyl)-1,2,4-triazol-3-one;
2-[2-(aminomethyl)-3,3-difluoro-allyl]-4-(6-bromo-3-pyridyl)-1,2,4-triazol-3-one;
2-[2-(aminomethyl)-3,3-difluoro-allyl]-4-(6-bromo-2-pyridyl)-1,2,4-triazol-3-one;
2-[2-(aminomethyl)-3,3-difluoro-allyl]-4-(4-bromo-2-pyridyl)-1,2,4-triazol-3-one;
2-[2-(aminomethyl)-3,3-difluoro-allyl]-4-(2-bromo-4-pyridyl)-1,2,4-triazol-3-one;
2-[2-(aminomethyl)-3,3-difluoro-allyl]-4-(5-bromo-3-methyl-2-pyridyl)-1,2,4-triazol-3-one;
2-[2-(aminomethyl)-3,3-difluoro-allyl]-4-(6-bromo-4-methyl-3-pyridyl)-1,2,4-triazol-3-one;
2-[2-(aminomethyl)-3,3-difluoro-allyl]-4-(6-bromo-5-methyl-3-pyridyl)-1,2,4-triazol-3-one;

2-[2-(aminomethyl)-3,3-difluoro-allyl]-4-(5-bromo-3-fluoro-2-pyridyl)-1,2,4-triazol-3-one;
2-[2-(aminomethyl)-3,3-difluoro-allyl]-4-(6-bromo-3-methyl-2-pyridyl)-1,2,4-triazol-3-one;
2-[2-(aminomethyl)-3,3-difluoro-allyl]-4-(5-bromopyrazin-2-yl)-1,2,4-triazol-3-one;
2-[2-(aminomethyl)-3,3-difluoro-allyl]-4-[3-(4-methylsulfonylphenyl)phenyl]-1,2,4-triazol-3-one;
2-[2-(aminomethyl)-3,3-difluoro-allyl]-4-[3-(4-piperazin-1-ylphenyl)phenyl]-1,2,4-triazol-3-one;
2-[2-(aminomethyl)-3,3-difluoro-allyl]-4-[3-[6-(trifluoromethyl)-3-pyridyl]phenyl]-1,2,4-triazol-3-one;
2-[2-(aminomethyl)-3,3-difluoro-allyl]-4-[3-[6-(dimethylamino)-3-pyridyl]phenyl]-1,2,4-triazol-3-one;
2-[2-(aminomethyl)-3,3-difluoro-allyl]-4-[3-(1,3-benzodioxol-5-yl)phenyl]-1,2,4-triazol-3-one;
6-[3-[1-[2-(aminomethyl)-3,3-difluoro-allyl]-5-oxo-1,2,4-triazol-4-yl]phenyl]-8-methyl-3,4-dihydro-1H-quinolin-2-one;
2-[2-(aminomethyl)-3,3-difluoro-allyl]-4-[3-(1-ethylpyrazol-4-yl)phenyl]-1,2,4-triazol-3-one;
2-[2-(aminomethyl)-3,3-difluoro-allyl]-4-[3-fluoro-4-(4-methylsulfonylphenyl)phenyl]-1,2,4-triazol-3-one;
2-[2-(aminomethyl)-3,3-difluoro-allyl]-4-[3-fluoro-4-(4-piperazin-1-ylphenyl)phenyl]-1,2,4-triazol-3-one;
2-[2-(aminomethyl)-3,3-difluoro-allyl]-4-[3-fluoro-4-[6-(trifluoromethyl)-3-pyridyl]phenyl]-1,2,4-triazol-3-one;
2-[2-(aminomethyl)-3,3-difluoro-allyl]-4-[4-[6-(dimethylamino)-3-pyridyl]-3-fluoro-phenyl]-1,2,4-triazol-3-one;
2-[2-(aminomethyl)-3,3-difluoro-allyl]-4-[4-(1,3-benzodioxol-5-yl)-3-fluoro-phenyl]-1,2,4-triazol-3-one;
6-[4-[1-[2-(aminomethyl)-3,3-difluoro-allyl]-5-oxo-1,2,4-triazol-4-yl]-2-fluoro-phenyl]-8-methyl-3,4-dihydro-1H-quinolin-2-one;
2-[2-(aminomethyl)-3,3-difluoro-allyl]-4-[4-(1-ethylpyrazol-4-yl)-3-fluoro-phenyl]-1,2,4-triazol-3-one;
2-[2-(aminomethyl)-3,3-difluoro-allyl]-4-[2-fluoro-4-(4-methylsulfonylphenyl)phenyl]-1,2,4-triazol-3-one;
2-[2-(aminomethyl)-3,3-difluoro-allyl]-4-[2-fluoro-4-(4-piperazin-1-ylphenyl)phenyl]-1,2,4-triazol-3-one;
2-[2-(aminomethyl)-3,3-difluoro-allyl]-4-[2-fluoro-4-[6-(trifluoromethyl)-3-pyridyl]phenyl]-1,2,4-triazol-3-one;
2-[2-(aminomethyl)-3,3-difluoro-allyl]-4-[4-[6-(dimethylamino)-3-pyridyl]-2-fluoro-phenyl]-1,2,4-triazol-3-one;
2-[2-(aminomethyl)-3,3-difluoro-allyl]-4-[4-(1,3-benzodioxol-5-yl)-2-fluoro-phenyl]-1,2,4-triazol-3-one;
6-[4-[1-[2-(aminomethyl)-3,3-difluoro-allyl]-5-oxo-1,2,4-triazol-4-yl]-3-fluoro-phenyl]-8-methyl-3,4-dihydro-1H-quinolin-2-one;
2-[2-(aminomethyl)-3,3-difluoro-allyl]-4-[4-(1-ethylpyrazol-4-yl)-2-fluoro-phenyl]-1,2,4-triazol-3-one;
2-[2-(aminomethyl)-3,3-difluoro-allyl]-4-[6-(4-methylsulfonylphenyl)-3-pyridyl]-1,2,4-triazol-3-one;
2-[2-(aminomethyl)-3,3-difluoro-allyl]-4-[6-(4-piperazin-1-ylphenyl)-3-pyridyl]-1,2,4-triazol-3-one;
2-[2-(aminomethyl)-3,3-difluoro-allyl]-4-[6-[6-(trifluoromethyl)-3-pyridyl]-3-pyridyl]-1,2,4-triazol-3-one;
2-[2-(aminomethyl)-3,3-difluoro-allyl]-4-[6-[6-(dimethylamino)-3-pyridyl]-3-pyridyl]-1,2,4-triazol-3-one;
2-[2-(aminomethyl)-3,3-difluoro-allyl]-4-[6-(1,3-benzodioxol-5-yl)-3-pyridyl]-1,2,4-triazol-3-one;
6-[5-[1-[2-(aminomethyl)-3,3-difluoro-allyl]-5-oxo-1,2,4-triazol-4-yl]-2-pyridyl]-8-methyl-3,4-dihydro-1H-quinolin-2-one;
6-[5-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[6-(1-ethylpyrazol-4-yl)-3-pyridyl]-1,2,4-triazol-3-one;
2-[2-(aminomethyl)-3,3-difluoro-allyl]-4-[6-(4-methylsulfonylphenyl)-2-pyridyl]-1,2,4-triazol-3-one;
2-[2-(aminomethyl)-3,3-difluoro-allyl]-4-[6-(4-piperazin-1-ylphenyl)-2-pyridyl]-1,2,4-triazol-3-one;
2-[2-(aminomethyl)-3,3-difluoro-allyl]-4-[6-[6-(trifluoromethyl)-3-pyridyl]-2-pyridyl]-1,2,4-triazol-3-one;
2-[2-(aminomethyl)-3,3-difluoro-allyl]-4-[6-[6-(dimethylamino)-3-pyridyl]-2-pyridyl]-1,2,4-triazol-3-one;
2-[2-(aminomethyl)-3,3-difluoro-allyl]-4-[6-(1,3-benzodioxol-5-yl)-2-pyridyl]-1,2,4-triazol-3-one;
6-[6-[1-[2-(aminomethyl)-3,3-difluoro-allyl]-5-oxo-1,2,4-triazol-4-yl]-2-pyridyl]-8-methyl-3,4-dihydro-1H-quinolin-2-one;
6-[6-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[6-(1-ethylpyrazol-4-yl)-2-pyridyl]-1,2,4-triazol-3-one;
2-[2-(aminomethyl)-3,3-difluoro-allyl]-4-[4-(4-methylsulfonylphenyl)-2-pyridyl]-1,2,4-triazol-3-one;
2-[2-(aminomethyl)-3,3-difluoro-allyl]-4-[4-(4-piperazin-1-ylphenyl)-2-pyridyl]-1,2,4-triazol-3-one;
2-[2-(aminomethyl)-3,3-difluoro-allyl]-4-[4-[6-(trifluoromethyl)-3-pyridyl]-2-pyridyl]-1,2,4-triazol-3-one;
2-[2-(aminomethyl)-3,3-difluoro-allyl]-4-[4-[6-(dimethylamino)-3-pyridyl]-2-pyridyl]-1,2,4-triazol-3-one;
2-[2-(aminomethyl)-3,3-difluoro-allyl]-4-[4-(1,3-benzodioxol-5-yl)-2-pyridyl]-1,2,4-triazol-3-one;
6-[2-[1-[2-(aminomethyl)-3,3-difluoro-allyl]-5-oxo-1,2,4-triazol-4-yl]-4-pyridyl]-8-methyl-3,4-dihydro-1H-quinolin-2-one;
2-[2-(aminomethyl)-3,3-difluoro-allyl]-4-[4-(1-ethylpyrazol-4-yl)-2-pyridyl]-1,2,4-triazol-3-one;
2-[2-(aminomethyl)-3,3-difluoro-allyl]-4-[2-(4-methylsulfonylphenyl)-4-pyridyl]-1,2,4-triazol-3-one;
2-[2-(aminomethyl)-3,3-difluoro-allyl]-4-[2-(4-piperazin-1-ylphenyl)-4-pyridyl]-1,2,4-triazol-3-one;
2-[2-(aminomethyl)-3,3-difluoro-allyl]-4-[2-[6-(dimethylamino)-3-pyridyl]-4-pyridyl]-1,2,4-triazol-3-one;
2-[2-(aminomethyl)-3,3-difluoro-allyl]-4-[2-(1,3-benzodioxol-5-yl)-4-pyridyl]-1,2,4-triazol-3-one;
6-[4-[1-[2-(aminomethyl)-3,3-difluoro-allyl]-5-oxo-1,2,4-triazol-4-yl]-2-pyridyl]-8-methyl-3,4-dihydro-1H-quinolin-2-one;
6-[4-[1-[2-(aminomethyl)-3,3-difluoro-allyl]-5-oxo-1,2,4-triazol-4-yl]-2-pyridyl]-1-methyl-3,4-dihydroquinolin-2-one;
2-[2-(aminomethyl)-3,3-difluoro-allyl]-4-[2-(1-ethylpyrazol-4-yl)-4-pyridyl]-1,2,4-triazol-3-one;
2-[2-(aminomethyl)-3,3-difluoro-allyl]-4-[3-methyl-5-(4-methylsulfonylphenyl)-2-pyridyl]-1,2,4-triazol-3-one;
2-[2-(aminomethyl)-3,3-difluoro-allyl]-4-[3-methyl-5-(4-piperazin-1-ylphenyl)-2-pyridyl]-1,2,4-triazol-3-one;
2-[2-(aminomethyl)-3,3-difluoro-allyl]-4-[3-methyl-5-[6-(trifluoromethyl)-3-pyridyl]-2-pyridyl]-1,2,4-triazol-3-one;
2-[2-(aminomethyl)-3,3-difluoro-allyl]-4-[5-[6-(dimethylamino)-3-pyridyl]-3-methyl-2-pyridyl]-1,2,4-triazol-3-one;

2-[2-(aminomethyl)-3,3-difluoro-allyl]-4-[5-(1,3-benzodioxol-5-yl)-3-methyl-2-pyridyl]-1,2,4-triazol-3-one;
6-[6-[1-[2-(aminomethyl)-3,3-difluoro-allyl]-5-oxo-1,2,4-triazol-4-yl]-5-methyl-3-pyridyl]-8-methyl-3,4-dihydro-1H-quinolin-2-one;
6-[6-[1-[2-(aminomethyl)-3,3-difluoro-allyl]-5-oxo-1,2,4-triazol-4-yl]-5-methyl-3-pyridyl]-1-methyl-3,4-dihydroquinolin-2-one;
2-[2-(aminomethyl)-3,3-difluoro-allyl]-4-[5-(1-ethylpyrazol-4-yl)-3-methyl-2-pyridyl]-1,2,4-triazol-3-one;
2-[2-(aminomethyl)-3,3-difluoro-allyl]-4-[5-methyl-6-(4-methylsulfonylphenyl)-3-pyridyl]-1,2,4-triazol-3-one;
2-[2-(aminomethyl)-3,3-difluoro-allyl]-4-[5-methyl-6-[6-(trifluoromethyl)-3-pyridyl]-3-pyridyl]-1,2,4-triazol-3-one;
2-[2-(aminomethyl)-3,3-difluoro-allyl]-4-[6-[6-(dimethylamino)-3-pyridyl]-5-methyl-3-pyridyl]-1,2,4-triazol-3-one;
2-[2-(aminomethyl)-3,3-difluoro-allyl]-4-[6-(1,3-benzodioxol-5-yl)-5-methyl-3-pyridyl]-1,2,4-triazol-3-one;
6-[5-[1-[2-(aminomethyl)-3,3-difluoro-allyl]-5-oxo-1,2,4-triazol-4-yl]-3-methyl-2-pyridyl]-8-methyl-3,4-dihydro-1H-quinolin-2-one;
6-[5-[1-[2-(aminomethyl)-3,3-difluoro-allyl]-5-oxo-1,2,4-triazol-4-yl]-3-methyl-2-pyridyl]-1-methyl-3,4-dihydroquinolin-2-one;
2-[2-(aminomethyl)-3,3-difluoro-allyl]-4-[3-fluoro-5-(4-methylsulfonylphenyl)-2-pyridyl]-1,2,4-triazol-3-one;
2-[2-(aminomethyl)-3,3-difluoro-allyl]-4-[3-fluoro-5-(4-piperazin-1-ylphenyl)-2-pyridyl]-1,2,4-triazol-3-one;
2-[2-(aminomethyl)-3,3-difluoro-allyl]-4-[3-fluoro-5-[6-(trifluoromethyl)-3-pyridyl]-2-pyridyl]-1,2,4-triazol-3-one;
2-[2-(aminomethyl)-3,3-difluoro-allyl]-4-[5-(1,3-benzodioxol-5-yl)-3-fluoro-2-pyridyl]-1,2,4-triazol-3-one;
6-[6-[1-[2-(aminomethyl)-3,3-difluoro-allyl]-5-oxo-1,2,4-triazol-4-yl]-5-fluoro-3-pyridyl]-8-methyl-3,4-dihydro-1H-quinolin-2-one;
6-[6-[1-[2-(aminomethyl)-3,3-difluoro-allyl]-5-oxo-1,2,4-triazol-4-yl]-5-fluoro-3-pyridyl]-1-methyl-3,4-dihydroquinolin-2-one;
2-[2-(aminomethyl)-3,3-difluoro-allyl]-4-[5-(1-ethylpyrazol-4-yl)-3-fluoro-2-pyridyl]-1,2,4-triazol-3-one;
2-[2-(aminomethyl)-3,3-difluoro-allyl]-4-[5-(4-methylsulfonylphenyl)-pyrazin-2-yl]-1,2,4-triazol-3-one;
2-[2-(aminomethyl)-3,3-difluoro-allyl]-4-[5-(4-piperazin-1-ylphenyl)pyrazin-2-yl]-1,2,4-triazol-3-one;
2-[2-(aminomethyl)-3,3-difluoro-allyl]-4-[5-[6-(trifluoromethyl)-3-pyridyl]pyrazin-2-yl]-1,2,4-triazol-3-one;
2-[2-(aminomethyl)-3,3-difluoro-allyl]-4-[5-[6-(dimethylamino)-3-pyridyl]pyrazin-2-yl]-1,2,4-triazol-3-one;
2-[2-(aminomethyl)-3,3-difluoro-allyl]-4-[5-(1,3-benzodioxol-5-yl)pyrazin-2-yl]-1,2,4-triazol-3-one;
6-[5-[1-[2-(aminomethyl)-3,3-difluoro-allyl]-5-oxo-1,2,4-triazol-4-yl]pyrazin-2-yl]-1-methyl-3,4-dihydro-1H-quinolin-2-one;
2-[2-(aminomethyl)-3,3-difluoro-allyl]-4-[5-(1-ethylpyrazol-4-yl)pyrazin-2-yl]-1,2,4-triazol-3-one;
2-[2-(aminomethyl)-3,3-difluoro-allyl]-4-[(4-benzyloxyphenyl)methyl]-1,2,4-triazol-3-one;
2-[2-(aminomethyl)-3,3-difluoro-allyl]-4-[(5-bromo-2-thienyl)methyl]-1,2,4-triazol-3-one;
2-[2-(aminomethyl)-3,3-difluoro-allyl]-4-[(4-bromo-2-thienyl)methyl]-1,2,4-triazol-3-one;
2-[2-(aminomethyl)-3,3-difluoro-allyl]-4-[(5-bromo-3-methyl-2-thienyl)methyl]-1,2,4-triazol-3-one;
4-[[5-(4-acetylphenyl)-2-thienyl]methyl]-2-[2-(aminomethyl)-3,3-difluoro-allyl]-1,2,4-triazol-3-one;
2-[2-(aminomethyl)-3,3-difluoro-allyl]-4-[[5-(4-methylsulfonylphenyl)-2-thienyl]methyl]-1,2,4-triazol-3-one;
2-[2-(aminomethyl)-3,3-difluoro-allyl]-4-[[5-(3-methylsulfonylphenyl)-2-thienyl]methyl]-1,2,4-triazol-3-one;
3-[5-[[1-[2-(aminomethyl)-3,3-difluoro-allyl]-5-oxo-1,2,4-triazol-4-yl]methyl]-2-thienyl]-N,N-dimethyl-benzenesulfonamide;
4-[5-[[1-[2-(aminomethyl)-3,3-difluoro-allyl]-5-oxo-1,2,4-triazol-4-yl]methyl]-2-thienyl]-N-methyl-benzamide;
2-[2-(aminomethyl)-3,3-difluoro-allyl]-4-[[5-(3,4,5-trimethoxyphenyl)-2-thienyl]methyl]-1,2,4-triazol-3-one;
2-[2-(aminomethyl)-3,3-difluoro-allyl]-4-[[5-(4-piperazin-1-ylphenyl)-2-thienyl]methyl]-1,2,4-triazol-3-one;
2-[2-(aminomethyl)-3,3-difluoro-allyl]-4-[[5-(3-piperazin-1-ylphenyl)-2-thienyl]methyl]-1,2,4-triazol-3-one;
4-[[5-[4-(4-acetylpiperazin-1-yl)phenyl]-2-thienyl]methyl]-2-[2-(aminomethyl)-3,3-difluoro-allyl]-1,2,4-triazol-3-one;
2-[2-(aminomethyl)-3,3-difluoro-allyl]-4-[[5-(4-morpholine-4-carbonyl)phenyl]-2-thienyl]methyl]-1,2,4-triazol-3-one;
2-[2-(aminomethyl)-3,3-difluoro-allyl]-4-[[5-[3-(1H-pyrazol-3-yl)phenyl]-2-thienyl]methyl]-1,2,4-triazol-3-one;
2-[2-(aminomethyl)-3,3-difluoro-allyl]-4-[[5-[6-(trifluoromethyl)-3-pyridyl]-2-thienyl]methyl]-1,2,4-triazol-3-one;
2-[2-(aminomethyl)-3,3-difluoro-allyl]-4-[[5-[6-(dimethylamino)-3-pyridyl]-2-thienyl]methyl]-1,2,4-triazol-3-one;
2-[2-(aminomethyl)-3,3-difluoro-allyl]-4-[[5-(6-methoxy-3-pyridyl)-2-thienyl]methyl]-1,2,4-triazol-3-one;
2-[2-(aminomethyl)-3,3-difluoro-allyl]-4-[[5-(6-piperazin-1-yl-3-pyridyl)-2-thienyl]methyl]-1,2,4-triazol-3-one;
2-[2-(aminomethyl)-3,3-difluoro-allyl]-4-[[5-[6-(dimethylamino)-5-fluoro-3-pyridyl]-2-thienyl]methyl]-1,2,4-triazol-3-one;
2-[2-(aminomethyl)-3,3-difluoro-allyl]-4-[[5-(2-aminopyrimidin-5-yl)-2-thienyl]methyl]-1,2,4-triazol-3-one;
2-[2-(aminomethyl)-3,3-difluoro-allyl]-4-[[5-(2-ethoxypyrimidin-5-yl)-2-thienyl]methyl]-1,2,4-triazol-3-one;
2-[2-(aminomethyl)-3,3-difluoro-allyl]-4-[[5-[2-(2-methoxyethylamino)pyrimidin-5-yl]-2-thienyl]methyl]-1,2,4-triazol-3-one;
2-[2-(aminomethyl)-3,3-difluoro-allyl]-4-[[5-(1-ethylpyrazol-4-yl)-2-thienyl]methyl]-1,2,4-triazol-3-one;
2-[2-(aminomethyl)-3,3-difluoro-allyl]-4-[[5-(2-chloro-3-methyl-imidazol-4-yl)-2-thienyl]methyl]-1,2,4-triazol-3-one;
5-[5-[[1-[2-(aminomethyl)-3,3-difluoro-allyl]-5-oxo-1,2,4-triazol-4-yl]methyl]-2-thienyl]-1-methyl-pyridin-2-one;
5-[5-[[1-[2-(aminomethyl)-3,3-difluoro-allyl]-5-oxo-1,2,4-triazol-4-yl]methyl]-2-thienyl]-1-ethyl-pyridin-2-one;

5-[5-[[1-[2-(aminomethyl)-3,3-difluoro-allyl]-5-oxo-1,2,
4-triazol-4-yl]methyl]-2-thienyl]-1-isopropyl-pyridin-
2-one;
2-[2-(aminomethyl)-3,3-difluoro-allyl]-4-[[5-(1-methyl-
3,6-dihydro-2H-pyridin-4-yl)-2-thienyl]methyl]-1,2,4-
triazol-3-one;
2-[2-(aminomethyl)-3,3-difluoro-allyl]-4-[[5-(1-acetyl-3,
6-dihydro-2H-pyridin-4-yl)-2-thienyl]methyl]-1,2,4-
triazol-3-one;
2-[2-(aminomethyl)-3,3-difluoro-allyl]-4-[[5-(1,3-benzo-
dioxol-5-yl)-2-thienyl]methyl]-1,2,4-triazol-3-one;
2-[2-(aminomethyl)-3,3-difluoro-allyl]-4-[[5-(1H-inda-
zol-6-yl)-2-thienyl]methyl]-1,2,4-triazol-3-one;
2-[2-(aminomethyl)-3,3-difluoro-allyl]-4-[[5-([1,2,4]tri-
azolo[1,5-a]pyridin-7-yl)-2-thienyl]methyl]-1,2,4-tri-
azol-3-one;
2-[2-(aminomethyl)-3,3-difluoro-allyl]-4-[[5-(2,1,3-ben-
zoxadiazol-5-yl)-2-thienyl]methyl]-1,2,4-triazol-3-
one;
5-[5-[[1-[2-(aminomethyl)-3,3-difluoro-allyl]-5-oxo-1,2,
4-triazol-4-yl]methyl]-2-thienyl]-7-fluoro-indolin-2-
one;
N-[6-[5-[[1-[2-(aminomethyl)-3,3-difluoro-allyl]-5-oxo-
1,2,4-triazol-4-yl]methyl]-2-thienyl]-1,3-benzothiazol-
2-yl]acetamide;
7-[5-[[1-[2-(aminomethyl)-3,3-difluoro-allyl]-5-oxo-1,2,
4-triazol-4-yl]methyl]-2-thienyl]-3,4-dihydro-2H-iso-
quinolin-1-one;
6-[5-[[1-[2-(aminomethyl)-3,3-difluoro-allyl]-5-oxo-1,2,
4-triazol-4-yl]methyl]-2-thienyl]-3,4-dihydro-1H-qui-
nolin-2-one;
6-[5-[[1-[2-(aminomethyl)-3,3-difluoro-allyl]-5-oxo-1,2,
4-triazol-4-yl]methyl]-2-thienyl]-8-methyl-3,4-di-
hydro-1H-quinolin-2-one;
6-[5-[[1-[2-(aminomethyl)-3,3-difluoro-allyl]-5-oxo-1,2,
4-triazol-4-yl]methyl]-2-thienyl]-8-methyl-1H-quino-
lin-2-one;
6-[5-[[1-[2-(aminomethyl)-3,3-difluoro-allyl]-5-oxo-1,2,
4-triazol-4-yl]methyl]-2-thienyl]-8-fluoro-3,4-di-
hydro-1H-quinolin-2-one;
6-[5-[[1-[2-(aminomethyl)-3,3-difluoro-allyl]-5-oxo-1,2,
4-triazol-4-yl]methyl]-2-thienyl]-8-fluoro-1H-quino-
lin-2-one;
6-[5-[[1-[2-(aminomethyl)-3,3-difluoro-allyl]-5-oxo-1,2,
4-triazol-4-yl]methyl]-2-thienyl]-1-methyl-3,4-dihyd-
roquinolin-2-one;
2-[2-(aminomethyl)-3,3-difluoro-allyl]-4-[[5-(5-methyl-
3,4-dihydro-2H-1,4-benzoxazin-6-yl)-2-thienyl]
methyl]-1,2,4-triazol-3-one;
2-[2-(aminomethyl)-3,3-difluoro-allyl]-4-[[5-(4-methyl-
2,3-dihydro-1,4-benzoxazin-7-yl)-2-thienyl]methyl]-1,
2,4-triazol-3-one;
6-[5-[[1-[2-(aminomethyl)-3,3-difluoro-allyl]-5-oxo-1,2,
4-triazol-4-yl]methyl]-2-thienyl]-4H-1,4-benzoxazin-
3-one;
7-[5-[[1-[2-(aminomethyl)-3,3-difluoro-allyl]-5-oxo-1,2,
4-triazol-4-yl]methyl]-2-thienyl]-1,4-dihydro-3,1-ben-
zoxazin-2-one;
6-[5-[[1-[2-(aminomethyl)-3,3-difluoro-allyl]-5-oxo-1,2,
4-triazol-4-yl]methyl]-2-thienyl]-1,4-dihydro-3,1-ben-
zoxazin-2-one;
7-[5-[[1-[2-(aminomethyl)-3,3-difluoro-allyl]-5-oxo-1,2,
4-triazol-4-yl]methyl]-2-thienyl]-4-methyl-1,4-benzo-
xazin-3-one;
2-[2-(aminomethyl)-3,3-difluoro-allyl]-4-[[5-(5,6,7,8-tet-
rahydro-1,8-naphthyridin-3-yl)-2-thienyl]methyl]-1,2,
4-triazol-3-one;
2-[2-(aminomethyl)-3,3-difluoro-allyl]-4-[[4-(4-methyl-
sulfonylphenyl)-2-thienyl]methyl]-1,2,4-triazol-3-one;
2-[2-(aminomethyl)-3,3-difluoro-allyl]-4-[[4-(4-piper-
azin-1-ylphenyl)-2-thienyl]methyl]-1,2,4-triazol-3-
one;
2-[2-(aminomethyl)-3,3-difluoro-allyl]-4-[[4-[6-(trifluo-
romethyl)-3-pyridyl]-2-thienyl]methyl]-1,2,4-triazol-
3-one;
2-[2-(aminomethyl)-3,3-difluoro-allyl]-4-[[4-[6-(dimeth-
ylamino)-3-pyridyl]-2-thienyl]methyl]-1,2,4-triazol-3-
one;
2-[2-(aminomethyl)-3,3-difluoro-allyl]-4-[[4-(1,3-benzo-
dioxol-5-yl)-2-thienyl]methyl]-1,2,4-triazol-3-one;
6-[5-[[1-[2-(aminomethyl)-3,3-difluoro-allyl]-5-oxo-1,2,
4-triazol-4-yl]methyl]-3-thienyl]-8-methyl-3,4-di-
hydro-1H-quinolin-2-one;
6-[5-[[1-[2-(aminomethyl)-3,3-difluoro-allyl]-5-oxo-1,2,
4-triazol-4-yl]methyl]-3-thienyl]-1-methyl-3,4-dihyd-
roquinolin-2-one;
2-[2-(aminomethyl)-3,3-difluoro-allyl]-4-[[4-(1-eth-
ylpyrazol-4-yl)-2-thienyl]methyl]-1,2,4-triazol-3-one;
2-[2-(aminomethyl)-3,3-difluoro-allyl]-4-[[3-methyl-5-
(4-methylsulfonylphenyl)-2-thienyl]methyl]-1,2,4-tri-
azol-3-one;
2-[2-(aminomethyl)-3,3-difluoro-allyl]-4-[[3-methyl-5-
(4-piperazin-1-ylphenyl)-2-thienyl]methyl]-1,2,4-tri-
azol-3-one;
2-[2-(aminomethyl)-3,3-difluoro-allyl]-4-[[3-methyl-5-
[6-(trifluoromethyl)-3-pyridyl]-2-thienyl]methyl]-1,2,
4-triazol-3-one;
2-[2-(aminomethyl)-3,3-difluoro-allyl]-4-[[5-[6-(dimeth-
ylamino)-3-pyridyl]-3-methyl-2-thienyl]methyl]-1,2,4-
triazol-3-one;
2-[2-(aminomethyl)-3,3-difluoro-allyl]-4-[[5-(1,3-benzo-
dioxol-5-yl)-3-methyl-2-thienyl]methyl]-1,2,4-triazol-
3-one;
2-[2-(aminomethyl)-3,3-difluoro-allyl]-4-[[5-(1-eth-
ylpyrazol-4-yl)-3-methyl-2-thienyl]methyl]-1,2,4-tri-
azol-3-one;
2-[2-(aminomethyl)-3,3-difluoro-allyl]-4-[6-[2-(1-meth-
ylpyrazol-4-yl)ethynyl]-2-pyridyl]-1,2,4-triazol-3-one;
7-[(E)-2-[5-[[1-[2-(aminomethyl)-3,3-difluoro-allyl]-5-
oxo-1,2,4-triazol-4-yl]methyl]-2-thienyl]vinyl]-1H-
pyrido[2,3-b][1,4]oxazin-2-one;
2-[2-(aminomethyl)-3,3-difluoro-allyl]-4-[[5-[2-[6-(dim-
ethylamino)-3-pyridyl]ethynyl]-2-thienyl]methyl]-1,2,
4-triazol-3-one;
2-[2-(aminomethyl)-3,3-difluoro-allyl]-4-[[5-[2-(6-mor-
pholino-3-pyridyl)ethynyl]-2-thienyl]methyl]-1,2,4-
triazol-3-one;
2-[2-(aminomethyl)-3,3-difluoro-allyl]-4-[[5-[2-(3,4-di-
hydro-2H-1,4-benzoxazin-6-yl)ethynyl]-2-thienyl]
methyl]-1,2,4-triazol-3-one;
6-[2-[5-[[1-[2-(aminomethyl)-3,3-difluoro-allyl]-5-oxo-
1,2,4-triazol-4-yl]methyl]-2-thienyl]ethynyl]-3,4-di-
hydro-1H-quinolin-2-one;
2-[2-(aminomethyl)-3,3-difluoro-allyl]-4-[[5-[2-(2,3-di-
hydro-1H-pyrido[2,3-b][1,4]oxazin-7-yl)ethynyl]-2-
thienyl]methyl]-1,2,4-triazol-3-one;
2-[2-(aminomethyl)-3,3-difluoro-allyl]-4-[[5-[2-(3,4-di-
hydro-2H-pyrido[3,2-b][1,4]oxazin-7-yl)ethynyl]-2-
thienyl]methyl]-1,2,4-triazol-3-one;
2-[2-(aminomethyl)-3,3-difluoro-allyl]-4-[[5-[2-(2,3-di-
hydro-1H-pyrido[2,3-b][1,4]oxazin-6-yl)ethynyl]-2-
thienyl]methyl]-1,2,4-triazol-3-one;

7-[2-[5-[[1-[2-(aminomethyl)-3,3-difluoro-allyl]-5-oxo-1,2,4-triazol-4-yl]methyl]-2-thienyl]ethynyl]-1H-pyrido[2,3-b][1,4]oxazin-2-one;

7-[2-[5-[[1-[2-(aminomethyl)-3,3-difluoro-allyl]-5-oxo-1,2,4-triazol-4-yl]methyl]-2-thienyl]ethynyl]-4H-pyrido[3,2-b][1,4]oxazin-3-one;

2-[2-(aminomethyl)-3,3-difluoro-allyl]-4-[[5-[2-(1-methylpyrazol-4-yl)ethynyl]-2-thienyl]methyl]-1,2,4-triazol-3-one;

2-[2-(aminomethyl)-3,3-difluoro-allyl]-4-[2-(2-thienyl)ethyl]-1,2,4-triazol-3-one;

2-[2-(aminomethyl)-3,3-difluoro-allyl]-4-[2-[5-(4-methylsulfonylphenyl)-2-thienyl]ethyl]-1,2,4-triazol-3-one;

2-[2-(aminomethyl)-3,3-difluoro-allyl]-4-[2-[5-(4-piperazin-1-ylphenyl)-2-thienyl]ethyl]-1,2,4-triazol-3-one;

2-[2-(aminomethyl)-3,3-difluoro-allyl]-4-[2-[5-[6-(trifluoromethyl)-3-pyridyl]-2-thienyl]ethyl]-1,2,4-triazol-3-one;

2-[2-(aminomethyl)-3,3-difluoro-allyl]-4-[2-[5-[6-(dimethylamino)-3-pyridyl]-2-thienyl]ethyl]-1,2,4-triazol-3-one;

2-[2-(aminomethyl)-3,3-difluoro-allyl]-4-[2-[5-(1,3-benzodioxol-5-yl)-2-thienyl]ethyl]-1,2,4-triazol-3-one;

6-[5-[2-[1-[2-(aminomethyl)-3,3-difluoro-allyl]-5-oxo-1,2,4-triazol-4-yl]ethyl]-2-thienyl]-8-methyl-3,4-dihydro-1H-quinolin-2-one;

6-[5-[2-[1-[2-(aminomethyl)-3,3-difluoro-allyl]-5-oxo-1,2,4-triazol-4-yl]ethyl]-2-thienyl]-1-methyl-3,4-dihydroquinolin-2-one;

2-[2-(aminomethyl)-3,3-difluoro-allyl]-4-[2-[5-(1-ethylpyrazol-4-yl)-2-thienyl]ethyl]-1,2,4-triazol-3-one;

3-[5-[[1-[2-(aminomethyl)-3,3-difluoro-allyl]-5-oxo-1,2,4-triazol-4-yl]methyl]-2-thienyl]-N,N-dimethyl-benzamide;

6-[5-[[1-[2-(aminomethyl)-3,3-difluoro-allyl]-5-oxo-1,2,4-triazol-4-yl]methyl]-2-thienyl]-3-methyl-1,4-dihydroquinazolin-2-one;

2-[2-(aminomethyl)-3,3-difluoro-allyl]-4-[[5-[1-(difluoromethyl)pyrazol-4-yl]-2-thienyl]methyl]-1,2,4-triazol-3-one;

2-[2-(aminomethyl)-3,3-difluoro-allyl]-4-[[5-(1-isopropylpyrazol-4-yl)-2-thienyl]methyl]-1,2,4-triazol-3-one;

2-[2-(aminomethyl)-3,3-difluoro-allyl]-4-[[5-[3-(11H-1,2,4-triazol-3-yl)phenyl]-2-thienyl]methyl]-1,2,4-triazol-3-one;

6-[5-[[1-[2-(aminomethyl)-3,3-difluoro-allyl]-5-oxo-1,2,4-triazol-4-yl]methyl]-3-thienyl]-3-methyl-1,4-dihydroquinazolin-2-one;

5-[5-[[1-[2-(aminomethyl)-3,3-difluoro-allyl]-5-oxo-1,2,4-triazol-4-yl]methyl]-3-thienyl]-1-isopropyl-pyridin-2-one;

4-[[4-[4-(4-acetylpiperazin-1-yl)phenyl]-2-thienyl]methyl]-2-[2-(aminomethyl)-3,3-difluoro-allyl]-1,2,4-triazol-3-one;

6-[5-[[1-[2-(aminomethyl)-3,3-difluoro-allyl]-5-oxo-1,2,4-triazol-4-yl]methyl]-3-thienyl]-8-fluoro-1H-quinolin-2-one;

5-[5-[[1-[2-(aminomethyl)-3,3-difluoro-allyl]-5-oxo-1,2,4-triazol-4-yl]methyl]-3-thienyl]-1-methyl-pyridin-2-one;

6-[5-[[1-[2-(aminomethyl)-3,3-difluoro-allyl]-5-oxo-1,2,4-triazol-4-yl]methyl]-3-thienyl]-1,4-dihydro-3,1-benzoxazin-2-one;

6-[5-[[1-[2-(aminomethyl)-3,3-difluoro-allyl]-5-oxo-1,2,4-triazol-4-yl]methyl]-3-thienyl]-3,4-dihydro-1H-quinolin-2-one;

5-[5-[[1-[2-(aminomethyl)-3,3-difluoro-allyl]-5-oxo-1,2,4-triazol-4-yl]methyl]-3-thienyl]-1-ethyl-pyridin-2-one;

2-[2-(aminomethyl)-3,3-difluoro-allyl]-4-[[4-[1-(difluoromethyl)pyrazol-4-yl]-2-thienyl]methyl]-1,2,4-triazol-3-one;

2-[2-(aminomethyl)-3,3-difluoro-allyl]-4-[[4-(1-isopropylpyrazol-4-yl)-2-thienyl]methyl]-1,2,4-triazol-3-one;

2-[2-(aminomethyl)-3,3-difluoro-allyl]-4-[[4-[3-(11H-1,2,4-triazol-3-yl)phenyl]-2-thienyl]methyl]-1,2,4-triazol-3-one;

2-[2-(aminomethyl)-3,3-difluoro-allyl]-4-[[6-(4-methylsulfonylphenyl)benzothiophen-2-yl]methyl]-1,2,4-triazol-3-one;

2-[2-(aminomethyl)-3,3-difluoro-allyl]-4-[[6-(4-piperazin-1-ylphenyl)benzothiophen-2-yl]methyl]-1,2,4-triazol-3-one;

2-[2-(aminomethyl)-3,3-difluoro-allyl]-4-[[6-[6-(trifluoromethyl)-3-pyridyl]benzothiophen-2-yl]methyl]-1,2,4-triazol-3-one;

2-[2-(aminomethyl)-3,3-difluoro-allyl]-4-[[6-[6-(dimethylamino)-3-pyridyl]benzothiophen-2-yl]methyl]-1,2,4-triazol-3-one;

2-[2-(aminomethyl)-3,3-difluoro-allyl]-4-[[6-(1,3-benzodioxol-5-yl)benzothiophen-2-yl]methyl]-1,2,4-triazol-3-one;

6-[2-[[1-[2-(aminomethyl)-3,3-difluoro-allyl]-5-oxo-1,2,4-triazol-4-yl]methyl]benzothiophen-6-yl]-8-methyl-3,4-dihydro-1H-quinolin-2-one;

6-[2-[[1-[2-(aminomethyl)-3,3-difluoro-allyl]-5-oxo-1,2,4-triazol-4-yl]methyl]benzothiophen-6-yl]-1-methyl-3,4-dihydroquinolin-2-one;

2-[2-(aminomethyl)-3,3-difluoro-allyl]-4-[[6-(1-ethylpyrazol-4-yl)benzothiophen-2-yl]methyl]-1,2,4-triazol-3-one;

2-[2-(aminomethyl)-3,3-difluoro-allyl]-4-[[5-(4-methylsulfonylphenyl)benzothiophen-2-yl]methyl]-1,2,4-triazol-3-one;

2-[2-(aminomethyl)-3,3-difluoro-allyl]-4-[[5-(4-piperazin-1-ylphenyl)benzothiophen-2-yl]methyl]-1,2,4-triazol-3-one;

5-[2-[[1-[2-(aminomethyl)-3,3-difluoro-allyl]-5-oxo-1,2,4-triazol-4-yl]methyl]benzothiophen-5-yl]-1-ethyl-pyridin-2-one;

2-[2-(aminomethyl)-3,3-difluoro-allyl]-4-[[5-[6-(dimethylamino)-3-pyridyl]benzothiophen-2-yl]methyl]-1,2,4-triazol-3-one;

2-[2-(aminomethyl)-3,3-difluoro-allyl]-4-[[5-(1,3-benzodioxol-5-yl)benzothiophen-2-yl]methyl]-1,2,4-triazol-3-one;

6-[2-[[1-[2-(aminomethyl)-3,3-difluoro-allyl]-5-oxo-1,2,4-triazol-4-yl]methyl]benzothiophen-5-yl]-8-methyl-3,4-dihydro-1H-quinolin-2-one;

6-[2-[[1-[2-(aminomethyl)-3,3-difluoro-allyl]-5-oxo-1,2,4-triazol-4-yl]methyl]benzothiophen-5-yl]-1-methyl-3,4-dihydroquinolin-2-one;

2-[2-(aminomethyl)-3,3-difluoro-allyl]-4-[[5-(1-ethylpyrazol-4-yl)benzothiophen-2-yl]methyl]-1,2,4-triazol-3-one;

2-[2-(aminomethyl)-3,3-difluoro-allyl]-4-[6-(6-piperazin-1-yl-3-pyridyl)-2-pyridyl]-1,2,4-triazol-3-one;

2-[2-(aminomethyl)-3,3-difluoro-allyl]-4-[6-[4-(morpholine-4-carbonyl)phenyl]-2-pyridyl]-1,2,4-triazol-3-one;

2-[2-(aminomethyl)-3,3-difluoro-allyl]-4-[6-(6-morpholino-3-pyridyl)-2-pyridyl]-1,2,4-triazol-3-one;

2-[2-(aminomethyl)-3,3-difluoro-allyl]-4-[6-(3-piperazin-1-ylphenyl)-2-pyridyl]-1,2,4-triazol-3-one;

2-[2-(aminomethyl)-3,3-difluoro-allyl]-4-[6-[3-(dimethylamino)-4-fluoro-phenyl]-2-pyridyl]-1,2,4-triazol-3-one;

5-[6-[1-[2-(aminomethyl)-3,3-difluoro-allyl]-5-oxo-1,2,4-triazol-4-yl]-2-pyridyl]-1-ethyl-pyridin-2-one;

7-[6-[1-[2-(aminomethyl)-3,3-difluoro-allyl]-5-oxo-1,2,4-triazol-4-yl]-2-pyridyl]-1,4-dihydro-3,1-benzoxazin-2-one;

2-[2-(aminomethyl)-3,3-difluoro-allyl]-4-[3-methyl-5-(6-piperazin-1-yl-3-pyridyl)-2-pyridyl]-1,2,4-triazol-3-one;

6-[6-[1-[2-(aminomethyl)-3,3-difluoro-allyl]-5-oxo-1,2,4-triazol-4-yl]-5-methyl-3-pyridyl]-4H-1,4-benzoxazin-3-one;

2-[2-(aminomethyl)-3,3-difluoro-allyl]-4-[5-[2-(2-methoxyethylamino)pyrimidin-5-yl]-3-methyl-2-pyridyl]-1,2,4-triazol-3-one;

2-[2-(aminomethyl)-3,3-difluoro-allyl]-4-[3-methyl-5-(4-methyl-2,3-dihydro-1,4-benzoxazin-7-yl)-2-pyridyl]-1,2,4-triazol-3-one;

2-[2-(aminomethyl)-3,3-difluoro-allyl]-4-[3-methyl-5-(3,4,5-trimethoxyphenyl)-2-pyridyl]-1,2,4-triazol-3-one;

2-[2-(aminomethyl)-3,3-difluoro-allyl]-4-[5-(6-methoxy-3-pyridyl)-3-methyl-2-pyridyl]-1,2,4-triazol-3-one;

4-[5-(2-amino-1,3-benzothiazol-5-yl)-3-methyl-2-pyridyl]-2-[2-(aminomethyl)-3,3-difluoro-allyl]-1,2,4-triazol-3-one;

2-[2-(aminomethyl)-3,3-difluoro-allyl]-4-[5-(2,1,3-benzoxadiazol-5-yl)-3-methyl-2-pyridyl]-1,2,4-triazol-3-one;

2-[2-(aminomethyl)-3,3-difluoro-allyl]-4-[3-methyl-5-(1H-pyrrolo[2,3-b]pyridin-5-yl)-2-pyridyl]-1,2,4-triazol-3-one;

2-[2-(aminomethyl)-3,3-difluoro-allyl]-4-[5-(1,3-benzoxazol-5-yl)-3-methyl-2-pyridyl]-1,2,4-triazol-3-one;

2-[2-(aminomethyl)-3,3-difluoro-allyl]-4-[3-methyl-5-[4-(2-oxopyrrolidin-1-yl)phenyl]-2-pyridyl]-1,2,4-triazol-3-one;

4-[5-(5-acetyl-2-thienyl)-3-methyl-2-pyridyl]-2-[2-(aminomethyl)-3,3-difluoro-allyl]-1,2,4-triazol-3-one;

2-[2-(aminomethyl)-3,3-difluoro-allyl]-4-[3-methyl-5-[3-(1H-pyrazol-3-yl)phenyl]-2-pyridyl]-1,2,4-triazol-3-one;

2-[2-(aminomethyl)-3,3-difluoro-allyl]-4-[5-(1H-indazol-6-yl)-3-methyl-2-pyridyl]-1,2,4-triazol-3-one;

2-[2-(aminomethyl)-3,3-difluoro-allyl]-4-[3-methyl-5-(3-methylsulfonylphenyl)-2-pyridyl]-1,2,4-triazol-3-one;

2-[2-(aminomethyl)-3,3-difluoro-allyl]-4-[3-methyl-5-(3-piperazin-1-ylphenyl)-2-pyridyl]-1,2,4-triazol-3-one;

2-[2-(aminomethyl)-3,3-difluoro-allyl]-4-[3-methyl-5-[4-(morpholine-4-carbonyl)phenyl]-2-pyridyl]-1,2,4-triazol-3-one;

2-[2-(aminomethyl)-3,3-difluoro-allyl]-4-[3-methyl-5-(4-morpholinophenyl)-2-pyridyl]-1,2,4-triazol-3-one;

4-[6-[1-[2-(aminomethyl)-3,3-difluoro-allyl]-5-oxo-1,2,4-triazol-4-yl]-5-methyl-3-pyridyl]-N,N-dimethylbenzenesulfonamide;

2-[2-(aminomethyl)-3,3-difluoro-allyl]-4-[3-methyl-5-[3-(1H-1,2,4-triazol-3-yl)phenyl]-2-pyridyl]-1,2,4-triazol-3-one;

2-[2-(aminomethyl)-3,3-difluoro-allyl]-4-[3-methyl-5-[2-(1-methylpyrazol-4-yl)ethynyl]-2-pyridyl]-1,2,4-triazol-3-one;

2-[2-(aminomethyl)-3,3-difluoro-allyl]-4-[5-[2-[6-(dimethylamino)-3-pyridyl]ethynyl]-3-methyl-2-pyridyl]-1,2,4-triazol-3-one;

2-[2-(aminomethyl)-3,3-difluoro-allyl]-4-[3-methyl-5-[2-(6-morpholino-3-pyridyl)ethynyl]-2-pyridyl]-1,2,4-triazol-3-one;

2-[2-(aminomethyl)-3,3-difluoro-allyl]-4-[5-[2-(3,4-dihydro-2H-1,4-benzoxazin-6-yl)ethynyl]-3-methyl-2-pyridyl]-1,2,4-triazol-3-one;

2-[2-(aminomethyl)-3,3-difluoro-allyl]-4-[5-[2-(2,3-dihydro-1H-pyrido[2,3-b][1,4]oxazin-7-yl)ethynyl]-3-methyl-2-pyridyl]-1,2,4-triazol-3-one;

2-[2-(aminomethyl)-3,3-difluoro-allyl]-4-[5-[2-(3,4-dihydro-2H-pyrido[3,2-b][1,4]oxazin-7-yl)ethynyl]-3-methyl-2-pyridyl]-1,2,4-triazol-3-one;

2-[2-(aminomethyl)-3,3-difluoro-allyl]-4-[5-[2-(2,3-dihydro-1H-pyrido[2,3-b][1,4]oxazin-6-yl)ethynyl]-3-methyl-2-pyridyl]-1,2,4-triazol-3-one;

7-[2-[6-[1-[2-(aminomethyl)-3,3-difluoro-allyl]-5-oxo-1,2,4-triazol-4-yl]-5-methyl-3-pyridyl]ethynyl]-1H-pyrido[2,3-b][1,4]oxazin-2-one;

7-[2-[6-[1-[2-(aminomethyl)-3,3-difluoro-allyl]-5-oxo-1,2,4-triazol-4-yl]-5-methyl-3-pyridyl]ethynyl]-4H-pyrido[3,2-b][1,4]oxazin-3-one;

6-[2-[6-[1-[2-(aminomethyl)-3,3-difluoro-allyl]-5-oxo-1,2,4-triazol-4-yl]-5-methyl-3-pyridyl]ethynyl]-3,4-dihydro-1H-quinolin-2-one;

6-[6-[1-[2-(aminomethyl)-3,3-difluoro-allyl]-5-oxo-1,2,4-triazol-4-yl]-5-methyl-3-pyridyl]-3-methyl-1,4-dihydroquinazolin-2-one;

2-[2-(aminomethyl)-3,3-difluoro-allyl]-4-[5-[1-(difluoromethyl)pyrazol-4-yl]-3-methyl-2-pyridyl]-1,2,4-triazol-3-one;

2-[2-(aminomethyl)-3,3-difluoro-allyl]-4-[5-(1-isopropylpyrazol-4-yl)-3-methyl-2-pyridyl]-1,2,4-triazol-3-one;

2-[2-(aminomethyl)-3,3-difluoro-allyl]-4-[2-methyl-3-(4-methylsulfonylphenyl)phenyl]-1,2,4-triazol-3-one;

2-[2-(aminomethyl)-3,3-difluoro-allyl]-4-[2-methyl-3-(4-piperazin-1-ylphenyl)phenyl]-1,2,4-triazol-3-one;

2-[2-(aminomethyl)-3,3-difluoro-allyl]-4-[2-methyl-3-[6-(trifluoromethyl)-3-pyridyl]phenyl]-1,2,4-triazol-3-one;

2-[2-(aminomethyl)-3,3-difluoro-allyl]-4-[3-[6-(dimethylamino)-3-pyridyl]-2-methyl-phenyl]-1,2,4-triazol-3-one;

2-[2-(aminomethyl)-3,3-difluoro-allyl]-4-[3-(1,3-benzodioxol-5-yl)-2-methyl-phenyl]-1,2,4-triazol-3-one;

6-[3-[1-[2-(aminomethyl)-3,3-difluoro-allyl]-5-oxo-1,2,4-triazol-4-yl]-2-methyl-phenyl]-8-methyl-3,4-dihydro-1H-quinolin-2-one;

6-[3-[1-[2-(aminomethyl)-3,3-difluoro-allyl]-5-oxo-1,2,4-triazol-4-yl]-2-methyl-phenyl]-1-methyl-3,4-dihydroquinolin-2-one;

2-[2-(aminomethyl)-3,3-difluoro-allyl]-4-[3-(1-ethylpyrazol-4-yl)-2-methyl-phenyl]-1,2,4-triazol-3-one;

2-[2-(aminomethyl)-3,3-difluoro-allyl]-4-[3-[1-(difluoromethyl)pyrazol-4-yl]-2-methyl-phenyl]-1,2,4-triazol-3-one;

2-[2-(aminomethyl)-3,3-difluoro-allyl]-4-[3-(1-isopropylpyrazol-4-yl)-2-methyl-phenyl]-1,2,4-triazol-3-one;

2-[2-(aminomethyl)-3,3-difluoro-allyl]-4-[2-methyl-3-[3-(1H-1,2,4-triazol-3-yl)phenyl]phenyl]-1,2,4-triazol-3-one;

2-[2-(aminomethyl)-3,3-difluoro-allyl]-4-[[4-(1-ethylpyrazol-4-yl)phenyl]methyl]-1,2,4-triazol-3-one;

2-[2-(aminomethyl)-3,3-difluoro-allyl]-4-[[4-(4-methylsulfonylphenyl)phenyl]methyl]-1,2,4-triazol-3-one;

2-[2-(aminomethyl)-3,3-difluoro-allyl]-4-[[4-(4-piper-azin-1-ylphenyl)phenyl]methyl]-1,2,4-triazol-3-one;
2-[2-(aminomethyl)-3,3-difluoro-allyl]-4-[[4-[6-(dimethylamino)-3-pyridyl]phenyl]methyl]-1,2,4-triazol-3-one;
2-[2-(aminomethyl)-3,3-difluoro-allyl]-4-[[4-(1,3-benzodioxol-5-yl)phenyl]methyl]-1,2,4-triazol-3-one;
6-[4-[[1-[2-(aminomethyl)-3,3-difluoro-allyl]-5-oxo-1,2,4-triazol-4-yl]methyl]phenyl]-8-methyl-3,4-dihydro-1H-quinolin-2-one;
5-[4-[[1-[2-(aminomethyl)-3,3-difluoro-allyl]-5-oxo-1,2,4-triazol-4-yl]methyl]phenyl]-1-ethyl-pyridin-2-one;
2-[2-(aminomethyl)-3,3-difluoro-allyl]-4-[[3-(1-ethylpyrazol-4-yl)phenyl]methyl]-1,2,4-triazol-3-one;
2-[2-(aminomethyl)-3,3-difluoro-allyl]-4-[[3-(4-methylsulfonylphenyl)phenyl]methyl]-1,2,4-triazol-3-one;
2-[2-(aminomethyl)-3,3-difluoro-allyl]-4-[[3-[6-(dimethylamino)-3-pyridyl]phenyl]methyl]-1,2,4-triazol-3-one;
2-[2-(aminomethyl)-3,3-difluoro-allyl]-4-[[3-(1,3-benzodioxol-5-yl)phenyl]methyl]-1,2,4-triazol-3-one;
6-[3-[[1-[2-(aminomethyl)-3,3-difluoro-allyl]-5-oxo-1,2,4-triazol-4-yl]methyl]phenyl]-8-methyl-3,4-dihydro-1H-quinolin-2-one;
6-[3-[[1-[2-(aminomethyl)-3,3-difluoro-allyl]-5-oxo-1,2,4-triazol-4-yl]methyl]phenyl]-1-methyl-3,4-dihydroquinolin-2-one;
5-[3-[[1-[2-(aminomethyl)-3,3-difluoro-allyl]-5-oxo-1,2,4-triazol-4-yl]methyl]phenyl]-1-ethyl-pyridin-2-one;
2-[2-(aminomethyl)-3,3-difluoro-allyl]-4-[[2-(1-ethylpyrazol-4-yl)phenyl]methyl]-1,2,4-triazol-3-one;
2-[2-(aminomethyl)-3,3-difluoro-allyl]-4-[[2-(4-methylsulfonylphenyl)phenyl]methyl]-1,2,4-triazol-3-one;
2-[2-(aminomethyl)-3,3-difluoro-allyl]-4-[[2-(4-piperazin-1-ylphenyl)phenyl]methyl]-1,2,4-triazol-3-one;
2-[2-(aminomethyl)-3,3-difluoro-allyl]-4-[[2-[6-(dimethylamino)-3-pyridyl]phenyl]methyl]-1,2,4-triazol-3-one;
2-[2-(aminomethyl)-3,3-difluoro-allyl]-4-[[2-(1,3-benzodioxol-5-yl)phenyl]methyl]-1,2,4-triazol-3-one;
6-[2-[[1-[2-(aminomethyl)-3,3-difluoro-allyl]-5-oxo-1,2,4-triazol-4-yl]methyl]phenyl]-8-methyl-3,4-dihydro-1H-quinolin-2-one;
6-[2-[[1-[2-(aminomethyl)-3,3-difluoro-allyl]-5-oxo-1,2,4-triazol-4-yl]methyl]phenyl]-1-methyl-3,4-dihydroquinolin-2-one;
5-[2-[[1-[2-(aminomethyl)-3,3-difluoro-allyl]-5-oxo-1,2,4-triazol-4-yl]methyl]phenyl]-1-ethyl-pyridin-2-one;
2-[2-(aminomethyl)-3,3-difluoro-allyl]-4-[[5-[4-(1-ethylpyrazol-4-yl)phenyl]-2-thienyl]methyl]-1,2,4-triazol-3-one;
2-[2-(aminomethyl)-3,3-difluoro-allyl]-4-[[5-[3-(1-ethylpyrazol-4-yl)phenyl]-2-thienyl]methyl]-1,2,4-triazol-3-one;
2-[2-(aminomethyl)-3,3-difluoro-allyl]-4-[[4-[4-(1-ethylpyrazol-4-yl)phenyl]-2-thienyl]methyl]-1,2,4-triazol-3-one;
2-[2-(aminomethyl)-3,3-difluoro-allyl]-4-[[4-[3-(1-ethylpyrazol-4-yl)phenyl]-2-thienyl]methyl]-1,2,4-triazol-3-one;
2-[2-(aminomethyl)-3,3-difluoro-allyl]-4-[5-[4-(1-ethylpyrazol-4-yl)phenyl]-3-methyl-2-pyridyl]-1,2,4-triazol-3-one;
2-[2-(aminomethyl)-3,3-difluoro-allyl]-4-[5-[3-(1-ethylpyrazol-4-yl)phenyl]-3-methyl-2-pyridyl]-1,2,4-triazol-3-one;
2-[2-(aminomethyl)-3,3-difluoro-allyl]-4-[[5-(1H-pyrazol-4-yl)-2-thienyl]methyl]-1,2,4-triazol-3-one;
2-[2-(aminomethyl)-3,3-difluoro-allyl]-4-[[5-(1-methylsulfonylpyrazol-4-yl)-2-thienyl]methyl]-1,2,4-triazol-3-one;
2-[2-(aminomethyl)-3,3-difluoro-allyl]-4-[[5-(1-cyclopropylsulfonylpyrazol-4-yl)-2-thienyl]methyl]-1,2,4-triazol-3-one;
2-[2-(aminomethyl)-3,3-difluoro-allyl]-4-[[5-[1-(cyclopropylmethyl)pyrazol-4-yl]-2-thienyl]methyl]-1,2,4-triazol-3-one;
2-[2-(aminomethyl)-3,3-difluoro-allyl]-4-[[5-(1-methylpyrazol-4-yl)-2-thienyl]methyl]-1,2,4-triazol-3-one;
2-[2-(aminomethyl)-3,3-difluoro-allyl]-4-[[5-(1-benzylpyrazol-4-yl)-2-thienyl]methyl]-1,2,4-triazol-3-one;
2-[2-(aminomethyl)-3,3-difluoro-allyl]-4-[[3-fluoro-5-(4-piperazin-1-ylphenyl)-2-thienyl]methyl]-1,2,4-triazol-3-one;
5-[5-[[1-[2-(aminomethyl)-3,3-difluoro-allyl]-5-oxo-1,2,4-triazol-4-yl]methyl]-4-fluoro-2-thienyl]-1-ethyl-pyridin-2-one;
2-[2-(aminomethyl)-3,3-difluoro-allyl]-4-[[5-(1,3-benzodioxol-5-yl)-3-fluoro-2-thienyl]methyl]-1,2,4-triazol-3-one;
6-[5-[[1-[2-(aminomethyl)-3,3-difluoro-allyl]-5-oxo-1,2,4-triazol-4-yl]methyl]-4-fluoro-2-thienyl]-1-methyl-3,4-dihydroquinolin-2-one;
2-[2-(aminomethyl)-3,3-difluoro-allyl]-4-[[5-(1-ethylpyrazol-4-yl)-3-fluoro-2-thienyl]methyl]-1,2,4-triazol-3-one;
2-(2-(aminomethyl)-3,3-difluoroallyl)-4-((5-(6-(dimethylamino)pyridin-3-yl)-3-fluorothiophen-2-yl)methyl)-2,4-dihydro-3H-1,2,4-triazol-3-one; and
6-(5-((1-(2-(aminomethyl)-3,3-difluoroallyl)-5-oxo-1,5-dihydro-4H-1,2,4-triazol-4-yl)methyl)-4-fluorothiophen-2-yl)-8-methyl-3,4-dihydroquinolin-2(1H)-one;
or a stereoisomer thereof, or a pharmaceutically acceptable salt thereof.

2. A pharmaceutical composition comprising the compound according to claim 1, or a stereoisomer thereof, or a pharmaceutically acceptable salt thereof, and at least one pharmaceutically acceptable excipient.

3. A compound which is 5-[5-[[1-[2-(aminomethyl)-3,3-difluoro-allyl]-5-oxo-1,2,4-triazol-4-yl]methyl]-2-thienyl]-7-fluoro-indolin-2-one, or a pharmaceutically acceptable salt thereof.

4. A compound which is 6-[5-[[1-[2-(aminomethyl)-3,3-difluoro-allyl]-5-oxo-1,2,4-triazol-4-yl]methyl]-2-thienyl]-8-methyl-1H-quinolin-2-one, or a pharmaceutically acceptable salt thereof.

5. A compound which is 7-[5-[[1-[2-(aminomethyl)-3,3-difluoro-allyl]-5-oxo-1,2,4-triazol-4-yl]methyl]-2-thienyl]-3,4-dihydro-2H-isoquinolin-1-one, or a pharmaceutically acceptable salt thereof.

6. A compound which is 2-[2-(aminomethyl)-3,3-difluoro-allyl]-4-[[5-([1,2,4]triazolo[1,5-a]pyridin-7-yl)-2-thienyl]methyl]-1,2,4-triazol-3-one, or a pharmaceutically acceptable salt thereof.

7. A compound which is 6-[5-[[1-[2-(aminomethyl)-3,3-difluoro-allyl]-5-oxo-1,2,4-triazol-4-yl]methyl]-2-thienyl]-8-fluoro-3,4-dihydro-1H-quinolin-2-one, or a pharmaceutically acceptable salt thereof.

8. A compound which is 2-[2-(aminomethyl)-3,3-difluoro-allyl]-4-[[5-(5,6,7,8-tetrahydro-1,8-naphthyridin-3-yl)-2-thienyl]methyl]-1,2,4-triazol-3-one, or a pharmaceutically acceptable salt thereof.

9. A compound which is 6-[5-[[1-[2-(aminomethyl)-3,3-difluoro-allyl]-5-oxo-1,2,4-triazol-4-yl]methyl]-2-thienyl]-8-fluoro-1H-quinolin-2-one, or a pharmaceutically acceptable salt thereof.

* * * * *